US012755814B2

(12) United States Patent
Thacker et al.

(10) Patent No.: US 12,755,814 B2
(45) Date of Patent: Oct. 6, 2026

(54) PLATFORMS, SYSTEMS, AND METHODS FOR RAPID FERMENTER SAMPLING

(71) Applicant: X Development LLC, Mountain View, CA (US)

(72) Inventors: Richard Eugene Thacker, Burlingame, CA (US); Thomas Jon Scherbart, Mountain View, CA (US)

(73) Assignee: X Development LLC, Mountain View, CA (US)

(*) Notice: Subject to any disclaimer, the term of this patent is extended or adjusted under 35 U.S.C. 154(b) by 0 days.

(21) Appl. No.: 19/337,758

(22) Filed: Sep. 23, 2025

(65) Prior Publication Data

US 2026/0071168 A1 Mar. 12, 2026

Related U.S. Application Data

(63) Continuation of application No. PCT/US2025/031891, filed on Jun. 2, 2025.

(Continued)

(51) Int. Cl.

*C12M 1/00* (2006.01)
*C12M 1/26* (2006.01)

(Continued)

(52) U.S. Cl.

CPC ............ *G16B 40/00* (2019.02); *C12M 23/12* (2013.01); *C12M 29/00* (2013.01); *C12M 33/14* (2013.01);

(Continued)

(58) Field of Classification Search

CPC ...... C12M 23/12; C12M 29/00; C12M 33/14; C12M 41/44; C12M 41/48; G01N 30/72;

(Continued)

(56) References Cited

U.S. PATENT DOCUMENTS 9,235,684 B2 1/2016 Prior et al.
11,456,053 B1 9/2022 Russo (Continued)

FOREIGN PATENT DOCUMENTS

WO WO 2023/015307 A1 2/2023

OTHER PUBLICATIONS

Bhardwaj et al. (Life (2022) vol. 12:20 pages).

(Continued)

*Primary Examiner* — Lydia Edwards
(74) *Attorney, Agent, or Firm* — Fish & Richardson P.C.

(57) ABSTRACT

Platforms, systems, and methods for rapid fermenter sampling. According to one aspect, there is provided A rapid sampling system for obtaining samples from a fermentation system, comprising: a sample inlet fluidly connected to the fermentation system; a pump fluidly connected to the sample inlet and configured to draw a sample from the fermentation system; a first valve fluidly connected to an outlet of the pump; a second valve fluidly connected to a liquid nitrogen chamber; a multi-well filter plate, wherein an individual well of the multi-well filter plate is configured to collect and filter the sample; a motorized base operatively connected to the multi-well filter plate configured to adjust a position of the multi-well filter plate; and a control unit including one or more processors and one or more memories operatively connected to the pump, the first valve, the second valve, and the motorized base.

12 Claims, 52 Drawing Sheets

Related U.S. Application Data

(60) Provisional application No. 63/803,471, filed on May 9, 2025, provisional application No. 63/655,575, filed on Jun. 3, 2024.

(51) Int. Cl.

| | |
|---|---|
| ***C12M 1/32*** | (2006.01) |
| ***C12M 1/34*** | (2006.01) |
| ***C12M 1/36*** | (2006.01) |
| ***G01N 30/02*** | (2006.01) |
| ***G01N 30/72*** | (2006.01) |
| ***G01N 30/86*** | (2006.01) |
| ***G06F 11/3604*** | (2025.01) |
| ***G06F 11/3668*** | (2025.01) |
| ***G06F 30/27*** | (2020.01) |
| ***G06N 3/0475*** | (2023.01) |
| ***G06N 3/091*** | (2023.01) |
| ***G06N 5/045*** | (2023.01) |
| ***G06Q 30/0201*** | (2023.01) |
| ***G16B 5/00*** | (2019.01) |
| ***G16B 20/00*** | (2019.01) |
| ***G16B 20/50*** | (2019.01) |
| ***G16B 25/10*** | (2019.01) |
| ***G16B 30/00*** | (2019.01) |
| ***G16B 30/10*** | (2019.01) |
| ***G16B 35/20*** | (2019.01) |
| ***G16B 40/00*** | (2019.01) |
| ***G16B 40/20*** | (2019.01) |
| ***G16B 40/30*** | (2019.01) |

(52) U.S. Cl.

CPC ............ *C12M 41/44* (2013.01); *C12M 41/48* (2013.01); *G01N 30/72* (2013.01); *G01N 30/8631* (2013.01); *G01N 30/8651* (2013.01); *G01N 30/8679* (2013.01); *G01N 30/8693* (2013.01); *G06F 11/3608* (2013.01); *G06F 11/3692* (2013.01); *G06F 30/27* (2020.01); *G06N 3/0475* (2023.01); *G06N 3/091* (2023.01); *G06N 5/045* (2013.01); *G06Q 30/0201* (2013.01); *G16B 5/00* (2019.02); *G16B 20/00* (2019.02); *G16B 20/50* (2019.02); *G16B 25/10* (2019.02); *G16B 30/00* (2019.02); *G16B 30/10* (2019.02); *G16B 35/20* (2019.02); *G16B 40/20* (2019.02); *G16B 40/30* (2019.02)

(58) Field of Classification Search

CPC ........... G01N 30/8631; G01N 30/8651; G01N 30/8679; G01N 30/8693; G06F 30/27; G06N 20/00; G06N 20/10; G06N 3/044; G06N 3/0442; G06N 3/045; G06N 3/0455; G06N 3/0475; G06N 3/08; G06N 3/088; G06N 3/091; G06N 5/01; G06N 5/045; G06N 7/01; G06Q 30/0201; G16B 20/00; G16B 20/20; G16B 20/50; G16B 25/10; G16B 30/00; G16B 30/10; G16B 35/20; G16B 40/00; G16B 40/20; G16B 40/30; G16B 5/00; G16B 5/20

See application file for complete search history.

(56) References Cited

U.S. PATENT DOCUMENTS

| | | | |
|---|---|---|---|
| 11,574,703 | B2 | 2/2023 | Abeliuk |
| 2006/0014302 | A1 | 1/2006 | Martinez et al. |
| 2014/0145074 | A1 | 5/2014 | Giles et al. |
| 2019/0060374 | A1 | 2/2019 | Hitchcock et al. |
| 2019/0225674 | A1 | 7/2019 | Lu |
| 2019/0332891 | A1 | 10/2019 | Lamkin et al. |
| 2019/0338364 | A1 | 11/2019 | Newman et al. |
| 2020/0168291 | A1 | 5/2020 | Chowdhury et al. |
| 2020/0211676 | A1 | 7/2020 | Perianayagam |
| 2021/0024918 | A1 | 1/2021 | Serber et al. |
| 2021/0063410 | A1 | 3/2021 | Wilcox et al. |
| 2021/0233605 | A1 | 7/2021 | Yoshikawa et al. |
| 2021/0366572 | A1 | 11/2021 | Zhang et al. |
| 2022/0301658 | A1 | 9/2022 | Zamft et al. |
| 2022/0374776 | A1 | 11/2022 | Liu |
| 2023/0045080 | A1 | 2/2023 | Marks |
| 2023/0281362 | A1 | 9/2023 | Ruggero |
| 2023/0313156 | A1 | 10/2023 | Zhu et al. |
| 2024/0047006 | A1 | 2/2024 | Pan |
| 2025/0259715 | A1 | 8/2025 | Crabtree |

OTHER PUBLICATIONS

Goshisht (ACS Omega (Feb. 19, 2024); vol. 9:9921-9945).

Liu et. al. "Pre-training of graph neural network for modeling effects of mutations on protein-protein binding affinity." arXiv preprintarXiv:2008.12473 (2020) (Year: 2020).

Liu T et al., scElmo: Embeddings from language models are good learners for single-cell data analysis. bioRxiv. Mar. 2024.

National Academies of Sciences, Engineering, and Medicine. 2002. Scientific Research in Education. Washington, DC: The National Academies Press. https://doi.Org/10.17226/10236:Chapter3; 44 pages.

Sieow et. al. "Synthetic biology meets machine learning" Computational Biology and Machine Learning for Metabolic Engineering and Synthetic Biology. New York, NY: Springer (2022) pp. 21-39 (Year: 2022).

Sinai et. al. "Variational auto-encoding of protein sequences." arXiv preprint arXiv:1712.03346 (2017). (Year: 2017).

Yu T etal., Machine learning-enabled retrobiosynthesis of molecules. Nature Catalysis. (Year: 2023).

De Mey et al., "Minimizing acetate formation in *E. coli* fermentations," Journal of Industrial Microbiology and Biotechnology, Nov. 2007, 34(11):689-700.

Arpino et al., "Tuning the dials of synthetic biology," Microbiology, Jul. 1, 2013, 159(Pt_7):1236-1253.

Gilman et al., "Statistical design of experiments for synthetic biology," ACS Synthetic Biology, Jan. 7, 2021, 10(1):1-18.

International Search Report and Written Opinion in International Appln. No. PCT/US2025/031891, mailed on Oct. 17, 2025, 33 pages.

Lee et al., "Systems strategies for developing industrial microbial strains," Nature Biotechnology, Oct. 8, 2015, 33(10):1061-1072.

Mathis et al., "Predicting prime editing efficiency and product purity by deep learning," Nature Biotechnology, Aug. 11, 2023, 41(8):1151-1159.

Nguyen et al., "Recent advances and prospects of computational methods for metabolite identification: a review with emphasis on machine learning approaches," Briefings in Bioinformatics, Aug. 6, 2018, 20(6):2028-2043.

Rebagay et al., "Studies and research concerning BNFP: on-line isotopic concentration monitors for reprocessing solutions," Allied-General Nuclear Services, No. AGNS-35900-2.4-107, Nov. 1980, 58 pages.

Shapira et al., "Tracking the emergence of synthetic biology," Scientometrics, 2017, 112(3):1439-1469.

Stage et al., "Lactobacillus rhamnosus GG genomic and phenotypic stability in an industrial production process," Applied and Environmental Microbiology, Mar. 2020, 86(6):e02780-19.

Xiao et al., "Metabolite identification and quantitation in LC-MS/MS-based metabolomics," TrAC Trends in Analytical Chemistry, Feb. 2012, 32:1-14.

Zhao et al., "A literature review of gene function prediction by modeling gene ontology," Frontiers in Genetics, Apr. 23, 2020, 11:400.

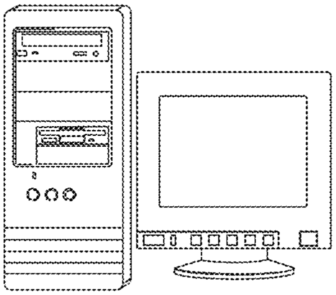

5202 integrate content of at least one publication data set relating to the biological strain and at least one proprietary data set including a set of parameters of a synthetic biological process in which the biological strain produces a functional output 5204 providing the integrated content as an input to a set of AI-based learning models 5206 generating, by at least one member of the set of AI-based learning models, a set of recommendations wherein the set of recommendations relate to modifications to a set of environmental parameters of the biological strain such that the set of recommendations enhance the production of the functional output by the biological strain

FIG. 12

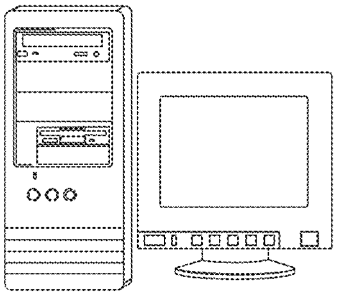

5302 integrate content of at least one publication data set relating to the biological strain and at least one proprietary data set including a set of parameters of a synthetic biological process in which the biological strain produces a functional output 5304 providing the integrated content as an input to a set of AI-based learning models 5306 generating, by at least one member of the set of AI-based learning models, a set of recommendations wherein the set of recommendations relate to modifications to a set of biological pathways such that the set of recommendations enhance the production of the functional output by the biological strain

FIG. 13

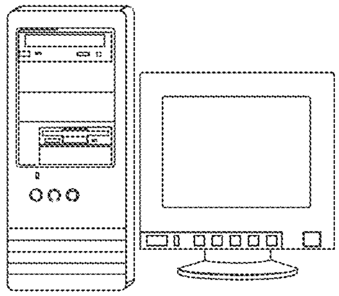

5402 integrate content of at least one publication data set relating to the biological strain and at least one proprietary data set including a set of parameters of a synthetic biological process in which the biological strain produces a functional output 5404 providing the integrated content as an input to a set of AI-based learning models 5406 generating, by at least one member of the set of AI-based learning models, a set of recommendations wherein the set of recommendations relate to modifications to a set of proteins and/or enzymes such that the set of recommendations enhance the production of the functional output by the biological strain

FIG. 14

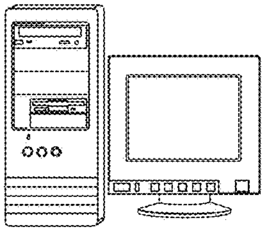

7702
collect a set of samples from a fermentation system at predetermined time increments 7704
prepare the set of samples for an analytical and mass spectrometry instrument 7706
generate raw measurement data associated with the samples and provide the data to an automated omics for generalization system 7708
determine a set of concentrations for a set of metabolites in the set of samples and output the set of concentrations

FIG. 24

Transformer Model 4302

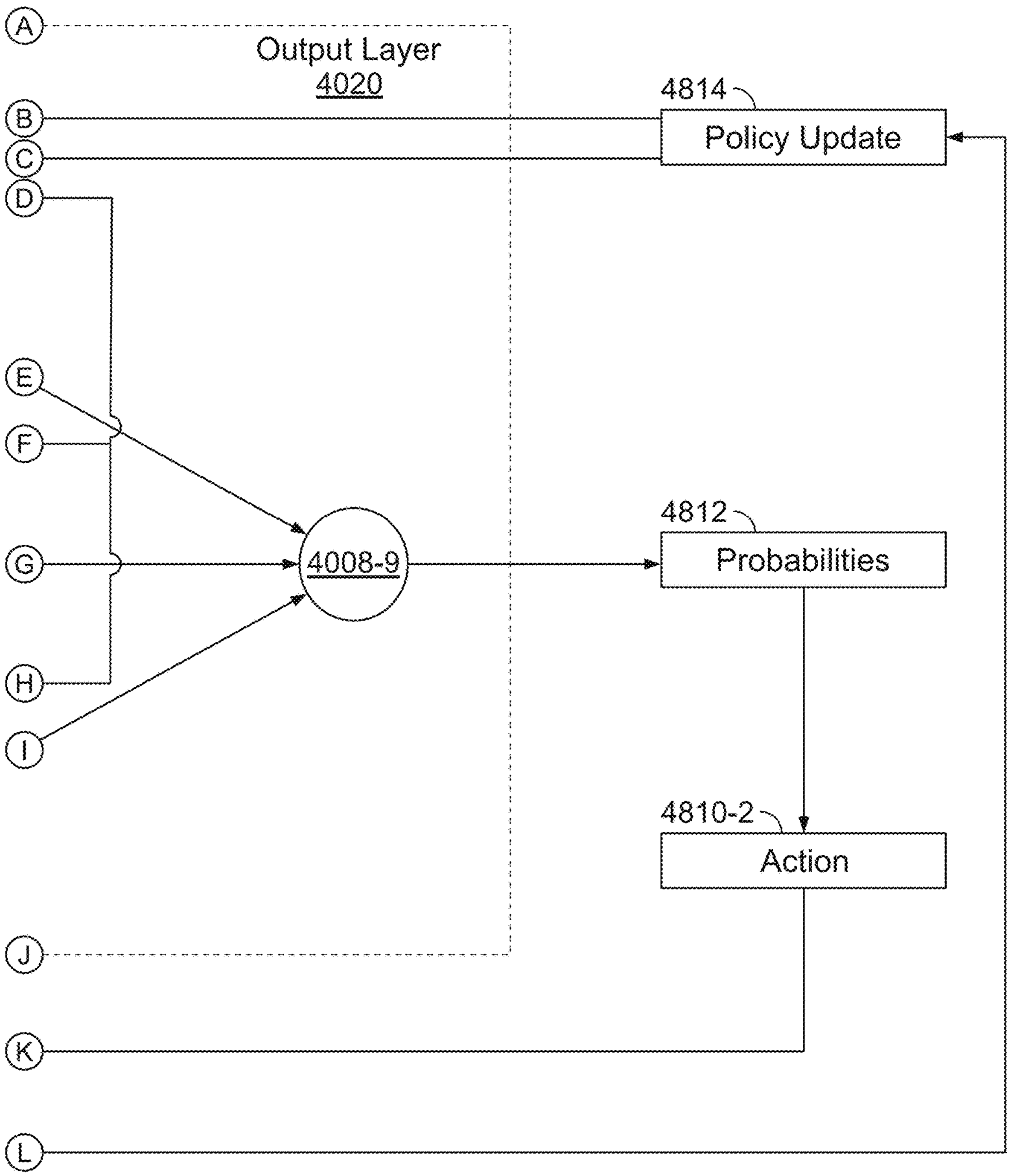
FIG. 48(Cont...)

PLATFORMS, SYSTEMS, AND METHODS FOR RAPID FERMENTER SAMPLING

CROSS-REFERENCE TO RELATED APPLICATIONS

This application is a continuation of PCT Application No. PCT/US2025/031891, filed on Jun. 2, 2025, which claims priority to U.S. Provisional Patent Application No. 63/655,575, filed on Jun. 3, 2024, and U.S. Provisional Patent Application No. 63/803,471, filed on May 9, 2025, and the disclosure of these applications are incorporated herein by reference in their entirety. Each of the aforementioned earlier-filed applications is hereby incorporated by reference in its entirety.

BACKGROUND

Most synthetic biology work today is lab-driven, and hence capital intensive, painstaking, expensive, and uncertain. However, the rapid development of AI models in general, as well as in pharma and specific segments within the life sciences, is poised to spur rapid innovation in AI-driven synthetic biology. Competition will emerge as AI, LLMs, and supporting technologies accelerate. These advancements could reduce barriers to entry, contributing to the emergence of a rapidly evolving research and development landscape and marketplace.

SUMMARY

Embodiments include an AI-guided synthetic biology development platform, systems, and methods substantially as shown and described.

Embodiments include a method for providing AI-guided synthetic biology development platform, systems, and methods substantially as shown and described.

In embodiments, a computer-implemented method for data integration in an AI-guided analytic platform for development of biologic synthesis processes may comprise: receiving, by a platform, biologic data from a plurality of databases, wherein the biologic data use different data formats and/or semantics; converting the received biologic data into at least one standardized data format to create an integrated dataset; processing the integrated dataset through at least one data normalization process to minimize batch-specific systemic variation; storing the normalized biologic data in a structured format that describes biologic components and their relationships to other components; applying at least one machine learning method to the normalized biologic data to generate at least one predictive model for synthetic biology design; and outputting at least one specification for biologic system design based on the at least one predictive model.

In embodiments, the data normalization processes used by the platform may include applying a Bayesian statistical model that incorporates prior knowledge about strain behavior, modeling different sources of variation including biological effects and technical factors, estimating strain performance while accounting for batch effects and other sources of systematic variability, batch effect correction, wherein a batch effect correction addresses systematic variations across at least one of a plurality of experimental runs, equipment, or operators, multi-modal data integration, or some other type of data normalization process.

In embodiments, multi-modal data integration may include data relating to at least one of an enzyme level, a metabolite concentration, or a gene expression level.

In embodiments, data normalization processes used by the platform may include standardized nomenclature across different data sources, quality control normalization, including flagging an anomalous data point, and/or flagging a well or sample that failed during an experiment.

In embodiments, data normalization processes used by the platform may include experiment normalization, such as experiment normalization to account for a variation across a plurality of experimental runs using a similar strain or condition. Experiment normalization used by the platform may implement a statistical method to minimize impact of a technical variation, and/or may use a control sample and spike-in standard for validation.

In embodiments, data normalization processes used by the platform may include cross-platform data harmonization, including but not limited to data harmonization that standardizes data from a plurality of experimental platforms and setups.

In embodiments, data normalization processes used by the platform may include time series data normalization, wherein the time series data normalization includes normalizing data relating to time-varying growth conditions, wherein the time series data normalization includes normalizing data relating to variations in a feed profile or fermentation parameter.

In embodiments, data normalization processes used by the platform may include knowledge graph-based normalization, including but not limited to knowledge graph-based normalization that represents biological entities and relationships in standardized format, knowledge graph-based normalization that associates information across a plurality of experiments or organisms, and/or knowledge graph-based normalization integrates a plurality of biological data types.

In embodiments, a predictive model used by the platform may include, but is not limited to, a long-short term memory model, a transformer model, a convolutional neural network model, a perceptron model, or a multi-modal deep learning architecture.

In embodiments, the platform may include a computer-implemented method for data quality assurance in an AI-guided analytic platform for development of biologic synthesis processes, comprising: collecting raw experimental data associated with a strain performance measurement; implementing a data normalization and quality control procedure to process the raw experimental data; validating a genotype of a strain through a data intake process; generating an analytical measure associated with quality control for the experimental data; identifying an outlier in an experimental dataset; maintaining metadata about an experimental condition or processing step; and storing processed and validated data in a knowledge graph structure that tracks data provenance from a raw experimental measurement to a processed value.

In embodiments, the platform may collect raw experimental data measuring key metabolites across a population of engineered strains, detecting and flagging anomalous data points through automated quality control, and/or identifying wells or samples that exhibit contamination or produce readouts outside expected ranges based on historical data.

In embodiments, the platform may include strain performance measurement that is an expression level, that is a metabolite concentration, that is growth rate measurement, and/or that is enzyme activity level.

In embodiments, the platform may include a system for ensuring data quality in an AI-guided analytic platform for development of a biologic synthesis process, comprising: one or more processors; memory storing instructions that, when executed by the one or more processors, cause the platform to implement a multi-objective optimization system for performing multi-objective optimizations of the biologic synthesis process, wherein the multi-objective optimization system comprises: a data intake and staging pipeline configured to: collect raw data from a plurality of experimental sources; convert the raw data into at least one standardized format; apply a quality assurance step to identify and correct error and inconsistency in the data; apply a normalization technique to remove a batch effect or technical variation; validate that the normalization technique preserve a specified biologic signal; and a knowledge management system configured to: maintain a log and audit trail for a platform data processing activity; track data lineage from a raw measurement to a processed value; and enable verification of a data processing step to confirm scientific validity.

In embodiments, the platform may include a method for hit identification in an AI-guided analytic platform for development of biologic synthesis processes, comprising: collecting raw experimental data on strain performance; normalizing the experimental data using a probabilistic approach to generate normalized strain performance data; representing strains as probability distributions over possible performance levels, wherein the probability distributions capture both a point estimate of the strain performance and uncertainty around the estimate; defining a hit based on the probability distributions by determining the strains having a specified probability of outperforming a parent strain by a predetermined margin; and identifying a promising strain for further investigation based on the defined hit.

In embodiments, defining a hit may comprise setting a threshold for minimum performance improvement over the parent strain, calculating a probability that each strain exceeds a threshold, and/or ranking strains based on their full performance distribution rather than point estimates.

In embodiments, the platform may include a method for hit identification in an AI-guided analytic platform for development of biologic synthesis processes, comprising: one or more processors; memory storing instructions that, when executed by the one or more processors, cause the platform to implement a multi-objective optimization system for performing multi-objective optimizations of the biologic synthesis processes, wherein the multi-objective optimization system comprises: performing data quality assurance on experimental strain performance data; applying a Bayesian data normalization process to the experimental strain performance data; generating probability distributions representing strain performance and associated uncertainty for a plurality of strains; identifying hits by comparing the probability distributions to defined at least one performance threshold, wherein the hits comprise strains exhibiting improved performance regarding a performance criterion relative to a reference strain; and outputting the identified hits for further optimization and investigation.

In embodiments, data quality assurance may include collecting metadata about experimental conditions, tracking data provenance from raw measurements through processing steps, and/or identifying and correcting errors or inconsistencies in the data.

In embodiments, the platform may include a system for integrating synthetic biology data in an AI-guided analytic platform for development of a biologic synthesis process, comprising: one or more processors; memory storing instructions that, when executed by the one or more processors, cause the platform to implement a multi-objective optimization system for performing multi-objective optimizations of biologic synthesis processes, wherein the multi-objective optimization system comprises: a data intake and staging pipeline configured to: collect biologic data from a plurality of data sources; integrate the collected biologic data into a computationally appropriate form; normalize the integrated biologic data using batch effect correction; validate quality and consistency of the normalized biologic data; store the validated biologic data in a structured format describing relationships between biologic entities; and a machine learning model configured to analyze the stored validated biologic data to generate at least one prediction for synthetic biology system design.

In embodiments, a structured data format may be a bipartite graph database structure, wherein the bipartite graph database structure organizes data into at least one molecule node and at least one process node, wherein the at least one molecule node represents at least one of a molecules, atomic elements, ions, compounds, nucleic acids, proteins, or macromolecules, wherein the at least one process node represents at least one of chemical reactions, protein folding, transport, regulatory interactions, or active site binding, and wherein connections between nodes indicate roles that create the relationships between a molecule and a process.

In embodiments, a structured data format may be a non-relational database format, a knowledge graph structure, or some other format type.

In embodiments, the platform may include a computer-implemented method for normalizing synthetic biology data in an AI-guided analytic platform for development of biologic synthesis processes, comprising: receiving experimental data associated with synthetic biology development from a plurality of sources; performing a data quality assurance on the received experimental data to identify at least one anomalous data point; applying a Bayesian statistical normalization model to the experimental data to: model a batch-specific systemic variation; account for a technical factor contributing to a batch effect; separate a biologic signal from the technical factor; and generate normalized synthetic biology data; and outputting the normalized synthetic biology data for use in a machine learning application.

In embodiments, data quality assurance may comprise detecting a well or sample that failed to grow properly, identifying samples exhibiting contamination, flagging a readout that falls outside an expected range based on historical data for a similar strain, and/or identifying a potential measurement error or mislabel in the experimental data.

In embodiments, modeling the batch-specific systemic variation may comprise constructing a plate notation model representing at least one strain effect, constructing a plate notation model representing at least one experimental effect, constructing a plate notation model representing at least one plate-to-plate variation, constructing a plate notation model representing at least one plate lot effect, and/or constructing a plate notation model representing at least one position effect of a sample on a plate. A plate notation model may provide a formal representation of at least one factor contributing to observed data.

In embodiments, the platform may include a system for normalizing synthetic biology experimental data in an AI-guided analytic platform for development of a biologic synthesis process, comprising: one or more processors;

memory storing instructions that, when executed by the one or more processors, cause the platform to implement a multi-objective optimization system for performing multi-objective optimizations of the biologic synthesis process, wherein the multi-objective optimization system comprises: intake raw experimental data from a plurality of synthetic biology experiments; apply a quality control process to identify an anomalous experimental data point: construct a hierarchical Bayesian model representing: a strain performance measurement; an experimental variability factor; and a batch effect; fit the hierarchical Bayesian model to the experimental data to infer underlying strain performance while accounting for at least one confounding factor; generate at least one uncertainty estimate for a normalized performance value; and output normalized experimental data with associated uncertainty estimates.

In embodiments, control processes used by the platform may include analyzing repeated measurements of strains across multiple plates, identifying a strain exhibiting inconsistent behavior when measured multiple times, detecting a systematic variation between a plurality of experimental runs of genetically identical strains, and/or flagging data points where strain performance variance exceeds an expected threshold.

In embodiments, constructing a hierarchical Bayesian model may comprise incorporating prior data relating to expected strain behavior, modeling multiple sources of experimental variability, representing relationships between a small-scale and a large-scale experiment, and/or generating at least one probability distribution that captures uncertainty in strain performance measurements.

In embodiments, the platform may include a computer-implemented method for handling batch effects in an AI-guided analytic platform for development of a biologic synthesis process, comprising: receiving biologic experimental data from a plurality of experiments; detecting a systematic variation between the experiments that is not related to a biologic factor of interest; applying a data normalization technique to minimize batch-specific systemic variation while preserving underlying biologic signals; generating probability distributions representing experimental outcomes to provide a summary of uncertainty; using a machine learning model to identify and correct batch effects directly from the data without requiring explicit modeling of all possible sources of variation; and outputting normalized biologic data with reduced batch effects for use in strain engineering.

In embodiments, the platform may include a method for managing batch effects in synthetic biology experiments in an AI-guided analytic platform for development of a biologic synthesis process, comprising: one or more processors; memory storing instructions that, when executed by the one or more processors, cause the platform to implement a multi-objective optimization system for performing multi-objective optimizations of biologic synthesis processes, wherein the multi-objective optimization system comprises: collect raw experimental data on strain performance across a plurality of experiments; implement a data normalization and quality control process to address variability between experiments of genetically identical strains; represent hits and non-hits as probability distributions; allow definition of at least one threshold for hit identification; apply an iterative splitting process to account for variation between constructs with identical genetic makeup; and output batch-effect corrected data suitable for machine learning model training and strain optimization.

In embodiments, the platform may include a computer-implemented method for iterative splitting in synthetic biology development in an AI-guided analytic platform for development of biologic synthesis processes, comprising: receiving data associated with sequences having identical genetic makeup but exhibiting different behaviors; initially labeling constructs with identical sequences as distinct entities; fitting a probabilistic model to observations of the constructs, wherein model accounts for experimental conditions and measurement techniques that influence construct behavior; processing the data through a data quality assurance pipeline to identify and validate variations between genetically identical constructs; and generating normalized data across different experimental sources based on a probabilistic batch correction model.

In embodiments, the platform may identify an observation that is unlikely to have been generated by a current probabilistic batch correction model; splitting the identified observation into separate entries with independent parameters; and refitting the probabilistic batch correction model after each splitting iteration, wherein fitting the probabilistic batch correction model comprises starting with a prior parameter that assumes constructs with identical sequences have identical activity, wherein fitting the probabilistic batch correction model comprises requiring empirical evidence to override a prior parameter, wherein fitting the probabilistic batch correction model comprises adjusting at least one model parameter based on an observed variation between identical sequences.

In embodiments, the platform may include a system for iterative data processing in synthetic biology development in an AI-guided analytic platform for development of biologic synthesis processes, comprising: one or more processors; memory storing instructions that, when executed by the one or more processors, cause the system to: receive biologic sequencing data containing systemic variation across multiple batches; implement an iterative splitting process that: identifies constructs with identical genetic sequences exhibiting different behaviors; labels the identified constructs as separate entities; applies a probabilistic model to account for experimental condition variations; flags observations that deviate from predicted model behavior to identify potential measurement errors or data inconsistencies; and generate normalized datasets that account for validated variations between genetically identical constructs while maintaining data quality assurance.

In embodiments, implementing the iterative splitting process may further comprise: maintaining sufficient anchor points between datasets to enable data combination across experimental sites; identifying when anchor points exhibit significantly different behaviors; and adjusting at least one model parameter to account for a validated difference while preserving ability to combine datasets.

In embodiments, the platform may estimate a scaffold parameter based on a validated construct variation; use the estimated scaffold parameter to calculate a more accurate expression estimate for a strain; and update the probabilistic model based on a refined expression estimate.

In embodiments, the platform may flag observations that deviate from predicted model behavior comprises: identifying a vertical outlier in a model fit visualization; calculating a probability assignment for each observation; and selecting an observation with a low probability assignment as a candidate for splitting.

In embodiments, the platform may include a computer-implemented method for training artificial intelligence models with specialized biologic data in an AI-guided analytic platform for development of a biologic synthesis process, comprising: collecting multimodal biologic data including at least one of a gene expression level, mRNA, metabolic reaction fluxes, or intracellular metabolite concentrations from biologic systems; processing the collected biologic data through data normalization and quality assurance steps to create model-ready data; and generating at least one output predicting an effect of genetic modification on a metabolite level or a reaction flux.

In embodiments, normalized biologic data may be converted from a first structured format to a second format suitable for model training.

In embodiments, one or more artificial intelligence models may be trained using the model-ready data to predict a cellular phenotype based on a genetic perturbation, wherein training the one or more artificial intelligence models comprises: using a knowledge graph to represent biological entities as nodes; representing relationships between entities as edges; and capturing biological relationships in a format appropriate for use by machine learning algorithms.

In embodiments, collecting multimodal biological data may comprise: obtaining RNA sequencing data for genome-wide gene expression levels; measuring metabolic reaction fluxes; and collecting metabolite concentration data using mass spectrometry, wherein the mass spectrometry is liquid chromatography-mass spectrometry, wherein the mass spectrometry is gas chromatography-mass spectrometry.

In embodiments, processing the collected multimodal biological data may comprise: identifying and correcting batch-specific systemic variation; standardizing nomenclature across different data sources; and correcting for missing data to ensure consistency across experimental setups.

In embodiments, the platform may include a system for specialized biologic data processing and model training in an AI-guided analytic platform for development of a biologic synthesis process, comprising: one or more processors; memory storing instructions that, when executed by the one or more processors, cause the platform to implement a multi-objective optimization system for performing multi-objective optimizations of biologic synthesis processes, wherein the multi-objective optimization system comprises: a data collection system configured to collect time-resolved metabolomics data from living cells; a data processing pipeline configured to: integrate multiple types of high-dimensional biologic data; normalize and correct batch effects in the biologic data; and transform the biologic data into a format suitable for machine learning.

In embodiments, the platform may use a data collection system that is a rapid sampling system, wherein the rapid sampling system comprises: automated sampling mechanisms for collecting standardized samples; near-instantaneous quenching of cellular metabolism; and integration with liquid chromatography-mass spectrometry and gas chromatography-mass spectrometry for metabolite analysis.

In embodiments, one or more artificial intelligence models may be trained using processed data to predict a cellular phenotype.

In embodiments, the data processing pipeline may be further configured to: track data lineage from a raw experimental measurement to a processed value; maintain detailed metadata about experimental conditions; and validate a normalization method using a control sample.

In embodiments, the platform may integrate multiple types of high-dimensional biological data that comprises: combining gene expression data from RNA sequencing; incorporating flux data from an isotope-labeled experiment; and merging a metabolite concentration measurement from mass spectrometry.

In embodiments, the platform may include a system for training specialized biologic models in an AI-guided analytic platform for development of biologic synthesis processes, comprising instructions that when executed cause a processor to: collect multimodal biologic data; process the collected multimodal biologic data through quality assurance steps to identify and correct errors or inconsistencies; employ multi-modal deep learning architectures with a separate encoding branch for different data modalities; combine encoded representations through fusion layers; and generate a prediction about cellular phenotypes based on the processed multimodal biologic data.

In embodiments, the multimodal biologic data may derive from at least one integrated sensor and/or automated sampling system.

In embodiments, the multi-modal deep learning architectures may comprise: the separate encoding branches for gene expression data; dedicated pathways for metabolite profile processing; and specialized branches for reaction flux analysis.

In embodiments, processing the collected multimodal biologic data may comprise: applying batch effect correction across experimental runs; normalizing data across different organisms and conditions; and ensuring data consistency for machine learning applications.

In embodiments, generating predictions may comprise: evaluating effects of genetic modifications on metabolic pathways; predicting changes in metabolite concentrations; and estimating reaction flux distributions in response to genetic perturbations.

In embodiments, the multi-modal deep learning architecture used by the platform may be a combination of a plurality of multi-modal deep learning architectures.

In some example embodiments, a method of generating a biologic product of a biologic synthesis process includes selecting a first biologic parent having a first feature; selecting a second biologic parent having a second feature; and selecting the biologic product based on an evaluation of a set of combinations of the first biologic parent and the second biologic parent.

In some example embodiments, a method of generating a biologic product of a biologic synthesis process includes selecting at least two objectives of the biologic product; selecting a biologic parent of the biologic product; and determining the biologic product based on an evaluation of the at least two objectives for a set of variants of the biologic parent.

In some example embodiments, an AI-guided analytic platform for development of biologic synthesis processes includes a multi-objective optimization system for performing multi-objective optimizations of the biologic synthesis processes; at least one multi-objective evaluation artificial intelligence model configured to evaluate a biologic product according to each of at least two objectives; and at least one variant evaluation module configured to generate a set of variants of a biologic parent and evaluate each variant of the set of variants of the biologic parent using the at least one multi-objective evaluation artificial intelligence model.

In some example embodiments, an AI-guided analytic platform for development of biologic synthesis processes includes one or more processors; and memory storing instructions that, when executed by the one or more processors, cause the platform to implement a multi-objective optimization system for performing multi-objective optimizations of the biologic synthesis processes, the system including at least one biologic synthesis simulation system that is configured to evaluate multiple objectives of the biologic synthesis processes based on simulation of the biologic synthesis processes.

In some example embodiments, a method of optimizing a biologic synthesis process includes identifying at least one bottleneck in the biologic synthesis process; evaluating a set of variants of the biologic synthesis process; and selecting an adjusted biologic synthesis process, wherein the adjusted biologic synthesis process includes at least one variant of the set of variants that reduces the at least one bottleneck of the biologic synthesis process.

In some example embodiments, a method of optimizing a biologic synthesis process includes identifying at least one bottleneck in the biologic synthesis process; determining, by at least one simulation of the biologic synthesis process, at least one cause of the at least one bottleneck; and selecting an adjusted biologic synthesis process, wherein the adjusted biologic synthesis process alters the biologic synthesis process to at least reduce the at least one cause of the at least one bottleneck of the biologic synthesis process.

In some example embodiments, an AI-guided analytic platform for development of biologic synthesis processes includes one or more processors and memory storing instructions that, when executed by the one or more processors, cause the AI-guided analytic platform to perform steps including, identifying at least one bottleneck in a biologic synthesis process; evaluating a set of variants of the biologic synthesis process; and selecting an adjusted biologic synthesis process, wherein the adjusted biologic synthesis process includes at least one variant of the set of variants that reduces the at least one bottleneck of the biologic synthesis process.

In some example embodiments, an AI-guided analytic platform for development of biologic synthesis processes includes one or more processors; and memory storing instructions that, when executed by the one or more processors, cause the AI-guided analytic platform to implement a system that evaluates the biologic synthesis processes, wherein the system includes at least one simulation system that is configured to simulate biologic synthesis processes to identify bottlenecks in the biologic synthesis processes.

In some aspects, the techniques described herein relate to a platform for generating a set of recommendations for modifications to a set of genes of a biological strain, including: a set of data integration facilities for integrating content of at least one publication data set relating to the biological strain and at least one proprietary data set including a set of parameters of a synthetic biological process in which the biological strain produces a functional output, wherein the output of data integration facilities is configured as an input to a set of artificial intelligence (AI)-based learning models; and at least one member of the set of AI-based learning models that is configured to generate a set of recommendations wherein the set of recommendations relates to modifications to a set of genes of the biological strain such that the set of recommendations enhance production of the functional output by the biological strain.

In some aspects, the techniques described herein relate to a platform, wherein the set of AI-based learning models includes at least one of a transformer model, a convolutional neural network, a deep learning model, a supervised model, a semi-supervised model, an unsupervised model, a reinforcement model, a long short-term memory (LSTM) model, a multi-layer perceptron, lin-log model, a large language model, a large protein model, or a protein language model.

In some aspects, the techniques described herein relate to a platform, wherein the at least one publication dataset includes at least one of: gene function description datasets, datasets from metabolic pathway databases, comparative genomics datasets, omics datasets, functional assay datasets, experiment result datasets, bioinformatics analyses datasets, regulatory study datasets, enzyme characterization datasets, case study datasets, or patent literature.

In some aspects, the techniques described herein relate to a platform, wherein the at least one proprietary dataset includes at least one of genetic parameters, metabolic parameters, growth and physiological parameters, environmental and culture conditions, process parameters, functional output parameters, regulatory and control parameters, phenotypic parameters, omics parameters, scale-up parameters, or energy consumption parameters.

In some aspects, the techniques described herein relate to a platform, wherein the set of recommendations relates to at least one of knockout mutations, overexpression of target genes, activation of specific genes, insertion of specific genes, gene knockdowns, site-directed mutagenesis, promoter engineering, codon optimization, gene fusion, allele replacement, creation of synthetic gene circuits, introduction of regulatory elements, or application of advanced genome editing technologies.

In some aspects, the techniques described herein relate to a platform, wherein the functional output includes at least one of fuel applications and solutions, industrial applications and solutions, consumer product applications and solutions, pharmaceutical applications and solutions, or medical applications and solutions.

In some aspects, the techniques described herein relate to a platform, further including a simulation engine, the simulation engine configured to: generate a plurality of simulated synthetic biological process scenarios in which the biological strain produces the functional output, wherein each process scenario has a different set of modifications to a set of genes; execute simulations for the plurality of simulated process scenarios; and generate simulation data based on the executed simulations; wherein the set of AI-based learning models is further configured to: receive the simulation data as additional input; and generate a set of recommendations based at least in part on the simulation data.

In some aspects, the techniques described herein relate to a platform, wherein the simulations involve a set of digital twins representing at least one of a biological strain digital twin, a gene digital twin, a genome digital twin, a pathway digital twin, a bioreactor digital twin, a protein digital twin, a metabolite digital twin, or an enzyme digital twin.

In some aspects, the techniques described herein relate to a method, including: integrating, by a set of data integration facilities, content of at least one publication data set relating to a biological strain and at least one proprietary data set including a set of parameters of a synthetic biological process in which the biological strain produces a functional output; providing the integrated content as input to a set of artificial intelligence (AI)-based learning models; and generating, by at least one member of the set of AI-based learning models, a set of recommendations wherein the set of recommendations relates to modifications to a set of genes of the biological strain such that the set of recommendations enhance production of the functional output by the biological strain.

In some aspects, the techniques described herein relate to a method, wherein the set of AI-based learning models includes at least one of a transformer model, a convolutional neural network, a deep learning model, a supervised model, a semi-supervised model, an unsupervised model, a reinforcement model, a long short-term memory (LSTM) model, a multi-layer perceptron, lin-log model, a large language model, a large protein model, or a protein language model.

In some aspects, the techniques described herein relate to a method, wherein the at least one publication dataset includes at least one of: gene function description datasets, datasets from metabolic pathway databases, comparative genomics datasets, omics datasets, functional assay datasets, experiment result datasets, bioinformatics analyses datasets, regulatory study datasets, enzyme characterization datasets, case study datasets, or patent literature.

In some aspects, the techniques described herein relate to a method, wherein the at least one proprietary dataset includes at least one of genetic parameters, metabolic parameters, growth and physiological parameters, environmental and culture conditions, process parameters, functional output parameters, regulatory and control parameters, phenotypic parameters, omics parameters, scale-up parameters, or energy consumption parameters.

In some aspects, the techniques described herein relate to a method, wherein the set of recommendations relates to at least one of knockout mutations, overexpression of target genes, activation of specific genes, insertion of specific genes, gene knockdowns, site-directed mutagenesis, promoter engineering, codon optimization, gene fusion, allele replacement, creation of synthetic gene circuits, introduction of regulatory elements, or application of advanced genome editing technologies.

In some aspects, the techniques described herein relate to a method, wherein the functional output includes at least one of fuel applications and solutions, industrial applications and solutions, consumer product applications and solutions, pharmaceutical applications and solutions, or medical applications and solutions.

In some aspects, the techniques described herein relate to a method, further including: generating, by a simulation engine, a plurality of simulated synthetic biological process scenarios in which the biological strain produces the functional output, wherein each process scenario has a different set of modifications to a set of genes; executing simulations for the plurality of simulated process scenarios; generating simulation data based on the executed simulations; receiving the simulation data as additional input to the set of AI-based learning models; and generating a set of recommendations based at least in part on the simulation data.

In some aspects, the techniques described herein relate to a method, wherein the simulations involve a set of digital twins representing at least one of a biological strain digital twin, a gene digital twin, a genome digital twin, a pathway digital twin, a bioreactor digital twin, a protein digital twin, a metabolite digital twin, or an enzyme digital twin. Platform for environmental/performance optimization.

In some aspects, the techniques described herein relate to a platform for generating a set of recommendations for modifications to a set of environmental parameters for a synthetic biological process in which a biological strain produces a functional output, including: a set of data integration facilities for integrating content of at least publication data set relating to the biological strain and at least one proprietary data set including a set of parameters of the synthetic biological process in which the biological strain produces the functional output, wherein the output of data integration facilities is configured as an input to a set of artificial intelligence (AI)-based learning models; and at least one member of the set of AI-based learning models that is configured to generate a set of recommendations wherein the set of recommendations relate to modifications to the set of environmental parameters of a synthetic biological process in which the biological strain produces a functional output such that the recommendations enhance production of the functional output by the biological strain.

In some aspects, the techniques described herein relate to a platform, wherein the set of AI-based learning models includes at least one of a transformer model, a convolutional neural network, a deep learning model, a supervised model, a semi-supervised model, an unsupervised model, a reinforcement model, a long short-term memory (LSTM) model, a multi-layer perceptron, lin-log model, a large language model, a large protein model, or a protein language model.

In some aspects, the techniques described herein relate to a platform, wherein the at least one publication dataset includes at least one of: gene function description datasets, datasets from metabolic pathway databases, comparative genomics datasets, omics datasets, functional assay datasets, experiment result datasets, bioinformatics analyses datasets, regulatory study datasets, enzyme characterization datasets, case study datasets, or patent literature.

In some aspects, the techniques described herein relate to a platform, wherein the at least one proprietary dataset includes at least one of genetic parameters, metabolic parameters, growth and physiological parameters, environmental and culture conditions, process parameters, functional output parameters, regulatory and control parameters, phenotypic parameters, omics parameters, scale-up parameters, or energy consumption parameters.

In some aspects, the techniques described herein relate to a platform, wherein the set of recommendations relates to modifications of at least one of temperature, pH level, oxygen supply, nutrient composition, fermentation time, stirring and mixing, inoculum size, light conditions, toxicity management, pressure, or salinity.

In some aspects, the techniques described herein relate to a platform, wherein the functional output includes at least one of fuel applications and solutions, industrial applications and solutions, consumer product applications and solutions, pharmaceutical applications and solutions, or medical applications and solutions.

In some aspects, the techniques described herein relate to a platform, further including a simulation engine, the simulation engine configured to: generate a plurality of simulated synthetic biological process scenarios in which the biological strain produces the functional output, wherein each process scenario has a different set of modifications to a set of environmental parameters; execute simulations for the plurality of simulated process scenarios; and generate simulation data based on the executed simulations; wherein the set of AI-based learning models is further configured to: receive the simulation data as additional input; and generate a set of recommendations based at least in part on the simulation data.

In some aspects, the techniques described herein relate to a platform, wherein the simulations involve a set of digital twins representing at least one of a biological strain digital twin, a gene digital twin, a genome digital twin, a pathway digital twin, a bioreactor digital twin, a protein digital twin, a metabolite digital twin, or an enzyme digital twin.

In some aspects, the techniques described herein relate to a method for generating a set of recommendations for modifications to a set of environmental parameters for a synthetic biological process in which a biological strain produces a functional output, including: integrating, by a set of data integration facilities, content of at least one publication data set relating to the biological strain and at least one proprietary data set including a set of parameters of the synthetic biological process in which the biological strain produces the functional output; providing the integrated content as input to a set of artificial intelligence (AI)-based learning models; and generating, by at least one member of the set of AI-based learning models, a set of recommendations wherein the set of recommendations relate to modifications to the set of environmental parameters of the synthetic biological process such that the recommendations enhance production of the functional output by the biological strain.

In some aspects, the techniques described herein relate to a method, wherein the set of AI-based learning models includes at least one of a transformer model, a convolutional neural network, a deep learning model, a supervised model, a semi-supervised model, an unsupervised model, a reinforcement model, a long short-term memory (LSTM) model, a multi-layer perceptron, lin-log model, a large language model, a large protein model, or a protein language model.

In some aspects, the techniques described herein relate to a method, wherein the at least one publication dataset includes at least one of: gene function description datasets, datasets from metabolic pathway databases, comparative genomics datasets, omics datasets, functional assay datasets, experiment result datasets, bioinformatics analyses datasets, regulatory study datasets, enzyme characterization datasets, case study datasets, or patent literature.

In some aspects, the techniques described herein relate to a method, wherein the at least one proprietary dataset includes at least one of genetic parameters, metabolic parameters, growth and physiological parameters, environmental and culture conditions, process parameters, functional output parameters, regulatory and control parameters, phenotypic parameters, omics parameters, scale-up parameters, or energy consumption parameters.

In some aspects, the techniques described herein relate to a method, wherein the set of recommendations relates to modifications of at least one of temperature, pH level, oxygen supply, nutrient composition, fermentation time, stirring and mixing, inoculum size, light conditions, toxicity management, pressure, or salinity.

In some aspects, the techniques described herein relate to a method, wherein the functional output includes at least one of fuel applications and solutions, industrial applications and solutions, consumer product applications and solutions, pharmaceutical applications and solutions, or medical applications and solutions.

In some aspects, the techniques described herein relate to a method, further including: generating, by a simulation engine, a plurality of simulated synthetic biological process scenarios in which the biological strain produces the functional output, wherein each process scenario has a different set of modifications to a set of environmental parameters; executing simulations for the plurality of simulated process scenarios; generating simulation data based on the executed simulations; receiving the simulation data as additional input to the set of AI-based learning models; and generating a set of recommendations based at least in part on the simulation data.

In some aspects, the techniques described herein relate to a method, wherein the simulations involve a set of digital twins representing at least one of a biological strain digital twin, a gene digital twin, a genome digital twin, a pathway digital twin, a bioreactor digital twin, a protein digital twin, a metabolite digital twin, or an enzyme digital twin.

In some aspects, the techniques described herein relate to a platform for generating a set of recommendations for modifications to a set of biological pathways associated with a process in which a biological strain produces a functional output, including: a set of data integration facilities for integrating content of at least one publication data set relating to the biological strain and at least one proprietary data set including a set of parameters of a synthetic biological process in which the biological strain produces the functional output, wherein the output of data integration facilities is configured as an input to a set of AI-based learning models and at least one member of the set of AI-based learning models that is configured to generate a set of recommendations wherein the set of recommendations relate to modifications to the set of biological pathways such that the recommendations enhance production of the functional output by the biological strain.

In some aspects, the techniques described herein relate to a platform, wherein the set of AI-based learning models includes at least one of a transformer model, a convolutional neural network, a deep learning model, a supervised model, a semi-supervised model, an unsupervised model, a reinforcement model, a long short-term memory (LSTM) model, a multi-layer perceptron, lin-log model, a large language model, a large protein model, or a protein language model.

In some aspects, the techniques described herein relate to a platform, wherein the at least one publication dataset includes at least one of: gene function description datasets, datasets from metabolic pathway databases, comparative genomics datasets, omics datasets, functional assay datasets, experiment result datasets, bioinformatics analyses datasets, regulatory study datasets, enzyme characterization datasets, case study datasets, or patent literature.

In some aspects, the techniques described herein relate to a platform, wherein the at least one proprietary dataset includes at least one of genetic parameters, metabolic parameters, growth and physiological parameters, environmental and culture conditions, process parameters, functional output parameters, regulatory and control parameters, phenotypic parameters, omics parameters, scale-up parameters, or energy consumption parameters.

In some aspects, the techniques described herein relate to a platform, wherein the set of recommendations relates to at least one of identification and overexpression of key enzymes, use of stronger or inducible promoters, knockout of competing pathways, pathway engineering, optimization of substrate utilization, feedback regulation modification, cofactor engineering, pathway flux redistribution, integration of pathways, or environmental adaptations.

In some aspects, the techniques described herein relate to a platform, wherein the functional output includes at least one of fuel applications and solutions, industrial applications and solutions, consumer product applications and solutions, pharmaceutical applications and solutions, or medical applications and solutions.

In some aspects, the techniques described herein relate to a platform, further including a simulation engine, the simulation engine configured to: generate a plurality of simulated synthetic biological process scenarios in which the biological strain produces the functional output, wherein each process scenario has a different set of modifications to a set of pathways; execute simulations for the plurality of simulated process scenarios; and generate simulation data based on the executed simulations; wherein the set of AI-based learning models is further configured to: receive the simulation data as additional input; and generate a set of recommendations based at least in part on the simulation data.

In some aspects, the techniques described herein relate to a platform, wherein the simulations involve a set of digital twins representing at least one of a biological strain digital twin, a synthetic biological process digital twin, a gene digital twin, a genome digital twin, a pathway digital twin, a bioreactor digital twin, a protein digital twin, a metabolite digital twin, or an enzyme digital twin.

In some aspects, the techniques described herein relate to a method for generating a set of recommendations for modifications to a set of biological pathways associated with a process in which a biological strain produces a functional output, including: integrating, by a set of data integration facilities, content of at least one publication data set relating to the biological strain and at least one proprietary data set including a set of parameters of a synthetic biological process in which the biological strain produces the functional output; providing the integrated content as input to a set of AI-based learning models; and generating, by at least one member of the set of AI-based learning models, a set of recommendations wherein the set of recommendations relate to modifications to the set of biological pathways such that the recommendations enhance production of the functional output by the biological strain.

In some aspects, the techniques described herein relate to a method, wherein the set of AI-based learning models includes at least one of a transformer model, a convolutional neural network, a deep learning model, a supervised model, a semi-supervised model, an unsupervised model, a reinforcement model, a long short-term memory (LSTM) model, a multi-layer perceptron, a lin-log model, a large language model, a large protein model, or a protein language model.

In some aspects, the techniques described herein relate to a method, wherein the at least one publication dataset includes at least one of: gene function description datasets, datasets from metabolic pathway databases, comparative genomics datasets, omics datasets, functional assay datasets, experiment result datasets, bioinformatics analyses datasets, regulatory study datasets, enzyme characterization datasets, case study datasets, or patent literature.

In some aspects, the techniques described herein relate to a method, wherein the at least one proprietary dataset includes at least one of genetic parameters, metabolic parameters, growth and physiological parameters, environmental and culture conditions, process parameters, functional output parameters, regulatory and control parameters, phenotypic parameters, omics parameters, scale-up parameters, or energy consumption parameters.

In some aspects, the techniques described herein relate to a method, wherein the set of recommendations relates to at least one of identification and overexpression of key enzymes, use of stronger or inducible promoters, knockout of competing pathways, pathway engineering, optimization of substrate utilization, feedback regulation modification, cofactor engineering, pathway flux redistribution, integration of pathways, or environmental adaptations.

In some aspects, the techniques described herein relate to a method, wherein the functional output includes at least one of fuel applications and solutions, industrial applications and solutions, consumer product applications and solutions, pharmaceutical applications and solutions, or medical applications and solutions.

In some aspects, the techniques described herein relate to a method, further including: generating, by a simulation engine, a plurality of simulated synthetic biological process scenarios in which the biological strain produces the functional output, wherein each process scenario has a different set of modifications to a set of pathways; executing, by the simulation engine, simulations for the plurality of simulated process scenarios; generating, by the simulation engine, simulation data based on the executed simulations; receiving, by the set of AI-based learning models, the simulation data as additional input; and generating, by the set of AI-based learning models, a set of recommendations based at least in part on the simulation data.

In some aspects, the techniques described herein relate to a method, wherein the simulations involve a set of digital twins representing at least one of a biological strain digital twin, a synthetic biological process digital twin, a gene digital twin, a genome digital twin, a pathway digital twin, a bioreactor digital twin, a protein digital twin, a metabolite digital twin, or an enzyme digital twin. Platform for Protein/Enzymes Optimization In some aspects, the techniques described herein relate to a platform for generating a set of recommendations for modification of a set of proteins and/or enzymes associated with a biological strain that produces a functional output, including: a set of data integration facilities for integrating content of at least one publication data set relating to the biological strain and at least one proprietary data set including a set of parameters of a synthetic biological process in which the biological strain produces the functional output, wherein the output of data integration facilities is configured as an input to a set of artificial intelligence (AI)-based learning models; and at least one member of the set of AI-based learning models that is configured to generate a set of recommendations wherein the set of recommendations relate to modifications to a set of proteins and/or enzymes such that the recommendations enhance production of the functional output by the biological strain.

In some aspects, the techniques described herein relate to a platform, wherein the set of AI-based learning models includes at least one of a transformer model, a convolutional neural network, a deep learning model, a supervised model, a semi-supervised model, an unsupervised model, a reinforcement model, a long short-term memory (LSTM) model, a multi-layer perceptron, a lin-log model, a large language model, a large protein model, or a protein language model.

In some aspects, the techniques described herein relate to a platform, wherein the at least one publication dataset includes at least one of: gene function description datasets, datasets from metabolic pathway databases, comparative genomics datasets, omics datasets, functional assay datasets, experiment result datasets, bioinformatics analyses datasets, regulatory study datasets, enzyme characterization datasets, case study datasets, or patent literature.

In some aspects, the techniques described herein relate to a platform, wherein the at least one proprietary dataset includes at least one of genetic parameters, metabolic parameters, growth and physiological parameters, environmental and culture conditions, process parameters, functional output parameters, regulatory and control parameters, phenotypic parameters, omics parameters, scale-up parameters, or energy consumption parameters.

In some aspects, the techniques described herein relate to a platform, wherein the set of recommendations relates to at least one of enzyme overexpression, use of stronger promoters, site-directed mutagenesis, construction of chimeric proteins, enhancement of cofactor interactions, alleviation of feedback inhibition, application of post-translational modifications, modification of enzyme localization, gene knockouts of competing enzymes, allosteric modulation, or integration of modular enzyme assemblies.

In some aspects, the techniques described herein relate to a platform, wherein the functional output includes at least one of fuel applications and solutions, industrial applications and solutions, consumer product applications and solutions, pharmaceutical applications and solutions, or medical applications and solutions.

In some aspects, the techniques described herein relate to a platform, further including a simulation engine, the simulation engine configured to: generate a plurality of simulated synthetic biological process scenarios in which the biological strain produces the functional output, wherein each process scenario has a different set of modifications to a set of proteins and/or enzymes; execute simulations for the plurality of simulated process scenarios; and generate simulation data based on the executed simulations; wherein the set of AI-based learning models is further configured to: receive the simulation data as additional input; and generate a set of recommendations based at least in part on the simulation data.

In some aspects, the techniques described herein relate to a platform, wherein the simulations involve a set of digital twins representing at least one of a biological strain digital twin, a gene digital twin, a genome digital twin, a pathway digital twin, a bioreactor digital twin, a protein digital twin, a metabolite digital twin, or an enzyme digital twin.

In some aspects, the techniques described herein relate to a method for generating a set of recommendations for modification of a set of proteins and/or enzymes associated with a biological strain that produces a functional output, including: integrating, by a set of data integration facilities, content of at least one publication data set relating to the biological strain and at least one proprietary data set including a set of parameters of a synthetic biological process in which the biological strain produces the functional output; providing the integrated content as input to a set of artificial intelligence (AI)-based learning models; and generating, by at least one member of the set of AI-based learning models, a set of recommendations wherein the set of recommendations relate to modifications to a set of proteins and/or enzymes associated with a biological strain such that the recommendations enhance production of the functional output by the biological strain.

In some aspects, the techniques described herein relate to a method, wherein the set of AI-based learning models includes at least one of a transformer model, a convolutional neural network, a deep learning model, a supervised model, a semi-supervised model, an unsupervised model, a reinforcement model, a long short-term memory (LSTM) model, a multi-layer perceptron, a lin-log model, a large language model, a large protein model, or a protein language model.

In some aspects, the techniques described herein relate to a method, wherein the at least one publication dataset includes at least one of: gene function description datasets, datasets from metabolic pathway databases, comparative genomics datasets, omics datasets, functional assay datasets, experiment result datasets, bioinformatics analyses datasets, regulatory study datasets, enzyme characterization datasets, case study datasets, or patent literature.

In some aspects, the techniques described herein relate to a method, wherein the at least one proprietary dataset includes at least one of genetic parameters, metabolic parameters, growth and physiological parameters, environmental and culture conditions, process parameters, functional output parameters, regulatory and control parameters, phenotypic parameters, omics parameters, scale-up parameters, or energy consumption parameters.

In some aspects, the techniques described herein relate to a method, wherein the set of recommendations relates to at least one of enzyme overexpression, use of stronger promoters, site-directed mutagenesis, construction of chimeric proteins, enhancement of cofactor interactions, alleviation of feedback inhibition, application of post-translational modifications, modification of enzyme localization, gene knockouts of competing enzymes, allosteric modulation, or integration of modular enzyme assemblies.

In some aspects, the techniques described herein relate to a method, wherein the functional output includes at least one of fuel applications and solutions, industrial applications and solutions, consumer product applications and solutions, pharmaceutical applications and solutions, or medical applications and solutions.

In some aspects, the techniques described herein relate to a method, further including: generating, by a simulation engine, a plurality of simulated synthetic biological process scenarios in which the biological strain produces the functional output, wherein each process scenario has a different set of modifications to a set of proteins and/or enzymes; executing, by the simulation engine, simulations for the plurality of simulated process scenarios; generating, by the simulation engine, simulation data based on the executed simulations; receiving, by the set of AI-based learning models, the simulation data as additional input; and generating, by the set of AI-based learning models, a set of recommendations based at least in part on the simulation data.

In some aspects, the techniques described herein relate to a method, wherein the simulations involve a set of digital twins representing at least one of a biological strain digital twin, a gene digital twin, a genome digital twin, a pathway digital twin, a bioreactor digital twin, a protein digital twin, a metabolite digital twin, or an enzyme digital twin.

In some aspects, the techniques described herein relate to a rapid sampling system for obtaining samples from a fermentation system, including: a sample inlet fluidly connected to the fermentation system; a pump fluidly connected to the sample inlet and configured to draw a sample from the fermentation system; a first valve fluidly connected to an outlet of the pump; a second valve fluidly connected to a liquid nitrogen chamber; a multi-well filter plate, wherein an individual well of the multi-well filter plate is configured to collect and filter a sample; a motorized base operatively connected to the multi-well filter plate configured to adjust a position of the multi-well filter plate; a control unit including one or more processors and one or more memories operatively connected to the pump, the first valve, the second valve, and the motorized base, the control unit configured to automatically initiate and perform a plurality of sampling operations at predetermined time intervals, wherein each sampling operation includes: controlling the operation of the pump to obtain a sample, controlling the operation of the first valve to dispense a sample into a first well of the multi-well filter plate; controlling the operation of the second valve to dispense liquid nitrogen into the first well of the multi-well filter plate; controlling the operation of the motorized base to move the multi-well filter plate to position a second well beneath the first valve and the second valve.

In some aspects, the techniques described herein relate to a rapid sampling system, further including a purge compressed air inlet fluidly connected to the first valve and operatively connected to the control unit, wherein the control unit is further configured to control operation of the first valve to dispense compressed air into the selected well before receiving the sample.

In some aspects, the techniques described herein relate to a rapid sampling system, further including a purge solvent inlet fluidly connected to the first valve and operatively connected to the control unit wherein the control unit is further configured to control operation of the first valve to dispense solvent into the selected well before obtaining the sample.

In some aspects, the techniques described herein relate to a rapid sampling system, further including a vacuum base wherein the vacuum base is operatively connected to the multi-well filter plate and operatively connected to the control unit wherein the control unit is further configured to control operation of the vacuum base to filter one or more wells of the multi-well filter plate.

In some aspects, the techniques described herein relate to a rapid sampling system, further including a carbon source inlet fluidly connected to the fermentation system and configured to dispense a carbon source into the fermentation system wherein the carbon source inlet is operatively connected to the control unit and wherein the initiation of the plurality of sampling operations is dependent on a dispensing of carbon by the carbon source inlet.

In some aspects, the techniques described herein relate to a rapid sampling system, further including a sampling loop.

In some aspects, the techniques described herein relate to a rapid sampling system, wherein the rapid sampling system is configured for a pilot scale.

In some aspects, the techniques described herein relate to a rapid sampling system, wherein the rapid sampling system is configured for industrial scale.

In some aspects, the techniques described herein relate to a rapid sampling system, wherein the first valve is an HPLC valve.

In some aspects, the techniques described herein relate to a rapid sampling system, wherein the second valve is a cryogenic valve.

In some aspects, the techniques described herein relate to a rapid sampling system, wherein the rapid sampling system is represented as a digital twin.

In some aspects, the techniques described herein relate to a rapid sampling system that is integrated with a mass and/or optical analytical system and an automated omics for generalization system.

In some aspects, the techniques described herein relate to a method for obtaining samples from a fermentation system, including: drawing, by a pump fluidly connected to a sample inlet, a sample from the fermentation system; dispensing, by a first valve fluidly connected to an outlet of the pump, a sample into a first well of a multi-well filter plate; dispensing, by a second valve fluidly connected to a liquid nitrogen chamber, liquid nitrogen into the first well of the multi-well filter plate; adjusting, by a motorized base operatively connected to the multi-well filter plate, a position of the multi-well filter plate to position a second well beneath the first valve and the second valve; and automatically initiating and performing, by a control unit, a plurality of sampling operations at predetermined time intervals.

In some aspects, the techniques described herein relate to a method, further including: dispensing, by the first valve, compressed air from a purge compressed air inlet into the selected well before receiving the sample.

In some aspects, the techniques described herein relate to a method, further including: dispensing, by the first valve, solvent from a purge solvent inlet into the selected well before obtaining the sample.

In some aspects, the techniques described herein relate to a method, further including: filtering, by a vacuum base operatively connected to the multi-well filter plate, one or more wells of the multi-well filter plate.

In some aspects, the techniques described herein relate to a method, further including: dispensing, by a carbon source inlet fluidly connected to the fermentation system, a carbon source into the fermentation system, wherein initiation of the plurality of sampling operations is dependent on the dispensing of the carbon source.

In some aspects, the techniques described herein relate to a method, further including utilizing a sampling loop.

In some aspects, the techniques described herein relate to a method, wherein the method is performed at pilot scale.

In some aspects, the techniques described herein relate to a method, wherein the method is performed at an industrial scale.

In some aspects, the techniques described herein relate to a method, wherein the first valve is an HPLC valve.

In some aspects, the techniques described herein relate to a method, wherein the second valve is a cryogenic valve.

In some aspects, the techniques described herein relate to a method, wherein the method is represented as a digital twin.

In some aspects, the techniques described herein relate to a method, wherein the method is integrated with a mass and/or optical analytical system and an automated omics for generalization system. Automated "Omics" for Generalization.

In some aspects, the techniques described herein relate to a method for converting raw data from an analytical and mass spectrometry instrument to model-ready data, the method including: receiving, by computing hardware, data from the analytical and mass spectrometry instrument wherein the data includes measurement data from a set of control samples and a set of test samples; extracting, by a computing hardware, a set of peak lists including a set of test peak lists and a set of control peak lists from the received data; compressing, by computer hardware, the extracted peak lists using a compression algorithm; identifying, by computer hardware, a set of metabolites that correspond to a set of peaks from the compressed peak lists by comparing a set of mass-to-charge ratios and a set of retention times associated with the set of peaks with the mass-to-charge ratios and retention times associated with known metabolites from a set of spectral databases; calculating, by computer hardware, a set of peak areas corresponding to the set of peaks; generating, by computer hardware, a calibration curve for each identified metabolite based on the calculated area from its corresponding peaks from the compressed set of control peak lists and its known concentration; calculating, by computer hardware, a set of concentrations for the set of identified metabolites associated with the peaks from the compressed set of test peak lists using the generated calibration curves; and generating, by computer hardware, a compilation of results.

In some aspects, the techniques described herein relate to a method, further including analyzing, by computer hardware, the identified peaks to determine a need for a deconvolution and/or window adjustment on one or more of the identified peaks, and, upon determination of said need, performing deconvolution and/or window adjustment on the one or more of the identified peaks.

In some aspects, the techniques described herein relate to a method, further including generating, by computer hardware, a quality control website wherein the quality control website presents a set of calibration curves representing the control samples and test samples for each of the metabolites of the set of metabolites.

In some aspects, the techniques described herein relate to a method, wherein the analytical and mass spectrometry instrument is a liquid chromatography-mass spectrometry (LC-MS) instrument, a gas chromatography-mass spectrometry (GC-MS) instrument, a quadruple time-of-flight (QTOF) mass spectrometry instrument, an ultraviolet-visible (UV-Vis) instrument, or a free induction decay (FID) instrument. In embodiments, the of analytical and mass spectrometry instrument may be a quadrupole mass spectrometry (QMS) instrument, a time-of-flight mass spectrometry (TOF-MS) instrument, an ion trap mass spectrometry instrument, an orbitrap mass spectrometry instrument, a sector mass spectrometry instrument, an electrospray ionization (ESI) instrument, a chemical ionization (CI) instrument, an electron ionization (EI) instrument, an atmospheric pressure chemical ionization (APCI) instrument, and an atmospheric pressure photoionization (APPI) instrument, among many others.

In some aspects, the techniques described herein relate to a method, further including comparing, by computer hardware, a set of fragmentation patterns from the set of peaks from the compressed peak lists with a set of fragmentation patterns from the set of spectral databases.

In some aspects, the techniques described herein relate to a method, further including applying, by computer hardware, a dilution factor to the set of concentrations.

In some aspects, the techniques described herein relate to a method, further including normalizing, by computer hardware, the concentrations to biomass content.

In some aspects, the techniques described herein relate to a system for converting raw data from an analytical and mass spectrometry instrument to model-ready data, including: computing hardware configured to: receive data from an analytical and mass spectrometry instrument wherein the data includes measurement data from a set of control samples and a set of test samples; extract a set of peak lists including a set of test peak lists and a set of control peak lists from the received data; compress the extracted peak lists using a compression algorithm; identify a set of metabolites that correspond to a set of peaks from the compressed peak lists by comparing a set of mass-to-charge ratios and a set of retention times associated with the set of peaks with the mass-to-charge ratios and retention times associated with known metabolites from a set of spectral databases; calculate a set of peak areas corresponding to the set of peaks; generate a calibration curve for each identified metabolite based on the calculated area from its corresponding peaks from the compressed set of control peak lists and its known concentrations; calculate a set of concentrations for the set of identified metabolites associated with the peaks from the compressed set of test peak lists using the generated calibration curves; and generate a compilation of results.

In some aspects, the techniques described herein relate to a system, wherein the computing hardware is further configured to analyze the identified peaks to determine a need for a deconvolution and/or window adjustment on one or more of the identified peaks, and, upon determination of said need, perform deconvolution and/or window adjustment on the one or more of the identified peaks.

In some aspects, the techniques described herein relate to a system, wherein the computing hardware is further configured to generate a quality control website wherein the quality control website presents a set of calibration curves for control samples and test samples for each of the metabolites of the set of metabolites.

In some aspects, the techniques described herein relate to a system, wherein the analytical and mass spectrometry instrument is a liquid chromatography-mass spectrometry (LC-MS) instrument, a gas chromatography-mass spectrometry (GC-MS) instrument, a quadruple time-of-flight (QTOF) mass spectrometry instrument, an ultraviolet-visible (UV-Vis) instrument, or a free induction decay (FID) instrument, a quadrupole mass spectrometry (QMS) instrument, a time-of-flight mass spectrometry (TOF-MS) instrument, an ion trap mass spectrometry instrument, an orbitrap mass spectrometry instrument, a sector mass spectrometry instrument, an electrospray ionization (ESI) instrument, a chemical ionization (CI) instrument, an electron ionization (EI) instrument, an atmospheric pressure chemical ionization (APCI) instrument, or an atmospheric pressure photoionization (APPI) instrument.

In some aspects, the techniques described herein relate to a system, wherein the computing hardware is further configured to compare a set of fragmentation patterns from the set of peaks from the compressed peak lists with a set of fragmentation patterns from the set of spectral databases.

In some aspects, the techniques described herein relate to a system, wherein the computing hardware is further configured to apply a dilution factor to the set of concentrations.

In some aspects, the techniques described herein relate to a system, wherein the computing hardware is further configured to normalize the concentrations to biomass content.

In some aspects, the techniques described herein relate to a system, including: a rapid sampling system configured to collect a set of samples from a fermentation system at predetermined time increments; a robotic handling system configured to obtain the set of samples from the rapid sampling system and prepare the samples for an analytical and mass spectrometry instrument; an analytical and mass spectrometry instrument configured to generate raw measurement data associated with the set of samples and provide the raw measurement data to an automated omics for generalization system; and an automated omics for generalization system configured to determine a set of concentrations for a set of metabolites in the set of samples based on the raw measurement data and output the set of concentrations.

In some aspects, the techniques described herein relate to a system, wherein the analytical and mass spectrometry instrument is a liquid chromatography-mass spectrometry (LC-MS) instrument, a gas chromatography-mass spectrometry (GC-MS) instrument, a quadruple time-of-flight (QTOF) mass spectrometry instrument, an ultraviolet-visible (UV-Vis) instrument, or a free induction decay (FID) instrument. In embodiments, the of analytical and mass spectrometry instrument may be a quadrupole mass spectrometry (QMS) instrument, a time-of-flight mass spectrometry (TOF-MS) instrument, an ion trap mass spectrometry instrument, an orbitrap mass spectrometry instrument, a sector mass spectrometry instrument, an electrospray ionization (ESI) instrument, a chemical ionization (CI) instrument, an electron ionization (EI) instrument, an atmospheric pressure chemical ionization (APCI) instrument, and an atmospheric pressure photoionization (APPI) instrument, among many others.

In some aspects, the techniques described herein relate to a system, wherein the system is further configured to provide the set of concentrations to an artificial intelligence (AI)-based learning model training system configured to train and/or retrain a set of AI-based learning models.

In some aspects, the techniques described herein relate to a system, wherein the system is further configured to provide the set of concentrations to a set of artificial intelligence (AI)-based learning models, wherein at least one member of the set of AI-based learning models is trained to identify one or more metabolite bottlenecks.

In some aspects, the techniques described herein relate to a system, wherein the set of AI-based learning models includes at least one of a transformer model, a convolutional neural network, a deep learning model, a supervised model, a semi-supervised model, an unsupervised model, a reinforcement model, a long short-term memory (LSTM) model, a multi-layer perceptron, a lin-log model, a large language model, a large protein model, or a protein language model.

In some aspects, the techniques described herein relate to a system, wherein the system is further configured to provide the set of concentrations to a set of artificial intelligence (AI)-based learning models, wherein at least one member of the set of AI-based learning models is trained to generate a set of recommendations for an intervention to a fermentation process in the fermentation system, wherein the set of recommendations includes at least one of a genetic modification, a process optimization, or an environmental adjustment.

In some aspects, the techniques described herein relate to a system, wherein the set of AI-based learning models includes at least one of a transformer model, a convolutional neural network, a deep learning model, a supervised model, a semi-supervised model, an unsupervised model, a reinforcement model, a long short-term memory (LSTM) model, a multi-layer perceptron, a lin-log model, a large language model, a large protein model, or a protein language model.

In some aspects, the techniques described herein relate to a system, wherein the system is further configured to calculate a flux of a metabolic pathway from the set of metabolite concentrations.

In some aspects, the techniques described herein relate to a system, wherein the system is further configured to provide the set of concentrations to a digital twin system, and wherein the digital twin system is configured to generate a digital twin representing a metabolic flux associated with a fermentation process in the fermentation system.

In some aspects, the techniques described herein relate to a system, wherein the system is further configured to calculate at least one of a predicted product yield measure, a fermentation productivity measure, a set of metabolite kinetic rates, or a set of pathway efficiency measures for a fermentation process in the fermentation system.

In some aspects, the techniques described herein relate to a system, wherein the system is configured to build a set of kinetic models for a fermentation process in the fermentation system.

In some aspects, the techniques described herein relate to a method for determining a set of concentrations for a set of metabolites from a fermentation system, the method including: collecting, by a rapid sampling system, a set of samples from a fermentation system at predetermined time increments; preparing, by a robotic handling system, the set of samples for an analytical and mass spectrometry instrument; generating, by the analytical and mass spectrometry instrument, raw measurement data associated with the set of samples; providing, by the analytical and mass spectroscopy instrument, the raw measurement data to an automated omics for generalization system; determining, by an automated omics for generalization system, a set of concentrations for a set of metabolites in the set of samples based on the raw measurement data; and outputting the set of concentrations.

In some aspects, the techniques described herein relate to a method, wherein the analytical and mass spectrometry instrument is a liquid chromatography-mass spectrometry (LC-MS) instrument, a gas chromatography-mass spectrometry (GC-MS) instrument, a quadruple time-of-flight (QTOF) mass spectrometry instrument, an ultraviolet-visible (UV-Vis) instrument, a free induction decay (FID) instrument, a quadrupole mass spectrometry (QMS) instrument, a time-of-flight mass spectrometry (TOF-MS) instrument, an ion trap mass spectrometry instrument, an orbitrap mass spectrometry instrument, a sector mass spectrometry instrument, an electrospray ionization (ESI) instrument, a chemical ionization (CI) instrument, an electron ionization (EI) instrument, an atmospheric pressure chemical ionization (APCI) instrument, or an atmospheric pressure photoionization (APPI) instrument.

In some aspects, the techniques described herein relate to a method, further including providing the set of concentrations to an artificial intelligence (AI)-based learning model training system configured to train and/or retrain a set of AI-based learning models.

In some aspects, the techniques described herein relate to a method, further including providing the set of concentrations to a set of artificial intelligence (AI)-based learning models, wherein at least one member of the set of AI-based learning models is trained to identify one or more metabolite bottlenecks.

In some aspects, the techniques described herein relate to a method, wherein the set of AI-based learning models includes at least one of a transformer model, a convolutional neural network, a deep learning model, a supervised model, a semi-supervised model, an unsupervised model, a reinforcement model, a long short-term memory (LSTM) model, a multi-layer perceptron, a lin-log model, a large language model, a large protein model, or a protein language model.

In some aspects, the techniques described herein relate to a method, further including providing the set of concentrations to a set of artificial intelligence (AI)-based learning models, wherein at least one member of the set of AI-based learning models is trained to generate a set of recommendations for an intervention to a fermentation process in the fermentation system, wherein the set of recommendations includes at least one of a genetic modification, a process optimization, or an environmental adjustment.

In some aspects, the techniques described herein relate to a method, wherein the set of AI-based learning models includes at least one of a transformer model, a convolutional neural network, a deep learning model, a supervised model, a semi-supervised model, an unsupervised model, a reinforcement model, a long short-term memory (LSTM) model, a multi-layer perceptron, a lin-log model, a large language model, a large protein model, or a protein language model.

In some aspects, the techniques described herein relate to a method, further including calculating a flux of a metabolic pathway from the set of metabolite concentrations.

In some aspects, the techniques described herein relate to a method, further including: providing the set of concentrations to a digital twin system; and generating, by the digital twin system, a digital twin representing a metabolic flux associated with a fermentation process in the fermentation system.

In some aspects, the techniques described herein relate to a method, further including calculating at least one of a predicted product yield measure, a fermentation productivity measure, a set of metabolite kinetic rates, or a set of pathway efficiency measures for a fermentation process in the fermentation system.

In some aspects, the techniques described herein relate to a method, further including building a set of kinetic models for a fermentation process in the fermentation system.

In some aspects, the techniques described herein relate to a computer-implemented method for data integration in an AI-guided synthetic biology development platform, including: receiving biological data from a plurality of experimental sources and databases; converting the received biological data into at least one standardized data format through a data intake and staging pipeline; processing the standardized biological data through a data normalization facility to minimize batch-specific systemic variation; storing the normalized biological data in a structured format that describes biological components and their relationships; applying at least one machine learning method to the normalized biological data to generate a predictive model for synthetic biology design; and outputting a specification for biological system optimization based on the predictive model.

In some aspects, the techniques described herein relate to a method, wherein the data normalization facility applies a Bayesian statistical model that incorporates prior knowledge about strain behavior.

In some aspects, the techniques described herein relate to a method, wherein processing the biological data includes modeling a source of variation including a biological effect.

In some aspects, the techniques described herein relate to a method, wherein the structured format includes a bipartite graph database structure organizing data into molecule nodes and process nodes.

In some aspects, the techniques described herein relate to a method, wherein the molecule nodes represent at least one of a molecule, atomic element, ion, compound, nucleic acid, protein, or macromolecule.

In some aspects, the techniques described herein relate to a method, wherein the process nodes represent at least one of a chemical reaction, protein folding, transport, regulatory interaction, or active site binding.

In some aspects, the techniques described herein relate to a method, wherein the data intake and staging pipeline includes an automated sampling mechanism for collecting a standardized sample.

In some aspects, the techniques described herein relate to a method, further including tracking data lineage from a raw experimental measurement to a processed value.

In some aspects, the techniques described herein relate to a method, wherein processing includes batch effect correction addressing systematic variation across experimental runs, equipment, or operators.

In some aspects, the techniques described herein relate to a method, further including validating data quality using a control sample.

In some aspects, the techniques described herein relate to a method, wherein receiving biological data includes collecting time-resolved metabolomic data from living cells.

In some aspects, the techniques described herein relate to a method, further including integrating a plurality of high-dimensional biological data types including at least one of gene expression data, flux data, or metabolite concentration measurement.

In some aspects, the techniques described herein relate to a method, wherein the machine learning method includes a neural network configured for processing biological parameter data.

In some aspects, the techniques described herein relate to a method, further including implementing an edge computing architecture for local processing of sensor data.

In some aspects, the techniques described herein relate to a method, further including maintaining metadata relating to an experimental condition.

In some aspects, the techniques described herein relate to a method, further including generating a visualization output of metabolic pathway performance.

In some aspects, the techniques described herein relate to a system for analytics-as-a-service in an AI-guided synthetic biology platform, including: one or more processors; memory storing instructions that, when executed by the one or more processors, cause a platform to: identify an appropriate analytic method based on assessment of a biological data characteristic; implement a data preparation procedure specific to a synthetic biology application; apply a machine learning model to analyze biological data and generate a prediction; perform a model validation procedure to ensure analytical reliability; create an audit trail documenting an analytic procedure and result; and generate technical documentation and visualization of an analytic finding.

In some aspects, the techniques described herein relate to a system, wherein identifying the appropriate analytical method includes evaluating at least one of a data type, distribution, or relationship in biological data.

In some aspects, the techniques described herein relate to a system, wherein the data preparation procedure includes automated feature engineering for a biological data type.

In some aspects, the techniques described herein relate to a system, wherein the machine learning model includes a protein language model for analyzing a protein sequence.

In some aspects, the techniques described herein relate to a system, further including implementing a distributed computing capability for handling computationally intensive analysis.

In some aspects, the techniques described herein relate to a system, wherein model validation includes both in-sample and out-of-sample testing.

In some aspects, the techniques described herein relate to a system, further including monitoring model performance over time and implementing a procedure to detect model degradation.

In some aspects, the techniques described herein relate to a system, wherein technical documentation includes at least one of a methodology description, assumption, or limitation.

In some aspects, the techniques described herein relate to a system, wherein the machine learning model includes a hybrid model combining mechanistic understanding with a machine learning method.

In some aspects, the techniques described herein relate to a system, further including implementing an automated model selection procedure.

In some aspects, the techniques described herein relate to a system, wherein model validation includes sensitivity analysis to evaluate model robustness.

In some aspects, the techniques described herein relate to a system, further including implementing a caching mechanism to improve processing efficiency.

In some aspects, the techniques described herein relate to a system, further including maintaining documentation of a standardization procedure.

In some aspects, the techniques described herein relate to a system, further including implementing a resource allocation procedure to optimize computational efficiency.

In some aspects, the techniques described herein relate to a system for data quality management in an AI-guided synthetic biology platform, including: a data intake and staging pipeline configured to: collect raw data from an experimental source; convert raw data into a standardized format; apply a quality assurance step to identify and correct an error; apply a normalization technique to remove a batch effect; validate that normalization preserves a biological signal; and a knowledge management system configured to: maintain an audit trail of data processing; track data lineage from a raw measurement to a processed value; enable verification of a data processing step; store validated data in a structured format describing a biological relationship; and generate a quality metric.

In some aspects, the techniques described herein relate to a system, wherein the quality assurance step includes detecting a well or sample that failed to grow properly.

In some aspects, the techniques described herein relate to a system, wherein the quality assurance step includes identifying a sample exhibiting contamination.

In some aspects, the techniques described herein relate to a system, wherein the quality assurance step includes flagging a readout that falls outside an expected range.

In some aspects, the techniques described herein relate to a system, wherein the normalization technique includes Bayesian statistical normalization.

In some aspects, the techniques described herein relate to a system, wherein the structured format includes a bipartite graph database structure.

In some aspects, the techniques described herein relate to a system, further including implementing an automated validation check.

In some aspects, the techniques described herein relate to a system, wherein tracking data lineage includes maintaining detailed metadata.

In some aspects, the techniques described herein relate to a system, further including implementing error handling and retry logic.

In some aspects, the techniques described herein relate to a system, wherein the quality metric includes completeness analysis.

In some aspects, the techniques described herein relate to a system, further including implementing a cross-reference validation technique.

In some aspects, the techniques described herein relate to a system, wherein the normalization technique includes batch effect correction.

In some aspects, the techniques described herein relate to a system, further including implementing an automated classification process.

In some aspects, the techniques described herein relate to a system, further including implementing a data enrichment capability.

In some aspects, the techniques described herein relate to a method for multi-modal data integration in an AI-guided synthetic biology platform, including: collecting time-resolved metabolomics data from a living cell through an automated sampling mechanism; integrating multiple types of high-dimensional biological data including at least one of gene expression, metabolic flux, or protein concentration measurement; normalizing the integrated biological data using batch effect correction; validating quality and consistency of the normalized biological data; storing the validated biological data in a structured format describing relationships between biological entities; and analyzing the stored validated biological data using a machine learning model to generate a prediction for synthetic biology system design.

In some aspects, the techniques described herein relate to a method, wherein the automated sampling mechanism includes near-instantaneous quenching of cellular metabolism.

In some aspects, the techniques described herein relate to a method, wherein integrating includes combining gene expression data from RNA sequencing.

In some aspects, the techniques described herein relate to a method, wherein integrating includes incorporating flux data from an isotope-labeled experiment.

In some aspects, the techniques described herein relate to a method, wherein integrating includes merging a metabolite concentration measurement from mass spectrometry.

In some aspects, the techniques described herein relate to a method, wherein normalizing includes applying a Bayesian statistical model.

In some aspects, the techniques described herein relate to a method, wherein the structured format is a knowledge graph structure.

In some aspects, the techniques described herein relate to a method, further including tracking data lineage from a raw measurement.

In some aspects, the techniques described herein relate to a method, further including maintaining detailed metadata about an experimental condition.

In some aspects, the techniques described herein relate to a method, wherein the machine learning model includes a neural network with a multi-headed attention mechanism.

In some aspects, the techniques described herein relate to a method, further including implementing a distributed computing capability.

In some aspects, the techniques described herein relate to a method, wherein validating includes using a control sample.

In some aspects, the techniques described herein relate to a method, further including generating a visualization output.

In some aspects, the techniques described herein relate to a method, wherein analyzing includes predicting strain performance.

In some aspects, the techniques described herein relate to a method, further including implementing an edge computing architecture.

In some aspects, the techniques described herein relate to a method, wherein storing includes maintaining an audit trail.

In some aspects, the techniques described herein relate to a system for real-time data processing in an AI-guided synthetic biology platform, including: one or more processors, each configured with an AI processing core optimized for biological data types; a data collection system configured to collect a continuous data stream from laboratory equipment; a data processing pipeline configured to: perform real-time normalization; integrate a plurality of data streams in parallel; implement edge computing for local data processing; apply a machine learning model for real-time analysis; and generate an automated alert or recommendation based on processed data.

In some aspects, the techniques described herein relate to a system, wherein the AI processing core includes a GPU configured for protein structure prediction.

In some aspects, the techniques described herein relate to a system, wherein the AI processing core includes an NPU optimized for metabolic pathway analysis.

In some aspects, the techniques described herein relate to a system, wherein the data stream includes bioreactor sensor data.

In some aspects, the techniques described herein relate to a system, wherein the data stream includes mass spectrometry data.

In some aspects, the techniques described herein relate to a system, wherein real-time normalization includes batch effect correction.

In some aspects, the techniques described herein relate to a system, further including implementing a load balancing algorithm.

In some aspects, the techniques described herein relate to a system, further including implementing an automated failover mechanism.

In some aspects, the techniques described herein relate to a system, wherein the machine learning model is a hybrid model.

In some aspects, the techniques described herein relate to a system, further including implementing a distributed computing capability.

In some aspects, the techniques described herein relate to a system, wherein the alert includes a quality control notification.

In some aspects, the techniques described herein relate to a system, further including generating a real-time visualization.

In some aspects, the techniques described herein relate to a system, wherein the recommendation includes a process parameter adjustment.

In some aspects, the techniques described herein relate to a system, further including implementing an automated validation check.

In some aspects, the techniques described herein relate to a method for data management in an AI-guided synthetic biology platform, including: implementing a knowledge graph structure to represent at least one biological entity; integrating experimental data, literature data, and proprietary data into the knowledge graph; maintaining data lineage and provenance tracking; applying a machine learning model to analyze graph relationships; generating a recommendation based on graph analysis; and providing an interactive visualization of the knowledge graph.

In some aspects, the techniques described herein relate to a method, wherein the biological entity includes at least one of a gene, protein, or metabolite.

In some aspects, the techniques described herein relate to a method, wherein relationships include a regulatory interaction and metabolic pathway.

In some aspects, the techniques described herein relate to a method, wherein the experimental data includes a time-series measurement.

In some aspects, the techniques described herein relate to a method, wherein literature data includes a published research finding.

In some aspects, the techniques described herein relate to a method, wherein proprietary data includes a strain performance datum.

In some aspects, the techniques described herein relate to a method, further including implementing automated data validation.

In some aspects, the techniques described herein relate to a method, wherein the machine learning model is a graph neural networks.

In some aspects, the techniques described herein relate to a method, further including maintaining an audit trails of changes.

In some aspects, the techniques described herein relate to a method, wherein visualization includes a network diagram.

In some aspects, the techniques described herein relate to a method, wherein the recommendation includes a strain optimization strategy.

In some aspects, the techniques described herein relate to a system for managing biological data in an AI-guided synthetic biology platform, including: a knowledge graph structure configured to: represent biological entities as nodes and their relationships as edges; store validated experimental data describing relationships between biological components; maintain data lineage from a raw measurement to a processed value; track a relationship between a strain, genetic design, experimental condition, and a performance datum; a machine learning system configured to: analyze the knowledge graph structure to identify a patterns or relationship; generate a prediction for synthetic biology system design; and provide a query capability for retrieving interconnected biological data.

In some aspects, the techniques described herein relate to a system, wherein biological entities include at least one of a gene, protein, metabolite, or strain.

In some aspects, the techniques described herein relate to a system, wherein relationships include at least one of a metabolic pathway, regulatory interaction, or protein-protein interaction.

In some aspects, the techniques described herein relate to a system, wherein experimental data includes time-resolved metabolomics data.

In some aspects, the techniques described herein relate to a system, wherein the knowledge graph enables retrieval of a strain that modifies a particular metabolic pathway.

In some aspects, the techniques described herein relate to a system, further including a visualization capability for exploring a graph relationship.

In some aspects, the techniques described herein relate to a system, wherein the machine learning system includes a graph neural network.

In some aspects, the techniques described herein relate to a system, further including automated validation of a data relationship.

In some aspects, the techniques described herein relate to a system, wherein data lineage includes experimental conditions metadata.

In some aspects, the techniques described herein relate to a system, further including version control for tracking graph changes.

In some aspects, the techniques described herein relate to a system, wherein a prediction includes a strain optimization recommendation.

In some aspects, the techniques described herein relate to a system, wherein the query capability includes filtering by pathway modifications.

In some aspects, the techniques described herein relate to a system, further including integration with an external biological database.

In some aspects, the techniques described herein relate to a system, wherein the knowledge graph maintains an audit trail.

In some aspects, the techniques described herein relate to a system, further including real-time updates from experimental data.

In some aspects, the techniques described herein relate to a computer-implemented method for structured biological data storage in an AI-guided synthetic biology platform, including: implementing a bipartite graph database structure organizing data into molecule nodes and process nodes; storing biological components and their relationships in the graph database structure; maintaining connections between nodes indicating roles in biological processes; integrating a plurality of high-dimensional biological data types; applying a machine learning method to analyze a graph relationship; and generating a prediction for synthetic biology optimization based on graph analysis.

In some aspects, the techniques described herein relate to a method, wherein molecule nodes represent at least one of an atomic element, ion, compound, nucleic acid, protein, or macromolecule.

In some aspects, the techniques described herein relate to a method, wherein process nodes represent at least one of a chemical reaction, protein folding, transport, regulatory interaction, or active site binding.

In some aspects, the techniques described herein relate to a method, wherein high-dimensional biological data includes gene expression data from RNA sequencing.

In some aspects, the techniques described herein relate to a method, wherein high-dimensional biological data includes flux data from isotope-labeled experiments.

In some aspects, the techniques described herein relate to a method, wherein high-dimensional biological data includes metabolite concentration measurements.

In some aspects, the techniques described herein relate to a method, further including implementing data normalization procedures.

In some aspects, the techniques described herein relate to a method, wherein the machine learning method is a hybrid model.

In some aspects, the techniques described herein relate to a method, further including maintaining data provenance tracking.

In some aspects, the techniques described herein relate to a method, wherein the prediction includes pathway bottleneck identification.

In some aspects, the techniques described herein relate to a method, further including implementing a quality control mechanism.

In some aspects, the techniques described herein relate to a method, wherein the graph relationship includes a metabolic pathway connection.

In some aspects, the techniques described herein relate to a method, further including generating a visualization output.

In some aspects, the techniques described herein relate to a method, wherein the machine learning method includes a neural network.

In some aspects, the techniques described herein relate to a method, further including implementing an automated validation check.

In some aspects, the techniques described herein relate to a method, wherein predictions include strain performance estimates.

In some aspects, the techniques described herein relate to a system for multi-modal data storage in an AI-guided synthetic biology platform, including: one or more processors; memory storing instructions that, when executed by the one or more processors, cause the platform to: implement a specialized data structure optimized for a biological data type; store time-series experimental data in a vector database; maintain a knowledge graph for biological relationship mapping; integrate structured and unstructured biological data; apply a machine learning model to analyze a cross-structure relationship; and generate a unified data presentation for decision support.

In some aspects, the techniques described herein relate to a system, wherein the specialized data structure includes a bipartite graph database.

In some aspects, the techniques described herein relate to a system, wherein time-series data includes a bioreactor sensor measurement.

In some aspects, the techniques described herein relate to a system, wherein time-series data includes a metabolomics measurement.

In some aspects, the techniques described herein relate to a system, wherein the knowledge graph represents a strain lineage.

In some aspects, the techniques described herein relate to a system, wherein structured data includes an experimental parameter.

In some aspects, the techniques described herein relate to a system, wherein unstructured data includes scientific literature.

In some aspects, the techniques described herein relate to a system, further including implementing a data normalization procedure.

In some aspects, the techniques described herein relate to a system, wherein the machine learning model is a hybrid architecture.

In some aspects, the techniques described herein relate to a system, further including maintaining an audit trail.

In some aspects, the techniques described herein relate to a system, wherein the unified presentation includes a visualization.

In some aspects, the techniques described herein relate to a system, further including implementing an automated validation check.

In some aspects, the techniques described herein relate to a system, wherein relationships include a metabolic pathway.

In some aspects, the techniques described herein relate to a system, wherein decision support includes a strain optimization recommendation.

In some aspects, the techniques described herein relate to a system for integrated data processing in an AI-guided synthetic biology platform, including: a data storage layer configured to: maintain a knowledge graph structure representing biological entities and relationships; store time-series experimental data in at least one vector database; track data lineage; an artificial intelligence layer configured to: analyze a data relationship using a machine learning model; generate a prediction for synthetic biology optimization; maintain a model performance metric; an automated processing layer configured to: implement a standardized data collection protocol; perform a quality control check; apply a normalization procedure; and an integration layer configured to: coordinate a data flow between system components; maintain a synchronized state across layers; and provide a unified access to platform capabilities.

In some aspects, the techniques described herein relate to a system, wherein the knowledge graph structure represents at least one of a gene, protein, metabolite or their interactions.

In some aspects, the techniques described herein relate to a system, wherein the machine learning model includes at least one of a foundation model, a mechanistic model, or a hybrid model.

In some aspects, the techniques described herein relate to a system, wherein quality control includes automated detection of anomalous data.

In some aspects, the techniques described herein relate to a system, wherein normalization procedures include a Bayesian statistical model.

In some aspects, the techniques described herein relate to a system, wherein data flow coordination includes automated staging and validation.

In some aspects, the techniques described herein relate to a system, wherein the integration layer implements standardized APIs.

In some aspects, the techniques described herein relate to a system, wherein the prediction includes a strain optimization recommendation.

In some aspects, the techniques described herein relate to a system, wherein the model metric includes performance tracking and validation.

In some aspects, the techniques described herein relate to a system, wherein data collection includes an automated sampling mechanism.

In some aspects, the techniques described herein relate to a system, wherein quality control includes control sample validation.

In some aspects, the techniques described herein relate to a system, wherein normalization preserves a biological signal.

In some aspects, the techniques described herein relate to a system, wherein coordination includes error handling.

In some aspects, the techniques described herein relate to a system, wherein synchronization includes version control.

In some aspects, the techniques described herein relate to a system, wherein access includes role-based permissions.

In some aspects, the techniques described herein relate to a system, wherein capabilities include a visualization tool.

In some aspects, the techniques described herein relate to a computer-implemented method for integrated synthetic biology data processing, including: receiving biological data through an automated collection mechanism; storing received data in a structured format optimized for a biological data type; processing stored data through a quality control and normalization pipeline; analyzing processed data using a machine learning model; maintaining a synchronized data state across platform components; generating a unified output for decision support; and tracking data transformation throughout the integrated process.

In some aspects, the techniques described herein relate to a method, wherein the collection mechanism includes sensor integration.

In some aspects, the techniques described herein relate to a method, wherein the structured format includes knowledge graphs.

In some aspects, the techniques described herein relate to a method, wherein quality control includes automated validation.

In some aspects, the techniques described herein relate to a method, wherein normalization includes batch effect correction.

In some aspects, the techniques described herein relate to a method, wherein the machine learning model includes a hybrid architecture.

In some aspects, the techniques described herein relate to a method, wherein synchronization includes state management.

In some aspects, the techniques described herein relate to a method, wherein the output includes a visualization capability.

In some aspects, the techniques described herein relate to a method, wherein tracking includes an audit trail.

In some aspects, the techniques described herein relate to a method, wherein processing includes error handling.

In some aspects, the techniques described herein relate to a method, wherein outputs include recommendations.

In some aspects, the techniques described herein relate to a method, wherein automated collection includes metadata capture.

In some aspects, the techniques described herein relate to a method, wherein validation includes a control sample.

In some aspects, the techniques described herein relate to a method, wherein synchronization includes a failover mechanism.

In some aspects, the techniques described herein relate to a system for coordinated synthetic biology workflow execution, including: one or more processors; memory storing instructions that, when executed by the one or more processors, cause a platform to: implement an automated data collection and storage process; coordinate a quality control and normalization workflow; manage a machine learning model execution; track workflow execution status; and generate integrated process documentation.

In some aspects, the techniques described herein relate to a system, wherein the collection process includes sensor integration.

In some aspects, the techniques described herein relate to a system, wherein quality control includes automated validation.

In some aspects, the techniques described herein relate to a system, wherein normalization includes a Bayesian model.

In some aspects, the techniques described herein relate to a system, wherein the machine learning includes model selection.

In some aspects, the techniques described herein relate to a system, wherein documentation includes a quality metric.

In some aspects, the techniques described herein relate to a system, wherein the workflow includes a validation step.

In some aspects, the techniques described herein relate to a system, wherein execution includes version control.

In some aspects, the techniques described herein relate to a system, wherein collection includes metadata capture.

In some aspects, the techniques described herein relate to a system, wherein validation includes a control sample.

In some aspects, the techniques described herein relate to a computer-implemented method for automated data handling in an AI-guided synthetic biology platform, including: receiving experimental data from a plurality of sources through an automated data sampling mechanism; implementing an automated validation check to ensure data integrity during transfer; applying an automated data normalization procedure to the received experimental data to standardize at least one data format and remove batch effects; performing an automated quality control to identify data anomalies; storing processed data with automated lineage metadata; and generating documentation summarizing the automated data handling.

In some aspects, the techniques described herein relate to a method, wherein automated data sampling mechanism includes near-instantaneous quenching of cellular metabolism.

In some aspects, the techniques described herein relate to a method, wherein the automated validation check verifies at least one of a data type, a value range, or a pattern.

In some aspects, the techniques described herein relate to a method, wherein the automated data normalization procedure includes a Bayesian statistical model.

In some aspects, the techniques described herein relate to a method, wherein quality control includes detecting a failed sample.

In some aspects, the techniques described herein relate to a method, wherein lineage tracking maintains metadata about an experimental condition.

In some aspects, the techniques described herein relate to a method, further including automated classification of a data sensitivity level.

In some aspects, the techniques described herein relate to a method, further including automated error handling and retry logic.

In some aspects, the techniques described herein relate to a method, wherein documentation includes a quality scorecard.

In some aspects, the techniques described herein relate to a method, further including automated batch effect correction.

In some aspects, the techniques described herein relate to a method, wherein validation includes cross-reference validation.

In some aspects, the techniques described herein relate to a method, further including automated data enrichment.

In some aspects, the techniques described herein relate to a method, wherein quality control includes a statistical check.

In some aspects, the techniques described herein relate to a method, further including automated format conversion.

In some aspects, the techniques described herein relate to a method, wherein documentation includes an audit trail.

In some aspects, the techniques described herein relate to a system for automated data processing in an AI-guided synthetic biology platform, including: one or more processors; memory storing instructions that, when executed by the one or more processors, cause the platform to: implement an automated ETL process for a biological data source; perform automated data quality assessment and validation; apply an automated normalization and standardization procedure; maintain an automated tracking of data transformation; generate automated documentation of a processing step; and provide an automated alert relating to a processing issue.

In some aspects, the techniques described herein relate to a system, wherein the ETL process handles structured and unstructured data.

In some aspects, the techniques described herein relate to a system, wherein quality assessment includes completeness analysis.

In some aspects, the techniques described herein relate to a system, wherein normalization includes batch effect correction.

In some aspects, the techniques described herein relate to a system, wherein tracking includes data lineage documentation.

In some aspects, the techniques described herein relate to a system, further including automated error detection.

In some aspects, the techniques described herein relate to a system, wherein documentation includes a processing history.

In some aspects, the techniques described herein relate to a system, further including automated data classification.

In some aspects, the techniques described herein relate to a system, wherein validation includes a control sample check.

In some aspects, the techniques described herein relate to a system, further including automated data format harmonization.

In some aspects, the techniques described herein relate to a system, wherein the alert relates to a quality threshold violation.

In some aspects, the techniques described herein relate to a system, further including automated metadata extraction.

In some aspects, the techniques described herein relate to a system, wherein processing includes outlier detection.

In some aspects, the techniques described herein relate to a system, further including automated version control.

In some aspects, the techniques described herein relate to a system, wherein documentation includes a quality metric.

In some aspects, the techniques described herein relate to a system, further including automated data staging.

In some aspects, the techniques described herein relate to a system for automated data integration in an AI-guided synthetic biology platform, including: a data intake pipeline configured to: automatically collect data from a plurality of experimental sources; perform automated data format standardization; implement an automated data quality control check; apply an automated data normalization procedure; a data management system configured to: maintain automated tracking of data processing; generate automated documentation; implement an automated data validation procedure; and provide an automated alert regarding verification of completed processing steps.

In some aspects, the techniques described herein relate to a system, wherein experimental sources include bioreactor sensors.

In some aspects, the techniques described herein relate to a system, wherein standardization includes unit conversion.

In some aspects, the techniques described herein relate to a system, wherein quality control includes anomaly detection.

In some aspects, the techniques described herein relate to a system, wherein normalization includes Bayesian models.

In some aspects, the techniques described herein relate to a system, wherein tracking includes an audit trail.

In some aspects, the techniques described herein relate to a system, wherein documentation includes a quality scorecard.

In some aspects, the techniques described herein relate to a system, wherein validation includes a control sample check.

In some aspects, the techniques described herein relate to a system, wherein an alert includes an error notification.

In some aspects, the techniques described herein relate to a system, further including automated data classification.

In some aspects, the techniques described herein relate to a system, wherein processing includes batch correction.

In some aspects, the techniques described herein relate to a system, further including automated metadata management.

In some aspects, the techniques described herein relate to a system, wherein validation includes cross-referencing.

In some aspects, the techniques described herein relate to a system, further including automated data enrichment.

In some aspects, the techniques described herein relate to a system, wherein documentation includes a processing log.

In some aspects, the techniques described herein relate to a system further including automated version tracking.

In some aspects, the techniques described herein relate to a system for machine learning-based analysis in an AI-guided synthetic biology platform, including: one or more processors configured with an AI processing core; memory storing instructions that, when executed by the one or more processors, cause the platform to: implement a multi-modal deep learning architecture with separate encoding branches for different data modalities; process gene expression data, metabolite profile, and reaction flux data through specialized neural network branches; combine encoded representations through fusion layers; generate at least one prediction about a cellular phenotype based on the processed multimodal biological data; and output a specification for biological system optimization based on the at least one prediction.

In some aspects, the techniques described herein relate to a system, wherein the AI processing core includes GPUs, NPUs, TPUs, or FPGAs optimized for biological data processing.

In some aspects, the techniques described herein relate to a system, wherein the multi-modal deep learning architecture includes transformer models.

In some aspects, the techniques described herein relate to a system, wherein specialized neural network branches include protein language models.

In some aspects, the techniques described herein relate to a system, wherein the at least one prediction includes a strain performance estimate.

In some aspects, the techniques described herein relate to a system, further including implementing a distributed computing capability.

In some aspects, the techniques described herein relate to a system, wherein fusion layers combine multiple types of biological embeddings.

In some aspects, the techniques described herein relate to a system, further including implementing automated model selection.

In some aspects, the techniques described herein relate to a system, wherein processing includes batch effect correction.

In some aspects, the techniques described herein relate to a system, further including maintaining model performance metrics.

In some aspects, the techniques described herein relate to a system, wherein the at least one prediction includes pathway bottleneck identification.

In some aspects, the techniques described herein relate to a system, further including implementing model validation procedures.

In some aspects, the techniques described herein relate to a system, wherein the deep learning architecture includes hybrid models.

In some aspects, the techniques described herein relate to a system, further including implementing edge computing capabilities.

In some aspects, the techniques described herein relate to a system, wherein the at least one prediction includes metabolic flux distributions.

In some aspects, the techniques described herein relate to a system, further including generating visualization outputs.

In some aspects, the techniques described herein relate to a computer-implemented method for AI-guided synthetic biology optimization, including: receiving biological data from a plurality of experimental sources; processing the biological data through a foundation model to generate a biological entity embedding; analyzing the embedding using a mechanistic model to characterize a biological process; combining the foundation model and the mechanistic model outputs through hybrid models; generating a prediction for synthetic biology system design; and implementing automated model construction to iteratively improve predictions based on new data.

In some aspects, the techniques described herein relate to a method, wherein the foundation model includes a genetic generalization model.

In some aspects, the techniques described herein relate to a method, wherein the foundation model includes a process generalization model.

In some aspects, the techniques described herein relate to a method, wherein the mechanistic model generates outputs characterizing a biological pathway.

In some aspects, the techniques described herein relate to a method, wherein hybrid models leverage respective strengths of individual models.

In some aspects, the techniques described herein relate to a method, further including implementing active learning capabilities.

In some aspects, the techniques described herein relate to a method, wherein the prediction includes a strain design specification.

In some aspects, the techniques described herein relate to a method, further including maintaining model performance tracking.

In some aspects, the techniques described herein relate to a method, wherein processing includes data normalization.

In some aspects, the techniques described herein relate to a method, further including implementing a validation procedure.

In some aspects, the techniques described herein relate to a method, wherein the prediction includes a process parameter optimization.

In some aspects, the techniques described herein relate to a method, further including implementing distributed computing.

In some aspects, the techniques described herein relate to a method, wherein the embedding includes a strain representation.

In some aspects, the techniques described herein relate to a method, further including maintaining an audit trail.

In some aspects, the techniques described herein relate to a method, wherein the prediction includes scale-up performance.

In some aspects, the techniques described herein relate to a method, further including generating a visualization output.

In some aspects, the techniques described herein relate to a computer-implemented method for data normalization in an AI-guided synthetic biology platform, including: receiving experimental data associated with synthetic biology development from a plurality of sources; processing the experimental data through a Bayesian statistical normalization model configured to: model batch-specific systemic variation; account for a technical factor contributing to a batch effect; separate a biological signal from a technical factor; validate that normalization preserved a specified biological signal; store the normalized data with tracked data lineage; and provide the normalized data to a machine learning model for analysis.

In some aspects, the techniques described herein relate to a method, wherein modeling batch-specific systemic variation includes constructing plate notation models representing a strain effect.

In some aspects, the techniques described herein relate to a method, wherein modeling includes representing an experimental effect and plate-to-plate variations.

In some aspects, the techniques described herein relate to a method, wherein the technical factor includes plate position effects.

In some aspects, the techniques described herein relate to a method, wherein the biological signal includes a metabolite concentration.

In some aspects, the techniques described herein relate to a method, wherein the biological signal includes an enzyme activity level.

In some aspects, the techniques described herein relate to a method, wherein the biological signal includes a gene expression level.

In some aspects, the techniques described herein relate to a method, further including implementing multi-modal data integration.

In some aspects, the techniques described herein relate to a method, wherein data lineage includes experimental conditions metadata.

In some aspects, the techniques described herein relate to a method, further including implementing cross-platform data harmonization.

In some aspects, the techniques described herein relate to a method, wherein normalization includes time series data normalization.

In some aspects, the techniques described herein relate to a method, further including implementing knowledge graph-based normalization.

In some aspects, the techniques described herein relate to a method, wherein the machine learning model includes a transformer model.

In some aspects, the techniques described herein relate to a method, wherein the machine learning model includes a neural network.

In some aspects, the techniques described herein relate to a method, further including generating a visualization output.

In some aspects, the techniques described herein relate to a method, further including maintaining an audit trail.

In some aspects, the techniques described herein relate to a system for quality control in an AI-guided synthetic biology platform, including: a data intake pipeline configured to: collect raw experimental data associated with a strain performance measurement; implement data normalization and quality control procedures; validate a strain genotype through an automated process; identify outlier data in an experimental dataset; maintain metadata about an experimental condition; a machine learning system configured to: analyze a quality control metric; generate an automated alert relating to detection of anomalous data; predict an expected measurement range based on historical data; and provide a recommendation for experimental validation.

In some aspects, the techniques described herein relate to a system, wherein the strain performance measurement includes a metabolite measurement.

In some aspects, the techniques described herein relate to a system, wherein the quality control procedure detects a failed growth sample.

In some aspects, the techniques described herein relate to a system, wherein the quality control procedure identifies contamination.

In some aspects, the techniques described herein relate to a system, wherein outlier detection uses statistical analysis.

In some aspects, the techniques described herein relate to a system, wherein metadata includes processing step information.

In some aspects, the techniques described herein relate to a system, further including implementing an automated validation check.

In some aspects, the techniques described herein relate to a system, wherein the alert includes a quality threshold violation.

In some aspects, the techniques described herein relate to a system, further including implementing an error handling procedure.

In some aspects, the techniques described herein relate to a system, wherein the quality metric includes completeness analysis.

In some aspects, the techniques described herein relate to a system, further including implementing cross-reference validation.

In some aspects, the techniques described herein relate to a system, wherein the recommendation includes control sample validation.

In some aspects, the techniques described herein relate to a system, further including implementing automated classification.

In some aspects, the techniques described herein relate to a system, wherein the quality metric includes a statistical check.

In some aspects, the techniques described herein relate to a system, further including generating a quality scorecard.

In some aspects, the techniques described herein relate to a system, further including maintaining an audit trail.

In some aspects, the techniques described herein relate to a system for integrated data quality management in an AI-guided synthetic biology platform, including: one or more processors; memory storing instructions that, when executed by the one or more processors, cause the platform to: implement an automated sampling mechanism for standardized data collection; apply a Bayesian normalization model to experimental data; perform an automated quality control check using a machine learning model; generate a probability distribution representing strain performance; and identify a high-performing strain based on normalized measurements.

In some aspects, the techniques described herein relate to a system, wherein the sampling mechanism includes metabolomics data collection.

In some aspects, the techniques described herein relate to a system, wherein the normalization model incorporates prior knowledge.

In some aspects, the techniques described herein relate to a system, wherein quality control includes anomaly detection.

In some aspects, the techniques described herein relate to a system, wherein the probability distribution includes an uncertainty estimate.

In some aspects, the techniques described herein relate to a system, further including implementing batch effect correction.

In some aspects, the techniques described herein relate to a system, wherein the machine learning model includes a hybrid model.

In some aspects, the techniques described herein relate to a system, further including maintaining a performance metric.

In some aspects, the techniques described herein relate to a system, wherein quality control includes control sample validation.

In some aspects, the techniques described herein relate to a system, further including implementing data enrichment.

In some aspects, the techniques described herein relate to a system, wherein normalization preserves a biological signal.

In some aspects, the techniques described herein relate to a system, further including implementing automated validation.

In some aspects, the techniques described herein relate to a system, wherein quality control includes a statistical check.

In some aspects, the techniques described herein relate to a system, further including generating documentation.

In some aspects, the techniques described herein relate to a system, further including maintaining an audit trail.

In some aspects, the techniques described herein relate to a platform for generating a set of recommendations associated with the production of a functional output by a biological strain, including: a set of data integration facilities for integrating content of at least one publication data set relating to the biological strain and at least one proprietary data set including a set of parameters of a synthetic biological process in which the biological strain produces the functional output, wherein an output of data integration facilities is configured as an input to a set of artificial intelligence (AI)-based learning models; and at least one member of the set of AI-based learning models that is configured to generate a set of recommendations wherein the set of recommendations relate to at least one of a set of modifications to a set of genes of the biological strain, a set of modifications to a set of environmental parameters for a synthetic biological process in which the biological strain produces the functional output, a set of modifications to a set of biological pathways associated with the synthetic biological process in which the biological strain produces the functional output, or a set of modifications to a set of proteins or enzymes associated with the biological strain; wherein that the set of recommendations enhance production of the functional output by the biological strain.

In some aspects, the techniques described herein relate to a platform, wherein the set of AI-based learning models includes at least one of a transformer model, a convolutional neural network, a deep learning model, a supervised model, a semi-supervised model, an unsupervised model, a reinforcement model, a long short-term memory (LSTM) model, a multi-layer perceptrons, a lin-log model, a large language model, a large protein model, or a protein language model.

In some aspects, the techniques described herein relate to a platform, wherein the at least one publication dataset includes at least one of: gene function description datasets, datasets from metabolic pathway databases, comparative genomics datasets, omics datasets, functional assay datasets, experiment result datasets, bioinformatics analyses datasets, regulatory study datasets, enzyme characterization datasets, case study datasets, or patent literature.

In some aspects, the techniques described herein relate to a platform, wherein the at least one proprietary dataset includes at least one of genetic parameters, metabolic parameters, growth and physiological parameters, environmental and culture conditions, process parameters, functional output parameters, regulatory and control parameters, phenotypic parameters, omics parameters, scale-up parameters, or energy consumption parameters.

In some aspects, the techniques described herein relate to a platform, wherein the set of recommendations relates to at least one of knockout mutations, overexpression of target genes, activation of specific genes, insertion of specific genes, gene knockdowns, site-directed mutagenesis, promoter engineering, codon optimization, gene fusion, allele replacement, creation of synthetic gene circuits, introduction of regulatory elements, or application of advanced genome editing technologies.

In some aspects, the techniques described herein relate to a platform, wherein the set of recommendations relates to modifications of at least one of temperature, pH level, oxygen supply, nutrient composition, fermentation time, stirring and mixing, inoculum size, light conditions, toxicity management, pressure, or salinity.

In some aspects, the techniques described herein relate to a platform, wherein the set of recommendations relates to at least one of identification and overexpression of key enzymes, use of stronger or inducible promoters, knockout of competing pathways, pathway engineering, optimization of substrate utilization, feedback regulation modification, cofactor engineering, pathway flux redistribution, integration of pathways, or environmental adaptations.

In some aspects, the techniques described herein relate to a platform, wherein the set of recommendations relates to at least one of enzyme overexpression, use of stronger promoters, site-directed mutagenesis, construction of chimeric proteins, enhancement of cofactor interactions, alleviation of feedback inhibition, application of post-translational modifications, modification of enzyme localization, gene knockouts of competing enzymes, allosteric modulation, or integration of modular enzyme assemblies.

In some aspects, the techniques described herein relate to a platform, wherein the functional output includes at least one of fuel applications and solutions, industrial applications and solutions, consumer product applications and solutions, pharmaceutical applications and solutions, or medical applications and solutions.

In some aspects, the techniques described herein relate to a platform, wherein the set of AI-based learning models is configured to process inputs in parallel across multiple AI Processing cores, wherein each processing core handles a subset of the input data.

In some aspects, the techniques described herein relate to a platform, wherein the set of AI-based learning models uses adaptive computation techniques that dynamically adjust a model's computational complexity based on input complexity.

In some aspects, the techniques described herein relate to a platform, wherein the data integration facilities use dedicated processing cores to perform data transformation or integration operations.

In some aspects, the techniques described herein relate to a method for generating a set of recommendations associated with the production of a functional output by a biological strain, including: integrating, by a set of data integration facilities, content of at least one publication data set relating to the biological strain and at least one proprietary data set including a set of parameters of a synthetic biological process in which the biological strain produces the functional output, wherein an output of data integration facilities is configured as an input to a set of artificial intelligence (AI)-based learning models; and generating, by at least one member of the set of AI-based learning models, a set of recommendations wherein the set of recommendations relate to at least one of a set of modifications to a set of genes of the biological strain, a set of modifications to a set of environmental parameters for a synthetic biological process in which the biological strain produces the functional output, a set of modifications to a set of biological pathways associated with the synthetic biological process in which the biological strain produces the functional output, or a set of modifications to a set of proteins or enzymes associated with the biological strain; wherein that the set of recommendations enhance production of the functional output by the biological strain.

In some aspects, the techniques described herein relate to a method, wherein the set of AI-based learning models includes at least one of a transformer model, a convolutional neural network, a deep learning model, a supervised model, a semi-supervised model, an unsupervised model, a reinforcement model, a long short-term memory (LSTM) model, a multi-layer perceptrons, a lin-log model, a large language model, a large protein model, or a protein language model.

In some aspects, the techniques described herein relate to a method, wherein the at least one publication dataset includes at least one of: gene function description datasets, datasets from metabolic pathway databases, comparative genomics datasets, omics datasets, functional assay datasets, experiment result datasets, bioinformatics analyses datasets, regulatory study datasets, enzyme characterization datasets, case study datasets, or patent literature.

In some aspects, the techniques described herein relate to a method, wherein the at least one proprietary dataset includes at least one of genetic parameters, metabolic parameters, growth and physiological parameters, environmental and culture conditions, process parameters, functional output parameters, regulatory and control parameters, phenotypic parameters, omics parameters, scale-up parameters, or energy consumption parameters.

In some aspects, the techniques described herein relate to a method, wherein the set of recommendations relates to at least one of knockout mutations, overexpression of target genes, activation of specific genes, insertion of specific genes, gene knockdowns, site-directed mutagenesis, promoter engineering, codon optimization, gene fusion, allele replacement, creation of synthetic gene circuits, introduction of regulatory elements, or application of advanced genome editing technologies.

In some aspects, the techniques described herein relate to a method, wherein the set of recommendations relates to modifications of at least one of temperature, pH level, oxygen supply, nutrient composition, fermentation time, stirring and mixing, inoculum size, light conditions, toxicity management, pressure, or salinity.

In some aspects, the techniques described herein relate to a method, wherein the set of recommendations relates to at least one of identification and overexpression of key enzymes, use of stronger or inducible promoters, knockout of competing pathways, pathway engineering, optimization of substrate utilization, feedback regulation modification, cofactor engineering, pathway flux redistribution, integration of pathways, or environmental adaptations.

In some aspects, the techniques described herein relate to a method, wherein the set of recommendations relates to at least one of enzyme overexpression, use of stronger promoters, site-directed mutagenesis, construction of chimeric proteins, enhancement of cofactor interactions, alleviation of feedback inhibition, application of post-translational modifications, modification of enzyme localization, gene knockouts of competing enzymes, allosteric modulation, or integration of modular enzyme assemblies.

In some aspects, the techniques described herein relate to a method, wherein the functional output includes at least one of fuel applications and solutions, industrial applications and solutions, consumer product applications and solutions, pharmaceutical applications and solutions, or medical applications and solutions.

In some aspects, the techniques described herein relate to a method, wherein processing the inputs by the set of AI-based learning models includes processing in parallel across multiple AI Processing cores, wherein each processing core handles a subset of the input data.

In some aspects, the techniques described herein relate to a method, wherein the set of AI-based learning models use adaptive computation techniques that dynamically adjust a model's computational complexity based on input complexity.

In some aspects, the techniques described herein relate to a method, wherein integrating the content includes using dedicated processing cores to perform data transformation or integration operations.

In some aspects, the techniques described herein relate to a platform for generating a set of recommendations associated with the production of a functional output by a biological strain, including: a set of data integration facilities configured to integrate the content of at least one publication data set relating to the biological strain and at least one proprietary data set including a set of parameters of a synthetic biological process in which the biological strain produces the functional output, wherein an output of data integration facilities is configured as an input to a set of artificial intelligence (AI)-based learning models; a simulation engine configured to: generate a plurality of synthetic biological process scenarios in which the biological strain produces the functional output, wherein each process scenario has a different set of modifications to at least one of a set of genes of the biological strain, a set of environmental parameters for the synthetic biological process in which the biological strain produces the functional output, a set of biological pathways associated with the synthetic biological process in which the biological strain produces the functional output, or a set of proteins or enzymes associated with the biological strain; execute simulations for the plurality of simulated process scenarios; generate simulation data based on the executed simulations wherein the simulation data is configured as an input to the set of AI-based learning models; and at least one member of the set of AI-based learning models that is configured to generate a set of recommendations wherein the set of recommendations relate to at least one of a set of modifications to a set of genes of the biological strain, a set of modifications to a set of environmental parameters for the synthetic biological process in which the biological strain produces the functional output, a set of modifications to the set of biological pathways associated with a synthetic biological process in which the biological strain produces the functional output, or a set of modifications to the set of proteins or enzymes associated with the biological strain; wherein that the set of recommendations enhance production of the functional output by the biological strain.

In some aspects, the techniques described herein relate to a platform, wherein the set of AI-based learning models includes at least one of a transformer model, a convolutional neural network, a deep learning model, a supervised model, a semi-supervised model, an unsupervised model, a reinforcement model, a long short-term memory (LSTM) model, a multi-layer perceptrons, a lin-log model, a large language model, a large protein model, or a protein language model.

In some aspects, the techniques described herein relate to a platform, wherein the at least one publication dataset includes at least one of: gene function description datasets, datasets from metabolic pathway databases, comparative genomics datasets, omics datasets, functional assay datasets, experiment result datasets, bioinformatics analyses datasets, regulatory study datasets, enzyme characterization datasets, case study datasets, or patent literature.

In some aspects, the techniques described herein relate to a platform, wherein the at least one proprietary dataset includes at least one of genetic parameters, metabolic parameters, growth and physiological parameters, environmental and culture conditions, process parameters, functional output parameters, regulatory and control parameters, phenotypic parameters, omics parameters, scale-up parameters, or energy consumption parameters.

In some aspects, the techniques described herein relate to a platform, wherein the set of recommendations relates to at least one of knockout mutations, overexpression of target genes, activation of specific genes, insertion of specific genes, gene knockdowns, site-directed mutagenesis, promoter engineering, codon optimization, gene fusion, allele replacement, creation of synthetic gene circuits, introduction of regulatory elements, or application of advanced genome editing technologies.

In some aspects, the techniques described herein relate to a platform, wherein the set of recommendations relates to modifications of at least one of temperature, pH level, oxygen supply, nutrient composition, fermentation time, stirring and mixing, inoculum size, light conditions, toxicity management, pressure, or salinity.

In some aspects, the techniques described herein relate to a platform, wherein the set of recommendations relates to at least one of identification and overexpression of key enzymes, use of stronger or inducible promoters, knockout of competing pathways, pathway engineering, optimization of substrate utilization, feedback regulation modification, cofactor engineering, pathway flux redistribution, integration of pathways, or environmental adaptations.

In some aspects, the techniques described herein relate to a platform, wherein the set of recommendations relates to at least one of enzyme overexpression, use of stronger promoters, site-directed mutagenesis, construction of chimeric proteins, enhancement of cofactor interactions, alleviation of feedback inhibition, application of post-translational modifications, modification of enzyme localization, gene knockouts of competing enzymes, allosteric modulation, or integration of modular enzyme assemblies.

In some aspects, the techniques described herein relate to a platform, wherein the functional output includes at least one of fuel applications and solutions, industrial applications and solutions, consumer product applications and solutions, pharmaceutical applications and solutions, or medical applications and solutions.

In some aspects, the techniques described herein relate to a platform, wherein the set of AI-based learning models is configured to process inputs in parallel across multiple AI Processing cores, wherein each processing core handles a subset of the input data.

In some aspects, the techniques described herein relate to a platform, wherein the set of AI-based learning models uses adaptive computation techniques that dynamically adjust a model's computational complexity based on input complexity.

In some aspects, the techniques described herein relate to a platform, wherein the data integration facilities use dedicated processing cores to perform data transformation or integration operations.

In some aspects, the techniques described herein relate to a platform, wherein the simulation engine uses distributed computing to parallelize the execution of simulations across a plurality of computing nodes.

In some aspects, the techniques described herein relate to a platform, wherein the simulation engine uses distributed computing to execute multiple simulations by batching neural network computations or distributing ODE integrations across a plurality of processing cores.

In some aspects, the techniques described herein relate to a method for generating a set of recommendations associated with the production of a functional output by a biological strain, including: integrating, by a set of data integration facilities, content of at least one publication data set relating to the biological strain and at least one proprietary data set including a set of parameters of a synthetic biological process in which the biological strain produces the functional output, wherein an output of data integration facilities is configured as an input to a set of artificial intelligence (AI)-based learning models; generating, by a simulation engine, a plurality of synthetic biological process scenarios in which the biological strain produces the functional output, wherein each process scenario has a different set of modifications to at least one of a set of genes of the biological strain, a set of environmental parameters for the synthetic biological process in which the biological strain produces the functional output, a set of biological pathways associated with the synthetic biological process in which the biological strain produces the functional output, or a set of proteins or enzymes associated with the biological strain; executing, by the simulation engine, simulations for the plurality of simulated process scenarios; generating, by the simulation engine, simulation data based on the executed simulations wherein the simulation data is configured as an input to the set of AI-based learning models; and generating, by at least one member of the set of AI-based learning models, a set of recommendations wherein the set of recommendations relate to at least one of a set of modifications to a set of genes of the biological strain, a set of modifications to a set of environmental parameters for the synthetic biological process in which the biological strain produces the functional output, a set of modifications to the set of biological pathways associated with a synthetic biological process in which the biological strain produces the functional output, or a set of modifications to the set of proteins or enzymes associated with the biological strain; wherein that the set of recommendations enhance production of the functional output by the biological strain.

In some aspects, the techniques described herein relate to a method, wherein the set of AI-based learning models includes at least one of a transformer model, a convolutional neural network, a deep learning model, a supervised model, a semi-supervised model, an unsupervised model, a reinforcement model, a long short-term memory (LSTM) model, a multi-layer perceptrons, a lin-log model, a large language model, a large protein model, or a protein language model.

In some aspects, the techniques described herein relate to a method, wherein the at least one publication dataset includes at least one of: gene function description datasets, datasets from metabolic pathway databases, comparative genomics datasets, omics datasets, functional assay datasets, experiment result datasets, bioinformatics analyses datasets, regulatory study datasets, enzyme characterization datasets, case study datasets, or patent literature.

In some aspects, the techniques described herein relate to a method, wherein the at least one proprietary dataset includes at least one of genetic parameters, metabolic parameters, growth and physiological parameters, environmental and culture conditions, process parameters, functional output parameters, regulatory and control parameters, phenotypic parameters, omics parameters, scale-up parameters, or energy consumption parameters.

In some aspects, the techniques described herein relate to a method, wherein the set of recommendations relates to at least one of knockout mutations, overexpression of target genes, activation of specific genes, insertion of specific genes, gene knockdowns, site-directed mutagenesis, promoter engineering, codon optimization, gene fusion, allele replacement, creation of synthetic gene circuits, introduction of regulatory elements, or application of advanced genome editing technologies.

In some aspects, the techniques described herein relate to a method, wherein the set of recommendations relates to modifications of at least one of temperature, pH level, oxygen supply, nutrient composition, fermentation time, stirring and mixing, inoculum size, light conditions, toxicity management, pressure, or salinity.

In some aspects, the techniques described herein relate to a method, wherein the set of recommendations relates to at least one of identification and overexpression of key enzymes, use of stronger or inducible promoters, knockout of competing pathways, pathway engineering, optimization of substrate utilization, feedback regulation modification, cofactor engineering, pathway flux redistribution, integration of pathways, or environmental adaptations.

In some aspects, the techniques described herein relate to a method, wherein the set of recommendations relates to at least one of enzyme overexpression, use of stronger promoters, site-directed mutagenesis, construction of chimeric proteins, enhancement of cofactor interactions, alleviation of feedback inhibition, application of post-translational modifications, modification of enzyme localization, gene knockouts of competing enzymes, allosteric modulation, or integration of modular enzyme assemblies.

In some aspects, the techniques described herein relate to a method, wherein the functional output includes at least one of fuel applications and solutions, industrial applications and solutions, consumer product applications and solutions, pharmaceutical applications and solutions, or medical applications and solutions.

In some aspects, the techniques described herein relate to a method, wherein processing the inputs by the set of AI-based learning models includes processing in parallel across multiple AI Processing cores, wherein each processing core handles a subset of the input data.

In some aspects, the techniques described herein relate to a method, wherein the set of AI-based learning models use adaptive computation techniques that dynamically adjust a model's computational complexity based on input complexity.

In some aspects, the techniques described herein relate to a method, wherein integrating the content includes using dedicated processing cores to perform data transformation or integration operations.

In some aspects, the techniques described herein relate to a method, wherein executing the simulations includes using distributed computing to parallelize the execution of simulations across a plurality of computing nodes.

In some aspects, the techniques described herein relate to a method, wherein executing the simulations includes using distributed computing to execute multiple simulations by batching neural network computations or distributing ODE integrations across a plurality.

In some aspects, the techniques described herein relate to a system for converting raw data from an analytical and mass spectrometry instrument to model-ready data, including: computing hardware configured to: receive data from an analytical and mass spectrometry instrument wherein the data includes measurement data from a set of control samples and a set of test samples; extract a set of peak lists including a set of test peak lists and a set of control peak lists from the received data; compress the extracted peak lists using a compression algorithm; identify a set of metabolites that correspond to a set of peaks from the compressed peak lists by comparing a set of mass-to-charge ratios and a set of retention times associated with the set of peaks with the mass-to-charge ratios and retention times associated with known metabolites from a set of spectral databases; calculate a set of peak areas corresponding to the set of peaks; generate a calibration curve for each identified metabolite based on the calculated area from its corresponding peaks from the compressed set of control peak lists and its known concentrations; calculate a set of concentrations for the set of identified metabolites associated with the peaks from the compressed set of test peak lists using the generated calibration curves; and generate a compilation of results.

In some aspects, the techniques described herein relate to a system, wherein the computing hardware is further configured to analyze the identified peaks to determine a need for a deconvolution and/or window adjustment on one or more of the identified peaks, and, upon determination of said need, perform deconvolution and/or window adjustment on the one or more of the identified peaks.

In some aspects, the techniques described herein relate to a system, wherein the computing hardware is further configured to generate a quality control website wherein the quality control website presents a set of calibration curves for control samples and test samples for each of the metabolites of the set of metabolites.

In some aspects, the techniques described herein relate to a system, wherein the analytical and mass spectrometry instrument is a liquid chromatography-mass spectrometry (LC-MS) instrument, a gas chromatography-mass spectrometry (GC-MS) instrument, a quadruple time-of-flight (QTOF) mass spectrometry instrument, an ultraviolet-visible (UV-Vis) instrument, or a free induction decay (FID) instrument, a quadrupole mass spectrometry (QMS) instrument, a time-of-flight mass spectrometry (TOF-MS) instrument, an ion trap mass spectrometry instrument, an orbitrap mass spectrometry instrument, a sector mass spectrometry instrument, an electrospray ionization (ESI) instrument, a chemical ionization (CI) instrument, an electron ionization (EI) instrument, an atmospheric pressure chemical ionization (APCI) instrument, or an atmospheric pressure photoionization (APPI) instrument.

In some aspects, the techniques described herein relate to a system, wherein the computing hardware is further configured to apply a dilution factor to the set of concentrations.

In some aspects, the techniques described herein relate to a system, wherein the computing hardware is further configured to normalize the concentrations to biomass content.

In some aspects, the techniques described herein relate to a system, wherein the system is integrated with a fermentation system and a rapid sampling system.

In some aspects, the techniques described herein relate to a system, further including comparing a set of fragmentation patterns associated with the set of peaks with the fragmentation patterns for a set of known metabolites from a set of spectral databases.

In some aspects, the techniques described herein relate to a method for converting raw data from an analytical and mass spectrometry instrument to model-ready data, including: receiving, by computing hardware, data from an analytical and mass spectrometry instrument wherein the data includes measurement data from a set of control samples and a set of test samples; extracting, by the computing hardware, a set of peak lists including a set of test peak lists and a set of control peak lists from the received data; compressing, by the computing hardware, the extracted peak lists using a compression algorithm; identifying, by the computing hardware, a set of metabolites that correspond to a set of peaks from the compressed peak lists by comparing a set of mass-to-charge ratios and a set of retention times associated with the set of peaks with the mass-to-charge ratios and retention times associated with known metabolites from a set of spectral databases; calculating, by the computing hardware, a set of peak areas corresponding to the set of peaks; generating, by the computing hardware, a calibration curve for each identified metabolite based on the calculated area from its corresponding peaks from the compressed set of control peak lists and its known concentrations; calculating, by the computing hardware, a set of concentrations for the set of identified metabolites associated with the peaks from the compressed set of test peak lists using the generated calibration curves; and generating, by the computing hardware, a compilation of results.

In some aspects, the techniques described herein relate to a method, further including analyzing the identified peaks to determine a need for a deconvolution and/or window adjustment on one or more of the identified peaks, and, upon determination of said need, performing deconvolution and/or window adjustment on the one or more of the identified peaks.

In some aspects, the techniques described herein relate to a method, further including generating a quality control website wherein the quality control website presents a set of calibration curves for control samples and test samples for each of the metabolites of the set of metabolites.

In some aspects, the techniques described herein relate to a method, wherein the analytical and mass spectrometry instrument is a liquid chromatography-mass spectrometry (LC-MS) instrument, a gas chromatography-mass spectrometry (GC-MS) instrument, a quadruple time-of-flight (QTOF) mass spectrometry instrument, an ultraviolet-visible (UV-Vis) instrument, or a free induction decay (FID) instrument, a quadrupole mass spectrometry (QMS) instrument, a time-of-flight mass spectrometry (TOF-MS) instrument, an ion trap mass spectrometry instrument, an orbitrap mass spectrometry instrument, a sector mass spectrometry instrument, an electrospray ionization (ESI) instrument, a chemical ionization (CI) instrument, an electron ionization (EI) instrument, an atmospheric pressure chemical ionization (APCI) instrument, or an atmospheric pressure photoionization (APPI) instrument.

In some aspects, the techniques described herein relate to a method, further including applying a dilution factor to the set of concentrations.

In some aspects, the techniques described herein relate to a method, further including normalizing the concentrations to biomass content.

In some aspects, the techniques described herein relate to a method, wherein the method is integrated with a fermentation system and a rapid sampling system.

In some aspects, the techniques described herein relate to a fermentation system including: a fermentation chamber configured to contain a fermentation medium; a plurality of sensors configured to measure fermentation parameters; a control system operatively coupled to the fermentation chamber and the plurality of sensors, the control system including: at least one processor; memory storing instructions that, when executed by the at least one processor, cause the control system to: receive sensor data from the plurality of sensors; process the sensor data using a set of AI-based learning models to determine a set of improved fermentation parameters; generate control signals based on the determined set of improved fermentation parameters; and adjust operating conditions of the fermentation chamber based on the control signals.

In some aspects, the techniques described herein relate to a fermentation system, wherein the set of AI-based learning models includes at least one of a transformer model, a convolutional neural network, a deep learning model, a supervised model, a semi-supervised model, an unsupervised model, a reinforcement model, a long short-term memory (LSTM) model, a multi-layer perceptrons, a lin-log model, a large language model, a large protein model, or a protein language model.

In some aspects, the techniques described herein relate to a fermentation system, wherein the fermentation system includes or is integrated with a rapid sampling system.

In some aspects, the techniques described herein relate to a fermentation system, wherein the fermentation system includes or is integrated with a rapid sampling system, an analytical and mass spectroscopy instrument, and an automated omics for generalization system.

In some aspects, the techniques described herein relate to a fermentation system, wherein the set of AI-based learning models are configured to process inputs in parallel across multiple AI Processing cores, wherein each processing core handles a subset of the input data.

In some aspects, the techniques described herein relate to a fermentation system, wherein the set of AI-based learning models use adaptive computation techniques that dynamically adjust a model's computational complexity based on input complexity.

In some aspects, the techniques described herein relate to a fermentation system, wherein the plurality of sensors includes at least two of: temperature sensors, pH sensors, dissolved oxygen sensors, biomass sensors, substrate concentration sensors, redox potential sensors, foam formation sensors, gas composition sensors, pressure sensors, flow rate sensors, conductivity sensors, turbidity sensors, viscosity sensors, cell viability sensors, weight sensors, acoustic sensors, optical density sensors, infrared sensors, fluorescence-based detection systems, enzymatic electrodes, biosensors, ion-selective electrodes, imaging sensors, and heat flux sensors.

In some aspects, the techniques described herein relate to a fermentation system, wherein the plurality of sensors includes at least one of a Raman sensor and a Near-Infrared (NIR) sensor.

In some aspects, the techniques described herein relate to a fermentation system, wherein the set of fermentation parameters include at least one of: temperature of the fermentation medium, pH level of the fermentation medium, dissolved oxygen concentration, pressure within the fermentation chamber, agitation rate, nutrient feed rate, substrate concentration, metabolite concentration, cell density, gas flow rate, foam level, viscosity of the fermentation medium, redox potential, carbon dioxide evolution rate, oxygen uptake rate, osmotic pressure, specific growth rate, product formation rate, yield coefficients, mass transfer coefficients, power input, mixing time, shear stress, or biomass morphology.

In some aspects, the techniques described herein relate to a fermentation system, wherein the control signals include signals to adjust at least one of: agitation speed of an impeller within the fermentation chamber, temperature of a heating or cooling element, flow rate of a nutrient feed pump, flow rate of an acid or base addition pump for pH control, flow rate of an antifoam addition pump, gas flow rate through a sparger, pressure within the fermentation chamber, substrate feed rate, harvest rate, mixing rate, aeration rate, or recirculation rate.

In some aspects, the techniques described herein relate to a fermentation system, wherein the fermentation system is configured as a mobile laboratory unit for deployment at remote locations.

In some aspects, the techniques described herein relate to a method of controlling a fermentation process including: containing a fermentation medium in a fermentation chamber; measuring fermentation parameters using a plurality of sensors; receiving sensor data from the plurality of sensors; processing the sensor data using a set of AI-based learning models to determine a set of improved fermentation parameters; generating control signals based on the determined set of improved fermentation parameters; and adjusting operating conditions of the fermentation chamber based on the control signals.

In some aspects, the techniques described herein relate to a method, wherein the set of AI-based learning models includes at least one of a transformer model, a convolutional neural network, a deep learning model, a supervised model, a semi-supervised model, an unsupervised model, a reinforcement model, a long short-term memory (LSTM) model, a multi-layer perceptrons, a lin-log model, a large language model, a large protein model, or a protein language model.

In some aspects, the techniques described herein relate to a method, further including sampling the fermentation medium using a rapid sampling system.

In some aspects, the techniques described herein relate to a method, further including: sampling the fermentation medium using a rapid sampling system; analyzing samples using an analytical and mass spectroscopy instrument; and processing sample data using an automated omics for generalization system.

In some aspects, the techniques described herein relate to a method, wherein processing the sensor data includes processing inputs in parallel across multiple AI Processing cores, wherein each processing core handles a subset of the input data.

In some aspects, the techniques described herein relate to a method, wherein processing the sensor data includes using adaptive computation techniques that dynamically adjust a model's computational complexity based on input complexity.

In some aspects, the techniques described herein relate to a method, wherein measuring fermentation parameters includes measuring at least two of: temperature, pH, dissolved oxygen, biomass, substrate concentration, redox potential, foam formation, gas composition, pressure, flow rates, conductivity, turbidity, viscosity, cell viability, weight, acoustic properties, optical density, infrared measurements, fluorescence, enzymatic activity, biosensor readings, ion concentrations, imaging data, and heat flux.

In some aspects, the techniques described herein relate to a method, wherein measuring fermentation parameters includes using at least one of a Raman sensor and a Near-Infrared (NIR) sensor.

In some aspects, the techniques described herein relate to a method, wherein the set of fermentation parameters include at least one of: temperature of the fermentation medium, pH level of the fermentation medium, dissolved oxygen concentration, pressure within the fermentation chamber, agitation rate, nutrient feed rate, substrate concentration, metabolite concentration, cell density, gas flow rate, foam level, viscosity of the fermentation medium, redox potential, carbon dioxide evolution rate, oxygen uptake rate, osmotic pressure, specific growth rate, product formation rate, yield coefficients, mass transfer coefficients, power input, mixing time, shear stress, or biomass morphology.

In some aspects, the techniques described herein relate to a method, wherein adjusting operating conditions includes adjusting at least one of: agitation speed of an impeller within the fermentation chamber, temperature of a heating or cooling element, flow rate of a nutrient feed pump, flow rate of an acid or base addition pump for pH control, flow rate of an antifoam addition pump, gas flow rate through a sparger, pressure within the fermentation chamber, substrate feed rate, harvest rate, mixing rate, aeration rate, or recirculation rate.

In some aspects, the techniques described herein relate to a method, further including: deploying the fermentation chamber, plurality set 5: AI-driven fermentation system with sensors-AI for data collection.

In some aspects, the techniques described herein relate to a fermentation system including: a fermentation chamber configured to contain a fermentation medium; a plurality of sensors configured to measure fermentation parameters; a control system operatively coupled to the fermentation chamber and the plurality of sensors, the control system including: at least one processor; memory storing instructions that, when executed by the at least one processor, cause the control system to: receive sensor data from the plurality of sensors; process the sensor data using a set of AI-based learning models to determine a set of fermentation parameters, wherein the determined fermentation parameters are configured to generate additional training data for improving the set of AI-based learning models; generate control signals based on the determined fermentation parameters; adjust operating conditions of the fermentation chamber based on the control signals; collect response data indicating effects of the adjusted operating conditions; update the set of AI-based learning models using the collected response data as additional training data.

In some aspects, the techniques described herein relate to a fermentation system, wherein the set of AI-based learning models includes at least one of a transformer model, a convolutional neural network, a deep learning model, a supervised model, a semi-supervised model, an unsupervised model, a reinforcement model, a long short-term memory (LSTM) model, a multi-layer perceptrons, a lin-log model, a large language model, a large protein model, or a protein language model.

In some aspects, the techniques described herein relate to a fermentation system, wherein the fermentation system includes or is integrated with a rapid sampling system.

In some aspects, the techniques described herein relate to a fermentation system, wherein the fermentation system includes or is integrated with a rapid sampling system, an analytical and mass spectroscopy instrument, and an automated omics for generalization system.

In some aspects, the techniques described herein relate to a fermentation system, wherein the set of AI-based learning models are configured to process inputs in parallel across multiple AI Processing cores, wherein each processing core handles a subset of the input data.

In some aspects, the techniques described herein relate to a fermentation system, wherein the set of AI-based learning models use adaptive computation techniques that dynamically adjust a model's computational complexity based on input complexity.

In some aspects, the techniques described herein relate to a fermentation system, wherein the plurality of sensors includes at least two of: temperature sensors, pH sensors, dissolved oxygen sensors, biomass sensors, substrate concentration sensors, redox potential sensors, foam formation sensors, gas composition sensors, pressure sensors, flow rate sensors, conductivity sensors, turbidity sensors, viscosity sensors, cell viability sensors, weight sensors, acoustic sensors, optical density sensors, infrared sensors, fluorescence-based detection systems, enzymatic electrodes, biosensors, ion-selective electrodes, imaging sensors, and heat flux sensors.

In some aspects, the techniques described herein relate to a fermentation system, wherein the plurality of sensors includes at least one of a Raman sensor and a Near-Infrared (NIR) sensor.

In some aspects, the techniques described herein relate to a fermentation system, wherein the set of fermentation parameters include at least one of: temperature of the fermentation medium, pH level of the fermentation medium, dissolved oxygen concentration, pressure within the fermentation chamber, agitation rate, nutrient feed rate, substrate concentration, metabolite concentration, cell density, gas flow rate, foam level, viscosity of the fermentation medium, redox potential, carbon dioxide evolution rate, oxygen uptake rate, osmotic pressure, specific growth rate, product formation rate, yield coefficients, mass transfer coefficients, power input, mixing time, shear stress, or biomass morphology.

In some aspects, the techniques described herein relate to a fermentation system, wherein the control signals include signals to adjust at least one of: agitation speed of an impeller within the fermentation chamber, temperature of a heating or cooling element, flow rate of a nutrient feed pump, flow rate of an acid or base addition pump for pH control, flow rate of an antifoam addition pump, gas flow rate through a sparger, pressure within the fermentation chamber, substrate feed rate, harvest rate, mixing rate, aeration rate, or recirculation rate.

In some aspects, the techniques described herein relate to a fermentation system, wherein the fermentation system is configured as a mobile laboratory unit for deployment at remote locations.

In some aspects, the techniques described herein relate to a method for controlling a fermentation process, including: receiving, by a control system, sensor data from a plurality of sensors configured to measure fermentation parameters of a fermentation chamber containing a fermentation medium; processing, by the control system, the sensor data using a set of AI-based learning models to determine a set of fermentation parameters, wherein the determined fermentation parameters are configured to generate additional training data for improving the set of AI-based learning models; generating, by the control system, control signals based on the determined fermentation parameters; adjusting, by the control system, operating conditions of the fermentation chamber based on the control signals; collecting, by the control system, response data indicating effects of the adjusted operating conditions; updating, by the control system, the set of AI-based learning models using the collected response data as additional training data.

In some aspects, the techniques described herein relate to a method, wherein the set of AI-based learning models includes at least one of a transformer model, a convolutional neural network, a deep learning model, a supervised model, a semi-supervised model, an unsupervised model, a reinforcement model, a long short-term memory (LSTM) model, a multi-layer perceptrons, a lin-log model, a large language model, a large protein model, or a protein language model.

In some aspects, the techniques described herein relate to a method, further including integrating the fermentation process with a rapid sampling system.

In some aspects, the techniques described herein relate to a method, further including integrating the fermentation process with a rapid sampling system, an analytical and mass spectroscopy instrument, and an automated omics for generalization system.

In some aspects, the techniques described herein relate to a method, wherein processing the sensor data includes processing inputs in parallel across multiple AI Processing cores, wherein each processing core handles a subset of the input data.

In some aspects, the techniques described herein relate to a method, wherein the set of AI-based learning models use adaptive computation techniques that dynamically adjust a model's computational complexity based on input complexity.

In some aspects, the techniques described herein relate to a method, wherein receiving the sensor data includes receiving data from at least two of: temperature sensors, pH sensors, dissolved oxygen sensors, biomass sensors, substrate concentration sensors, redox potential sensors, foam formation sensors, gas composition sensors, pressure sensors, flow rate sensors, conductivity sensors, turbidity sensors, viscosity sensors, cell viability sensors, weight sensors, acoustic sensors, optical density sensors, infrared sensors, fluorescence-based detection systems, enzymatic electrodes, biosensors, ion-selective electrodes, imaging sensors, and heat flux sensors.

In some aspects, the techniques described herein relate to a method, wherein receiving the sensor data includes receiving data from at least one of a Raman sensor and a Near-Infrared (NIR) sensor.

In some aspects, the techniques described herein relate to a method, wherein the set of fermentation parameters include at least one of: temperature of the fermentation medium, pH level of the fermentation medium, dissolved oxygen concentration, pressure within the fermentation chamber, agitation rate, nutrient feed rate, substrate concentration, metabolite concentration, cell density, gas flow rate, foam level, viscosity of the fermentation medium, redox potential, carbon dioxide evolution rate, oxygen uptake rate, osmotic pressure, specific growth rate, product formation rate, yield coefficients, mass transfer coefficients, power input, mixing time, shear stress, or biomass morphology.

In some aspects, the techniques described herein relate to a method, wherein generating the control signals includes generating signals to adjust at least one of: agitation speed of an impeller within the fermentation chamber, temperature of a heating or cooling element, flow rate of a nutrient feed pump, flow rate of an acid or base addition pump for pH control, flow rate of an antifoam addition pump, gas flow rate through a sparger, pressure within the fermentation chamber, substrate feed rate, harvest rate, mixing rate, aeration rate, or recirculation rate.

In some aspects, the techniques described herein relate to a method for predicting performance of a strain of a biologic organism, the method comprising: receiving, by a platform, information about the strain of a biologic organism, wherein the information describes one or more genetic edits associated with the strain; generating, by the platform, a set of embeddings based on the information about the strain of the biologic organism; receiving, by the platform, a set of bioreactor process conditions; and generating, by the platform, a prediction of a performance of the strain of the biologic organism in a bioreactor based on inputting both the set of embeddings and the bioreactor process conditions to a pre-trained genetic generalization model, wherein the pre-trained genetic generalization model is trained using training data for a plurality of strains of the biologic organism, wherein the training data comprises: information about corresponding genetic edits for the plurality of strains of the biologic organism; information about corresponding bioreactor process conditions for the plurality of strains of the biologic organism; and target data indicating corresponding performance for the plurality of strains of the biologic organism.

In some aspects, the techniques described herein relate to a method, wherein the bioreactor process conditions comprise at least one of bioreactor volume, temperature, pH, dissolved oxygen level, feed rate, or agitation speed.

In some aspects, the techniques described herein relate to a method, wherein the prediction of the performance of the strain indicates at least one of a growth rate, a metabolite production rate, a byproduct formation rate, a protein expression level, or a titer.

In some aspects, the techniques described herein relate to a method, wherein generating the set of embeddings comprises inputting the information about the strain of the biologic organism to one or more embeddings models, wherein the one or more embedding models include at least one of a GenePT model, a Proteinfer model, a pFBA-PCA model, or a GO-PCA model.

In some aspects, the techniques described herein relate to a method, wherein the one or more embeddings models comprise two or more embeddings models, the method further comprising aggregating the respective embeddings generated by the two or more embedding models to create the set of genetic embeddings.

In some aspects, the techniques described herein relate to a method, wherein the pre-trained genetic generalization model comprises a first stage that generates a strain embedding characterizing the strain of the biologic organism and a second stage that generates the prediction based on the strain embedding. In some embodiments, the first stage is one or more of a long-short term memory (LSTM) model, a transformer model, or a convolutional neural network (CNN) model. Additionally or alternatively, the second stage is a multi-layer perceptron.

In some aspects, the techniques described herein relate to a method, wherein the pre-trained genetic generalization model is an ensemble of multiple pre-trained genetic generalization models.

In some aspects, the techniques described herein relate to a method, wherein the set of embeddings encodes the one or more genetic edits.

In some aspects, the techniques described herein relate to a method, wherein the information about the strain comprises information about a base strain of the biologic organism. In some embodiments, the one or more genetic edits are with respect to the base strain, wherein the information about the one or more genetic edits comprises information indicating one or more gene knockouts, gene overexpressions, or gene underexpressions.

In some aspects, the techniques described herein relate to a system for predicting performance of a strain of a biologic organism, the system comprising: one or more processors; and memory storing instructions that, when executed by the one or more processors, cause the system to: receive information about the strain of a biologic organism, wherein the information describes one or more genetic edits associated with the strain; generate a set of embeddings based on the information about the strain of the biologic organism; receive a set of bioreactor process conditions; and generate a prediction of a performance of the strain of the biologic organism in a bioreactor based on inputting both the set of embeddings and the bioreactor process conditions to a pre-trained genetic generalization model, wherein the pre-trained genetic generalization model is trained using training data for a plurality of strains of the biologic organism, wherein the training data comprises: information about corresponding genetic edits for the plurality of strains of the biologic organism; information about corresponding bioreactor process conditions for the plurality of strains of the biologic organism; and target data indicating corresponding performance for the plurality of strains of the biologic organism.

In some aspects, the techniques described herein relate to a system, wherein the bioreactor process conditions comprise at least one of bioreactor volume, temperature, pH, dissolved oxygen level, feed rate, or agitation speed.

In some aspects, the techniques described herein relate to a system, wherein the prediction of the performance of the strain indicates at least one of a growth rate, a metabolite production rate, a byproduct formation rate, a protein expression level, or a titer.

In some aspects, the techniques described herein relate to a system, wherein generating the set of embeddings comprises inputting the information about the strain of the biologic organism to two or more embeddings models, wherein the embeddings models include at least one of a GenePT model, a Proteinfer model, a pFBA-PCA model, or a GO-PCA model, and wherein the system aggregates the respective embeddings generated by the two or more embedding models to create the set of genetic embeddings.

In some aspects, the techniques described herein relate to a system, wherein the pre-trained genetic generalization model comprises: a first stage that generates a strain embedding characterizing the strain of the biologic organism, wherein the first stage is one or more of a long-short term memory (LSTM) model, a transformer model, or a convolutional neural network (CNN) model; and a second stage that generates the prediction based on the strain embedding, wherein the second stage is a multi-layer perceptron.

In some aspects, the techniques described herein relate to a system, wherein the pre-trained genetic generalization model is an ensemble of multiple pre-trained genetic generalization models.

In some aspects, the techniques described herein relate to a system, wherein the set of embeddings encodes the one or more genetic edits.

In some aspects, the techniques described herein relate to a system, wherein the information about the strain comprises information about a base strain of the biologic organism, wherein the one or more genetic edits are with respect to the base strain, and wherein the information about the one or more genetic edits comprises information indicating one or more gene knockouts, gene overexpressions, or gene underexpressions.

In some aspects, the techniques described herein relate to a method comprising: receiving, by a platform, a first training dataset comprising a plurality of sets of genetic edits corresponding to a plurality of strains of a biologic organism, wherein the first training dataset further comprises a first target, wherein the first target comprises fitness data for the plurality of strains of the biologic organism; pre-training, by the platform, a genetic generalization model using the first training dataset, wherein the pre-training comprises training embeddings for the plurality of sets of genetic edits; receiving, by the platform, a second training dataset smaller than the first training dataset, wherein the second training dataset comprises: information about genetic edits for a second plurality of strains, wherein the second plurality of strains are different from the first plurality of strains; and information about at least one second target, wherein the at least one second target is different from the first target; and fine-tuning, by the platform, the pre-trained genetic generalization model using the second training dataset to generate a second genetic generalization model that is trained to predict the at least one second target.

In some aspects, the techniques described herein relate to a method, wherein the at least one second target comprises at least one of a bioreactor growth rate, a metabolite production rate, a byproduct formation rate, or a titer.

In some aspects, the techniques described herein relate to a method, wherein the second plurality of strains are strains of a different biologic organism than the first plurality of strains.

In some aspects, the techniques described herein relate to a method, wherein the second plurality of strains are strains of the same biologic organism as the first plurality of strains.

In some aspects, the techniques described herein relate to a method, wherein the genetic generalization model comprises a first stage that generates a strain embedding and a second stage that generates a prediction based on the strain embedding, wherein the fine-tuning comprises updating parameters of the second stage to predict the second target. In some embodiments, the fine-tuning comprises replacing at least a portion of the second stage with new layers trained to predict the second target. Additionally or alternatively, the fine-tuning uses a lower learning rate for the fine-tuning as compared to the pre-training. Additionally or alternatively, the first stage is one or more of a long-short term memory (LSTM) model, a transformer model, or a convolutional neural network (CNN) model. Additionally or alternatively, the second stage is a multi-layer perceptron.

In some aspects, the techniques described herein relate to a method, wherein the embeddings are generated at least in part by processing gene descriptions using a large language model prior to the pre-training.

In some aspects, the techniques described herein relate to a method, wherein the embeddings are trainable parameters during the pre-training such that they are iteratively updated during the pre-training.

In some aspects, the techniques described herein relate to a method, wherein the plurality of sets of genetic edits comprise information indicating that each genetic edit is at least one of a gene knockout, a gene overexpression, or a gene underexpression.

In some aspects, the techniques described herein relate to a system comprising: one or more processors; and memory storing instructions that, when executed by the processor, cause the system to: receive a first training dataset comprising a plurality of sets of genetic edits corresponding to a plurality of strains of a biologic organism, wherein the first training dataset further comprises a first target, wherein the first target comprises fitness data for the plurality of strains of the biologic organism; pre-train a genetic generalization model using the first training dataset, wherein the pre-training comprises training embeddings for the plurality of sets of genetic edits; receive a second training dataset smaller than the first training dataset, wherein the second training dataset comprises: information about genetic edits for a second plurality of strains, wherein the second plurality of strains are different from the first plurality of strains; information about at least one second target, wherein the at least one second target is different from the first target; and fine-tune the pre-trained genetic generalization model using the second training dataset to generate a second genetic generalization model that is trained to predict the at least one second target.

In some aspects, the techniques described herein relate to a system, wherein the at least one second target comprises at least one of a bioreactor growth rate, a metabolite production rate, a byproduct formation rate, or a titer.

In some aspects, the techniques described herein relate to a system, wherein the genetic generalization model comprises a first stage that generates a strain embedding and a second stage that generates a prediction based on the strain embedding, wherein the fine-tuning comprises updating parameters of the second stage to predict the second target. In some embodiments, the fine-tuning comprises replacing at least a portion of the second stage with new layers trained to predict the second target. Additionally or alternatively, the fine-tuning uses a lower learning rate for the fine-tuning as compared to the pre-training. Additionally or alternatively, the first stage is one or more of a long-short term memory (LSTM) model, a transformer model, or a convolutional neural network (CNN) model, wherein the second stage is a multi-layer perceptron. Additionally or alternatively, the embeddings are generated at least in part by processing gene descriptions using a large language model prior to the pre-training; and the embeddings are trainable parameters during the pre-training such that they are iteratively updated during the pre-training.

In some aspects, the techniques described herein relate to a system, wherein the plurality of sets of genetic edits comprise information indicating that each genetic edit is at least one of a gene knockout, a gene overexpression, or a gene underexpression.

In some aspects, the techniques described herein relate to a method comprising: receiving, by a platform, information about a strain of a biologic organism, wherein the information describes one or more genetic edits associated with the strain; generating, by the platform, a set of embeddings based on the information about the strain of the biologic organism; receiving, by the platform, a set of bioreactor process conditions for a bioreactor containing the strain; generating, by the platform, at least one prediction of performance of the strain using a pre-trained genetic generalization model that processes both the set of embeddings and the set of bioreactor process conditions, wherein the pre-trained genetic generalization model is trained using training data comprising: information about genetic edits for a plurality of strains; information about corresponding bioreactor process conditions for the plurality of strains; and target data indicating corresponding performance of the plurality of strains with respect to the corresponding bioreactor process conditions; determining, by the platform, adjusted bioreactor process conditions based on the at least one prediction of performance; and automatically adjusting controls of the bioreactor based on the adjusted bioreactor process conditions.

In some aspects, the techniques described herein relate to a method, wherein automatically adjusting controls comprises real-time adjustment of at least one of feed rates, pH levels, temperature, or dissolved oxygen levels of the bioreactor.

In some aspects, the techniques described herein relate to a method, wherein determining the adjusted bioreactor process conditions comprises: generating multiple predictions of performance for different combinations of bioreactor process conditions; and selecting the adjusted bioreactor process conditions based on the generated multiple predictions.

In some aspects, the techniques described herein relate to a method, further comprising: continuously monitoring performance of the strain in the bioreactor; generating updated predictions based on the monitored performance; and iteratively adjusting the controls based on the updated predictions.

In some aspects, the techniques described herein relate to a method, wherein the method is performed by a laboratory automation system, the method further comprising: automatically logging the adjustments to the controls and corresponding performance results; and using the logged adjustments and performance results to update the pre-trained genetic generalization model.

In some aspects, the techniques described herein relate to a method, further comprising: predicting strain stability under the adjusted bioreactor process conditions; and implementing automated quality control measures based on the predicted strain stability.

In some aspects, the techniques described herein relate to a method, wherein generating the set of embeddings comprises using one or more of a GenePT model, a Proteinfer model, a pFBA-PCA model, or a GO-PCA model.

In some aspects, the techniques described herein relate to a method, wherein the pre-trained genetic generalization model comprises: a first stage that generates a strain embedding characterizing the strain of the biologic organism; and a second stage that generates the at least one prediction based on the strain embedding. In some embodiments, the first stage is one or more of a long-short term memory (LSTM) model, a transformer model, or a convolutional neural network (CNN) model. Additionally or alternatively, the second stage is a multi-layer perceptron.

In some aspects, the techniques described herein relate to a method, wherein the pre-trained genetic generalization model is an ensemble of multiple pre-trained genetic generalization models.

In some aspects, the techniques described herein relate to a method, wherein the set of embeddings encodes genetic edits associated with the strain of the biologic organism.

In some aspects, the techniques described herein relate to a method, wherein the information about the strain comprises information about a base strain. In some embodiments, the information about the strain comprises information indicating that the one or more genetic edits include one or more gene knockouts, gene overexpressions, or gene underexpressions with respect to the base strain.

In some aspects, the techniques described herein relate to a system comprising: one or more processors; and memory storing instructions that, when executed by the processor, cause the system to: receive information about a strain of a biologic organism, wherein the information describes one or more genetic edits associated with the strain; generate a set of embeddings based on the information about the strain of the biologic organism; receive a set of bioreactor process conditions for a bioreactor containing the strain; generate at least one prediction of performance of the strain using a pre-trained genetic generalization model that processes both the set of embeddings and the set of bioreactor process conditions, wherein the pre-trained genetic generalization model is trained using training data comprising: information about genetic edits for a plurality of strains; information about corresponding bioreactor process conditions for the plurality of strains; and target data indicating corresponding performance of the plurality of strains with respect to the corresponding bioreactor process conditions; determine adjusted bioreactor process conditions based on the at least one prediction of performance; and automatically adjust controls of the bioreactor based on the adjusted bioreactor process conditions.

In some aspects, the techniques described herein relate to a system, wherein: automatically adjusting controls comprises real-time adjustment of at least one of feed rates, pH levels, temperature, or dissolved oxygen levels of the bioreactor; and determining the adjusted bioreactor process conditions comprises: generating multiple predictions of performance for different combinations of bioreactor process conditions; and selecting the adjusted bioreactor process conditions based on the generated multiple predictions.

In some aspects, the techniques described herein relate to a system, wherein the instructions further cause the system to: continuously monitor performance of the strain in the bioreactor; generate updated predictions based on the monitored performance; and iteratively adjust the controls based on the updated predictions.

In some aspects, the techniques described herein relate to a system, wherein the instructions further cause the system to: automatically log the adjustments to the controls and corresponding performance results; use the logged adjustments and performance results to update the pre-trained genetic generalization model.

In some aspects, the techniques described herein relate to a system, wherein the pre-trained genetic generalization model comprises: a first stage that generates a strain embedding characterizing the strain of the biologic organism, wherein the first stage is one or more of a long-short term memory (LSTM) model, a transformer model, or a convolutional neural network (CNN) model; and a second stage that generates the at least one prediction based on the strain embedding, wherein the second stage is a multi-layer perceptron.

In some aspects, the techniques described herein relate to a system, wherein: the information about the strain comprises information about a base strain; and the information about the strain comprises information indicating that the one or more genetic edits include one or more gene knockouts, gene overexpressions, or gene underexpressions with respect to the base strain.

In some aspects, the techniques described herein relate to a platform for synthetic biology development, the platform comprising: a data collection system configured to collect performance data for a plurality of synthetic biologic products and market data comprising costs for synthetic biology development inputs; a synthetic biology development system configured to predict performance of the synthetic biologic products under different process conditions; a techno-economic analysis system configured to: generate economic viability predictions by analyzing the predicted performance and process conditions using one or more artificial intelligence models trained on historical data, wherein the historical data includes historical market data; wherein the synthetic biology development system is further configured to prioritize development of synthetic biology products based on the predicted performance and the economic viability predictions.

In some aspects, the techniques described herein relate to a platform, wherein prioritizing development comprises: generating risk-adjusted economic predictions for each synthetic biology product; ranking products based on probability of commercial success; and adjusting development resource allocation based on the rankings.

In some aspects, the techniques described herein relate to a platform, wherein the market data further comprises one or more of feedstock costs, energy costs, labor costs, capital costs, equipment costs, or product market prices.

In some aspects, the techniques described herein relate to a platform, wherein the techno-economic analysis system is further configured to: identify economic thresholds for commercial viability; monitor performance data with respect to the economic thresholds; and automatically adjust development priorities when performance data indicates a particular economic threshold will not be met.

In some aspects, the techniques described herein relate to a platform, wherein the synthetic biology development system generates economic viability predictions for a plurality of parallel development paths for multiple synthetic biology products, wherein the synthetic biology is configured to dynamically allocate development resources between the parallel development paths based on comparing the economic viability predictions.

In some aspects, the techniques described herein relate to a platform, wherein the one or more artificial intelligence models comprise one or more of a convolutional neural network, a long-short term memory (LSTM), and a transformer neural network.

In some aspects, the techniques described herein relate to a platform, wherein the performance data comprises one or more of yield data, titer data, productivity data, stability data, or growth rate data.

In some aspects, the techniques described herein relate to a platform, wherein the process conditions comprise one or more of temperature, pH, nutrient concentrations, dissolved oxygen levels, mixing speed, gas flow rates, or nutrient feeding rates.

In some aspects, the techniques described herein relate to a platform, wherein the historical data further comprises historical production data indicating relationships between production factors and economic outcomes.

In some aspects, the techniques described herein relate to a platform, wherein the techno-economic analysis system is further configured to simulate scale-up costs for different production scenarios.

In some aspects, the techniques described herein relate to a platform, wherein the techno-economic analysis system is further configured to predict market-dependent revenue potential.

In some aspects, the techniques described herein relate to a platform, wherein the techno-economic analysis system is further configured to calculate economic metrics, including return on investment and payback period.

In some aspects, the techniques described herein relate to a platform, wherein the data collection system continuously collects the performance data and market data, and wherein the techno-economic analysis system continuously updates the economic viability predictions during development of the synthetic biology products.

In some aspects, the techniques described herein relate to a method for synthetic biology development, the method comprising: collecting, by one or more processors of a synthetic biology platform, performance data for a plurality of synthetic biologic products and market data comprising costs for synthetic biology development inputs; predicting, by the one or more processors, performance of the synthetic biologic products under different process conditions; generating, by the one or more processors, economic viability predictions by analyzing the predicted performance and process conditions using one or more artificial intelligence models trained on historical data, wherein the historical data includes historical market data; and prioritizing, by the one or more processors, development of synthetic biology products based on the predicted performance and the economic viability predictions.

In some aspects, the techniques described herein relate to a method, wherein prioritizing development comprises: generating risk-adjusted economic predictions for each synthetic biology product; ranking products based on probability of commercial success; and adjusting development resource allocation based on the rankings.

In some aspects, the techniques described herein relate to a method, wherein the market data further comprises one or more of feedstock costs, energy costs, labor costs, capital costs, equipment costs, or product market prices.

In some aspects, the techniques described herein relate to a method, further comprising: identifying economic thresholds for commercial viability; monitoring performance data with respect to the economic thresholds; and automatically adjusting development priorities when performance data indicates a particular economic threshold will not be met.

In some aspects, the techniques described herein relate to a method, wherein generating economic viability predictions comprises generating economic viability predictions for a plurality of parallel development paths for multiple synthetic biology products, wherein prioritizing development comprises dynamically allocating development resources between the parallel development paths based on comparing the economic viability predictions.

In some aspects, the techniques described herein relate to a method, wherein the performance data comprises one or more of yield data, titer data, productivity data, stability data, or growth rate data, and wherein the process conditions comprise one or more of temperature, pH, nutrient concentrations, dissolved oxygen levels, mixing speed, gas flow rates, or nutrient feeding rates.

In some aspects, the techniques described herein relate to a method, wherein collecting the performance data and the market data and generating the economic viability predictions occur continuously during development of the synthetic biology products.

In some aspects, the techniques described herein relate to a platform for synthetic biology development, the platform comprising: a data collection facility configured to collect strain data for a plurality of biological strain candidates and to receive assay data from biological strain experiments, wherein the strain data comprises biological information for each strain candidate; a prototype prediction system configured to: generate initial fitness predictions for the strain candidates using one or more first artificial intelligence models trained on historical strain performance data; and identify an initial subset of the strain candidates based on the initial fitness predictions; a scale-up prediction system configured to: receive, from the data collection facility, assay data for the initial subset of the strain candidates; analyze the assay data and the strain data using one or more second artificial intelligence models; generate scale-up performance predictions for predicting strain performance under bioreactor production conditions; and select at least one strain candidate for production based on the scale-up performance predictions.

In some aspects, the techniques described herein relate to a platform, wherein the biological information comprises one or more of genetic edits, metabolic pathway data, or strain library information.

In some aspects, the techniques described herein relate to a platform, wherein the assay data comprises one or more of yield data, titer data, productivity data, stability data, or growth rate data.

In some aspects, the techniques described herein relate to a platform, wherein the one or more first artificial intelligence models comprise one or more of a convolutional neural network, a long-short term memory (LSTM) network, or a transformer neural network.

In some aspects, the techniques described herein relate to a platform, wherein the one or more second artificial intelligence models are trained using a training data set that includes correlations between plate assay data and data collected during bioreactor production.

In some aspects, the techniques described herein relate to a platform, wherein the bioreactor production conditions comprise one or more of temperature profiles, pH setpoints, nutrient concentrations, dissolved oxygen levels, mixing speeds, gas flow rates, or nutrient feeding rates.

In some aspects, the techniques described herein relate to a platform, wherein the scale-up prediction system is further configured to: continuously collect performance data during production of the selected at least one strain candidate; and update the scale-up performance predictions based on the continuously collected performance data.

In some aspects, the techniques described herein relate to a platform, wherein the data collection facility is configured to receive the assay data for the initial subset of the strain candidates after the generation of the initial fitness predictions, wherein the prototype prediction system is further configured to re-train the one or more first artificial intelligence models using the assay data.

In some aspects, the techniques described herein relate to a platform, wherein the scale-up prediction system is configured to generate embeddings that identify strain-specific sensitivities to process conditions that may affect performance at production scale.

In some aspects, the techniques described herein relate to a platform, wherein the one or more second artificial intelligence models comprise at least one ensemble model configured to generate uncertainty estimates for the scale-up performance predictions.

In some aspects, the techniques described herein relate to a platform, wherein the scale-up prediction system is configured to generate a digital twin simulation of at least one production facility, wherein the one or more second artificial intelligence models are configured to generate scale-up performance predictions based on data from the digital twin simulation.

In some aspects, the techniques described herein relate to a method for synthetic biology development, the method comprising: collecting strain data for a plurality of biological strain candidates, wherein the strain data comprises biological information for each strain candidate; generating initial fitness predictions for the strain candidates using one or more first artificial intelligence models trained on historical strain performance data; identifying an initial subset of the strain candidates based on the initial fitness predictions; receiving assay data from plate assays of the initial subset of the strain candidates; processing the assay data and the strain data using one or more second artificial intelligence models, wherein the processing comprises generating scale-up performance predictions for predicting strain performance under bioreactor production conditions; and selecting at least one strain candidate for production based on the scale-up performance predictions.

In some aspects, the techniques described herein relate to a method, wherein the biological information comprises one or more of genetic edits, metabolic pathway data, or strain library information, and wherein the assay data comprises one or more of yield data, titer data, productivity data, stability data, or growth rate data.

In some aspects, the techniques described herein relate to a method, wherein the one or more second artificial intelligence models are trained using a training data set that includes correlations between plate assay data and data collected during bioreactor production.

In some aspects, the techniques described herein relate to a method, further comprising: continuously collecting performance data during production of the selected at least one strain candidate; and updating the scale-up performance predictions based on the continuously collected performance data.

In some aspects, the techniques described herein relate to a method, further comprising generating a digital twin simulation of at least one production facility, wherein the one or more second artificial intelligence models generate the scale-up performance predictions based on data from the digital twin simulation. In some embodiments, the digital twin simulation comprises a simulation of one or more of equipment configurations, operational parameters, environmental conditions, process control settings, material flows, or quality measurements.

In some aspects, the techniques described herein relate to a method, further comprising re-training the one or more first artificial intelligence models using the assay data received from the plate assays.

In some aspects, the techniques described herein relate to a method, wherein processing the assay data comprises generating embeddings that identify strain-specific sensitivities to process conditions that may affect performance at production scale.

In some aspects, the techniques described herein relate to a method, wherein the one or more second artificial intelligence models comprise at least one ensemble model, and wherein the method further comprises generating uncertainty estimates for the scale-up performance predictions using the ensemble model.

BRIEF DESCRIPTION OF THE DRAWINGS

The present disclosure will become more fully understood from the detailed description and the accompanying drawings.

FIG. 12 is a flowchart illustrating example environment and/or performance optimization methods, according to some embodiments.

FIG. 13 is a flowchart illustrating example pathway optimization methods according to some embodiments.

FIG. 14 is a flowchart illustrating example protein and/or enzyme optimization methods, according to some embodiments.

FIG. 24 is a flowchart illustrating an example rapid sampling and omics for generalization method according to some embodiments.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

Figure 1:
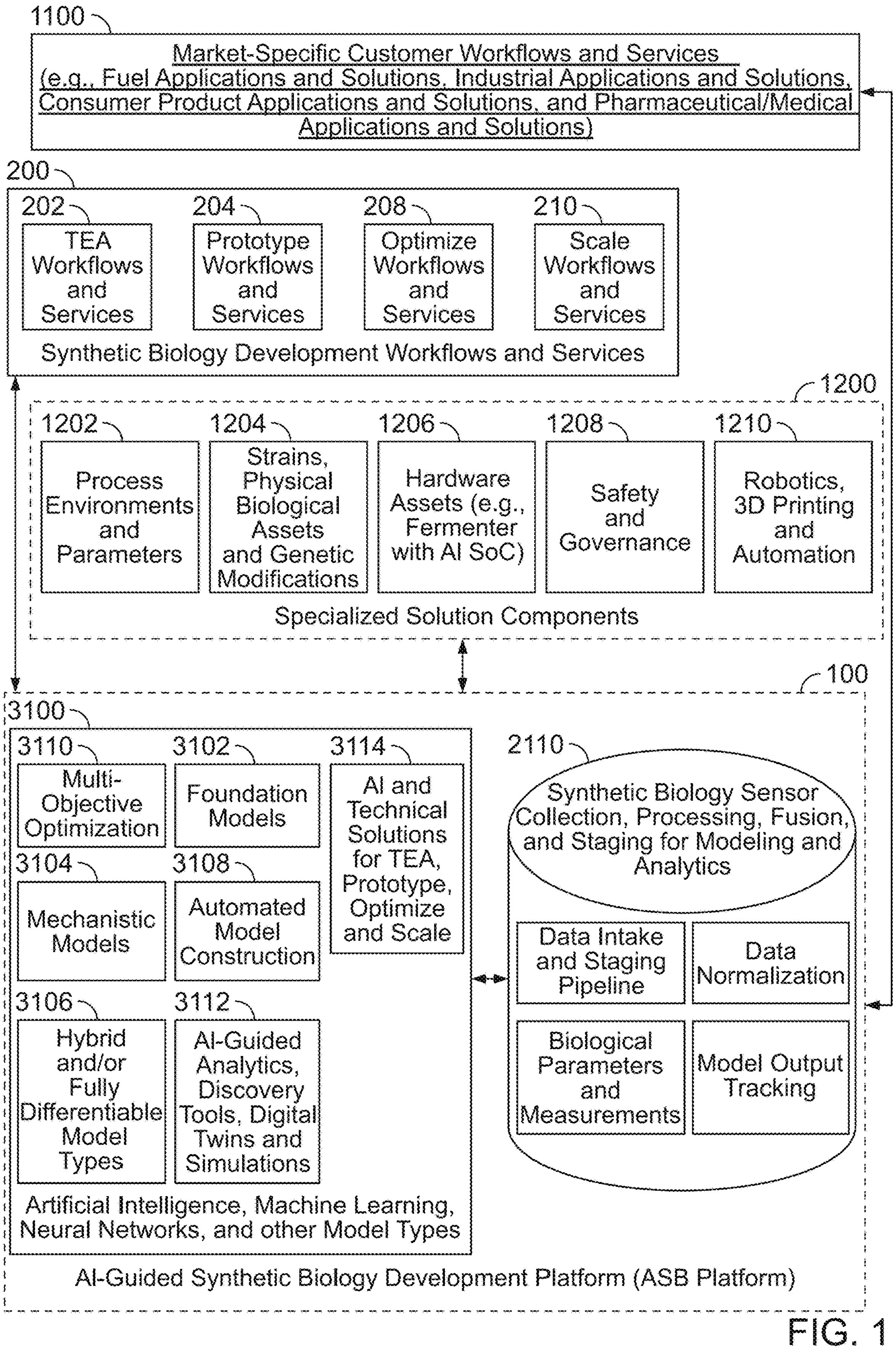
FIG. 1 is a schematic diagram detailing a platform and a multi-objective optimization module that operates in tandem with other elements and resources of the platform, according to some embodiments.

FIG. 1: Introduction of Platform and Main Elements

Techniques described herein provide novel approaches to accelerating synthetic biology research and development through the integration of computing hardware and advanced artificial intelligence capabilities. The platform described herein provides technical solutions that address fundamental computational and engineering challenges in synthetic biology development, including optimizing complex biological systems across multiple objectives (from strain development to commercial-scale production), hardware-constrained limitations of traditional laboratory data processing (e.g., screening) approaches, computational difficulties in modeling and predicting performance translation from laboratory to commercial scale, and technical constraints in rapidly iterating through design-build-test cycles with limited data. By leveraging AI models, data management, and specialized workflow components in various ways, the platform described herein can accelerate synthetic biology development across a range of applications.

The platform's architecture enables the flexible deployment of multiple AI models, including the integration of foundation models, mechanistic models, and/or hybrid models for the various tasks described herein. The platform provides technical solutions that enable efficient model training even with sparse initial datasets, enable real-time techno-economic analysis (TEA) to select for and optimize commercial viability, use specialized neural network architectures for automated identification and optimization of genetic modifications and biosynthetic pathways, deploy a plurality of models (e.g., using distributed/parallel computing architectures) to enable prediction and improvement of scale-up performance, implement optimized data integration pipelines across heterogeneous data types, provide systematic governance and risk management throughout the development process, and other technical benefits.

As described herein, the platform may leverage distributed and/or parallel processing architectures that use multiple computing nodes to reduce computation time and/or enable processing of larger datasets. The platform may also leverage specialized machine learning model architectures, distributed data management systems, hardware-optimized workflows, and the like to accelerate synthetic biology development while reducing computational and other resource consumption compared to other methods, for example by reducing the number of experimental iterations needed for a strain design workflow. The platform may further integrate with laboratory and/or commercial equipment, such as bioreactors and other equipment described herein.

AI-Guided Synthetic Biology ("ASB") Platform.

In embodiments, an AI-Guided Synthetic Biology Development Platform 100 (the "ASB Platform"), with a range of components, services, modules, entities, workflows and other elements that are configured to enable the acceleration, through the use of artificial intelligence and other supporting technologies, of research and development at all stages of synthetic biology projects, from initial prototyping of candidate strains and other biological entities, to optimization of the biological entities and the environments and processes by which they will produce useful outputs, and to the scaling up of production to commercially valuable levels. With the use of an appropriately configured set of advanced artificial intelligence models, the ASB Platform can enable an accelerated path to successful development of synthetic biology products and processes even when starting datasets are sparsely populated. FIG. 1 depicts an exemplary embodiment of entities and interactions of an ASB Platform 100. It should be understood that the ASB Platform 100 may comprise various subsets of such entities and interactions, as well as additional elements. The ASB Platform may be arranged in a wide range of architectures and topologies, such as software-as-a-service (SaaS), platform-as-a-service (PaaS) and infrastructure-as-a-service (IaaS) architectures, such as comprising a set of services, such as microservices, configured to operate on cloud computing, enterprise computing, and other computing architectures.

The AI models 3100 may be implemented using specialized computing hardware to improve processing efficiency and reduce resource consumption. For example, the platform may use graphics processing units (GPUs), neural processing units (NPUs), tensor processing units (TPUs), and/or other such processing cores for AI model training and/or inference operations such as matrix computations. Additionally or alternatively, the platform may use field-programmable gate arrays (FPGAs) or other customizable hardware to provide optimized implementations of the functions described herein. These hardware optimizations may enable faster and/or more efficient processing of large biological datasets and/or complex model architectures. Specific hardware configurations and optimizations may vary by model, task, workflow, etc., examples of which are detailed elsewhere herein.

In embodiments, a platform topology may comprise a set of artificial intelligence, neural network, machine learning, or other models, or "AI Models 3100," each of which may be configured to operate as a standalone model, or which may operate in various hybrid, serial, parallel, loop and other topologies as disclosed elsewhere herein. Model types may include those depicted in FIG. 1, or any of the other types of models disclosed herein or in the documents incorporated herein by reference, including, without limitation, feedback neural networks, feed forward neural networks, convolutional neural networks, gated recurrent neural networks, positional encoders, transformer models, foundation models, large language models, and others. Model types may be configured and trained to enable (e.g., to embed) specific capabilities, including granular modeling of mechanistic and kinetic behaviors of biological entities and flows, including genetics of strains, process environment parameters, and many others.

Figure 2:
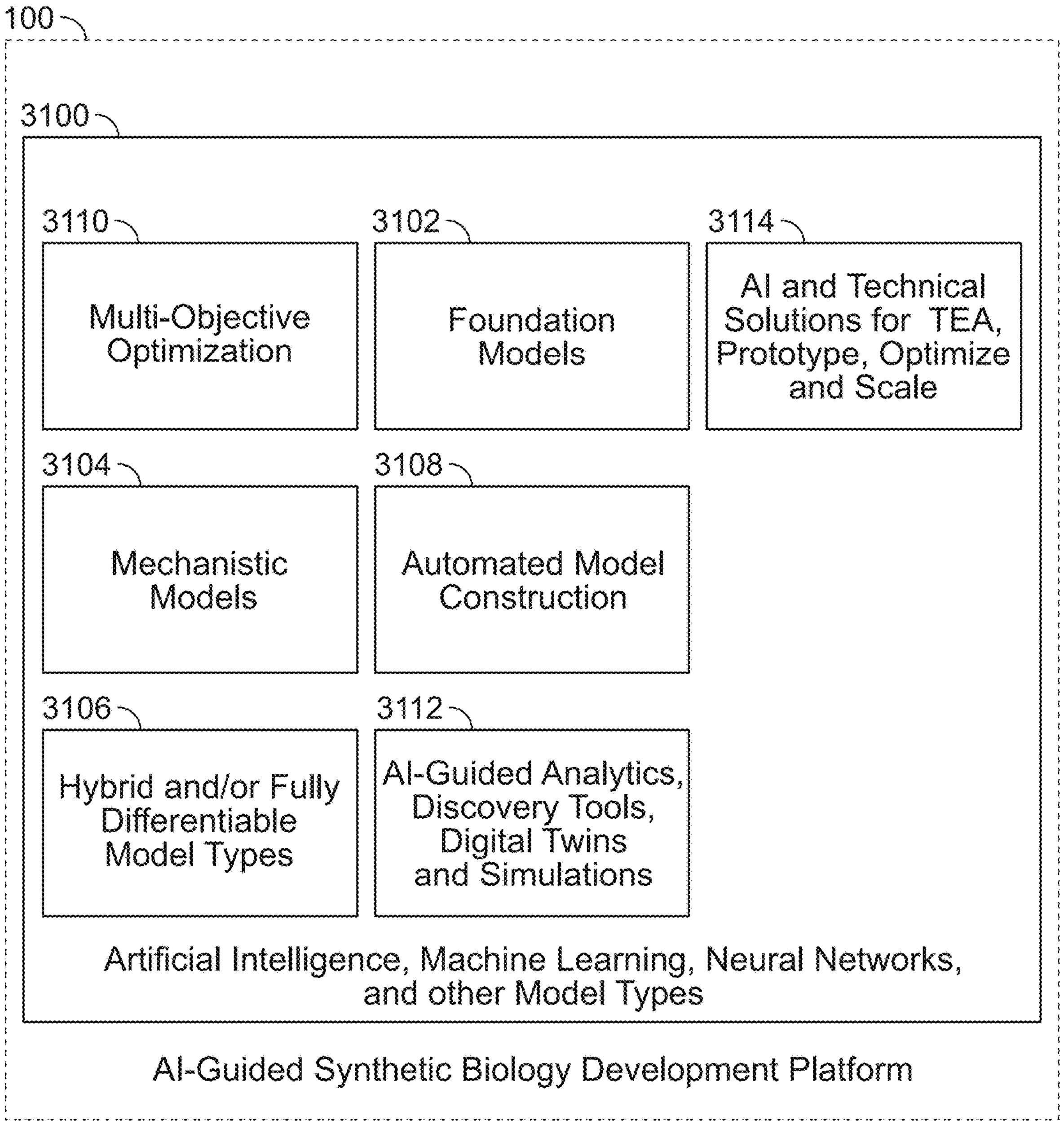
FIG. 2 is a schematic diagram detailing a prototype system that typically involves exploration of candidate strains of biological entities that have the potential to produce, as an output, a molecule that is desired for its commercial or other beneficial properties, according to some embodiments.

With reference to FIGS. 1 and 2, the AI models 3100 may include multi-objective optimization models 3110 that are configured to enable simultaneous optimization across multiple parameters (e.g., yield, cost, process efficiency, etc.). The AI models 3100 may further include foundation models 3102 that may provide various predictions for proposed biological systems and that can be fine-tuned for specific applications. For example, the foundation models 3102 may include genetic generalization models, process generalization models, and/or other types of models described in more detail elsewhere herein. The AI models 3100 may further include mechanistic models 3104, which may generate outputs characterizing biological processes and pathways. Additionally, the AI models may include hybrid models 3106 that may combine multiple types of models to leverage the respective strengths of individual models. In embodiments, automated model construction capabilities 3108 may enable rapid development and/or iteration of new models as additional data becomes available. Furthermore, AI-guided analytics, discovery tools, digital twins, and simulations 3112 provide simulation and visualization capabilities. The AI models may further include AI and technical solution models for TEA, prototype, optimize, and scale 3114, which may support specific workflows/operations described in detail elsewhere herein. The AI models may also be used to generate specific recommendations across multiple optimization domains. Specific functions and applications of the AI models are described in more detail below.

The ASB Platform 100 may further comprise various data sources, such as involving sensor data collection, data processing, data and sensor fusion, and data staging for synthetic biology modeling and analytics, collectively referred to as "AI-ready data 2110." In embodiments, the AI-ready data 2110 may be stored and/or processed into specialized data structures optimized for biological data and/or machine learning processing, examples of which are described in more detail below. These and other specialized data representations may enable more efficient storage and/or better model training and inference. Various elements of AI-ready data 2110 may be used as inputs for AI Models 3100, as well as to enable higher-level solution components of the ASB Platform 100. Data collection, extraction, processing, transformation, loading, normalization, storage and other techniques may include any of the techniques disclosed herein or in the documents incorporated by reference herein, or as would be understood by one of ordinary skill in the art, including use of distributed data storage, data storage structures suitable for staging data for processing by AI models (e.g., graph database, vector database, and others), and the like. For example, a data intake and staging pipeline may collect and preliminarily process various types of data. A data normalization process (described elsewhere herein) may normalize data to provide consistency and compatibility across different data sources. A data integration process (described elsewhere herein) may integrate various data types while maintaining data segregation and security protocols. The platform may use biological parameters and measurements derived from experimental and/or operational data for various purposes (e.g., training). The platform may also store model output tracking data to enable systematic evaluation of model performance and iterative improvement.

Figure 5:
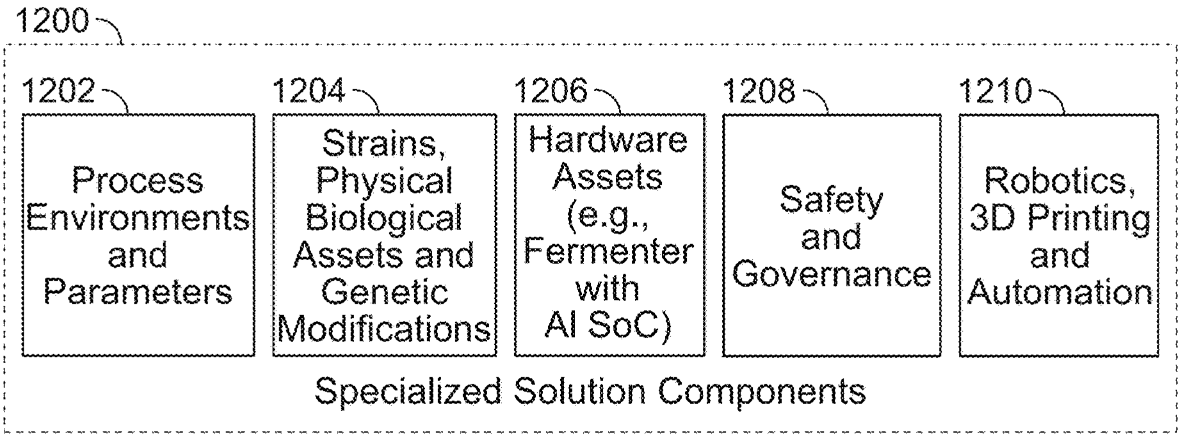
FIG. 5 is a schematic diagram that details specialized solution components, according to some embodiments.

In embodiments, AI models also produce insights, such as the relevance of specific genetic modifications, that can enable specialized solution components 1200 are applicable and extensible across multiple end-market solutions, as shown in FIG. 5. These solution components can include specifications for appropriate process environments and parameters, strains of biological organisms, genetic modifications can be predicted to yield desired effects, hardware components (including fermenters and other biological process hardware, robotics, 3D printers, and automation systems), software, firmware and other information technology components that can be used in synthetic biology processes, systems for providing safety, governance, compliance and similar guidance for synthetic biology processes and products, and the like. All of these elements work together to create a flywheel for industry growth by expanding favorable economics to a growing universe of materials.

Figure 4:
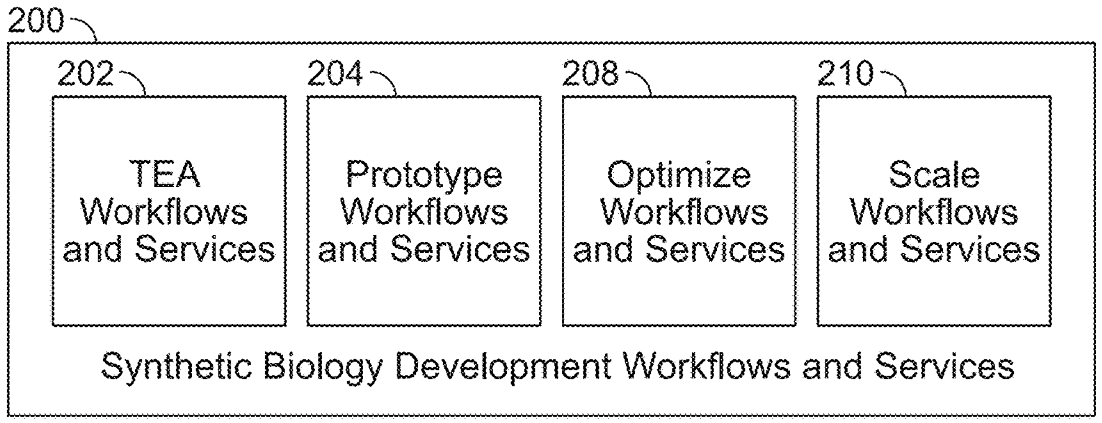
FIG. 4 is a schematic diagram that details synthetic biology development workflows and services, according to some embodiments.

In embodiments, the ASB Platform 100 may include a set of configured solutions, each configured to enable a set of services and workflows that are specific to a distinct phase of synthetic biology research and development, referred to herein as "core platform systems 200." With reference to FIG. 4, the core platform systems 200 may be configured as a single, unified system, or each may be configured to enable a specific phase or capability that is commonly required in synthetic biology development projects. For example, a prototype system 204 may be configured to enable the exploratory or prototyping phase of development of a synthetic biology system, such as involving identification of and experimentation with candidate strains and variants that may be capable of producing a desired output product. Similarly, an optimize system 208 may be configured to enable the optimization phase of development, where various elements of biological entities, process parameters (environmental controls, feedstock elements, genetic modifications, and many others), and other elements are rapidly and iteratively improved, guided by AI specifications and recommendations, to improve the productivity and quality of the outputs of a synthetic biology product or system. Further, a scale-up system 210 may be configured to enable the scale-up phase of synthetic biology development, where entities and processes that were developed in the laboratory during the prototyping phase and improved at small scale (e.g., in fermenters) in the optimization phase are further adjusted, based on AI recommendations and specifications and iterative improvement, to improve the yield of a synthetic biology system (such as in larger scale commercial production environments, where imperfect conditions, such as lower quality feedstocks, less controlled environmental parameters, and other factors are likely to be present).

In embodiments, the various core systems 200, including the prototype system 204, the optimize system 208, the scale-up system 210, and the TEA system 202, may be any system described herein that is capable of implementing prototype workflows and services, optimize workflows and services, scale-up workflows and services, or TEA workflows and services respectively. Thus, it should be understood that although the workflows and services may in some cases be described as being performed by specific core systems, they may also be performed by the other systems described herein that are capable of implementing the workflows and services, running AI models, etc.

Various configurations of AI models 3100 (FIGS. 1 and 2), including hybrid models, may be configured in the workflows of the respective prototype system 204, optimize system 208 and/or scale-up system 210 to provide the most effective set of predictions, recommendations, specifications, instructions, orchestration, automation, and other outputs and capabilities needed to support successful R&D projects. Each system may benefit from a particular configuration of AI models 3100 that is created to suit the needs of that system, as further described elsewhere in this disclosure.

In embodiments, the ASB platform 100 may include a techno-economic analysis system, or TEA system 202, which may include a variety of analytic models, AI models, expert models, and the like, which operate on technical and economic input data to provide outputs relevant to the commercial viability of a synthetic biology project, product, or system. This may include outputs that predict, under various scenarios, the likely unit economics for a synthetic biology organism based on predicted input costs (e.g., feedstock prices), output value (e.g., the market price of a product produced by the organism or system), capital costs (including the cost of equipment needed to produce a product in a commercial environment, borrowing costs, and the like), operating costs, and the like. The TEA system 202 may include machine learning and AI systems that are trained to predict relevant economic variables based on input data. The TEA system 202 may include a suite of analytic tools, such as econometric tools that frame predictions based on statistical parameters of certainty or uncertainty, including regression models and many others. The TEA system 202 may include simulation capabilities, such as random walk, random forest, and similar algorithms. The TEA system 202 may include various algorithms that are helpful for processing technical subject matter, such as clustering algorithms (e.g., k-means clustering) that can be used to group entities (such as organisms, genetics, and other biological entities or factors, environmental parameters, and the like) based on similarities.

The TEA system 202, prototype system 204, optimize system 208 and/or scale-up system 210 may be configured to enable iteration and feedback among them, such as where one of them provides feedback or feed forward inputs to the other, allowing outcomes at each phase to be used for learning and inputs at other phases. As noted above, outputs may include insights that are applicable across various phases of multiple projects, with replicable or extensible outputs being candidates for inclusion as specialized solution components 1200, as shown in FIG. 5.

In embodiments, elements of one or more of the TEA system 202, prototype system 204, optimize system 208 and/or scale-up system 210, as well as optionally some set of specialized solution components 1200, may be configured as a system, platform, system-of-systems, or the like of the ASB Platform 100 to enable a market-specific workflow, service, product, or solution, referred to herein as an "end-market solution 1100." Thus, embodiments of the ASB Platform 100 may include ones that are specifically configured to enable particular types of end-market research and development solutions and outputs, such as for pharmaceuticals, fuels, specialty chemicals, waste remediation, and many others.

In embodiments, various platform components may iteratively optimize one or more of the AI models 3100 based on feedback data. For example, the platform may collect data from hardware assets 1206 (e.g., AI-enabled fermenters) (in real-time or otherwise) and provide the data to mechanistic models 3104 and/or hybrid models 3106 in order to iteratively and/or continuously optimize process parameters 1202. As another example, the platform may collect predictions about strain performance from various AI models and use these predictions to trigger automated adjustments to robotics and automation systems 1210 for subsequent experimental iterations. As these examples demonstrate, the platform may leverage the data generated by any of the models and/or equipment described herein to create self-improving feedback loops by feeding the data into other models, using the data to retrain models, using model predictions to adjust operational parameters including hardware parameters and/or process parameters, and/or the like, such that any component's outputs may be used to continuously and iteratively improve performance of other components. The platform 100 may use these and other feedback loops to reduce computation by providing targeted model updates that improve prediction accuracy. More specific examples of optimizing the platform using feedback loops are described herein.

The platform 100 may also improve AI models by comparing predictions generated by any of the TEA system 202, prototype system 204, optimize system 208 and/or scale-up system 210 to later data gained from experiments (e.g., assays, production runs, etc.). Based on the comparison, the platform 100 may generate a loss signal that can be used to update the AI models used to generate the predictions. Some data (e.g., data related to failed prototypes or production runs) may be weighted more heavily for updating the models.

Prototype System

Referring to FIG. 2, further details of various embodiments of the prototype system 204 are provided. The prototype system 204 typically involves exploration of candidate strains of biological entities (e.g., microbes, including various strains of bacteria, yeast, algae, fungi, mammalian cells, plants, or the like) that have the potential to produce, as an output, a molecule that is desired for its commercial or other beneficial properties (e.g., medical or wellness effects, use as a fuel, use as a catalysts or additive to a process, or many others). In many cases, the volume of production is small, such that laboratory experiments have historically been the state of the art for testing and prototyping new strains for their potential commercial application. Artificial intelligence, such as using various AI models 3100, may be used to dramatically accelerate the historical laboratory-based processes of prototyping new strains and variants.

Figure 3:
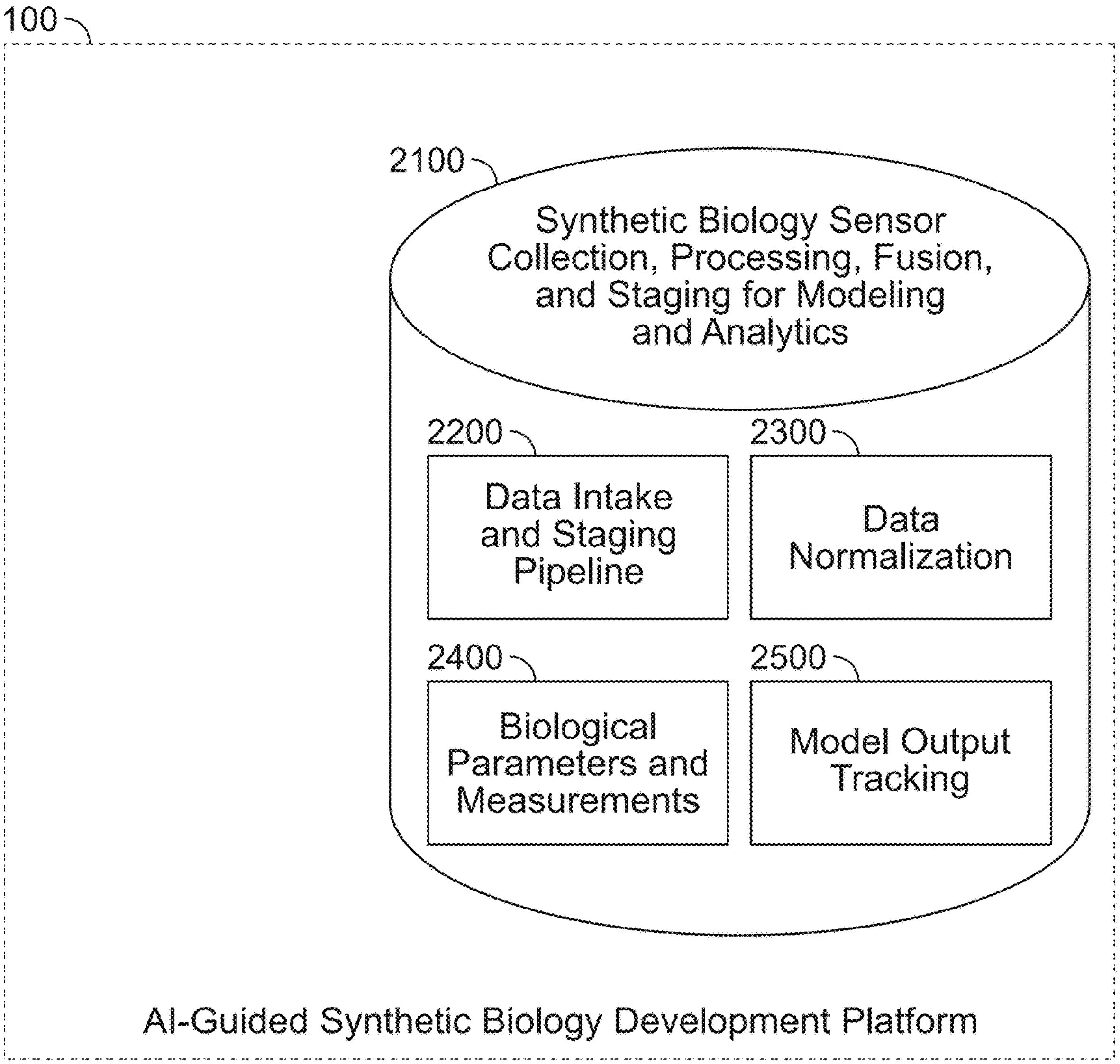
FIG. 3 is a schematic diagram that details synthetic biology sensor collection, processing, fusion, and staging for modeling and analytics, according to some embodiments.
Figure 7:
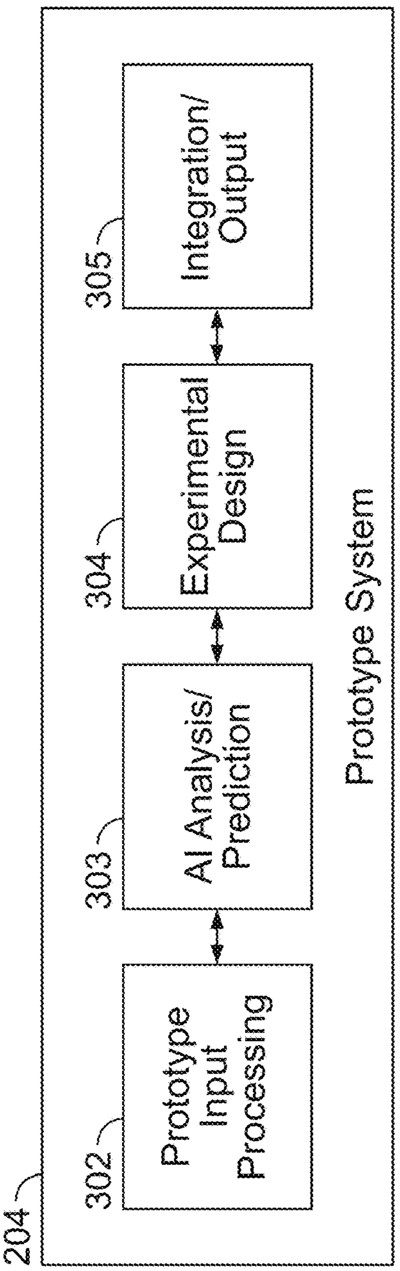
FIG. 7 is a schematic diagram that details additional example components of a prototype system for implementing prototype systems and workflows, according to some embodiments.

Additional example components of a prototype system 204 for implementing prototype systems and workflows are shown at FIG. 7. As shown in the figure, the prototype system 204 may include a prototype input processing component 302 that is configured to collect, normalize, and/or prepare data from multiple sources for use in prototyping workflows. In embodiments, the input processing component 302 may receive and/or process experimental data, target molecule specifications, strain library information, known pathway data, and/or other inputs. In embodiments, the input processing component 302 may leverage the platform's data intake pipeline and normalization capabilities (described elsewhere herein) to ensure data consistency and quality. Additionally or alternatively, the input processing component 302 may maintain and update a knowledge base that captures relationships between strains, pathways, genes, observed outcomes, etc. This data may be processed, stored, and used for various use cases of the prototype systems 204 and/or other systems. For example, the data may be used for training and/or fine-tuning of AI models 3100 and/or for any other use cases described herein. The input processing component 302 may be implemented by the facility for synthetic biology sensor collection, processing, fusion, and staging for modeling and analytics 2100 described below, as shown in FIG. 3. As described below, this facility may use dedicated processing cores to handle data preprocessing tasks. For example, sequence alignment operations may be performed using GPUs or other AI processing cores to reduce processing time. The input processing component 302 may implement distributed storage and/or processing architectures that enable parallel processing of multiple data streams from different experimental sources simultaneously.

In embodiments, the prototype system 204 may include an AI analysis and prediction component 303 that leverages various AI models 3100 to generate insights and/or predictions about prototyping candidates. For example, the AI analysis and prediction component 303 may use foundation models 3102, such as genetic generalization models or other models, to predict the performance of different candidate base strains under various conditions. As another example, the AI analysis and prediction component 303 may use mechanistic models 3104 to analyze biosynthetic pathways and/or may use hybrid models 3106 to combine multiple types of models to predict enzyme effectiveness within particular pathways. In embodiments, any of the AI models 3100 described herein may be used by the prototype system 204 for analysis and/or prediction, such as using protein language models to predict enzyme function, using Lin-Log models to estimate metabolic flux distributions, or using neural networks to predict strain performance from genetic modifications.

In embodiments, the prototype system 204 may include an experimental design component 304 that uses AI predictions and/or recommendations to generate experimental plans. For example, the experimental design component 304 may generate assay testing plans for testing multiple strain variants under particular conditions, specify sets of genetic modifications to test in parallel, determine optimal sampling times, generate control experiments to validate specific hypotheses, and/or the like. As another example, the experimental design component 304 may generate experimental sequences that efficiently test combinations of pathway modifications in a way that minimizes the total number of experiments needed. The experimental design component 304 may specify validation experiments (e.g., by generating control strain configurations, specifying replication requirements, determining which analytical measurements are needed to confirm predicted behaviors, etc.), allocate laboratory resources (e.g., by scheduling equipment usage based on experiment priorities and duration, determining optimal batch sizes for parallel testing, etc.), establish testing timelines (which may include analyzing predicted growth rates to determine testing durations, scheduling sampling points based on expected production curves, coordinating automated sample collection and analysis, etc.), and/or the like. In embodiments, the experimental design component 304 may interface with specialized solution components 1200, such as hardware assets 1206 and robotics/automation systems 1210, to enable efficient execution of experiments, as shown in FIG. 5. For example, the experimental design component 304 may output operational parameters including process parameters for adjusting automated equipment, output robotic handling instructions for automated strain construction, generate and/or coordinate data for input to AI-enabled fermenters, and the like. The experimental design component 304 may thereby implement real-time control based on AI predictions. For example, the component may dynamically adjust fermentation parameters (e.g., temperature, pH, oxygen levels) of bioreactors or other equipment based on real-time sensor data and model predictions derived therefrom, enabling automated optimization of growth conditions. These and other automated control loops described herein can significantly improve experimental efficiency while reducing human error. In embodiments, the experimental design component 304 may incorporate feedback from previous experiments to continuously improve experimental design. For example, the experimental design component 304 may adjust sampling frequencies to capture additional data as necessary based on previous experiments, modify various parameters based on unexpected strain behaviors, revise strain selections based on observed experimental performance and/or variability, and the like.

In embodiments, the prototype system 204 may include an integration and output component 305 that manages results, facilitates feedback loops, and prepares for subsequent development phases. More specifically, the integration and output component 305 layer may output experimental outcome data to other systems and/or users, provide data as feedback to the TEA system 202 or other systems, prepare successful prototypes for the optimization system 208, and/or the like. As specific examples, the integration and output component 305 may generate comparative analyses of strain performance across different conditions by synthesizing outputs of multiple experiments, create visualizations or other analyses of metabolic pathway performance, compile outcome data into training datasets that include correlations between genetic modifications and phenotypic outcomes, generate lists of strains that meet performance thresholds for advancement to an optimization phase, and/or the like. The integration and output component 305 may further generate analytical data that may be used by the TEA system to generate updated cost projections. This analytical data may include, for example, calculating actual versus predicted yields, identifying unexpected process requirements, quantifying resource usage across different strain variants, and the like. The integration and output component 305 may also update the platform's knowledge base with new insights about strain behavior, pathway effectiveness, and/or process parameters, thus providing more information for future prototyping experiments. In embodiments, the integration and output component 305 implements efficient data structures and algorithms optimized for handling large-scale biological data. For example, the component 305 may employ specialized compression algorithms for biological sequence data, enabling efficient storage and retrieval of large-scale experimental results. These and other specialized structures and algorithms may enable reduced memory usage and faster query performance compared to traditional databases while also maintaining data integrity across multiple experimental iterations.

In embodiments of a prototyping system 204, an AI model can be used, among other things, to understand and predict the behaviors of many different candidate base strains under many different kinds of conditions, to facilitate development of a candidate set of base strains and selection of ones on which to conduct further experimentation and development. For example, the AI analysis and prediction component 303 may use foundation models 3102 to predict strain tolerance to different process conditions, growth characteristics under various media formulations, and/or production capabilities for target molecules, as described in more detail elsewhere herein. The AI analysis and prediction component 303 may also analyze strain libraries to identify candidates with desired genetic characteristics and/or to predict the effects of specific genetic modifications on strain performance.

In other embodiments of a prototyping system 204, an AI model can be used for pathway selection, such as to identify biosynthetic chemical pathways (i.e., efficient routes from an initial biochemical state (e.g., chemical structure, physiological structure, or the like) to another. For example, the AI analysis and prediction component 303 may use mechanistic models 3104 to evaluate multiple potential pathways based on various requirements. The experimental design component 304 may then generate experiments to validate these predictions and identify optimal pathway configurations. Pathways for strain development, cultivation and a wide range of other applications can be prototyped with the assistance of an AI model, thereby accelerating the process of identification of a favorable pathway for a desired outcome (e.g., production of a target molecule using a host strain).

In other embodiments of a prototyping system 204, an AI model can be used for enzyme selection, including which enzymes are likely to be effective within particular pathways. For example, the AI analysis and prediction component 303 may use protein language models to predict enzyme function, stability, and/or activity under different conditions. The AI analysis and prediction component 303 may also use hybrid models 3106 to evaluate enzyme compatibility within specific pathway configurations by leveraging different types of models within a hybrid architecture.

In other embodiments of a prototyping system 204, an AI model can be used for host organism selection, such as among bacteria, fungi, yeast, algae, mammalian cells, plants, or the like. For example, the AI analysis and prediction component 303 may evaluate potential host organisms based on their predicted ability to express target pathways, tolerance to process conditions, genetic manipulation requirements, scaling characteristics, etc. The TEA system 202 may also incorporate these predictions to assess the economic viability of different host organisms based on cultivation requirements and/or expected performance at scale.

In each case, an AI model 3100, or a set of them, may be configured and trained iteratively over time based on outcomes, to predict the biological states and flows of all entities involved in the production of a desired molecule by the operation of a host organism, via selected pathways, moderated by selected enzymes, on an input (such as a feedstock) to produce an output. The integration and output component 305 may facilitate this iterative improvement by capturing experimental outcomes and updating the platform's knowledge base (e.g., including training and/or fine-tuning data sets), thereby enabling models to iteratively train to improve learning from each additional prototyping cycle and thereby improve predictive accuracy.

The above features and functionalities are only some examples of the operation of the prototype system 204. The disclosure provides additional details elsewhere herein of prototype workflows and services. It should be understood that any of these workflows and services can be performed by the prototype system 204 or the components thereof. It should also be understood that the workflows and services described above with respect to the prototype system 204 can be performed by other systems and components described elsewhere herein that are capable of implementing prototype workflows and services, executing AI models, and/or the like.

Optimize System

In the optimize system 208, an AI model 3100, or a set of them, may similarly be configured and trained iteratively over time based on outcomes, to predict the biological states and flows of all entities involved in the production of a desired molecule by the operation of a host organism, via selected pathways, moderated by selected enzymes, on an input (such as a feedstock) to product an output. The optimize system 208 may typically be involved at the stage of research and development where it is understood that a host can produce a desired output molecule, but there remains a large amount of uncertainty about operational parameters including the ideal inputs, genetics, process parameters, and other dimensions to enable commercially viable levels of production (i.e., ones in which the unit economics are expected to be favorable).

Figure 8:
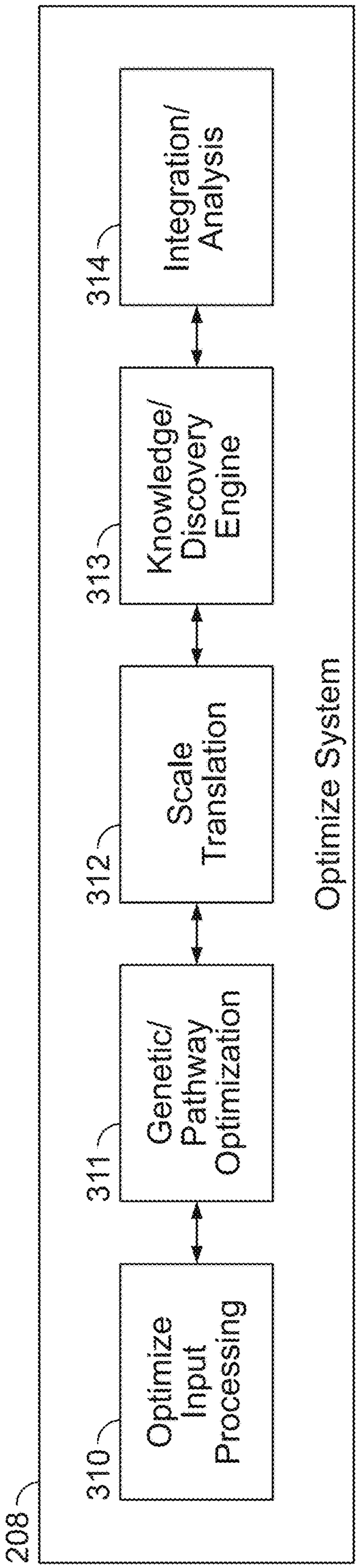
FIG. 8 is a schematic diagram that details example embodiments of an optimize system, according to some embodiments.

FIG. 8 illustrates additional details of an example optimize system 208. As shown in the figure, the optimize system 208 may include an optimization input processing component 310 that is configured to collect, process, and prepare data for optimization workflows. In embodiments, the input processing component 310 may receive and process outputs from the prototype system 204, including successful strain candidates, validated pathway configurations, initial performance data, and the like. The optimization input processing component may also collect optimization-specific data such as scale-up parameters, process conditions, equipment specifications, and economic constraints (e.g., from the TEA system 202). In embodiments, the input processing component 310 may leverage the platform's data intake pipeline and normalization capabilities to ensure consistency across different experimental scales and conditions, in a similar way as described for the prototype input processing 302.

In embodiments, the optimization input processing component 310 may maintain and update data sets that capture relationships between strain performance and various optimization parameters. For example, these data sets may include correlations between genetic modifications and phenotypic outcomes at different scales, historical data about successful scale-up strategies, documented process parameter sensitivities, and/or optimization constraints specific to different market applications. The optimize system 208 may use these or similar data sets to identify patterns to inform optimization strategies, such as by recognizing common bottlenecks in similar pathways, identifying genetic modifications that consistently improve scale-up performance, determining process conditions that tend to maintain consistent performance in particular situations (e.g., for certain organisms, strains, processes, scales, etc.), or the like.

With reference to FIGS. 3 and 8, the optimization input processing component 310 may be implemented by the facility for synthetic biology sensor collection, processing, fusion, and staging for modeling and analytics 2100, as described herein. The component 310 may implement methods that are optimized for biological optimization and/or scale-up data. When processing biological data, the input processing component 310 may process input sequences representing process parameters with temporal information (e.g., temporal embeddings), for example, such that the inputs are annotated with time data for each parameter state. The input processing component 310 may collate training data to include paired examples of input and outcome data (e.g., process parameters, scale-up outcomes) collected from laboratory and industrial-scale experiments. In embodiments, the input processing component 310 uses AI processing cores for processing multiple data streams from different scales simultaneously, thereby enabling real-time optimization of process parameters.

In embodiments, the optimization input processing component 310 may prepare data for use by various AI models 3100 that are involved in optimization tasks. For example, the optimization input processing component 310 may format genetic sequence data for analysis by protein language models, prepare process parameter datasets for mechanistic models 3104, structure experimental results for training hybrid models 3106, or perform other such training preparation steps as described elsewhere herein. In embodiments, the optimization input processing component 310 may also implement quality control measures for optimization data, such as by validating consistency of measurements across different scales, identifying potential experimental or data artifacts that may impact optimization predictions, and/or flagging unexpected deviations in performance for further investigation.

In embodiments, an optimize system 208 can be used to understand, analyze and optimize various biosynthetic pathways that are involved in the host's production of a molecule. Existing pathways may be understood (e.g., from the prototyping phase), but adjustments to inputs, environmental parameters, and other factors may be explored and selected by AI models 3100 of the platform ASB Platform 100 to increase the amount of production for a given amount of feedstock, to improve the quality of the outputs, or the like. For example, the genetic and pathway optimization component 311 may use AI models 3100 to identify opportunities to increase production yield for a given amount of feedstock, improve the purity or quality of outputs, reduce byproduct formation, and/or the like.

In other embodiments, an optimize system 208 can be used to design/engineer new pathways. For example, the genetic and pathway optimization component 311 may use mechanistic models 3104 to predict the effectiveness of novel pathway configurations, hybrid models 3106 to evaluate combinations of existing pathway elements, and/or foundation models 3102 to identify other pathways for desired products. In embodiments, the genetic and pathway optimization component 311 may generate and evaluate multiple pathway alternatives simultaneously, rank them based on predicted performance metrics, and/or recommend specific modifications for experimental validation.

In other embodiments, an optimize system 208 can be used to evaluate the impact of metabolic engineering (overexpressing gene, introducing new enzyme). For example, the genetic and pathway optimization component 311 may leverage protein language models to predict the effects of these genetic modifications, use mechanistic models 3104 to simulate changes resulting from these modifications, and/or employ hybrid models 3106 to evaluate the combined effects of multiple modifications. In embodiments, the genetic and pathway optimization component 311 may generate recommendations for specific genetic modifications based on predicted impacts on pathway efficiency, product yield, strain stability, and/or other performance metrics.

In other embodiments, an optimize system 208 can be used to optimize performance. For example, the genetic and pathway optimization component 311 may integrate output data from experimental results to iteratively refine its optimization strategies and predictions.

In other embodiments, an optimize system 208 can be used to identify problems, such as the presence of biosynthetic pathway bottlenecks that can be removed with adjustments to various operational parameters, including genetic modification, process parameters, environmental parameters, or the like. The genetic and pathway optimization component 311 may use AI models 3100 trained on pathway data, metabolomics data, and/or other experimental results to identify specific bottlenecks or inefficiencies. The genetic and pathway optimization component 311 may then recommend various adjustments to remove the bottlenecks using the various AI models 3100 described herein. In embodiments, the genetic and pathway optimization component 311 may prioritize recommended modifications based on predicted impact, implementation complexity, and/or economic considerations provided by the TEA system 202. For example, the genetic and pathway optimization component 311 may recommend overexpressing a particular gene if the models predict this modification would significantly improve yield with minimal process changes, while more complex modifications involving multiple genetic changes might be a lower priority despite potentially higher yields due to increased implementation complexity and development time.

In other embodiments, an optimize system 208 can be used to optimize proteins. In such embodiments, the optimize system 208 can operate as a genetic generalization system (e.g., using genetic generalization models described elsewhere herein), such as to predict the effects of various prospective genetic edits process conditions are assumed to be held constant. A genetic generalization model may be trained to generalize and predict the effects of a set of edits that have not been observed based on the effects of edits that have historically been observed. Among other benefits, this may reduce the need for expensive, high throughput laboratory screening (such as high throughput assays, plates, and the like). As the model predicts the performance of as-yet-unobserved synthetic biology designs screening can be directed to more relevant process conditions earlier in the research and development process, thereby accelerating the overall timeline of development. In embodiments, this may include enabling design screening directly in bioreactors, which is otherwise very challenging, because the rate of experimental throughput is much lower. Overall, such models may reduce the data requirements to find successes by applying genetic edits that have been seen to perform well and generalizing them to other designs that can perform as well or better in various applications.

The optimize system thus provides a technical improvement to the field of genetic engineering by enabling rapid assessment and prototyping of genetic edits to strains using a machine learning model. The optimize system can thus perform an automated search through a space of genetic edits to identify a combination of genetic edits that are predicted to enhance performance of a strain on a synthetic biologic task. The identified genetic edits can then be applied to the strain, and the optimized strain can be deployed to perform synthetic biology tasks.

In other embodiments, an optimize system 208 can be used to recommend genetic edits. Genetic information and other relevant data, such as process environment data, output product data, and the like can be fed into an AI Model 3100 that provides a set of embeddings that predict the outcome of a particular genetic edit given variations in the organism in which the modification takes place, modifications of the process environment, and modifications of the desired output product, among other factors. In embodiments, the genetic and pathway optimization component 311 may rank recommended genetic edits based on predicted effectiveness, confidence levels, and/or alignment with optimization objectives provided by the TEA system 202 or other platform components.

In other embodiments, an optimize system 208 can be used to optimize strain genetics for performance at the target scale of commercial operations. This may include models that predict outcomes of strain genetics under imperfect conditions, such as where feedstocks are somewhat impure, temperature control is imperfect, and the like. For example, the genetic and pathway optimization component 311 may use hybrid models 3106 that combine mechanistic models of cellular responses with modes trained on empirical data from scale-up experiments to predict strain robustness under variable conditions. In embodiments, the genetic and pathway optimization component 311 may recommend genetic modifications specifically designed to improve strain stability and performance based on data indicating a set of imperfect conditions, such as by introducing certain genes that maintain pathway function across a broader range of conditions.

In other embodiments, an optimize system 208 can employ a set of gene function models, such as machine learning models that are pretrained generally on variety of data sets relevant to a host. For example, such models capture the broad characteristics of gene function that are stable across organisms. If there is data demonstrating the performance of some subset of genes for a particular molecule, a gene function model may also generalize what other genes might do that that have not yet been tested. In embodiments, this may include, for example, model predicted gene function with a mechanistic AI model and use the outputs to recommendations maximally informant set of initial screens to perform in order to explore the impact of a set of genes across function space. As additional rounds of data come in, performance of designs in a given project or product can be used to recommend what designs should be tested next. This can enable discovery of high-performing gene edits, including ones that are not related to known biosynthetic pathways, early enough in a project to accelerate overall research and development success. As noted above, this can occur without the need for expensive high throughput screening or automation systems.

In these and certain other embodiments, gene function models are focused on predicting or understanding the function of genes in biosynthetic pathways. With a set of different gene function models, each comprising a representation of gene function, a dataset can be generated that captures the relative rate of growth of cells after particular sets of genes have been knocked out. A model can take a set of initial embeddings, concatenate them to each other, feed the concatenated data into a neural network, train the neural network on fitness data and use the training to develop not only a hybrid embedding for information from the existing models, but also additional information. Over time, with more and more supervised datasets, a better general purpose representation of gene edits emerges and performs very well across a range of tasks.

In embodiments, an optimize system 208 can combine a set of gene function models and with a set of pathway function models. The genetic and pathway optimization component 311 may use hybrid models 3106 that simultaneously process genetic modification data and pathway data. The hybrid models 3106 may predict how specific genetic changes affect activity within a pathway context, predict how pathway modifications influence the expression or regulation of particular genes, identify synergistic effects between genetic modifications and pathway engineering, and/or optimize both genetic and pathway parameters simultaneously. Therefore, hybrid models may enable comprehensive optimization strategies that account for both genetic and metabolic factors affecting strain performance.

In embodiments, an optimize system 208 can employ a set of gene knockout models, which may be taught to predict behavior of single gene edits (knockouts) from phenotypes of knockouts of other genes. For example, the genetic and pathway optimization component 311 may train models to detect patterns in how different gene knockouts affect strain behavior, identify functional relationships between genes based on similarity of knockout phenotypes, predict the effects of untested knockouts based on these relationships, recommend specific knockout experiments to produce desired outcomes, and/or the like. In embodiments, knockout predictions may be used to prioritize genetic modifications for testing and reduce the number of experiments needed to achieve optimization goals.

In embodiments, the scale translation component 312 may use supervised modeling to understand and optimize the relationship between different experimental scales. Scale translation is useful in a common situation in which the researcher does not know in advance what the best way is to undertake a process, such as fermentation. Depending on the end product sought, the host organism that may produce the product, the pathways of the host organism used, and the like, there is a need to learn the relationship between a laboratory assay (e.g., conducted on a plate) and a larger scale assay (e.g., conducted in a fermentation tank). The scale translation component 312 may be configured to predict and optimize the performance of a larger scale assay (e.g., a tank assay), given a set of data about the performance in a smaller scale assay (e.g., a plate assay).

The scale translation component 312 may use distributed computing techniques to process multi-scale biological data. For example, the scale translation component 312 may allocate (or request allocation from another component of platform 100) processing nodes to process data from different experimental scales in parallel, with AI processing cores (e.g., GPUs, NPUs, TPUs, FPGAs, etc.) performing specific computational tasks such as sequence alignment, metabolic flux analysis, etc. These techniques may optimize processing of large datasets without causing excessive latency in generating scale-up predictions. Additionally or alternatively, the scale translation component 312 may dynamically adjust resource allocation (e.g., the number and/or type of processing nodes/cores assigned to the optimize system 208) based on computational demands to enable efficient processing of varying experimental loads.

The inputs to a supervised model trained by the scale translation component 312 may include, for each strain, the genetics of that strain (e.g., an encoded genotype), a set of process features (e.g., physical characteristics) that characterize the process environment in the smaller and larger scale environments, such as reactor volume, feed rate, and many others. The scale translation component 312 may then train models to predict targets at various different scales. These targets may range from basic metrics such as product yield to more sophisticated measures of granular characteristics or parameters of the process or the outputs, such as measures of salt density, amount of acid, amount of substrate or feedstock consumed, and many others. The scale translation component 312 may train supervised models using very rich data sets that are collected in fermentation bioreactors, where very detailed characteristics of process and output product are measured in granular detail over defined periods of time. In embodiments of supervised modeling, the scale translation component 312 may run experiments in parallel with the same strain used in both small-scale environments (e.g., plates) and large-scale environments (e.g., fermentation tanks), so that the models can capture relationships by which small-scale and large-scale performance is correlated (e.g., a relationship between plate performance and tank performance). Where tank performance is poorly correlated and negative in relation to plate performance, the scale translation component 312 can identify and eliminate false positives in plate-based models; conversely, where tank performance is more positive than expected based on models of plate performance, the scale translation component 312 can recognize and address false negatives. Over time, the scale translation component 312 may iteratively improve a plate or other small-scale experiment model via supervised learning, in part based on correlation to large-scale experiment performance, to do a better and better job of predicting performance in a tank or other larger-scale environment.

In embodiments, over a period of time, the scale translation component 312 may train models that are more sophisticated in terms of how strain genetics are represented, with models reflecting gene embedding features being trained, based on the discovery of where small scale, (e.g., plate) performance is over- or under-estimated by the plate assay relative to large-scale performance (e.g., in tanks), as described elsewhere herein. Understanding what genetics are involved when prediction is difficult can help generalize to other similar examples to predict when false negatives or false positives are more likely to arise from a small-scale assay. With a set of examples of over- or under-estimation of large-scale performance in a training set involving similar embeddings (such as of gene function), a model can be trained to predict which results from a plate-based or other small-scale model are most likely to produce false negatives, and those instances can be elevated in priority for further experimentation or screening, notwithstanding unfavorable predictions in a small-scale model.

In embodiments, the scale translation component 312 may evolve genetic generalization models to sufficient predictive capability that plate-based or other small-scale assays are unnecessary. Selection of what strains and process environments to test in bioreactors can become sufficiently effective that it is economically advantageous to advance to that stage of experimentation, cutting out time and cost involved in laboratory screening. In other embodiments, a combination of genetic generalization models and plate-based assays can be used, with appropriate comparison, checks and balances, to create a fast, highly efficient pipeline of candidates for larger-scale experimentation, such as bioreactors or fermentation tanks.

In embodiments, the scale translation component 312 may train models that use richer plate assay data, such as by using inputs that include aspects other than genetic representation features. The input data may include analytical chemistry of media used on plate-based assays, tranportomics (i.e., the understanding of the array of ion channels and transporters expressed in cell membranes), and other representations that improve the ability to create accurate signature performance in plates and that more accurately generalizes to predict what will happen in tanks with related hosts strains, genetic modifications, process environment features, and output products. Thus, training sets with similar effects on measurements (i.e., "assay fingerprints") can be generalized to tank performance.

In some embodiments, the scale translation component 312 may, for example, generalize from successful tank experiments based on gene functions/embeddings. This can be done with tank data alone (i.e., screening from bioreactors), or related plate data can be supplied, which is likely to lead to better predictions. In other embodiments, the scale translation component 312 may generalize from tank experiment successes based on a plate data signature to recommend a set of genetic edits. These elements can also be combined to provide a richer model and a richer assay, with the expectation that gene embeddings and richer plate data could synergistically improve performance.

In embodiments, the scale translation component 312 can (instead of or in addition to using a single model) use an ensemble set of models and active learning, so that selection of strains, tests, and experiments provide together a balance of exploration and exploitation to identify regions of gene function space that are not well characterized in a model, as described elsewhere herein. Any single supervised model may have low predictive value and high uncertainty, especially with the expected limitations on dataset size. However, by incorporating model uncertainty into predictions (e.g., by generating model ensembles), a researcher can use active learning to balance exploration and exploitation. Supervised modeling may be used, for example: to generalize from tank experiment successes based on gene functions/embeddings; to generalize tank performance data based on plate signature data for gene edits; and/or to combine gene embeddings and rich plate data.

In other embodiments, an optimize system 208 can be used to design for scale. This may include, in embodiments, a knowledge and discovery engine 313 for best practices. The knowledge and discovery engine 313 may systematically collect, analyze, and leverage information from multiple sources to inform scale-up strategies. For example, the engine 313 may perform scientific and patent literature analysis using natural language processing models (e.g., LLMs) to extract relevant scale-up methodologies and to record documented successes and failures from published sources. Additionally or alternatively, the engine 313 may process historical scale-up data generated by the platform 100, including successful and unsuccessful attempts at scaling various strains and processes and the data captured therefrom. Additionally or alternatively, the engine 313 may analyze and process data indicating industry best practices for strain development and scale-up, such as strategies for maintaining strain stability at larger scales in general and/or for particular organisms, equipment, processes, media, and/or the like, methods for adapting strains to industrial feedstocks, method for improving strain robustness in variable conditions, guidelines for process parameter adjustment across scales and in varying conditions, and other methods for managing other strain performance characteristics during scale-up. In some embodiments, the engine 313 may generate training data using this data by translating natural language data into training data using various natural language models. These generated training data sets may be used for any of the models described herein. For example, the knowledge and discovery engine 313 may provide training data to the scale translation component 312 to train models for scale-up predictions and recommendations.

In embodiments, supervised modeling may not be possible due to the scale, location, timing, or other elements of the commercial scale-up environment. In this case, the scale translation component 312 may implement scale-down modeling strategies. For example, the scale translation component 312 may analyze parameters of a target condition and replicate, in a scale-down model, as many of the conditions as possible to make supervised learning possible. This may include collecting various "'omics" to characterize the strain biology in the target condition: designing a platform host for robustness across conditions rather than peak performance in any one condition; identifying optimal fermentation processes for any particular strain in few experiments; developing a set of environmental requirements of the host that depend on the genetic modifications of the host to make the product, and the like.

In other embodiments, an optimize system 208 can use AI for screening experiment selection. For example, the genetic and pathway optimization component 311 may analyze strain modification data and send instructions to the prototype system 204 to conduct specific screening experiments. The instructions may indicate which genetic variants to test first, which pathway modifications to combine, what experimental conditions to use based on predictions of likely performance improvements, etc. The prototype system 204 may then execute the screening experiments and return the results to the optimize system 208 for further analysis/optimization.

In other embodiments, an optimize system 208 can use AI to predict outcomes of scaling production of a molecule. For example, the scale translation component 312 may analyze production data at different scales to generate predictions of performance at larger scales. The predictions may include anticipated yields, potential bottlenecks, required process adjustments, optimal operating conditions, etc. In some cases, the prototype system 204 may execute test runs to validate the predictions and return the actual performance data to the optimize system 208 for further analysis and/or to update the predictive models.

In other embodiments, an optimize system 208 can use AI for understanding plate to tank transitions. For example, the scale translation component 312 may analyze correlations between plate-based and tank-based experimental results to develop predictive models of scale-up behavior. These models may account for differences in operational parameters such as environmental conditions, strain behavior, metabolic changes, process parameters, etc. In some cases, the prototype system 204 may conduct parallel experiments at both scales to validate these correlations and return the results to the optimize system 208 for further analysis/optimization/training of the models.

In other embodiments, an optimize system 208 can use gene embedding to identify untested potential high performers and neural networks and hybrid models for combining plate and tank data. For example, various models described herein may use gene embeddings as inputs to predict which untested genetic variants are likely to perform well (including at larger scales). These predictions may incorporate plate-based screening data and/or tank-based production data using various neural network models described elsewhere herein. In some cases, the prototype system 204 may test predicted high performers and return the results to the optimize system 208 for validation and/or re-training of the models.

In other embodiments, an optimize system 208 can use strain embedding to identify untested potential high performers and neural networks and hybrid models for combining plate and tank data. As described elsewhere herein, a strain embedding may be a more comprehensive embedding that characterizes an entire strain, rather than one or more genetic modifications to a strain. The optimize system 208 may use strain embeddings as described elsewhere herein, and may instruct the prototype system 204 to validate predictions, gather additional data for training, etc.

In other embodiments, an optimize system 208 can be used to identify signatures in plate data that help predict tank performance and neural networks and hybrid models for combining plate and tank data. Plate data signatures may include patterns in plate-based experimental data that have been found to correlate with specific tank performance outcomes, which may be distinct from the genetic or strain-level characteristics described above. The optimize system 208 may instruct the prototype system 204 to validate signature-based predictions, gather additional correlation data, etc.

In other embodiments, an optimize system 208 can use AI to optimize any biomanufacturing processes using the principles and techniques described herein.

In other embodiments, an optimize system 208 can use models for scaling in product design.

In other embodiments, an optimize system 208 can be used as a process generalization system. Process generalization may include identifying common patterns and principles across different processes and applying knowledge related to these patterns to new situations. For example, when the genetic and pathway optimization component 311 discovers a successful optimization strategy for one pathway, the optimization 208 may attempt to generalize this strategy to similar pathways or metabolic contexts. Similarly, when the scale translation component 312 identifies successful scale-up operational parameters for one molecule, these insights may be generalized to inform scale-up predictions for molecules with similar chemical properties or production requirements. The prototype system 204 may assist in validating these generalized approaches by testing their applicability across different specific cases.

The optimize system 208 may implement process generalization using various AI models. In some embodiments, the optimize system 208 may train specific generalization models that learn to identify similarities between different processes and extract generalizable features. These models may use techniques such as transfer learning to adapt knowledge from well-characterized processes to new ones or meta-learning to learn how to better adapt to new processes. In other embodiments, the system may implement generalization as part of its existing optimization models (e.g., genetic generalization models) by incorporating appropriate feature representations that capture process similarities. The optimize system 208 may also maintain databases of process patterns and associated contextual metadata, which may be used for rule-based and/or learning-based generalization. As with other aspects of the system, predictions that involve process generalizations may be validated through targeted experiments using the prototype system 204, with results used to refine the generalization capabilities.

In other embodiments, an optimize system 208 can be used to predict tank performance from plate performance. For example, the scale translation component 312 may use models to analyze performance indicators from plate-based experiments (e.g., growth rates, product titers, metabolite data, etc.) to predict corresponding performance in tank environments. These model predictions may account for known scaling effects. For example, the models may be trained on data that illustrates the known scaling effects so that the models encode knowledge of the effects. In some cases, the prototype system 204 may validate scale-up predictions by running parallel plate and tank experiments, with results returned to the optimize system 208 for model refinement.

In other embodiments, an optimize system 208 can be used to predict optimal process conditions for strains in tanks. For example, the scale translation component 312 may analyze strain characteristics and historical tank performance data to recommend specific processes or other operational parameters (e.g., temperature profiles, pH setpoints, feeding strategies, etc.) that are likely to optimize strain performance at tank scale. These predictions may incorporate data characterizing strain-specific sensitivities, metabolic requirements, etc. In some cases, the prototype system 204 may test predicted optimal conditions and provide feedback to the optimize system 208 for validation and/or refinement of the prediction models.

In other embodiments, an optimize system 208 can use technical, economic, and physical limitations to predict performance of a scaled production process. For example, the scale translation component 312 may generate and/or compare predictions based on data indicating equipment capabilities, raw material costs, energy requirements, and/or physical space limitations to predict or compare predictions of production outcomes at commercial scale. The optimize system 208 may use these constraints to guide optimization strategies and/or may instruct the prototype system 204 to validate critical aspects of the predictions where possible.

In other embodiments, an optimize system 208 can use properties of the product molecule and required downstream processing to predict performance in assays, in tanks or bioreactors and/or in scale-up environments using the models described herein. Downstream processing may include operations that take place after biosynthesis (e.g., fermentation) to recover, purify, and/or concentrate a target biological output from a complex mixture of cells, media components, and byproducts. Downstream processing can involve various steps, including, but not limited to, cell harvesting, debris removal, separation (e.g., via centrifugation, depth filtration, tangential flow filtration, liquid-liquid extraction, etc.), purification (e.g., via chromatography, precipitation, membrane separations, etc.), polishing, and formulation (e.g., concentration via dialysis or ultrafiltration, buffering or stabilization, lypholization, etc.). Because these steps may influence the overall process efficiency, cost, and/or the final yield and/or condition of the product, the optimize system 208 may generate predictions that take these factors into account. For example, the optimize system 208 may, using predictive models, selectively compare two potential host strains, where one produces a high titer but requires more complex and/or more costly downstream processing as compared to another that produces a lower titer but requires less complex or less costly downstream processing. By analyzing anticipated downstream processing requirements, the optimize system 208 can select which strain may lead to a more efficient and/or overall cost-effective process (e.g., even if an initial titer is lower). In embodiments, the optimize system 208 may exchange data and/or predictions with the TEA system 202 (described in more detail elsewhere) to incorporate cost factors for downstream processing. The optimize system 208 may generate predictions and/or optimizations associated with a variety of downstream processing techniques, including any of the downstream processing techniques described herein. In addition, the optimize system 208 may receive feedback data from the results of actual downstream processing to improve prediction models used for optimization, as described elsewhere herein.

In other embodiments, an optimize system 208 can use environmental requirements of the host that are independent of the target molecule to predict performance using the models described herein.

In other embodiments, an optimize system 208 can use the AI models described herein to optimize the yield of target molecules in a supervised learning process.

In other embodiments, an optimize system 208 can use the AI models described herein to optimize performance of target molecule.

In other embodiments, an optimize system 208 can use the AI models described herein to optimize purification of target molecule.

The optimize system 208 may further include an integration/analysis component 314 to process outputs from various system components. For example, the integration/analysis component 314 may combine and analyze predictions generated by the genetic/pathway optimization component 311, the scale translation component 312, and other systems/components described herein to rank proposed optimizations, compare predictions, generate more comprehensive recommendations, and/or the like. For example, the integration/analysis component 314 may identify potential conflicts between different optimizations (e.g., based on detecting that proposed recommendations conflict with each other, that proposed genetic modifications may not combine synergistically, etc.). Additionally or alternatively, the integration/analysis component 314 evaluates trade-offs between multiple competing objectives as described elsewhere herein. Additionally or alternatively, the integration/analysis component 314 may rank predictions, including prioritizing recommendations based on predicted impact, implementation feasibility, and/or confidence levels. In some embodiments, the integration/analysis component 314 may balance genetic optimization suggestions against scale-up constraints by evaluating whether proposed genetic modifications are likely to maintain their benefits at larger scales based on historical scale-up data, or combine strain performance predictions with process generalization insights by detecting common patterns in successful strain-process combinations. In some cases, the prototype system 204 may validate these integrated recommendations through targeted experiments, with results returned to the optimize system 208 for further refinement.

The optimize system 208 may directly interface with industrial control systems to implement real-time process optimization based on any of the AI predictions described herein. For example, the optimize system 208 may dynamically adjust fermentation parameters across production equipment based on real-time sensor data and model predictions, thereby enabling automated optimization of production conditions. The optimize system 208 may therefore provide automated control loops that can significantly improve production efficiency and/or reduce resource consumption.

The above features and functionalities are only some examples of the operation of the optimize system 208. The disclosure provides additional details elsewhere herein of optimizing workflows and services. It should be understood that any of these workflows and services can be performed by the optimize system 208 or the components thereof. It should also be understood that the workflows and services described above with respect to the scale system 208 can be performed by other systems and components described elsewhere herein that are capable of implementing optimized workflows and services, executing AI models, and/or the like.

Scale-Up System

In embodiments, a scale-up system 210 may be used to predict and improve important factors in the commercial scale-up of production, such as the amount of material produced given a set of inputs, the cost of the inputs required (e.g., reducing the need for more expensive feedstocks), the time required for production, the capital or labor requirements for production, downstream processing associated with scaled production, or other factors. Techniques similar to those described in connection with the optimize system 208 may be used, including supervised models that model genetic functions, impact of process environment parameters (including upstream during biosynthesis and downstream during processing), and predictive accuracy between assay-based models, tank/fermentation models, and commercial production models that may encompass production up to and including downstream processing. In embodiments, the scale-up system 210 may predict downstream processing performance and the platform 100 may gather actual downstream processing results as feedback data. The platform may use this and other feedback data to influence other systems (e.g., for prototype strain design, selection of strain candidates, strain and process optimizations, etc.) as described herein.

Figure 9:
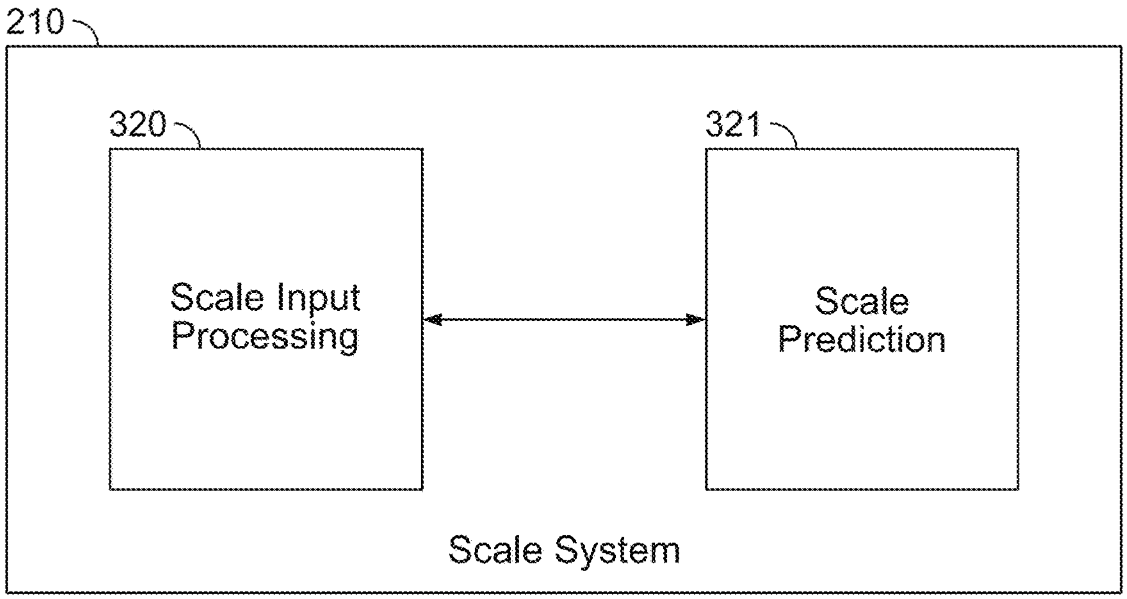
FIG. 9 is a schematic diagram that details example embodiments of a scale-up system, according to some embodiments.

FIG. 9 illustrates additional details of an example scale-up system 210. As shown in the figure, the scale-up system 210 may include a scale input processing component 320 that is configured to collect, process, and prepare data for use in process scale-up predictions. In embodiments, the input processing component 320 may receive performance data for an optimized strain or set of strains (e.g., from the optimize system 208) and associated data, including predicted and/or observed strain behavior under various conditions (e.g., process conditions), and/or other strain-specific data that may impact commercial scale production. In embodiments, the input processing component 320 may also receive economic constraints, targets, and/or other relevant data generated by the TEA system 202 (e.g., required production volumes, acceptable cost ranges, equipment availability, and/or other economic parameters that may influence process design decisions).

In embodiments, the input processing component 320 may collect and process data about potential process configurations, including available equipment specifications, available control systems, target operating procedures, and/or other operational parameters that may affect production scale outcomes. In some cases, this data may be specific to a particular client or a set of production systems that will be used for production scale operations. The data may include, for example, data about specific industrial fermentation equipment and/or associated downstream processing equipment (e.g., centrifuges, filtration systems, chromatography equipment, crystallizers, lyophilizers, etc.), available/planned feeding strategies, purification protocols, temperature control systems, mixing configurations, and/or other relevant process variables including upstream and/or downstream processing operations. The input processing component 320 may also collect scale-up data that captures relationships between laboratory-scale strain performance (and/or other associated lab-scale variables such as recovery efficiencies) and industrial-scale process outcomes, including product yield, purity after commercial scale downstream processing, and/or the like. Such comprehensive scale-up data may enable predictions that cross scales/stages of the prototype/optimize/scale process, including downstream processing. Moreover, the ongoing collection and updating of data provides a feedback loop that may affect operation of each stage/system of a synthetic biology development process.

The data received by the input processing system 320 may be generated by the prototype system 204, the optimize system 208, the TEA system 202, the facility that will implement the commercial scale production, manufacturers of the equipment used by the production facility, or other third parties. In some cases, while the optimize system 208 may predict and/or optimize performance with respect to particular sets of process conditions, the predictions generated by the scale system 210 may be generated based on data for specific sets of equipment or other process conditions (e.g., specific feedstocks) that will actually or likely be used at commercial scale. Additionally or alternatively, the scale system 210 may use AI models that are fine-tuned (e.g., from foundation models) on manufacturer-specific data, such as specific sets of equipment used by a particular manufacturer, inputs and processes used by the manufacturer, historic data generated by the manufacturer, and/or the like.

In embodiments, the input processing component 320 may prepare the received data for use by various AI models involved in commercial scale prediction tasks. For example, the input processing component 320 may normalize data, align timestamps for time-series data, handle missing or incomplete data, and/or perform other preprocessing steps needed for effective model training and prediction. The input processing component may also implement quality control measures for data, such as identifying potential data anomalies, validating consistency across different data sources, and/or flagging unusual patterns that may impact prediction accuracy.

In embodiments, the scale-up system 210 may include a scale-up prediction component 321 that uses AI models to predict production outcomes at commercial scale. The scale-up prediction component 321 may receive processed data from the input processing component 320 and generate predictions about how optimized strains will perform under specific commercial production conditions. For example, the scale-up prediction component 321 may predict production volumes, yields, and/or quality metrics when using particular combinations of equipment, feedstocks, and process or other operational parameters that will be used in actual production.

In embodiments, the scale-up prediction component 321 may use various types of AI models that are specifically trained and/or fine-tuned for commercial scale prediction. For example, the scale-up prediction component may use models that have been trained on historical data from specific manufacturers or facilities to predict how strains will perform with their particular equipment configurations and operating procedures. These manufacturer-specific models may capture patterns involving strain behavior and the specific characteristics of production equipment, such as how mixing patterns or temperature control systems in particular equipment affect strain performance, how different feedstock qualities impact yields, or the like. In embodiments, the scale prediction component 321 may train the models by fine-tuning foundation models 3102 (e.g., the models used for optimizing system 208 and/or other foundation models) using data that is specific to a production process.

In some implementations, the scale-up prediction component 321 may use one or more of the AI models described herein to process data from industrial bioprocesses. These models may combine various layers, such as layers for extracting temporal patterns from sensor data streams (e.g., pH, temperature, oxygen readings, etc.), layers for capturing long-range dependencies in process parameters over time, layers for integrating static process parameters (e.g., equipment specifications, strain characteristics), and/or the like. These AI models may be trained and/or executed for inference using AI processing cores (e.g., TPUs, FPGAs) as described elsewhere herein, which may enable real-time processing of high-frequency sensor data streams.

In embodiments, the scale-up prediction component 321 may use AI models 3100 to generate predictions at different levels of detail and/or time scales. For example, the scale-up prediction component may predict batch-level outcomes (e.g., production volumes, quality metrics) and/or longer-term performance patterns (e.g., consistency across multiple batches). The predictions may incorporate facility-specific factors that may reflect facility-specific conditions, such as typical operating schedules, maintenance patterns, operator training levels, and other real-world considerations that may affect production outcomes.

In embodiments, the scale-up prediction component 321 may update its predictions based on actual production data as it becomes available. For example, when initial production runs are completed, the scale-up prediction component 321 may re-train AI models 3100 based on comparing predicted versus actual outcomes. This feedback loop may help improve prediction accuracy for specific production environments over time. The scale-up prediction component 321 may also analyze and identify patterns in prediction errors that suggest potential adjustments to the production process and/or optimization targets for the strain.

The scale-up system 210 may implement distributed training across multiple computing nodes to handle large volumes of historical production data. For example, the training process may use a set of nodes to process subsets of the training data in parallel and a central component to aggregate model updates. Using distributed training, the scale-up system 210 can enable training on datasets that are too large for single-machine processing. The scale-up system 210 may dynamically adjust the number of nodes based on data volume and/or desired training speed.

In some implementations, the scale-up system 210 may use digital twins to create virtual representations of specific production facilities. The digital twins may maintain real-time synchronized states of equipment configurations and operational parameters, including environmental conditions, process control settings, material flows, quality measurements, and/or the like. In embodiments, the scale-up system 210 (or another system) may use the digital twin for rapid simulation of process modifications without disrupting actual production.

The above features and functionalities are only some examples of the operation of the scale-up system 210. The disclosure provides additional details elsewhere herein of scale-up workflows and services. It should be understood that any of these workflows and services can be performed by the scale-up system 210 or the components thereof. It should also be understood that the workflows and services described above with respect to the scale system 210 can be performed by other systems and components described elsewhere herein that are capable of implementing scale workflows and services, executing AI models, and/or the like.

In some cases, a "laboratory-scale biological process" can refer to a biological process conducted on a small scale for purposes such as feasibility testing, process optimization, or proof-of-concept studies. Laboratory-scale processes may be carried out in bench-top equipment (e.g., flasks, shake tubes, or small bioreactors), and involve limited volumes of materials, lower throughput, and less stringent process control compared to commercial-scale operations.

In some cases, a "commercial-scale biological process" can refer to a biological process carried out at a scale that involves significantly larger volumes of input materials, higher production throughput, more rigorous quality control, and more sophisticated process automation and infrastructure compared to laboratory-scale processes. These processes can be implemented in large bioreactors, fermentation tanks, or production facilities designed for continuous or large-batch operation.

The scale-up system thus provides a technical solution to technical problems that arise when scaling up laboratory-scale biological processes to commercial-scale biological processes. For instance, the scale-up system can optimize experimental conditions, operational conditions, and biological strains in order to enable laboratory-scale biological processes to be successfully conducted at commercial scale.

Techno-Economic Analyses System

In embodiments, the TEA system 202 can be used to enable techno-economic analyses of a process, such as to predict the unit economics of commercial production of a product using a process with a host strain, its genetic functions and biosynthetic pathways, the process environment (including feedstocks), and the like. This may include a software system that automatically collects and manages input data sets (such as the market costs of input feedstocks, capital costs, labor costs, overhead and the like; the market prices of output products, and other factors), performs calculations on the data sets, and presents economic measures, such as predicted unit economics (marginal profit), capital economics (e.g., time to return on investment, IRR, or the like), and other measures, such as in an analytic dashboard. In embodiments, inputs to the TEA system may be systematically varied, such as in scenario planning, to provide sensitivity analyses (e.g., how sensitive unit economics are to the cost of feedstocks). This may include, for example, the price of sugar, the price of fuel and the like, where high volumes of production can produce dramatic swings in economic viability based on the relative prices of inputs and outputs.

In embodiments, the TEA system 202 may use AI processing cores (e.g., GPUs, NPUs, TPUs, FPGAs, etc.) to enable real-time analysis of large-scale economic datasets. The TEA system 202 may implement parallel processing algorithms that distribute computational tasks across multiple processing nodes, enabling simultaneous analysis of multiple economic scenarios. For example, the TEA system 202 may employ a distributed computing architecture where different nodes simultaneously process different combinations of input parameters (e.g., feedstock costs, process conditions, strain characteristics) to identify optimal operating conditions.

In embodiments, the TEA system 202 may be included in the orchestration of a set of recommendations, such as for experiments and/or for selection of strains, process environments, inputs, and the like, such that recommendations include factors such as volatility. For example, a strain that produces a lower marginal unit profit when generating an output product may nevertheless be promoted over a strain that produces a higher one, if the former uses an input feedstock that has historically been very stable in price. Depending on the preferences of the enterprise, a high probability of a profit, even if smaller, may be preferred over a higher profit with a greater likelihood of a large loss. Thus, the TEA system 202 may be tuned to the risk tolerance of the user, such that the tolerance is automatically factored into overall recommendations.

In embodiments, the TEA system 202 automatically collects and processes data from relevant markets and from the other systems of the ASB Platform 100, such as scanning thousands of molecules to identify the best commercialization opportunities based on what other models of the TEA system 202 predict can be produced across a set of host strains, genetic functions, pathways, and products. The TEA system 202 may generate economic viability predictions for a plurality of parallel development paths for multiple synthetic biology products simultaneously. The TEA system 202 may then dynamically allocate development resources between the parallel development paths based on comparative economic viability predictions. For example, the TEA system 202 may adjust the distribution of computational resources, laboratory capacity, and/or human expertise across multiple competing biological strains based on an economic and/or technical predictions for each. Thus, the TEA system 202 may shorten development times and maximize a return on development investment by continuously directing resources to the most promising development paths as new data becomes available.

Figure 10:
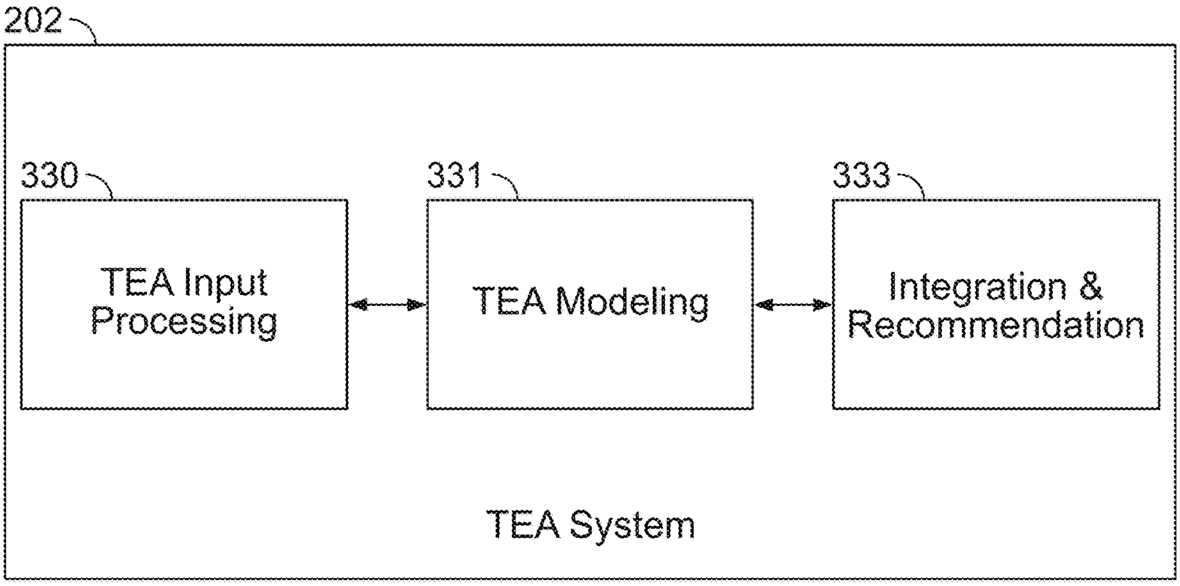
FIG. 10 is a schematic diagram that details example embodiments of a technoeconomic analyses (TEA) system, according to some embodiments.

FIG. 10 illustrates additional details of an example TEA system 202. As shown in the figure, the TEA system 202 may include a TEA input processing component 330 that is configured to collect, normalize, and prepare data for techno-economic analysis. In embodiments, the input processing component 330 may automatically collect and process market data (e.g., prices of feedstocks, energy costs, labor costs, capital costs, equipment costs, product market prices), production data (e.g., yield data, equipment costs, labor requirements), and other economic data from various internal and external sources. The data may include data used by and/or generated by any of the systems or components described herein, as well as external market data. In embodiments, the input processing component 330 may compile the collected data into training data sets that may be updated over time. The input processing component 330 may implement automated data collection pipelines that regularly update price trends, market conditions, and other dynamic factors that affect economic analysis.

With reference to FIGS. 3 and 8, the input processing component 330 may be implemented by the facility for synthetic biology sensor collection, processing, fusion, and staging for modeling and analytics 2100 described below. The input processing component 330 may implement data structures and algorithms that are optimized for efficient processing of time-series economic data. For example, the input processing component 330 may use specialized indexes (e.g., compressed bitmap indexes) for rapid querying of historical price data, specialized tree data structures for efficient range queries across time periods, and/or the like. The input processing component 330 may also employ adaptive sampling techniques that automatically adjust data collection frequency based on market volatility, such as by reducing frequency and therefore computational overhead during stable periods and increasing frequency to achieve higher temporal resolution during periods of rapid change.

In embodiments, the input processing component 330 may process and prepare historical data sets that capture relationships between various production factors and economic factors. For example, these data sets may capture historical price fluctuations for different feedstocks, patterns in energy costs, relationships between production scale and unit costs, and/or other economic patterns that may inform predictions. The input processing component 330 may also collect and process data about market trends for different molecules, including demand patterns, competitive dynamics, regulatory changes that may affect markets, and other factors that may influence commercial opportunity assessment. In embodiments, the historical data sets may include correlations and/or other relationships between production factors and economic outcomes. For example, historical production data may be collected from the prototype system, optimize system, and/or scale up system for previous fermentation runs, and correlated with commercial production data documenting specific production parameters and economic results including yields, conversion efficiencies, processing costs, product quality, etc. By incorporating comprehensive historical production and cost data, the TEA system 202 may have sufficient data to train AI models to learn patterns that link various operational parameters to economic outcomes, as well as to provide other predictions described herein. The TEA system 202 may also regularly update the historical data sets as additional data is received, as well as retrain AI models, thereby identifying additional correlations and improving predication accuracy over time.

In embodiments, the input processing component 330 may prepare data for use by various AI models involved in economic analysis and prediction. For example, the input processing component may normalize price data across different time periods and regions, align different data sources for consistent analysis, handle missing or incomplete data, and/or perform other preprocessing steps needed for effective model training and prediction. The input processing component 330 may also implement quality control measures for economic data, such as identifying anomalous price movements, validating consistency across different data sources, and/or flagging unusual patterns that may impact prediction accuracy.

In embodiments, the TEA system 202 may include a TEA modeling component 331 that uses various AI models to generate economic predictions using data generated other platform systems combined with market data. For example, the TEA modeling component 331 may combine strain performance predictions from the optimize system 208 (e.g., predicted yields, required process conditions) and/or scale-up predictions from the scale system 210 (e.g., expected production volumes, equipment requirements) with market data (e.g., feedstock costs, energy costs, product prices, commercial viability data, etc.) to predict unit economics for specific strain/process combinations. In embodiments, the TEA modeling component 331 may use various AI models to identify correlations between the various data generated by the prototype system, optimize system, and/or scale-up system and cost or other market factors to identify operational parameters that are driving higher costs. In embodiments, the TEA modeling component 331 may generate economic viability predictions by analyzing predicted performance and/or process conditions using one or more artificial intelligence models trained on historical data, wherein the historical data includes the historical market data described herein. The platform 100 may use the economic viability predictions to prioritize development of synthetic biology products based on the predicted performance/or and the economic viability predictions, thereby allocating resources efficiently to projects with the highest probability of technical and/or commercial success. In embodiments, the TEA modeling component 331 may identify economic thresholds for commercial viability for each product under development (e.g., minimum yield requirements, maximum allowable input costs, minimum selling prices, and required margins, etc.). The TEA modeling component 331 may monitor performance data with respect to the economic thresholds throughout the development process. When performance data indicates that a particular economic threshold will not be met, the platform may automatically adjust development priorities, which may include reallocating resources, modifying development targets, or in some cases, recommending termination of development paths that are not economically viable. In embodiments, the TEA modeling component 331 may feed its predictions back to other platform systems to guide strain and/or process development. For example, predictions about which feedstocks are likely to remain cost-effective may influence strain optimization targets in the optimize system 208. Similarly, predictions about minimum viable production volumes may inform scale-up requirements analyzed by the scale system 210. The input processing component may also identify economic constraints that should be considered during strain design, such as maximum allowable feedstock costs, minimum required yields to achieve target margins, and/or the like.

The TEA modeling component 331 may be configured to predict market-dependent revenue potential for synthetic biology products by incorporating market size data, competitive positioning data, potential market share capture data, pricing strategies, and/or market growth trajectories. In embodiments, the TEA modeling component 331 may analyze current market conditions and/or forecast future market developments. These market-dependent revenue predictions may be dynamically updated as new market intelligence becomes available, thereby enabling the platform to continuously reassess commercial opportunities as market conditions evolve.

The TEA system 202 may generate a plurality of economic metrics, including return on investment (ROI) calculations that are based on total capital expenditure, time-weighted returns, and/or risk-adjusted expectations. Additionally or alternatively, the TEA system 202 may generate payback period analyses that determine the time required to recover initial investments under various scenarios, net present value calculations that discount future cash flows to assess current value, and/or internal rate of return computations that enable comparison with alternative investment opportunities. The TEA system 202 may use configurable discount rates and/or time horizons for these metrics, thereby allowing users to customize economic assessments for their specific financial requirements and/or investment strategies. These and other economic metrics described herein may be generated by the TEA system 202 at various scales, including for individual strains and/or processes as well as for overall development programs (e.g., for multiple competing biological strains) and/or product portfolios.

The TEA modeling component 331 may use machine learning architectures optimized for processing heterogeneous economic and biological data. For example, the AI models may include convolutional neural networks for processing time-series market data, graph neural networks for analyzing metabolic pathway relationships, and/or neural networks that use attention mechanisms for identifying relevant correlations between economic and biological parameters. Moreover, each of these example models may be combined using a hybrid architecture. This example hybrid architecture may be trained using multi-task learning that simultaneously optimizes for multiple economic and technical objectives using the multi-objective training system described in more detail below. The TEA modeling component 331 may also implement efficient batch processing techniques that enable training on large datasets, as described elsewhere herein.

In embodiments, the TEA modeling component 331 may train AI models using training data including strain performance data, scale-up data, and/or economic data in combination. The AI models may learn patterns that help predict which combinations of strain characteristics and/or process parameters are most likely to achieve economic objectives. For example, models may learn to identify relationships between specific metabolic pathways and production costs, or between strain stability characteristics and long-term economic viability at scale. The models may be periodically retrained as new production data and economic outcomes become available, improving their predictive accuracy over time.

In embodiments, the TEA system 202 may include an integration and recommendation component 332 that combines economic predictions with other platform data to support development decisions. For example, the integration and recommendation component 332 may process inputs including economic predictions from the TEA modeling component 331, strain performance data and predictions from the optimize system 208, scale-up predictions from the scale system 210, and/or user-provided parameters such as business objectives and constraints. These combined datasets may be used to generate comparative analyses, such as ranking different strain candidates based on both their predicted technical performance and economic outcomes. The integration and recommendation component 332 may generate risk-adjusted economic predictions for each synthetic biology product, may rank products based on probability of commercial success, and may provide recommendations for adjusting development resource allocation based on the rankings. For example, the integration and recommendation component 332 can rank products based on probability of commercial success, taking into account an expected economic performance of a biological strain (e.g., as indicated by predictions generated by the modeling component 331) and any associated risks and uncertainties. Based on the rankings, the integration and recommendation component 332 may provide recommendations for adjusting development resource allocation of the ASB platform across multiple biological strains (which may be the same or different organisms). This risk-adjusted prioritization approach allows the platform to balance high-potential opportunities against risks. The analyses generated by the integration and recommendation component 332 may include standardized metrics, visualizations, and/or reports that may assist in evaluating development options, such as dashboards that show predicted yields, costs, and margins for different strain candidates, confidence intervals, risk factors, etc.

Market-Specific Customer Workflows and Services (End-Market Solutions 1100)

Referring to FIG. 1, the ASB platform 100 includes market-specific customer workflows and services, referred to herein as "end-market solutions 1100." In embodiments, end-market solutions 1100 (FIG. 6) may comprise research and/or development workflows, processes, services, products, solutions, outputs, and the like that are customized to specific types of end-markets, solutions, and applications. In embodiments, end-market solutions 1100 may comprise fuel applications and/or solutions, industrial applications and/or solutions, consumer product applications and/or solutions, pharmaceutical and/or medical applications and/or solutions, and many others. In embodiments, the end-market applications and solutions (e.g., for fuel, industrial, consumer product, pharmaceutical and/or medical) may be specific to the host/strain types (e.g., bacteria, algae, fungi, mammalian cells, yeast, and/or plants) and/or specific to particular hosts/strains.

In implementations, the platform 100 may efficiently implement the end-market solutions 1100 using computing architectures that are optimized for specific market applications. For example, the platform 100 may employ distributed computing nodes that parallelize computational tasks across multiple processing nodes, where each node specializes in a particular market-specific analysis (e.g., where one node optimizes fermentation parameters while another node simultaneously generates metabolic pathway predictions). As another example, the platform 100 may execute market-specific machine learning models that process structured input data that comprises industry-specific parameters (e.g., for biofuel applications, input vectors containing fermentation conditions, metabolite concentrations, and/or enzyme activity levels encoded as numerical arrays). The platform 100 may use AI processing cores (e.g., GPUs, NPUs, TPUs, FPGAs, etc.) configured to efficiently process specific types of biological data for particular markets, such as protein structure prediction in pharmaceutical applications, real-time processing of fermentation sensor data in biofuel applications, metabolomics data in food/beverage applications, and/or the like.

Figure 6:
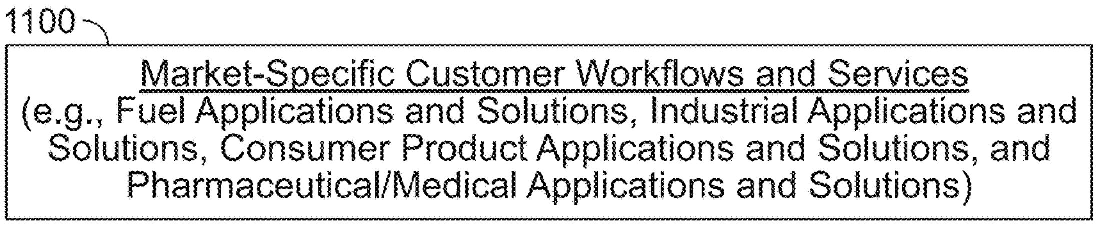
FIG. 6 is a schematic diagram that details market-specific customer workflows and services, according to some embodiments.

With reference to FIG. 6, the end-market solutions 1100 are configured to guide users through the complex phases of synthetic biology product development, including the prototyping phase, the optimization phase, and the scale-up phase for particular industry segments. Customer engagements and/or other synthetic biology projects may commence at different stages of research and/or product development and/or may have different requirements, and thus, may only need to leverage a subset of the workflows and/or services supplied by end-market solutions 1100. For example, a customer with a base strain already developed (e.g., completion of a prototype phase) may arrange for an engagement that leverages the workflows and/or services of the optimization and scaling phases but not the workflows and/or services of the prototype phase. Additionally, end-market solutions 1100 may encompass techno-economic analysis services that are specific to a particular type of market solution.

In embodiments, an end-market solution 1100 may be enabled by the functionalities of the prototype system 204, the optimize system 208, the scale-up system 210, the TEA system 202 (FIG. 4), the elements of 3100 (e.g., machine learning models, artificial intelligence models, deep learning models, mechanistic models, digital twins, simulations, and the like), the elements of the facility for synthetic biology sensor collection, processing, fusion, and staging for modeling and analytics 2100 (e.g., data intake and staging, data normalization, data fusion, and the like), the specialized solution components 1200, and/or other elements of ASB platform 100 to provide industry-specific workflows and/or services to achieve the objectives of various synthetic biology research and development projects and/or engagements with customers.

In some implementations, end-market solutions 1100 includes biosynthetic fuel research and development workflows, processes, services, products, solutions, and outputs for many categories of biofuels, including aviation and marine biofuels, biosynthetic methanol, biosynthetic ethanol, biodiesel, biobutanol, biosynthetic fuel additives, biosynthetic isooctane, biosynthetic lubricants, and the like. Biofuel development workflows and services may focus on leveraging genetically engineered hosts or strains (e.g., bacteria, fungi, yeast, algae, plants, and mammalian cells), which are then optimized for the efficient conversion of biomass into desired fuel products. For instance, biosynthetic methanol workflows and services may be centered on the engineering of microbial strains capable of metabolizing carbon sources into methanol through a series of enzymatic reactions.

In embodiments, the end-market solutions 1100 may include industrial applications and solutions such as chemicals and materials, fibers and textiles, mining solutions, industrial sensors, agriculture and aquaculture solutions, and the like. In embodiments, an end-market solutions 1100 may comprise workflows and services for TEA analysis, design, optimization, and/or manufacturing of biosynthetic industrial enzymes and/or other specialized catalysts for industrial processes, biosynthetic dies and/or pigments, biosynthetic commodity chemicals, biosynthetic alkanediols, biosynthetic 1,4-Butanediol (BDO), biosynthetic purified terephthalic acid (PTA), biosynthetic peroxides and/or other organic acids, biopolymers, biosynthetic biodegradable plastics, biosynthetic biodegradable polyhydroxyalkanoates (PHA), biosynthetic biosurfactants, biosynthetic sophorolipids, biosynthetic building materials, biosynthetic cement, biosynthetic hydrophobic industrial materials, biosynthetic products that digest plastic, biosynthetic products that digest waste material, and biosynthetic negative carbon materials. BDO is a versatile intermediate used in the production of plastics, elastic fibers, and polyurethanes. In embodiments, the end-market solution 1100 to develop biosynthetic BDO may target the use of engineered strains to ferment sugars into BDO, offering a renewable alternative to petrochemical methods. The widespread adoption of bio-BDO could lead to a significant reduction in carbon dioxide emissions, with the potential to eliminate millions of tons of carbon dioxide annually. In embodiments, the workflows and services for the development of biosynthetic building materials, such as bio-cement, may be aimed at utilizing microorganisms like algae or bacteria that precipitate calcium carbonate. This innovative approach to cement production not only mimics natural processes but also contributes to carbon sequestration, enhancing the sustainability of construction materials.

In embodiments, end-market solutions 1100 (FIG. 6) may provide workflows and services for the design, optimization, and/or manufacturing of biosynthetic fibers and textiles, including, but not limited to, biosynthetic polyester, biosynthetic polyamide, biosynthetic polypropylene, biosynthetic cellulosics, biosynthetic natural fibers, biosynthetic spider silk, biosynthetic silkworm silk, biosynthetic wool, and biosynthetic cotton, among many others. In one example, the research and development solutions for biosynthetic textiles may involve converting carbon dioxide into organic compounds that can be spun into fibers and textiles. Such a process not only produces sustainable fabrics, but also contributes to the reduction of atmospheric carbon dioxide levels, aligning with global efforts to mitigate climate change.

In some implementations, the end-market solutions 1100 may include solutions for bioleaching, biomining, and/or bioremediation processes. Biosynthetic approaches to mineral extraction are not only more environmentally friendly, reducing the need for harsh chemicals and high energy inputs, but also allow for the recovery of metals from low-grade ores that would otherwise be uneconomical to process. The workflows and services for biosynthetic products configured for bioremediation may be focused on utilizing microorganisms and enzymes that are capable of breaking down and neutralizing toxic compounds commonly found in mining waste, such as heavy metals and cyanides. Bioremediation processes can leverage biosynthetic products that are designed to restore contaminated sites to a state where they can support ecosystems and prevent the spread of pollutants to surrounding areas.

In embodiments, the end-market solutions 1100 provide research and development workflows and services for biosynthetic industrial sensors, which may be centered on leveraging biological molecules such as enzymes, antibodies, or nucleic acids that exhibit specific binding or catalytic properties. These biological components may be integrated into sensor devices to detect the presence of target substances with high specificity. The biosynthetic sensors can be tailored to monitor a wide range of industrial parameters, including the detection of pollutants, measurement of metabolite concentrations, and monitoring of process conditions. The biosynthetic industrial sensor solutions may further involve identifying and engineering biological recognition elements that can interact with the target analyte. These elements may then be coupled with transducers that convert the biological interaction into a measurable electrical signal.

In embodiments, the end-market solutions 1100 may include solutions for agriculture and/or aquaculture applications, including, but not limited to, biosynthetic fertilizers, biosynthetic pesticides, biosynthetic herbicides, biosynthetic fungicides, biosynthetic nematicides, biosynthetic crop protection agents, microbes configured for nitrogen optimization and/or fixation in crops, biosynthetic products for carbon sequestration, biosynthetic animal feed, biosynthetic animal probiotics, biosynthetic animal medicines, biosynthetic bioluminescent plants, and the like. The workflows and services for development of biosynthetic pesticides, herbicides, fungicides, nematicides, and other crop protection agents, for example, may be geared towards harnessing the natural defense mechanisms found in the plant microbiome, enhancing strains for improved pest control, nutrient acquisition, and resistance to crop diseases. By targeting specific pests and pathogens with precision, these biosynthetic products can reduce the collateral environmental impact often associated with broad-spectrum chemical agents.

In embodiments, the end-market solutions 1100 may include research and development solutions and/or industry-specific techno-economic analysis services for consumer products such as food and beverages, consumer goods, nutraceuticals, and the like.

In embodiments, food and beverage applications and solutions may include biosynthetic food, biosynthetic beverages, biosynthetic palm oils, biosynthetic flavors, biosynthetic milk components, biosynthetic milk proteins, biosynthetic casein, biosynthetic human milk sugar (HMO), biosynthetic baby formulas, biosynthetic meat substitutes, and many others. In examples, the provision of research and development workflows and services may be directed to commercial yeast strains and processes for protein production. These engineered yeasts can produce high-quality proteins that can be used as ingredients in a variety of food products, offering a sustainable alternative to traditional animal-based proteins.

In embodiments, consumer good applications and solutions may include, but are not limited to, biosynthetic personal care products, biosynthetic cosmetics, biosynthetic retinol, biosynthetic fragrances, biosynthetic skin care products, biosynthetic home care products, biosynthetic cleaning materials, and biosynthetic laundry detergent. For instance, the services and workflows for the development of biosynthetic cleaning materials may incorporate the engineering of bacteria to break down stains and soils, providing a powerful and eco-friendly cleaning solution. In another example, the end-market solutions 1100 for biosynthetic laundry detergent may focus on creating detergents that are effective at low temperatures and biodegradable, reducing energy consumption and minimizing water pollution.

In embodiments, the end-market solutions 1100 comprise nutraceutical applications and solutions, including biosynthetic vitamins, biosynthetic antioxidants, biosynthetic phytochemicals, biosynthetic cannabinoids, biosynthetic carotenoids, biosynthetic flavonoids, biosynthetic terpenes, biosynthetic polyunsaturated fatty acids, and the like. For example, end-market solutions 1100 may include research and development workflows and services for compounds such as cannabichromene (CBC) and cannabigerol (CBG). These non-psychoactive cannabinoids have potential therapeutic benefits, and the biosynthetic approach may supply compounds that are free from the contaminants and variability associated with plant extraction methods.

In embodiments, the end-market solutions 1100 may include pharmaceutical and/or medical applications and solutions, which may comprise biosynthetic pharmaceuticals, enzymes that act as biocatalysts in active pharmaceutical ingredient manufacturing, cell therapies, biosynthetic vaccines and/or vaccine components, biosynthetic squalene, therapeutic enzymes, biosynthetic heparin, therapeutic bacteria, living medicines, biosynthetic probiotics, biosynthetic antibody therapeutics, biosynthetic personalized medicines, biosynthetic medical devices, biosynthetic medical diagnostic devices, and biosynthetic medical sensors, among many others. For instance, the workflows and services of end-market solutions 1100 may be used to develop cell therapies such as chimeric antigen receptor T-cell (CAR-T) therapies, which may involve the genetic modification of T-cells to target and destroy cancer cells.

The market-specific customer workflows and services of end-market solutions 1100 offer a diverse array of solutions for enabling the biosynthesis of products tailored to specific market needs, supporting end-to-end solution development, from genetic engineering to scalable manufacturing, with a focus on sustainability, efficiency, and market compliance.

Facility for Synthetic Biology Sensor Collection, Processing, Fusion, and Staging for Modeling and Analytics In embodiments, the ASB Platform 100 may include a facility for synthetic biology sensor collection, processing, fusion, and staging for modeling and analytics 2100, and may handle and process a wide range of biological data for the purpose of constructing and analyzing models that simulate biological systems. The methods and systems may include a data intake and staging pipeline 2200, a data normalization facility 2300, biological parameters and measurements 2400, and model output tracking 2500. The data intake and staging pipeline 2200 may receive and store biological or other data, including but not limited to data regarding molecules, reactions, gene regulatory networks, intracellular transport, and other biological aspects. Data may be from a plurality of sources, such as from public literature, electronic sources, manual entry, or direct electronic form from experiments. Data may be stored in structured formats, allowing for detailed descriptions of biological objects and their relationships to other objects. In embodiments, the facility for synthetic biology sensor collection, processing, fusion, and staging for modeling and analytics 2100 may be implemented using hardware that is optimized for high-throughput sensor data processing. For example, the facility for synthetic biology sensor collection, processing, fusion, and staging for modeling and analytics 2100 may use field-programmable gate arrays (FPGAs) configured for parallel processing of multiple sensor data streams, application-specific integrated circuits (ASICs) designed for efficient processing of particular biological data types, and/or the like. The facility for synthetic biology sensor collection, processing, fusion, and staging for modeling and analytics 2100 may implement data compression algorithms that are optimized for biological sensor data.

In embodiments, the ASB Platform 100 may include a compiler 7904 that receives inputs regarding a specific biological system and desired modeling technique from an input engine 7908. The compiler may retrieve a subset of biological data associated with the biological system and use, for example, a configuration module 7910 and a model generator 7912 to generate a model that simulates the behavior of the biological system. Processes performed by the model configuration system include, but are not limited to, data repository and management, advanced data compilation and model generation, diverse modeling techniques, user interfaces, simulation and analysis, integration of experimental data, in silico experiments, and collaborative and iterative development. In embodiments, data repository and management may include storing a comprehensive knowledge base of biological data from a plurality of sources, managing data related to multiple biological systems, including genes, proteins, biochemical reactions, and allowing for the revision and updating of biological data by administrators or contributors. In embodiments, advanced data compilation and model generation may include converting biological data from a first structured format to a second format suitable for the selected modeling technique, and generating computational models based on the selected modeling technique and model configuration data without requiring additional technical inputs from the user. In embodiments, modeling techniques may include a range of modeling methodologies, including ordinary differential equations (ODEs), partial differential equations (PDEs), Flux Balance Analyses, Monte-Carlo simulations, Boolean networks, or some other type of modeling technique, and allow for the selection of hybrid modeling techniques that combine more than one type of modeling approach. In embodiments, user interfaces may be provided for inputting selections related to biological systems, behaviors, conditions, modeling techniques, and graphical output formats, and provide tools for adding, editing, and validating biological data entries. In embodiments, simulation and analysis methods and systems may execute models to simulate the behavior of biological systems and generate results, and produce graphical outputs, including dynamic and static representations, to visualize the simulation outcomes. In embodiments, the integration of experimental data may utilize empirical data to fine-tune model generation and incorporate new relationships into models, and support model-driven and experiment-driven approaches to enhance the understanding of biological systems. The ASB Platform 100 may run multiple in silico experiments to reduce the need for wet-lab experiments and guide experimental priorities, and use simulated behavior to interpret experimental results, such as RNA expression studies and metabolomics.

The compiler 7904 may use specialized processing techniques to optimize model generation. For example, the compiler 7904 may implement adaptive time-stepping algorithms (e.g., for ODEs) that automatically adjust computational granularity based on system dynamics to reduce computation overhead. The compiler 7904 may also implement parallel processing techniques (e.g., for Monte-Carlo simulations), such as by distributing individual simulation runs across multiple processing cores or nodes.

In embodiments, the ASB Platform 100 may include modular system components, including interconnected modules such as a data repository, compiler, output engine, and input engine to facilitate aspects of model generation and execution. In embodiments, the ASB Platform 100 may include aspects of a client-server model having client computing devices presenting user interfaces generated by the ASB Platform 100, with inputs sent over a network to a server system. The ASB Platform 100 may retrieve biological data from external sources such as databases, websites, and RSS feeds, and may include integration capabilities with these external systems. The ASB Platform 100 includes a flexible and scalable architecture designed to be applicable in contexts beyond biological systems including, but not limited to, chemical systems, physical systems, and materials science systems.

In embodiments, the modular system components may be implemented using a microservices architecture that enables flexible scaling and deployment of individual components. For example, the data repository module may provide a distributed database microservice with features such as automatic sharding based on data type and access patterns to enable efficient handling of heterogeneous biological data at scale. In embodiments, the platform 100 may implement load balancing algorithms that route requests based on computational intensity, data locality, or the like. In embodiments, the platform 100 may implement automated failover mechanisms that maintain system availability when individual modules and/or processing nodes fail, for example, with backup nodes automatically taking over processing tasks after a failure detection.

Data Intake and Staging Pipeline

In embodiments, the ASB Platform 100 may include a data intake and staging pipeline 2200. Data may derive from a plurality of biological data sources including, but not limited to, publicly available literature, electronic databases, websites, RSS feeds, inferred data, simulated data, model data, and direct inputs from experiments. Data used by the ASB Platform 100 may be retrieved automatically, including automatically collected according to a schedule, or entered manually by users, for example, administrators of a model configuration system 7900. Biological data may be received in electronic form directly from experiments, such as results produced by in silico modeling and/or other experiments.

In embodiments, the data intake and staging pipeline 2200 may use one or more AI processing cores (e.g., GPUs, NPUs, TPUs, FPGAs, etc.) for processing incoming biological data streams. For example, when processing high-throughput sequencing data, the pipeline may employ the AI processing cores for efficient parallel processing of nucleotide sequence data. The data intake and staging pipeline 2200 may implement adaptive data buffering mechanisms that automatically adjust buffer sizes based on input data rates and/or available system resources.

In embodiments, the data intake and staging pipeline 2200 may include a plurality of data repositories and include facilities for structured data storage and management. A data repository of the data intake and staging pipeline 2200 may store biological data, which may include information related to genes, RNA transcripts, proteins, biochemical reactions, and other biological aspects. The repository may also store models, model configuration data, and graphical outputs generated by the compiler 7904, or some other type of data. Biological data may be stored in a structured format within the data repository 7902, which describes details of a given biological object and its relationships to other objects. This structured format may allow for analytic descriptions and relationships, facilitating the use of editing tools and navigation of such relationships. The data intake and staging pipeline 2200 may include data quality and maintenance processes allowing for changes, supplements, and/or removals to ensure data fidelity and to ensure that the biological data is comprehensive, accurate, and readily available for generating models that simulate the behavior of biological systems.

The intake and staging pipeline 2200 may use data structures that are optimized for biological data types in the structured data storage and management. For example, the storage may use tries and/or suffix trees for efficient storage and retrieval of sequence data, knowledge graph databases optimized for storing and traversing biological pathway information, and/or the like. In embodiments, the storage may use data partitioning schemes that co-locate frequently accessed data on high-performance storage devices while migrating less frequently accessed data to lower-cost storage tiers, thereby balancing performance and cost for the large data sets described herein.

In embodiments, the platform, as described herein, may be used for data integration and mining for synthetic biology design and to facilitate the modeling of information about biological parts and their relationships and the automation of biological engineering. In order to design predictable biological systems that allow complex systems to be successfully designed and built, synthetic biological systems may be developed via the composition of simple, modular components. To ensure that the resulting synthetic systems behave in a predictable fashion, the parts and modules used for biological systems engineering, and the context in which they are deployed, need to be well-understood and well-characterized. However, the lack of well-characterized parts and modular devices, confounded by our limited understanding of biology, is widely recognized as limiting the scale and complexity of current engineered biological systems.

In embodiments, the identification, characterization, and development of new modular parts, devices, and systems requires access to large amounts of biological knowledge. This knowledge must be gathered, integrated, and made accessible to system designers. Furthermore, this knowledge must also be made available in a computationally appropriate form in order to support other platform functions, including but not limited to automation, simulation, machine learning, computer aided design and the like. Obtaining such information may present challenges due to, for example, information being scattered over multiple databases and database types, which use different formats and/or have different semantics. Bringing together such complex, heterogeneous, disparate data sets in a form that will best inform the platform in an integrated data set format may allow the data to be more efficiently computationally mined and modeled, and to be used in robust machine learning methods and systems.

In embodiments, the platform 100 may implement data fusion algorithms for combining heterogeneous biological data types. For example, when integrating metabolomic and transcriptomic data, the platform 100 may use neural network architectures designed to handle different sampling rates or other such differences between the heterogeneous data. The platform 100 may use distributed computing resources to parallelize data integration/fusion tasks, with load balancing algorithms that handle differences in data locality and/or computational intensity for different integration operations. These processes may leverage specialized hardware of the platform 100. For example, the platform 100 may parallelize data fusion algorithms using AI processing cores (e.g., GPUs, NPUs, TPUs, FPGAS, etc.), allowing simultaneous processing of multiple data streams and significantly reducing computation time. Additionally or alternatively, the platform 100 may use field-programmable gate arrays (FPGAs) with custom logic to perform real-time data normalization or other functions, enabling the platform to handle high-throughput data ingestion. Additionally or alternatively, the platform 100 may use AI processing cores to perform specific data compression tasks to allow for high-efficiency storage management. These techniques are examples that illustrate how the platform 100 may efficiently use AI processing cores to achieve technical benefits, including reduced latency in data processing, increased throughput for handling large datasets, and/or the ability to perform complex computations in real-time.

In embodiments, data mining may require data integration techniques that align disparate representations and semantics to produce a unified set and/or domain model. This model may then be mined to extract the necessary information without the need to repeatedly visit large numbers of separate data resources. Traditional methods include data warehousing, where data from multiple databases are drawn together into a single database. In federated data integration, the data may remain in separate databases that are queried in parallel, and the results may be integrated before being returned to the user. One challenge in data integration may arise from a lack of agreement on data formats and/or a variation in the meaning(s) of the data (sometimes referred to as "semantics"). Semantically well-defined electronic representations of data for their integration may increase the utility and value of data. As one example, one data integration technology developed to exploit unified semantics on the Internet, called Semantic Web technology, encourages the use of common data representation formats for data, allowing data to be shared across boundaries and easing the integration process. The ontologies that underpin the Semantic Web concept may be used to standardize data representation by adding computationally tractable meaning to the syntax of data entities and the relationships between them. In this respect, similar ontologies may be used on other data types, sources and formats to identify, integrate, and organize large amounts of complex data that may be used by the platform.

In embodiments, data integration technologies have become increasingly necessary for modeling, accessing, and exchanging large datasets in the life sciences. Numerous databases now provide data in the Resource Description Framework (RDF) format. These databases use standard terms from biological ontologies for the annotation of biological concepts and their interactions.

In embodiments, Synthetic Biology Open Language (SBOL) may be used to integrate and exchange information about biological designs and their component parts. SBOL may be used, in part, to exchange sequence-based information and capture additional types of design components such as proteins and compounds and the functional relationships between them.

In embodiments, the ASB Platform 100 may provide systems and methods for the efficient onboarding and continuous engagement of partners in a computational biology environment. The ASB Platform 100 may be designed to streamline the ingestion, quality assurance, and preparation of partner data for modeling purposes, thereby reducing the time and resource burden on computational biology and engineering teams. The data intake and staging pipeline 2200 may include a set of command line interface (CLI) tools and a standardized data model and/or plurality of data models that enable self-service data loading into a central data repository, such as BigQuery or some other data tool. This may allow parties, such as solutions engineers or others, to independently load client data without reliance on a software engineering team, addressing a bottleneck in the traditional data preparation process. The data intake and staging pipeline 2200 may include a standardized, queryable strain registry database table that serves as a "source of truth" for built strains. This registry may enable parties, like solutions engineers or others, to verify the novelty of candidate strains during a design phase, reducing the time and potential for error associated with manual inspections of client-supplied documents. The data intake and staging pipeline 2200 may include a multi-step process for importing new datasets and updating existing datasets with new data. This process may include the use of CLI tools for transforming and loading data into BigQuery or some other data tool, generating configuration files for data ingestion, and performing transformations to harmonize raw data into an analysis-ready schema. The method may also provide for the versioning of data with timestamps to maintain a historical record of data loads. The system and method of the data intake and staging pipeline 2200 may be modular and encapsulated within a structured framework, with configuration files reducing the need for partner-specific code. The system may be adaptable to various data types and file formats and include error detection and logging capabilities to ensure data integrity and provide a scalable solution for managing partner data in a computational biology context, enhancing efficiency and accuracy in the data preparation and strain verification processes.

In embodiments, the data intake and staging pipeline 2200 may implement specialized error detection and correction algorithms optimized for biological data types. For example, when processing sequencing data, the data intake and staging pipeline 2200 may employ machine learning models trained to identify and correct common sequencing errors. The data intake and staging pipeline 2200 may also use compression algorithms that exploit common patterns in biological data to achieve higher compression ratios than general-purpose compression algorithms.

Data Normalization Facility

In embodiments, the ASB Platform 100 may include a data normalization facility 2300. In an example, biological data may be stored in structured formats within a data repository which may involve organizing the data into a consistent format that is suitable for modeling and analysis. A data configuration module may compile biological and/or other data to produce model configuration data in a second structured format that is specific to a selected modeling technique. This step may involve normalizing data to fit the requirements of the modeling technique. A compiler may convert biological data from one format to another, including a data normalization process, to ensure compatibility with different modeling methodologies.

In embodiments, the data normalization facility 2300 may use hardware configurations that accelerate normalization processing. For example, AI processing cores (e.g., GPUs, NPUs, TPUs, FPGAs, etc.) may be configured for parallel processing of large-scale biological datasets. As another example, field-programmable gate arrays (FPGAs) or other programmable cores may be programmed with custom logic for the specific normalization algorithms that are described below. The data normalization facility 2300 may implement adaptive hardware resource allocation, for example by automatically scaling computational resources based on volume/complexity of data flows. The data normalization facility 2300 may store biological data using specialized data structures, as mentioned above for the data intake and staging pipeline 2200.

In embodiments, the platform, as described herein, may use data normalization and batch effect correction as components of the data analysis pipeline in synthetic biology and strain engineering. These processes may ensure the reliability and reproducibility of experimental results, as well as enable effective machine learning applications in the field. As the complexity and scale of biological experiments continue to increase, the development of more sophisticated and robust normalization methods will be crucial for advancing the understanding of biological systems and our ability to engineer them for useful applications.

In embodiments, data normalization and merging methods and systems may be used by the platform to minimize batch-specific systemic variation in biological sequencing data. As biology and synthetic biology experimentation increases in complexity, there is an increasing need to align and co-analyze larger and more diverse outputs of workflows. However, small and often uncontrollable technical variations in sample collection and data processing may manifest as noticeable effects that confound data interpretation. This systemic variation may be referred to as "batch-effect" and may pose an obstacle to data interpretation, in part, by confounding biologically-derived variation of experimental interest with technically-derived variation. An inability to discern the source of a particular signal may lead to, for example, over-interpretation of data, where systemic variation arising from technical differences may be interpreted as a biologically driven phenotypic difference. In an example, batch-effects may confound data interpretation, in part, by presenting as an over-merging or under-merging of cell types. An uncorrected batch-effect may cause similar cell populations between samples to appear divergent. Conversely, batch-effect may also cause two biologically distinct populations to appear similar due to a shared technical signal.

In embodiments, data normalization and batch effect processes may be components in the analysis and interpretation of biological data performed by the platform as described herein, including, for example, in the context of strain engineering and synthetic biology. These processes may promote and improve the accuracy and reliability of experimental results derived from the platform and its associated systems and methods, as well as for enabling effective machine learning applications.

One of the challenges in biological data analysis is the presence of batch effects, which can significantly impact the interpretation of experimental results. Batch effects refer to systematic variations in data that are not related to the biological factors of interest, but rather to technical or experimental factors such as different experimental runs, equipment, or operators, or some other factor and/or potentially confounding variable. These effects may obscure true biological signals, including results bearing a causal relationship to an experimental outcome, and lead to incorrect conclusions if not properly addressed.

In an example of one batch effect in strain engineering experiments, variation in performance may be observed across different experimental runs, even when using the same strain and experimental conditions, such as equipment, environment and the like. This variability can be substantial, with some studies reporting differences of up to 100% in measured values for the same strain across different experiments. Such large variations impede accurate assessment of the impact of genetic modifications or other experimental interventions, as the batch effects can overshadow the true biological effects of interest. To address these challenges, in part, researchers may use data normalization techniques. These methods aim to remove or minimize the impact of batch effects while preserving the underlying biological signals of interest.

In embodiments, one approach to data normalization may involve the use of Bayesian statistical methods, which can incorporate prior knowledge and provide a more comprehensive picture of, for example, the uncertainty in data. In an example of a Bayesian approach to data normalization, plate notation models may be used. Plate notation models may be used to provide a formal way of describing various factors that contribute to the observed data, including both the biological effects of interest and the technical factors that may give rise to batch effects. By explicitly modeling these different sources of variation, plate notation models may separate the true biological signals from the confounding technical factors. In an example of a plate notation model for strain engineering data, the observed measurements may be modeled as a combination of several factors. These may include the true biological effect of the strain, the effect of the specific experiment or batch, and other technical factors such as the position of the sample on the plate. By estimating these different components simultaneously, the model can provide a more accurate estimate of the true biological effects while accounting for the various sources of technical variation.

One of the key advantages of using Bayesian methods for data normalization is the methods' ability to handle complex experimental designs and incorporate prior knowledge. For example, if certain strains or conditions are known to be more variable than others, this information can be incorporated into the model as prior distributions. Similarly, if certain types of batch effects are known to be present in an experimental setup (e.g., the equipment used), these may be explicitly modeled and accounted for in the analysis. Another aspect of data normalization that may be performed by the platform in strain engineering is the handling of different types of data. Experiments may produce multimodal data, including measurements of enzyme levels, metabolite concentrations, and gene expression levels. Effective normalization techniques need to be able to handle these diverse data types and integrate them into a coherent analysis framework.

The platform thus leverages Bayesian statistical normalization to provide technical improvements to technical fields such as computer technology and machine learning technology. In particular, Bayesian statistical normalization can allow for experimental data to be cleaned and normalized by an approach that can explicitly account for uncertainty in the data, thus producing higher quality data for use in downstream training of machine learning models. The higher quality of the training data can enable machine learning training to be performed more efficiently, e.g., over fewer training iterations and using less training data than would otherwise be required, which provides an improvement to computer technology and machine learning technology.

In embodiments, by utilizing effective data normalization techniques, the platform may be able to better reach the goal of creating "model-ready" data for machine learning applications in synthetic biology. Model-ready data refers to data that has been processed and normalized in such a way that it can be effectively used as input for machine learning models. This typically involves not only addressing batch effects but also standardizing nomenclature, handling missing data, and ensuring consistency across different data sources. One of the challenges in creating model-ready data is the need to integrate information from multiple sources and experimental setups. For example, data from different organisms or different experimental conditions may need to be combined to train more general and robust models. This may require consideration of how to normalize and integrate data across these different contexts while preserving the relevant biological information. In an example, one approach to addressing these challenges is the use of knowledge graphs to represent biological entities and their relationships. Knowledge graphs may provide a flexible framework for integrating diverse types of biological data and can help in linking information across different experiments, organisms, and data types. By representing biological entities as nodes in a graph and their relationships as edges, knowledge graphs may capture complex biological relationships in a way that is amenable to both human interpretation and machine learning algorithms.

In embodiments, the process of creating model-ready data may involve several steps, including data intake, quality assurance, and normalization. The data intake process involves collecting raw data from various sources and converting it into a standardized format. Quality assurance steps are then applied to identify and correct any errors or inconsistencies in the data. Finally, normalization techniques are applied to remove batch effects and other sources of technical variation. One of the challenges in this process is to ensure that the normalization techniques do not inadvertently remove important biological signals along with the technical noise. This requires validation of the normalization methods, for example, by using known control samples or spike-in standards. It also highlights the importance of maintaining detailed metadata about the experimental conditions and processing steps, as this information can be crucial for interpreting the normalized data and assessing the reliability of any downstream analyses. As experimental techniques in the fields of synthetic biology and strain engineering become more sophisticated and the volume of data continues to grow, there is an ongoing need for more advanced and robust normalization methods. This includes the development of methods that can handle increasingly complex experimental designs, integrate diverse data types, and scale to large datasets.

The training data used by the machine learning models described herein may be compiled from biological datasets sourced from public databases, experimental results, and/or synthetic data generated through in silico modeling. Each training example may include a model input, such as gene expression levels or metabolite concentrations, and a corresponding target output, such as predicted strain performance metrics. The platform 100 may acquire data using standardized experimental assays and/or laboratory or commercial scale testing, including RNA sequencing for gene expression analysis, mass spectrometry for metabolite profiling, etc.

In embodiments, the platform, as described herein, may use machine learning methods that can learn to identify and correct for batch effects directly from the data, without requiring explicit modeling of all possible sources of variation. Such approaches may handle more complex and subtle batch effects that are difficult to model explicitly.

In embodiments, the platform, as described herein, may create and use standardized benchmarks and validation datasets for assessing the performance of different normalization methods. Such resources may improve the accuracy of comparisons of different experimental approaches and identify the most effective methods for different types of experimental data and analysis goals.

In embodiments, the platform may include systems and methods for data quality assurance and hit identification for use in AI-guided synthetic biology systems, methods and experimental and analytic techniques, as described herein. Ensuring data quality and accurately identifying hits are critical processes that underpin the success of strain engineering efforts. The platform may include methods and systems for performing data quality assurance and hit identification in, for example, the context of iterative strain design and optimization workflows.

In an example embodiment, data quality assurance may begin at the point of data collection from experimental assays. When measuring strain performance, it is common to encounter significant variability between experimental runs, even when testing genetically identical strains. This variability can arise from differences in experimental conditions, measurement noise, and other factors that are difficult to control precisely. To address this challenge, a robust data normalization and quality control pipeline may be used by the platform. An early step in this pipeline may be to collect raw experimental data on strain performance. This may involve measuring key metabolites or other phenotypes of interest across a population of engineered strains. The raw data may then be passed through an automated quality control process to identify and flag any anomalous data points. This may include detecting wells or samples that failed to grow properly, exhibited contamination, or produced readouts that fall well outside the expected range based on historical data for similar strains. Once anomalous data points have been flagged, the platform may perform batch correction and normalization. This process enables comparisons between strains tested in different experimental batches or at different times. The normalization procedure leverages Bayesian statistical techniques to model and account for batch effects and other sources of systematic variability. In an example, a hierarchical Bayesian model may be constructed to represent the various factors influencing strain performance measurements. This model may incorporate prior knowledge about expected strain behavior, experimental variability, and batch effects. By fitting this model to the experimental data, it becomes possible to infer the true underlying strain performance while accounting for confounding factors. The Bayesian normalization has advantages over simpler normalization methods. First, it provides a principled way to incorporate prior knowledge and expectations about strain behavior. This can be particularly valuable when working with limited data, as is often the case in the early stages of a strain engineering project. Second, the Bayesian framework naturally produces uncertainty estimates around the normalized performance values. This uncertainty information may assist downstream hit identification and decision-making processes.

In embodiments, once the data has been normalized and quality-controlled, the platform may identify promising hits for further investigation and optimization. In the context of strain engineering, a "hit" typically refers to a strain that exhibits improved performance relative to the parent strain or other reference points. However, defining and identifying hits in a rigorous and reproducible manner can be challenging, particularly when working with "noisy" biological data. To address this challenge, the platform may use a probabilistic approach to hit identification. For example, rather than simply applying a fixed threshold to the normalized performance data, strains may be represented as probability distributions over possible performance levels. These distributions may capture both the point estimate of strain performance as well as the uncertainty around that estimate derived from the Bayesian normalization process. With strains represented as probability distributions, it becomes possible to define hits in a more nuanced and flexible manner. For example, a hit may be defined as a strain that has a certain probability (e.g., 90%) of outperforming the parent strain by a specified margin. Alternatively, hits may be identified based on the probability of exceeding absolute performance thresholds.

In embodiments, the probabilistic framework(s) for hit identification used by the platform may offer several advantages over traditional methods. First, the probabilistic framework(s) may account for uncertainty in strain performance estimates, reducing the risk of false positives or negatives due to experimental noise. Second, the probabilistic framework(s) may allow for more fine-grained ranking and prioritization of hits based on the full performance distribution rather than just point estimates. Finally, the probabilistic framework(s) may provide a flexible way for researchers to tune the hit identification criteria based on their specific goals and risk tolerance for a given project. Thus, the probabilistic framework for hit identification provides a technical improvement to the technical field of strain engineering by explicitly accounting for uncertainty in strain performance, which can facilitate automated strain optimization to be performed more efficiently, e.g., over fewer optimization rounds. For instance, in some cases, the probabilistic framework for hit identification can be used as a scoring mechanism to drive an optimization process such as a genetic optimization process, and this optimization can be performed more efficiently due to manner in which the probabilistic framework accounts for uncertainty.

In embodiments, to support this probabilistic hit identification approach, interactive visualization tools may be used by the platform. These tools may allow researchers to explore the performance distributions of different strains, adjust hit criteria, and quickly identify the most promising candidates for further investigation. The visualizations may include elements like density plots showing the overlapping performance distributions of different strains, as well as summary statistics and hit probabilities based on user-defined criteria.

In embodiments, in addition to identifying individual strain hits, the quality-controlled and normalized data may be used to train machine learning models for predicting strain performance. These predictive models may be used by the platform for AI-guided strain design pipelines, allowing for in silico exploration of the vast space of possible genetic modifications. The data quality assurance and normalization procedures described herein may also be used to ensure that these models are trained on reliable, comparable data from across multiple experiments and time points.

In embodiments, one class of models for strain performance prediction is long short-term memory (LSTM) neural networks. These recurrent neural network architectures may be well-suited to capturing the complex temporal dynamics often present in biological systems. By training LSTM models on time-series data of strain performance across multiple generations of engineering, it may become possible to predict not just the immediate effects of genetic modifications, but also how strains are likely to evolve and adapt over time. One challenge in training these predictive models is the limited amount of data typically available, especially in the early stages of a strain engineering project. To address this, transfer learning techniques may be employed to leverage knowledge gained from previous related projects. For example, a base LSTM model might be pre-trained on a large dataset of historical strain engineering results across multiple organisms and pathways. This base model may then be fine-tuned on the specific data for the current project, allowing for improved predictive performance even with limited project-specific data. The platform thus provides a technical improvement to machine learning technology by addressing the technical problem of training data scarcity. In more detail, effectively training machine learning models may be infeasible in the absence of large quantities of high quality training data. Training data scarcity can cause technical issues such as over-fitting during machine learning training, e.g., where the machine learning model models the training data too precisely, including noise or anomalies, thereby reducing its ability to generalize to new, unseen data. Pre-training the machine learning model can enrich the initial parameter values of the machine learning model using training data for a separate task, and can enable the machine learning model to subsequently be rapidly and efficiently fine-tuned to perform a specific machine learning task.

The platform 100 may train the machine learning models using objective functions tailored to their specific tasks. For example, the training may use a cross-entropy loss function to measure the discrepancy between predicted class probabilities and actual class labels. As another example, the training may use a mean squared error (MSE) loss function to measure the difference between predicted continuous values and true values. The training processes described herein can minimize loss functions through optimization algorithms such as stochastic gradient descent (SGD), thereby refining model parameters to enhance predictive accuracy.

In embodiments, another important consideration in model training is how to handle the multi-modal nature of much biological data. In addition to the primary performance metrics (e.g., product titers), there may be other relevant data streams such as gene expression levels, metabolite profiles, and growth rates. Integrating these diverse data types into a unified predictive model may significantly improve predictive accuracy and provide deeper insights into the underlying biological mechanisms driving strain performance. To this end, multi-modal deep learning architectures may be used by the platform that can integrate heterogeneous biological data types. These architectures may involve separate encoding branches for each data modality (e.g., one for gene expression data, another for metabolite profiles), followed by fusion layers that combine the encoded representations. By jointly training on multiple data types, these models may capture complex interactions and dependencies that might be missed when considering each data stream in isolation. The trained predictive models may serve as a foundation for in silico strain design and optimization. By rapidly evaluating the predicted performance of millions of potential genetic designs, it becomes possible to identify promising candidates for experimental validation. However, effectively exploring the vast space of possible designs requires sophisticated optimization algorithms. In an example embodiment, one approach used by the platform may be multi-objective optimization, which allows for simultaneous optimization of multiple, potentially competing strain characteristics. For example, one might want to maximize both product titer and yield while minimizing unwanted byproducts. Techniques like Pareto optimization can be used to identify designs that achieve optimal trade-offs between these different objectives.

In embodiments, to further improve the efficiency of the strain design process, active learning techniques may be employed. Rather than simply selecting the top predicted designs for experimental validation, active learning algorithms may strategically choose designs that will be most informative for improving model accuracy. This may involve selecting designs in underexplored regions of the genetic design space or designs where the model has high uncertainty in its predictions.

In embodiments, as experimental validation data is collected for the AI-designed strains, this data may be fed back into the data quality assurance and normalization pipeline described earlier. This creates a closed-loop learning system where each iteration of the design-build-test-learn cycle improves both the quality of the underlying data and the accuracy of the predictive models. To support this iterative optimization process, the platform may use data management and tracking systems. For example, a knowledge graph approach may be used to represent the complex relationships between strains, genetic designs, experimental conditions, and performance data. This knowledge graph may serve as a unified data model, allowing for seamless integration of data from multiple sources and experiments. The knowledge graph may be structured around key biological entities such as genes, proteins, metabolites, and reactions. Experimental data and strain designs may then be linked to these core biological entities, creating a rich network of relationships. This structure may allow for powerful querying and analysis capabilities. For example, one may retrieve all strains that modify a particular metabolic pathway, along with their associated performance data across multiple experiments.

By representing data in this interconnected manner, the knowledge graph may enable sophisticated reasoning and inference capabilities. Machine learning models may be trained directly on the graph structure, allowing them to capture complex higher-order relationships that might be missed in more traditional tabular data representations. This graph-based learning approach may be used for tasks such as predicting the effects of combinatorial genetic modifications, where the impact of multiple simultaneous changes can be highly non-linear and context-dependent.

In embodiments, the knowledge graph may be used by the platform to ensure data provenance and reproducibility. Data, from raw experimental measurements to processed and normalized values, may be tracked along with its full lineage. This may allow researchers to trace the origins of any data point and understand how it has been processed and transformed. Such transparency may assist in maintaining scientific rigor and enabling effective collaboration in large-scale strain engineering projects. To make the wealth of data and insights captured in the knowledge graph accessible to researchers, a suite of interactive visualization and exploration tools of the platform may be used. These tools may allow users to navigate the complex network of biological entities and experimental data, uncovering hidden patterns and relationships. For example, network visualization techniques may be used to reveal clusters of genetically similar strains or to highlight unexpected correlations between genetic modifications and phenotypic outcomes.

In embodiments, the data quality assurance, hit identification, and knowledge management systems described herein may form the foundation AI-guided strain engineering performed by the platform. By ensuring high-quality, comparable data across experiments, accurately identifying promising strain candidates, and enabling sophisticated predictive modeling, the platform may accelerate the strain optimization process. This integrated approach of the platform may also provide the ability to learn and improve over time. As more data is collected and processed through the systems and methods of the platform, as described herein, the underlying models and knowledge representations may become increasingly accurate and comprehensive. This may create a virtuous cycle where each iteration of the strain engineering process becomes more efficient and effective than the last.

In embodiments, the platform design may be highly flexible and adaptable to different organisms and engineering objectives. While the core data processing and modeling frameworks may share characteristics, the specific metrics, thresholds, and optimization criteria may be customized for each project. This may allow the same underlying technology to be applied across a wide range of synthetic biology applications, from, for example, biofuel production to pharmaceutical manufacturing.

In embodiments, the platform may enhance the capabilities of AI-guided strain engineering platform through, for example, the integration of mechanistic modeling approaches with the data-driven machine learning methods described herein. By incorporating known biological constraints and mechanisms into the predictive models, it may be possible to improve generalization performance and reduce the amount of experimental data required to make accurate predictions. The application of advanced natural language processing techniques to automatically extract relevant information from scientific literature and patents may be used by the platform. By continuously updating, for example, the knowledge graph, or some other data tracking means, with the latest published findings, the platform may provide current synthetic biology knowledge to researchers, automatically incorporating new insights into its predictive models and design algorithms on a continuous, real-time, on-going basis. In part as a result of such capabilities, the platform may accelerate the pace of strain engineering and optimization. By combining rigorous data quality assurance, sophisticated hit identification, and powerful predictive modeling, the platform may navigate the vast space of potential genetic designs with improved speed and precision, and derive new applications in, for example, sustainable chemical production, bioremediation, and medical biotechnology, driving forward the field of synthetic biology and its real-world impact.

In embodiments, the platform, as described herein, may use an iterative splitting process to address challenges in data integration and model training for synthetic biology applications. This process may improve the accuracy and reliability of predictions made by machine learning models, particularly in scenarios where there may be inconsistencies or errors in the underlying data. In embodiments, sequences with identical genetic makeup may not always behave similarly due to various factors such as experimental conditions, measurement errors, biological variability, or some other factor. Traditional approaches often assume that constructs with the same sequence would exhibit identical behavior, which can lead to inaccuracies in model predictions. To overcome this limitation, the iterative splitting process used by the platform may begin, for example, by initially labeling constructs with identical sequences as distinct entities. This approach acknowledges the potential for variation even among genetically identical constructs. The process may then proceed to fit a probabilistic batch correction model to all available observations. This model may take into account various factors that might influence the behavior of constructs, such as experimental conditions and measurement techniques, or some other factor.

In embodiments, once a probabilistic model has been fitted to the data, the model may be used to identify observations that are unlikely to have been generated by the current model. This step may allow for the detection of potential inconsistencies or errors in the data. By flagging these outliers, the process may then split them into separate entries. This splitting may create independent parameters for these constructs, effectively treating them as distinct entities rather than assuming they should behave identically based solely on their genetic sequence.

This process may be iterative as these steps are repeated multiple times. After each round of splitting and model fitting, the process may reassess the data, identifying new potential outliers and refining the model's predictions. This iterative approach may allow for continuous improvement of a model's accuracy and its ability to capture the true variability present in biological systems.

In embodiments, iterative splitting processes may handle complex biological data where the relationship between genetic sequence and phenotype may not be straightforward. By allowing for the possibility of variation among genetically identical constructs, the process may capture nuances that might be missed by more traditional approaches. This is particularly valuable in synthetic biology methods, where small variations in experimental conditions or cellular environments can have significant impacts on the behavior of engineered organisms.

The iterative splitting process may also address the challenge of integrating data from different sources or experiments. In synthetic biology, data often comes from multiple experiments, potentially conducted under different conditions or using different measurement techniques. By using a probabilistic batch correction model and allowing for the splitting of seemingly identical constructs, the process may effectively normalize data across these different sources, improving the overall quality and consistency of the dataset used for model training. The iterative splitting approach may help identify potential errors or inconsistencies in the experimental data itself. By flagging observations that do not fit well with a current model, the process may highlight areas where there may be measurement errors, mislabeling, or other issues with the data. This may be invaluable for quality control and can help researchers identify and correct problems in their experimental protocols or data collection processes.

In embodiments, iterative splitting processes used by the platform, as described herein, may better account for the complex relationship between genetic sequences and observed phenotypes, and allow for more accurate and reliable predictions. This, in turn, can lead to more effective strain engineering strategies and improved outcomes in synthetic biology applications. Iterative splitting may allow researchers to make better use of the vast amounts of data generated, accounting for the inherent variability and complexity of biological systems. By improving the accuracy and reliability of predictive models, these approaches used by the platform may accelerate the development of new biotechnology applications and enhance understanding of complex biological processes. The iterative splitting process thus provides technical improvements to the technical field of strain engineering, e.g., by enabling identification of biological strains that can perform synthetic biology tasks more effectively. Further, the iterative splitting process provides technical improvements to the technical field of machine learning, e.g., by enabling cleaning and normalization of training data by removing batch effects which can enable machine learning models to be trained more efficiently, e.g., over fewer training iterations and using less training data than would otherwise be required.

In embodiments, the platform, as described herein, may use systems and methods of specialized data collection and biological modelling processing for collecting, processing, and utilizing specialized biological data to enable advanced modeling and optimization of cellular processes. The specialized data collection and biological modelling processing techniques used by the platform may allow for the integration of multiple types of high-dimensional biological data, including gene expression levels, metabolic reaction fluxes, and intracellular metabolite concentrations, to build comprehensive models of cellular metabolism and gene regulation. These models may then be used to predict and optimize cellular phenotypes for biotechnology applications.

As will be described below and throughout this specification, the high-dimensional biological data that is collected and processed by the platform has a high dimensionality and complexity that is well beyond what could be analyzed in the human mind or using simple arithmetic. Rather, the volume and complexity of the specialized data requires processing by automated approaches such as by training machine learning models on the specialized data, and then using the trained machine learning models for inference, e.g., to predict effects of genetic modifications. In some cases, some or all of the high-dimensional biological data can be acquired by a rapid sampling system, and the platform can train and use the machine learning model in tandem with the rapid sampling system. For instance, the platform can perform active learning by identifying data points for which the machine learning model has a high associated prediction uncertainty, and then provide instructions to the rapid sampling system to automatically collect experimental data regarding these data points which can then be used for re-training the machine learning model.

In embodiments, the platform may use a rapid sampling system that enables the collection of time-resolved metabolomics data from living cells with heightened temporal resolution. This system may allow for the near-instantaneous quenching of cellular metabolism, preserving an accurate snapshot of the metabolic state at a given time point. The rapid sampling device may integrate with standard laboratory fermentation equipment and may automatically collect samples at defined time intervals or in response to specific triggers. The rapid sampling system may comprise a series of microfluidic channels and valves that can rapidly divert a small volume of cell culture from a bioreactor into a quenching solution. The quenching solution, typically a cold organic solvent, halts all enzymatic activity within milliseconds. This preserves the concentrations of labile metabolites that might otherwise be rapidly consumed or produced by cellular enzymes. The quenched samples are then automatically transferred to a collection vessel for subsequent metabolite extraction and analysis. By enabling the collection of metabolomics data with sub-second temporal resolution, the platform's systems and methods may allow for the capture of rapid metabolic dynamics that were previously unobservable. This high-resolution time-course data is invaluable for parameterizing kinetic models of metabolism and for observing the propagation of perturbations through metabolic networks. The ability to observe these fast metabolic responses may provide new insights into cellular regulation and adaptation.

In embodiments, the platform, as described herein, may incorporate techniques for measuring intracellular metabolic fluxes. Metabolic fluxes represent the rates of conversion between metabolites and provide a quantitative description of the activity of metabolic pathways. One approach for measuring intracellular fluxes utilizes isotope labeling experiments, where cells are fed isotopically labeled substrates (e.g., 13C-glucose) and the propagation of the label through the metabolic network is tracked over time.

In embodiments, the rapid sampling system may be used in conjunction with isotope labeling experiments to obtain time-resolved labeling data. This may allow for the observation of isotope incorporation dynamics with improved temporal resolution over traditional methods. By fitting this high-resolution isotope labeling data to metabolic models, accurate estimates of intracellular fluxes may be obtained. This flux data may provide a quantitative readout of pathway activities that complement the metabolite concentration data.

In embodiments, to complete a multi-omic dataset, gene expression levels may be measured using RNA sequencing (RNA-seq) or other high-throughput transcriptomics methods. By measuring transcript levels for all genes in the organism, a genome-wide view of gene regulation may be obtained. This expression data may be integrated with the metabolomics and fluxomics data to build comprehensive models of cellular physiology that span from gene regulation to metabolic activity. In embodiments, the collection of this multi-omic dataset—comprising gene expression, metabolite levels, and metabolic fluxes—may provide a rich, high-dimensional view of cellular state. However, fully leveraging this complex data for modeling and engineering applications requires sophisticated computational approaches. To this end, novel machine learning techniques, as described herein, may be used by the platform to integrate and extract insights from these diverse data types.

In embodiments, the platform may use genetic generalization models that can predict cellular phenotypes based on genetic perturbations. These models take as input a description of genetic modifications (e.g., gene knockouts, overexpressions) and predict the resulting changes in metabolite levels, fluxes, and other phenotypes of interest. By training on large datasets of genotype-phenotype pairs, these models deployed by the platform may learn to generalize patterns and predict the effects of novel genetic perturbations. The genetic generalization models may utilize advanced neural network architectures, such as long short-term memory (LSTM) networks, as described herein, to capture the complex relationships between genotypes and phenotypes. The genetic perturbations may be encoded using embeddings derived from protein language models or genome-scale metabolic models. These embeddings may provide a rich representation of gene function that allows the model to reason about the effects of perturbing different genes.

In embodiments, to handle the diverse types of input data, the platform may use models that employ a multi-modal architecture that can process different data modalities (e.g., gene expression, metabolomics) in parallel before integrating them to make predictions. This may allow the models to leverage available data types while respecting their distinct statistical properties. The multi-modal approach may also provide flexibility, allowing predictions to be made even when some data types are unavailable for a given sample. A challenge in training these models may include handling data from diverse experimental conditions and organisms. To address this, transfer learning approaches may be employed by the platform to leverage large public datasets (e.g., genome-wide knockout screens) to pre-train the models before fine-tuning on smaller, more specialized datasets. This may allow the models to learn general principles of cellular function that can then be adapted to specific use cases.

As a specific example, the ASB Platform 100 may use a neural network architecture that includes an input layer that receives gene expression vectors and/or metabolite concentration vectors as inputs, embedding layer(s) that convert categorical genetic modifications into dense vector representations, attention layer(s) that use self-attention mechanisms to capture dependencies between different genes and metabolites, pooling layer(s) that aggregate the embeddings using average pooling to create a unified representation, and/or fully connected layer(s) that process the pooled embeddings to generate the final prediction of strain performance. This architecture may enable the integration of diverse data types and facilitate the extraction of complex patterns essential for accurate strain performance prediction.

The ASB Platform 100 may represent input data for the models in structured formats tailored to each data type. For example, the platform 100 may encode genetic sequences as embeddings (e.g., where each embedding may correspond to a nucleotide). Techniques for generating embeddings are described elsewhere herein. As another example, the platform 100 may normalize metabolite concentration data and represent such data as continuous numerical vectors that may be input to a model.

In embodiments, the platform may use genetic generalization models that are trained using a multi-task learning approach, where multiple related prediction tasks (e.g., predicting different metabolites or fluxes) are learned simultaneously. This may encourage the model to learn generalizable features that are relevant across multiple cellular processes. The platform may balance the contributions of different tasks and datasets during training to avoid overfitting to any single data source.

In embodiments, to handle the uncertainty inherent in biological data and predictions, the platform may use models that can be designed to output probabilistic predictions rather than point estimates. This may be achieved using Bayesian neural network techniques or by training ensembles of models. The probabilistic outputs may allow for rigorous quantification of prediction uncertainty, which is critical for guiding experimental design and decision-making in biotechnology applications. In addition to the neural network-based approaches, mechanistic modeling techniques may also be employed by the platform to leverage prior knowledge of cellular biochemistry. One such approach is the use of lin-log models, as described herein, which provide a simplified kinetic description of metabolic reactions. These models express reaction rates as linear functions of the logarithms of metabolite concentrations and enzyme levels. This formulation may capture key properties of enzyme kinetics while remaining computationally tractable for large-scale modeling. Lin-log models are particularly well-suited for integrating the multi-omic datasets collected using the rapid sampling system. The models can be parameterized using a combination of metabolite concentrations, enzyme levels (inferred from gene expression data), and metabolic fluxes. This may allow for the creation of genome-scale kinetic models that can predict metabolic dynamics and steady-state fluxes.

The lin-log approach may capture complex regulatory effects, including allosteric regulation and transcriptional feedback, within a relatively simple mathematical framework. This may make it possible to model large metabolic networks with hundreds or thousands of reactions while retaining mechanistic interpretability. The models may also be updated as new data becomes available, allowing for iterative refinement as more experiments are performed. In embodiments, to fully leverage the predictive power of these models for strain engineering, the platform may use multi-objective optimization techniques. These methods may allow for the simultaneous optimization of multiple cellular properties, such as product yield, growth rate, and byproduct formation. By framing strain design as a multi-objective optimization problem, trade-offs between different engineering goals can be explicitly explored.

In embodiments, the multi-objective optimization algorithms used by the platform may employ techniques from evolutionary computation, such as genetic algorithms and particle swarm optimization, to efficiently search the high-dimensional space of possible genetic interventions. The genetic generalization models may be used as surrogate models within the optimization loop, allowing for rapid in silico evaluation of candidate designs. This may enable the exploration of a much larger design space than would be possible through experimental approaches alone.

In embodiments, to handle the inherent uncertainty in biological systems and model predictions, robust optimization techniques may be employed by the platform. These methods may use designs that perform well across a range of possible scenarios, accounting for both experimental variability and model uncertainty, and which may lead to the identification of genetic designs that are more likely to translate successfully from in silico predictions to experimental implementation. In embodiment, the multi-objective optimization framework may also incorporate experimental design considerations, such as the cost and feasibility of implementing different genetic modifications. This may allow for the generation of practically realizable strain designs that balance performance improvements with implementation complexity. The optimization may also suggest sets of strains to build for testing, maximizing information gain to improve model accuracy in subsequent iterations.

In embodiments, to support the analysis and interpretation of the large datasets and model outputs generated by the methods used by the platform, advanced visualization and exploration tools may be used. These tools may allow researchers to interactively explore high-dimensional datasets, visualize predicted metabolic states, and examine the trade-offs between different engineering objectives. Network-based visualizations may be used to represent metabolic pathways and regulatory interactions, with data overlays showing predicted or measured changes in metabolite levels, fluxes, and gene expression. In an example, the use of interactive Pareto fronts to display the results of multi-objective optimizations may be used by the platform. These plots show the trade-offs between different objectives and allow users to explore the characteristics of different optimal designs. Linked views allow for drilling down into the specific genetic modifications and predicted metabolic changes associated with each point on the Pareto front.

In embodiments, to ensure the reliability and reproducibility of data analysis pipelines created by the platform, automation and quality control measures may be implemented. Automated data processing workflows may handle the normalization, filtering, and integration of raw data from various experimental platforms. These workflows may incorporate best practices for handling common issues in biological data, such as batch effects and missing values, as described herein. Quality control metrics may be automatically calculated and visualized for each dataset, allowing for rapid identification of potential issues or outliers. Statistical methods for outlier detection and batch correction may be applied to ensure data consistency across experiments. Version control systems may be used to track changes in data processing pipelines and model implementations, ensuring reproducibility and facilitating collaboration.

To handle the large volumes of data generated by high-throughput experiments, scalable data storage and computation infrastructure may be used by the platform. This may include distributed file systems for efficient storage and retrieval of large datasets, as well as cloud-based computation platforms for running computationally intensive modeling and optimization tasks. Container-based deployment by the platform may ensure consistency across different computing environments.

In embodiments, the systems and methods of the platform may be designed with modularity and extensibility in mind, allowing for the easy incorporation of new data types, modeling approaches, and optimization algorithms as they are developed. Application programming interfaces (APIs) may provide programmatic access to data and models, facilitating integration with existing bioinformatics tools and workflows.

In embodiments, a computer-implemented method for data integration in an AI-guided analytic platform for development of biologic synthesis processes may comprise: receiving, by a platform, biologic data from a plurality of databases, wherein the biologic data use different data formats and/or semantics; converting the received biologic data into at least one standardized data format to create an integrated dataset; processing the integrated dataset through at least one data normalization process to minimize batch-specific systemic variation; storing the normalized biologic data in a structured format that describes biologic components and their relationships to other components; applying at least one machine learning method to the normalized biologic data to generate at least one predictive model for synthetic biology design; and outputting at least one specification for biologic system design based on the at least one predictive model.

In embodiments, the data normalization processes used by the platform may include applying a Bayesian statistical model that incorporates prior knowledge about strain behavior, modeling different sources of variation including biological effects and technical factors, estimating strain performance while accounting for batch effects and other sources of systematic variability, batch effect correction, wherein a batch effect correction addresses systematic variations across at least one of a plurality of experimental runs, equipment, or operators, multi-modal data integration, or some other type of data normalization process.

In embodiments, multi-modal data integration may include data relating to at least one of an enzyme level, a metabolite concentration, or a gene expression level.

In embodiments, data normalization processes used by the platform may include standardized nomenclature across different data sources, quality control normalization, including flagging an anomalous data point, and/or flagging a well or sample that failed during an experiment.

In embodiments, data normalization processes used by the platform may include experiment normalization, such as experiment normalization to account for a variation across a plurality of experimental runs using a similar strain or condition. Experiment normalization used by the platform may implement a statistical method to minimize impact of a technical variation, and/or may use a control sample and spike-in standard for validation.

In embodiments, data normalization processes used by the platform may include cross-platform data harmonization, including but not limited to data harmonization that standardizes data from a plurality of experimental platforms and setups.

In embodiments, data normalization processes used by the platform may include time series data normalization, wherein the time series data normalization includes normalizing data relating to time-varying growth conditions, wherein the time series data normalization includes normalizing data relating to variations in a feed profile or fermentation parameter.

In embodiments, data normalization processes used by the platform may include knowledge graph-based normalization, including but not limited to knowledge graph-based normalization that represents biological entities and relationships in standardized format, knowledge graph-based normalization that associates information across a plurality of experiments or organisms, and/or knowledge graph-based normalization integrates a plurality of biological data types.

In embodiments, a predictive model used by the platform may include, but is not limited to, a long-short term memory model, a transformer model, a convolutional neural network model, a perceptron model, or a multi-modal deep learning architecture including, but not limited to, at least one of a feed forward neural network, a feedback neural network, a convolutional neural network, a gated recurrent neural network, a long short-term memory network, a transformer model, a foundation model, a large language model, a single and multi-layer perceptron network, a recurrent neural network, a dual-process artificial neural network, a radial basis function neural network, a self-organizing neural network, a modular neural network, a physical neural network, a multi-layered neural network, a autoencoder neural network, a probabilistic neural network, a time delay neural network, a regulatory feedback neural network, a hopfield neural network, a boltzmann machine neural network, a self-organizing map (SOM) neural network, a learning vector quantization (LVQ) neural network, a echo state neural network, a bi-directional neural network, a hierarchical neural network, a stochastic neural network, a genetic scale RNN neural network, a committee of machines neural network, a associative neural network, a instantaneously trained neural network, a spiking neural network, a neocognitron neural network, a dynamic neural network, a cascading neural network, a neuro-fuzzy neural network, a compositional pattern-producing neural network, a memory neural network, a hierarchical temporal memory neural network, a deep feed forward neural network, a gated recurrent unit neural network, a variational auto encoder neural network, a de-noising auto encoder neural network, a sparse auto-encoder neural network, a markov chain neural network, a restricted boltzmann machine neural network, a deep belief neural network, a deep convolutional neural network, a de-convolutional neural network, a deep convolutional inverse graphics neural network, a generative adversarial neural network, a liquid state machine neural network, an extreme learning machine neural network, a deep residual neural network, a neural turing machine neural network, and a holographic associative memory neural network.

In embodiments, the platform may include a computer-implemented method for data quality assurance in an AI-guided analytic platform for development of biologic synthesis processes, comprising: collecting raw experimental data associated with a strain performance measurement; implementing a data normalization and quality control procedure to process the raw experimental data; validating a genotype of a strain through a data intake process; generating an analytical measure associated with quality control for the experimental data; identifying an outlier in an experimental dataset; maintaining metadata about an experimental condition or processing step; and storing processed and validated data in a knowledge graph structure that tracks data provenance from a raw experimental measurement to a processed value.

In embodiments, the platform may collect raw experimental data measuring key metabolites across a population of engineered strains, detecting and flagging anomalous data points through automated quality control, and/or identifying wells or samples that exhibit contamination or produce readouts outside expected ranges based on historical data.

In embodiments, the platform may include strain performance measurement that is an expression level, that is a metabolite concentration, that is growth rate measurement, and/or that is enzyme activity level.

In embodiments, the platform may include a system for ensuring data quality in an AI-guided analytic platform for development of a biologic synthesis process, comprising: one or more processors; memory storing instructions that, when executed by the one or more processors, cause the platform to implement a multi-objective optimization system for performing multi-objective optimizations of the biologic synthesis process, wherein the multi-objective optimization system comprises: a data intake and staging pipeline configured to: collect raw data from a plurality of experimental sources; convert the raw data into at least one standardized format; apply a quality assurance step to identify and correct error and inconsistency in the data; apply a normalization technique to remove a batch effect or technical variation; validate that the normalization technique preserve a specified biologic signal; and a knowledge management system configured to: maintain a log and audit trail for a platform data processing activity; track data lineage from a raw measurement to a processed value; and enable verification of a data processing step to confirm scientific validity.

In embodiments, the platform may include a method for hit identification in an AI-guided analytic platform for development of biologic synthesis processes, comprising: collecting raw experimental data on strain performance; normalizing the experimental data using a probabilistic approach to generate normalized strain performance data; representing strains as probability distributions over possible performance levels, wherein the probability distributions capture both a point estimate of the strain performance and uncertainty around the estimate; defining a hit based on the probability distributions by determining the strains having a specified probability of outperforming a parent strain by a predetermined margin; and identifying a promising strain for further investigation based on the defined hit.

In embodiments, defining a hit may comprise setting a threshold for minimum performance improvement over the parent strain, calculating a probability that each strain exceeds a threshold, and/or ranking strains based on their full performance distribution rather than point estimates.

In embodiments, the platform may include a method for hit identification in an AI-guided analytic platform for development of biologic synthesis processes, comprising: one or more processors; memory storing instructions that, when executed by the one or more processors, cause the platform to implement a multi-objective optimization system for performing multi-objective optimizations of the biologic synthesis processes, wherein the multi-objective optimization system comprises: performing data quality assurance on experimental strain performance data; applying a Bayesian data normalization process to the experimental strain performance data; generating probability distributions representing strain performance and associated uncertainty for a plurality of strains; identifying hits by comparing the probability distributions to defined at least one performance threshold, wherein the hits comprise strains exhibiting improved performance regarding a performance criterion relative to a reference strain; and outputting the identified hits for further optimization and investigation.

In embodiments, data quality assurance may include collecting metadata about experimental conditions, tracking data provenance from raw measurements through processing steps, and/or identifying and correcting errors or inconsistencies in the data.

In embodiments, the platform may include a system for integrating synthetic biology data in an AI-guided analytic platform for development of a biologic synthesis process, comprising: one or more processors; memory storing instructions that, when executed by the one or more processors, cause the platform to implement a multi-objective optimization system for performing multi-objective optimizations of biologic synthesis processes, wherein the multi-objective optimization system comprises: a data intake and staging pipeline configured to: collect biologic data from a plurality of data sources; integrate the collected biologic data into a computationally appropriate form; normalize the integrated biologic data using batch effect correction; validate quality and consistency of the normalized biologic data; store the validated biologic data in a structured format describing relationships between biologic entities; and a machine learning model configured to analyze the stored validated biologic data to generate at least one prediction for synthetic biology system design.

In embodiments, a structured data format may be a bipartite graph database structure, wherein the bipartite graph database structure organizes data into at least one molecule node and at least one process node, wherein the at least one molecule node represents at least one of a molecules, atomic elements, ions, compounds, nucleic acids, proteins, or macromolecules, wherein the at least one process node represents at least one of chemical reactions, protein folding, transport, regulatory interactions, or active site binding, and wherein connections between nodes indicate roles that create the relationships between a molecule and a process.

In embodiments, a structured data format may be a non-relational database format, a knowledge graph structure, or some other format type.

In embodiments, the platform may include a computer-implemented method for normalizing synthetic biology data in an AI-guided analytic platform for development of biologic synthesis processes, comprising: receiving experimental data associated with synthetic biology development from a plurality of sources; performing a data quality assurance on the received experimental data to identify at least one anomalous data point; applying a Bayesian statistical normalization model to the experimental data to: model a batch-specific systemic variation; account for a technical factor contributing to a batch effect; separate a biologic signal from the technical factor; and generate normalized synthetic biology data; and outputting the normalized synthetic biology data for use in a machine learning application.

In embodiments, data quality assurance may comprise detecting a well or sample that failed to grow properly, identifying samples exhibiting contamination, flagging a readout that fall outside an expected range based on historical data for a similar strain, and/or identifying a potential measurement error or mislabel in the experimental data.

In embodiments, modeling the batch-specific systemic variation may comprise constructing a plate notation model representing at least one strain effect, constructing a plate notation model representing at least one experimental effect, constructing a plate notation model representing at least one plate-to-plate variation, constructing a plate notation model representing at least one plate lot effect, and/or constructing a plate notation model representing at least one position effect of a sample on a plate. A plate notation model may provide a formal representation of at least one factor contributing to observed data.

In embodiments, the platform may include a system for normalizing synthetic biology experimental data in an AI-guided analytic platform for development of a biologic synthesis process, comprising: one or more processors; memory storing instructions that, when executed by the one or more processors, cause the platform to implement a multi-objective optimization system for performing multi-objective optimizations of the biologic synthesis process, wherein the multi-objective optimization system comprises: intake raw experimental data from a plurality of synthetic biology experiments; apply a quality control process to identify an anomalous experimental data point: construct a hierarchical Bayesian model representing: a strain performance measurement; an experimental variability factor; and a batch effect; fit the hierarchical Bayesian model to the experimental data to infer underlying strain performance while accounting for at least one confounding factor; generate at least one uncertainty estimate for a normalized performance value; and output normalized experimental data with associated uncertainty estimates.

In embodiments, control processes used by the platform may include analyzing repeated measurements of strains across multiple plates, identifying a strain exhibiting inconsistent behavior when measured multiple times, detecting a systematic variation between a plurality of experimental runs of genetically identical strains, and/or flagging data points where strain performance variance exceeds an expected threshold.

In embodiments, constructing a hierarchical Bayesian model may comprise incorporating prior data relating to expected strain behavior, modeling multiple sources of experimental variability, representing relationships between a small-scale and a large-scale experiment, and/or generating at least one probability distribution that captures uncertainty in strain performance measurements.

In embodiments, the platform may include a computer-implemented method for handling batch effects in an AI-guided analytic platform for development of a biologic synthesis process, comprising: receiving biologic experimental data from a plurality of experiments; detecting a systematic variation between the experiments that is not related to a biologic factor of interest; applying a data normalization technique to minimize batch-specific systemic variation while preserving underlying biologic signals; generating probability distributions representing experimental outcomes to provide a summary of uncertainty; using a machine learning model to identify and correct batch effects directly from the data without requiring explicit modeling of all possible sources of variation; and outputting normalized biologic data with reduced batch effects for use in strain engineering.

In embodiments, the platform may include a method for managing batch effects in synthetic biology experiments in an AI-guided analytic platform for development of a biologic synthesis process, comprising: one or more processors; memory storing instructions that, when executed by the one or more processors, cause the platform to implement a multi-objective optimization system for performing multi-objective optimizations of biologic synthesis processes, wherein the multi-objective optimization system comprises: collect raw experimental data on strain performance across a plurality of experiments; implement a data normalization and quality control process to address variability between experiments of genetically identical strains; represent hits and non-hits as probability distributions; allow definition of at least one threshold for hit identification; apply an iterative splitting process to account for variation between constructs with identical genetic makeup; and output batch-effect corrected data suitable for machine learning model training and strain optimization.

In embodiments, the platform may include a computer-implemented method for iterative splitting in synthetic biology development in an AI-guided analytic platform for development of biologic synthesis processes, comprising: receiving data associated with sequences having identical genetic makeup but exhibiting different behaviors; initially labeling constructs with identical sequences as distinct entities; fitting a probabilistic model to observations of the constructs, wherein model accounts for experimental conditions and measurement techniques that influence construct behavior; processing the data through a data quality assurance pipeline to identify and validate variations between genetically identical constructs; and generating normalized data across different experimental sources based on a probabilistic batch correction model.

In embodiments, the platform may identify an observation that is unlikely to have been generated by a current probabilistic batch correction model; splitting the identified observation into separate entries with independent parameters; and refitting the probabilistic batch correction model after each splitting iteration, wherein fitting the probabilistic batch correction model comprises starting with a prior parameter that assumes constructs with identical sequences have identical activity, wherein fitting the probabilistic batch correction model comprises requiring empirical evidence to override a prior parameter, wherein fitting the probabilistic batch correction model comprises adjusting at least one model parameter based on an observed variation between identical sequences.

In embodiments, the platform may include a system for iterative data processing in synthetic biology development in an AI-guided analytic platform for development of biologic synthesis processes, comprising: one or more processors; memory storing instructions that, when executed by the one or more processors, cause the system to: receive biologic sequencing data containing systemic variation across multiple batches; implement an iterative splitting process that: identifies constructs with identical genetic sequences exhibiting different behaviors; labels the identified constructs as separate entities; applies a probabilistic model to account for experimental condition variations; flags observations that deviate from predicted model behavior to identify potential measurement errors or data inconsistencies; and generate normalized datasets that account for validated variations between genetically identical constructs while maintaining data quality assurance.

In embodiments, implementing the iterative splitting process may further comprise: maintaining sufficient anchor points between datasets to enable data combination across experimental sites; identifying when anchor points exhibit significantly different behaviors; and adjusting at least one model parameter to account for a validated difference while preserving ability to combine datasets.

In embodiments, the platform may estimate a scaffold parameter based on a validated construct variation; use the estimated scaffold parameter to calculate a more accurate expression estimate for a strain; and update the probabilistic model based on a refined expression estimate.

In embodiments, the platform may flag observations that deviate from predicted model behavior comprises: identifying a vertical outlier in a model fit visualization; calculating a probability assignment for each observation; and selecting an observation with a low probability assignment as a candidate for splitting.

In embodiments, the platform may include a computer-implemented method for training artificial intelligence models with specialized biologic data in an AI-guided analytic platform for development of a biologic synthesis process, comprising: collecting multimodal biologic data including at least one of a gene expression level, mRNA, metabolic reaction fluxes, or intracellular metabolite concentrations from biologic systems; processing the collected biologic data through data normalization and quality assurance steps to create model-ready data; and generating at least one output predicting an effect of genetic modification on a metabolite level or a reaction flux.

In embodiments, normalized biologic data may be converted from a first structured format to a second format suitable for model training.

In embodiments, one or more artificial intelligence models may be trained using the model-ready data to predict a cellular phenotype based on a genetic perturbation, wherein training the one or more artificial intelligence models comprises: using a knowledge graph to represent biological entities as nodes; representing relationships between entities as edges; and capturing biological relationships in a format appropriate for use by machine learning algorithms.

In embodiments, collecting multimodal biological data may comprise: obtaining RNA sequencing data for genome-wide gene expression levels; measuring metabolic reaction fluxes; and collecting metabolite concentration data using mass spectrometry, wherein the mass spectrometry is liquid chromatography-mass spectrometry, wherein the mass spectrometry is gas chromatography-mass spectrometry.

In embodiments, processing the collected multimodal biological data may comprise: identifying and correcting batch-specific systemic variation; standardizing nomenclature across different data sources; and correcting for missing data to ensure consistency across experimental setups.

In embodiments, the platform may include a system for specialized biologic data processing and model training in an AI-guided analytic platform for development of a biologic synthesis process, comprising: one or more processors; memory storing instructions that, when executed by the one or more processors, cause the platform to implement a multi-objective optimization system for performing multi-objective optimizations of biologic synthesis processes, wherein the multi-objective optimization system comprises: a data collection system configured to collect time-resolved metabolomics data from living cells; a data processing pipeline configured to: integrate multiple types of high-dimensional biologic data; normalize and correct batch effects in the biologic data; and transform the biologic data into a format suitable for machine learning.

In embodiments, the platform may use a data collection system that is a rapid sampling system, wherein the rapid sampling system comprises: automated sampling mechanisms for collecting standardized samples; near-instantaneous quenching of cellular metabolism; and integration with liquid chromatography-mass spectrometry and gas chromatography-mass spectrometry for metabolite analysis.

In embodiments, one or more artificial intelligence models may be trained using processed data to predict a cellular phenotype.

In embodiments, the data processing pipeline may be further configured to: track data lineage from a raw experimental measurement to a processed value; maintain detailed metadata about experimental conditions; and validate a normalization method using a control sample.

In embodiments, the platform may integrate multiple types of high-dimensional biological data comprises: combining gene expression data from RNA sequencing; incorporating flux data from an isotope-labeled experiment; and merging a metabolite concentration measurement from mass spectrometry.

In embodiments, the platform may include a system for training specialized biologic models in an AI-guided analytic platform for development of biologic synthesis processes, comprising instructions that when executed cause a processor to: collect multimodal biologic data; process the collected multimodal biologic data through quality assurance steps to identify and correct errors or inconsistencies; employ multi-modal deep learning architectures with a separate encoding branch for different data modalities; combine encoded representations through fusion layers; and generate a prediction about cellular phenotypes based on the processed multimodal biologic data.

In embodiments, the multimodal biologic data may derive from at least one integrated sensor and/or automated sampling system.

In embodiments, the multi-modal deep learning architectures may comprise: the separate encoding branches for gene expression data; dedicated pathways for metabolite profile processing; and specialized branches for reaction flux analysis.

In embodiments, processing the collected multimodal biologic data may comprise: applying batch effect correction across experimental runs; normalizing data across different organisms and conditions; and ensuring data consistency for machine learning applications.

In embodiments, generating predictions may comprise: evaluating effects of genetic modifications on metabolic pathways; predicting changes in metabolite concentrations; and estimating reaction flux distributions in response to genetic perturbations.

In embodiments, the multi-modal deep learning architecture used by the platform may be a combination of a plurality of multi-modal deep learning architectures.

The data normalization facility provides a technical improvement to machine learning technology by enabling more efficient machine learning training and more accurate machine learning inference. More specifically, as outlined above, the data normalization facility can integrate biologic data from a plurality of databases and then normalize the biologic data to minimize batch-specific systemic variation. The normalized biologic data can then be used for training machine learning models. The normalization can enable more efficient machine learning training, e.g., by reducing the likely of over-fitting, and by reducing the amount of training data and the number of training iterations required for the machine learning model to achieve an acceptable performance. Further, trained machine learning model can achieve a higher prediction accuracy as a result of the normalization, e.g., because the normalization removes errors, inconsistencies, and irrelevant variations in the biologic data, thereby allowing the machine learning model to learn more accurate and generalizable patterns.

Biological Parameters and Measurements Facility

In embodiments, the ASB Platform 100 may include a biological parameters and measurements facility 2400 that includes systems and methods for receiving, transmitting, storing, analyzing and compiling biological parameters and measurements for use by the ASB Platform 100. In an example, a configuration module 7910 of the ASB Platform 100 may compile biological data, parameters and/or measurements to produce model configuration data that is suitable for a selected modeling technique. In another example, a model generator 7912 of the ASB Platform 100 may select technical parameters that fit the goals for modeling the behavior of a biological system while accounting for constraints of the selected modeling technique. These technical parameters may be based on biological data, parameters and/or measurements stored at least in part in the biological parameters and measurements facility 2400 and relevant to the system being modeled. In embodiments, biological data, parameters and/or measurements may include measurements related to various biological systems, such as information on genes, RNA transcripts, proteins, biochemical reactions, and more. Biological data, parameters and/or measurements may be stored in structured formats within, for example, a data repository 7902, which describes the details of biological objects and their relationships. This structured data may include biological data, parameters and/or measurements that are fundamental to the processes being modeled.

In embodiments, the biological parameters and measurements facility 2400 may use data structures that are optimized for efficient storage and retrieval of biological parameters and measurements, as mentioned above for the data intake and staging pipeline 2200. Additionally or alternatively, the biological parameters and measurements facility 2400 may implement caching mechanisms that store frequently accessed biological parameters in high-speed memory and store historical and/or less frequently accessed data in lower-cost storage tiers.

In embodiments, the biological parameters and measurements facility 2400 may validate data to ensure data quality and consistency. For example, the facility may use machine learning models trained on known-good biological parameters to detect anomalous measurements, verify that values are within designated ranges that are defined based on physically possible parameter values for specific biological systems (e.g., discarding values that are outside the range), and/or the like. In embodiments, the biological parameters and measurements facility 2400 may maintain audit logs that specify parameter modifications, where the audit logs may include metadata about measurement conditions, instrument calibration status, data processing steps, and/or the like.

In embodiments, the biological parameters and measurements facility 2400 may use data access patterns that are optimized for different types of biological measurements. For example, the biological parameters and measurements facility 2400 may use (e.g., when retrieving biological data for any of the operations described herein) prefetch algorithms that predict which parameters will be needed based on historical access patterns, model requirements, or other values. The biological parameters and measurements facility 2400 may also use parameter-specific compression algorithms for storage that maintain precision for different types of biological measurements. In embodiments, the biological parameters and measurements facility 2400 may provide interfaces (e.g., via APIs) for real-time streaming of biological parameters from laboratory instruments.

In embodiments, referring to FIG. 1, the ASB platform 100 may include a facility for data-as-a-service (DaaS) functionality encompassing an ecosystem of interconnected processes and mechanisms designed to discover, obtain, transmit, transform and analyze data, including data from third parties that are external to the ASB platform 100, as well as report on modeling and other analytic results and processes. Data identification processes may serve as a foundation of DaaS implementation, beginning with comprehensive source discovery mechanisms. These mechanisms may employ scanning technologies to systematically catalog available data sources throughout an enterprise ecosystem, including but not limited to laboratory, pharmaceutical, or experimental data repositories. The discovery process may identify various data types and formats, ranging from structured databases to unstructured data and/or document repositories, and create mappings of data relationships and dependencies to establish and record lineages between different data elements, sources and types. DaaS processes, as described herein, may evaluate data reliability and authenticity evaluation during the data discovery and identification phase, for example employing algorithms to assess the credibility and trustworthiness of each data source.

In embodiments, metadata analysis may comprise a component of the identification process, where the system conducts detailed examination and extraction of metadata attributes. This process may involve categorization of data elements based on their characteristics, such as experimental or business context. The system may create data dictionaries that serve as reference points for understanding data structure and meaning and established data lineage paths that track the origin and transformation of data elements throughout a DaaS lifecycle. Automated classification processes may include the use of machine learning algorithms to recognize content patterns and categorize information effectively. These algorithms may analyze data content to determine sensitivity levels and apply appropriate classifications. The DaaS system, as described herein, may include governance elements to identify and tag information sensitive information (e.g., proprietary or trade secret data, personally identifiable information and the like) to ensure compliance with organization rules and/or external regulations, such as governmental, while simultaneously categorizing information to facilitate proper data governance and usage.

In embodiments, DaaS functionality may include data import mechanisms employing ingestion methods to accommodate different data sources and requirements. Batch processing capabilities may handle large volumes of historical data, while real-time streaming mechanisms may process continuous data flows from active sources, including third party sources that are external to the ASB platform 100. API-based integration may enable connectivity with external systems and services, and file-based transfers may support traditional data exchange methods. The extraction process within the import mechanism may handle a plurality of data formats and parse structured and unstructured data, converting file formats into standardized structures for processing. The system may include robust capabilities for handling compressed files and managing encrypted data, ensuring data security throughout the import process.

In embodiments, DaaS functionality may include connection management for maintaining data handling, procurement and ingestion through multiple protocol support. The system may implement authentication management to ensure secure data access, while connection pooling may optimize resource utilization. Error handling and retry logic may be used to ensure reliable data transmission even in challenging network conditions.

In embodiments, DaaS functionality may include data quality assessment such as implementing validation rules to ensure data integrity. These rules may verify data types, check value ranges, and validate patterns to maintain consistency. The DaaS system may perform referential integrity validation to ensure relationships between data elements remain intact and accurate.

In embodiments, DaaS functionality may include completeness analysis within a quality assessment framework to systematically evaluate data for missing values and required fields. For example, the DaaS system may analyze data density to identify potential gaps in coverage and measure various metrics to quantify data completeness and ensure that data meets specified quality standards before proceeding to further processing stages.

In embodiments, DaaS functionality may include accuracy verification and cross-reference validation techniques to confirm data correctness. For example, historical trend analysis may identify potential anomalies in data patterns, while statistical anomaly detection algorithms may flag suspicious values for review. The DaaS system may ensure compliance with established business rules, maintaining data quality standards throughout the process.

In embodiments, DaaS functionality may include data transformation processes and data normalization procedures that standardize data formats and resolve inconsistencies. These procedures may eliminate redundancies in the data while optimizing data structures for efficient processing and storage, requiring, for example, less computer processes power and/or time, less physical data storage requirements, consolidation of computing resources and the like. The DaaS system may employ algorithms to identify and handle outliers, conducting thorough impact assessments before applying automated corrections.

In embodiments, DaaS functionality may include a data transformation phase that includes data enrichment capabilities that integrate reference data from authoritative sources. The DaaS system may calculate derived values based on, for example rules or information derived from other data or analytic resources (e.g., information known about *E. coli* genetics) and add contextual information to enhance data utility. Relationship mapping procedures may establish connections between different data elements, creating a rich network of interrelated information.

In embodiments, DaaS functionality may include data standardization for implementing format harmonization procedures. These procedures may ensure or improve consistency across different data sources through common data model mapping and format conversion rules. The DaaS system may apply, for example, unit standardization to ensure measurement consistency and normalize character encoding to prevent interpretation errors.

In embodiments, DaaS functionality may include semantic alignment within the standardization framework to improve consistency in terminology and meaning across different data sources. The DaaS system may maintain standard code sets and/or unified naming conventions to facilitate clear communication and understanding. For example, common taxonomies may provide a structured framework for organizing and categorizing information. The DaaS system may utilize a structural unification process to align schemas from different sources into a coherent whole. Techniques, including but not limited to field mapping procedures may improve consistency of representation of similar data elements, while relationship standardization may maintain proper connections between different data entities. Hierarchy normalization may establish clear organizational structures within the data.

In embodiments, DaaS functionality may include quality control mechanisms to maintain continuous monitoring of data quality through the automated DaaS processes. These systems may track a plurality of quality metrics and generate detailed scorecards to assess data health. Alert mechanisms may notify appropriate personnel of quality issues, while performance monitoring may ensure efficient system operation.

In embodiments, DaaS functionality may include error management procedures within the quality control framework to provide systematic approaches to handling data issues. For example, the DaaS system may implement resolution workflows to address identified problems and conduct root cause analysis to prevent future occurrences. Comprehensive correction tracking may maintain records of all modifications made to the data.

In embodiments, DaaS functionality may include the creation of audit trails to provide detailed documentation of system activities and changes. For example, the DaaS system may capture processing history and track changes to data elements, maintaining records of user actions and system modifications. Such comprehensive logging may ensure transparency and accountability in data management.

In embodiments, DaaS functionality may include data integration processes for coordinating multiple data sources. For example, schema mapping procedures may align different data structures, while identity resolution may ensure consistent entity representation across sources. Reference data management may maintain consistency in shared information elements.

In embodiments, DaaS functionality may include transformation rules within the integration framework for implementing business logic and validation criteria. For example, the DaaS system may handle exceptions according to defined procedures and maintain consistent processing across different data sources. Output generation may ensure proper format compliance and manage delivery scheduling effectively.

In embodiments, DaaS functionality may include performance optimization processes to ensure efficient processing through parallel computation and sophisticated resource allocation. For example, cache management and query optimization techniques may be used to improve system responsiveness, while scalability features may enable the system to handle growing data volumes effectively.

In embodiments, DaaS functionality may include security and compliance processes for implementing comprehensive access controls and data protection measures. For example, the DaaS system may maintain authentication and authorization mechanisms, while activity monitoring may ensure proper system usage. Data protection may include encryption standards and privacy controls to safeguard sensitive information.

In embodiments, DaaS functionality may include reporting and analytics capabilities to provide detailed insights into system operation and data quality. For example, quality reporting may generate metrics and trend analysis, while operational analytics may track system performance and resource utilization. Business intelligence features may support decision-making through visualization and predictive analysis capabilities, as described herein.

In embodiments, that DaaS system may include analytics-as-a-service (AaaS) representing an ecosystem of analytical capabilities designed to transform raw data into actionable insights through automated, intelligent processes, including the AI, machine learning, neural networking methodologies and processes as described herein. In embodiments, the AaaS processes may identify appropriate analytical methods based at least in part on an assessment of data characteristics and analytic objectives. The system may employ classification algorithms to evaluate data types, distributions, and relationships, determining which analytical approaches would yield the most meaningful results. This intelligent method selection process may consider factors such as data volume, velocity, variety, and veracity to recommend appropriate analytical techniques.

In embodiments, the AaaS system may include a library of analytical methods, ranging from descriptive statistics to advanced machine learning algorithms. It may evaluate the applicability of different methods based on data characteristics, sample sizes, and statistical power requirements. The selection process may also consider computational efficiency and resource requirements to ensure optimal performance. Improving the computation efficiency may lessen the computational power, time and cost associated with analysis on the ASB platform 100. Method identification may incorporate automated validation procedures to verify the suitability of selected analytical approaches. These procedures may examine assumptions about data distributions, independence, and other statistical prerequisites. The system may provide documentation of method selection criteria and potential limitations to ensure transparency in the analytical process.

In embodiments, the AaaS system may include data import processes, such as utilizing ETL (Extract, Transform, Load) capabilities to gather data from diverse sources. The system may support multiple data formats and protocols, implementing parsing algorithms to handle structured, semi-structured, and unstructured data. Import procedures may include automated validation checks to ensure data integrity during the transfer process. Data preparation may involve cleaning and standardization procedures. The system may identify and handle missing values through various imputation methods, considering the statistical implications of different approaches, and implement outlier detection algorithms that consider both univariate and multivariate relationships in the data. The preparation phase may include automated feature engineering capabilities that create derived variables and transform existing features to improve analytical effectiveness. The system may employ dimension reduction techniques when appropriate, identifying and preserving the most informative aspects of high-dimensional datasets.

In embodiments, the AaaS system may include quality assurance procedures that encompass multiple layers of validation to ensure data reliability and analytical integrity. For example, the system may perform statistical checks to verify data distributions, identify anomalies, and assess data quality metrics. These checks may include, for example, tests for normality, homoscedasticity, and other statistical properties relevant to the chosen analytical methods. The validation processes may include automated assessment of data completeness and consistency across different sources. The system may implement cross-validation procedures to ensure the robustness of analytical results and maintain detailed quality scorecards that track various metrics throughout the analytical processes. Data quality monitoring may extend to the evaluation of temporal stability and trend analysis. The system may identify potential data drift and concept drift, implementing appropriate adjustments to maintain analytical accuracy over time and provide documentation of quality issues and remediation actions taken.

In embodiments, the AaaS system may include a modeling phase employing algorithms to construct and validate analytical models. For example, the system may implement automated model selection procedures that evaluate multiple approaches based on performance metrics and business requirements and consider factors such as model complexity, interpretability, and computational efficiency in the selection process. Model development may include comprehensive parameter optimization through techniques such as grid search and Bayesian optimization. The system may implement cross-validation procedures to assess model stability and generalization capability and maintain documentation of model specifications, training procedures, and validation results. The analysis phase may include automated interpretation of results, generating insights and recommendations based on model outputs. The system may implement visualization techniques to communicate findings and provide detailed documentation of analytical procedures and assumptions to ensure transparency and reproducibility.

In embodiments, the AaaS system may include model validation procedures encompassing a plurality of approaches to ensure analytical reliability. For example, the system may implement both in-sample and out-of-sample testing to assess model performance and conduct sensitivity analyses to evaluate model robustness under different conditions and assumptions. Testing procedures may include automated assessment of model assumptions and limitations. The system may identify potential issues, including but not limited to multicollinearity, heteroscedasticity, and other statistical violations that could affect model validity, and provide documentation of validation procedures and results. The validation processes may include automated monitoring of model performance over time, and implementing procedures to detect model degradation and trigger retraining when necessary. The system may maintain audit trails of model changes and performance metrics.

In embodiments, the AaaS system may include data standardization procedures to improve consistency across different sources and formats. For example, the system may implement normalization techniques that consider statistical properties and business or experimental requirements, while maintaining documentation of standardization procedures and transformations applied. Integration capabilities may enable the combination of data from a plurality of sources while maintaining data quality and consistency. The system may implement entity resolution and record linkage procedures to ensure accurate data combination and provide documentation of integration procedures and any assumptions made during the process. The standardization process may include, for example, the automated handling of different measurement scales and units. The system may implement conversion procedures to ensure consistency across different data sources, and maintain documentation of standardization rules and procedures.

In embodiments, the AaaS system may include performance optimization to improve processing of large-scale analytical workloads. For example, the system may implement distributed computing capabilities to handle computationally intensive analyses and employ caching mechanisms to improve processing efficiency. Scaling capabilities may enable the system to handle growing data volumes and analytical complexity. The system may implement automated resource allocation procedures to optimize computational efficiency and provide monitoring of system performance and resource utilization. The optimization processes may include automated procedures for managing analytical workflows and implementing scheduling algorithms to maximize resource utilization, as well as maintaining documentation of performance metrics and optimization procedures.

In embodiments, the AaaS system may include security measures to improve the protection of sensitive data and analytical results. For example, the system may implement access controls and encryption procedures and maintain audit trails of analytical activities and data access. Compliance procedures may ensure adherence to relevant regulations and standards. The system may implement automated checks for compliance requirements and provide documentation of compliance procedures and controls implemented.

In embodiments, the AaaS system may include a reporting framework for providing documentation of analytical procedures and results. For example, the system may generate detailed technical documentation including methodology descriptions, assumptions, and limitations and implement visualization capabilities to communicate analytic findings, results and recommendations. Documentation may include automated generation of model cards and analytical reports. The system may maintain audit trails of analytical procedures and decisions and provide documentation of quality metrics, validation results, and performance indicators.

In embodiments, the DaaS and AaaS systems, as described herein, may be applied to optimize metabolic pathways for improved production of target molecules. An example workflow may begin with the DaaS system collecting and integrating data from multiple experimental sources through its data intake and staging pipeline. The system may automatically process raw metabolomics data, applying normalization techniques to remove batch effects and technical variations while preserving the biological signal. The AaaS system may then employ specialized AI models to analyze the normalized data and generate recommendations for pathway modifications. The ASB platform 100 may utilize hybrid models that combine mechanistic understanding of metabolic networks with machine learning to predict the outcomes of a plurality of pathway configurations. Through this process, the system may identify bottlenecks in the metabolic network and suggest specific genetic modifications to improve flux through desired pathways. Expected outcomes may include optimized strain designs with enhanced production capabilities, validated through both in silico predictions and experimental validation. The system may maintain audit trails of modifications and their impacts on pathway performance.

In embodiments, the ASB platform 100 may implement fermentation optimization workflows utilizing the DaaS system to continuously collect real-time data from, for example, bioreactor sensors and analytical instruments. The system may implement automated sampling mechanisms, as described herein, for collecting standardized samples and integrate with analytical instruments for metabolite analysis. This data may be automatically normalized and processed to account for variations in experimental conditions.

In embodiments, the AaaS system may apply machine learning models to analyze the processed fermentation data and generate recommendations for process parameters. The system may evaluate multiple objectives simultaneously, including, for example, titer, rate, and yield, while considering practical constraints of commercial-scale production. The ABS platform 100 digital twin capabilities may enable simulation of different process scenarios before implementation, reducing experimental iterations. Expected outcomes may include optimized fermentation protocols with improved productivity and reduced variability. The system may generate documentation of process modifications and their impacts on performance metrics.

In embodiments, for strain engineering applications, the DaaS system may integrate genetic modification data with phenotypic measurements and process parameters. The system may maintain data lineage tracking from raw measurements to processed values, enabling verification of the data processing steps.

In embodiments, the AaaS system may employ neural network architectures for automated identification and optimization of genetic modifications. The platform may use distributed computing architectures to enable prediction and improvement of scale-up performance, implementing optimized data integration pipelines across heterogeneous data types. The system may generate recommendations for genetic modifications that are predicted to perform well at commercial scale. These recommendations may be based on historical performance data, simulated outcomes, or some other parameter(s), using the platform's digital twin capabilities. Expected outcomes may include strain designs that maintain desired performance characteristics during scale-up.

In embodiments, the ASB platform 100 may create protein engineering workflows and use the DaaS system to collect and integrate, for example, protein sequence data, structural information, and functional assay results. The system may implement specialized data structures optimized for biological data and machine learning processing.

In embodiments, the AaaS system may utilize protein language models and other AI approaches to predict protein function and optimize protein sequences for desired properties. The platform may generate and evaluate multiple protein variants simultaneously, considering multiple objectives such as activity, stability, and expression levels. Expected outcomes may include engineered proteins with improved functional properties, supported by both computational predictions and experimental validation data. The system may maintain records of protein variants and their performance characteristics.

In embodiments, the DaaS system may implement quality control mechanisms for synthetic biology workflows, including but not limited to automated validation checks and standardization procedures. The system may track data quality metrics throughout the development process and generate detailed scorecards to assess data health.

In embodiments, the AaaS system may apply machine learning models to detect anomalies and potential quality issues in real-time. The platform may maintain audit trails of process modifications and their impacts on product quality and ensure compliance with relevant regulations and standards through automated checks and documentation. Expected outcomes may include improved process consistency, reduced quality deviations, and documentation for regulatory compliance. The system may generate reports of quality control measures and their effectiveness.

In embodiments, the data intake and staging pipeline of the ASB platform 100 may implement specialized ETL capabilities designed for synthetic biology data sources. The pipeline may include automated sampling mechanisms for collecting standardized samples with near-instantaneous quenching of cellular metabolism. This system may integrate with liquid chromatography-mass spectrometry and gas chromatography-mass spectrometry for metabolite analysis. The pipeline may employ parallel processing architectures using multiple processing nodes that specialize in different aspects of the data processing workflow. For example, one node may optimize fermentation parameters while another simultaneously generates metabolic pathway predictions. The system utilizes AI processing cores (GPUs, NPUs, TPUs, FPGAs) configured for efficient processing of specific types of biological data, such as protein structure prediction in pharmaceutical applications and real-time processing of fermentation sensor data.

In embodiments, the normalization pipeline may implement a Bayesian statistical model incorporating prior knowledge about strain behavior while modeling different sources of variation, including biological effects and technical factors. The system may apply batch effect correction to address systematic variations across experimental runs, equipment, and operators. Quality control processes may include, for example, automated detection of wells or samples that failed to grow properly, identification of contamination, flagging of readouts that fall outside expected ranges based on historical data, and identification of potential measurement errors or mislabeling. The system may maintain metadata about experimental conditions and validate normalization methods using control samples.

In embodiments, the ASB platform 100 may implement specialized data structures optimized for biological data processing, including but not limited to bipartite graph database structures that organize data into molecule nodes and process nodes. Molecule nodes may represent atomic elements, ions, compounds, nucleic acids, proteins, or macromolecules, while process nodes may represent chemical reactions, protein folding, transport, regulatory interactions, or active site binding. The integration pipeline may combine multiple types of high-dimensional biological data, including gene expression data from RNA sequencing, flux data from isotope-labeled experiments, and metabolite concentration measurements from mass spectrometry. The system may employ edge computing architectures that enable local processing of sensor data to reduce latency and network bandwidth requirements.

In embodiments, the ASB platform 100 may implement distributed computing frameworks to optimize computational efficiency in model training and inference. Model training may be distributed across multiple AI processing nodes operating in parallel, with specialized cores configured for common biological sequence analysis operations like sequence alignment or fold prediction. The system may employ a multi-headed attention mechanism where separate attention heads process different types of parameters (genetic, metabolic, environmental) in parallel before integration. The platform may implement automated model selection procedures that evaluate multiple approaches based on performance metrics and biological requirements, considering factors such as model complexity, interpretability, and computational efficiency.

In embodiments, a scale-up prediction pipeline may utilize hybrid models that combine mechanistic understanding with machine learning approaches. The system may implement digital twin capabilities representing, for example, biological strain characteristics, synthetic biological processes, genes, genomes, pathways, bioreactors, proteins, metabolites, and enzymes. The pipeline may employ specialized neural network architectures for automated identification and optimization of genetic modifications, with distributed computing architectures enabling prediction and improvement of scale-up performance. The system may implement load balancing algorithms that route requests based on computational intensity and data locality, with automated failover mechanisms that maintain system availability when individual modules or processing nodes fail.

In embodiments, the ASB platform 100 may implement comprehensive visualization and exploration tools that enable users to navigate complex networks of biological entities and experimental data. The system may employ network visualization techniques to reveal clusters of genetically similar strains and highlight correlations between genetic modifications and phenotypic outcomes. These visualization capabilities may be specifically designed to communicate analytical findings and support decision-making through predictive analysis. The platform may provide interactive visualization and exploration tools that allow researchers to examine high-dimensional datasets, visualize predicted metabolic states, and analyze trade-offs between different engineering objectives. Network-based visualizations may represent metabolic pathways and regulatory interactions, with data overlays showing, for example, predicted or measured changes in metabolite levels, fluxes, and gene expression. The system may implement interactive Pareto fronts to display multi-objective optimization results, allowing users to explore the characteristics of different optimal designs through linked views that enable drilling down into specific genetic modifications and predicted metabolic changes.

In embodiments, the ASB platform 100 may provide documentation for research and engineering users that includes methodology descriptions, assumptions, and limitations. This documentation may include model cards that specify model characteristics, training procedures, and validation results. The platform may maintain quality scorecards that track various metrics throughout the analytical processes, enabling researchers to assess data quality and analytical integrity.

In embodiments, the ASB platform 100 may provide operational analytics dashboards that track system performance and resource utilization. These dashboards may include visualization of quality metrics, trend analysis, and performance indicators that enable engineering teams, or others, to monitor and optimize process efficiency. The platform may generate comparative analyses of strain performance across different conditions by synthesizing outputs of multiple experiments and may create visualizations of metabolic pathway performance.

In embodiments, the ASB platform 100 may provide documentation for management users, implementing business intelligence features that support decision-making through visualization capabilities. The system may generate unified data presentations that communicate analytics results and recommendations in an accessible format. These reports may include, for example, visualization of techno-economic analysis results, enabling assessment of commercial viability and process optimization opportunities.

In embodiments, the ASB platform 100 may provide documentation for audit trails and generate detailed reports documenting system activities and changes. This may include tracking of data lineage from raw measurements to processed values, maintaining records of user actions and system modifications. The system may generate documentation of compliance procedures and controls, ensuring transparency and accountability in data management.

In embodiments, the platform may provide real-time visualization of experimental data through integration with laboratory and commercial equipment. This may include monitoring of, for example, bioreactor parameters, analytical instrument outputs, and process conditions. The system may implement edge computing architectures that enable local processing and visualization of sensor data to reduce latency and network bandwidth requirements.

In embodiments, the platform may utilize knowledge graph approaches to represent complex relationships between, for example, strains, genetic designs, experimental conditions, and performance data. This unified data model may enable querying and visualization capabilities, allowing users to retrieve and visualize strains that modify particular metabolic pathways along with their associated performance data across multiple experiments.

Model Output Tracking Facility

In embodiments, the ASB Platform 100 may include a model output tracking facility 2500 for tracking and presenting model outputs, which includes the generation of graphical representations of simulation results, storage of model data for later use, and customizable user interfaces for viewing and interacting with the model outputs. The model output tracking facility 2500 may be designed to provide users with clear and accessible information about the outcomes of their biological simulations.

In embodiments, the model output tracking facility 2500 may include systems and methods for optimizing the selection and presentation of candidate designs in the computational biology environment of the ASB Platform 100. The model output tracking facility 2500 may be designed to address inefficiencies in preparing and filtering lists of candidate designs to share with, for example, customers, standardizing the manual filtering process, and establishing a method to link edits to the corresponding model or dataset. The model output tracking facility 2500 may include a central database for storing model predictions along with metadata describing the model and dataset from which they were generated. The model output tracking facility 2500 may include a "human-in-the-loop," code-driven process to standardize, document, and accelerate manual filtering. The model output tracking facility 2500 may include storing model predictions and associated metadata in a central database to facilitate retrieval and analysis. In an example, the model output tracking facility 2500 may utilize a Python API to interact with the database for operations such as loading model predictions, querying, filtering, and aggregating model predictions into design batches, and recording provenance about design batches and build/test status updates from partners. The model output tracking facility 2500 may implement a data model to capture raw model predictions, annotations, and partner-ready design batches, enabling joins and cross-referencing with client datasets. The model output tracking facility 2500 may employ a user process that includes running a model against candidates to obtain a list of scored design candidates, analyzing and filtering scored candidates, and exporting the final list for presentation to the client. The model output tracking facility 2500 may provide a structured approach to managing model outputs, enhancing the efficiency and traceability of the design selection process. The model output tracking facility 2500 may leverage advanced data management techniques and a collaborative API to improve the accuracy and speed of preparing candidate designs for customer, or other's review.

In an embodiment, provided herein is an ASB Platform 100 for synthetic biology development having a data intake pipeline configured to manage the intake of data associated with synthetic biology development.

In an embodiment, provided herein is an ASB Platform 100 for synthetic biology development having a customer data ingestion toolkit configured for processing customer data associated with synthetic biology development.

In an embodiment, provided herein is an ASB Platform 100 for synthetic biology development having a data intake pipeline having schema definition system configured to infer a consistent schema configuration for a set of data files.

In an embodiment, provided herein is an ASB Platform 100 for synthetic biology development having a data intake pipeline having a system for validating genotypes.

In an embodiment, provided herein is an ASB Platform 100 for synthetic biology development having a data intake pipeline having a system for generating an analytical measure associated with quality control (QC) for data associated with synthetic biology development.

In an embodiment, provided herein is an ASB Platform 100 for synthetic biology development having a data intake pipeline having a system configured to identify outliers in a dataset wherein the dataset is associated with synthetic biology development.

In an embodiment, provided herein is an ASB Platform 100 for synthetic biology development having a data intake pipeline having a system for prioritizing control strains.

In an embodiment, provided herein is an ASB Platform 100 for synthetic biology development having a data intake pipeline having a system configured to design a set of experiments associated with synthetic biology development.

In an embodiment, provided herein is an ASB Platform 100 for synthetic biology development having a data intake pipeline having a queryable strain registry.

In an embodiment, provided herein is an ASB Platform 100 for synthetic biology development having a data intake pipeline having a system for importing a new dataset associated with synthetic biology development.

In an embodiment, provided herein is an ASB Platform 100 for synthetic biology development having a data intake pipeline having a system for updating a dataset with new data wherein the new data is associated with synthetic biology development.

In an embodiment, provided herein is an ASB Platform 100 for synthetic biology development having a data intake pipeline having a system for storing model parameters and/or outputs wherein the models are associated with synthetic biology development.

In an embodiment, provided herein is an ASB Platform 100 for synthetic biology development having a data collection system configured to automatically collect data wherein the data is associated with synthetic biology development.

In an embodiment, provided herein is an ASB Platform 100 for synthetic biology development having a data aggregation system configured to automatically aggregate data wherein the data is associated with synthetic biology development.

In an embodiment, provided herein is an ASB Platform 100 for synthetic biology development having a data processing system configured to automatically process data wherein the data is associated with synthetic biology development.

In an embodiment, provided herein is an ASB Platform 100 for synthetic biology development having a data storage system configured to store data wherein the data is associated with synthetic biology development.

In an embodiment, provided herein is an ASB Platform 100 for synthetic biology development having a distributed ledger system configured to store data wherein the data is associated with synthetic biology development.

In an embodiment, provided herein is an ASB Platform 100 for synthetic biology development having a blockchain system configured to store data wherein the data is associated with synthetic biology development.

In an embodiment, provided herein is an ASB Platform 100 for synthetic biology development having a blockchain system configured to represent strain lineage.

In an embodiment, provided herein is an ASB Platform 100 for synthetic biology development having a data normalization system configured for normalizing data associated with synthetic biology development.

In an embodiment, provided herein is an ASB Platform 100 for synthetic biology development having a data normalization system configured to perform Bayesian data normalization for data associated with synthetic biology development.

In an embodiment, provided herein is an ASB Platform 100 for synthetic biology development having a data normalization system configured for normalizing data associated with synthetic biology development having a system configured to identify the optimal model of data generation.

In an embodiment, provided herein is an ASB Platform 100 for synthetic biology development having a data normalization system configured for normalizing data associated with synthetic biology development having a system configured to estimate batch effects.

In an embodiment, provided herein is an ASB Platform 100 for synthetic biology development having a system for automatically collecting biological parameters and measurements.

In an embodiment, provided herein is an ASB Platform 100 for synthetic biology development having a system configured to generate an analytical measure associated with fermentation.

In an embodiment, provided herein is an ASB Platform 100 for synthetic biology development having a system configured to generate an analytical measure associated with carbon balance in fermentation.

In an embodiment, provided herein is an ASB Platform 100 for synthetic biology development having a system configured to estimate normalized yield associated with fermentation.

In an embodiment, provided herein is an ASB Platform 100 for synthetic biology development having a system configured to monitor flow rate and/or other metrics associated with fermentation.

In an embodiment, provided herein is an ASB Platform 100 for synthetic biology development having a sensor and/or data fusion system configured to combine data from multiple sensors and/or data sources wherein the data is associated with synthetic biology development.

In an embodiment, provided herein is an ASB Platform 100 for synthetic biology development having a model output tracking system configured for tracking model outputs wherein the model outputs are associated with synthetic biology development.

In an embodiment, provided herein is an ASB Platform 100 for synthetic biology development having a model output tracking system having a database to store model predictions wherein the model predictions are associated with synthetic biology development.

In an embodiment, provided herein is an ASB Platform 100 for synthetic biology development having a model output tracking system having an application programming interface (API).

In an embodiment, provided herein is an ASB Platform 100 for synthetic biology development having a model output tracking system having a system for running a model against candidate strains to obtain a list of scored design candidate strains.

In an embodiment, provided herein is an ASB Platform 100 for synthetic biology development having a model output tracking system having a system for analyzing and/or filtering a list of scored candidate strains.

In an embodiment, provided herein is an ASB Platform 100 for synthetic biology development having a model output tracking system having a candidate strain scoring system.

Specialized Solution Components

Referring to FIG. 1, the ASB platform 100 includes specialized solution components 1200. The specialized solution components 1200 may include process environments and parameters 1202; strains, physical biological assets, and genetic modifications 1204; hardware assets 1206; safety and governance system 1208; and robotics, 3D printing, and automation 1210.

In embodiments, the specialized solution components 1200 may further include one or more of the outputs of the prototype system 204, optimize system 208, and/or scale-up system 210, but only where such outputs are repeatable or extensible across multiple synthetic biology projects and/or customer engagements. In embodiments, these outputs may be added to process environments and parameters 1202 or strains, physical biological assets, and genetic modifications 1204.

In some implementations, the process environments and parameters 1202 may comprise specifications for improved or optimized synthetic biology process settings. The process environments and parameters 1202 are the specific variables that govern the operation and control of biological systems engineered in synthetic biology. In embodiments, the process environments and parameters 1202 may be fine-tuned through iterative cycles of design, testing, and modification to achieve a desired outcome and may be applicable to multiple synthetic biology projects and/or customer engagements. In embodiments, the process environments and parameters 1202 may include genetic parameters (e.g., gene expression levels, promoter strength, ribosome binding site (RBS) efficiency, codon optimization, and the like), environmental parameters (e.g., temperatures, pressures, pH levels, oxygen levels, and the like), cultural parameters (e.g., media composition, cell density, agitation and/or aeration, and the like), metabolic parameters (e.g., substrate concentration, product concentration, enzyme kinetics, and the like), operational parameters (e.g., bioreactor operation conditions, induction timing and concentration, harvest time, and the like), molecular parameters (e.g., vector design, chassis selection, and the like), process control parameters (e.g., feedback control loops, sensor and actuator control systems, and the like), and any process environments and/or parameters described throughout this disclosure. In embodiments, the process environments and parameters 1202 can be stored in the data storage systems provided by the facility for synthetic biology sensor collection, processing, fusion, and staging for modeling and analytics 2100. In embodiments, process environments and parameters 1202 may be managed and/or stored in a set of data structures. In embodiments, the data structures may comprise arrays or lists; key-value pairs (e.g., dictionaries or hash tables); structures or records; trees (e.g., binary search trees); graphs; linked lists; queues and stacks; sets; vectors; tuples; object-oriented classes or objects; databases (e.g., relational or NoSQL), JSON, XML, or YML files; or the like. In implementations, a data structure for storing process environments and parameters 1202 may comprise a key-value pairing mechanism, wherein each key corresponds to a unique process parameter identifier, and each value is the associated setting for the parameter; a hierarchical organization capability, enabling nested sub-parameters under a primary parameter key; a metadata inclusion feature for additional information associated with each key-value pair, and a serialization and deserialization functionality that allows the conversion of the data structure into a standardized format (e.g., JSON or XML) for storage, transmission, and the like.

With reference to FIG. 5, the specialized solution components 1200 may comprise strains, physical biological assets, and genetic modifications 1204. In embodiments, strains may refer to specific genetic variants or subtypes of microorganisms (e.g., bacteria, yeast, and the like) that have been genetically modified and/or engineered to have certain properties or to perform specific functions. Such modifications may include the addition, deletion, or alteration of genes within the organism's genome to enable it to produce a desired product, such as a compound used in a pharmaceutical, or to execute a particular biochemical reaction or pathway. In embodiments, the strains may be chassis strains that operate as standardized platforms for further genetic modification and development and provide a reliable and consistent starting point for the development of new biological systems. The strains may include bacteria (e.g., gram-negative *E. coli* or gram-positive *Bacillus*), yeast (e.g., *Saccharomyces, Pichia*, or *Yarrowia*), filamentous fungi (e.g., *Aspergillus*), algae (e.g., *Chlorella* or Cyanobacteria), mammalian cells (e.g., Chinese hamster ovary), plants, and the like. Common organisms that are used as chassis strains include *Escherichia coli* (*E. coli*), *Saccharomyces cerevisiae* (Baker's yeast). *Bacillus subtilis*, and *Pseudomonas putida*. In embodiments, chassis strain and other strain information may be stored or represented in data structures, including relational databases, object-oriented databases, NoSQL databases, JSON files, XML files, YAML files, custom data structures in programming languages, hierarchical data structures (e.g., trees), flat files (e.g., CSV, TSV), linked data structures, data frames or tables in data analysis libraries, and the like.

In embodiments, physical biological assets may refer to tangible materials that are derived from or used in synthetic biology development. In embodiments, physical biological assets may comprise microbial strains, cell lines, plasmids, DNA libraries, synthetic genes and gene circuits, proteins, enzymes, biological samples, biochemicals, seed stocks, viral vectors, and nucleic acid constructs, among many others. In embodiments, the physical biological assets may be the outputs of the prototype system 204, optimize system 208, and/or scale-up system 210.

Genetic modifications may refer to deliberate alteration of an organism's genetic material to change its properties or behavior in a directed way. These modifications are achieved through a number of techniques and/or technologies that enable addition, deletion, or editing within an organism's genome. Genetic modification types may include, but are not limited to, gene insertion, gene deletion (knockout), gene editing, gene silencing (knockdown), gene replacement, pathway engineering, genome shuffling, synthetic genomes, transgenic modifications, and cisgenic modifications. In embodiments, genetic modifications may be stored as genetic sequence databases (e.g., GenBank, EBML, DDBJ), laboratory information management systems (LIMS), plasmid repositories, bioinformatics tools and software, custom databases and data structures, ontologies (e.g., SBOL), blockchain systems, and the like. In some implementations, genetic modifications may be stored or represented in data structures, including relational databases, NoSQL databases, graph databases, vectors, object-oriented databases, hierarchical data structures (e.g., trees), JSON files, XML files, YAML files, custom data structures in programming languages, flat files (e.g., CSV or TSV), binary data formats, linked data structures, data frames or tables in data analysis libraries, and the like.

In embodiments, hardware assets 1206 may comprise AI system-on-chip (SoC) hardware configurations and embodiments configured to perform tasks associated with synthetic biology development, including local data collection, process optimization and/or improvements, model-guided fermentation, and the like. AI SoCs may refer to specialized integrated circuits designed to process and/or execute AI and machine learning tasks. In embodiments, AI SoCs may comprise CPUs, GPUs, NPUs, memory, DSPs, and the like. AI SoCs may include I/O interfaces and may be equipped with wireless communication capabilities. The AI SoCs may include machine learning framework support for frameworks including TensorFlow, PyTorch, ONNX, and the like. In implementations, AI SoCs may be embodied in fermenters, plates, tanks, DNA synthesizers, centrifuges, thermal cyclers, spectrophotometers, imaging systems, incubators, shakers, liquid handling systems (e.g., pipetting robots), turbidostats, chemostats, and biological process hardware, including any biological process hardware described throughout this disclosure.

In some implementations, the AI SoCs may include customizable processing cores (e.g., FPGAs) that may be optimized for specific synthetic biology computations. For example, the processing cores may be configured with custom instruction sets for common biological sequence analysis operations, such as sequence alignment or fold prediction. The AI SoCs may include a variety of cores that are configured for different mathematical operations used in different tasks, such as matrix operations for metabolic flux analysis or convolution operations for image-based analysis.

In embodiments, hardware assets 1206 may comprise smart plates, smart tanks, and other smart biological process hardware. These smart plates, smart tanks, and other smart biological process hardware may be equipped with integrated sensors, microfluidic channels that enable precise manipulation and control of liquids, automated sampling, real-time monitoring, data connectivity, and high-throughput screening. As described above, the smart plates, smart tanks, and other smart biological process hardware may be configured with AI SoCs to enhance their capabilities and enabling real-time data analysis, image processing and analysis, predictive modeling, automated decision-making, remote monitoring, high-throughput data processing, and the like. Smart synthetic biology hardware could enable autonomous execution of complex tasks.

In embodiments, the smart biological process hardware may implement edge computing architectures that enable local processing of sensor data to reduce latency and network bandwidth requirements. For example, the smart hardware may include embedded processors that perform real-time analysis (e.g., of growth curves or other sensor data), which may be used locally at the edge or remotely by the platform 100 to trigger automated sampling of and/or adjustment of conditions based on detected anomalies. The smart biological process hardware may also implement compression algorithms that are optimized for biological time series data to enable more efficient transmission of high-frequency sensor readings (e.g., to the platform 100).

In embodiments, hardware assets 1206 may comprise extended reality (XR) systems, including, but not limited to, virtual reality (VR) systems, augmented reality (AR) systems, and mixed reality (MR) systems. The XR systems can provide immersive synthetic biology experiences, interaction, collaboration, the enhanced viewing of simulations, the overlay of digital content and/or contextual information on a real-world environment, training, and the like. For example, a VR system could enable a synthetic biologist to be immersed in a virtual biomanufacturing environment. In another example, a synthetic biologist wearing an AR headset in a laboratory may be able to view an overlay of critical process parameters and experimental outputs. XR systems provide tools and platforms for experiencing synthetic biology content in ways that transcend the traditional boundaries between the physical and digital worlds.

In some implementations, hardware assets 1206 may comprise optical and machine vision systems configured for monitoring synthetic biology experiments, biomanufacturing activities, and the like. The optical and machine vision systems may provide safety and security monitoring, experiment observation and remote monitoring, operational oversight of equipment, verification or visual confirmation of steps in various synthetic biology protocols, data collection and analysis, documentation and record keeping, and quality control, among many others.

In embodiments, the optical and machine vision systems may use image processing pipelines optimized for biological samples. For example, the optical and machine vision systems may utilize convolutional neural network (CNN) models trained to analyze microscopy images to determine various relevant features (e.g., cell count, cell size distribution, growth patterns, etc.). In embodiments, the optical and machine vision systems may use sufficient processing cores to implement real-time image processing directly on raw sensor data streams, for example to enable immediate detection of process deviations (e.g., contamination events or unexpected growth patterns). The optical and machine vision systems may use any of the specialized hardware described herein (e.g., AI processing cores) for image processing operations (e.g., including running AI models, using edge detection algorithms, pattern recognition algorithms, etc.).

In implementations, the specialized solution components 1200 may comprise a safety and governance system 1208. Safety and governance system 1208 may be configured to establish protocols, policies, and/or mechanisms to maintain the integrity, security, and reliability of ASB platform 100 and its subsystems, with particular focus on the AI and machine learning models of 3100. In embodiments, safety and governance system 1208 may ensure that the ASB platform 100 and the elements thereof comply with relevant laws, regulations and industry standards associated with synthetic biology, data protection, and AI. Safety and governance system 1208 may be configured to assess and mitigate risks associated with the deployment and operation of AI and ML machine learning models, including potential biases, errors, and the like. In some implementations, safety and governance system 1208 may oversee the development, validation, deployment, and maintenance of the models of 3100 and/or manage data access, quality, and integrity of the data used by the models of 3100. Further, safety and governance system 1208 may be configured to maintain logs and/or audit trails for activities within ASB platform 100, deploy mechanisms for responding to safety incidents (e.g., model deactivation), perform monitoring, reporting, and ethical oversight, and the like. Additionally, the safety and governance system 1208 may perform risk analysis for the outputs of the prototype system 204, optimize system 208, and/or scale-up system 210 to ensure such outputs are safe for humans, environmentally friendly, and the like.

In implementations, the specialized solution components 1200 may comprise robotics, 3D printing, and automation 1210. The robotics of 1210 may comprise robots and/or robotic handlings systems configured to perform synthetic biology tasks, including laboratory tasks, screening tasks, biomanufacturing tasks, and the like. In embodiments, the robotics may help drive a semi-automated or fully-automated laboratory and/or a semi-automated and/or fully-automated biomanufacturing facility. The 3D printers of 1210 may be configured to print synthetic biology products, including physical biological assets, and in some embodiments, may be configured to print the outputs of the prototype system 204, optimize system 208, and/or scale-up system 210. In embodiments, the 3D printers may include software and/or firmware such as design software (e.g., CAD), slicing software, printer control software, scanning software, G-code interpretation firmware, motion control firmware, temperature management firmware, sensor feedback firmware, user interface firmware, error handling firmware, and the like.

Artificial Intelligence and Machine Learning

In embodiments, the ASB Platform 100 may include a set of artificial intelligence, machine learning, neural networks, and other model types 3100. In some embodiments, at least a portion of the set of artificial intelligence and/or machine learning models 3100 may be provided as a component and/or layer of the ASB Platform 100, and may be utilized by the other components of the ASB Platform 100 (e.g., the synthetic biology development workflows and services 200 and/or the specialized solution components 1200) through cross-component and/or cross-layer communication and interoperation, such as through one or more application programming interfaces (APIs). Alternatively or additionally, at least a portion of the set of artificial intelligence and/or machine learning models 3100 may be provided as a library and/or software development kit (SDK) that may be integrated with one or more other components of the ASB Platform 100. The set of artificial intelligence, machine learning, neural networks, and other model types 3100 may perform various forms of artificial intelligence logic for use in the ASB Platform 100, such as analyzing data, transforming data (e.g., summarization, validation, normalization, supplementation, curation, aggregation, filtering, or the like), and/or generating synthetic data.

The platform 100 may train and/or execute any of the AI models described herein using distributed computing frameworks to optimize computational efficiency. For example, model training and/or inference may be distributed across multiple AI processing nodes (e.g., GPU clusters) operating in parallel. In embodiments, the platform 100 may speed up inference operations using model quantization and/or batching to reduce memory usage. The platform 100 may use preprocess data (e.g., as described above with respect to the intake/staging/normalization facilities) using distributed computing frameworks for handling large-scale biological datasets. Thus, the platform 100 may generate predictions in real-time using optimized inference pipelines with reduced latency. The AI processing nodes may use AI processing cores (e.g., GPUs, NPUs, TPUs, FPGAs, etc.) that are optimized for operations common in machine learning computations, such as matrix multiplication and/or convolution operations.

In embodiments, the set of artificial intelligence, machine learning, neural networks, and other model types 3100 includes a set of foundation models 3102 that are generated, trained, and/or deployed for various purposes within the ASB Platform 100. In some embodiments, one or more of the foundation models 3102 are generated by and/or for the ASB Platform 100 based on a set of model hyperparameters (e.g., a model type, model external and/or internal structure, model processing techniques such as activation functions) and further developed for particular purposes within the ASB Platform 100. In some embodiments, one or more of the foundation models 3102 are received from another source (e.g., an external model library) and are added to the set of artificial intelligence, machine learning, neural networks, and other model types 3100. In some such cases, one or more foundation models 3102 may be adapted for use by the ASB Platform 100. For example, a pretrained foundation model 3102 may have been partially trained on a general-purpose task (e.g., generating content based on a prompt, or analyzing the molecular structures of various compositions) and may be further trained to perform one or more specific tasks within the ASB Platform 100 (e.g., generating specific forms of content based on prompts associated with particular contexts, or analyzing the molecular structures of one or more particular classes of compositions).

The foundation models 3102 may be configured to use specific input and output representations that are optimized for biological data. For example, when processing strain variants, the inputs may be encoded as a sequence of embeddings, where each embedding represents characteristics of genetic modifications or strain features. The platform 100 may generate embeddings that are predefined encodings of variant characteristics and/or that are learned embeddings trained along with the model, as described elsewhere herein. The models 3102 may be configured to output a score distribution over possible strain modifications or process adjustments, enabling probabilistic selection of variants and conditions based on confidence scores.

The set of foundation models 3102 may include a wide range of different types of neural networks, machine learning systems, artificial intelligence systems, and the like, including (without limitation) single- and multi-layer perceptron networks, convolutional networks (CNNs), recurrent neural networks (RNNs), dual-process artificial neural networks (DPANN), feed-forward neural networks, radial basis function neural networks, self-organizing neural networks (e.g., Kohonen self-organizing neural networks), modular neural networks, artificial neural networks, physical neural networks, multi-layered neural networks, convolutional neural networks, hybrids of neural networks with other expert systems (e.g., hybrid fuzzy logic-neural network systems), autoencoder neural networks, probabilistic neural networks, time delay neural networks, convolutional neural networks, regulatory feedback neural networks, radial basis function neural networks, recurrent neural networks, Hopfield neural networks, Boltzmann machine neural networks, self-organizing map (SOM) neural networks, learning vector quantization (LVQ) neural networks, fully recurrent neural networks, simple recurrent neural networks, echo state neural networks, long short-term memory neural networks, bi-directional neural networks, hierarchical neural networks, stochastic neural networks, genetic scale RNN neural networks, committee of machines neural networks, associative neural networks, physical neural networks, instantaneously trained neural networks, spiking neural networks, neocognitron neural networks, dynamic neural networks, cascading neural networks, neuro-fuzzy neural networks, compositional pattern-producing neural networks, memory neural networks, hierarchical temporal memory neural networks, deep feed forward neural networks, gated recurrent unit (GCU) neural networks, auto encoder neural networks, variational auto encoder neural networks, denoising auto encoder neural networks, sparse auto-encoder neural networks, Markov chain neural networks, restricted Boltzmann machine neural networks, deep belief neural networks, deep convolutional neural networks, de-convolutional neural networks, deep convolutional inverse graphics neural networks, generative adversarial neural networks, liquid state machine neural networks, extreme learning machine neural networks, echo state neural networks, deep residual neural networks, support vector machine neural networks, neural Turing machine neural networks, and/or holographic associative memory neural networks, or hybrids or combinations of the foregoing, or combinations with other expert systems, such as rule-based systems, model-based systems (including ones based on physical models, statistical models, flow-based models, biological models, biomimetic models, decision trees, random forests, Bayesian networks, Gaussian mixture models (GMMs), generative adversarial networks (GANs), diffusion probabilistic models, and large language models (LLMs). The set foundation models 3102 may be expanded as additional foundation models 3102 are developed, refined, extended, and/or received from other sources.

Each foundation model 3102 may be trained using specific objective functions that are optimized for different biological applications. For example, the platform 100 may train a model 3102 on classification tasks (e.g., identifying protein functions, process bottlenecks, etc.) using cross-entropy objective functions. For regression tasks (e.g., predicting binding affinities, predicting yield or titer), the platform 100 may train a model 3102 using squared-error objective functions. The objective function may calculate a discrepancy between predicted outputs and target outputs, and the platform 100 may apply iterative optimization techniques such as stochastic gradient descent. The training process may use specific technical optimizations. For example, the platform 100 may perform gradient computation using mixed precision training to reduce memory usage. The platform 100 may also implement model checkpointing and/or early stopping to optimize training efficiency. In an example implementation, a particular neural network architecture may include an input layer, one or more attention layer(s) processing input embeddings, a pooling layer that generates a pooled embedding, and/or one or more fully connected layer(s) processing the pooled embedding to generate the output.

In embodiments, the set of artificial intelligence, machine learning, neural networks, and other model types 3100 includes one or more mechanistic models 3104 that embody mathematical representations of fundamental scientific and/or technical processes, such as laws of physics, chemistry, biology, or the like. While many foundation models 3102 may perform statistical and/or stochastic analysis of input data, many mechanistic model 3104 perform a deterministic analysis of input data based on the modeled scientific and/or technical processes. In some embodiments, a mechanistic model 3104 may be configured to receive input relating to an initial, current, predicted, and/or proposed state of a composition, article, entity, environment, or the like. The mechanistic model 3104 may process the state according to the modeled scientific and/or technical processes to generate various forms of logical analysis, such as predictions of an updated state, analyses of structure or content of the input (e.g., active structures within a biological composition), outcomes of the scientific and/or technical processes (e.g., products of various biological and/or chemical processes), or the like. In some embodiments, one or more mechanistic models 3104 may perform probabilistic analysis, such as statistical distributions of possible outcomes of chemical reactions with predicted likelihoods and/or conditional features of the respective outcomes.

In embodiments, the set of artificial intelligence, machine learning, neural networks, and other model types 3100 includes one or more hybrid and/or fully differentiable model types 3106. For example, the set of artificial intelligence, machine learning, neural networks, and other model types 3100 may include a hybrid of two or more foundation models 3102, such as an ensemble of two or more artificial neural networks that perform analysis of input data in tandem, or a sequential aggregation of a convolutional neural network with one or more fully-connected layers of an artificial neural network. The hybrid model types 3106 may include a first artificial intelligence model that evaluates an output of one or more additional artificial intelligence models (e.g., a "blender" model that selects one or more models that correspond to a particular input and/or selects among alternative outputs of various models based on the particular input). The hybrid model types 3106 may include an adversarial architecture, such as a generator network that generates content and a discriminator network that critically evaluates the generated content, and/or an adversarial training process (e.g., training a discriminator model to distinguish between authentic and synthetic content, and training a generator model to generate synthetic content that the discriminator model classifies as authentic content). The hybrid model types 3106 may include self-reflection features, such as a first model that critically evaluates an output of a second model, and/or that guides the development of a second model to generate improved output. For example, a generator foundation model 3102 may generate synthetic composition candidates, and a mechanistic model 3104 may evaluate various features of the synthetic composition candidates (e.g., efficacy, biocompatibility, biosimilarity, desirable and/or undesirable interactions, side effects, dosage, or the like) to determine the suitability of synthetic composition candidates for various scenarios.

In some embodiments, one or more artificial intelligence models included in the set of artificial intelligence, machine learning, neural networks, and other model types 3100 may be fully differentiable, such that the various architectural features of the artificial intelligence model can be differentially related to various performance features of the artificial intelligence model. For example, in a backpropagation artificial neural network, the relationship between various architectural features of the artificial neural network and an output of the artificial neural network for a given input can be differentially modeled. During training, the delta between an actual output of the artificial neural network for a given training sample and a desired output for the training sample (e.g., a label for the training sample) may be determined. Based on the delta, adjustments of individual neuron parameters of the artificial neural network (e.g., weights and biases associating each neuron with other neurons) may be adjusted based on the delta and the differential relationships of the parameters. In some embodiments, combinations of various fully-differentiable models may result in a fully-differentiable hybrid model. For example, a hybrid including a fully-differentiable convolutional neural network followed by a fully-differentiable artificial neural network may enable training deltas to be differentially backpropagated through both models to improve the performance of the hybrid.

In embodiments, the set of artificial intelligence, machine learning, neural networks, and other model types 3100 includes automated model construction 3108. In some embodiments, the automated model construction 3108 may involve generating an artificial intelligence model based on a description of an objective, context, capability, task, or the like (e.g., a request for a classification capability involving a particular data set may prompt an automated model construction 3108 involving an instantiation of a classifier neural network that is suitable for the data set, and an automated training, testing, and/or deployment of the model for the classification task). In some embodiments, the automated model construction 3108 may involve an automated determination of an architecture for an artificial intelligence model for a particular objective, context, capability, task, or the like (e.g., a hyperparameter search that evaluates various model types, configurations, activation functions, and training and/or testing techniques). In some embodiments, the automated model construction 3108 may involve experimental training of various candidate models and a selection of a suitable model based on performance comparisons of the candidate models. In some embodiments, the automated model construction 3108 may select and/or perform various forms of training, including unsupervised training (e.g., automated cluster determination), supervised training (e.g., automated training based on a training data set that associates samples with determined labels), semi-supervised training (e.g., automated training with occasional involvement of human experts to provide labels for ambiguous and/or borderline training data samples), or the like. In some embodiments, the automated model construction 3108 may add an automatically developed model to the set of foundation models 3102 and/or mechanistic models 3104 (e.g., to provide a new capability that is not already satisfied by the set of foundation models 3102). In some embodiments, the automated model construction 3108 may initiate a retraining, refinement, and/or replacement of one or more existing foundation models 3102 and/or mechanistic models 3104. For example, upon determining a performance deficiency of a foundation model 3102 (e.g., systemic classification errors, systemic bias, performance drift, or susceptibility to adversarial attack), the automated model construction 3108 may automatically generate a substitute artificial intelligence model and may replace the foundation model 3102 with the substitute artificial intelligence model.

In embodiments, the set of artificial intelligence, machine learning, neural networks, and other model types 3100 includes multi-objective optimization 3110. For example, a particular scenario or task, such as a development of a composition for a pharmaceutical target or a biological pathway, may involve a set of objectives, such as effectiveness, efficiency, consistency, rate, safety, cost, compatibility, or the like. Multi-objective optimization 3110 may seek to optimize the set of objectives, such as analyzing various candidates and/or alternatives, predicting outcomes for each objective, and holistically comparing the set of outcomes over the entire set of candidates and/or alternatives. In embodiments, the multi-objective optimization 3110 may prioritize the respective objectives, such as classifying various objectives as higher priority (including essential priority) and other objectives as lower priority, attributing and/or adjusting weights among the objectives, and/or defining thresholds for one or more outcomes. In some embodiments, the multi-objective optimization 3110 may include a scoring mechanism that enables holistic comparisons of the candidates and/or alternatives. In some embodiments, the multi-objective optimization 3110 may proscriptively, retrospectively, and/or iteratively refine the set of objectives, such as adding new objectives, clarifying objectives, and/or adjusting weights of the objectives (e.g., based on the results of simulations of selected candidates and/or alternatives). In some embodiments, the multi-objective optimization 3110 may determine a set of selected candidates with comparative combinations of optimized outcomes (e.g., each selected candidate may exhibit good performance on some objectives and lower performance on other objectives). In some such embodiments, the multi-objective optimization 3110 may present summaries of the reasons for selecting various candidates (e.g., a first candidate that exhibits strong biological effectiveness and a second candidate that exhibits wide biocompatibility and/or lower cost).

In embodiments, the set of artificial intelligence, machine learning, neural networks, and other model types 3100 includes AI-guided analytics, discovery tools, digital twins, and simulations 3112. For example, the AI-guided analytics may include simulations of physical, chemical, and/or biological processes associated with a synthetic pharmaceutical composition developed by AI models. Outcomes of the simulations (e.g., pharmaceutical effectiveness, efficiency, and/or biocompatibility) may be provided as input to the AI models to produce improved pharmaceutical compositions with improved outcomes (e.g., improved pharmaceutical effectiveness, efficiency, and/or biocompatibility). Discovery tools may be used to identify features of the simulation for additional development and/or exploration (e.g., a simulation of a biologic pathway associated with a condition may result in an automated identification of targets that may alter the biologic pathway and the features of synthetic compositions that may achieve such alterations). One or more digital twins may be included in simulations to model various features of the simulation (e.g., biological organisms, organs, immunologic pathways, or the like), and the performance and/or outcomes of the digital twins during the simulation may be included in the resulting analysis (e.g., the immunologic response of an organism to various forms of a synthetic pharmaceutical composition).

In embodiments, the set of artificial intelligence, machine learning, neural networks, and other model types 3100 includes AI and technical solutions for techno-economic analysis (TEA), prototype, and scale 3114. For example, simulations of synthesis processes may include an evaluation of features such as material and reagent costs, equipment, reaction rates, reaction product quality, yield, and consistency. Such determinations may yield economic analysis of the synthesis processes, such as an overall cost, production volume, timelines, risks, and/or value. The AI models may experiment with the synthesis processes to determine opportunities for adjustment that may produce improved techno-economic analyses (e.g., greater yield, faster production, higher quality, or greater value). The techno-economic analyses of a synthetic process may include evaluations of opportunity cost (e.g., the comparative advantages of applying available resources to various synthetic processes) and/or market considerations (e.g., the technical and/or economic value derived by optimizing various aspects of a synthetic process). Techno-economic analysis may be performed and/or applied in a retrospective mode (e.g., evaluation of the outcomes of a candidate and/or proposed synthetic process) and/or a prospective mode (e.g., desired adjustments of a synthetic process that could yield technical and/or economic improvements, such as increased binding to a particular interaction site and/or selectivity for a particular biological pathway). Techno-economic analysis derived from a first processes may result in a determination of principles and/or optimizations that may be applied to other processes (e.g., adjustments to a first synthetic process that produce improved yield may be evaluated for application to similar synthetic processes for which improved yield would provide a substantial technical and/or economic benefit).

AI-Guided Synthetic Biology Development Optimization Platform Optimization Platform In embodiments, the platform 100 may be configured to optimize and/or improve aspects of the production of a functional output by a biological strain. For example, the platform 100 may be configured to generate a set of recommendations wherein the recommendations relate to a set of modifications to a set of genes of the biological strain, a set of modifications to a set of environmental parameters for a synthetic biological process in which the biological strain produces the functional output, a set of modifications to a set of biological pathways associated with the synthetic biological process in which the biological strain produces the functional output, and/or a set of modifications to a set of proteins or enzymes associated with the biological strain. Such recommendations may be used to improve, enhance, and/or optimize the production of a functional output by the biological strain.

In embodiments, a biological strain may refer to a genetically distinct variant or subtype of a biological organism, including microorganisms such as bacteria, fungi, and viruses, or any of the other biological organisms or microorganisms described throughout this disclosure and the documents incorporated herein by reference, that exhibits specific phenotypic or genotypic characteristics that distinguish it from other members of the same species.

Functional outputs may refer to outputs involved in the production of fuel applications and solutions (e.g., methanol, ethanol, biodiesel, fuel additives, and lubricants), industrial applications and solutions (e.g., chemicals and materials, fibers and textiles, mining, industrial sensors, agriculture, and aquaculture), consumer product applications and solutions (e.g., food and beverage, consumer goods, and nutraceuticals), and pharmaceutical and medical applications and solutions (e.g., cell therapies, vaccines, personalized medicines, and medical sensors), among many others, and including any of the applications and solutions described throughout this disclosure and the documents incorporated herein by reference.

Enhancements to functional outputs by the biological strain may include, for example, improved performance, the production of novel compounds, cost reduction, sustainability, pathogen resistance, bioremediation capabilities, customization for specific environments, compliance with regulatory standards, and many others. Improved performance, for example, could include an increase in product yield, efficiency, and/or robustness of the biological strain, making it more effective for specific applications such as biofuel production.

The platform 100 may include data integration facilities having various components and functionalities designed to combine and unify data sets from multiple data sources. The platform 100 may be configured to generate a set of recommendations for modifications a set of modifications to the set of genes of the biological strain, a set of modifications to a set of environmental parameters for the synthetic biological process in which the biological strain produces the functional output, a set of modifications to the set of biological pathways associated with the synthetic biological process in which the biological strain produces the functional output, and/or a set of modifications to a set of proteins or enzymes associated with the biological strain, the set of data integration facilities integrates the content of at least one publication data set relating to the biological strain and at least one proprietary data set including a set of parameters of a synthetic biological process in which the biological strain produces a functional output.

In embodiments, the data integration facilities may refer to various capabilities of the synthetic biology sensor collection, processing, fusion, and staging for modeling and analytics system 2100. The data integration facilities may enable the consolidation of diverse data types and formats from different systems, databases, applications, and the like. This aggregation of the data can be for a range of applications, including advanced analytics, machine learning model training and/or retraining, and machine learning model execution, among many others.

In embodiments, the data integration facilities may use dedicated processing cores, such as field-programmable gate arrays (FPGAs) or application-specific integrated circuits (ASICs), to perform high-speed data transformation and integration operations. In embodiments, the data integration facilities may use a sufficient number of processing cores to enable real-time integration of streaming sensor data with historical datasets. The processing cores may be configured to perform parallel processing of multiple data streams simultaneously, with dedicated circuits for common data transformation operations such as normalization, formatting, validation, etc.

The data integration facilities may provide data extraction mechanisms to connect to and retrieve information from various sources, including relational databases, NoSQL databases, flat files, APIs, and cloud storage systems, among many others. The data integration facilities may also offer tools for data transformation, enabling data cleaning, data normalization, and the conversion of data into a consistent format. This may involve data mapping, data type conversion, and the application of operational rules or calculations.

Furthermore, the data integration facilities may include mechanisms for data loading, supporting the transfer of transformed data into target systems such as data warehouses, data lakes, or analytical databases. Real-time integration capabilities can be incorporated to process and integrate data in near real-time, ensuring up-to-date information. To maintain data quality throughout the integration process, the data integration facilities may provide features for ensuring data accuracy, completeness, and consistency.

In some implementations, the data integration facilities may comprise metadata management tools for capturing, storing, and managing metadata, providing context and lineage for integrated data. The data integration facilities can also include scheduling and automation capabilities, allowing the streamlining of data integration processes, reducing manual intervention and ensuring timely data updates. Error handling mechanisms and detailed logging capabilities can be used to track and troubleshoot data integration issues.

The data integration facilities may incorporate security and compliance features to ensure data protection, access control, and adherence to relevant client and/or partner contracts, industry practices, regulations, standards, and the like throughout the integration process.

In embodiments, the data integration facilities may include a sensor and data fusion system, expanding the capabilities of platform 100 to handle diverse data sources and complex integration scenarios. Sensor and/or data fusion systems enable the aggregation and processing of data from multiple sensors, sensor networks, and data sources. The sensor and data fusion system can synchronize and correlate data from disparate sensors and data sources, accounting for variations in data formats, sampling rates, and measurement units. The sensor and data fusion system can combine data from multiple sources to derive more accurate, complete, or reliable information than what could be obtained from any individual source alone. In the context of data integration facilities, sensor and data fusion capabilities can be applied to merge information from various databases, real-time streams, and external systems, which may involve techniques such as probabilistic inference, statistical analysis, or machine learning algorithms to reconcile conflicting data points and extract meaningful insights.

The data integration facilities can be configured to automatically integrate relevant data from data sources using different mechanisms. For instance, the data integration facilities of the platform 100 may incorporate natural language processing (NLP) and machine learning algorithms to analyze and categorize scientific literature, publications, texts, and the like, enabling understanding of the content, context, and relevance of publications to specific areas or topics associated with synthetic biology development. In embodiments, an automated web scraping component could be implemented to continuously scan and retrieve new data from data sources such as publications from reputable scientific journals, preprint servers, and academic databases, ensuring that the data integration facilities have access to the most up-to-date research literature. In implementations, the data integration facilities could utilize semantic analysis techniques to extract key information from data sources. For example, the data integration facilities could use semantic analysis techniques to extract specific information from scientific papers, such as methodologies, results, and conclusions. This extracted data could then be structured and integrated into the knowledge base facilities of the platform. The platform 100 could employ text summarization algorithms to generate concise overviews of integrated publications, making it easier to determine the main points of relevant research. An ontology-based integration system could be implemented to map concepts and terminology, ensuring consistent interpretation of integrated literature. In embodiments, the data integration facilities of the platform may incorporate knowledge graphs that enhance the ability to manage, understand, and utilize data from multiple sources.

The platform 100 may include components for processing and storing data. A data processing component may prepare raw data for use in modeling and/or analysis. An integration/API layer may enable communications between platform components and external systems. A data storage component may store raw data, processed data, integrated data, model outputs, and/or the like. The platform 100 may provide results and visualizations to users through the visualization and reporting component, and the platform can interact with third-party systems (e.g., to receive third party data, use third party models such as large language models) via the integration/API layer.

The platform 100 may include components for generating user interfaces and/or controlling external equipment. An equipment control component may interface with and/or control laboratory equipment (e.g., based on a model that determines optimal environmental conditions). A visualization and reporting component may present unified data, analytics, results, and the like to users and may receive user inputs and/or instructions.

Other functions of the data integration facilities may include compressing, decompressing, encoding, decoding, and otherwise processing data packets, signals, and other information as it exchanged among the systems and/or subsystems of platform, such as transforming data from one format or protocol to another as needed in order for one system or subsystem to consume output from another.

The data integration facilities may integrate data from a diverse range of data sources, including publication data sets relating to biological strains, proprietary data sets relating to biological strains, client- or partner-specific data (e.g., operational data, client requirements, and client contracts), public databases (e.g., GenBank, UniProt, KEGG, EcoCyc, and ChEMBL), scientific literature (e.g., research articles, theses and dissertations, and patents and patent applications), experimental data (e.g., laboratory results, plate-based assay results, full-scale bioreactor results, and high-throughput screening results), metagenomic and transcriptomic data (e.g., environmental genomes and RNA-Seq data), data from bioinformatics tools (e.g., pathway analysis software and gene editing tools), fermentation data (e.g., process monitoring data, historical production data), market research (e.g., industry reports, surveys, and feedback), regulatory data, news data, simulation and modeling data, synthetic data, and many others.

The platform 100 may utilize a variety of publication datasets in the optimization of strains, focusing on several key types of data that provide insights into genetic functions, metabolic pathways, and other relevant biological information. Publication data sets relating to biological strains may include gene function descriptions (e.g., gene annotations and functional genomics studies), metabolic pathway databases (e.g., pathway maps and pathway reconstruction studies), comparative genomics (e.g., comparative studies and phylogenetic analyses), "omics" data (e.g., transcriptomic data such as RNA-Seq data and proteomics data), functional assays and experiments (e.g., experimental data and high-throughput screening results), bioinformatics analyses (e.g., computational predictions and network analyses), regulatory studies (e.g., gene regulation studies), enzyme characterization (e.g., enzyme function studies, mutagenesis studies), case studies, and patent literature, among many others.

The publication data sets may include functional descriptions of genes from relevant databases (e.g., the EcoCyc™ database). This data may include information about genetic modifications made to strains and information about a corresponding target phenotype or other property of interest (e.g., production of a specific metabolite, growth rate under certain conditions, or fitness). In implementations, the publication datasets related to strains could be published knockout fitness experiment results for strains like *E. coli.*

In embodiments, the platform 100 may utilize proprietary data sets in the optimization of strains, the generation of recommendations to improve the functional outputs by the strains, and other synthetic biology development optimizations and/or improvements. The platform 100 may obtain proprietary data for a specific optimization task, which may be provided by a client or partner and/or may be provided for a particular application.

The platform 100 may interact with external systems including test equipment, production equipment (e.g., tanks), and third-party systems. These external systems provide data to the platform and receive control instructions and/or insights from it, thereby enabling a design-build-test-learn (DBTL) cycle. The components of platform 100 may interact in various ways to enable synthetic biology development optimization and/or improvement recommendations. For example, the platform 100 may receive data from test equipment and/or production equipment, process that data using the data processing component and store the processed data in the data storage. In embodiments, the platform 100 may receive data for different strains with results indicating the performance of the strain in both plate assays and in tanks (bioreactors).

The proprietary data sets may include a set of parameters of a synthetic biological process in which the biological strain produces the functional output. In embodiments, a synthetic biological process may refer to the engineered manipulation of a biological strain to systematically produce a specific functional output. The proprietary data sets may comprise genetic parameters (e.g., gene copy number, plasmid copy number, base strain information, integration sites, promoter information, edits on plasmids, and ribosome binding sites), metabolic parameters (e.g., metabolite concentrations, reaction fluxes, flux distribution, byproduct formation rates, enzyme activity levels, energy charge and ATP levels, cofactor availability, redox balance, substrate uptake rates, product inhibition and feedback regulation, metabolic pathway efficiency, oxygen uptake rate, metabolic burden, enzyme kinetics [Km, Vmax], and metabolite channeling), growth and physiological parameters (e.g., growth rate, biomass yield, oxygen consumption rate, cell viability, cell density, and stress indicators), environmental and culture conditions (e.g., temperature, inducer concentrations, nutrient availability, pH levels, salinity, osmotic pressure, culture medium composition, $CO_2$ levels, light exposure, osmolyte concentrations, redox potential, and humidity and evaporation rates), process parameters (e.g., induction timing, culture volume and scale, fermentation conditions, agitation speed, shaking rate, oxygen levels and aeration rates, pressure conditions, mode of operation [batch, fed-batch, continuous], nutrient feed strategies and feed rates, sampling frequency and methods, harvesting methods, bioreactor type and configuration, mixing times, mass transfer coefficients, scalability factors, scale-dependent kinetics, power input per unit volume, and energy inputs), functional output parameters (e.g., product yield, productivity rate, product purity, product titer, specific productivity, volumetric productivity, conversion efficiency, product stability, and overall process yield), regulatory and control parameters (e.g., regulatory network configurations and feedback control mechanisms), phenotypic parameters (e.g., cell morphology, colony appearance, motility, biofilm formation, stress resistance, metabolic activity indicators, growth phase characteristics, protein expression levels, protein stability and folding, post-translational modifications, mRNA stability, and protein localization), "omics" parameters (e.g., transcriptomics, proteomics, genomics, and metabolomics), scale-up parameters (e.g., mixing times, mass transfer coefficients, scalability factors, scale-dependent kinetics, power input per unit volume, hydraulic retention time, oxygen transfer rate, shear stress levels, temperature control efficiency, pH control and stability, foam control, scalability of nutrient feed strategies, and scale-dependent kinetics), and energy consumption parameters (e.g., energy inputs, power input per unit volume, total energy input, power consumption by agitator, aeration energy cost, cooling and heating energy consumption, energy efficiency of filtration and separation systems, energy recovery systems, power usage effectiveness (PUE), operational load patterns, maintenance and downtime energy costs, automated energy management systems, energy benchmarking and monitoring, and renewable energy integration), among many others.

The various neural networks of the platform 100 may be optimized for processing the biological parameter data and/or genetic modification data. In some applications, the neural networks may use a multi-headed attention mechanism where separate attention heads process different types of parameters (e.g., genetic, metabolic, environmental) in parallel before combining their outputs, thereby efficiently processing heterogeneous parameter data. The attention mechanism may leverage a plurality of processing cores (e.g., GPUs, NPUs, TPUs, FPGAs, etc.) to compute attention weights in parallel.

In embodiments, the output of the data integration facilities is configured as an input or otherwise provided to a set of artificial intelligence (AI)-based learning models. The AI-based learning models are configured to process and analyze the integrated data to generate insights, predictions, recommendations, decision support, simulations, control instructions, and the like based on patterns and relationships identified within the data. The AI-based learning models may also be configured to perform optimization tasks, detection and/or identification tasks, and many others.

The set of AI-based learning models may comprise various architectures and approaches to machine learning, including but not limited to: transformer models, convolutional neural networks, deep learning models, supervised models, semi-supervised models, unsupervised models, reinforcement models, long short-term memory (LSTM) models, multi-layer perceptron, lin-log models, large language models, large protein models, and protein language models, among many others.

The AI-based learning models may be implemented using various architectural configurations and combinations to optimize performance for specific tasks. For example, a hybrid architecture may combine an LSTM model with a multi-layer perceptron, where the LSTM processes functional embeddings information for genetic edits to generate strain embeddings, which are then fed into the multi-layer perceptron to produce targeted recommendations to achieve fitness targets or other desired outcomes.

In embodiments, the AI-based learning models may be configured to process inputs in parallel across multiple AI processing cores (e.g., GPUs, NPUs, TPUs, FPGAs, etc.), with each processing core handling a subset of the input data. For example, when processing multiple gene sequences simultaneously, the platform 100 may assign each sequence to a separate processing core, enabling concurrent analysis of multiple genetic modifications. Additionally or alternatively, the platform 100 may implement model compression techniques to reduce computational resource requirements while maintaining prediction accuracy. Such techniques may include quantization of model weights (e.g., from 32-bit floating point to 8-bit integers), pruning of network connections, knowledge distillation from larger to smaller models, low-rank factorization of weight matrices, and/or the like. To handle large-scale data processing efficiently, the platform 100 may implement streaming data processing pipelines that process data in chunks rather than loading entire datasets into memory, efficient data structures optimized for biological sequence data, caching mechanisms for frequently accessed model parameters, adaptive batch sizing based on available computational resources, and/or the like.

The platform may support flexible model architectures to accommodate different analytical requirements. These include transformer-based architectures that leverage attention mechanisms for processing sequential data, ensemble and/or hybrid architectures that combine multiple model types to improve robustness and performance, and other specialized architectures tailored to specific use cases. The AI-based learning models may incorporate parallel input layers to process multiple data streams simultaneously, enabling more comprehensive analysis of complex datasets.

The models can be configured with different optimization strategies, loss functions, and training approaches based on the specific requirements of the analysis task. This includes the ability to fine-tune model parameters, implement custom activation functions, and incorporate domain-specific constraints to ensure the generated outputs align with biological and experimental constraints.

In embodiments, at least one member of the of the set of AI-based learning models may be configured to generate a set of recommendations wherein the recommendations relate to a set of modifications to a set of genes of the biological strain, a set of modifications to a set of environmental parameters for the synthetic biological process in which the biological strain produces the functional output, a set of modifications to the set of biological pathways associated with the synthetic biological process in which the biological strain produces the functional output, and/or a set of modifications to the set of proteins or enzymes associated with the biological strain such that the recommendations enhance the production of the functional output by the biological strain.

The platform 100 may execute the set of AI-based learning models using adaptive computation techniques that dynamically adjust a model's computational complexity based on input complexity. For example, when processing simple parameter sets, the platform 100 may execute the AI-based learning model using a reduced number of layers or attention heads to conserve computational resources. Conversely, for complex parameter sets requiring more detailed analysis, the platform 100 may dynamically configure the AI-based learning model to activate additional layers and/or computational pathways.

Enhancing the production of a functional output by a biological strain can involve several types of gene modifications, including knockout mutations, overexpression of target genes, activation of specific genes, insertion of specific genes, gene knockdowns, site-directed mutagenesis, promoter engineering, codon optimization, gene fusion, allele replacement, the creation of synthetic gene circuits, introduction of regulatory elements, and the application of advanced genome editing technologies such as CRISPR/Cas9, among others. By modifying strain genetics, the production of functional outputs from biological strains may be improved.

In some embodiments, a first member of the set of AI-based learning models may be configured to generate embeddings, which are continuous vector representations that capture semantic relationships and functional attributes of a gene, while a second member of the set of AI-based learning models may be configured to generate the gene modification recommendations.

For example, a first member of the set of AI-based learning models may generate "GenePT" embeddings using large language models (LLMs) that process textual descriptions of gene functions. To generate GenePT embeddings, the platform may extract functional descriptions of genes from relevant databases (e.g., the EcoCyc™ database). The platform may then take the extracted text (which may include information about the gene's role, associated metabolic pathways, enzymatic functions, interactions, and the like) and input the text into one or more pre-trained LLMs (e.g., models developed by OpenAI™, Google™, Meta™, etc.), which may be running remotely and/or locally on the platform 100. The LLM may process the textual description and produce an embedding. Because LLMs are trained on vast amounts of textual data, they are capable of inferring relationships between different genes based on the context provided in the textual descriptions.

In another example, the platform 100 may generate embeddings using Proteinfer, a pre-trained convolutional neural network (CNN) that predicts protein functions. More specifically, the Proteinfer model analyzes the amino acid sequences of proteins encoded by genes and generates embeddings that capture structural and functional features of the proteins. The Proteinfer model may use a deep learning architecture trained on datasets containing protein sequences labeled with enzyme function codes, gene ontology (GO) terms, and/or other functional annotations. Therefore, Proteinfer embeddings may indicate information about enzymatic activities, active sites, structural motifs, and/or the like. For instance, two isomerase enzymes with similar active sites but different sequences may have embeddings that reflect their functional similarities despite the different sequences.

In embodiments, the platform 100 may generate embeddings using protein language models such as ESM2. These protein language models are trained on large amounts of protein sequences to generate predictions of sequences in a similar way as how language models predict words in a sentence. The protein language models also generate embeddings that capture both local and global structural features of proteins, such as secondary structures, domains, and folding patterns. The embeddings from protein language models provide additional information that may complement the functional information provided by the GenePT embeddings, Proteinfer embeddings, and/or other such embeddings. Other embedding techniques that may be used by the platform 100 are described elsewhere herein.

Modification of environmental parameters may significantly enhance the production of outputs by biological strains, and such modifications may include temperature, pH level, oxygen supply, nutrient composition, fermentation time, stirring and mixing, inoculum size, light conditions (e.g., for phototrophic organisms), toxicity management, pressure, salinity, dissolved oxygen levels, carbon dioxide levels, and many others.

For example, adjusting the temperature to an optimal temperature for a biological strain can enhance metabolic activity and enzyme efficiency, leading to higher product yields. In another example, gradually changing pH during a fermentation process can promote specific metabolic pathways leading to increased output. In yet another example, adjusting the aeration rate can optimize oxygen availability for aerobic processes, enhancing cell growth and product formation. By modifying certain environmental parameters, the production of functional outputs from biological strains may be improved.

To improve the production of a functional output from the biological strain, modifications to biological pathways may include identification and overexpression of key enzymes that are critical for the desired biosynthetic pathway, the use of stronger or inducible promoters, the knockout of competing pathways, pathway engineering, optimization of substrate utilization, feedback regulation modification, cofactor engineering, pathway flux redistribution, integration of pathways, environmental adaptations, and the like.

The set of recommendations for modifications to biological pathways may relate to overexpression of pathway enzymes, which may involve gene amplification, or increasing the copy number of genes encoding key enzymes in the pathway to enhance enzyme levels and boost metabolic flux, or the use of stronger promoters or inducible promoters to drive higher expression levels of target enzymes. Another potential modification may involve the knockout of competing pathways, using gene deletion to identify and knockout genes involved in competing pathways that divert precursors away from the desired product or pathway disruption by targeting enzymes that catalyze side reactions. Pathway engineering modification recommendations may involve synthetic pathway construction, which refers to the designing and implementing of new metabolic pathways that convert substrates into target products, or the engineering of modular pathways that can be combined or reconfigured to optimize production. Recommendations to optimize substrate utilization may relate to substrate specificity modification or the utilization of alternative carbon sources. Feedback regulation modification recommendations might involve the elimination of feedback inhibition by modifying or knocking out genes that encode for regulatory proteins inhibiting key enzymes in response to high product concentrations or could involve the implementation of synthetic feedback systems that allow fine-tuning of enzyme activity based on real-time product levels. Cofactor engineering modification recommendations can include cofactor supply enhancement (e.g., increasing the availability of NADPH or ADP) or cofactor regeneration by engineering pathways that regenerate cofactors efficiently. Recommendations related to pathway flux redistribution may involve metabolic flux analysis, or the use of computational models to identify bottlenecks and the modification of the pathway to redistribute flux toward the desired output, or enzyme kinetics optimization by modifying enzyme kinetics (e.g., affinity or turnover number) through directed evolution or site-directed mutagenesis to enhance overall pathway efficiency. Modifications involving integration of pathways might refer to pathway coupling or cross-pathway regulation by implementing regulatory mechanisms that synchronize the operation of multiple pathways to optimize overall production. Recommendations to adjust environmental adaptations could involve condition-specific modifications, such as by modifying pathways to respond favorably to specific environmental conditions (e.g., temperature or pH) to enhance product yield or stress tolerance engineering, which refers to enhancing pathways to improve strain tolerance to byproducts or inhibitory compounds generated during production. By recommending pathway optimization modifications, the performance of biological strains in producing desired functional outputs can be significantly enhanced.

To enhance the production of a functional output of the biological strain, modifications can be made to a set of proteins and/or enzymes associated with the strain. Recommendations for modifications can relate to enzyme overexpression, which could involve increased gene copies (e.g., amplifying the genes encoding key enzymes to increase their abundance within the cell) or the use of stronger promoters to drive higher expression. Additionally, site-directed mutagenesis may be employed to introduce targeted mutations in an enzyme's active site, thereby enhancing its catalytic efficiency, substrate specificity, or stability. Constructing chimeric proteins by fusing domains from different enzymes can also combine beneficial traits, such as increased stability and improved catalytic activity. Modifications to cofactor interactions, such as enhancing cofactor affinity through active site alterations or engineering regeneration pathways, can optimize enzymatic reactions. To alleviate feedback inhibition, one can disable regulatory sites or introduce synthetic regulation mechanisms that adjust enzyme activity based on product concentrations. Post-translational modifications can be strategically applied to influence enzyme performance, with alterations aimed at enhancing stability or activity through phosphorylation, glycosylation, or ubiquitination. Additionally, modifying enzyme localization to target specific cellular compartments or anchoring them to membranes can enhance their interaction with substrates, while gene knockouts may remove competing enzymes, ensuring that more substrates are funneled toward the desired pathway. Allosteric modulation techniques, such as engineering allosteric sites for small molecule interaction, can provide dynamic regulation of enzyme activity, allowing for improved product formation. Other modification approaches can integrate modular enzyme assemblies that work synergistically within the metabolic framework, creating novel pathways that significantly enhance product yield and flow, ultimately optimizing the overall production capabilities of the biological strain. These strategies, tailored to the specific biological context and desired product, can lead to substantial improvements in metabolic efficiency and overall production capabilities.

In embodiments, the platform 100 may include a simulation engine that is configured to generate and execute simulations for different process scenarios in which the biological strain produces the functional output, wherein each process scenario has different modifications to genes, environmental parameters, biological pathways, and/or proteins or enzymes associated with the biological strain. The simulation engine can generate multiple simulated process scenarios, where each scenario tests different modifications. The simulation engine executes these scenarios and generates simulation data based on the results.

The simulation data generated from these simulations can be received as additional input by the set of AI-based learning models. This simulation data, along with other data inputs, can be used by the set of AI-based learning models to generate recommendations. The recommendations can be based at least in part on analyzing the outcomes and results captured in the simulation data. In some embodiments, the simulation data may be integrated with other data by the data integration facilities before being provided to the set of AI-based learning models.

The platform's ability to incorporate simulation data as an additional input allows it to leverage both real experimental data and simulated outcomes when generating recommendations. This combination of actual and simulated data provides a more comprehensive basis for the platform's recommendation capabilities.

In some embodiments, the simulation engine may use digital twins in the execution of its simulations. In embodiments, the platform 100 may include a digital twin system configured to generate and/or manage digital twins. Such digital twins may include biological strain digital twins, synthetic biological process digital twins, gene digital twins, genome digital twins, pathway digital twins, bioreactor and/or fermentation system digital twins, protein digital twins, metabolite digital twins, enzyme digital twins, and digital twins representing any of the synthetic biology entities described throughout this disclosure and documents incorporated herein.

In embodiments, the simulation engine may employ distributed computing techniques to parallelize the execution of digital twin simulations across multiple computing nodes. For example, each node may be responsible for simulating specific aspects of a biological system (e.g., metabolic pathways, environmental conditions, genetic expressions, etc.) or other systems that are represented by the digital twin. The platform 100 may then aggregate results using a synchronization layer that maintains temporal consistency across simulations. This and other examples of distributed approaches can enable fast simulation of complex biological systems.

The simulation engine may be configured to perform a sensitivity analysis across multiple parameters simultaneously. This capability enables the platform to identify which combinations of modifications have the most significant impact on the desired functional output. The engine can systematically vary parameters within defined ranges while monitoring system responses, generating comprehensive sensitivity maps that highlight key control points in the biological system.

In embodiments, the simulation engine incorporates machine learning-based prediction models that can estimate the outcomes of proposed modifications before running full simulations. These predictive capabilities help optimize the simulation pipeline by prioritizing the most promising scenarios for detailed analysis. The prediction models may be continuously refined using both historical simulation results and real experimental data to improve their accuracy over time.

The platform's simulation engine may also include specialized modules for modeling stochastic biological processes. These modules account for the inherent randomness and variability in biological systems by incorporating probabilistic elements into the simulations. This stochastic modeling capability provides more realistic predictions of system behavior and helps identify potential failure modes or edge cases that deterministic approaches might miss.

In embodiments, the simulation engine maintains a comprehensive library of standardized simulation components that can be assembled into custom workflows. These components may include pre-configured digital twins, common biological pathways, standard operating conditions, and frequently used genetic modifications. This modular approach accelerates the setup of new simulations while ensuring consistency across different simulation scenarios.

The platform may include visualization tools integrated with the simulation engine that enable real-time monitoring and analysis of simulation progress. These tools can generate interactive dashboards displaying key performance indicators, pathway flux distributions, and other relevant metrics. The visualization capabilities help users identify trends and patterns in the simulation data that might not be apparent from numerical results alone.

For example, the simulation engine may be utilized to optimize the production of a target protein in a bacterial strain. The engine would first generate multiple simulation scenarios testing various combinations of genetic modifications and environmental conditions. In one scenario, the engine might simulate increasing the copy number of genes encoding rate-limiting enzymes while simultaneously adjusting temperature and PH levels in the bioreactor digital twin. The distributed computing system would parallelize these calculations, with separate nodes handling the metabolic flux analysis, protein expression modeling, and environmental parameter simulations. The synchronization layer would then integrate these parallel computations to maintain temporal consistency throughout the simulated fermentation process.

As the simulation progresses, the engine would continuously monitor key performance indicators such as protein yield, metabolic burden on the host cell, and resource utilization efficiency. The stochastic modeling modules would account for biological variability by running multiple iterations of each scenario with probabilistic variations in parameters such as gene expression levels and enzyme kinetics. The resulting simulation data would be analyzed by the platform's AI-based learning models, which could then recommend specific genetic modifications and process conditions most likely to achieve optimal protein production while maintaining cell viability and process stability.

Platform for Cell Optimization

Figure 11:
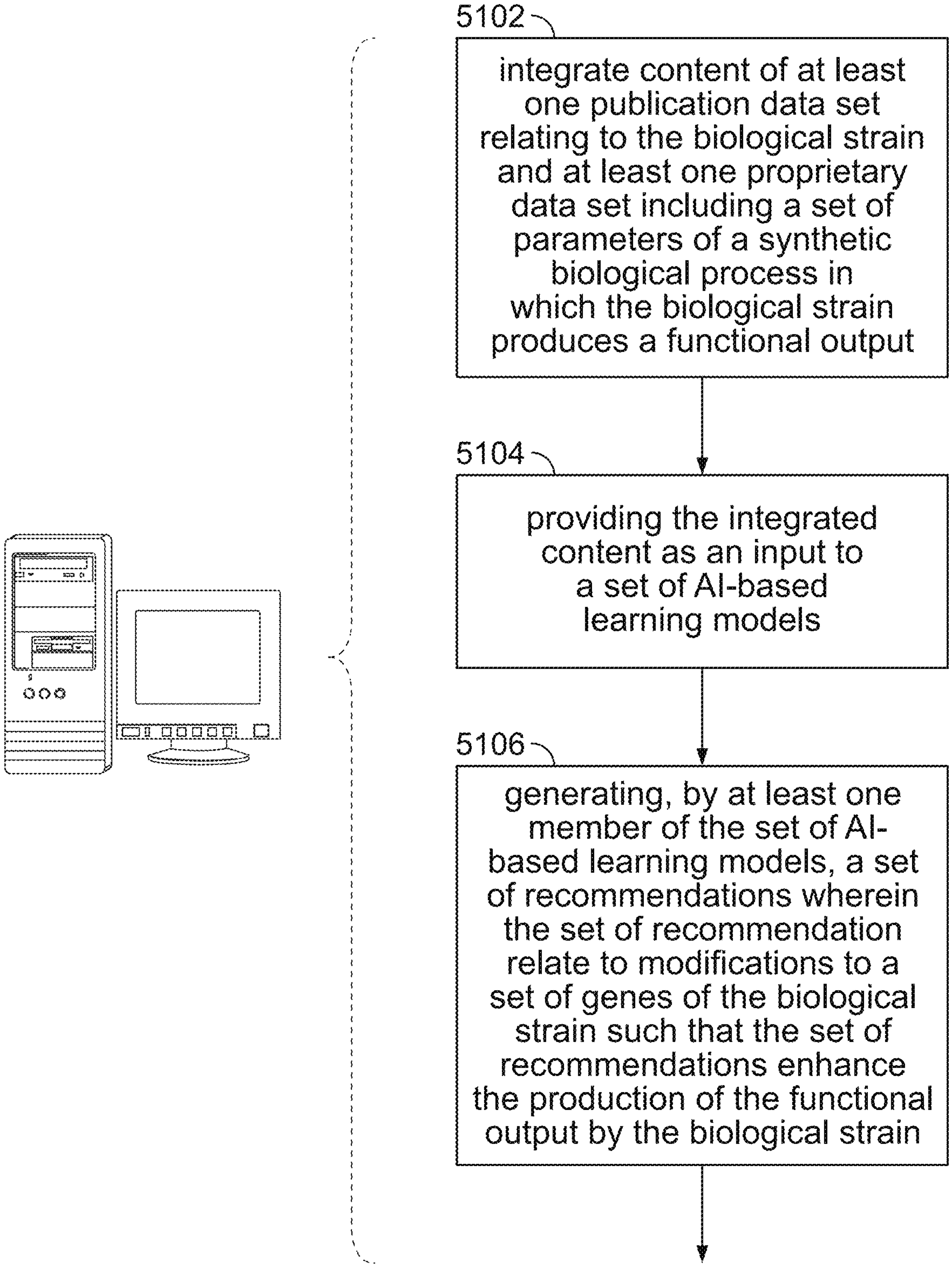
FIG. 11 is a flowchart illustrating example cell optimization methods, according to some embodiments.

Referring to FIG. 11, the platform 100 may be configured to generate a set of recommendations for modifications to a set of genes of a biological strain. Such recommendations may be used to enhance the production of a functional output by the biological strain.

In embodiments, a biological strain may refer to a genetically distinct variant or subtype of a biological organism, including microorganisms such as bacteria, fungi, and viruses, or any of the other biological organisms or microorganisms described throughout this disclosure and the documents incorporated herein by reference, that exhibits specific phenotypic or genotypic characteristics that distinguish it from other members of the same species.

Functional outputs may refer to outputs involved in the production of fuel applications and solutions (e.g., methanol, ethanol, biodiesel, fuel additives, and lubricants), industrial applications and solutions (e.g., chemicals and materials, fibers and textiles, mining, industrial sensors, agriculture, and aquaculture), consumer product applications and solutions (e.g., food and beverage, consumer goods, and nutraceuticals), and pharmaceutical and medical applications and solutions (e.g., cell therapies, vaccines, personalized medicines, and medical sensors), among many others, and including any of the applications and solutions described throughout this disclosure and the documents incorporated herein by reference.

Enhancements to functional outputs by the biological strain may include, for example, improved performance, the production of novel compounds, cost reduction, sustainability, pathogen resistance, bioremediation capabilities, customization for specific environments, compliance with regulatory standards, and many others. Improved performance, for example, could include an increase in product yield, efficiency, and/or robustness of the biological strain, making it more effective for specific applications such as biofuel production.

The platform 100 may include data integration facilities having various components and functionalities designed to combine and unify data sets from multiple data sources. In a method for generating a set of recommendations for modifications to a set of genes of a biological strain, described at 5102-5106, at 5102, the set of data integration facilities integrates the content of at least one publication data set relating to the biological strain and at least one proprietary data set including a set of parameters of a synthetic biological process in which the biological strain produces a functional output.

In embodiments, the data integration facilities may refer to various capabilities of the synthetic biology sensor collection, processing, fusion, and staging for modeling and analytics system 2100. The data integration facilities may enable the consolidation of diverse data types and formats from different systems, databases, applications, and the like. This aggregation prepares the data for a range of applications, including advanced analytics, machine learning model training and/or retraining, and machine learning model execution, among many others.

The data integration facilities may provide data extraction mechanisms to connect to and retrieve information from various sources, including relational databases, NoSQL databases, flat files, APIs, and cloud storage systems, among many others. The data integration facilities may also offer tools for data transformation, enabling data cleaning, data normalization, and the conversion of data into a consistent format. This may involve data mapping, data type conversion, and the application of operational rules or calculations.

Furthermore, the set of data integration facilities may include mechanisms for data loading, supporting the transfer of transformed data into target systems such as data warehouses, data lakes, or analytical databases. Real-time integration capabilities can be incorporated to process and integrate data in near real-time, ensuring up-to-date information. To maintain data quality throughout the integration process, the data integration facilities may provide features for ensuring data accuracy, completeness, and consistency.

In some implementations, the data integration facilities may comprise metadata management tools for capturing, storing, and managing metadata, providing context and lineage for integrated data. The data integration facilities can also include scheduling and automation capabilities, allowing the streamlining of data integration processes, reducing manual intervention and ensuring timely data updates. Error handling mechanisms and detailed logging capabilities can be used to track and troubleshoot data integration issues.

The data integration facilities may incorporate security and compliance features to ensure data protection, access control, and adherence to relevant client and/or partner contracts, industry practices, regulations, standards, and the like throughout the integration process.

In embodiments, the data integration facilities may include a sensor and data fusion system, expanding the capabilities of platform 100 to handle diverse data sources and complex integration scenarios. Sensor and/or data fusion systems enable the aggregation and processing of data from multiple sensors, sensor networks, and data sources. The sensor and data fusion system can synchronize and correlate data from disparate sensors and data sources, accounting for variations in data formats, sampling rates, and measurement units. The sensor and data fusion system can combine data from multiple sources to derive more accurate, complete, or reliable information than what could be obtained from any individual source alone. In the context of data integration facilities, sensor and data fusion capabilities can be applied to merge information from various databases, real-time streams, and external systems, which may involve techniques such as probabilistic inference, statistical analysis, or machine learning algorithms to reconcile conflicting data points and extract meaningful insights.

The data integration facilities can be configured to automatically integrate relevant data from data sources using different mechanisms. For instance, the data integration facilities of the platform 100 may incorporate natural language processing (NLP) and machine learning algorithms to analyze and categorize scientific literature, publications, texts, and the like, enabling understanding of the content, context, and relevance of publications to specific areas or topics associated with synthetic biology development. In embodiments, an automated web scraping component could be implemented to continuously scan and retrieve new data from data sources such as publications from reputable scientific journals, preprint servers, and academic databases, ensuring that the data integration facilities have access to the most up-to-date research literature. In implementations, the data integration facilities could utilize semantic analysis techniques to extract key information from data sources. For example, the data integration facilities could use semantic analysis techniques to extract specific information from scientific papers, such as methodologies, results, and conclusions. This extracted data could then be structured and integrated into the knowledge base facilities of the platform. The platform 100 could employ text summarization algorithms to generate concise overviews of integrated publications, making it easier to determine the main points of relevant research. An ontology-based integration system could be implemented to map concepts and terminology, ensuring consistent interpretation of integrated literature. In embodiments, the data integration facilities of the platform may incorporate knowledge graphs that enhance the ability to manage, understand, and utilize data from multiple sources.

The platform 100 may include components for processing and storing data. A data processing component may prepare raw data for use in modeling and/or analysis. An integration/API layer may enable communications between platform components and external systems. A data storage component may store raw data, processed data, integrated data, model outputs, and/or the like. The platform 100 may provide results and visualizations to users through the visualization and reporting component, and the platform can interact with third-party systems (e.g., to receive third party data, use third party models such as large language models) via the integration/API layer.

The platform 100 may include components for generating user interfaces and/or controlling external equipment. An equipment control component may interface with and/or control laboratory equipment (e.g., based on a model that determines optimal environmental conditions). A visualization and reporting component may present unified data, analytics, results, and the like to users and may receive user inputs and/or instructions.

Other functions of the data integration facilities may include compressing, decompressing, encoding, decoding, and otherwise processing data packets, signals, and other information as it exchanged among the systems and/or subsystems of platform, such as transforming data from one format or protocol to another as needed in order for one system or subsystem to consume output from another.

The data integration facilities may integrate data from a diverse range of data sources, including publication data sets relating to biological strains, proprietary data sets relating to biological strains, client- or partner-specific data (e.g., operational data, client requirements, and client contracts), public databases (e.g., GenBank, UniProt, KEGG, EcoCyc, and ChEMBL), scientific literature (e.g., research articles, theses and dissertations, and patents and patent applications), experimental data (e.g., laboratory results, plate-based assay results, full-scale bioreactor results, and high-throughput screening results), metagenomic and transcriptomic data (e.g., environmental genomes and RNA-Seq data), data from bioinformatics tools (e.g., pathway analysis software and gene editing tools), fermentation data (e.g., process monitoring data, historical production data), market research (e.g., industry reports, surveys, and feedback), regulatory data, simulation and modeling data, synthetic data, and many others.

The platform 100 may utilize a variety of publication datasets in the optimization of strains, focusing on several key types of data that provide insights into genetic functions, metabolic pathways, and other relevant biological information. Publication data sets relating to biological strains may include gene function descriptions (e.g., gene annotations and functional genomics studies), metabolic pathway databases (e.g., pathway maps and pathway reconstruction studies), comparative genomics (e.g., comparative studies and phylogenetic analyses), "omics" data (e.g., transcriptomic data such as RNA-Seq data and proteomics data), functional assays and experiments (e.g., experimental data and high-throughput screening results), bioinformatics analyses (e.g., computational predictions and network analyses), regulatory studies (e.g., gene regulation studies), enzyme characterization (e.g., enzyme function studies, mutagenesis studies), case studies, and patent literature, among many others.

The publication data sets may include functional descriptions of genes from relevant databases (e.g., the EcoCyc™ database). This data may include information about genetic modifications made to strains and information about a corresponding target phenotype or other property of interest (e.g., production of a specific metabolite, growth rate under certain conditions, or fitness). In implementations, the publication datasets related to strains could be published knockout fitness experiment results for strains like *E. coli.*

In embodiments, the platform 100 may utilize proprietary data sets in the optimization of strains and/or the generation of recommendations to modify the genetics of strains to improve the functional outputs by the strains. The platform 100 may obtain proprietary data for a specific optimization task, which may be provided by a client or partner and/or may be provided for a particular application.

The platform 100 may interact with external systems including test equipment, production equipment (e.g., tanks), and third-party systems. These external systems provide data to the platform and receive control instructions and/or insights from it, thereby enabling a design-build-test-learn (DBTL) cycle. The components of platform 100 may interact in various ways to enable strain genetics optimization recommendations. For example, the platform 100 may receive data from test equipment and/or production equipment, process that data using the data processing component and store the processed data in the data storage. In embodiments, the platform 100 may receive data for different strains with results indicating the performance of the strain in both plate assays and in tanks (bioreactors).

The proprietary data sets may include a set of parameters of a synthetic biological process in which the biological strain produces the functional output. In embodiments, a synthetic biological process may refer to the engineered manipulation of a biological strain to systematically produce a specific functional output. The proprietary data sets may comprise genetic parameters (e.g., gene copy number, plasmid copy number, base strain information, integration sites, promoter information, edits on plasmids, and ribosome binding sites), metabolic parameters (e.g., metabolite concentrations, reaction fluxes, flux distribution, byproduct formation rates, enzyme activity levels, energy charge and ATP levels, cofactor availability, redox balance, substrate uptake rates, product inhibition and feedback regulation, metabolic pathway efficiency, oxygen uptake rate, metabolic burden, enzyme kinetics [Km, Vmax], and metabolite channeling), growth and physiological parameters (e.g., growth rate, biomass yield, oxygen consumption rate, cell viability, cell density, and stress indicators), environmental and culture conditions (e.g., temperature, inducer concentrations, nutrient availability, pH levels, salinity, osmotic pressure, culture medium composition, $CO_2$ levels, light exposure, osmolyte concentrations, redox potential, and humidity and evaporation rates), process parameters (e.g., induction timing, culture volume and scale, fermentation conditions, agitation speed, shaking rate, oxygen levels and aeration rates, pressure conditions, mode of operation [batch, fed-batch, continuous], nutrient feed strategies and feed rates, sampling frequency and methods, harvesting methods, bioreactor type and configuration, mixing times, mass transfer coefficients, scalability factors, scale-dependent kinetics, power input per unit volume, and energy inputs), functional output parameters (e.g., product yield, productivity rate, product purity, product titer, specific productivity, volumetric productivity, conversion efficiency, product stability, and overall process yield), regulatory and control parameters (e.g., regulatory network configurations and feedback control mechanisms), phenotypic parameters (e.g., cell morphology, colony appearance, motility, biofilm formation, stress resistance, metabolic activity indicators, growth phase characteristics, protein expression levels, protein stability and folding, post-translational modifications, mRNA stability, and protein localization), "omics" parameters (e.g., transcriptomics, proteomics, genomics, and metabolomics), scale-up parameters (e.g., mixing times, mass transfer coefficients, scalability factors, scale-dependent kinetics, power input per unit volume, hydraulic retention time, oxygen transfer rate, shear stress levels, temperature control efficiency, pH control and stability, foam control, scalability of nutrient feed strategies, and scale-dependent kinetics), and energy consumption parameters (e.g., energy inputs, power input per unit volume, total energy input, power consumption by agitator, aeration energy cost, cooling and heating energy consumption, energy efficiency of filtration and separation systems, energy recovery systems, power usage effectiveness (PUE), operational load patterns, maintenance and downtime energy costs, automated energy management systems, energy benchmarking and monitoring, and renewable energy integration), among many others.

In embodiments, at 5104, the output of the data integration facilities is configured as an input or otherwise provided to a set of artificial intelligence (AI)-based learning models. The AI-based learning models are configured to process and analyze the integrated data to generate insights, predictions, recommendations, decision support, control instructions, and the like based on patterns and relationships identified within the data.

The set of AI-based learning models may comprise various architectures and approaches to machine learning, including but not limited to: transformer models, convolutional neural networks, deep learning models, supervised models, semi-supervised models, unsupervised models, reinforcement models, long short-term memory (LSTM) models, multi-layer perceptron, lin-log models, large language models, large protein models, and protein language models.

The AI-based learning models may be implemented using various architectural configurations and combinations to optimize performance for specific tasks. For example, a hybrid architecture may combine an LSTM model with a multi-layer perceptron, where the LSTM processes functional embeddings information for genetic edits to generate strain embeddings, which are then fed into the multi-layer perceptron to produce targeted recommendations to achieve fitness targets or other desired outcomes.

In embodiments, the AI-based learning models may be configured to process inputs in parallel across multiple AI processing cores (e.g., GPUs, NPUs, TPUs, FPGAs, etc.), with each processing core handling a subset of the input data. For example, when processing multiple gene sequences simultaneously, the platform 100 may assign each sequence to a separate processing core, enabling concurrent analysis of multiple genetic modifications. Additionally or alternatively, the platform 100 may implement model compression techniques to reduce computational resource requirements while maintaining prediction accuracy. Such techniques may include quantization of model weights (e.g., from 32-bit floating point to 8-bit integers), pruning of network connections, knowledge distillation from larger to smaller models, low-rank factorization of weight matrices, and/or the like. To handle large-scale data processing efficiently, the platform 100 may implement streaming data processing pipelines that process data in chunks rather than loading entire datasets into memory, efficient data structures optimized for biological sequence data, caching mechanisms for frequently accessed model parameters, adaptive batch sizing based on available computational resources, and/or the like.

The platform supports flexible model architectures to accommodate different analytical requirements. These include transformer-based architectures that leverage attention mechanisms for processing sequential data, ensemble and/or hybrid architectures that combine multiple model types to improve robustness and performance, and other specialized architectures tailored to specific use cases. The AI-based learning models may incorporate parallel input layers to process multiple data streams simultaneously, enabling more comprehensive analysis of complex datasets.

The models can be configured with different optimization strategies, loss functions, and training approaches based on the specific requirements of the analysis task. This includes the ability to fine-tune model parameters, implement custom activation functions, and incorporate domain-specific constraints to ensure the generated outputs align with biological and experimental constraints.

In embodiments, at 5106, at least one member of the of the set of AI-based learning models may be configured to generate a set of recommendations for modifications to a set of genes of the biological strain such that the recommendations enhance the production of the functional output by the biological strain.

Enhancing the production of a functional output by a biological strain can involve several types of gene modifications, including knockout mutations, overexpression of target genes, activation of specific genes, insertion of specific genes, gene knockdowns, site-directed mutagenesis, promoter engineering, codon optimization, gene fusion, allele replacement, the creation of synthetic gene circuits, introduction of regulatory elements, and the application of advanced genome editing technologies such as CRISPR/Cas9, among others. By modifying strain genetics, the production of functional outputs from biological strains may be improved.

In some embodiments, a first member of the set of AI-based learning models may be configured to generate embeddings, which are continuous vector representations that capture semantic relationships and functional attributes of a gene, while a second member of the set of AI-based learning models may be configured to generate the gene modification recommendations.

For example, a first member of the set of AI-based learning models may generate “GenePT” embeddings using large language models (LLMs) that process textual descriptions of gene functions. To generate GenePT embeddings, the platform may extract functional descriptions of genes from relevant databases (e.g., the EcoCyc™ database). The platform may then take the extracted text (which may include information about the gene’s role, associated metabolic pathways, enzymatic functions, interactions, and the like) and input the text into one or more pre-trained LLMs (e.g., models developed by OpenAI™, Google™, Meta™, etc.), which may be running remotely and/or locally on the platform 100. The LLM may process the textual description and produce an embedding. Because LLMs are trained on vast amounts of textual data, they are capable of inferring relationships between different genes based on the context provided in the textual descriptions.

In another example, the platform 100 may generate embeddings using Proteinfer, a pre-trained convolutional neural network (CNN) that predicts protein functions. More specifically, the Proteinfer model analyzes the amino acid sequences of proteins encoded by genes and generates embeddings that capture structural and functional features of the proteins. The Proteinfer model may use a deep learning architecture trained on datasets containing protein sequences labeled with enzyme function codes, gene ontology (GO) terms, and/or other functional annotations. Therefore, Proteinfer embeddings may indicate information about enzymatic activities, active sites, structural motifs, and/or the like. For instance, two isomerase enzymes with similar active sites but different sequences may have embeddings that reflect their functional similarities despite the different sequences.

In embodiments, the platform 100 may generate embeddings using protein language models such as ESM2. These protein language models are trained on large amounts of protein sequences to generate predictions of sequences in a similar way as how language models predict words in a sentence. The protein language models also generate embeddings that capture both local and global structural features of proteins, such as secondary structures, domains, and folding patterns. The embeddings from protein language models provide additional information that may complement the functional information provided by the GenePT embeddings, Proteinfer embeddings, and/or other such embeddings. Other embedding techniques that may be used by the platform 100 are described elsewhere herein.

In embodiments, the platform 100 may include a simulation engine that is configured to generate and execute simulations for different process scenarios in which the biological strain produces the functional output, wherein each process scenario has a different set of modifications to a set of genes. The simulation engine can generate multiple simulated process scenarios, where each scenario tests different modifications to a set of genes. The simulation engine executes these scenarios and generates simulation data based on the results.

The simulation data generated from these simulations can be received as additional input by the set of AI-based learning models. This simulation data, along with other data inputs, can be used by the set of AI-based learning models to generate recommendations. The recommendations can be based at least in part on analyzing the outcomes and results captured in the simulation data. In some embodiments, the simulation data may be integrated with other data by the data integration facilities before being provided to the set of AI-based learning models.

The platform's ability to incorporate simulation data as an additional input allows it to leverage both real experimental data and simulated outcomes when generating recommendations. This combination of actual and simulated data provides a more comprehensive basis for the platform's recommendation capabilities. Put another way, the platform leverages simulation data to provide a technical solution to the technical problem of scarcity of real-world experimental data, which may be available only in very limited amounts (or not at all) and can be expensive and difficult to obtain. Further, using simulation data during training can provide technical solutions to technical problems that arise during machine learning training, such as over-fitting, e.g., when AI-based learning models are trained to fit the training data so closely that they captures noise or irrelevant patterns, thereby reducing their ability to generalize and perform accurately on new or unseen data. Augmenting the real-world experimental data with simulated training data can increase the amount of available training data and reduce the likelihood of overfitting, thus improving generalization performance of the AI-based learning models.

In some embodiments, the simulation engine may use digital twins in the execution of its simulations. In embodiments, the platform 100 may include a digital twin system configured to generate and/or manage digital twins. The digital twins may include biological strain digital twins, synthetic biological process digital twins, gene digital twins, genome digital twins, pathway digital twins, bioreactor and/or fermentation system digital twins, protein digital twins, metabolite digital twins, enzyme digital twins, and digital twins representing any of the synthetic biology entities described throughout this disclosure and documents incorporated herein.

The set of recommendations generated by the set of AI-based learning models can be provided for use in any of a variety of possible downstream processes. For instance, in some cases, the set of recommendations are provided to a user on a display of a user device. As another example, actions can be performed in a real-world physical system to implement the recommendations generated by the AI-based learning models. In some cases, instructions to perform real-world actions to implement the recommendations generated by the AI-based learning models can be transmitted to a physical experimental system, and the physical experimental system can execute those instructions in order to implement the recommendations generated by the AI-based learning models. In some cases, the recommendations generated by the AI-based learning models can be implemented in the real-world by a process that involves at least some manual human intervention.

In some cases, after real-world actions are performed to implement the recommendations generated by the AI-based learning models, data characterizing the effects of those actions can be gathered, e.g., by one or more sensors. This data can then be fed back into a machine learning training algorithm for re-training the AI-based learning models. The re-training process can improve the accuracy of predictions and recommendations generated by the AI-based learning models. In some cases, new recommendations can be generated using the re-trained AI-based learning models, and real-world actions can be performed to implement the new recommendations.

In some cases, the term "digital twin" can refer to a digital representation of a physical object, system, or process that is dynamically updated to reflect changes in the state, condition, or behavior of its real-world counterpart. The digital twin may include one or more models, data sets, or simulations that mirror the attributes, operations, or performance of the physical entity, and may be used for monitoring, analysis, prediction, or control purposes.

Platform for Environment and Performance Optimization

Referring to FIG. 12, the platform 100 may be configured to generate a set of recommendations for modifications to a set of environmental parameters for a synthetic biological process in which a biological strain produces a functional output. Such recommendations may be used to enhance the production of the functional output by the biological strain.

In embodiments, a biological strain may refer to a genetically distinct variant or subtype of a biological organism, including microorganisms such as bacteria, fungi, and viruses, or any of the other biological organisms or microorganisms described throughout this disclosure and documents the documents incorporated herein by reference, that exhibits specific phenotypic or genotypic characteristics that distinguish it from other members of the same species.

Functional outputs may refer to outputs involved in the production of fuel applications and solutions (e.g., methanol, ethanol, biodiesel, fuel additives, and lubricants), industrial applications and solutions (e.g., chemicals and materials, fibers and textiles, mining, industrial sensors, agriculture, and aquaculture), consumer product applications and solutions (e.g., food and beverage, consumer goods, and nutraceuticals), and pharmaceutical and medical applications and solutions (e.g., cell therapies, vaccines, personalized medicines, and medical sensors), among many others.

Enhancements to functional outputs by the biological strain may include, for example, improved performance, the production of novel compounds, cost reduction, sustainability, pathogen resistance, bioremediation capabilities, customization for specific environments, compliance with regulatory standards, and many others, including any of the enhancements discussed throughout this disclosure and the documents incorporated herein by reference. Improved performance, for example, could include an increase in product yield, efficiency, and/or robustness of the biological strain, making it more effective for specific applications such as biofuel production.

The platform 100 may include data integration facilities having various components and functionalities designed to combine and unify data sets from multiple data sources. In a method for generating a set of recommendations for modifications to a set of environmental parameters for a synthetic biological process, described at 5202-5206, at 5202, the set of data integration facilities integrates the content of at least one publication data set relating to the biological strain and at least one proprietary data set including a set of parameters of a synthetic biological process in which the biological strain produces a functional output.

In embodiments, the data integration facilities may refer to various capabilities of the synthetic biology sensor collection, processing, fusion, and staging for modeling and analytics system 2100. The data integration facilities may enable the consolidation of diverse data types and formats from different systems, databases, applications, and the like. This aggregation prepares the data for a range of applications, including advanced analytics, machine learning model training and retraining, and machine learning model execution, among many others.

In embodiments, the data integration facilities may use dedicated processing cores, such as field-programmable gate arrays (FPGAs) or application-specific integrated circuits (ASICs), to perform high-speed data transformation and integration operations. In embodiments, the data integration facilities may use a sufficient number of processing cores to enable real-time integration of streaming sensor data with historical datasets. The processing cores may be configured to perform parallel processing of multiple data streams simultaneously, with dedicated circuits for common data transformation operations such as normalization, formatting, validation, etc.

The data integration facilities may provide data extraction mechanisms to connect to and retrieve information from various sources, including relational databases, NoSQL databases, flat files, APIs, and cloud storage systems, among many others. The data integration facilities may also offer tools for data transformation, enabling data cleaning, data normalization, and the conversion of data into a consistent format. This may involve data mapping, data type conversion, and the application of operational rules or calculations.

Furthermore, the set of data integration facilities may include mechanisms for data loading, supporting the transfer of transformed data into target systems such as data warehouses, data lakes, or analytical databases. Real-time integration capabilities can be incorporated to process and integrate data in near real-time, ensuring up-to-date information. To maintain data quality throughout the integration process, the data integration facilities may provide features for ensuring data accuracy, completeness, and consistency.

In some implementations, the data integration facilities may comprise metadata management tools for capturing, storing, and managing metadata, providing context and lineage for integrated data. The data integration facilities can also include scheduling and automation capabilities, allowing the streamlining of data integration processes, reducing manual intervention and ensuring timely data updates. Error handling mechanisms and detailed logging capabilities can be used to track and troubleshoot integration issues.

The data integration facilities may incorporate security and compliance features to ensure data protection, access control, and adherence to relevant client or partner contracts, industry practices, regulations, standards, and the like throughout the integration process. These various components can work in concert to consolidate data assets and improve data quality.

In embodiments, the data integration facilities may include a sensor and data fusion system, expanding the capabilities of platform 100 to handle diverse data sources and complex integration scenarios. Sensor and/or data fusion systems enable the aggregation and processing of data from multiple sensors, sensor networks, and data sources. The sensor and data fusion system can synchronize and correlate data from disparate sensors and data sources, accounting for variations in data formats, sampling rates, and measurement units. The sensor and data fusion system can combine data from multiple sources to derive more accurate, complete, or reliable information than what could be obtained from any individual source alone. In the context of data integration facilities, sensor and data fusion capabilities can be applied to merge information from various databases, real-time streams, and external systems, which may involve techniques such as probabilistic inference, statistical analysis, or machine learning algorithms to reconcile conflicting data points and extract meaningful insights.

The data integration facilities can be configured to automatically integrate relevant data from data sources using different mechanisms. For instance, the data integration facilities of the platform 100 may incorporate natural language processing (NLP) and machine learning algorithms to analyze and categorize scientific literature, publications, texts, and the like, enabling understanding of the content, context, and relevance of publications to specific research areas or topics associated with synthetic biology development. In embodiments, an automated web scraping component could be implemented to continuously scan and retrieve new data from data sources such as publications from reputable scientific journals, preprint servers, and academic databases, ensuring that the data integration facilities have access to the most up-to-date research literature. In implementations, the data integration facilities could utilize semantic analysis techniques to extract key information from data sources. For example, the data integration facilities could use semantic analysis techniques to extract specific information from scientific papers, such as methodologies, results, and conclusions. This extracted data could then be structured and integrated into the knowledge base of the platform. The platform 100 could employ text summarization algorithms to generate concise overviews of integrated publications, making it easier to determine the main points of relevant research. An ontology-based integration system could be implemented to map concepts and terminology, ensuring consistent interpretation of integrated literature. In embodiments, the data integration facilities of the platform may incorporate knowledge graphs that enhance the ability to manage, understand, and utilize data from multiple sources.

The platform 100 may include components for processing and storing data. A data processing component may prepare raw data for use in modeling and/or analysis. An integration/API layer may enable communications between platform components and external systems. A data storage component may store raw data, processed data, model outputs, and/or the like. The platform 100 may provide results and visualizations to users through the visualization and reporting component, and the platform can interact with third-party systems (e.g., to receive third party data, use third party models such as large language models) via the integration/API layer.

The platform 100 may include components for generating user interfaces and/or controlling external equipment. An equipment control component may interface with and/or control laboratory equipment (e.g., based on a model that determines optimal environmental conditions). The visualization and reporting component may present unified data, analytics, results, and the like to users and may receive user inputs and/or instructions.

Other functions of the data integration facilities may include compressing, decompressing, encoding, decoding, and otherwise processing data packets, signals, and other information as it exchanged among the systems and/or subsystems of platform, such as transforming data from one format or protocol to another as needed in order for one system or subsystem to consume output from another.

The data integration facilities may integrate data from a diverse range of data sources, including publication data sets relating to biological strains, proprietary data sets relating to biological strains, client- or partner-specific data (e.g., operational data, client requirements, and client contracts), public databases (e.g., GenBank, UniProt, KEGG, EcoCyc, and ChEMBL), scientific literature (e.g., research articles, theses and dissertations, and patents and patent applications), experimental data (e.g., laboratory results, plate-based assay results, full-scale bioreactor results, and high-throughput screening results), metagenomic and transcriptomic data (e.g., environmental genomes and RNA-Seq data), data from bioinformatics tools (e.g., pathway analysis software and gene editing tools), fermentation data (e.g., process monitoring data, historical production data), market research (e.g., industry reports, surveys, and feedback), regulatory data, simulation and modeling data, synthetic data, and many others.

The platform 100 may utilize a variety of publication datasets in the optimization of environmental conditions, focusing on several key types of data that provide insights into genetic functions, metabolic pathways, and other relevant biological information. Publication data sets relating to biological strains may include gene function descriptions (e.g., gene annotations and functional genomics studies), metabolic pathway databases (e.g., pathway maps and pathway reconstruction studies), comparative genomics (e.g., comparative studies and phylogenetic analyses), "omics" data (e.g., transcriptomic data such as RNA-Seq data and proteomics data), functional assays and experiments (e.g., experimental data and high-throughput screening results), bioinformatics analyses (e.g., computational predictions and network analyses), regulatory studies (e.g., gene regulation studies), enzyme characterization (e.g., enzyme function studies, mutagenesis studies), case studies, and patent literature, among many others.

The publication data sets may include functional descriptions of genes from relevant databases (e.g., the EcoCyc™ database). This data may include information about genetic modifications made to strains and information about a corresponding target phenotype or other property of interest (e.g., production of a specific metabolite, growth rate under certain conditions, or fitness). In implementations, the publication datasets related to strains could be published knock-out fitness experiment results for strains like *E. coli.*

In embodiments, the platform 100 may utilize proprietary data sets in the optimization of environmental conditions. The platform 100 may obtain proprietary data for a specific optimization task, which may be provided by a client and/or partner and/or may be provided for a particular application.

The platform 100 may interact with external systems including test equipment, production equipment (e.g., tanks), and third-party systems. These external systems may provide data to the platform and receive control instructions and/or insights from it. The components of platform 100 may interact in various ways to enable environmental optimization recommendations. For example, the platform 100 may receive data from test equipment and/or production equipment, process that data using the data processing component and store the processed data in the data storage. In embodiments, the platform 100 may receive data for different strains with results indicating the performance of the strain in both plate assays and in tanks (bioreactors).

The proprietary data sets may include a set of parameters of a synthetic biological process in which the biological strain produces the functional output. In embodiments, a synthetic biological process may refer to the engineered manipulation of a biological strain to systematically produce a specific functional output. The proprietary data sets may comprise genetic parameters (e.g., gene copy number, plasmid copy number, base strain information, integration sites, promoter information, edits on plasmids, and ribosome binding sites), metabolic parameters (e.g., metabolite concentrations, reaction fluxes, flux distribution, byproduct formation rates, enzyme activity levels, energy charge and ATP levels, cofactor availability, redox balance, substrate uptake rates, product inhibition and feedback regulation, metabolic pathway efficiency, oxygen uptake rate, metabolic burden, enzyme kinetics [Km, Vmax], and metabolite channeling), growth and physiological parameters (e.g., growth rate, biomass yield, oxygen consumption rate, cell viability, cell density, and stress indicators), environmental and culture conditions (e.g., temperature, inducer concentrations, nutrient availability, pH levels, salinity, osmotic pressure, culture medium composition, $CO_2$ levels, light exposure, osmolyte concentrations, redox potential, and humidity and evaporation rates), process parameters (e.g., induction timing, culture volume and scale, fermentation conditions, agitation speed, shaking rate, oxygen levels and aeration rates, pressure conditions, mode of operation [batch, fed-batch, continuous], nutrient feed strategies and feed rates, sampling frequency and methods, harvesting methods, bioreactor type and configuration, mixing times, mass transfer coefficients, scalability factors, scale-dependent kinetics, power input per unit volume, and energy inputs), functional output parameters (e.g., product yield, productivity rate, product purity, product titer, specific productivity, volumetric productivity, conversion efficiency, product stability, and overall process yield), regulatory and control parameters (e.g., regulatory network configurations and feedback control mechanisms), phenotypic parameters (e.g., cell morphology, colony appearance, motility, biofilm formation, stress resistance, metabolic activity indicators, growth phase characteristics, protein expression levels, protein stability and folding, post-translational modifications. mRNA stability, and protein localization), "omics" parameters (e.g., transcriptomics, proteomics, genomics, and metabolomics), scale-up parameters (e.g., mixing times, mass transfer coefficients, scalability factors, scale-dependent kinetics, power input per unit volume, hydraulic retention time, oxygen transfer rate, shear stress levels, temperature control efficiency, pH control and stability, foam control, scalability of nutrient feed strategies, and scale-dependent kinetics), and energy consumption parameters (e.g., energy inputs, power input per unit volume, total energy input, power consumption by agitator, aeration energy cost, cooling and heating energy consumption, energy efficiency of filtration and separation systems, energy recovery systems, power usage effectiveness (PUE), operational load patterns, maintenance and downtime energy costs, automated energy management systems, energy benchmarking and monitoring, and renewable energy integration), among many others.

The various neural networks of the platform 100 may be optimized for processing the biological parameter data. In some applications, the neural networks may use a multi-headed attention mechanism where separate attention heads process different types of parameters (e.g., genetic, metabolic, environmental) in parallel before combining their outputs, thereby efficiently processing heterogeneous parameter data. The attention mechanism may leverage a plurality of processing cores (e.g., GPUs, NPUs, TPUs, FPGAs, etc.) to compute attention weights in parallel.

In embodiments, at 5204, the output of the data integration facilities is configured as an input or otherwise provided to a set of artificial intelligence (AI)-based learning models. The AI-based learning models are configured to process and analyze the integrated data to generate insights, predictions, recommendations, decision support, control instructions, and the like based on patterns and relationships identified within the data.

The set of AI-based learning models may comprise various architectures and approaches to machine learning, including but not limited to: transformer models, convolutional neural networks, deep learning models, supervised models, semi-supervised models, unsupervised models, reinforcement models, long short-term memory (LSTM) models, multi-layer perceptron, lin-log models, large language models, large protein models, and protein language models.

The AI-based learning models may be implemented using various architectural configurations and combinations to optimize performance for specific tasks. For example, a hybrid architecture may combine an LSTM model with a multi-layer perceptron, where the LSTM processes functional embeddings information for genetic edits to generate strain embeddings, which are then fed into the multi-layer perceptron to produce targeted recommendations to achieve fitness targets or other desired outcomes.

The platform supports flexible model architectures to accommodate different analytical requirements. These include transformer-based architectures that leverage attention mechanisms for processing sequential data, ensemble and/or hybrid architectures that combine multiple model types to improve robustness and performance, and other specialized architectures tailored to specific use cases. The AI-based learning models may incorporate parallel input layers to process multiple data streams simultaneously, enabling more comprehensive analysis of complex datasets.

The models can be configured with different optimization strategies, loss functions, and training approaches based on the specific requirements of the analysis task. This includes the ability to fine-tune model parameters, implement custom activation functions, and incorporate domain-specific constraints to ensure the generated outputs align with biological and experimental constraints.

In embodiments, at 5206, at least one member of the of the set of AI-based learning models may be configured to generate a set of recommendations for modifications to a set of environmental parameters for a process in which a biological strain produces a functional output such that the set of recommendations can enhance the production of the functional output by the biological strain.

The platform 100 may execute the set of AI-based learning models using adaptive computation techniques that dynamically adjust a model's computational complexity based on input complexity. For example, when processing simple parameter sets, the platform 100 may execute the AI-based learning model using a reduced number of layers or attention heads to conserve computational resources. Conversely, for complex parameter sets requiring more detailed analysis, the platform 100 may dynamically configure the AI-based learning model to activate additional layers and/or computational pathways.

Modification of environmental parameters may significantly enhance the production of outputs by biological strains, and may include temperature, pH level, oxygen supply, nutrient composition, fermentation time, stirring and mixing, light conditions (e.g., for phototrophic organisms), toxicity management, pressure, salinity, dissolved oxygen levels, carbon dioxide levels, and many others.

For example, adjusting the temperature to an optimal temperature for a biological strain can enhance metabolic activity and enzyme efficiency, leading to higher product yields. In another example, gradually changing pH during a fermentation process can promote specific metabolic pathways leading to increased output. In yet another example, adjusting the aeration rate can optimize oxygen availability for aerobic processes, enhancing cell growth and product formation. By modifying certain environmental parameters, the production of functional outputs from biological strains may be improved.

In embodiments, the platform 100 may include a simulation engine that is configured to generate and execute simulations for different process scenarios in which the biological strain produces the functional output, wherein each process scenario has a different set of modifications to a set of environmental parameters. The simulation engine can generate multiple simulated process scenarios, where each scenario tests different modifications to a set of environmental parameters. The simulation engine executes these scenarios and generates simulation data based on the results.

The simulation data generated from these simulations can be received as additional input by the set of AI-based learning models. This simulation data, along with other data inputs, can be used by the set of AI-based learning models to generate recommendations. The recommendations can be based at least in part on analyzing the outcomes and results captured in the simulation data. In some embodiments, the simulation data may be integrated with other data by the data integration facilities before being provided to the set of AI-based learning models.

The platform's ability to incorporate simulation data as an additional input allows it to leverage both real experimental data and simulated outcomes when generating recommendations. This combination of actual and simulated data provides a more comprehensive basis for the platform's recommendation capabilities.

In some embodiments, the simulation engine may use digital twins in the execution of its simulations. In embodiments, the platform 100 may include a digital twin system configured to generate and/or manage digital twins. The digital twins may include biological strain digital twins, synthetic biological process digital twins, gene digital twins, genome digital twins, pathway digital twins, bioreactor and/or fermentation system digital twins, protein digital twins, metabolite digital twins, enzyme digital twins, and digital twins representing any of the synthetic biology entities described throughout this disclosure and documents incorporated herein.

In embodiments, the simulation engine may employ distributed computing techniques to parallelize the execution of digital twin simulations across multiple computing nodes. For example, each node may be responsible for simulating specific aspects of a biological system (e.g., metabolic pathways, environmental conditions, genetic expressions, etc.) or other systems that are represented by the digital twin. The platform 100 may then aggregate results using a synchronization layer that maintains temporal consistency across simulations. This and other examples of distributed approaches can enable fast simulation of complex biological systems.

Additionally or alternatively, the simulation engine may use distributed computing techniques (e.g., GPU-based parallelization) to efficiently execute multiple simulations by batching neural network computations and/or distributing ODE integrations across processing cores. In some of these implementations, the platform may execute multiple ODE simulations in parallel using a neural ODE simulator that optimizes processing core (e.g., GPU) utilization. In embodiments, the platform 100 may coordinate batch sizes and/or memory allocation to maximize computational efficiency.

Platform for Pathway Optimization

Referring to FIG. 13, the platform 100 may be configured to generate a set of recommendations for modifications to a set of biological pathways in a process in which a biological strain produces a functional output. Such recommendations may be used to enhance the production of the functional output by the biological strain.

In embodiments, a biological strain may refer to a genetically distinct variant or subtype of a biological organism, including microorganisms such as bacteria, fungi, and viruses, or any of the other biological organisms or microorganisms described throughout this disclosure and documents the documents incorporated herein by reference, that exhibits specific phenotypic or genotypic characteristics that distinguish it from other members of the same species.

Functional outputs may refer to outputs involved in the production of fuel applications and solutions (e.g., methanol, ethanol, biodiesel, fuel additives, and lubricants), industrial applications and solutions (e.g., chemicals and materials, fibers and textiles, mining, industrial sensors, agriculture, and aquaculture), consumer product applications and solutions (e.g., food and beverage, consumer goods, and nutraceuticals), and pharmaceutical and medical applications and solutions (e.g., cell therapies, vaccines, personalized medicines, and medical sensors), among many others.

Enhancements to functional outputs by the biological strain may include, for example, improved performance, the production of novel compounds, cost reduction, sustainability, pathogen resistance, bioremediation capabilities, customization for specific environments, compliance with regulatory standards, and many others, including any of the enhancements discussed throughout this disclosure and the documents incorporated herein by reference. Improved performance, for example, could include an increase in product yield, efficiency, and/or robustness of the biological strain, making it more effective for specific applications such as biofuel production.

The platform 100 may include data integration facilities having various components and functionalities designed to combine and unify data sets from multiple data sources. In a method for generating a set of recommendations for modifications to a set of pathways associated with a process in which a biological strain produces a functional output, described at 5302-5306, at 5302, the set of data integration facilities integrates the content of at least one publication data set relating to the biological strain and at least one proprietary data set including a set of parameters of a synthetic biological process in which the biological strain produces a functional output.

In embodiments, the data integration facilities may refer to various capabilities of the synthetic biology sensor collection, processing, fusion, and staging for modeling and analytics system 2100. The data integration facilities may enable the consolidation of diverse data types and formats from different systems, databases, applications, and the like. This aggregation prepares the data for a range of applications, including advanced analytics, machine learning model training and retraining, and machine learning model execution, among many others.

In embodiments, the data integration facilities may use dedicated processing cores, such as field-programmable gate arrays (FPGAs) or application-specific integrated circuits (ASICs), to perform high-speed data transformation and integration operations. In embodiments, the data integration facilities may use a sufficient number of processing cores to enable real-time integration of streaming sensor data with historical datasets. The processing cores may be configured to perform parallel processing of multiple data streams simultaneously, with dedicated circuits for common data transformation operations such as normalization, formatting, validation, etc.

The data integration facilities may provide data extraction mechanisms to connect to and retrieve information from various sources, including relational databases, NoSQL databases, flat files, APIs, and cloud storage systems, among many others. The data integration facilities may also offer tools for data transformation, enabling data cleaning, data normalization, and the conversion of data into a consistent format. This may involve data mapping, data type conversion, and the application of operational rules or calculations.

Furthermore, the set of data integration facilities may include mechanisms for data loading, supporting the transfer of transformed data into target systems such as data warehouses, data lakes, or analytical databases. Real-time integration capabilities can be incorporated to process and integrate data in near real-time, ensuring up-to-date information. To maintain data quality throughout the integration process, the data integration facilities may provide features for ensuring data accuracy, completeness, and consistency.

In some implementations, the data integration facilities may comprise metadata management tools for capturing, storing, and managing metadata, providing context and lineage for integrated data. The data integration facilities can also include scheduling and automation capabilities, allowing the streamlining of data integration processes, reducing manual intervention and ensuring timely data updates. Error handling mechanisms and detailed logging capabilities can be used to track and troubleshoot integration issues.

The data integration facilities may incorporate security and compliance features to ensure data protection, access control, and adherence to relevant client or partner contracts, industry practices, regulations, standards, and the like throughout the integration process. These various components can work in concert to consolidate data assets and improve data quality.

In embodiments, the data integration facilities may include a sensor and data fusion system, expanding the capabilities of platform 100 to handle diverse data sources and complex integration scenarios. Sensor and/or data fusion systems enable the aggregation and processing of data from multiple sensors, sensor networks, and data sources. The sensor and data fusion system can synchronize and correlate data from disparate sensors and data sources, accounting for variations in data formats, sampling rates, and measurement units. The sensor and data fusion system can combine data from multiple sources to derive more accurate, complete, or reliable information than what could be obtained from any individual source alone. In the context of data integration facilities, sensor and data fusion capabilities can be applied to merge information from various databases, real-time streams, and external systems, which may involve techniques such as probabilistic inference, statistical analysis, or machine learning algorithms to reconcile conflicting data points and extract meaningful insights.

The data integration facilities can be configured to automatically integrate relevant data from data sources using different mechanisms. For instance, the data integration facilities of the platform 100 may incorporate natural language processing (NLP) and machine learning algorithms to analyze and categorize scientific literature, publications, texts, and the like, enabling understanding of the content, context, and relevance of publications to specific research areas or topics associated with synthetic biology development. In embodiments, an automated web scraping component could be implemented to continuously scan and retrieve new data from data sources such as publications from reputable scientific journals, preprint servers, and academic databases, ensuring that the data integration facilities have access to the most up-to-date research literature. In implementations, the data integration facilities could utilize semantic analysis techniques to extract key information from data sources. For example, the data integration facilities could use semantic analysis techniques to extract specific information from scientific papers, such as methodologies, results, and conclusions. This extracted data could then be structured and integrated into the knowledge base of the platform. The platform 100 could employ text summarization algorithms to generate concise overviews of integrated publications, making it easier to determine the main points of relevant research. An ontology-based integration system could be implemented to map concepts and terminology, ensuring consistent interpretation of integrated literature. In embodiments, the data integration facilities of the platform may incorporate knowledge graphs that enhance the ability to manage, understand, and utilize data from multiple sources.

The platform 100 may further comprise components for processing and storing data. A data processing component may prepare raw data for use in modeling and/or analysis. An integration/API layer may enable communications between platform components and external systems. A data storage component may store raw data, processed data, model outputs, and/or the like. The platform 100 may provide results and visualizations to users through the visualization and reporting component, and the platform can interact with third-party systems (e.g., to receive third party data, use third party models such as large language models) via the integration/API layer.

The platform 100 may include components for generating user interfaces and/or controlling external equipment. An equipment control component may interface with and/or control laboratory equipment (e.g., based on a model that determines optimal environmental conditions). A visualization and reporting component may present unified data, analytics, results, and the like to users and may receive user inputs and/or instructions.

Other functions of the data integration facilities may include compressing, decompressing, encoding, decoding, and otherwise processing data packets, signals, and other information as it exchanged among the systems and/or subsystems of platform, such as transforming data from one format or protocol to another as needed in order for one system or subsystem to consume output from another.

The data integration facilities may integrate data from a diverse range of data sources, including publication data sets relating to biological strains, proprietary data sets relating to biological strains, client- or partner-specific data (e.g., operational data, client requirements, and client contracts), public databases (e.g., GenBank, UniProt, KEGG, EcoCyc, and ChEMBL), scientific literature (e.g., research articles, theses and dissertations, and patents and patent applications), experimental data (e.g., laboratory results, plate-based assay results, full-scale bioreactor results, and high-throughput screening results), metagenomic and transcriptomic data (e.g., environmental genomes and RNA-Seq data), data from bioinformatics tools (e.g., pathway analysis software and gene editing tools), fermentation data (e.g., process monitoring data, historical production data), market research (e.g., industry reports, surveys, and feedback), regulatory data, simulation and modeling data, synthetic data, and many others.

The platform 100 may utilize a variety of publication datasets in the optimization of pathways, focusing on several key types of data that provide insights into genetic functions, metabolic pathways, and other relevant biological information. Publication data sets relating to biological strains may include gene function descriptions (e.g., gene annotations and functional genomics studies), metabolic pathway databases (e.g., pathway maps and pathway reconstruction studies), comparative genomics (e.g., comparative studies and phylogenetic analyses), "omics" data (e.g., transcriptomic data such as RNA-Seq data and proteomics data), functional assays and experiments (e.g., experimental data and high-throughput screening results), bioinformatics analyses (e.g., computational predictions and network analyses), regulatory studies (e.g., gene regulation studies), enzyme characterization (e.g., enzyme function studies, mutagenesis studies), case studies, and patent literature, among many others.

The publication data sets may include functional descriptions of genes from relevant databases (e.g., the EcoCyc™ database). This data may include information about genetic modifications made to strains and information about a corresponding target phenotype or other property of interest (e.g., production of a specific metabolite, growth rate under certain conditions, or fitness). In implementations, the publication datasets related to strains could be published knockout fitness experiment results for strains like *E. coli*.

In embodiments, the platform 100 may utilize proprietary data sets in the optimization of pathways. The platform 100 may obtain proprietary data for a specific optimization task, which may be provided by a client or partner and/or may be provided for a particular application.

The platform 100 may interact with external systems including test equipment, production equipment (e.g., tanks), and third-party systems. These external systems provide data to the platform and receive control instructions and/or insights from it. The components of platform 100 may interact in various ways to enable pathway optimization recommendations. For example, the platform 100 may receive data from test equipment and/or production equipment, process that data using the data processing component and store the processed data in the data storage. In embodiments, the platform 100 may receive data for different strains with results indicating the performance of the strain in both plate assays and in tanks (bioreactors).

The proprietary data sets may include a set of parameters of a synthetic biological process in which the biological strain produces the functional output. In embodiments, a synthetic biological process may refer to the engineered manipulation of a biological strain to systematically produce a specific functional output. The proprietary data sets may comprise genetic parameters (e.g., gene copy number, plasmid copy number, base strain information, integration sites, promoter information, edits on plasmids, and ribosome binding sites), metabolic parameters (e.g., metabolite concentrations, reaction fluxes, flux distribution, byproduct formation rates, enzyme activity levels, energy charge and ATP levels, cofactor availability, redox balance, substrate uptake rates, product inhibition and feedback regulation, metabolic pathway efficiency, oxygen uptake rate, metabolic burden, enzyme kinetics [Km, Vmax], and metabolite channeling), growth and physiological parameters (e.g., growth rate, biomass yield, oxygen consumption rate, cell viability, cell density, and stress indicators), environmental and culture conditions (e.g., temperature, inducer concentrations, nutrient availability, pH levels, salinity, osmotic pressure, culture medium composition, $CO_2$ levels, light exposure, osmolyte concentrations, redox potential, and humidity and evaporation rates), process parameters (e.g., induction timing, culture volume and scale, fermentation conditions, agitation speed, shaking rate, oxygen levels and aeration rates, pressure conditions, mode of operation [batch, fed-batch, continuous], nutrient feed strategies and feed rates, sampling frequency and methods, harvesting methods, bioreactor type and configuration, mixing times, mass transfer coefficients, scalability factors, scale-dependent kinetics, power input per unit volume, and energy inputs), functional output parameters (e.g., product yield, productivity rate, product purity, product titer, specific productivity, volumetric productivity, conversion efficiency, product stability, and overall process yield), regulatory and control parameters (e.g., regulatory network configurations and feedback control mechanisms), phenotypic parameters (e.g., cell morphology, colony appearance, motility, biofilm formation, stress resistance, metabolic activity indicators, growth phase characteristics, protein expression levels, protein stability and folding, post-translational modifications. mRNA stability, and protein localization), "omics" parameters (e.g., transcriptomics, proteomics, genomics, and metabolomics), scale-up parameters (e.g., mixing times, mass transfer coefficients, scalability factors, scale-dependent kinetics, power input per unit volume, hydraulic retention time, oxygen transfer rate, shear stress levels, temperature control efficiency, pH control and stability, foam control, scalability of nutrient feed strategies, and scale-dependent kinetics), and energy consumption parameters (e.g., energy inputs, power input per unit volume, total energy input, power consumption by agitator, aeration energy cost, cooling and heating energy consumption, energy efficiency of filtration and separation systems, energy recovery systems, power usage effectiveness (PUE), operational load patterns, maintenance and downtime energy costs, automated energy management systems, energy benchmarking and monitoring, and renewable energy integration), among many others.

The proprietary data sets may include certain types of genetic modification data such as values indicating the base strain, each edit on plasmids, the copy number of the plasmids, the promoters that are used, the integration sites, and/or the like. The proprietary data sets may also include complementary information such as metabolite levels, gene expression data, and/or reaction fluxes. These additional data values may provide additional context for the genetic modifications, enabling models to obtain a more comprehensive understanding of the effects of genetic edits.

The various neural networks of the platform 100 may be optimized for processing the biological parameter data and/or genetic modification data. In some applications, the neural networks may use a multi-headed attention mechanism where separate attention heads process different types of parameters (e.g., genetic, metabolic, environmental) in parallel before combining their outputs, thereby efficiently processing heterogeneous parameter data. The attention mechanism may leverage a plurality of processing cores (e.g., GPUs, NPUs, TPUs, FPGAs, etc.) to compute attention weights in parallel.

In embodiments, at 5304, the output of the data integration facilities is configured as an input or otherwise provided to a set of artificial intelligence (AI)-based learning models. The set of AI-based learning models are configured to process and analyze the integrated data to generate insights, predictions, recommendations, decision support, control instructions, or the like based on patterns and relationships identified within the data.

The set of AI-based learning models may comprise various architectures and approaches to machine learning, including but not limited to: transformer models, convolutional neural networks, deep learning models, supervised models, semi-supervised models, unsupervised models, reinforcement models, long short-term memory (LSTM) models, multi-layer perceptron, lin-log models, large language models, large protein models, and protein language models.

The AI-based learning models may be implemented using various architectural configurations and combinations to optimize performance for specific tasks. For example, a hybrid architecture may combine an LSTM model with a multi-layer perceptron, where the LSTM processes functional embeddings information for genetic edits to generate strain embeddings, which are then fed into the multi-layer perceptron to produce targeted recommendations to achieve fitness targets or other desired outcomes.

The platform supports flexible model architectures to accommodate different analytical requirements. These include transformer-based architectures that leverage attention mechanisms for processing sequential data, ensemble and/or hybrid architectures that combine multiple model types to improve robustness and performance, and other specialized architectures tailored to specific use cases. The AI-based learning models may incorporate parallel input layers to process multiple data streams simultaneously, enabling more comprehensive analysis of complex datasets.

The models can be configured with different optimization strategies, loss functions, and training approaches based on the specific requirements of the analysis task. This includes the ability to fine-tune model parameters, implement custom activation functions, and incorporate domain-specific constraints to ensure the generated outputs align with biological and experimental constraints.

In embodiments, at 5306, at least one member of the of the set of AI-based learning models may be configured to generate a set of recommendations for modifications to a set of biological pathways associated with a process in which a biological strain produces a functional output such that the recommendations can enhance the production of the functional output by the biological strain.

The platform 100 may execute the set of AI-based learning models using adaptive computation techniques that dynamically adjust a model's computational complexity based on input complexity. For example, when processing simple parameter sets, the platform 100 may execute the AI-based learning model using a reduced number of layers or attention heads to conserve computational resources. Conversely, for complex parameter sets requiring more detailed analysis, the platform 100 may dynamically configure the AI-based learning model to activate additional layers and/or computational pathways.

To improve the production of a functional output from the biological strain, modifications to biological pathways may include identification and overexpression of key enzymes that are critical for the desired biosynthetic pathway, the use of stronger or inducible promoters, the knockout of competing pathways, pathway engineering, optimization of substrate utilization, feedback regulation modification, cofactor engineering, pathway flux redistribution, integration of pathways, environmental adaptations, and the like.

The set of recommendations for modifications may relate to overexpression of pathway enzymes, which may involve gene amplification, or increasing the copy number of genes encoding key enzymes in the pathway to enhance enzyme levels and boost metabolic flux, or the use of stronger promoters or inducible promoters to drive higher expression levels of target enzymes. Another potential modification may involve the knockout of competing pathways, using gene deletion to identify and knockout genes involved in competing pathways that divert precursors away from the desired product or pathway disruption by targeting enzymes that catalyze side reactions. Pathway engineering modification recommendations may involve synthetic pathway construction, which refers to the designing and implementing of new metabolic pathways that convert substrates into target products, or the engineering of modular pathways that can be combined or reconfigured to optimize production. Recommendations to optimize substrate utilization may relate to substrate specificity modification or the utilization of alternative carbon sources. Feedback regulation modification recommendations might involve the elimination of feedback inhibition by modifying or knocking out genes that encode for regulatory proteins inhibiting key enzymes in response to high product concentrations or could involve the implementation of synthetic feedback systems that allow fine-tuning of enzyme activity based on real-time product levels. Cofactor engineering modification recommendations can include cofactor supply enhancement (e.g., increasing the availability of NADPH or ADP) or cofactor regeneration by engineering pathways that regenerate cofactors efficiently. Recommendations related to pathway flux redistribution may involve metabolic flux analysis, or the use of computational models to identify bottlenecks and the modification of the pathway to redistribute flux toward the desired output, or enzyme kinetics optimization by modifying enzyme kinetics (e.g., affinity or turnover number) through directed evolution or site-directed mutagenesis to enhance overall pathway efficiency. Modifications involving integration of pathways might refer to pathway coupling or cross-pathway regulation by implementing regulatory mechanisms that synchronize the operation of multiple pathways to optimize overall production. Recommendations to adjust environmental adaptations could involve condition-specific modifications, such as by modifying pathways to respond favorably to specific environmental conditions (e.g., temperature or pH) to enhance product yield or stress tolerance engineering, which refers to enhancing pathways to improve strain tolerance to byproducts or inhibitory compounds generated during production. By recommending pathway optimization modifications, the performance of biological strains in producing desired functional outputs can be significantly enhanced.

In embodiments, the platform 100 may include a simulation engine that is configured to generate and execute simulations for different process scenarios in which the biological strain produces the functional output, wherein each process scenario has a different set of modifications to a set of pathways. The simulation engine can generate multiple simulated process scenarios, where each scenario tests different modifications to a set of pathways. The simulation engine executes these scenarios and generates simulation data based on the results.

The simulation data generated from these simulations can be received as additional input by the set of AI-based learning models. This simulation data, along with other data inputs, can be used by the set of AI-based learning models to generate recommendations. The recommendations can be based at least in part on analyzing the outcomes and results captured in the simulation data. In some embodiments, the simulation data may be integrated with other data by the data integration facilities before being provided to the set of AI-based learning models.

The platform's ability to incorporate simulation data as an additional input allows it to leverage both real experimental data and simulated outcomes when generating recommendations. This combination of actual and simulated data provides a more comprehensive basis for the platform's recommendation capabilities.

In some embodiments, the simulation engine may use digital twins in the execution of its simulations. In embodiments, the platform 100 may include a digital twin system configured to generate and/or manage digital twins. The digital twins may include biological strain digital twins, synthetic biological process digital twins, gene digital twins, genome digital twins, pathway digital twins, bioreactor and/or fermentation system digital twins, protein digital twins, metabolite digital twins, enzyme digital twins, and digital twins representing any of the synthetic biology entities described throughout this disclosure and documents incorporated herein.

In embodiments, the simulation engine may employ distributed computing techniques to parallelize the execution of digital twin simulations across multiple computing nodes. For example, each node may be responsible for simulating specific aspects of a biological system (e.g., metabolic pathways, environmental conditions, genetic expressions, etc.) or other systems that are represented by the digital twin. The platform 100 may then aggregate results using a synchronization layer that maintains temporal consistency across simulations. This and other example distributed approaches can enable fast simulation of complex biological systems.

Platform for Protein and Enzyme Optimization

Referring to FIG. 14, the platform 100 may be configured to generate a set of recommendations for modifications to a set of proteins and/or enzymes associated with a biological strain. Such recommendations may be used to enhance the production of a functional output by the biological strain.

In embodiments, a biological strain may refer to a genetically distinct variant or subtype of a biological organism, including microorganisms such as bacteria, fungi, and viruses, or any of the other biological organisms or microorganisms described throughout this disclosure and documents the documents incorporated herein by reference, that exhibits specific phenotypic or genotypic characteristics that distinguish it from other members of the same species.

Functional outputs may refer to outputs involved in the production of fuel applications and solutions (e.g., methanol, ethanol, biodiesel, fuel additives, and lubricants), industrial applications and solutions (e.g., chemicals and materials, fibers and textiles, mining, industrial sensors, agriculture, and aquaculture), consumer product applications and solutions (e.g., food and beverage, consumer goods, and nutraceuticals), and pharmaceutical and medical applications and solutions (e.g., cell therapies, vaccines, personalized medicines, and medical sensors), among many others.

Enhancements to functional outputs by the biological strain may include, for example, improved performance, the production of novel compounds, cost reduction, sustainability, pathogen resistance, bioremediation capabilities, customization for specific environments, compliance with regulatory standards, and many others, including any of the enhancements discussed throughout this disclosure and the documents incorporated herein by reference. Improved performance, for example, could include an increase in product yield, efficiency, and/or robustness of the biological strain, making it more effective for specific applications such as biofuel production.

The platform 100 may include data integration facilities having various components and functionalities designed to combine and unify data sets from multiple data sources. In a method for generating a set of recommendations for modifications to a set of proteins and/or enzymes associated biological strain, described at 5402-5406, at 5402, the set of data integration facilities integrates the content of at least one publication data set relating to the biological strain and at least one proprietary data set including a set of parameters of a synthetic biological process in which the biological strain produces a functional output.

In embodiments, the data integration facilities may refer to various capabilities of the synthetic biology sensor collection, processing, fusion, and staging for modeling and analytics system 2100. The data integration facilities may enable the consolidation of diverse data types and formats from different systems, databases, applications, and the like. This aggregation prepares the data for a range of applications, including advanced analytics, machine learning model training and retraining, and machine learning model execution, among many others. In some embodiments, the data integration facilities may be configured to integrate the content of at least one publication data set relating to a biological strain and at least one proprietary data set including a set of parameters of a workflow in which the biological strain produces a functional output.

In embodiments, the data integration facilities may use dedicated processing cores, such as field-programmable gate arrays (FPGAs) or application-specific integrated circuits (ASICs), to perform high-speed data transformation and integration operations. In embodiments, the data integration facilities may use a sufficient number of processing cores to enable real-time integration of streaming sensor data with historical datasets. The processing cores may be configured to perform parallel processing of multiple data streams simultaneously, with dedicated circuits for common data transformation operations such as normalization, formatting, validation, etc.

The data integration facilities may provide data extraction mechanisms to connect to and retrieve information from various sources, including relational databases, NoSQL databases, flat files, APIs, and cloud storage systems, among many others. The data integration facilities may also offer tools for data transformation, enabling data cleaning, data normalization, and the conversion of data into a consistent format. This may involve data mapping, data type conversion, and the application of operational rules or calculations.

Furthermore, the set of data integration facilities may include mechanisms for data loading, supporting the transfer of transformed data into target systems such as data warehouses, data lakes, or analytical databases. Real-time integration capabilities can be incorporated to process and integrate data in near real-time, ensuring up-to-date information. To maintain data quality throughout the integration process, the data integration facilities may provide features for ensuring data accuracy, completeness, and consistency.

In some implementations, the data integration facilities may comprise metadata management tools for capturing, storing, and managing metadata, providing context and lineage for integrated data. The data integration facilities can also include scheduling and automation capabilities, allowing the streamlining of data integration processes, reducing manual intervention and ensuring timely data updates. Error handling mechanisms and detailed logging capabilities can be used to track and troubleshoot integration issues.

The data integration facilities may incorporate security and compliance features to ensure data protection, access control, and adherence to relevant client or partner contracts, industry practices, regulations, standards, and the like throughout the integration process. These various components can work in concert to consolidate data assets and improve data quality.

In embodiments, the data integration facilities may include a sensor and data fusion system, expanding the capabilities of platform 100 to handle diverse data sources and complex integration scenarios. Sensor and/or data fusion systems enable the aggregation and processing of data from multiple sensors, sensor networks, and data sources. The sensor and data fusion system can synchronize and correlate data from disparate sensors and sources, accounting for variations in data formats, sampling rates, and measurement units. The sensor and data fusion system can combine data from multiple sources to derive more accurate, complete, or reliable information than what could be obtained from any individual source alone. In the context of data integration facilities, sensor and data fusion capabilities can be applied to merge information from various databases, real-time streams, and external systems, which may involve techniques such as probabilistic inference, statistical analysis, or machine learning algorithms to reconcile conflicting data points and extract meaningful insights.

The data integration facilities can be configured to automatically integrate relevant data from data sources using different mechanisms. For instance, the data integration facilities of the platform 100 may incorporate natural language processing (NLP) and machine learning algorithms to analyze and categorize scientific literature, publications, texts, and the like, enabling understanding of the content, context, and relevance of publications to specific research areas or topics associated with synthetic biology development. In embodiments, an automated web scraping component could be implemented to continuously scan and retrieve new data from data sources such as publications from reputable scientific journals, preprint servers, and academic databases, ensuring that the data integration facilities have access to the most up-to-date research literature. In implementations, the data integration facilities could utilize semantic analysis techniques to extract key information from data sources. For example, the data integration facilities could use semantic analysis techniques to extract specific information from scientific papers, such as methodologies, results, and conclusions. This extracted data could then be structured and integrated into the knowledge base of the platform. The platform 100 could employ text summarization algorithms to generate concise overviews of integrated publications, making it easier to determine the main points of relevant research. An ontology-based integration system could be implemented to map concepts and terminology, ensuring consistent interpretation of integrated literature. In embodiments, the data integration facilities of the platform may incorporate knowledge graphs that enhance the ability to manage, understand, and utilize data from multiple sources.

The platform 100 may include components for processing and storing data. A data processing component may prepare raw data for use in modeling and/or analysis. An integration/API layer may enable communications between platform components and external systems. A data storage component may store raw data, processed data, model outputs, and/or the like. The platform 100 may provide results and visualizations to users through the visualization and reporting component, and the platform can interact with third-party systems (e.g., to receive third party data, use third party models such as large language models) via the integration/API layer.

The platform 100 may include components for generating user interfaces and/or controlling external equipment. An equipment control component may interface with and/or control laboratory equipment (e.g., based on a model that determines optimal environmental conditions). A visualization and reporting component may present unified data, analytics, results, and the like to users and may receive user inputs and/or instructions.

Other functions of the data integration facilities may include compressing, decompressing, encoding, decoding, and otherwise processing data packets, signals, and other information as it exchanged among the systems and/or subsystems of platform, such as transforming data from one format or protocol to another as needed in order for one system or subsystem to consume output from another.

The data integration facilities may integrate data from a diverse range of data sources, including publication data sets relating to biological strains, proprietary data sets relating to biological strains, client- or partner-specific data (e.g., operational data, client requirements, and client contracts), public databases (e.g., GenBank, UniProt, KEGG, EcoCyc, and ChEMBL), scientific literature (e.g., research articles, theses and dissertations, and patents and patent applications), experimental data (e.g., laboratory results, plate-based assay results, full-scale bioreactor results, and high-throughput screening results), metagenomic and transcriptomic data (e.g., environmental genomes and RNA-Seq data), data from bioinformatics tools (e.g., pathway analysis software and gene editing tools), fermentation data (e.g., process monitoring data, historical production data), market research (e.g., industry reports, surveys, and feedback), regulatory data, simulation and modeling data, synthetic data, and many others.

The platform 100 may utilize a variety of publication datasets in the optimization of proteins and/or enzymes, focusing on several key types of data that provide insights into genetic functions, metabolic pathways, and other relevant biological information. Publication data sets relating to biological strains may include gene function descriptions (e.g., gene annotations and functional genomics studies), metabolic pathway databases (e.g., pathway maps and pathway reconstruction studies), comparative genomics (e.g., comparative studies and phylogenetic analyses), "omics" data (e.g., transcriptomic data such as RNA-Seq data and proteomics data), functional assays and experiments (e.g., experimental data and high-throughput screening results), bioinformatics analyses (e.g., computational predictions and network analyses), regulatory studies (e.g., gene regulation studies), enzyme characterization (e.g., enzyme function studies, mutagenesis studies), case studies, and patent literature, among many others.

The publication data sets may include functional descriptions of genes from relevant databases (e.g., the EcoCyc™ database). This data may include information about genetic modifications made to strains and information about a corresponding target phenotype or other property of interest (e.g., production of a specific metabolite, growth rate under certain conditions, or fitness). In implementations, the publication datasets related to strains could be published knockout fitness experiment results for strains like *E. coli.*

In embodiments, the platform 100 may utilize proprietary data sets in the optimization of proteins and/or enzymes. The platform 100 may obtain proprietary data for a specific optimization task, which may be provided by a partner and/or may be provided for a particular application.

The platform 100 may interact with external systems including test equipment, production equipment (e.g., tanks), and third-party systems. These external systems provide data to the platform and receive control instructions and/or insights from it, thereby enabling a design-build-test-learn (DBTL) cycle. The components of platform 100 may interact in various ways to enable protein and/or enzyme optimization recommendations. For example, the platform 100 may receive data from test equipment and/or production equipment, process that data using the data processing component and store the processed data in the data storage. In embodiments, the platform 100 may receive data for different strains with results indicating the performance of the strain in both plate assays and in tanks (bioreactors).

The proprietary data sets may include a set of parameters of a synthetic biological process in which the biological strain produces the functional output. In embodiments, a synthetic biological process may refer to the engineered manipulation of a biological strain to systematically produce a specific functional output. The proprietary data sets may comprise genetic parameters (e.g., gene copy number, plasmid copy number, base strain information, integration sites, promoter information, edits on plasmids, and ribosome binding sites), metabolic parameters (e.g., metabolite concentrations, reaction fluxes, flux distribution, byproduct formation rates, enzyme activity levels, energy charge and ATP levels, cofactor availability, redox balance, substrate uptake rates, product inhibition and feedback regulation, metabolic pathway efficiency, oxygen uptake rate, metabolic burden, enzyme kinetics [Km, Vmax], and metabolite channeling), growth and physiological parameters (e.g., growth rate, biomass yield, oxygen consumption rate, cell viability, cell density, and stress indicators), environmental and culture conditions (e.g., temperature, inducer concentrations, nutrient availability, pH levels, salinity, osmotic pressure, culture medium composition, $CO_2$ levels, light exposure, osmolyte concentrations, redox potential, and humidity and evaporation rates), process parameters (e.g., induction timing, culture volume and scale, fermentation conditions, agitation speed, shaking rate, oxygen levels and aeration rates, pressure conditions, mode of operation [batch, fed-batch, continuous], nutrient feed strategies and feed rates, sampling frequency and methods, harvesting methods, bioreactor type and configuration, mixing times, mass transfer coefficients, scalability factors, scale-dependent kinetics, power input per unit volume, and energy inputs), functional output parameters (e.g., product yield, productivity rate, product purity, product titer, specific productivity, volumetric productivity, conversion efficiency, product stability, and overall process yield), regulatory and control parameters (e.g., regulatory network configurations and feedback control mechanisms), phenotypic parameters (e.g., cell morphology, colony appearance, motility, biofilm formation, stress resistance, metabolic activity indicators, growth phase characteristics, protein expression levels, protein stability and folding, post-translational modifications, mRNA stability, and protein localization), "omics" parameters (e.g., transcriptomics, proteomics, genomics, and metabolomics), scale-up parameters (e.g., mixing times, mass transfer coefficients, scalability factors, scale-dependent kinetics, power input per unit volume, hydraulic retention time, oxygen transfer rate, shear stress levels, temperature control efficiency, pH control and stability, foam control, scalability of nutrient feed strategies, and scale-dependent kinetics), and energy consumption parameters (e.g., energy inputs, power input per unit volume, total energy input, power consumption by agitator, aeration energy cost, cooling and heating energy consumption, energy efficiency of filtration and separation systems, energy recovery systems, power usage effectiveness (PUE), operational load patterns, maintenance and downtime energy costs, automated energy management systems, energy benchmarking and monitoring, and renewable energy integration), among many others.

The proprietary data sets may include certain types of genetic modification data such as values indicating the base strain, each edit on plasmids, the copy number of the plasmids, the promoters that are used, the integration sites, and/or the like. The proprietary data sets may also include complementary information such as metabolite levels, gene expression data, and/or reaction fluxes. These additional data values may provide additional context for the genetic modifications, enabling models to obtain a more comprehensive understanding of the effects of genetic edits.

The various neural networks of the platform 100 may be optimized for processing the biological parameter data. In some applications, the neural networks may use a multi-headed attention mechanism where separate attention heads process different types of parameters (e.g., genetic, metabolic, environmental) in parallel before combining their outputs, thereby efficiently processing heterogeneous parameter data. The attention mechanism may leverage a plurality of processing cores (e.g., GPUs, NPUs, TPUs, FPGAs, etc.) to compute attention weights in parallel.

In embodiments, at 5404, the output of the data integration facilities is configured as an input or otherwise provided to a set of artificial intelligence (AI)-based learning models. The set of AI-based learning models is configured to process and analyze the integrated data to generate insights, predictions, and recommendations based on patterns and relationships identified within the data.

The set of AI-based learning models may comprise various architectures and approaches to machine learning, including but not limited to: transformer models, convolutional neural networks, deep learning models, supervised models, semi-supervised models, unsupervised models, reinforcement models, long short-term memory (LSTM) models, multi-layer perceptron, lin-log models, large language models, large protein models, and protein language models.

The AI-based learning models may be implemented using various architectural configurations and combinations to optimize performance for specific tasks. For example, a hybrid architecture may combine an LSTM model with a multi-layer perceptron, where the LSTM processes functional embeddings information for genetic edits to generate strain embeddings, which are then fed into the multi-layer perceptron to produce targeted recommendations such as fitness targets or other desired outcomes.

The platform supports flexible model architectures to accommodate different analytical requirements. These include transformer-based architectures that leverage attention mechanisms for processing sequential data, ensemble and/or hybrid architectures that combine multiple model types to improve robustness and performance, and other specialized architectures tailored to specific use cases. The AI-based learning models may incorporate parallel input layers to process multiple data streams simultaneously, enabling more comprehensive analysis of complex datasets.

The models can be configured with different optimization strategies, loss functions, and training approaches based on the specific requirements of the analysis task. This includes the ability to fine-tune model parameters, implement custom activation functions, and incorporate domain-specific constraints to ensure the generated outputs align with biological and experimental constraints.

In embodiments, at 5406, at least one member of the of the set of AI-based learning models may be configured to generate a set of recommendations for modifications to a set of proteins and/or enzymes associated with a process in which a biological strain produces a functional output such that the recommendations enhance the production of the functional output by the biological strain.

The platform 100 may execute the set of AI-based learning models using adaptive computation techniques that dynamically adjust a model's computational complexity based on input complexity. For example, when processing simple parameter sets, the platform 100 may execute the AI-based learning model using a reduced number of layers or attention heads to conserve computational resources. Conversely, for complex parameter sets requiring more detailed analysis, the platform 100 may dynamically configure the AI-based learning model to activate additional layers and/or computational pathways.

To enhance the production of a functional output of the biological strain, modifications can be made to a set of proteins and/or enzymes associated with the strain. Recommendations for modifications can relate to enzyme overexpression, which could involve increased gene copies (e.g., amplifying the genes encoding key enzymes to increase their abundance within the cell) or the use of stronger promoters to drive higher expression. Additionally, site-directed mutagenesis may be employed to introduce targeted mutations in an enzyme's active site, thereby enhancing its catalytic efficiency, substrate specificity, or stability. Constructing chimeric proteins by fusing domains from different enzymes can also combine beneficial traits, such as increased stability and improved catalytic activity. Modifications to cofactor interactions, such as enhancing cofactor affinity through active site alterations or engineering regeneration pathways, can optimize enzymatic reactions. To alleviate feedback inhibition, one can disable regulatory sites or introduce synthetic regulation mechanisms that adjust enzyme activity based on product concentrations. Post-translational modifications can be strategically applied to influence enzyme performance, with alterations aimed at enhancing stability or activity through phosphorylation, glycosylation, or ubiquitination. Additionally, modifying enzyme localization to target specific cellular compartments or anchoring them to membranes can enhance their interaction with substrates, while gene knockouts may remove competing enzymes, ensuring that more substrates are funneled toward the desired pathway. Allosteric modulation techniques, such as engineering allosteric sites for small molecule interaction, can provide dynamic regulation of enzyme activity, allowing for improved product formation. Other modification approaches can integrate modular enzyme assemblies that work synergistically within the metabolic framework, creating novel pathways that significantly enhance product yield and flow, ultimately optimizing the overall production capabilities of the biological strain. These strategies, tailored to the specific biological context and desired product, can lead to substantial improvements in metabolic efficiency and overall production capabilities.

In embodiments, the platform 100 may include a simulation engine that is configured to generate and execute simulations for different process scenarios in which the biological strain produces the functional output, wherein each process scenario has a different set of modifications to a set of proteins and/or enzymes. The simulation engine can generate multiple simulated process scenarios, where each scenario tests different modifications to a set of proteins and/or enzymes. The simulation engine executes these scenarios and generates simulation data based on the results.

The simulation data generated from these simulations can be received as additional input by the set of AI-based learning models. This simulation data, along with other data inputs, can be used by the set of AI-based learning models to generate recommendations. The recommendations can be based at least in part on analyzing the outcomes and results captured in the simulation data. In some embodiments, the simulation data may be integrated with other data by the data integration facilities before being provided to the set of AI-based learning models.

The platform's ability to incorporate simulation data as an additional input allows it to leverage both real experimental data and simulated outcomes when generating recommendations. This combination of actual and simulated data provides a more comprehensive basis for the platform's recommendation capabilities.

In some embodiments, the simulation engine may use digital twins in the execution of its simulations. In embodiments, the platform 100 may include a digital twin system configured to generate and/or manage digital twins. The digital twins may include biological strain digital twins, synthetic biological process digital twins, gene digital twins, genome digital twins, pathway digital twins, bioreactor and/or fermentation system digital twins, protein digital twins, metabolite digital twins, enzyme digital twins, and digital twins representing any of the synthetic biology entities described throughout this disclosure and documents incorporated herein.

In embodiments, the simulation engine may employ distributed computing techniques to parallelize the execution of digital twin simulations across multiple computing nodes. For example, each node may be responsible for simulating specific aspects of a biological system (e.g., metabolic pathways, environmental conditions, genetic expressions, etc.) or other systems that are represented by the digital twin. The platform 100 may then aggregate results using a synchronization layer that maintains temporal consistency across simulations. This and other examples of distributed approaches can enable fast simulation of complex biological systems.

Platform for Genetic Generalization-Overview

Genetic generalization models are models that are able to predict the effects of "unseen" genetic edits (e.g., genetic edits that have not been previously tested for a phenotype of interest in a specific system and/or process conditions). These models may be used to improve processes involved in strain development, testing, and production. Current processes often require the use of expensive and time-consuming screening (e.g., using plate-based assays) to identify promising genetic designs, followed by a process of optimizing production conditions in bioreactors for the most promising candidates. In addition to the cost and time required, the screening process can often overlook potential high-performing strains due to false negatives (e.g., where a particular strain does not perform well in plate assays but performs wells in bioreactors under certain process conditions), false positives (e.g., where a particular strain performs well in plate assays but does not perform well in bioreactors at production scale), worse performance in a fermenter, or other such errors or oversights.

Genetic generalization models, as described herein, improve the scaling-up process by providing technological solutions that predict the effects of genetic edits in untested scenarios based on previously observed data. For example, the models can use the outcomes of previous tests on strains that have other genetic edits to predict the performance of a strain with a new set of genetic edits. If these models can accurately predict performance, they can enhance the strain development process by reducing the number of experiments needed, including reducing or eliminating the need for extensive high-throughput screening in some applications. Additionally, better genetic generalization models may provide computation efficiency improvements by reducing the time and compute spent exploring the genetic edit space, thereby decreasing processing time compared to other experimental methods.

In many cases, genetic generalization models may simplify the prediction problem by predicting the effects of unseen genetic edits while holding process conditions constant. In some cases, the models may predict performance in assays by generalizing from the performance of other genetic edits in assays. Additionally or alternatively, some genetic generalization models may have the ability to directly predict strain performance in relevant process conditions (e.g., in bioreactors).

Another technical challenge in strain engineering is process generalization, which includes optimizing bioreactor conditions for specific strains based on limited data (e.g., data regarding performance in other process conditions while holding genotype constant). Process generalization may reduce the need to iteratively adjust relevant process variables (e.g., feed profiles, pH, carbon sources, etc.), which can be time-consuming and resource-intensive. Although aspects of process generalization may be considered a separate problem from genetic generalization, in some cases, the genetic generalization models that are described herein may perform some aspects of process generalization (e.g., by directly predicting the performance of genetic edits in specific sets of production conditions). These predictions can be used to automatically adjust bioreactor parameters (e.g., in real-time during production), providing direct control over production conditions based on model outputs that are generated during production. For example, the platform may automatically adjust bioreactor feed rates, pH levels, temperature, and/or other parameters described herein based on predicted strain performance under different conditions.

The genetic generalization models described herein, therefore, provide a technological solution that improves strain development by tightening the feedback loop between genetic and process engineering. In other words, by predicting the performance of genetic edits, the number of iterations required to find a successful production-scale process is reduced. The genetic generalization models, therefore, can improve engineering efficiency, assist in the identification of processes that yield higher production, and otherwise improve design for scale engineering.

In embodiments, the genetic generalization models described herein may use novel and innovative techniques for representing genetic edits and predicting their impacts on strain performance. For example, the models may make use of specialized gene embeddings that allow for functional representation(s) of genetic edits. Unlike simpler (e.g., one-hot) encoding methods, specialized gene embeddings may provide a function-aware vector representation of gene sequences and/or modifications. These embeddings capture not only the presence or absence of genetic edits but also encode information about the genes' functions, their roles in metabolic pathways, and/or their potential interactions with other genes. The use of specialized gene embeddings may enhance the models' abilities to generalize across unseen genetic edits by leveraging pre-trained models that incorporate extensive biological knowledge.

The genetic generalization models may aggregate information from multiple embedding techniques, as described in more detail herein. Distinct embedding techniques may each contribute distinct information about gene functions, enzymatic roles, pathway contexts, and/or the like. By aggregating the distinct embeddings, the models may work with a more comprehensive set of information describing genetic functions, thereby enabling more accurate predictions of strain performance.

The genetic generalization models described herein may use various architectures, of which specific examples are described herein. For example, Long Short-Term Memory (LSTM) neural networks and/or transformer-based architectures may be suitable for handling sequences of gene embeddings and modeling complex genotypes. These architectures may use attention mechanisms and/or positional encodings to model the spatial relationships between genetic edits, enabling the capture of global and/or local genetic interaction patterns. These and other architectures described herein may be able to predict complex interactions that result from the combined effect of multiple genetic edits, such as non-additive genetic interactions. Therefore, the trained models that are described herein may provide improved predictions based on information about complex edits to strain genetics.

In embodiments, a method for predicting performance associated with genetic edits may include receiving, by a platform, information about a biologic product, wherein the information includes a description of at least a portion of the biologic product in an expression language; generating, by the platform, a set of edits of the biologic product based on the description the at least a portion of the biologic product in the expression language; and generating, by the platform, a performance prediction for each edit of the set of edits of the biologic product based on a pre-trained genetic generalization model applied to each edit of the set of edits.

In embodiments, the biologic product includes a protein, the expression language includes a protein expression language, and the information includes a description of at least a portion of the protein in the protein expression language.

In embodiments, the expression language is based on one or more embedding models, the embedding models include at least one of a GenePT model, a Proteinfer model, a pFBA-PCA model, or a GO-PCA model, and the method further comprising aggregating a set of multi-dimensional vectors generated by the two or more embedding models to create the set of edits.

In embodiments, at least one edit of the set of edits includes an expression of the edit in the expression language.

In embodiments, the description of the at least a portion of the biologic product includes a description of at least one of a structural feature of the at least a portion of the biologic product, a functional feature of the at least a portion of the biologic product, a source of the at least a portion of the biologic product, a metabolic pathway associated with the at least a portion of the biologic product, or a biologic condition associated with the at least a portion of the biologic product.

In embodiments, the description of at least a portion of the biologic product is generated from at least one of a description of the at least a portion of the biologic product in at least one natural-language information source, or a representation of the at least a portion of the biologic product in a knowledge graph.

In embodiments, the description of at least a portion of the biologic product is generated by a language machine learning model that has been trained to generate descriptions of at least portions of biologic products in the expression language.

In embodiments, generating the set of edits includes generating a description of at least one edit of the set of edits, and the description of the at least one edit includes a description of at least one of a structural feature of the at least one edit of the biologic product, a functional feature of the at least one edit of the biologic product, a source of the at least one edit of the biologic product, a metabolic pathway associated with the at least one edit of the biologic product, or a biologic condition associated with the at least one edit of the biologic product.

In embodiments, the description of the at least one edit of the set of edits is generated from at least one of a description of the at least a portion of the biologic product in at least one natural-language information source, or a representation of the at least a portion of the biologic product in a knowledge graph.

In embodiments, the description of the at least one edit of the set of edits is generated by a language machine learning model that has been trained to generate descriptions of edits of biologic products.

In embodiments, the method further includes generating, by the platform, a representation of the biologic product edited by the set of edits, wherein the representation includes a description in the expression language of at least a portion of the biologic product edited by the set of edits.

For example, a platform may represent biologic parents, products, and/or synthesis processes in an expression language. For instance, a protein language may represent various proteins or portions thereof as a set of embeddings determined according to a set of protein language embeddings. The protein language embeddings may be determined by a protein language model (PLM), such as ESM2, ProtT5, or Ankh. A protein or portion thereof may be represented as a sequence of embeddings in the protein language, which may be generated by applying a protein language embedding model to another representation of the protein, such as an amino acid sequence and/or a structural model. Biologic parents (e.g., protein parents), or portions thereof (e.g., a portion of a protein that includes a set of amino acids comprising a binding site or other relevant feature of the protein), may be represented based on their embeddings in the protein language. Embeddings may also be developed for biologic synthesis process (e.g., processing steps that include one or more relevant portions of one or more biologic parents, such as a step of processing a protein, represented by a first expression in the expression language, with another protein as an enzyme, represented by a second expression in the expression language). A biologic product of the biologic synthesis process may also be represented according to an expression language (e.g., modeling a biologic product as a sequence of embeddings, each representing one or more subsets of one or more amino acids of the biologic product). The embeddings in the expression language may indicate and/or may be associated with various aspects of the represented portions of the biologic parent(s), biologic synthesis process, and/or biologic products, such as a structural feature of the at least a portion of the biologic product (e.g., a type, identifier, configuration, and/or shape of a binding site of a protein), a functional feature of the at least a portion of the biologic product (e.g., an affinity of a portion of a biologic parent and/or product for another protein, such as a capability of a binding site of an enzyme to bind to a binding site of a target protein), a source of the at least a portion of the biologic product (e.g., a strain in which the portion of a biologic parent and/or biologic product was discovered, naturally arises, and/or has been and/or may be inserted through natural mutations and/or strain engineering), a metabolic pathway associated with the at least a portion of the biologic product (e.g., an association between a binding site and/or capability of a protein and a metabolic pathway that relies upon the binding site and/or capability of the protein), or a biologic condition associated with the at least a portion of the biologic product (e.g., a trait, phenotype, and/or pathology of a strain or organism that is associated which a binding site of a protein). Representing biologic parents, biologic synthesis processes, and/or biologic products according to an expression language may standardize the biologic parents, biologic synthesis processes, and/or biologic products across various databases, models, information sources, or the like (e.g., enabling a first machine learning model that evaluates proteins to be combined with a second machine learning model that simulates a biologic synthesis process to produce a hybrid machine learning model that is capable of simulating the effect of a particular biologic parent on a biologic synthesis process).

Expression languages may also be used to represent edits of one or more biologic parents, biologic products, or the like. For example, a strain may be or may have been engineered by an edit to include, exclude, substitute, or otherwise alter a particular portion of a DNA sequence, RNA sequence, protein, metabolic product, or the like. The edit may be represented in the expression language (e.g., as an embedding or sequence of embeddings included in and/or generated by an embedding model). For example, a protein language model may receive, as input, one or more embeddings that represent a protein or a portion thereof, and an indication of a particular alteration of a particular portion of the protein. The protein language model may generate, as output, one or more embeddings that represent the edit of the protein or the portion thereof. The embeddings in the expression language may indicate and/or may be associated with various aspects of the edit of the biologic parent(s), biologic synthesis process, and/or biologic products, such as a structural edit of the at least a portion of the biologic product (e.g., an alteration of a type, identifier, configuration, and/or shape of a binding site of a protein), a functional edit of the at least a portion of the biologic product (e.g., an alteration of an affinity of a portion of a biologic parent and/or product for another protein, such as a capability of a binding site of an enzyme to bind to a binding site of a target protein), a source of an edit of a portion of the biologic product (e.g., a strain in which an edit of a portion of a biologic parent and/or biologic product was discovered, naturally arises, and/or has been and/or may be inserted through natural mutations and/or strain engineering), a metabolic pathway associated with the edit of the biologic product (e.g., an association between an edit of a binding site and/or capability of a protein and a metabolic pathway that is affected by the edit of the binding site and/or capability of the protein), or a biologic condition associated with the edit of at least a portion of the biologic product (e.g., an edit of a trait, phenotype, and/or pathology of a strain or organism that is associated which a binding site of a protein). Representing edits according to an expression language may standardize the edits across various databases, models, information sources, or the like (e.g., enabling a first machine learning model that evaluates proteins to be combined with a second machine learning model that evaluates the effects of various types of edits to various proteins to produce a hybrid machine learning model that is capable of determining the effect of an edit applied to a particular biologic parent, biologic synthesis process, and/or biologic product).

In embodiments, expressions of various biologic parents, biologic synthesis processes, and/or biologic products, and/or edits thereof, may be generated by a machine learning model. For example, a protein language embedding model may be trained on a corpus of information about various biologic parents, biologic synthesis processes, and/or biologic products, and/or edits thereof, such as databases of proteins and/or scientific journals that relate thereto. The protein language embedding model may be configured, through training, to generate an embedding language as an asset of embeddings that represent various aspects of the biologic parents, biologic synthesis processes, and/or biologic products. The protein language embedding model may then receive, as input, a protein (e.g., based on its name, identifier, amino acid sequence, progenitor DNA sequence, structure, or the like). Based on the input, the protein language embedding model may generate the embedding thereof for storage and/or further processing.

Platform Including Genetic Generalization Models

The genetic generalization models described herein may be training and/or executed for inference using AI processing cores (e.g., GPUs, NPUs, TPUs, FPGAs, etc.). The platform 100 may use the AI processing cores in parallel to speed up predictions and/or enable the generation of multiple predictions simultaneously.

Figure 15:
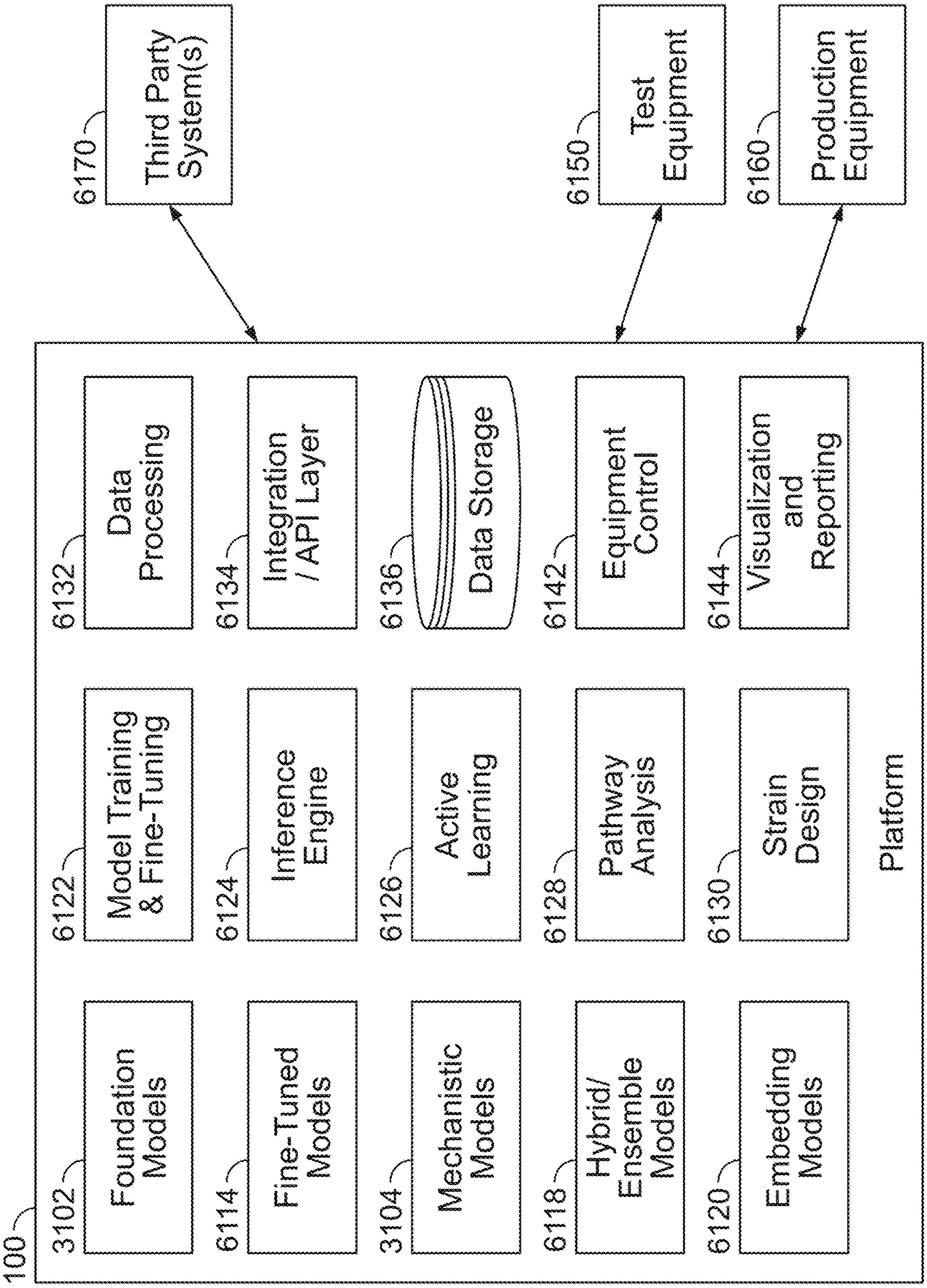
FIG. 15 is a schematic diagram that presents a platform as described herein according to some embodiments.

FIG. 15 shows another view of the platform 100 that includes genetic generalization models and a plurality of components that use the models to generate genetic generalization predictions and interact with the predictions provided by these models. It should be noted that other data, modules, components, and the like may be present within the platform 100 and/or may be used by the platform for other purposes, as shown in other figures. In embodiments, the platform 100 may be implemented using a distributed computing architecture, where different components/functions may be executed across multiple processing nodes to optimize computational speed and efficiency. For example, the inference engine 6124 may use AI processing cores (e.g., GPUs, NPUs, TPUs, FPGAS, etc.) for parallel processing of multiple predictions, the data processing component 6132 may leverage distributed data processing frameworks for handling large-scale experimental data, and/or the like. A distributed and/or parallel processing architecture may enable reduced latency in generating predictions and/or improved scalability for processing larger datasets.

The platform 100 may include various types of models used in genetic generalization and strain engineering. These include foundation models 3102, which may include pre-trained genetic generalization models that serve as a basis for the development of a variety of models that are specialized for certain tasks (e.g., fine-tuned models 6114). The foundation models 3102 may use various machine learning architectures, such as transformer-based networks with multiple attention layers that process sequences of gene embeddings, as described in more detail below. The models 3102 may be trained using objective functions specifically designed for genetic prediction tasks, such as cross-entropy loss for categorical predictions (e.g., strain viability categories), mean squared error loss for continuous predictions (e.g., production yields), and/or the like. The training process may include minimizing the discrepancy between predicted outputs and actual experimental results across a diverse set of training examples, where each training example includes input genetic modifications represented as sequences of gene embeddings and corresponding target outputs such as measured strain performance metrics.

A foundation model 3102 may be a large-scale machine learning model trained using comprehensive biological datasets. Example architectures for the foundation models 3102 are described elsewhere herein. In genetic generalization applications, the training of the model 3102 may enable the discovery of relationships between genetic modifications and phenotypic outcomes. The foundation models 3102 may then be used for transfer learning (as described in more detail below), where the learned representations can be adapted to specific prediction tasks via fine-tuning.

The platform may further include mechanistic models 3104, such as Lin-Log models, which may be used to analyze metabolic pathways and strain behavior based on known biological mechanisms. For example, the platform may use mechanistic models 3104 to inform an active learning process that incorporates genetic generalization predictions, as well as for other purposes. The platform may further include hybrid/ensemble models 6118 that combine multiple model types (e.g., multiple foundation models 3102, fine-tuned models 6114, and/or mechanistic models 3104) to provide more robust predictions. The platform may include embedding models 6120 that generate specialized gene embeddings to capture functional relationships between genes and genetic modifications. As described in more detail below, these embeddings may enable better foundation models 3102 for genetic generalization.

The platform 100 may further include a variety of functional components. For example, a model training & fine-tuning component 6122 may perform tasks including development and refinement of models based on available data. An inference engine 6124 may generate predictions using trained models. The inference engine 6124 may implement optimized computational techniques that reduce memory usage and processing time compared to other methods. For example, the inference engine 6124 may use batch processing and/or model quantization techniques to enable efficient processing of multiple prediction requests simultaneously, while maintaining prediction accuracy.

An active learning component 6126 may guide the iterative improvement of models and/or strain designs by suggesting new experiments based on the outcomes of past experiments and/or other considerations. A pathway analysis component 6128 may examine metabolic pathways to inform strain design decisions. The strain design component 6130 may propose new genetic modifications for improved strain performance based on the outputs of other components.

The platform may further include components for processing and storing data. A data processing component 6132 may prepare raw data for use in modeling and/or analysis. For example, the data processing component 6132 may implement data normalization and/or feature extraction algorithms to prepare experimental data for model input. Such techniques may include batch effect correction using statistical methods, automated quality control filtering, and/or transformation of raw experimental measurements into standardized formats suitable for model training and inference. In embodiments, the data processing component 6132 may be implemented by the facility for synthetic biology sensor collection, processing, fusion, and staging for modeling and analytics 2100. An integration/API layer 6134 may enable communications between platform components and external systems. A data storage component 6136 may store raw data, processed data, model outputs, and/or the like.

The platform may also include components for generating user interfaces and/or controlling external equipment. An equipment control component 6142 may interface with and/or control laboratory equipment (e.g., based on genetic generalization predictions). In embodiments, the equipment control component 6142 receives inputs that include model predictions and generates outputs that include specific control parameters for laboratory equipment, thereby enabling real-time optimization of experimental conditions. For example, the equipment control component 6142 may automatically adjust bioreactor parameters such as temperature, pH, and/or nutrient feed rates based on model predictions of optimal growth conditions for specific genetic modifications. The equipment control component 6142 may implement an automated control system that provides closed-loop feedback between model predictions and experimental outcomes, thereby improving the efficiency (e.g., speed, number of iterations, etc.) of iterative strain development processes.

A visualization & reporting component 6144 may present results to users and may receive user inputs and/or instructions.

The platform 100 may interact with external systems, including test equipment 6150, production equipment 6160, and third-party systems 6170. These external systems provide data to the platform and receive control instructions and/or predictions from it, thereby enabling a design-build-test-learn (DBTL) cycle for strain engineering.

The components of platform 100 may interact in various ways to enable genetic generalization and strain optimization. For example, the platform 100 may receive data from test equipment 6150 and/or production equipment 6160, process that data using the data processing component 6132 and store the processed data in the data storage 6136. The platform 100 may then provide the processed data to the model training & fine-tuning component 6122 to train the foundation models 3102, fine-tune the foundation models 3102, and/or otherwise improve the various models of the platform 100. The platform 100 may use the inference engine 6124 to execute the trained models to make predictions. The platform 100 may then use these predictions for strain design 6130, and/or to generate decisions about future experiments via the active learning component 6126. The platform 100 may provide results and visualizations to users through the visualization & reporting component 6144, and the platform can interact with third-party systems 6170 (e.g., to receive third party data, use third party models such as large language models) via the integration/API layer 6134.

Modeling Scenarios

Genetic generalization predictions can be categorized into three scenarios based on data availability and modeling feasibility: (1) cases where supervised modeling is not needed, (2) cases where supervised modeling is possible due to available data, and (3) cases where supervised modeling is not possible due to data limitations. Each of these scenarios may require different modeling strategies and have distinct applications in product development processes. The platform 100 may use different techniques for operating in the different scenarios, which may provide a technical improvement to computational efficiency that adaptively selects appropriate modeling strategies. For example, in scenario one, the platform may use lightweight inference methods that consume minimal computational resources, while in scenario two, the platform may use the more sophisticated machine learning models described below, which may use parallel processing capabilities of the platform 100 (e.g., for training and/or inference) to handle complex prediction tasks.

In the first scenario, supervised modeling may not be required because the general requirements for cultivating a particular host may already be well-established. For example, there may be existing “best practice conditions” for some organisms (e.g., industrial *E. coli* fermentation), known genetic strategies to improve strain performance, etc. These may include a “standard package” of edits that reduce overflow metabolism, strategies for making chromosomal edits rather than using plasmids, methods for two-step activation of pathways without chemical inducers, and/or the like. In some of these cases, screening assays can be set up to match target conditions from the outset.

To address the first scenario, the genetic generalization predictions described herein may not be necessary and/or may be supplemented by strategies that include identifying best practices for specific hosts and evaluating the best practices in different types of fermentation (e.g., including their limitations and effectiveness). Additionally or alternatively, the platform may analyze (e.g., using AI solutions such as LLMs) relevant literature (which may include publications, patents, and/or other sources) to identify information on best practices for different hosts. In some cases, the platform may use such information to guide the development of strains based on these known best practices. Additionally or alternatively, these best practices may be supplemented or even improved by the use of genetic generalization predictions, which may identify other high performing strains, iteratively improve on known best practices, etc. In embodiments, the platform 100 may then directly interface with laboratory automation systems, for example by automatically translating identified strategies into executable protocols for robotic systems and/or automated bioreactors. The platform may therefore enable real-time adjustment of experimental parameters based on established best practices and/or ongoing learning from genetic generalization predictions.

In the second scenario, supervised modeling is possible. For example, the platform may be able to assemble training data sets that include a sufficient number of data points for different strains with results indicating the performance of the strain in both plate assays and in tanks (bioreactors). Various genetic generalization models may be trained on the training data sets and used for genetic generalization (e.g., to predict bioreactor performance for strains previously tested in plates, or not previously tested at all). Example predictive models that are especially suitable for the second scenario are described in the following disclosures below.

In a third scenario, supervised modeling may not be possible. For example, data measuring the performance of strains in large scale bioreactors may be limited. In these cases, the platform may perform various analytics on the physical parameters of a target condition (e.g., oxygenation, heterogeneity, etc.) and provide instructions for replicating the target condition in a scaled down model (e.g., a smaller bioreactor). Using smaller bioreactors, additional data may be generated and the platform may therefore collect sufficient data for training a supervised model (i.e., moving into the second scenario). Additionally or alternatively, the platform may collect “omics” data (e.g., proteomics, transcriptomics, metabolomics, etc.) to characterize strain biology in the target condition and compensate, for example based on a loss of pathway gene expressions, activation of stress response pathways, etc. Additionally or alternatively, the platform may accept a certain amount of uncertainty regarding predictions (e.g., in large scale bioreactors for which data is limited) and therefore may optimize for robustness across conditions rather than peak performance in a narrower set of specific process conditions.

The platform 100 may perform analyses of physical parameters and omics data in the third scenario that may be accelerated through the use of distributed computing resources. For example, the platform 100 may process proteomics data in parallel across multiple compute nodes, with AI processing cores handling the computation for pathway analysis. The platform 100 may use a distributed architecture to process large-scale omics datasets efficiently, reducing the time required to characterize strain biology in target conditions.

Example Predictive Models

The platform described herein may train and use one or more of various types of genetic generalization models, which may use various methods to provide predictions for genetic generalization. Each of these models may be foundation models 3102, and/or may be further fine-tuned to generate fine-tuned models 6114. An example ensemble model 6120 is also described with respect to FIG. 16F. These examples illustrate certain drawbacks of overly simplified methods as well as how to iteratively develop more highly performant genetic generalization models. In these examples, models are described in terms of inputs and outputs. More detailed descriptions of specific model architectures are provided in later sections and elsewhere herein.

Figure 16A:
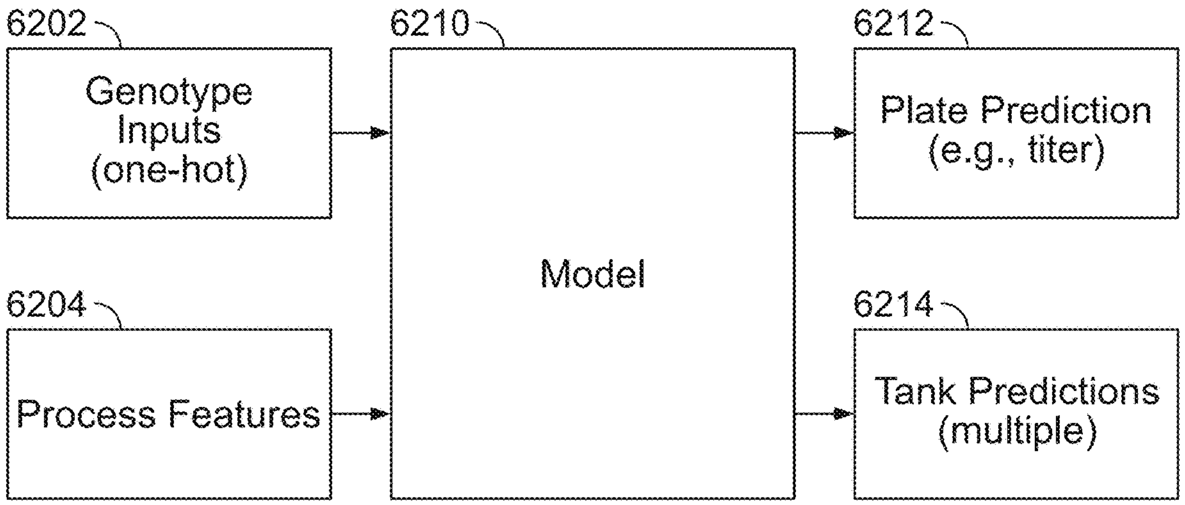
FIGS. 16A, 16B, 16C, 16D, 16E, and 16F are schematic diagrams that illustrate examples of genetic generalization models according to some embodiments.

A first example model 6210 may be trained to predict plate and tank performance based on genotype and process inputs, as shown in FIG. 16A. The model 6210 is provided herein to illustrate certain weaknesses of models that do not use sufficient information to accurately predict performance, especially at production scale. These weaknesses are explained in more detail below. However, it should be noted that the model 6210 may be useful in certain use cases, for example, as a model within a larger ensemble model.

The model may receive inputs including genotype inputs 6202 that describe the genetics of each strain, as well as process features 6204 that characterize the physical conditions in plate and/or tank fermentations (e.g., reactor volume, feed rate, etc.). In the illustrated example, the genotype inputs 6202 are one-hot encoded, which is a simple encoding method that may be used for a basic model. (Other input techniques using embeddings are described below for other models). For example, each one-hot data value may indicate the presence or absence of a particular genetic modification. The genotype inputs 6202 may therefore be a vector of binary input values, where each value represents the presence or absence of a modification.

The model 6210 shown in FIG. 16A predicts various output features, including one or more plate features (e.g., titer) and one or more tank features (e.g., bioreactor conditions and/or sensor readings). The model 6210 may be a neural network and may use one of the various architectures described in more detail elsewhere herein. Alternatively, the model may be a simpler model, such as a regression model.

The platform 100 may train a basic model 6210 using a dataset of strains that have been tested in plate and/or tank conditions. For each strain, the dataset may include the one-hot encoded genotype and process features for plate and/or tank conditions as input data as well as measured performance metrics (e.g., titer for plates, various metrics for tanks, as illustrated in FIG. 16A) as the target outputs. In embodiments, the platform may collect the data and normalize, transform, and/or otherwise preprocess the data (e.g., to ensure all features are on a similar scale) before training begins. Depending on the model architecture, training may involve various steps. The platform 100 may train the model 6210 (and/or other models described herein) using a training pipeline that comprises preprocessing input data using normalization techniques as described elsewhere herein. The training pipeline may train using techniques such as an adaptive learning rate schedule (e.g., to optimize convergence), mini-batch processing (e.g., to enable efficient parallel computation), early stopping based on validation performance (e.g., to prevent overfitting), distributed training across multiple computing nodes (e.g., when dealing with large-scale datasets), and/or the like. A training objective function may be configured as a combination (e.g., a weighted combination) of one or more of a primary regression loss (e.g., mean squared error) for performance prediction, regularization terms (e.g., to prevent overfitting), and/or optional auxiliary losses (e.g., to leverage additional biological constraints). Additional example steps for training a neural network are described below with respect to FIG. 19.

Figure 16B:
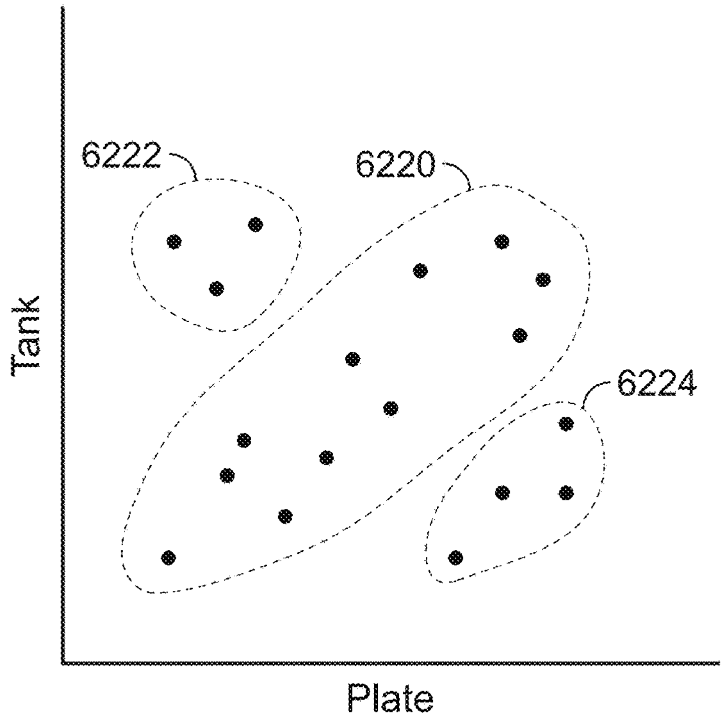

Certain weaknesses of the model 6210 may be described with respect to FIG. 16B, which illustrates examples of how a strain's tank performance may generally correlate with the strain's plate performance, but there may be outliers that deviate from this trend. For example, many data points (shown in group 6220) may follow a general correlation between plate and tank performance, but there may be false positives and false negatives (shown in groups 6222 and 6224), where plate performance does not accurately predict tank performance.

The model 6210 may have a limited ability to accurately predict performance for strains that have been tested only in plates but not in tanks, which is one aspect of the genetic generalization problem as described above. For example, the model may have trouble distinguishing false positives and false negatives (shown in groups 6222 and 6224 in FIG. 16B) from strains that perform well in both plates and tanks. In other words, the model may be too simple for robust genetic generalization, which may be due (at least in part) to using an overly simple encoding method for the genotype inputs, which may therefore limit the model's ability to generalize sufficiently. For example, the model may not have enough information to accurately identify specific strains that may deviate from the general correlation between plate and tank performance (e.g., the model may not be able to identify the false positives and negatives that may be of particular interest in strain development). Specifically, the one-hot encoding of genotypes may not capture the functional relationships between genes or the impact of specific combinations of genetic modifications. Additionally, the model may not account for complex interactions between genetic modifications and process conditions. In some cases, the limited plate assay data (e.g., only titer) also may not provide sufficient information to differentiate strains that might perform differently in tank conditions. More sophisticated models (described in more detail below) remedy these limitations in various ways.

Figure 16C:
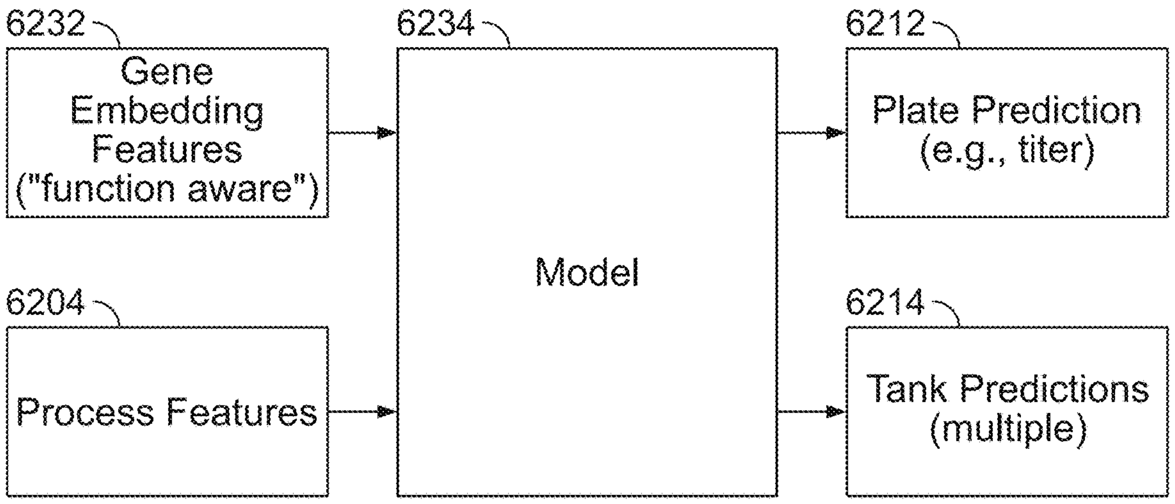

FIG. 16C illustrates a model 6234 that includes an improvement to how strain genetics are represented for the inputs as compared to the model 6210. In the model 6234, the one-hot encoded genotype inputs of the previous model are replaced with more sophisticated gene embedding features 6232 that are "function-aware," meaning they capture more detailed information about the genetic modifications and their potential impacts on strain performance. Unlike the binary representation used for one-hot encoding, these gene embeddings encode functional relationships between genes and the potential effects of specific genetic modifications. The embeddings provide this capability by reducing input dimensionality through learned dense representations and therefore enable efficient parallel processing of genetic information. Models that use the embeddings may implement attention mechanisms to capture gene interactions and/or may use special neural network layers for embedding processing. The generation of embeddings is described in more detail below. The embeddings allow the model to recognize patterns in genetic modifications that may lead to unexpected performance in tank conditions compared to plate assays, as well as to better predict false positives and false negatives. For example, when the model receives inputs describing strains where plate performance either over- or under-estimates tank performance, the model may still be able to make accurate predictions for tank performance (i.e., identify false positives or false negatives) because the model may have been trained on other strains with similar genetic embeddings/functions. Thus, the model is more capable of generalizing to strains that are similar in terms of embeddings to strains within the training data set that were false negatives or false positives based on the plate assay.

In embodiments, the inputs to the any of the models described herein (e.g., model 6234) may include bioreactor process inputs that characterize one or more conditions of a bioreactor. In these embodiments, the model may have been trained to predict fitness with respect to a specific set of bioreactor process conditions (e.g., one or more of bioreactor volume, temperature, pH, dissolved oxygen level, feed rate, agitation speed, any of the sensor measurements described elsewhere herein, any bioreactor settings, and/or the like). Thus, by inputting bioreactor process inputs, the model may predict one or more targets (e.g., fitness) with respect to the particular set of conditions represented by the bioreactor process inputs. In these embodiments, the bioreactor process inputs may be represented in the same embedding space as the embeddings for the genetic edits, in a different embedding space (e.g., in an embedding space with a reduced number of dimensions that may be input into a separate input layer and/or converted into the same embedding space used by the genetic inputs), or otherwise, for example by using parallel input layers.

The model 6234 (as well as models 6244, 6248 described more below) may be constructed using various architectures. For example, as described in more detail below, an LSTM model may be used together with a multi-layer perceptron model. Alternative model architectures may include transformer-based architectures, ensemble/hybrid architectures, and other example architectures described elsewhere herein. In some embodiments, the model 6234 may include parallel input layers configured to handle the embedding features (which may have very high dimensionality) and the process features (which may not use embeddings and thus may have lower dimensionality).

Similarly as for the model 6210 of FIG. 16A, the platform may train the model 6234 (and/or the models 6244, 6248) using a dataset of strains that have been tested in plate and/or tank conditions. For each strain, the dataset may include the gene embedding features and process features for plate and/or tank conditions as input data as well as measured performance metrics (e.g., titer for plates, various metrics for tanks) as the target outputs. In embodiments, the platform may preprocess the input data features using any relevant techniques. The gene embedding features may be generated as described in more detail below.

Thus, the model of FIG. 16C can predict points that deviate from the main trend line (e.g., points within groups 6222 and/or 6224 as shown in FIG. 16B), even for unseen genetic edits (e.g., edits for which the previous model 6210 may have generated less accurate predictions). In other words, the model can learn from examples in the training set with similar embeddings or functions.

Additionally, the use of embeddings can enable the reduction or elimination of the need for plate assays entirely (e.g., by not requiring plate target data in the training data set). For example, the model may learn to generalize from one set of strains tested in bioreactors in order to predict the likely tank performance of another set of strains. However, it should be noted that because plates are often largely predictive of tank performance, the illustrated model that uses plate data for training may (in some cases) provide a more comprehensive strain evaluation at the cost of still requiring plate assays.

Figure 16D:
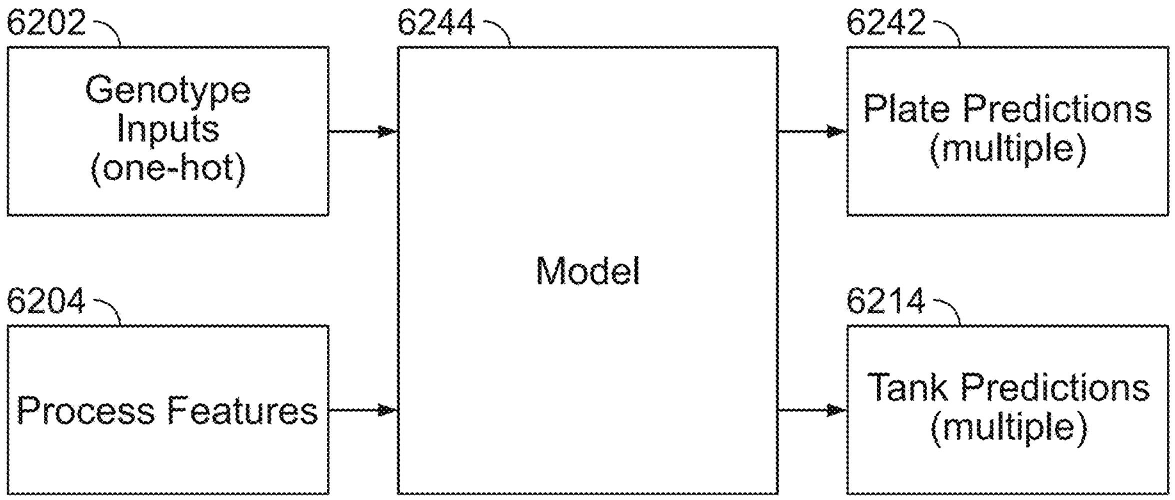

A third model 6244 shown in FIG. 16D provides another improvement to the first model 6210. Instead of enhancing the genetic representation as for the model 6234 of FIG. 16C, the model 6244 of FIG. 16D uses additional target data based on outcome data collected from plate assays. In other words, as shown in FIG. 16D, the model reverts to using one-hot encoded genotype inputs, but trains on multiple plate targets 6242 instead of just titer. These additional measurements provide a more comprehensive measure of strain performance in plates. The additional target data may include (e.g., in addition to titer), targets that characterize an analytical chemistry of the media, targets that specify "omics" data (e.g., transcriptomics), and/or targets that characterize other relevant biochemical or physiological measurements. By training on a richer set of data from plate assays, the model can better identify patterns that may correlate with tank performance. The model therefore trains on (and potentially generates) multiple plate predictions that provide an "assay fingerprint" that better characterizes strain behavior, allowing for better prediction of tank performance even without using gene embeddings. In some cases, these assay fingerprints may be generated by intermediate layers of the models described herein, and/or may be output by a first model and/or input to a second model that predicts fitness for the strain corresponding to the assay fingerprint.

The advantages of the model shown in FIG. 16D include achieving improved genetic generalization without requiring complex embeddings (e.g., maintaining the computational efficiency of one-hot encodings). If there are examples in the training set with similar assay fingerprints, the model(s) 6244 have been trained on sufficient information to generalize to other strains and thereby generate improved predictions for tank performance. In other words, the model of FIG. 16D is an alternative strategy (as compared to the model of FIG. 16C) for addressing the genetic generalization problem that enriches the experimental data rather than the genetic representation. The model 6244 of FIG. 16D may be particularly valuable when collecting additional experimental data is easier (e.g., faster and/or more economical) than developing sophisticated genetic embeddings. However, the model 6244 may require more extensive and therefore more expensive plate assays.

Figure 16E:
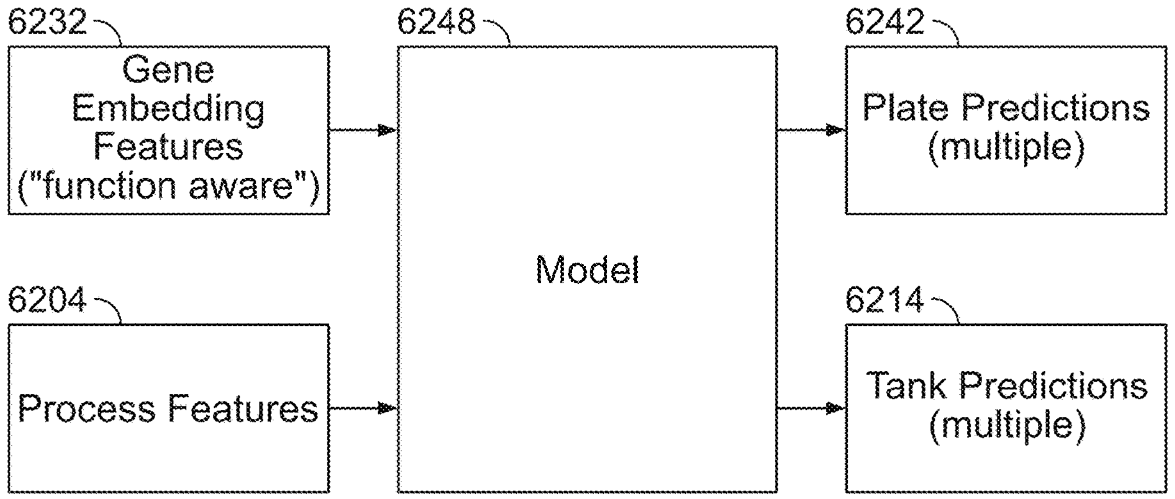

The model 6248 of FIG. 16E combines the strengths of the model 6234 and the model 6244 by using both function-aware gene embedding features 6232 as inputs, as well as by incorporating multiple plate targets 6242 that provide a more comprehensive assay fingerprint. The model 6248 therefore leverages both the improved genetic representation and the richer experimental data, which may provide a synergistic effect that increases predictive power and the capability of identifying false positives and negatives.

Figure 16F:
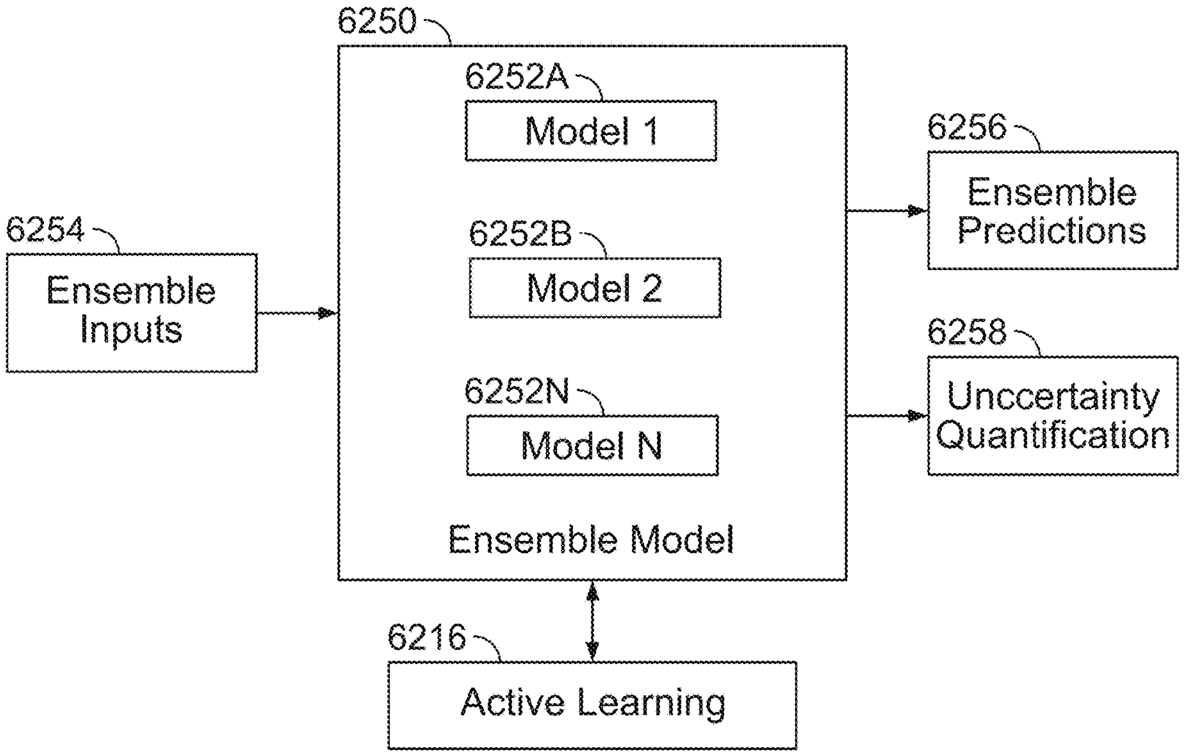

Another iteration shown in FIG. 16F may leverage ensemble modeling and active learning. The ensemble model 6250 may incorporate several individual models 6252A-N and may generate ensemble predictions 6256 that are based on the outputs of each of the multiple individual models 6252A-N. The individual models 6252A-N may have different architectures (e.g., neural networks, random forests, gradient boosting machines, etc.), may use different hyperparameters, may be trained on different subsets of a training data set, may use different combinations of genetic representations and plate assay data as inputs and outputs (e.g., the individual models may include any or all of the models 6210, 6234, 6244, 6248), and/or the like. In embodiments, the ensemble predictions 6256 may be a weighted combination of the predictions output by each individual model 6252.

The platform 100 may use an active learning process wherein the platform 100 actively selects which strains to test next in order to explore unknown genetic modifications while also targeting the most promising genetic modifications. For example, the active learning process may involve identifying regions of gene function "space" that are not well characterized by the current models, then selecting experiments based on which areas of the unexplored space are most likely to prove useful and/or provide additional data to improve the training of the models. As shown in FIG. 16F, the ensemble model may generate both ensemble predictions as well as uncertainty quantifications for untested strains.

The platform may use an active learning component 6126 to select strains for testing based on predicted performance (as indicated by ensemble predictions 6256) and an uncertainty quantification 6258. The active learning component 6126 may generate instructions for collecting new experimental data, which may involve performing additional experiments and collecting the data therefrom. After the data is collected, the platform 100 may update (e.g., retrain and/or fine-tune) one or more of the models 6252 within the ensemble model using the new data. The experiment and update process may then iteratively repeat, which may continuously improve the performance of the model 6250 as a whole.

In some cases, the ensemble models 6250 may include mechanistic models 3104, such as Lin-Log models, to provide additional outputs that may be used, for example, to better characterize strain behavior. For example, pathway optimization information generated by Lin-Log models could be used in various ways (e.g., to inform the selection of genetic targets for analysis, to guide the active learning process, etc.). This is merely one example explanation of how an integration of mechanistic models and genetic generalization models in an active learning process may allow better exploration of the design space and/or more efficiently identify high-performing strains.

The platform 100 may communicate control instructions based on predictions/outputs of any of the models described above to automated laboratory systems to actively control fermentation parameters in real time based on predicted strain performance. For example, the model outputs may be used to automatically adjust temperature, pH, and/or nutrient feed rates in bioreactors to optimize strain growth conditions.

Specialized Gene Embeddings

In embodiments, the genetic generalization models (e.g., foundation models 3102, fine-tuned models 6114) may use one or more specialized gene embeddings (briefly discussed above with regard to FIGS. 16C, 16E, 16F) to represent genetic edits functionally within genetic generalization models. Simpler encoding methods may represent genes or genetic edits as binary vectors indicating the presence or absence of each gene (e.g., one-hot encoding of knockout data). Although one-hot encoding and other simar methods are straightforward and simple, the one-hot inputs may not adequately capture the functional similarities or relationships between genes. For example, two separate genetic modifications may interact in unforeseen ways because genes may interact with each other in ways that are not necessarily additive. Such interactions are more likely as additional genetic edits are introduced. Consequently, models relying on one-hot encoding of single gene edits (e.g., knockouts) may struggle to generalize to unseen genetic edits, limiting the predictive capabilities of models that are trained on such inputs.

To address these and other limitations, the genetic generalization models described herein may use specialized gene embeddings that may provide function-aware vector representations of genes and/or gene modifications. In some cases, a specialized gene embedding may still correspond to a single gene edit, but instead of merely encoding whether the gene has been edited or not, the input may include an embeddings vector that represents additional data about the single gene edit. For example, the embeddings may capture various types of semantic and/or functional information about each gene, such as their roles in metabolic pathways, enzymatic activities, known interactions with other genes, etc. By training on the additional data provided by embeddings, the genetic generalization models can better generalize from known genetic edits to predict the performance of untested or unseen genetic designs.

Several techniques may be employed to generate gene embeddings that each contribute distinct information about gene function(s). The models used to generate the embeddings may be described herein as embedding models 6120.

In embodiments, the platform 100 may generate "GenePT" embeddings using large language models (LLMs) that process textual descriptions of gene functions. To generate GenePT embeddings, the platform may extract functional descriptions of genes from relevant databases (e.g., the EcoCyc™ database). The platform may then take the extracted text (which may include information about the gene's role, associated metabolic pathways, enzymatic functions, interactions, etc.) and input the text into one or more pre-trained LLMs (e.g., models developed by OpenAI™, Google™, Meta™, etc.), which may be running remotely and/or locally on the platform 100. The LLM may process the textual description and produce a continuous vector representation (i.e., embedding) that captures semantic relationships and functional attributes of the gene. Because LLMs are trained on vast amounts of textual data, they are capable of inferring relationships between different genes based on the context provided in the textual descriptions. In other words, if two genes have similar functional descriptions, their vector embeddings as generated using the GenePT technique may be similar.

In embodiments, the LLM used for GenePT embeddings may include multiple transformer layers with multi-head self-attention mechanisms. Each layer may process the input text through parallel attention heads that compute query, key, and value representations to capture different aspects of the textual relationships. The platform 100 may extract (or receive from another device that is executing the LLM) the output embeddings from an intermediate layer of the model, where the embeddings may be formatted as vectors of high dimensionality (e.g., 768 or 1024 dimensions) that capture the contextual representation of the gene descriptions.

In embodiments, the platform 100 may generate embeddings using Proteinfer, a pre-trained convolutional neural network (CNN) that predicts protein functions. More specifically, the Proteinfer model analyzes the amino acid sequences of proteins encoded by genes and generates embeddings that capture structural and functional features of the proteins. The Proteinfer model may use a deep learning architecture trained on datasets containing protein sequences labeled with enzyme function codes, gene ontology (GO) terms, and/or other functional annotations. Therefore, Proteinfer embeddings may indicate information about enzymatic activities, active sites, structural motifs, and/or the like. For instance, two isomerase enzymes with similar active sites but different sequences may have embeddings that reflect their functional similarities despite the different sequences.

In embodiments, the platform 100 may generate embeddings using protein language models such as ESM2. These protein language models are trained on large amounts of protein sequences to generate predictions of sequences in a similar way as how language models predict words in a sentence. The protein language models also generate embeddings that capture both local and global structural features of proteins, such as secondary structures, domains, and folding patterns. The embeddings from protein language models provide additional information that may complement the functional information provided by the GenePT embeddings, Proteinfer embeddings, and/or other such embeddings.

Figure 17A:
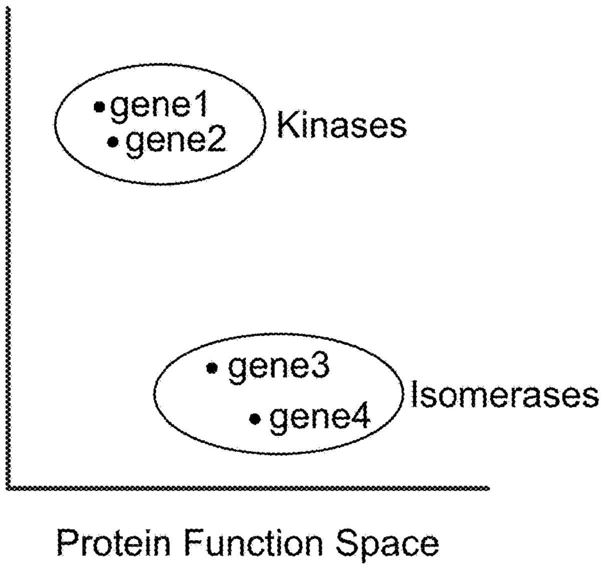
FIGS. 17A and 17B are schematic diagrams that illustrate different types of genetic embeddings according to some embodiments.

In embodiments, the platform 100 may use multiple embeddings generated using different methods to provide more comprehensive data describing the functions of specific genes. An example of how different embedding methods may provide more comprehensive gene information is shown with respect to FIG. 17A-B. As shown in FIG. 17A, one or more embeddings may encode information about protein function. For example, these embeddings may indicate groupings of genes that perform a specific function, such as a first grouping of genes that are kinases and a second grouping of genes that are isomerases. The embeddings may indicate that example genes (gene1 and gene2) are both kinases because they appear close together within the embedding space. Thus, even if the training data for training a model includes examples of genetic edits involving gene1 but no examples of genetic edits involving gene2, the model may be able to generalize its knowledge regarding gene1 to the unseen gene2 edit. Similarly, the embeddings may include information about other groupings, such as a group of isomerases including gene3 and gene4, as shown in FIG. 17A.

Figure 17B:
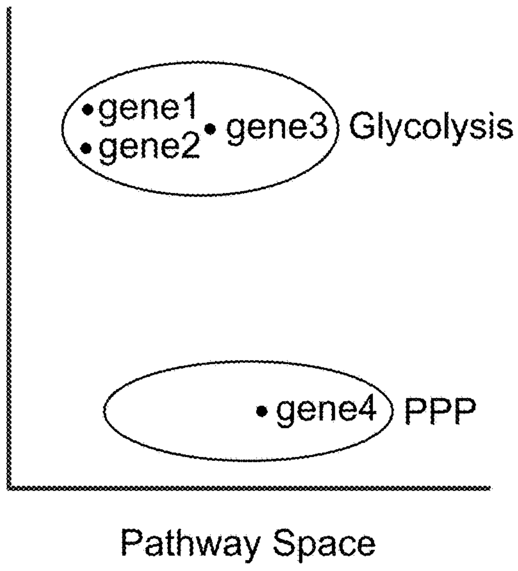

FIG. 17B, by contrast, shows a different embedding space that is based on gene-pathway relationships. In this example, the embedding space may place genes at different positionings reflecting the different data used to generate the embeddings. For example, gene1, gene2, and gene3 may each be close together in the embedding space of FIG. 17B because they are each involved in glycolysis, whereas gene4 may be further away within the embeddings space because it is not involved in glycolysis.

The platform 100 may use various types of embeddings, including the above-described GenePT embeddings, Proteinfer embeddings, and/or ESM2 embeddings that are generated using pre-trained models. Additionally or alternatively, the platform may use other techniques, such as pFBA-PCA embeddings that are generated by simulating gene knockouts in a genome scale metabolic model (e.g., performing parsimonious Flux Balance Analysis (pFBA) to obtain genome-wide reaction fluxes for each knockout, and then applying Principal Component Analysis (PCA) to generate a low-dimensional representation of the flux profile for each gene knockout). Additionally or alternatively, the platform may use embeddings generated using gene ontology (GO) pathway terms followed by PCA (GO-PCA). Additionally or alternatively, the platform may use embeddings generated using other flux analysis methods, such as Flux Variability Analysis (FVA), Flux Scanning based on Enforced Objective Flux (FSEOF), or Flux Variability Scanning based on Enforced Objective Flux (FVSEOF), followed by dimensionality reduction.

The genetic generalization models described herein may use embeddings that are combined from multiple sources into a composite representation. The composite representation may combine different individual embedding vectors into a single comprehensive embedding vector. For example, the platform 100 may combine a GenePT embedding vector, a Proteinfer embedding vector, and/or a protein language model embedding vector into a composite representative vector. The platform may then input the composite representation vector into a genetic generalization model, which may generate a prediction based on the composite input.

In embodiments, the platform 100 may generate and process the embeddings using parallelized processing across multiple processing units. For example, the platform may generate different embeddings (GenePT, Proteinfer, etc.) simultaneously on separate dedicated hardware (e.g., GPUs, NPUs, TPUs, FPGAs, etc.). Using a parallel processing architecture may significantly reduce the computational latency compared to sequential processing approaches.

Experimentally, a combination of functional embeddings generated using pre-trained LLMs and embeddings generated using a pathway representation (e.g., the pFBA-PCA technique described above) provide substantial amounts of generalization. For example, in testing involving training a model on data gathered from a large number of *E. coli* knockout fitness experiments, a neural network model using a concatenation of GenePT and pFBA-PCA embeddings was able to predict the fitness of unseen genetic knockouts from the test data set with an R-squared value of about 0.5. This experimental result demonstrates substantial generalization performance using a simple concatenation of two different types of vector embeddings, illustrating the merit of the use of composite embeddings as described herein.

Composite embeddings as described herein provide several technical advantages over conventional (e.g., one-hot) encoding methods. For example, the composite embeddings reduce the dimensionality of the input space while preserving functional relationships, thereby enabling more efficient memory usage and faster model training. Second, the composite embeddings enable the model to process previously unseen genetic modifications by leveraging learned functional similarities, thereby addressing a technical challenge in biological prediction tasks. Third, the platform may use different modules to generate multiple embeddings, which allows for dynamic updating of the system as new genetic information becomes available without requiring complete model retraining.

The platform may also generate embeddings that encode information about genetic modifications beyond single edits. For example, the embeddings may include values indicating the base strain, each edit on plasmids, the copy number of the plasmids, the promoters that are used, the integration sites, etc. Any or all of the embedding methods described above or other embedding methods may be used to encode information about these or other features.

Example Model Architectures

Figure 18A:
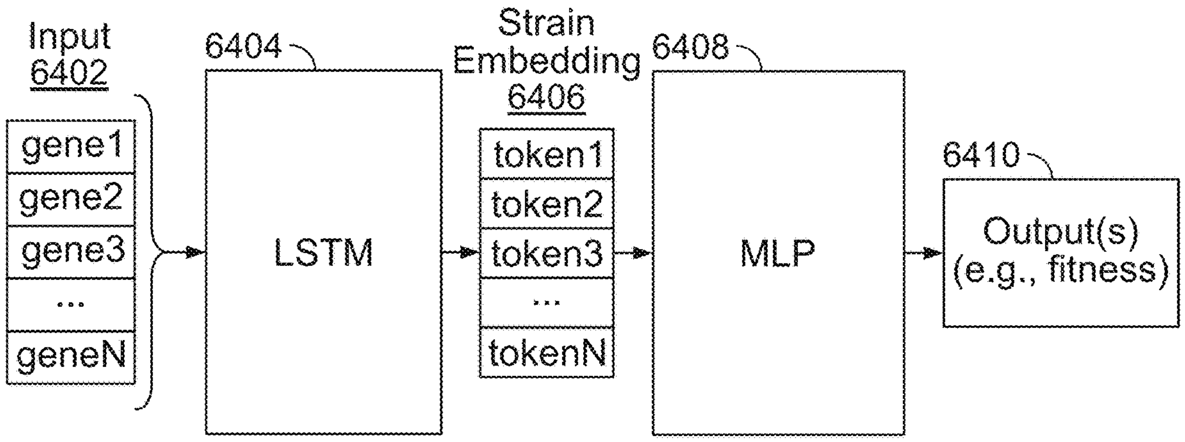
FIGS. 18A, 18B, and 18C are schematic diagrams that illustrate specific genetic generalization model architectures that generate intermediate strain embeddings according to some embodiments.
Figure 18B:
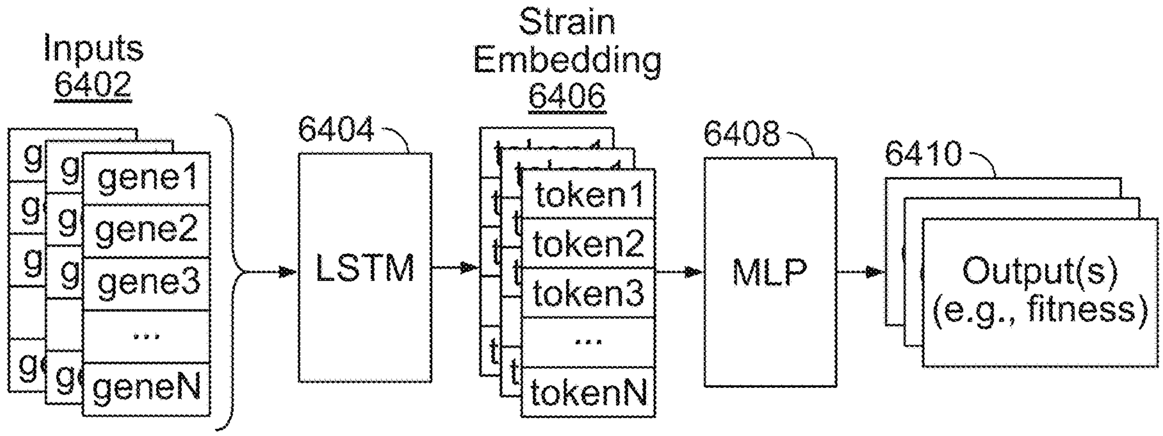

The models described herein may use various types of architectures, of which a few specific examples are described in detail herein to illustrate the relevant principles. It should be understood that other types of model architectures will occur to a person skilled in the art. A first example architecture for generating predictions using genetic embeddings information using a hybrid LSTM-MLP (multi-layer perceptron) model is illustrated in FIG. 18A. In the example of FIG. 18A, example inputs 6402 comprising functional embeddings information for genetic edits are provided to an LSTM 6404 stage, which in turn generates a strain embedding 6406 for input into a multi-layer perceptron 6408 stage. The multi-layer perceptron 6408 then outputs one or more predictions (e.g., a fitness target and/or other targets described elsewhere herein). Although FIGS. 18A-18B illustrate examples of using an LSTM-MLP model for genetic generalization, a person of ordinary skill will recognize that the illustrated model may be adapted to use other inputs and/or generate other outputs as described elsewhere herein.

In the example of FIG. 18A, a single type of embedding may be used to generate the embeddings for each token of the inputs 6402. For example, a first input may include embeddings for a first genetic edit (e.g., an edit in relation to gene1), a second input may include embeddings for a second genetic edit (e.g., an edit in relation to gene2), and so on. In some cases, the input for each genetic edit may further include a value indicating the type of modification (e.g., knockout, overexpression, underexpression). The value may be encoded as a two-dimensional value (e.g., if less than 4 types of modifications are valid inputs). Additionally or alternatively, the modification value may be a separate input that may be its own embedding (e.g., where each modification value appears immediately before or after the gene embedding to which it pertains).

The LSTM 6404 may be trained to output a strain embedding 6406, which may be a single fixed-length vector that represents the entire set of genetic modifications. The strain embedding may thereby capture complex interactions between multiple genetic edits in a single embedding. Although not shown, one or more process features (as described above with respect to FIG. 2) may also be used as inputs to either of the two stages. For example, after the LSTM generates a strain embedding, both the strain embedding and one or more process features may be input into the MLP.

The example two stage model provides a first LSTM stage that can handle any number of genetic edits (e.g., from 1 to N) while outputting a single representation (the strain embedding 6406) of the genetic modification as a whole. An LSTM may be useful for its ability to process variable-length sequences while capturing information about the interactions between different genetic modifications. Additionally, LSTMs have the ability to analyze non-linear combinations of inputs, which allows the LSTM 6404 to learn how various genetic edits may interact. The LSTM 6404 therefore has the ability to handle sets of genetic modifications that are not additive (e.g., the edits may have synergistic or antagonistic effects). The LSTM 6404 may also perform a dimensionality reduction, taking the various input values (each of which may include hundreds of values if the embeddings space has hundreds of dimensions) into a reduced strain embedding that encodes the most important information about the modification. For example, during the training process, the gating mechanisms of the LSTM may learn to provide more or less weight to certain edits or combinations of edits, thereby enabling an effective reduction of dimensionality prior to input to the multi-layer perceptron. In other words, the LSTM may generate a strain embedding that encodes an understanding of the interactions between edits, while the MLP may predict fitness or other performance outcomes based on the overall strain embedding.

FIG. 18B illustrates one example method of handling multiple embedding techniques. In the illustrated example, multiple inputs 6402 are generated, where each input may include embeddings generated using a different type of embedding. For example, a first input may include embeddings generated using GenePT, a second input may include embeddings generated using pFBA-PCA, and so on. In embodiments, the inputs may each be provided in turn as several forward passes, such that the LSTM 6404 may generate a different strain embedding 6406 for each corresponding input 6402, and the MLP 6408 in turn may generate a different prediction 6410 for each input 6402. In embodiments, the predictions may then be averaged (e.g., using a weighted average) or analyzed in combination. Additionally or alternatively, other methods may be used to combine the different types of embeddings. For example, the inputs 6402 may be aggregated (e.g., such that each of the embeddings for gene1 are combined into a single token for gene1, each of the embeddings for gene2 are combined into a single token for gene2, etc.) using concatenation or some other operation, then passed into the LSTM using a single forward pass to generate a single string embedding 6406 and a single set of prediction output(s) 6410. Additionally or alternatively, as another variant, the LSTM may generate multiple strain embeddings 6406 as shown, then combine the multiple strain embeddings (e.g., using concatenation or another aggregation method) into a single strain embedding, which may be provided to the MLP 6408 in a single forward pass to generate a single set of prediction output(s) 6410.

Additionally, the LSTM 6404 may be replaced with a transformer. Like an LSTM, a transformer is capable of processing variable length sequences, finding relationships between the input tokens, and outputting a fixed length embedding. Transformers have some benefits and drawbacks as compared to LSTMs. In some cases, transformers may handle longer sequences better than LSTMs, which may be beneficial when the inputs 6402 include a large number of genetic edits, a large amount of information about each edit, and/or a large amount of input tokens describing other aspects of a genetic modification (as described elsewhere herein). A transformer's attention mechanism may also allow the transformer to detect the interactions between each genetic edit based on the attention values that characterize the relationship between each pairing of input tokens. The attention mechanism can work well even for "long range" dependencies (e.g., dependencies between input tokens that may be far apart in the input 6402). Additionally, transformers allow for better parallelization, which can be leveraged by providing additional hardware (e.g., more GPUs) to speed up training and/or inference, to use more parameters in the models to achieve better performance, and/or the like. However, transformers may need additional hardware due to more complex computation (especially when dealing with long sequences of inputs) and may require more data to train effectively.

The platform 100 may implement transformer-based or other models using AI processing cores (e.g., GPUs, NPUs, TPUs, FPGAs, etc.) that are optimized for attention mechanism computations. The cores may distribute the attention computations across multiple processing units by partitioning an input sequence into chunks and computing attention scores in parallel. This distributed attention processing enables processing of longer input sequences (e.g., for strains with many genetic modifications) while maintaining low latency. The platform 100 may dynamically adjust the batch size and/or sequence length based on available hardware resources to optimize throughput.

Several other specific architectures are contemplated. A two stage convolutional neural network (CNN)+MLP hybrid model may use a CNN to perform a similar role as the LSTM 6404 (e.g., to capture local patterns and interactions between nearby edits or other encoded inputs described elsewhere herein). As another example, a graph neural network (GNN)+MLP hybrid model may be used. In this case, the GNN may represent genetic edits (or other inputs as described elsewhere herein) as nodes in a graph (e.g., with edges presenting potential interactions between edits or other inputs). For example, the GNN may be able to process the graph to generate a strain embedding and feed the strain embedding into an MLP for prediction. As another example, a hierarchical attention network (HAN)+MLP hybrid model may use the HAN to group edits in various ways (e.g., by type, pathway, etc.) and process each group with an attention mechanism. The HAN may then use another level of attention to combine group representations into a strain embedding, then feed the strain embedding into an MLP to generate prediction(s).

An example CNN+MLP architecture may employ one or more convolutional layers with varying filter sizes (e.g., 3, 5, 7, etc.) to capture different scales of genetic modification interactions. Each convolutional layer may be followed by batch normalization and an activation function (e.g., ReLU). This architecture may include residual connections to facilitate gradient flow during training and enable learning of both simple and complex interaction patterns. The model may include a pooling layer for pooling convolutional layer outputs using max and/or average pooling operations. The model may then concatenate outputs before feeding the concatenated outputs into the MLP stage.

Several of the architectures described herein provide specific technical improvements over conventional approaches. For example, a HAN+MLP model may reduce computational complexity using a hierarchical structure, thereby enabling efficient inference even for complex sets of inputs. A GNN+MLP architecture may capture both local and global interaction patterns that may be represented using a genetic modification network, thereby providing better predictions that take into account the various interactions between edits or other inputs. A CNN+MLP architecture may use local convolution operations to reduce memory requirements compared to fully-connected architectures while maintaining prediction accuracy.

These examples represent only some possible variants. For example, any of the models described above or elsewhere herein may be used without multiple stages. In other words, the various first stages described above may be trained to directly output a prediction instead of outputting a strain embedding for input into an MLP. Additionally, any of the models described herein (whether hybrid/multi-stage or not) may be combined into an ensemble model, as described above for FIG. 16F. Other variants are also possible.

The platform 100 may implement any of the models described herein in real-time strain engineering systems. For example, the models can be deployed in (or in communication with) automated laboratory systems that dynamically select subsequent genetic modifications based on predicted outcomes, enabling closed-loop optimization of strain design. These models may use the hardware optimizations described elsewhere herein to enable real-time decision-making, thereby enabling more automated strain construction processes.

Two-Step Training

In embodiments, the platform may use a two-step training process for pre-training a foundation model 3102 on data and one or more general targets such as fitness or other performance targets, then performing supervised learning (and/or fine-tuning) using a smaller data set that may be specific to a particular use case (e.g., a customer use case) and/or a particular target (e.g., a target variable for a particular customer) to generate a fine-tuned model 6114.

The platform 100 may use objective functions tailored to each stage. For example, during pre-training, the model may use one or more of cross-entropy loss for classification tasks (e.g., predicting discrete phenotype categories), mean squared error loss for regression tasks (e.g., predicting continuous fitness values), and/or a contrastive loss term that ensures similar genetic modifications produce similar strain embeddings. Each loss term may be weighted by a corresponding hyperparameter that controls its relative importance.

In the pre-training step, the platform may obtain one or more larger data sets describing, for example, the results (phenotypes) of single gene knockouts for an organism. Multiple datasets may describe different phenotypes for the knockouts. These data sets may be used to pre-train any of the models described herein as foundation models 3102 that can predict at least a fitness value (e.g., using the embeddings described above). The pre-training may use a large amount of data that allows the model to develop knowledge about the embeddings for each gene.

Other data may be present in the training data set. For example, the training data may include other types of genetic modification data such as values indicating the base strain, each edit on plasmids, the copy number of the plasmids, the promoters that are used, the integration sites, and/or the like. Additionally or alternatively, the training data set may include complementary information such as metabolite levels, gene expression data, and/or reaction fluxes. These additional data values may provide additional context for the genetic modifications, thereby enabling the trained model to obtain a more comprehensive understanding of the effects of genetic edits. In some cases, the model may integrate diverse data types (e.g., using a multi-modal structure) to better capture complex interactions between genetic changes and cellular metabolism.

During pre-training, the embeddings may be learnable parameters, such that the model can start with the initial (e.g., LLM-generated) embeddings but then refine them over time during the learning process. Thus, the model may gradually fine-tune the embeddings over time to better capture the patterns in the training data sets. In other words, as part of learning to predict phenotypes from training data (e.g., knockout data), the model may adjust the embeddings to tailor them to the task being learned. After pre-training, the refined embeddings may be used instead of the LLM embeddings.

Figure 18C:
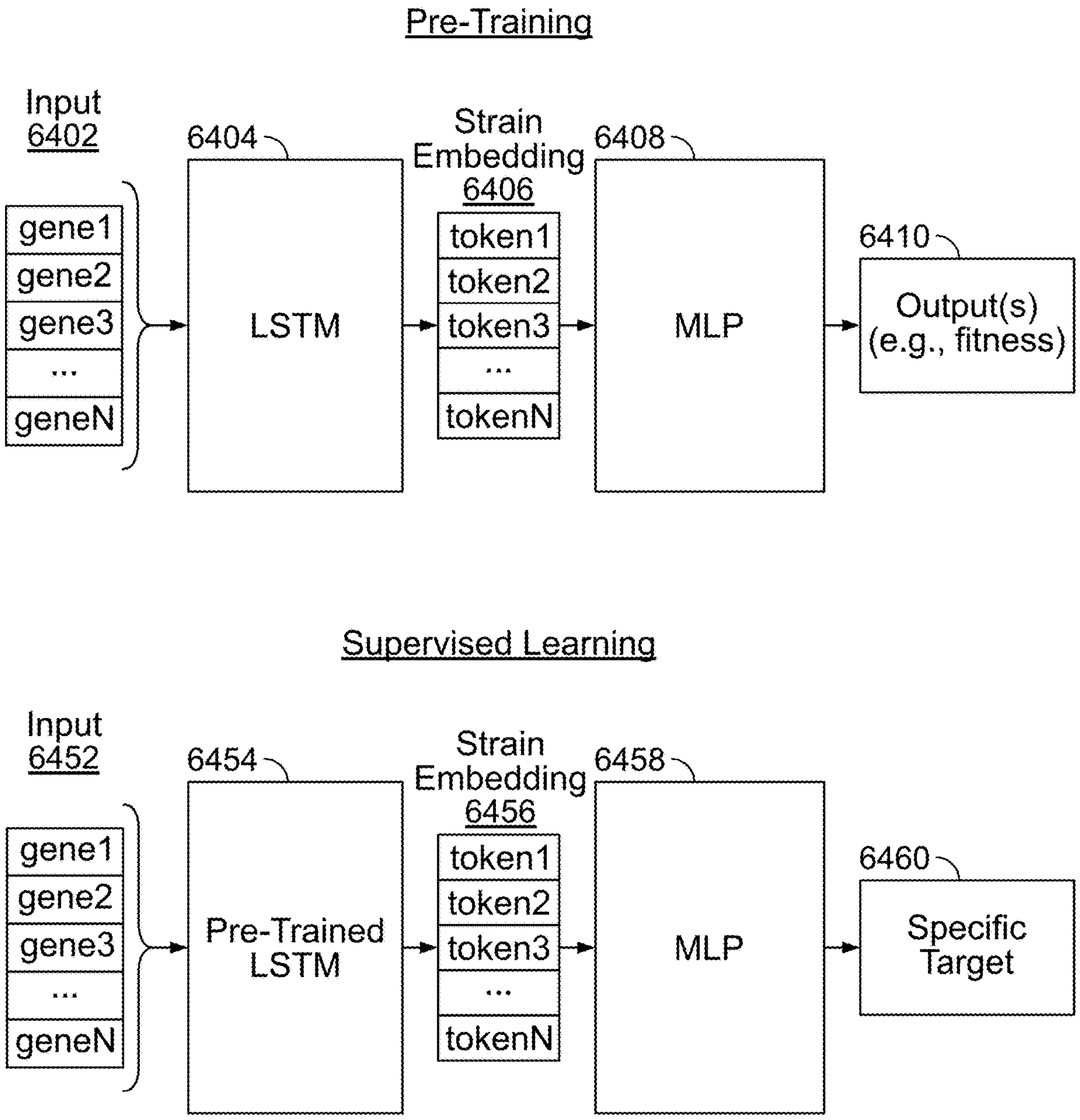

During a second step of training, the platform may train or fine-tune a foundation model 3102 using a new training data set to generate a fine-tuned model 6114 that can predict a new target, the specific target 6460. As shown in FIG. 18C, after pre-training, the supervised learning step starts with the pre-trained LSTM 6454 (e.g., or a transformer, or any other type of model used as a first stage), then trains the model to output a specific target 6460. In some cases, supervised learning may start by discarding the MLP 6408 of the foundation model 3102 and replacing it with a new MLP 6458 that can be trained to predict the specific target 6460. Alternatively, the model may fine tune the pre-trained MLP 6408 of the foundation model 3102 using the new training data set, or use a hybrid architecture that may replace certain layers of the MLP 6408 (e.g., one or more final layers of the MLP 6458) in order to retain some learning while also allowing adaptation to the final task.

Figure 19:
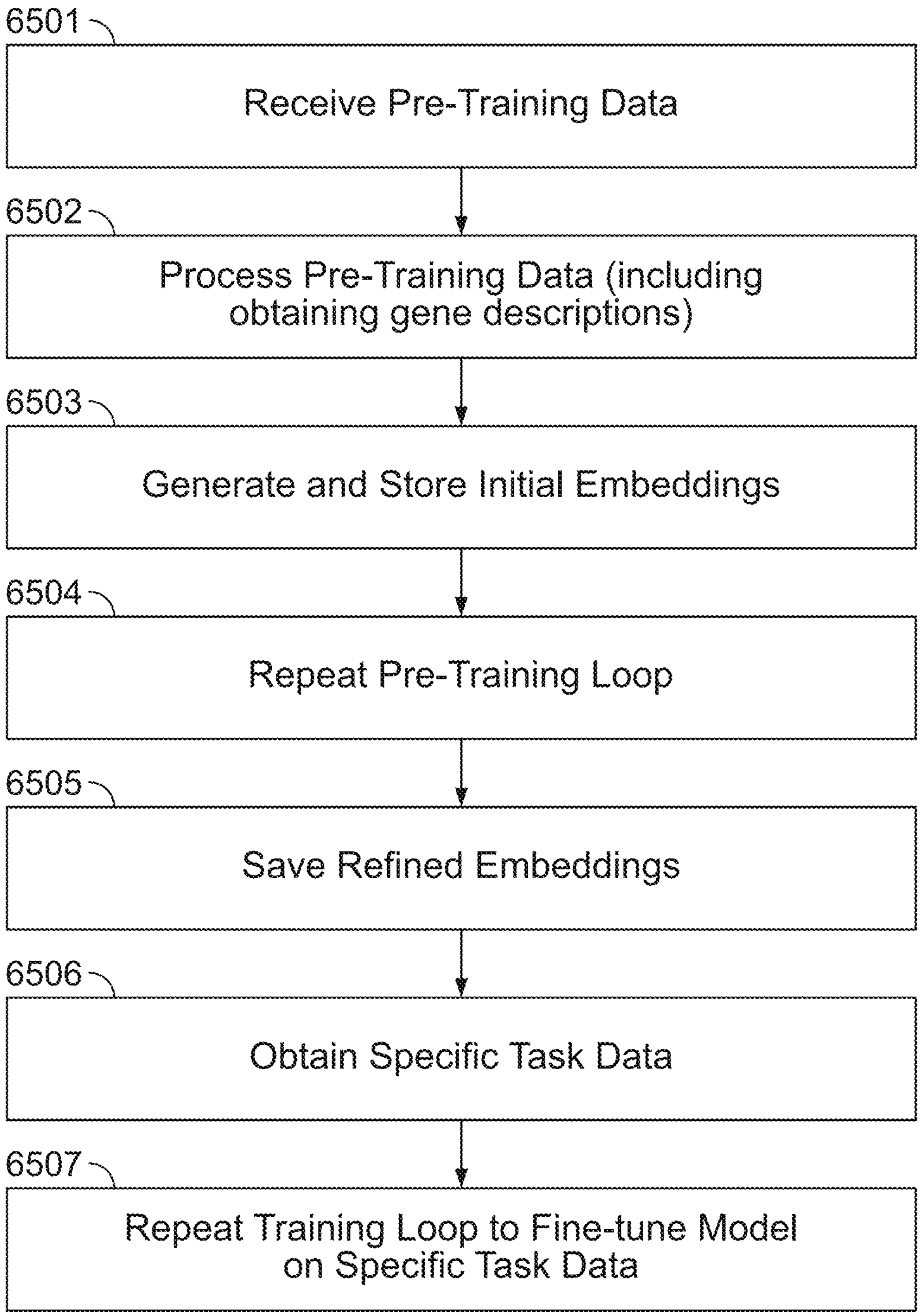
FIG. 19 is a schematic diagram that illustrates examples of a method for pre-training and fine-tuning a genetic generalization model according to some embodiments.

FIG. 19 illustrates a method for performing the two-step training process described above.

At 6501, the platform receives a comprehensive dataset for pre-training (e.g., information about gene knockouts in a particular organism). The dataset may include, for each gene in the organism's genome, data on the phenotypic effects observed when that gene is knocked out or otherwise modified. The phenotypic effects may vary depending on the specific dataset and may include measures such as growth rate, metabolite production, or other observable characteristics.

At 6502, the platform 100 may process the dataset to prepare it for use in the model. The processing may include organizing the data into a structured format suitable for input into the neural network. Additionally, the platform may obtain detailed descriptions of each gene involved in the experiments (e.g., from one or more third party databases). These descriptions may be retrieved from biological databases and/or generated through analysis of scientific literature. The descriptions may provide context about the known and/or hypothesized functions of each gene, the role of each gene in metabolic pathways, and/or other relevant biological information.

At 6503, the platform may generate initial embeddings for each gene and edit type (e.g., knockout, overexpression, underexpression, etc.) in the dataset, as well as any other genetic modification information (examples of which are described elsewhere herein). The platform may generate the embeddings by querying a large language model (LLM), which may be running locally or remotely, where the query includes the gene descriptions. The LLM may process the descriptions and output vector representations (embeddings) that capture semantic information about each gene's function and characteristics. In some cases, the platform may also query the LLM with edit type information to cause the LLM to generate embeddings for edit types using general descriptions of the edit types. The platform may then store the initial embeddings generated by the LLM in a database or lookup table for efficient retrieval during the training process.

At 6504, the platform may pre-train the model using a series of looping training steps to iteratively refine the model's understanding of genetic modifications and their effects. The training steps may begin with batch preparation, where a batch of training examples from the training data set is prepared (e.g., where each training example includes a set of genetic modifications and a resulting phenotype). Next, the platform may, for each genetic modification in the batch, retrieve the corresponding embeddings from storage. Next, the platform may input a sequence of embeddings corresponding to the genetic modifications from the training data as inputs to the model. The model may process these inputs (i.e., a forward pass) and output a strain embedding (e.g., by an LSTM stage) and/or a prediction (e.g., an MLP stage). Next, the platform may compare the predicted phenotype to the actual phenotype from the training data and calculate a loss value based on the comparison. Next, the platform may backpropagate the loss value through the network, computing gradients for the model parameters (which may include weights of the MLP, LSTM, and/or other stages as well as the embeddings themselves). Next, the platform may update the model parameters (which may optionally include updating the embeddings) based on the computed gradients, thereby refining the model's ability to generate predictions based on the training data examples. The platform may repeat the training process in a loop for multiple epochs, which may include processing the entire pre-training dataset multiple times to progressively improve the model's performance.

The platform 100 may perform the training processes using distributed computing architecture optimized for parallel processing, including multiple processing cores (e.g., GPUs, NPUs, TPUs, FPGAs, etc.) that process different batches simultaneously using data parallelism. In embodiments, the platform 100 may synchronize model parameters across parallel processing devices using an all-reduce operation. The platform 100 may perform gradient computation and parameter updates using mixed-precision training to reduce memory usage while maintaining numerical stability. The platform 100 may dynamically adjust batch sizes based on available memory to maximize GPU utilization.

In embodiments, upon completion of the pre-training loop, at 6505 the platform may save the refined embeddings to storage (e.g., replacing the initial embeddings generated by the LLM). In these embodiments, the refined embeddings may incorporate both the initial knowledge provided by the LLM (or other source of embeddings) and additional knowledge gained by the training using the pre-training dataset. Thus, the refined embeddings may capture better information about gene functions as revealed by the pre-training data examples. In this example, the platform may train/update the weights of the trained model (e.g., LSTM stage) to encode multiple genetic modifications into a strain representation.

At 6506, after pre-training, the platform may obtain data for a specific prediction task, which may be provided by a partner and/or may be provided for a particular application. The data may include information about genetic modifications made to strains and information about a corresponding target phenotype or other property of interest (e.g., production of a specific metabolite, growth rate under certain conditions, fitness, etc.). In some cases, the specific prediction task dataset may be smaller than the pre-training data, representing a specific application or research question at hand.

At 6507, the platform may repeat the training steps to fine-tune the model on the specific task data. The fine-tuning process may adapt the general knowledge gained during pre-training to a more specific prediction task. Prior to fine-tuning, the platform may load the pre-trained model from step 6504 and any refined embeddings generated at 6505. In some cases, the platform may replace some layers of the pre-trained model (e.g., some or all of the MLP stage) with a new MLP for the specific task. Alternatively, the previous MLP may be retained and fine-tuned. The platform may then train as described above for 6504, including batch preparation using the specific task data, a forward pass, calculation of a loss value, backpropagation, and parameter updates (which may include or omit further refinement of the embeddings). In some cases, the platform may adjust the learning rate at 6507 as compared to the learning rate for step 6504. For example, the platform may use a lower learning rate (e.g., adjust the weights by a reduced amount for each parameter update step) for a stage that generates an intermediate strain embedding (e.g., the LSTM stage) at 6507 as compared to 6504. Additionally or alternatively, the platform may use a higher learning rate for a stage that generates the specific task prediction (e.g., MLP stage).

In embodiments, the platform may run the fine-tuning loop of at 6507 for fewer epochs than the pre-training loop at 6504 (e.g., because the model is already initialized with relevant knowledge). The platform may continue the training loop until the model's performance on a validation set plateaus and/or reaches a satisfactory level. Upon completion of fine-tuning, the resulting model may be capable of making accurate predictions for the specific task because the model was trained on both the pre-training data (which may include a large number of more general examples) and the specific task data (which may include a smaller number of specific examples for a specific task).

In embodiments, the fine-tuning process may use one or more technical optimizations, including gradient freezing in early layers (e.g., to preserve learned feature representations), progressive layer unfreezing (e.g., to gradually adapt the model), learning rate scheduling (e.g., using a cosine decay with warm restarts), dropout rate adjustment (e.g., based on the size of the fine-tuning dataset), and/or the like. These techniques may help reduce forgetting during transfer learning while maintaining adaptation to specific tasks.

Two-stage training (e.g., fine-tuning a foundation model) provides several technical advantages, including reduced computational resource requirements (e.g., by leveraging transfer learning from the pre-trained model), improved model generalization through the combination of large-scale pre-training data and task-specific fine-tuning, more efficient memory usage (e.g., through the learned compressed strain embeddings), and an ability to handle previously unseen genetic modifications (e.g., by leveraging the learned functional relationships). These advantages and improvements enable the platform to process complex genetic modifications more efficiently while maintaining prediction accuracy.

The platform 100 may use the foundation models 3102 and/or the fine-tuned models 6114 for real-time control of laboratory automation systems by, for example, dynamically adjusting fermentation parameters based on predicted strain performance, automatically selecting optimal genetic modifications during strain engineering, real-time quality control through continuous monitoring and prediction, and/or the like. These practical applications reduce experimental iteration time and improve resource efficiency.

Inference Using Aggregated Gene Embeddings

Figure 20:
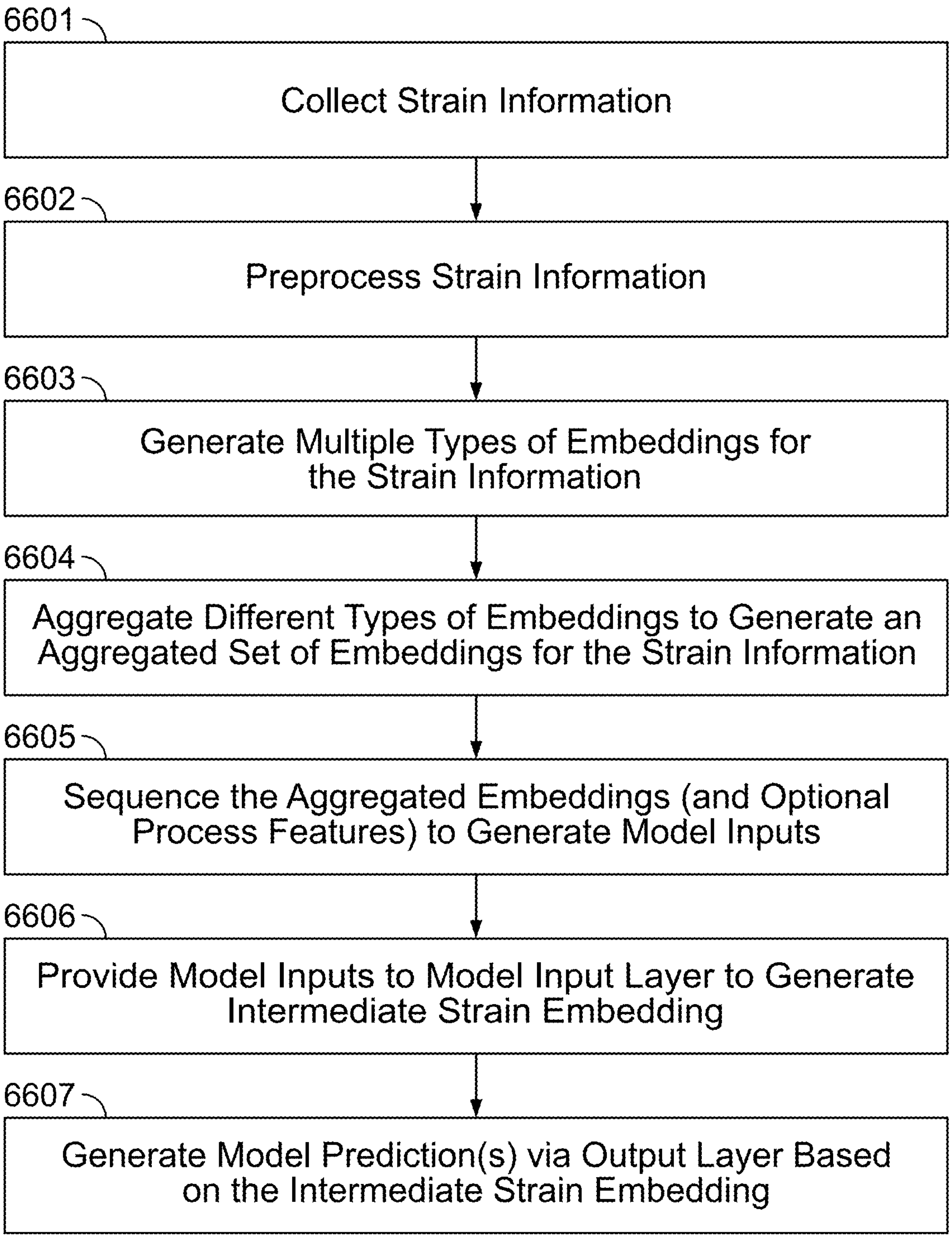
FIG. 20 is a schematic diagram that illustrates an example method of generating a prediction using a genetic generalization model according to some embodiments.

FIG. 20 illustrates an example method that describes inference steps for a genetic generalization model that uses aggregated embeddings. The method involves processing input data representing genetic modifications, generating multiple gene embeddings for each modification, combining these embeddings, and feeding the embeddings to a trained model to predict target outcomes such as strain fitness.

At 6601, the platform may receive a description of a strain, including the strain's genetic modifications. The description may include single-gene edit information and/or may include more comprehensive information such as base strain information, information describing multiple genetic edits, which may include knockouts, overexpressions, and underexpressions, information about plasmid-based modifications (e.g., copy numbers), promoter information for each genetic edit, integration sites for chromosomal modifications, and/or the like.

At 6602, the strain description information may be preprocessed and/or any additional relevant information may be retrieved. For example, for each gene listed in the strain information as a genetic modification, the platform may retrieve any relevant information that may be necessary for generating embeddings (e.g., if embeddings were not pregenerated for the specific gene in question), such as functional descriptions (e.g., textual descriptions of gene functions extracted from biological databases), protein sequences (e.g., amino acid sequences of the proteins encoded by the genes) obtained from sequence databases, functional annotations (e.g., Enzyme Commission (EC) numbers, Gene Ontology (GO) terms, and other annotations indicating enzymatic functions and biological processes), and/or the like. The platform may also preprocess each component of the strain description and/or additional information into a format suitable for embedding lookup and/or generation.

At 6603, the platform may generate and/or look up embeddings for each element of the strain description. For example, the platform may retrieve corresponding embeddings from pre-computed lookup tables. Additionally or alternatively, the platform may generate embeddings using one or more techniques of the embedding were not precomputed.

The platform may generate and/or look up multiple types of embeddings, which may capture different aspects of genetic function. For example, that platform may generate and/or look up GenePT embeddings, FBA-PCA embeddings, and/or the like for each gene involved in the genetic modifications. Additionally or alternatively, the platform may generate and/or look up edit type embeddings representing each type of genetic modification (e.g., knockout, overexpression, etc.). Additionally or alternatively, that platform may generate and/or look up plasmid embeddings representing plasmid characteristics, promoter embeddings that capture the characteristics of each promoter used in the genetic modifications, integration site embeddings that represent integration sites, etc.

As an example, the platform may generate a first embedding [a1, a2, a3] (although this example embedding only has three values, a real embedding may have many hundreds of values, each corresponding to a dimension in the embedding space) for a specific genetic edit and a second embedding [b1, b2, b3] for the same genetic edit using a different embedding method. In embodiments, the platform may also prepend or append additional value(s) to the embedding, such as a value indicating the type of genetic edit (e.g., a value m indicating whether an edit is a knockout, underexpression, or overexpression), yielding example embeddings such as [a1, a2, a3, m] and/or [b1, b2, b3, m].

At 6604, the platform may optionally aggregate multiple embedding types to create a more comprehensive embedding for each genetic modification. For example, the platform may concatenate multiple embeddings for a particular genetic edit. In some cases, the platform may use other aggregation methods, some examples of which are described below.

In the concatenation method, the platform joins embedding from different sources end-to-end to form a longer vector. For example, a GenePT embedding [a1, a2, a3] and an FBA-PCA embedding [b1, b2, b3] for a gene may be concatenated to yield the concatenated embedding [a1, a2, a3, b1, b2, b3]. It should be noted that in this example, extra values (e.g., a value m indicating a type of modification) are not appended to the embedding; however, the platform may generate a concatenated embedding with a copy of the additional values prepended or appended).

Additionally or alternatively, the platform may use a weighted sum method of aggregating embeddings. In this method, the platform may combine embeddings using weighted sum (e.g., where the weights may be parameters that can be learned during the training process). For example, given weights w1 and w2 and example embeddings [a1, a2, a3] and [b1, b2, b3], the platform may generate a combined embedding [w1a1+w2b1, w1a2+w2b2, w1a3+w2b3]. This method may have the advantage of maintaining the same dimensionality of embeddings whether or not the embeddings are aggregated.

Additionally or alternatively, the platform may use a small model (e.g., neural network) to learn how to best combine the different embeddings into more comprehensive embeddings for each genetic edit. For example, the platform may input two example embeddings [a1, a2, a3] and [b1, b2, b3] into a trained neural network, which may output a combined embedding for the corresponding genetic edit. (It may be noted that although an LSTM stage described above may perform a similar role for combining embeddings for individual genetic edits into a strain embedding, the neural network described in this example may combine multiple individual embeddings for a genetic edit into a single combined embedding for a genetic edit.)

Additionally or alternatively, the platform may use multiplication to generate a product of the two embeddings vectors. For example, the platform may combine a first matrix A (including a first type of embeddings) and second matrix B (including a second type of embeddings) to generate a tensor product C that captures, for example, pairwise interactions between the elements of A and B.

Other aggregations are possible, and it should be understood that the above methods are merely exemplary ways of aggregating multiple embeddings to create a set of more comprehensive embeddings for the genetic edit information.

At 6605, the platform may arrange the comprehensive embedding vectors for all genetic modifications into a sequence that may be used as model inputs. The combined inputs, therefore, represent the entire set of modifications made to the strain. The platform may arrange the combined input values in any way, such as by the order of modifications, the relative positions of integration sites, and/or the like. For some types of models, the ordering of the inputs may not matter.

Additionally, in cases in which process features are being input to the model to generate predictions for a specific process (e.g., as described above for FIGS. 16A-F), the process features may be added as model inputs. For example, the model may use a hybrid architecture whereby process features are input via a parallel path into a separate network (e.g., such that the genetic embeddings are processed via an LSTM or other stage that generates a strain embedding, whereas the process inputs are processed via an MLP or some other dedicated process features stage). Additionally or alternatively, the platform may skip inputting the process features into a first stage in favor of fusing the features into an intermediate strain embedding before the inputs are provided to a final (e.g., MLP) stage. These strategies are example methods of processing process features in parallel, but other example methods may be used to generate predictions for certain process features that may specified as inputs to the mode.

At 6606, the platform may provide the model inputs (e.g., the sequence(s) of combined embedding vectors and/or process features) to input layer(s) of the model (e.g., an input layer of an LSTM and/or other initial stage of a neural network). The LSTM or other first stage may process the embeddings sequence, capturing the interactions and/or cumulative effects of the various genetic modifications, as described above. The LSTM may output a strain embedding (e.g., a fixed-length vector representing the entire strain).

At 6607, the platform may provide the strain embedding to a second/final stage (e.g., an MLP neural network) to generate the final prediction(s). As described above, the platform may have trained the MLP to map the strain embedding to the target phenotype or task specific performance metric(s). The MLP thus processes the strain embedding and outputs one or more prediction(s) for the target metric(s) (e.g., fitness, metabolite production rate). In some cases, the prediction(s) may include confidence intervals or uncertainty estimates. In some embodiments, the MLP may also receive one or more process conditions and predict the performance of the strain in the designated process conditions. The process conditions may be any of the process conditions described herein.

It should be noted that in some cases, the model may not use two stages in the way described above. For example, the model may directly predict the target variable without generating an intermediate strain embedding.

The platform 100 may optimize the inference process for low-latency prediction using techniques that may include batch processing of multiple strain predictions, model quantization to enable faster computation with reduced precision, parallel processing of different embedding types across multiple compute units, and/or the like. These optimizations may help enable strain prediction with lower latencies.

After generating the prediction(s), the platform may perform various analyses using the prediction(s) and/or other information. For example, the platform may perform contribution analyses that analyze the relative contributions of different genetic modifications to a final prediction, thereby identifying which factors influence strain performance. Additionally or alternatively, the platform may use active learning methods as described above to iteratively find more performant strains and/or explore the space of strain modifications.

The platform 100 may use the generated predictions in various applications, including real-time strain engineering (e.g., using the predictions to generating guidance for laboratory automation workflows), dynamic adjustment of fermentation parameters based on predicted strain performance, automated quality control systems that predict strain stability, optimization of industrial-scale bioprocesses using continuous monitoring and prediction, and/or the like. In embodiments, the platform 100 may integrate with laboratory management systems to automatically log predictions, trigger automated responses based on prediction results, and/or the like.

Rapid Sampling System

Figure 21:
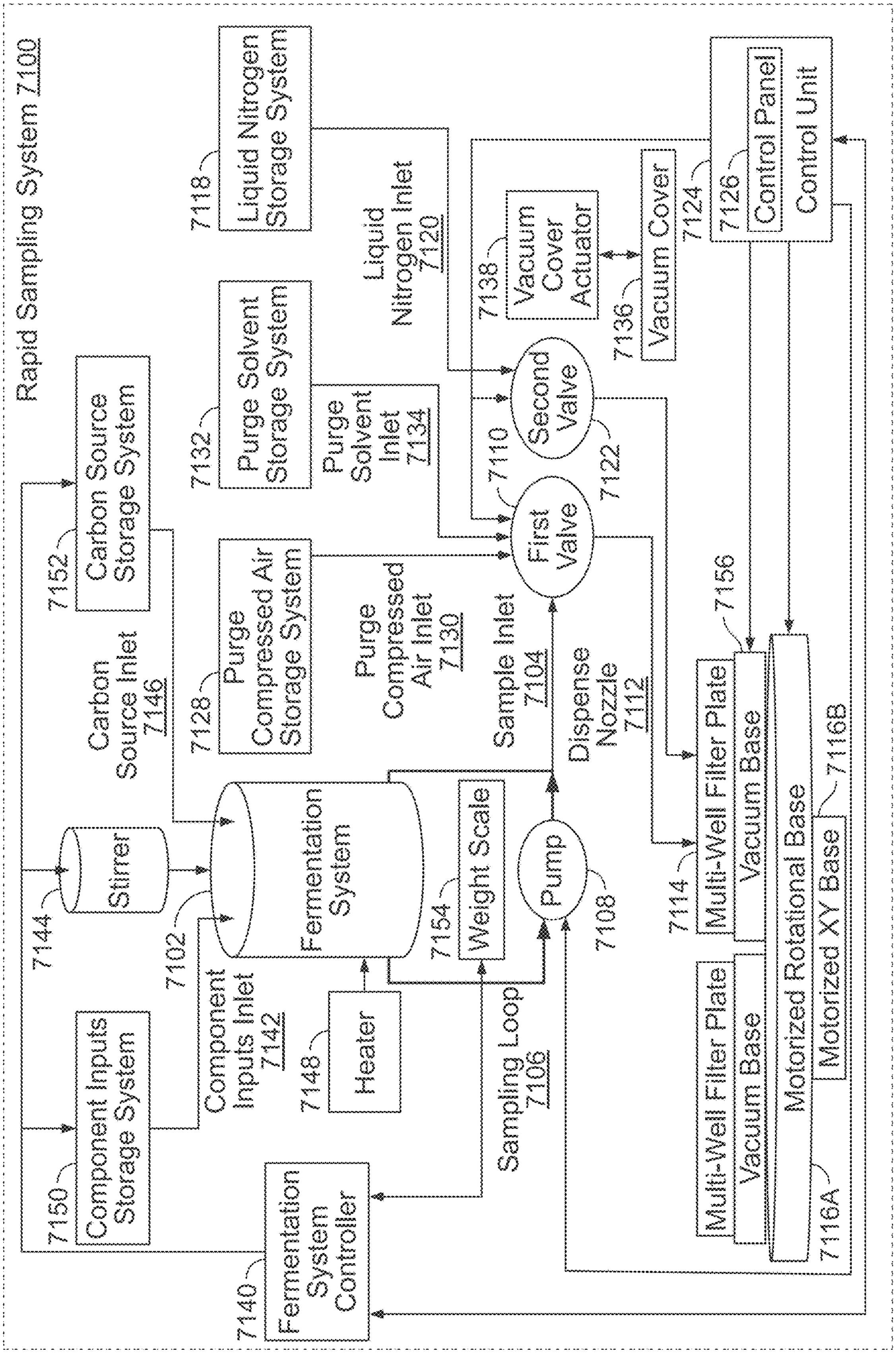
FIG. 21 is a schematic illustrating an example rapid sampling system according to some embodiments.

Referring to FIG. 21, the platform 100 can include and/or integrate with a rapid sampling system 7100. The rapid sampling system 7100 is configured to collect samples from a fermentation system 7102 at rapid predetermined time increments (e.g., every five seconds), enabling users to closely monitor metabolic processes inside the fermentation system. The rapid sampling system 7100 enables high-resolution temporal monitoring of metabolic processes, allowing users to track enzyme activity and/or metabolite accumulation with unprecedented precision compared to traditional sampling methods. Additionally, the automated handling of the samples by the rapid sampling system 7100 minimizes the variations that can arise from manual sample handling. This enhanced monitoring capability facilitates the identification of metabolic bottlenecks through real-time observation of metabolite buildups. The rapid sampling system enables granular analysis of carbon flux, revealing the flow of carbon-containing compounds through metabolic pathways. By mapping these metabolic flows and identifying rate-limiting steps, users can implement targeted interventions in fermentation processes, such as adjusting enzyme expression levels or modifying substrate concentrations. This approach allows precise optimization of metabolic efficiency and product yields through strategic manipulation of identified bottlenecks and flux patterns. The rapid sampling system 7100 is capable of operating at any practical fermentation scale, including pilot scale and industrial scale.

The rapid sampling system 7100 may have a sample inlet 7104 fluidly connected to the fermentation system 7102. In some embodiments, the sample inlet 7104 may be fluidly connected to a sampling loop 7106 that is driven by a pump 7108, dispensing some fluid of the sampling loop 7106 into the sample inlet 7104 and allowing the remaining fluid of the sampling loop to re-enter the fermentation system. The pump 7108 is fluidly connected to the sample inlet 7104 and configured to draw a sample from the fermentation system, through the sampling loop 7106, through the pump 7108, and into the sample inlet 7104.

The rapid sampling system 7100 includes a first valve 7110 fluidly connected to the outlet of the pump 7108 and fluidly connected to sample inlet 7104 and configured to receive a sample from the sample inlet 7104. In embodiments, the first valve 7110 may be an HPLC valve, which regulates the flow of samples and other fluids (e.g., purge compressed air and purge solvent). The first valve 7110 may be operatively connected to a dispense nozzle 7112 configured for precisely releasing the samples and the other fluids and directing the flow of fluid from the valve to specific well targets, ensuring accurate placement and minimizing waste or spillage. A selected well of the multi-well filter plate 7114 may be positioned, by a motorized base, directly below the first valve 7110 and its dispense nozzle 7112, such that samples and other fluids can be dispensed into the selected well.

The rapid sampling system 7100 may also include a liquid nitrogen storage system 7118 for storing liquid nitrogen that is fluidly connected to a liquid nitrogen inlet 7120. A second valve 7122 may be fluidly connected to the liquid nitrogen inlet 7120 and configured to dispense liquid nitrogen into a select well of the multi-well filter plate. In implementations, the selected well of the multi-well filter plate 7114 may be positioned, by the motorized base, directly below the second valve 7122 in order to receive the liquid nitrogen in the selected well. The second valve 7122 may be a cryogenic valve, which is designed to handle the low temperatures of the liquid nitrogen. The liquid nitrogen "quenches" the metabolism of the sample, rapidly halting all metabolic activities and preserving the current state of the metabolites in the sample, such that an accurate snapshot of the metabolites can be determined for a specific time. While liquid nitrogen rapidly freezes the cells, it also maintains the structural integrity of the cells. Without quenching, enzymes may continue to metabolize substrates even after sampling, which can alter metabolite concentrations and lead to inaccurate data and analysis.

The multi-well filter plate 7114 of the rapid sampling system 7100 may have a plurality of wells wherein individual wells can be designed to collect and filter samples deposited in the wells by the first valve 7110. The multi-well filter plate 7114 may be operatively coupled to a motorized base that is configured to adjust the position of the multi-well filter plate such that a first well may be positioned directly underneath the first valve. In embodiments, the motorized base comprises a motorized rotational base 7116A and a motorized XY base 7116B, collectively enabling comprehensive movement within the horizontal plane.

The rapid sampling system 7100 comprises a control unit 7124 having one or more processors and one or more memories wherein the control unit 7124 is configured to control rapid sampling system operations. The control unit 7124 may comprise microcontrollers or programmable logic controllers (PLCs) that execute control algorithms, input/output (I/O) modules that facilitate communication between the control unit 7124 and external devices, a power supply that provides the necessary electrical power for the control unit's operation and connected components, and connectivity interfaces that enable communication with other systems, networks, and/or user interfaces (e.g., Ethernet, USB, serial ports, and the like). The control unit 7124 may be operatively connected to the pump, the first valve, the second valve, the motorized base, and other components of the rapid sampling system 7100. The control unit 7124 may be configured to automatically initiate and perform a plurality of sampling operations at predetermined time intervals (e.g., every five seconds), wherein each sampling operation comprises steps 7202-7208. The control unit 7124 may integrate with a control panel 7126, which acts as the interface through with operators interact with the rapid sampling system 7100, allowing operators to send commands and receive feedback. For example, operators may be able to send commands related to the timing of sampling operations or the desired flow rate of sample through the pump through the control panel 7126. The control panel 7126 may comprise buttons and switches, displays and indicators, knobs and dials, touchscreens, and/or safety features (e.g., emergency stop buttons, interlocks, and warning signals).

Figure 22:
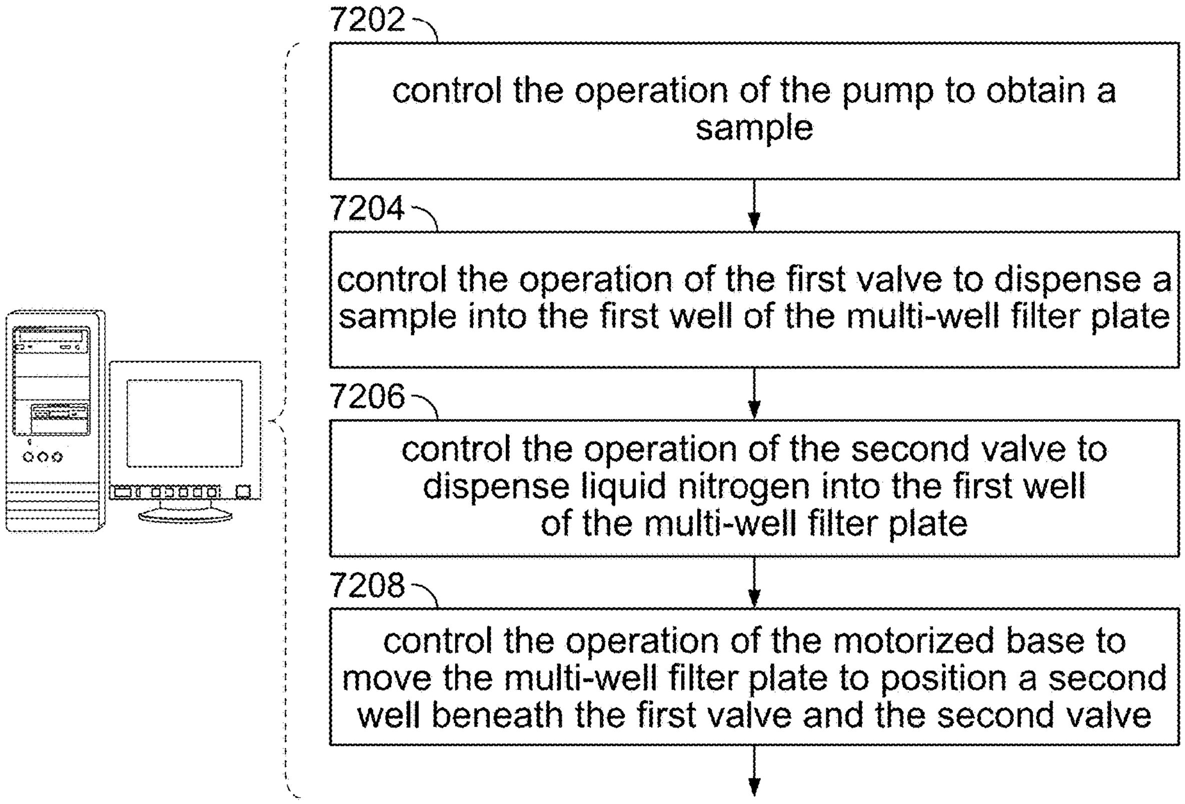
FIG. 22 is a flowchart illustrating an example rapid sampling system control unit method according to some embodiments.

Referring to FIG. 22, at 7202, the control unit 7124 controls the operation of the pump 7108 to draw a sample from the fermentation system 7102, through the sampling loop 7106 and pump 7108 and into the sample inlet 7104. In embodiments, the pump may be a peristaltic pump, or roller pump, which is configured to move fluid using positive displacement. In some embodiments, the control unit 7124 may control the flow rate of the pump 7108.

At 7204, the control unit 7124 controls the operation of the first valve 7110 to dispense a sample, through the dispense nozzle 7112, into a first well of the multi-well filter plate 7114.

At 7206, the control unit 7124 controls the operation of the second valve 7122 to dispense liquid nitrogen into the first well of the multi-well filter plate 7114 to quench the metabolism of the sample in the first well. In embodiments, the second valve 7122 is placed directly adjacent to the first valve 7110 such that both the first and second valve 7122 can dispense sample and liquid nitrogen, respectively, into the first well. In other embodiments, the motorized base may move the first well from directly under the first valve 7110 to directly under the second valve 7122 after the first valve 7110 dispenses the sample into the first well such that the second valve 7122 can dispense the liquid nitrogen into the first well to "quench" the metabolism of the sample.

At 7208, the control unit 7124 controls the operation of the motorized base to move the multi-well filter plate to position a second well beneath the first valve and the second valve.

In embodiments, the rapid sampling system 7100 further comprises a purge compressed air storage system 7128, which is fluidly connected to a purge compressed air inlet 7130. The purge compressed air can be used to dry and/or remove particulates from a selected well before it receives a sample. The purge compressed air inlet 7130 may be fluidly connected to the first valve 7110. The purge compressed air inlet 7130 can be operatively connected to the control unit, wherein the control unit is further configured to control operation of the first valve 7110 to dispense compressed air to a select well. In some embodiments, the purge compressed air inlet may be fluidly connected to a third valve, or a separate valve than the first valve that dispenses the sample.

The rapid sampling system 7100 may be equipped with a purge solvent storage system 7132 that is fluidly connected to a purge solvent inlet 7134. The purge solvent inlet 7134 may be fluidly connected to the first valve 7110. The control unit 7124, which is operatively connected to the first valve 7110, may be configured to control operation of the first valve to dispense solvent to clean a selected valve before receiving the sample. In some embodiments, the purge solvent inlet may be fluidly connected to a third valve or a fourth valve rather than the first valve that dispenses the sample. For example, the first valve may dispense the sample, the second valve may dispense the liquid nitrogen, and the third valve may dispense both the purge compressed air and purge solvent. In another example, the first valve may dispense the sample, the second valve may dispense the liquid nitrogen, the third valve may dispense the purge compressed air, and the fourth valve may dispense the purge solvent.

In implementations, the rapid sampling system 7100 further comprises a vacuum base 7156 wherein the vacuum base 7156 is operatively connected to the multi-well filter plate and operatively connected to the control unit wherein the control unit is further configured to control operation of the vacuum base 7156 to filter one or more wells of the multi-well filter plate. The rapid sampling system 7100 may also include a vacuum cover 7136 and a vacuum cover actuator 7138.

The fermentation system 7102 may include a fermentation system controller 7140 having one or more processors and one or more memories that controls the operations of the fermentation system 7102. The fermentation system 7102 may be fluidly connected to a component inputs inlet 7142, a stirrer 7144, and a carbon source inlet 7146 and operatively connected to a heater 7148. The component inputs inlet 7142 may be fluidly connected to a component inputs storage system 7150 that stores fermentation system inputs. The fermentation system controller 7140 may be operatively connected to component inputs inlet 7142 and cause the component inputs inlet 7142 to dispense fermentation inputs (e.g., microorganisms and pH control agents) into the fermentation system 7102. The fermentation system controller 7140 may be operatively connected to the stirrer 7144 and cause the stirrer to stir the contents of the fermentation system 7102. The fermentation system controller 7140 may be operatively connected to the heater 7148 and cause the heater 7148 to heat the contents of the fermentation system 7102.

A carbon source storage system 7152 may be fluidly connected to the carbon source inlet 7146. The fermentation system controller 7140 may be operatively connected to the carbon source inlet 7146, which may be operatively and/or fluidly connected to the fermentation system 7102 and may be configured to dispense a carbon source into the fermentation system 7102. In embodiments, the carbon source may be a labeled carbon source such as Carbon-13 or Carbon-14, which are isotopes of carbon. The use of a labeled carbon enables the understanding of carbon distribution in the resulting metabolites, revealing how carbon is being channeled through the metabolic network, essentially acting as a "tracer" to map out the metabolic flux within the fermentation system. In some implementations, the fermentation system controller 7140 is operatively coupled to the control unit 7124 and the initiation of the plurality of sampling operations is dependent on the dispensing of carbon by the carbon source inlet.

The fermentation system controller 7140 may be operatively connected to a weight scale 7154 for biomass monitoring and measurement, assessing feedstock utilization, process control and automation (e.g., automated feeding systems), maintaining liquid levels and preventing overflow, leak detection, data collection for scale-up and reproducibility, and the like.

The rapid sampling system may be connected to an automated "omics" for generalization, or auto-OMG system. For example, the control unit of the rapid sampling system 7100 may be integrated with and/or connected with the auto-OMG system, which enables certain measurements of the samples collected by the rapid sampling system 7100.

The control unit 7124 of the rapid sampling system 7100 may be integrated with an analytical and mass spectrometry instrument and/or the auto-OMG system through a coordinated control architecture that manages the physical handling and analysis of samples. The control unit 7124 of the rapid sampling system 7100 can automate the collection of physical samples from the source material and coordinate the physical transfer of these samples to the analytical and mass spectrometry instrument. In embodiments, this physical transfer may be implemented using robotics and/or robotic handling systems, which may also be integrated with the control unit 7124, the analytical and mass spectrometry instrument, the robot(s) and/or robotic handling systems, and/or the auto-OMG system. This integration enables timing coordination between sample extraction and subsequent measurements by the analytical and mass spectrometry instrument, where the rapid sampling system's control unit 7124 signals the robot(s) and/or robotic handling systems when a new physical sample is ready for measurement and ensures proper sample positioning for accurate analysis.

In embodiments, the control unit 7124 of the rapid sampling system 7100 may be integrated with other systems, including concentration measurement systems and devices that enable concentration measurements of metabolites in the samples collected by the rapid sampling system 7100.

In embodiments, the platform 100 may include a digital twin system configured to generate and/or manage a digital twin of the rapid sampling system and/or its components.

Automated Omics for Generalization (Auto-OMG)

Figure 23:
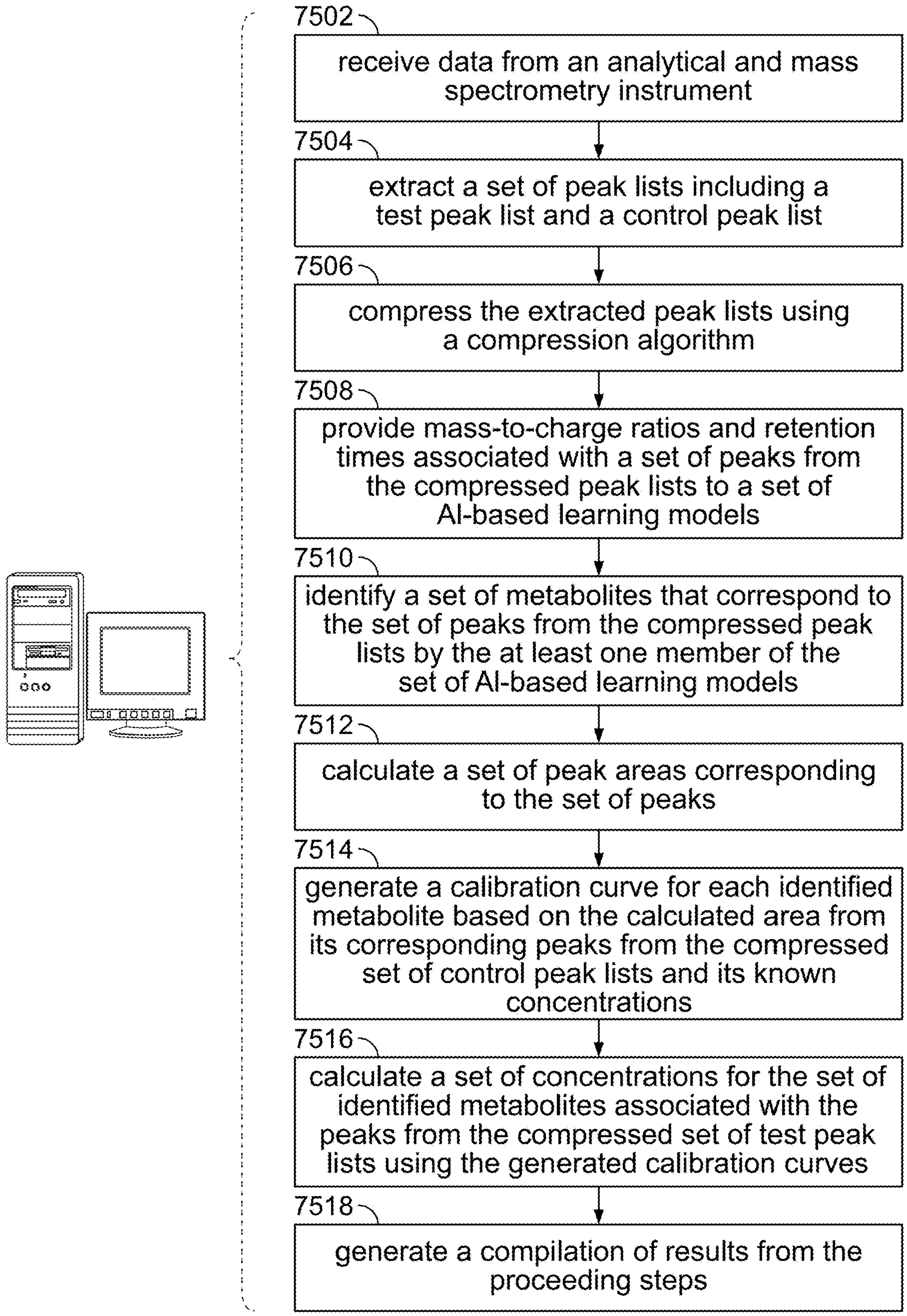
FIG. 23 is a flowchart illustrating an example omics for generalization method according to some embodiments.

Referring to FIG. 23, the platform 100 includes an automated "omics" for generalization (auto-OMG) system. The auto-OMG system may be configured to convert raw data from an analytical and mass spectrometry instrument to model-ready data. In embodiments, the auto-OMG system comprises the analytical and mass spectrometry instrument, while in other embodiments, the auto-OMG system integrates and/or interfaces with the analytical and mass spectrometry instrument. In embodiments, the auto-OMG system comprises computing hardware, including one or more processors and one or more memories.

The analytical and mass spectrometry instrument may be a liquid chromatography-mass spectrometry (LC-MS) instrument, a gas chromatography-mass spectrometry (GC-MS) instrument, a quadruple time-of-flight (QTOF) mass spectrometry instrument, an ultraviolet-visible (UV-Vis) instrument, or a free induction decay (FID) instrument. In embodiments, the of analytical and mass spectrometry instrument may be a quadrupole mass spectrometry (QMS) instrument, a time-of-flight mass spectrometry (TOF-MS) instrument, an ion trap mass spectrometry instrument, an orbitrap mass spectrometry instrument, a sector mass spectrometry instrument, an electrospray ionization (ESI) instrument, a chemical ionization (CI) instrument, an electron ionization (EI) instrument, an atmospheric pressure chemical ionization (APCI) instrument, and an atmospheric pressure photoionization (APPI) instrument, among many others.

In embodiments, the auto-OMG system facilitates the generation and analysis of "omics" data, which refers to fields of study in biology that involve large-scale datasets to analyze various biological molecules and their roles in an organism, "Omics" data may comprise metabolomics data, transcriptomics data, fluxomics data, proteomics data, and genomics data, epigenomics data, lipidomics data, glycomics data, microbiomics data, exposomics data, phenomics data, foodomics data, and toxicogenomics data.

The auto-OMG system enables the detection and quantification of metabolites (e.g., sugars and amino acids) that are present in an organism or microorganism in a sample. For example, in order to determine whether a genetic edit has altered one or more pathways, it is important to determine the quantification of metabolites being used by the one or more pathways.

The auto-OMG system may be configured to execute a method on computing hardware that converts raw data from an analytical and mass spectrometry instrument to model-ready data, the method comprising steps 7502-7516. In some embodiments, the method is executed on an auto-OMG server.

At 7502, the auto-OMG system receives and/or downloads data from an analytical and mass spectrometry instrument wherein the data includes data from a set of control samples and a set of test samples. The test samples, for example, may be sourced from the rapid sampling system and may be transferred from the rapid sampling system by a robotic handling system or robot, which may handle any preparation required for the analytical and mass spectrometry instrument. Analytical and mass spectrometry instruments, such as liquid chromatography-mass spectrometry (LC-MS) systems, generate extensive raw spectral and temporal data for both control (e.g., reference) samples and test samples directly from the instrument. Control samples labeled with heavy carbon isotopes (e.g., Carbon-13 and Carbon-14) produce distinct mass-to-charge (m/z) ratios, intensity profiles, and retention times that appear as specific signal patterns in the raw data, serving as internal standards for accurate calibration and normalization of measurements. Test samples generate spectra accompanied by retention timing information, which are essential for the subsequent identification and differentiation of metabolites based on their unique retention times and mass signatures. In embodiments, the auto-OMG system includes a network interface configured to establish a communication link with the analytical and mass spectrometry instrument. The network interface may comprise an ethernet connection, wireless connection, or other suitable data communication protocol for receiving instrument data. The auto-OMG system receives the data by establishing a connection to the analytical instrument through the network interface and initiating a data transfer session. During the data transfer session, data from both the control samples and test samples can be transmitted from the instrument's data storage to the auto-OMG system's local memory. The network interface manages the data transmission protocols to ensure complete and accurate transfer of all data.

At 7504, the auto-OMG system extracts peak lists from the received data. The auto-OMG system processes the received data to extract peak lists by analyzing the spectral and temporal information using peak detection algorithms. Specifically, the auto-OMG system can identify local maxima within the mass spectrometry data that exceed predetermined intensity thresholds, marking these as potential peaks. For each detected peak, the auto-OMG system extracts key parameters including the mass-to-charge ratio, signal intensity, and chromatographic retention time. The extracted peak information can then be organized into structured data arrays or peak lists, with separate peak lists maintained for the control samples and test samples (e.g., control peak lists and test peak lists). In embodiments, the peak detection algorithm can incorporate noise filtering and baseline correction to ensure only genuine analytical signals are captured in the peak lists. Additionally, the auto-OMG system may apply peak deconvolution algorithms to resolve overlapping peaks and ensure accurate representation of co-eluting metabolites in the final peak lists.

At 7506, the auto-OMG system compresses the extracted peak lists using a compression algorithm. The auto-OMG system may organize the peak list data into structured formats optimized for compression operations. A compression algorithm can then be applied to reduce data size while maintaining critical information integrity, wherein the algorithm may utilize lossless compression techniques, run-length encoding for repeated intensity values, dictionary-based compression for common peak patterns, and/or arithmetic coding for efficient numerical sequence encoding. The compression maintains the integrity of mass/charge ratio measurements, accuracy of intensity values, temporal relationships between peaks, and other essential peak characteristics throughout the process. The auto-OMG system may generate compressed peak list data with optimized compression ratios based on the specific data characteristics. The auto-OMG system can thus use data compression techniques to provide a technical solution to technical problems arising from storing and processing large datasets representing measurement data generated by the analytical and mass spectrometry instrument.

At 7508, the auto-OMG system prepares inputs for a set of AI-based learning models that are trained to identify a set of metabolites that correspond to a set of peaks from the compressed peak lists by providing the mass-to-charge ratios and/or retention times associated with the set of peaks to a set of artificial intelligence (AI)-based learning models wherein at least one member of the set of AI-based learning models is trained on a training data set of mass-to-charge ratios and/or retention times to identify metabolites. In embodiments, the training data set may include spectral databases, publication data sets, experimental data, and/or the like. Additionally, or alternatively, in some embodiments, the at least one member of the set of AI-models may be trained on a training data set including fragmentation patterns, and fragmentation patterns from the set of peaks may be provided to the set of AI-based learning models in the identification of metabolites. In embodiments, the set of AI-based learning models includes at least one of a transformer model, a convolutional neural network, a deep learning model, a supervised model, a semi-supervised model, an unsupervised model, a reinforcement model, a long short-term memory (LSTM) model, a multi-layer perceptron model, lin-log model, and a large language model.

In embodiments where neural networks are used, the AI-based learning model may include an encoder-decoder architecture configured to process mass spectrometry data. For example, the encoder may comprise one or more convolutional layers that process mass spectrometry data such as mass-to-charge ratio and retention time data as a 2D input, where one dimension represents the mass-to-charge ratio range and the other represents the retention time range. In embodiments, the decoder may output probability distributions over possible metabolite identifications. The AI-based learning model may be trained using a cross-entropy loss function to minimize identification errors. In particular implementations, the neural network may include attention mechanisms that learn to focus on specific peak characteristics that are most informative for metabolite identification.

Alternatively (e.g., instead of or in addition to using AI/ML approaches), the metabolites may be identified by comparing and/or matching the mass-to-charge ratios and/or retention times associated with the set of peaks with the mass-to-charge ratios and/or retention times from a set of spectral databases for known metabolites, where the database may store information about each known metabolite, including information about corresponding retention times for the metabolite, mass-to-charge ratios for the metabolite, fragmentation patterns for the metabolite, and the like. The platform may, for example, perform lookups on the spectral databases using the mass-to-charge ratio and/or retention time data to find matching and/or partially matching metabolites (where partial matches may be based on matching within tolerance ranges for mass-to-charge ratios and/or retention times). In embodiments, fragmentation patterns can also be used in the identification of metabolites by comparing and/or matching fragmentation patterns from the compressed peak lists to fragmentation patterns in the set of spectral databases.

At 7510, in embodiments in which AI-based learning models are used, the platform 100 may execute (e.g., run inference) at least one member of the set of AI-based learning models using the inputs prepared at step 7508 to identify a set of metabolites associated with the set of peaks from the set of compressed peak lists using the provided mass-to-charge ratios and/or retention times. In some embodiments, the at least one member of the set of AI-based learning models uses provided fragmentation patterns in the identification of metabolites.

At 7512, the auto-OMG system calculates a set of peak areas corresponding to the set of identified peaks from the compressed peak lists. The peak area calculation for each peak may be performed by using mathematical integration where the function representing the peak is defined and the relevant range of the x-axis is integrated.

At 7514, the auto-OMG system generates a calibration curve for each identified metabolite by using the calculated areas from its corresponding peaks from the compressed control peak lists and its known concentrations (e.g., at preparation). Calibration curves are constructed by plotting the peak areas of the control peaks against their known concentrations, establishing a linear relationship that can be used to determine the concentrations of metabolites in test samples. The linear relationship may be expressed by a calibration curve equation.

At 7516, the auto-OMG system calculates a set of concentrations for the set of identified metabolites associated with the test peaks using the generated calibration curves and/or calibration curve equations and the test peak areas. In some embodiments, the auto-OMG system corrects for sample dilution and/or biomass content and adjusts the metabolite concentrations to reflect absolute amounts of the metabolites in the original biological sample. During sample preparation, the original sample may be diluted to make it compatible with the analytical and mass spectrometry instrument. For example, a sample may be extracted in a specific volume of solvent, and additional dilutions may be required to meet the concentration range of the calibration curve. A cumulative dilution factor can be determined and multiplied by the raw concentration from the calibration curve to adjust back to the original concentration in the undiluted sample. In some embodiments, the auto-OMG system can normalize to biomass content to further correct the concentration. Biomass may be measured as cell dry weight, protein content, or cell count. Once the concentration is adjusted for dilution, it can be normalized by dividing by the biomass amount, which allows the reporting of concentration in terms of the sample's original dry weight, cell count, or protein content.

In embodiments, the auto-OMG system analyzes the identified peaks to determine a need for a deconvolution and/or windowing adjustment on one or more of the identified peaks, and, upon determination of said need, performing deconvolution and/or windowing adjustment on the one or more of the identified peaks. Deconvolution may refer to the process of resolving complex signals or overlapping peaks into their original components. Deconvolution may be necessary to separate co-eluting compounds, interpreting isotopic patterns, converting multiple charge states into a single mass (e.g., neutral mass), resolving fragmentation spectra, and the like. The auto-OMG system may include a set of models trained to determine whether a deconvolution and/or windowing adjustment is appropriate and to automatically perform the deconvolution and/or windowing adjustment. For example, the set of models may be trained to identify and when peak shapes that are the result of column loading issues (e.g., a column loading issue in an LC-MS spectrometer causes an M-shaped peak) and should not be de-convoluted. In another example, the set of models may be trained to identify, in the peaks and/or spectral data, when structural isomers (e.g., leucine and isoleucine) co-elute perform a deconvolution. Windowing adjustments may be required, for example, when multiple metabolites exit a liquid chromatography column at the same time and overlap. In embodiments, the set of models may be trained to identify the need for windowing adjustment and perform the needed adjustment.

In some embodiments, the auto-OMG system generates a quality control (QC) website. The QC website may present a set of calibration curves representing the control samples and test samples for each of the metabolites of the set of metabolites for each run, aggregated data (e.g., mass-to-charge ratios and retention times) from each run, spectral data, peaks, and the like. In embodiments, the QC website allows an operator to link back to the raw experimental data. In some embodiments, the QC website allows operators to perform a manual deconvolution and/or windowing adjustment on one or more of the peaks.

The auto-OMG system may be configured to identify and/or quantify metabolites for which there are no controls. For example, the set of AI-based learning models may include at least one member trained on a training data set of mass-to-charge ratios, retention times, and/or fragmentation patterns to identify metabolites associated with a set of peaks. For identified metabolites without associated control peaks, control samples for such metabolites can be prepared and subsequently measured using the analytical and mass spectrometry instrument, allowing calibration curves to be generated and quantification to be performed as described above.

In some embodiments, at 7518, the auto-OMG system generates a compilation of results from the preceding steps. In embodiments, the auto-OMG system outputs the set of concentrations for the set of identified metabolites associated with the test peaks from the compressed peak list to a user interface, to a set of AI models, to an analytical system, to a model training system, to an external system, or the like.

In some cases, the auto-OMG system presents a visual representation of concentrations of the identified metabolites associated with the test peaks for presentation on a display of a user device. The auto-OMG system can generate the concentrations more efficiently and with higher accuracy than would otherwise be possible by integrating data compression techniques and AI-based learning models. These advantages extend to the visual representation of the concentrations of the identified metabolites, which can be generated with higher accuracy and with lower latency than would otherwise by possible as a result of the synergistic combination of the compression techniques and the AI-based learning models.

Generally, measurement data generated from the analytical and mass spectrometry instrument is high-dimensional and complex. For instance, the measurement data can include spectra that comprise mass-to-charge ratios (m/z values) and intensity values for each m/z. Even a single sample can produce spectra with thousands of peaks, representing a large number of molecular species or fragments. Measurement data generated by the analytical and mass spectrometry instrument thus has a complexity that is well beyond what could be practically analyzed in the human mind or using simple arithmetic. The auto-OMG system provides an automated process for analyzing and extracting features from measurement data generated by the analytical and mass spectrometry instrument using AI-based learning models which are trained by machine learning training techniques.

Rapid Sampling and Automated Omics for Generalization (Auto OMG) System

In embodiments, a rapid sampling and auto-OMG system comprises a rapid sampling system, an analytical and mass spectrometry instrument, and an automated omics for generalization (auto-OMG) system. In some embodiments, the rapid sampling and auto-OMG system further comprises a fermentation system and/or a robot and/or robotic handling system. In embodiments, the rapid sampling and auto-OMG system comprises one or more memories and one or more processors and is configured to collect a set of samples from a fermentation system and determine the concentration of a set of metabolites in the set of samples.

The rapid sampling system may be integrated with the analytical and mass spectrometry instrument, the auto-OMG system, and the robot and/or robotic handling system through a coordinated control architecture that manages the physical handling and analysis of samples. The control unit of the rapid sampling system can automate the collection of physical samples from the fermentation system and coordinate with the robot and/or robotic handling system to manage the physical transfer of these samples to the analytical and mass spectrometry instrument. This integration enables timing coordination between sample extraction and subsequent measurements by the auto-OMG system, where the rapid sampling system's control unit signals the robot and/or robotic handling system when a new physical sample is ready for measurement.

In embodiments, the coordinated control architecture may use distributed processing to manage multiple sampling and analysis operations in parallel. For example, the platform 100 may deploy multiple processing nodes to simultaneously handle sample collection timing, robotic transfer coordination, and/or instrument control, thereby allowing multiple parallel operations in real-time.

Referring to FIG. 24, at 7702, the rapid sampling system is configured to collect a set of samples from a fermentation system at predetermined time increments.

At 7704, the robot and/or robotic handling system may be configured to obtain the set of samples from the rapid sampling system and prepare the samples for the analytical and mass spectrometry instrument.

At 7706, the analytical and mass spectrometry instrument is configured to generate raw measurement data associated with the set of samples and provide the raw measurement data to the auto-OMG system.

At 7708, the auto-OMG system is configured to determine a set of concentrations for a set of metabolites in the samples based on the raw measurement data and output the set of concentrations.

In implementations, the rapid sampling and auto-OMG system may be configured to provide the set of concentrations to an artificial intelligence (AI)-based learning model training system. The concentration values may be used to train and/or retrain models trained by the AI-based learning model training system.

The rapid sampling and auto-OMG system may be configured to provide the set of concentrations to a set of artificial intelligence (AI)-based learning models, wherein at least one member of the set of AI-based learning models is trained to identify one or more metabolite bottlenecks. In embodiments, the set of AI-based learning models includes at least one of a transformer model, a convolutional neural network, a deep learning model, a supervised model, a semi-supervised model, an unsupervised model, a reinforcement model, a long short-term memory (LSTM) model, a multi-layer perceptron, a lin-log model, a large language model, a large protein model, or a protein language model. For example, suppose there is a high concentration of a precursor metabolite (e.g., glucose-6-phosphate in glycolysis) compared to downstream metabolites. This could indicate a bottleneck at a key enzymatic step that processes this precursor. For instance, if glucose-6-phosphate is accumulating but levels of fructose-6-phosphate (the next step in glycolysis) are low, it may suggest that phosphoglucose isomerase is limiting the flow through this pathway. Adjustments such as increasing the enzyme's expression, optimizing pH for its activity, or adding cofactors could relieve this bottleneck.

In some embodiments, the rapid sampling and auto-OMG system may be configured to provide the set of concentrations to a set of artificial intelligence (AI)-based learning models, wherein at least one member of the set of AI-based learning models is trained to generate a set of recommendations for an intervention to a fermentation process in the fermentation system, wherein the set of recommendations includes at least one of a genetic modification, a process improvement, and an environmental adjustment. The set of AI-based learning models includes at least one of a transformer model, a convolutional neural network, a deep learning model, a supervised model, a semi-supervised model, an unsupervised model, a reinforcement model, a long short-term memory (LSTM) model, a multi-layer perceptron, a lin-log model, a large language model, a large protein model, or a protein language model. For example, if the metabolite concentration indicates a bottleneck at a particular step, overexpressing the enzyme responsible for that reaction (e.g., through gene amplification or using a stronger promoter) could increase flow through the pathway and increase production. In another example, if metabolite concentration indicates the accumulation of unwanted byproducts, the nutrient feeding strategy could be adjusted in a process improvement. In yet another example, if metabolite concentrations suggest that a pathway's enzymes are underperforming (e.g., low product levels with an accumulation of upstream intermediates), it might indicate that the temperature is suboptimal for enzyme activity. Raising the temperature slightly can increase reaction rates, pushing intermediates forward and enhancing the overall pathway flux.

The rapid sampling and auto-OMG system may be configured to calculate the flux of a metabolic pathway for a fermentation in the fermentation system from the set of metabolite concentrations. Metabolite concentrations at multiple time points may be determined, and by calculating the rate of change of each metabolite concentration over time, the fluxes in and out of each metabolite can be determined. In some embodiments, the rapid sampling and auto-OMG system may provide the metabolite concentrations and/or metabolite fluxes to a digital twin of a metabolic pathway. The digital twin of the metabolic pathway could then model and/or simulate the flux of the real-world metabolic pathway.

In embodiments, the rapid sampling and auto-OMG system may be configured to calculate at least one of a predicted product yield measure, a fermentation productivity measure, a set of metabolite kinetic rates, or a set of pathway efficiencies for a fermentation process in the fermentation system. The rapid sampling and auto-OMG system can calculate these key fermentation metrics using measured metabolite concentration data.

For product yield calculations, the system first establishes baseline concentrations of all relevant metabolites at the start of fermentation. It then continuously monitors changes in both substrate and product concentrations throughout the process. The theoretical maximum yield is calculated based on stoichiometric equations and initial substrate concentrations. The actual yield is determined by comparing the measured final product concentration against this theoretical maximum, expressing the result as a percentage efficiency.

Fermentation productivity measurements involve precise temporal tracking of product formation. The rapid sampling and auto-OMG system records product concentrations from samples taken at regular intervals (e.g., at predetermined intervals) throughout the duration of a fermentation. These time-series measurements allow for calculation of both instantaneous and average productivity rates. The system can also determine specific productivity phases, such as lag phase, exponential phase, and stationary phase, by analyzing the rate changes over time.

Metabolite kinetic rate calculations require analysis of multiple concentration measurements over time. The system tracks the simultaneous changes in various metabolite concentrations, including substrates, intermediates, products, and biomass. From these measurements, it calculates instantaneous rates of change using differential analysis of concentration versus time data. The system also determines specific rates by normalizing these values to biomass concentration, providing insights into cellular metabolism efficiency. Additionally, it can calculate average rates over defined time intervals to smooth out short-term fluctuations and identify broader trends.

Pathway efficiency calculations involve complex analysis of metabolite interconversion throughout the biochemical pathway. The system measures concentrations of all key intermediates in the metabolic pathway at regular intervals. It then calculates conversion efficiencies between each step by comparing actual concentration ratios to theoretical stoichiometric ratios. The system performs carbon balance analysis by tracking the distribution of carbon atoms through various metabolites. Energy efficiency calculations are made by analyzing the concentration changes of energy-carrying molecules like ATP and NADH. These combined analyses provide a comprehensive view of pathway performance and help identify potential metabolic bottlenecks.

In embodiments, the rapid sampling and auto-OMG system may be configured to build a set of kinetic models for a fermentation process in the fermentation system using the set of determined metabolite concentrations. The rapid sampling and auto-OMG system builds kinetic models by utilizing the measured metabolite concentration data to construct mathematical representations of the fermentation process dynamics. Initially, the rapid sampling and auto-OMG system analyzes time-series concentration data for all measured metabolites to identify key relationships and patterns between different species. These relationships are then expressed as differential equations that describe the rates of change of each metabolite concentration over time. The rapid sampling and auto-OMG system incorporates various kinetic parameters, such as maximum reaction rates (Vmax) and substrate affinities (Km), which are estimated by fitting the concentration data to established enzyme kinetic equations like Michaelis-Menten kinetics. Multiple model structures may be evaluated, ranging from simple first-order kinetics to more complex models that account for substrate inhibition, product inhibition, and cellular growth dynamics. The rapid sampling and auto-OMG system can refine these models through iterative optimization, comparing model predictions against actual measured concentration profiles to minimize prediction errors. Advanced statistical techniques can be employed to assess model quality and determine confidence intervals for the estimated parameters. The resulting set of kinetic models can include both mechanistic models based on known biochemical pathways and empirical models that capture observed behavior patterns. These models can then be used to predict metabolite concentrations under different operating conditions, optimize process parameters, and identify rate-limiting steps in the fermentation process.

Multi-Objective Optimization and Comparative Analysis Approach

Overview

In the field of biotechnology, many scenarios involve a biologic synthesis process for the production of a biologic product, such as a DNA sequence, an RNA sequence, a protein such as an enzyme, a metabolic precursor, a cell or cell line, a strain of a biological species, or the like. The biologic synthesis process may involve a research process, such as a generation of a microbe of a particular genotype and/or phenotype for testing, or a protein that may be a pharmaceutical candidate for the treatment of a biologic pathway associated with a disease. The biologic synthesis process may involve an industrial process to generate biologic materials for other purposes, such as the synthesis of a protein that is used as a precursor or catalyst in the synthesis of other biologic materials, or in other fields, such as an enzyme that degrades pollutants for remediation processes. The biologic synthesis process may involve a pharmaceutical process to generate pharmaceutically active materials to be dispensed in healthcare. The biologic synthesis processes may involve various synthesis settings (e.g., culturing strains on plates, replicating a DNA sequence via polymerase chain reaction (PCR), or fermentation processes occurring in biological fermentation tanks) and/or scales (e.g., small-scale synthesis for research, individual-scale synthesis for personalized medicine, and/or large-scale synthesis for mass production and distribution).

In such scenarios, a biologic synthesis process may be designed to promote and/or maintain a particular objective. Alternatively or additionally, the biologic synthesis process involving a biologic product may be designed to promote and/or maintain a particular feature of the biologic product. For example, synthesis processes to generate a strain may be developed with the objective of amplifying the yield of the synthesis process per unit of time. Synthesis processes to generate an enzyme via a metabolic pathway may be developed with the objective of maintaining or increasing the effectiveness of the enzyme, such as the activity and/or rate of the enzyme to convert substrate materials into further biologic products. Synthesis processes to generate a pharmaceutical candidate may be developed with the objective of maintaining or increasing the effectiveness of treating a particular condition, such as a magnitude of increase or decrease of a metabolic pathway related to the condition. Synthesis processes involving the synthesis of a protein product from DNA and/or RNA may be developed with the objective of amplifying the rate of transcription and/or translation to increase the rate of production of the protein product. Many biologic synthesis processes begin with the identification of a biologic parent (e.g., a parent DNA or RNA sequence, a parent protein such as an enzyme, a parent cell line, or a parent strain of a microbe) having a particular feature, and the biologic synthesis process may be designed to promote an objective of the biologic synthesis process and/or a feature of the biologic parent. For example, a biologic synthesis process may produce a protein product that is commonly in a metabolic pathway and that may have an identified effect on the metabolic pathway. It may be desirable to modify the biologic synthesis process to promote an objective of the biologic synthesis process (e.g., to increase a yield of the protein product) or to promote a feature of the biologic product (e.g., to reduce unintended activity of the protein product that causes undesirable side-effects of the biologic synthesis process and/or a metabolic pathway in which the protein product is to be used). In order to promote an objective of the biologic synthesis process or to promote a feature of the biologic product, researchers may experiment with modifications of various parameters of the biologic synthesis process (e.g., temperature, pressure, the presence and components of reactants and/or nutrients, or the order and/or timing of steps of the biologic synthesis process) and may capture measurements of the experiments that indicate an effect of the modified parameters on the objective of the biologic synthesis process or the feature of the biologic product. Alternatively or additionally, researchers may conduct computer simulations of the biologic synthesis process with modifications of various parameters of the biologic synthesis process and may examine the results of the computer simulation to identify an effect of the modified parameters on the objective of the biologic synthesis process or the feature of the biologic product. The results of the experiments and/or simulations may enable the researchers to identify modifications of the biologic synthesis process that provide improvements of the objective of the biologic synthesis process or the feature of the biologic product.

In many biotechnology scenarios, it may be desirable to pursue multiple objectives of a biologic synthesis process. For example, in addition to increasing an overall yield of the synthesis of a protein product (e.g., a volume of the protein product generated at the completion of the biologic synthesis process), it may also be desirable to increase a rate of the biologic synthesis process (e.g., the amount of time required to complete the biologic synthesis process), a consistency of the biologic synthesis process (e.g., reducing variance in the yield and/or failures of the biologic synthesis process to produce the protein product), and/an efficiency of the biologic synthesis process (e.g., an amount of precursor material required to complete the biologic synthesis process). The multiple objectives may be related (e.g., increasing a yield of the biologic synthesis process as well as a rate of the biologic synthesis process), competitive (e.g., increasing a yield of the biologic synthesis process while also reducing a volume of precursor materials), or at least partially unrelated (e.g., increasing a yield of the biologic synthesis process while also preserving the materials for reuse in subsequent biologic synthesis processes). In such scenarios, modifications that improve or maintain a first objective of the biologic synthesis process (e.g., improving yield) might also detrimentally affect a second objective of the biologic synthesis process (e.g., increasing the volume of precursor materials to increase the yield, resulting in a higher-yield process that requires more precursor materials). In some cases, a modification that improves or maintains a first objective of the biologic synthesis process might detrimentally affect a second objective of the biologic synthesis process that researchers are not monitoring or pursuing (e.g., a modification that increases a yield of the biologic synthesis process, but that also reduces a desired activity or effectiveness of the biologic product on a metabolic pathway).

Alternatively or additionally, in many such scenarios, it may be desirable to improve or maintain multiple features of a biologic product. For example, in addition to increasing an activity a protein product (e.g., a magnitude of an effect of an pharmaceutical candidate product on a metabolic pathway), it may also be desirable to maintain a selectivity of the pharmaceutical candidate product in the context of the metabolic pathway (e.g., avoiding undesired interactions between the modified biologic product and other metabolic pathways that could result in undesired side-effects). The multiple features may be related (e.g., increasing both an activation and a selectivity of the biologic product), competitive (e.g., increasing a transcription and/or translation of a protein product from DNA and/or RNA sequences while also increasing the accuracy and/or consistency of the transcription and/or translation processes), or at least partially unrelated (e.g., increasing or maintaining an activity of a biologic product in a first metabolic pathway to treat a first disease while also increasing the activity of the biologic product in a second, unrelated metabolic pathway to treat a second disease). In such scenarios, modifications that improve or maintain a first feature of the biologic product (e.g., activity) might also detrimentally affect a second feature of the biologic product (e.g., selectivity). In some cases, a modification that improves or maintains a first feature of the biologic product might detrimentally affect a second feature of the biologic product that researchers are not monitoring or pursuing (e.g., a modification that increases an activity of the biologic product, but that also introduces undesirable interactions with other metabolic pathways that result in undesired side-effects).

Presented herein are techniques for pursuing multiple objectives in the development (e.g., discovery, adaptation, optimization, refinement, or the like) of a biologic synthesis process, and/or for pursuing multiple features of a biologic product (e.g., the activity, selectivity, and efficiency of a synthesized enzyme in the context of a particular metabolic pathway).

Comparative Analysis Approaches

Figure 25:
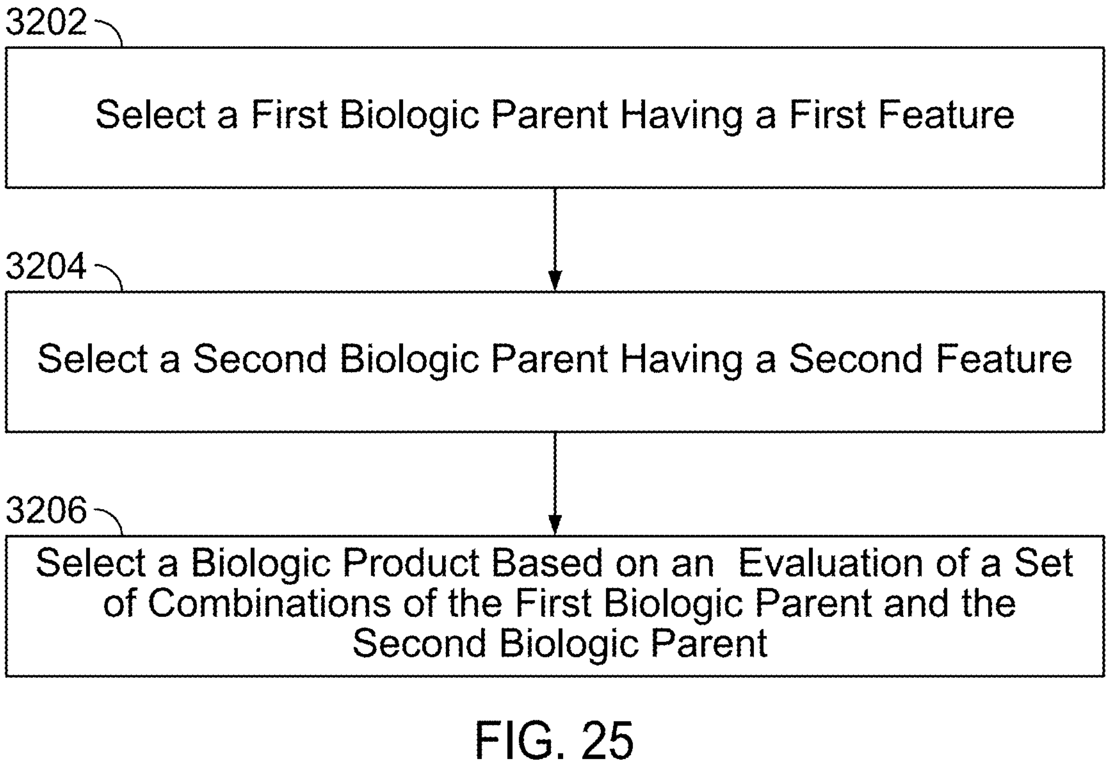
FIG. 25 is a flowchart that presents an example method of generating a biologic product of a biologic synthesis process according to some example embodiments.

FIG. 25 is a flowchart that presents an example method of generating a biologic product of a biologic synthesis process according to some example embodiments. The example method of FIG. 25 (which may be referred to as a Comparative Analysis Approach) may be performed, for example, by the Multi-Objective Optimization Module 3110 of the platform of FIG. 1.

The example flowchart of FIG. 25 includes a step 3202 of selecting a first biologic parent having a first feature. The first biologic parent may represent a biologic material having a desirable first feature that is to be included, maintained, and/or improved in the biologic product. For example, the first biologic parent may include a first DNA sequence including a first gene that, when expressed, causes a protein product transcribed (from the first DNA sequence to a first mRNA sequence) and translated (from the first mRNA sequence to the protein product) to include a first feature, such as an activity of binding to a particular binding site, an inclusion in a metabolic process, a suitability as a precursor for another biologic process, or the like. The first biologic parent may include a first protein having a first feature that is to be included in a protein product that is a variant of the first protein, such as an activity of binding to a particular binding site, an inclusion in a metabolic process, a suitability as a precursor for another biologic process, or the like. The first biologic parent may include a first cell line or strain of a microbe having a first feature, such as an expression of a particular enzyme or other protein, a performance of a metabolic pathway, or a characteristic within an environment of the first cell line or strain. The first biologic parent may include a first biologic synthesis process that produces a first biologic product, such as a biological fermentation process occurring in a biological fermentation tank that produces the first biologic product, wherein the biological fermentation process includes a first feature such as a yield, a reaction rate, or a consistency. Other examples of the first biologic parent include an enzyme protein, a non-enzyme protein, a DNA sequence, an RNA sequence, a plasmid, a metabolite, a biologic strain, a DNA synthesis process, an RNA synthesis process, a protein synthesis process, a metabolite synthesis process, a metabolic process, at least one pathway of a metabolic system, a plate growth process, a bioreactor process, or a downstream purification process. Other examples of the first feature include a product expression feature, a product activation feature, a product reaction feature, an enzyme cleaning feature, a product stability feature, a product biocompatibility feature, a process rate feature, a process catalyzation rate feature, a process efficiency feature, a process cost feature, or a process yield feature.

The example flowchart of FIG. 25 includes a step 3204 of selecting a second biologic parent having a second feature. The second biologic parent may represent a biologic material having a desirable second feature that is also to be included, maintained, and/or improved in the biologic product. For example, the second biologic parent may include a second DNA sequence including a second gene that, when expressed, causes a protein product transcribed (from the second DNA sequence to a second mRNA sequence) and translated (from the second mRNA sequence to the protein product) to include a second feature, such as an activity of binding to a particular binding site, an inclusion in a metabolic process, a suitability as a precursor for another biologic process, or the like. The second biologic parent may include a second protein having a second feature that is to be included in a protein product that is a variant of the second protein, such as an activity of binding to a particular binding site, an inclusion in a metabolic process, a suitability as a precursor for another biologic process, or the like. The second biologic parent may include a second cell line or strain of a microbe having a second feature, such as an expression of a particular enzyme or other protein, a performance of a metabolic pathway, or a characteristic within an environment of the second cell line or strain. The second biologic parent may include a second biologic synthesis process that produces a second biologic product, such as a biological fermentation process occurring in a biological fermentation tank that produces the second biologic product, wherein the biological fermentation process includes a second feature such as a yield, a reaction rate, or a consistency. The second feature may be related to the first feature (e.g., increasing both an activation and a selectivity of the biologic product), competitive with the first feature (e.g., increasing a transcription and/or translation of a protein product from DNA and/or RNA sequences while also increasing the accuracy and/or consistency of the transcription and/or translation processes), or at least partially unrelated to the first feature (e.g., increasing or maintaining an activity of a biologic product in a first metabolic pathway to treat a first disease while also increasing the activity of the biologic product in a second, unrelated metabolic pathway to treat a second disease). Other examples of the second biologic parent include an enzyme protein, a non-enzyme protein, a DNA sequence, an RNA sequence, a plasmid, a metabolite, a biologic strain, a DNA synthesis process, an RNA synthesis process, a protein synthesis process, a metabolite synthesis process, a metabolic process, at least one pathway of a metabolic system, a plate growth process, a bioreactor process, or a downstream purification process. Other examples of the second feature include a product expression feature, a product activation feature, a product reaction feature, an enzyme cleaning feature, a product stability feature, a product biocompatibility feature, a process rate feature, a process catalyzation rate feature, a process efficiency feature, a process cost feature, or a process yield feature.

The example flowchart of FIG. 25 includes a step 3206 of selecting a biologic product based on an evaluation of a set of combinations of the first biologic parent and the second biologic parent. The evaluation may include a simulation of at least one combination of the first biologic parent and the second biologic parent (e.g., a protein product based on the first biologic parent with an edit to include a portion and/or feature of the second biologic parent). The evaluation may include a laboratory experiment that involves generating and measuring at least one combination of the first biologic parent and the second biologic parent (e.g., a protein product based on the first biologic parent with an edit to include a portion and/or feature of the second biologic parent). The evaluation may be based on a scoring and/or weighting of the measurements of the first feature and the second feature. The evaluation may include evaluating a set of candidates selected from a set of combinations. The set of candidates may be selected from the set of combinations based on a ranking of the combinations (e.g., based on a viability and/or measurements, estimates, and/or predictions of the first feature and/or the second feature of the respective combinations). The set of candidates may be iteratively identified and evaluated (e.g., first evaluating a first top n-ranked candidates to determine high-performing combinations, and then evaluating a next top n-ranked candidates that may be similar to or different than previously evaluated combinations). The evaluation of the set of candidates may continue until a desired number of high-performing combinations are determined.

In embodiments, the platform 100 may evaluate sets of candidates to identify combinations using AI processing cores (e.g., GPUs, NPUs, TPUs, FPGAs, etc.) that are configured to efficiently process multiple combinations in parallel. For example, when evaluating protein combinations, the platform 100 may simultaneously compute structural predictions for multiple variant sequences. The platform 100 may optionally implement a distributed computing architecture where different processing cores evaluate different subsets of combinations simultaneously, with results aggregated by the platform 100 as a central coordinator.

Figure 26:
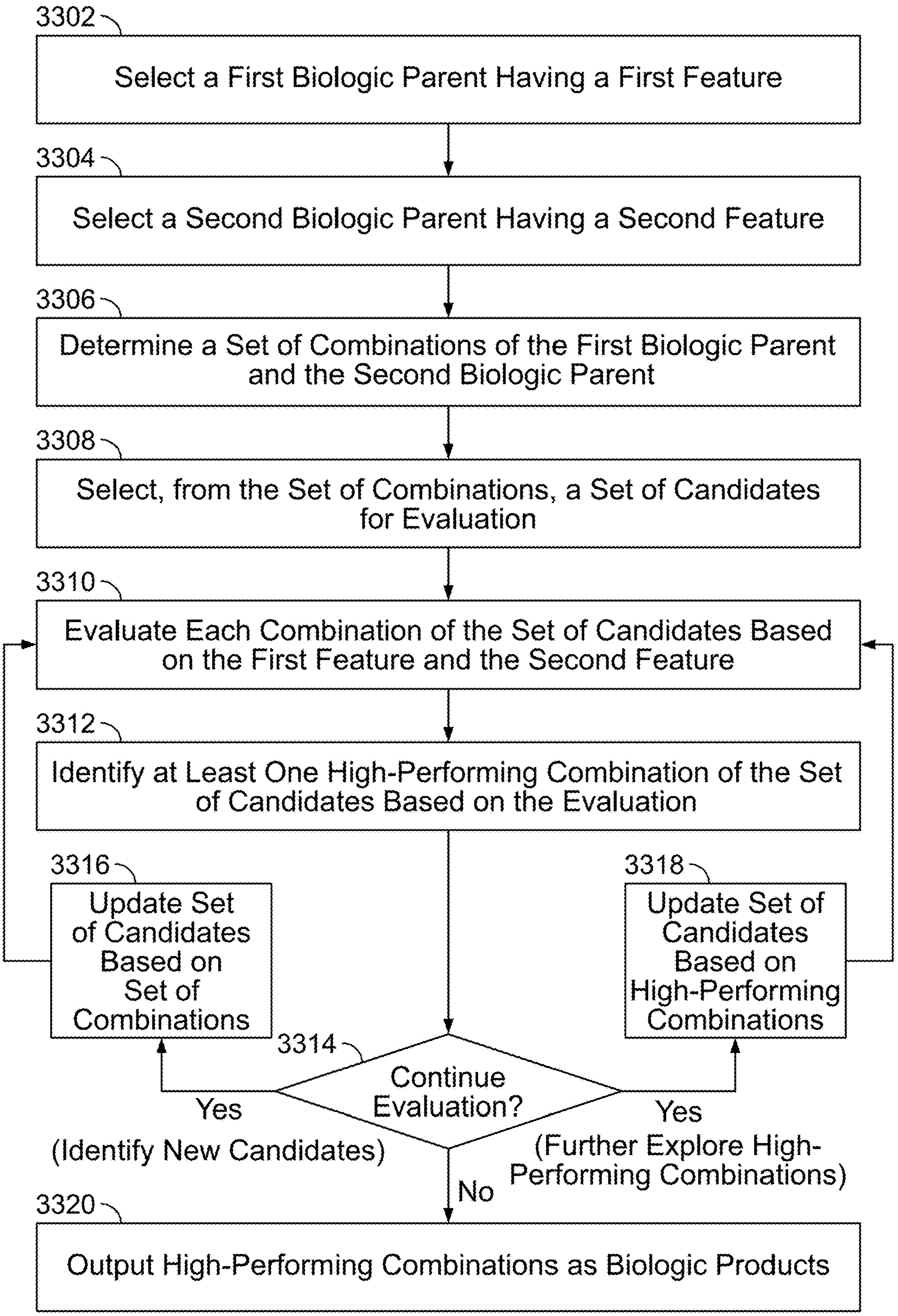
FIG. 26 is another flowchart that presents an example method of generating a biologic product of a biologic synthesis process according to some example embodiments.

FIG. 26 is another flowchart that presents an example method of generating a biologic product of a biologic synthesis process according to some example embodiments. The flowchart of FIG. 26 is a more detailed version of the flowchart of FIG. 25 that may be included and/or performed in some example embodiments. The example method of 26 (which may be referred to as a Comparative Analysis Approach) may be performed, for example, by the Multi-Objective Optimization Module 3110 of the platform of FIG. 1.

The example flowchart of FIG. 26 includes a step 3302 of selecting a first biologic parent having a first feature. The first biologic parent may represent a biologic material having a desirable first feature that is to be included, maintained, and/or improved in the biologic product. For example, the first biologic parent may include a first DNA sequence including a first gene that, when expressed, causes a protein product transcribed (from the first DNA sequence to a first mRNA sequence) and translated (from the first mRNA sequence to the protein product) to include a first feature, such as an activity of binding to a particular binding site, an inclusion in a metabolic process, a suitability as a precursor for another biologic process, or the like. The first biologic parent may include a first protein having a first feature that is to be included in a protein product that is a variant of the first protein, such as an activity of binding to a particular binding site, an inclusion in a metabolic process, a suitability as a precursor for another biologic process, or the like. The first biologic parent may include a first cell line or strain of a microbe having a first feature, such as an expression of a particular enzyme or other protein, a performance of a metabolic pathway, or a characteristic within an environment of the first cell line or strain. The first biologic parent may include a first biologic synthesis process that produces a first biologic product, such as a biological fermentation process occurring in a biological fermentation tank that produces the first biologic product, wherein the biological fermentation process includes a first feature such as a yield, a reaction rate, or a consistency. Other examples of the first biologic parent include an enzyme protein, a non-enzyme protein, a DNA sequence, an RNA sequence, a plasmid, a metabolite, a biologic strain, a DNA synthesis process, an RNA synthesis process, a protein synthesis process, a metabolite synthesis process, a metabolic process, at least one pathway of a metabolic system, a plate growth process, a bioreactor process, or a downstream purification process. Other examples of the first feature include a product expression feature, a product activation feature, a product reaction feature, an enzyme cleaning feature, a product stability feature, a product biocompatibility feature, a process rate feature, a process catalyzation rate feature, a process efficiency feature, a process cost feature, or a process yield feature.

The example flowchart of FIG. 26 includes a step 3304 of selecting a second biologic parent having a second feature. The second biologic parent may represent a biologic material having a desirable second feature that is also to be included, maintained, and/or improved in the biologic product. For example, the second biologic parent may include a second DNA sequence including a second gene that, when expressed, causes a protein product transcribed (from the second DNA sequence to a second mRNA sequence) and translated (from the second mRNA sequence to the protein product) to include a second feature, such as an activity of binding to a particular binding site, an inclusion in a metabolic process, a suitability as a precursor for another biologic process, or the like. The second biologic parent may include a second protein having a second feature that is to be included in a protein product that is a variant of the second protein, such as an activity of binding to a particular binding site, an inclusion in a metabolic process, a suitability as a precursor for another biologic process, or the like. The second biologic parent may include a second cell line or strain of a microbe having a second feature, such as an expression of a particular enzyme or other protein, a performance of a metabolic pathway, or a characteristic within an environment of the second cell line or strain. The second biologic parent may include a second biologic synthesis process that produces a second biologic product, such as a biological fermentation process occurring in a biological fermentation tank that produces the second biologic product, wherein the biological fermentation process includes a second feature such as a yield, a reaction rate, or a consistency. The second feature may be related to the first feature (e.g., increasing both an activation and a selectivity of the biologic product), competitive with the first feature (e.g., increasing a transcription and/or translation of a protein product from DNA and/or RNA sequences while also increasing the accuracy and/or consistency of the transcription and/or translation processes), or at least partially unrelated to the first feature (e.g., increasing or maintaining an activity of a biologic product in a first metabolic pathway to treat a first disease while also increasing the activity of the biologic product in a second, unrelated metabolic pathway to treat a second disease). Other examples of the second biologic parent include an enzyme protein, a non-enzyme protein, a DNA sequence, an RNA sequence, a plasmid, a metabolite, a biologic strain, a DNA synthesis process, an RNA synthesis process, a protein synthesis process, a metabolite synthesis process, a metabolic process, at least one pathway of a metabolic system, a plate growth process, a bioreactor process, or a downstream purification process. Other examples of the second feature include a product expression feature, a product activation feature, a product reaction feature, an enzyme cleaning feature, a product stability feature, a product biocompatibility feature, a process rate feature, a process catalyzation rate feature, a process efficiency feature, a process cost feature, or a process yield feature.

The example flowchart of FIG. 26 includes 3306 of determining a set of combinations of the first biologic parent and the second biologic parent. The set of combinations may be determined by combining at least a portion of the first biologic parent (e.g., a first subsequence or a first gene within a first DNA sequence) and at least a portion of the second biologic parent (e.g., a second subsequence or a second gene within a second DNA sequence). The set of combinations may be determined by selecting the first biologic parent and introducing one or more edits based on the second biologic parent (e.g., replacing a gene, DNA subsequence, or sequence of protein residues of the first biologic parent with a gene, DNA subsequence, or sequence of protein residues of the second biologic parent, and otherwise maintaining the features of the first biologic parent in the combination). The set of combinations may be determined by altering and/or substituting at least one property or parameter of the first biologic parent (e.g., a first biologic synthesis process for producing a biologic product in a biologic fermentation tank) with at least one property or parameter of the second biologic parent (e.g., adding or substituting a reactant included in a second biologic synthesis process for a reactant included in the first biologic synthesis process). Each combination of the set of combinations may include a number of edits with respect to the first biologic parent (e.g., single edits of the first biologic parent that involve changing one property, parameter, or feature of the first biologic parent, such as replacing one DNA subsequence or set of protein residues with a DNA subsequence or set of protein residues of the second biologic parent, and/or double edits of the first biologic parent that involve changing two distinct properties, parameters, or features of the first biologic parent, such as replacing two DNA subsequences or sets of protein residues with DNA subsequences or sets of protein residues of the second biologic parent). If the biologic parents and the combinations are biologic synthesis processes, the edits may include a combination of one or more steps of the first biologic parent with one or more steps of the second biologic parent (e.g., a combination of all of the steps of the first biologic parent and one step of the second biologic parent, or a substitution of one step of the first biologic parent with one or more steps of the second biologic parent).

The example flowchart of FIG. 26 includes a step 3308 of selecting, from the set of combinations, a set of candidates for evaluation. The selecting may be based, for example, on an edit distance between each combination and the first biologic parent and/or second biologic parent (e.g., single edits vs. double edits, or more conservative and/or less numerous edits of a DNA subsequence, gene, sequence of protein residues, biologic synthesis process parameters, or the like vs. more extensive and/or more numerous edits of a DNA subsequence, gene, sequence of protein residues, biologic synthesis process parameters, or the like). The selecting may be based on a distance between each combination and the first biologic parent and/or second biologic parent in an embedding space, which may be based on a biologic product language model, such as a protein language model. The selecting may be based on a ranking of the combinations (e.g., comparing previously untested combinations and choosing those with a highest predicted performance).

The example flowchart of FIG. 26 includes a step 3310 of evaluating each combination of the set of candidates based on the first feature and the second feature. The evaluating may include, for example, a joint comparison of the first feature of the first biologic parent with the first feature of the candidate and the second feature of the second biologic parent with the second feature of the candidate. The evaluating may be based on a laboratory experiment that involves synthesizing each combination of the set of candidates and measuring the first feature and/or the second feature for each combination of the set of candidates. The evaluating may be based on a simulation of each combination of the set of candidates in a simulated environment and a measurement of the first feature and/or the second feature in the simulation for each combination of the set of candidates.

The platform 100 may use machine learning models trained to predict features of combinations. In some embodiments, a machine learning model may include one or more of an encoder that processes input sequences representing combinations to generate embeddings, where each embedding represents features of a respective combination in a learned latent space, one or more transformer layers that process the embeddings using self-attention mechanisms to capture relationships between different regions of the combinations, and prediction heads that generate scores for the first and second features. The model may be trained using an objective function that uses one or more loss terms, such as a cross-entropy loss for discrete features and/or a mean squared error loss for continuous features. Training data may be obtained from historical laboratory experiments and may be augmented using techniques such as masked language modeling on biological sequences.

The example flowchart of FIG. 26 includes a step 3312 of identifying at least one high-performing combination of the set of candidates based on the evaluation. The identifying of high-performing combinations may include, for instance, a comparison of one or more scores with each combination of the set of candidates (e.g., a sum and/or product of the scores of the first and second features for each combination). The identifying of high-performing combinations may include comparing one or more scores of each combination with one or more thresholds (e.g., identifying high-performing combinations that at least maintain, and preferably improve, the first feature relative to the first biologic parent and/or that at least maintain, and preferably improve, the second feature relative to the second biologic parent). The identifying of high-performing combinations may include mapping a vector representation of each combination to an embedding space and identifying the high-performing combinations based on the locations of the combinations within the embedding space. The identifying of high-performing combinations may include ranking the combinations (e.g., according to one or more scores of each combination) and selecting one or more combinations as high-performing combinations based on the ranking. Each combination that is identified as high-performing combinations may be added to a set of high-performing combinations that also includes other high-performing combinations from the same evaluation and/or other evaluations, such as prior evaluations of other sets of candidates.

In embodiments, the platform 100 may use neural networks for the mapping of combinations to embedding spaces. For example, the platform 100 may employ protein language models or other techniques to generate contextual embeddings that capture biological properties, as described elsewhere herein. The platform 100 may optionally implement caching mechanisms to store frequently accessed embeddings and thereby reduce computational overhead for repeated analysis of similar combinations.

The example flowchart of FIG. 26 includes a step 3314 of determining whether to continue evaluation of candidates of the set of combinations. If the set of high-performing combinations includes at least a desired or target number of high-performing combinations, or if the set of high-performing combinations includes at least one high-performing combination that satisfies at least one target criterion (e.g., at least maintaining the first feature of the first biologic parent and at least exhibiting the second feature of the second biologic parent), the evaluation may continue to step 3320. If the set of high-performing combinations does not include at least a desired or target number of high-performing combinations and/or does not include at least one high-performing combination that satisfies at least one target criterion, the evaluation may evaluate additional sets of candidates. If at least one high-performing combination has been identified, the evaluation may proceed to step 3318 by including, in the set of candidates, at least one additional combination that is based on at least one of the high-performing combinations (e.g., a depth-based search in a proximity of the at least one high-performing combination). Alternatively or additionally, the evaluation may proceed to step 3316 by including, in the set of candidates, at least one additional combination from the set of combinations (e.g., a breadth-based search of additional combinations that are not in a proximity of the previously evaluated combinations).

The example flowchart of FIG. 26 includes a step 3320 of outputting the high-performing combinations as biologic products. The outputting may include, for example, presenting a report of the high-performing combinations based on the evaluation. The outputting may include presenting a report of the performance of the high-performing combinations (e.g., a result of a laboratory experiment and/or simulation that demonstrates the high performance of the identified high-performing combinations). The outputting may include presenting an explanation of the high-performing combinations (e.g., an explanation of the features of the first biologic parent and of the second biologic parent that are included in the high-performing combination, and/or an explanation of the manner in which the high-performing combination achieves the high performance). The outputting may include initiating one or more biologic synthesis processes to synthesize an amount of at least one of the high-performing combinations (e.g., automatically initiating a biologic fermentation process to synthesize the high-performing combination for automated, human-supervised, and/or human-led evaluation). If the high-performing combinations are biologic synthesis processes, the outputting may include initiating the biologic synthesis process to evaluate one or more results of the high-performing biologic synthesis process.

In some example embodiments, selecting a biologic product and/or biologic synthesis process based on a comparative analysis approach and/or multi-objective optimization approach may improve a hit rate and/or efficiency of determining high-performing biologic products as variants and/or combinations of one or more parents. Such example embodiments may yield a set of variants of the biologic parent that increases a number of determined variants, which may improve at least one of the at least two objectives relative to the biologic parent. The platform thus provides a technical improvement to the field of biologic product engineering by enabling efficient identification and generation of biologic variants that have improved properties.

Multi-Objective Optimization Approaches

Figure 27:
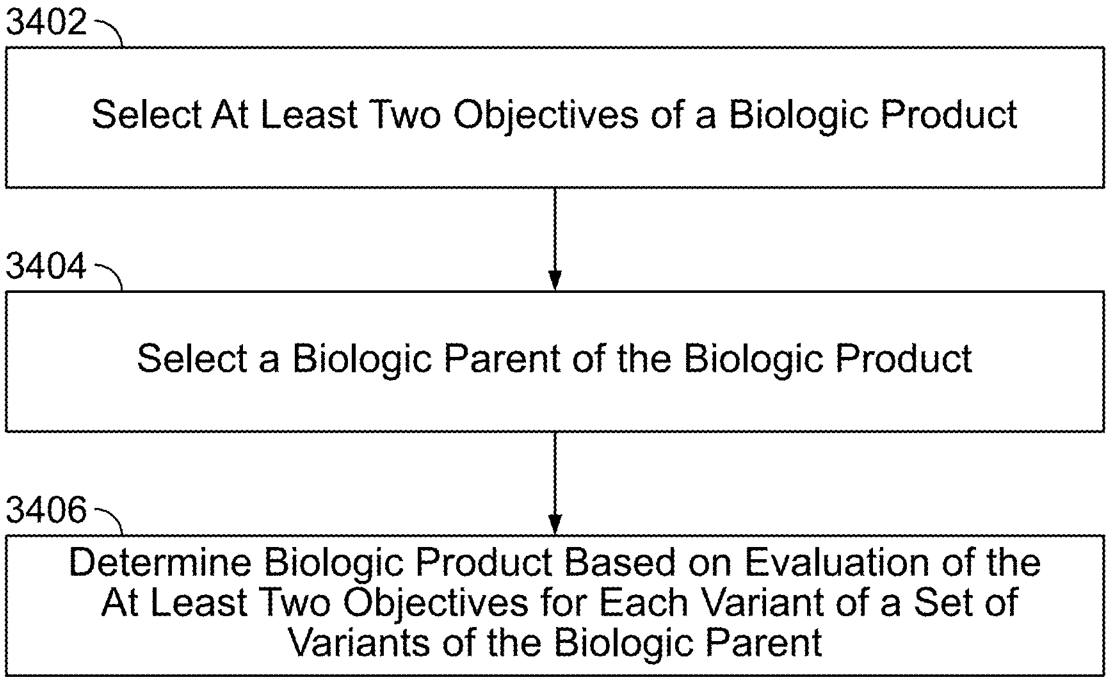
FIG. 27 is another flowchart that presents an example method of generating a biologic product of a biologic synthesis process according to some example embodiments.

FIG. 27 is another flowchart that presents an example method of generating a biologic product of a biologic synthesis process according to some example embodiments. The example method of FIG. 27 (which may be referred to as a Multi-Objective Optimization Approach) may be performed, for example, by the Multi-Objective Optimization Module 3110 of the platform of FIG. 1.

The example flowchart of FIG. 27 includes a step 3402 of selecting at least two objectives of a biologic product. The at least two objectives may include, for example, an objective of synthesizing a biologic product with an activity of binding to a particular binding site, an inclusion in a metabolic process, a suitability as a precursor for another biologic process, or the like. The at least two objectives may include an objective of synthesizing a biologic product that expresses a particular enzyme or other protein, that performs a metabolic pathway, or that exhibits a characteristic within an environment. The at least two objectives may include an objective of determining a biologic synthesis process that includes an objective such as a yield, a reaction rate, or a consistency of a biologic product. Other examples of objectives include a product expression objective, a product activation objective, a product reaction objective, an enzyme cleaning objective, a product stability objective, a product biocompatibility objective, a process rate objective, a process catalyzation rate objective, a process efficiency objective, a process cost objective, or a process yield objective.

The example flowchart of FIG. 27 includes a step 3404 of selecting a biologic parent of the biologic product. The biologic parent may include, for example, a DNA sequence, an RNA sequence, a protein such as an enzyme, a metabolic precursor, a cell or cell line, a strain of a biological species, or the like. The biologic parent may be or may include a material from which the biologic product is synthesized, such as a metabolic precursor that is included in a metabolic pathway to produce the biologic product, or a DNA or RNA sequence that can be transcribed and/or translated to synthesize the biologic product. The biologic parent may be or may include a material that is similar to the biologic product, and that is to be modified to generate the biologic product (e.g., a DNA sequence that is to be edited to produce an edited DNA sequence as the biologic product). The biologic parent may include a biologic synthesis process that generates one or more biologic products. The biologic parent may be selected based on at least one of the at two objectives selected for the biologic product (e.g., selecting a biologic parent that at least partially exhibits the at least two objectives, wherein the biologic product to be determined improves upon at least one of the at least two objectives of the biologic parent). The biologic parent may be selected based on an objective of improving at least one feature of the biologic parent (e.g., maintaining at least one desirable feature of the biologic parent and improving at least one undesirable feature of the biologic parent, or adding a new feature to the biologic parent).

The example flowchart of FIG. 27 includes a step 3406 of selecting a biologic product based on an evaluation of the at least two objectives for each variant of a set of variants of the biologic parent. The evaluation may include a simulation of at least one variant of the parent (e.g., a protein product based on the biologic parent with an edit to a portion of the biologic parent). The evaluation may include a laboratory experiment that involves generating and measuring at least one variant of the biologic parent (e.g., a protein product based on the biologic parent with an edit to a portion of the biologic parent). The evaluation may be based on a scoring and/or weighting of the measurements of each of the at least two objectives of the biologic product. The evaluation may include evaluating a set of variants selected from a set of variants. The set of candidates may be selected from the set of variants based on a ranking of the variants (e.g., based on a viability and/or measurements, estimates, and/or predictions of the at least two objectives of the respective variants). The set of candidates may be iteratively identified and evaluated (e.g., first evaluating a first top-ranked candidates to determine high-performing variants, and then evaluating a next top n-ranked candidates that may be similar to or different than previously evaluated variants). The evaluation of the set of candidates may continue until a desired number of high-performing variants are determined.

Figure 28:
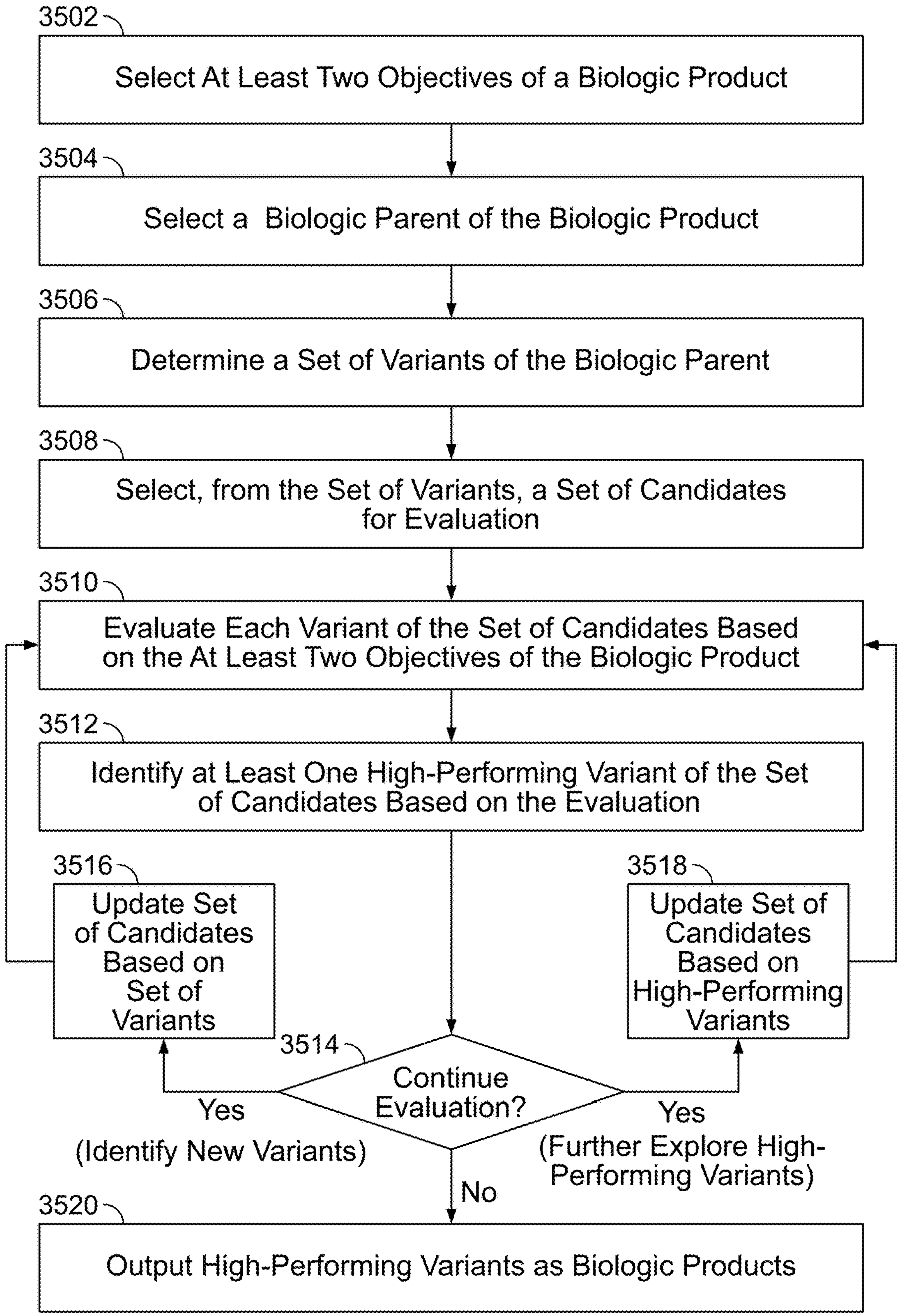
FIG. 28 is another flowchart that presents an example method of generating a biologic product of a biologic synthesis process according to some example embodiments.

FIG. 28 is another flowchart that presents an example method of generating a biologic product of a biologic synthesis process according to some example embodiments. The flowchart of FIG. 28 is a more detailed version of the flowchart of FIG. 27 that may be included and/or performed in some example embodiments. The example method of FIG. 28 (which may be referred to as a Multi-Objective Optimization Approach) may be performed, for example, by the Multi-Objective Optimization Module 3110 of the platform of FIG. 1.

The example flowchart of FIG. 28 includes a step 3502 of selecting at least two objectives of a biologic product. The at least two objectives may include, for example, an objective of synthesizing a biologic product with an activity of binding to a particular binding site, an inclusion in a metabolic process, a suitability as a precursor for another biologic process, or the like. The at least two objectives may include an objective of synthesizing a biologic product that expresses a particular enzyme or other protein, that performs a metabolic pathway, or that exhibits a characteristic within an environment. The at least two objectives may include an objective of determining a biologic synthesis process that includes an objective such as a yield, a reaction rate, or a consistency of a biologic product. Other examples of objectives include a product expression objective, a product activation objective, a product reaction objective, an enzyme cleaning objective, a product stability objective, a product biocompatibility objective, a process rate objective, a process catalyzation rate objective, a process efficiency objective, a process cost objective, or a process yield objective.

The example flowchart of FIG. 28 includes a step 3504 of selecting a biologic parent of the biologic product. The biologic parent may include, for example, a DNA sequence, an RNA sequence, a protein such as an enzyme, a metabolic precursor, a cell or cell line, a strain of a biological species, or the like. The biologic parent may be or may include a material from which the biologic product is synthesized, such as a metabolic precursor that is included in a metabolic pathway to produce the biologic product, or a DNA or RNA sequence that can be transcribed and/or translated to synthesize the biologic product. The biologic parent may be or may include a material that is similar to the biologic product, and that is to be modified to generate the biologic product (e.g., a DNA sequence that is to be edited to produce an edited DNA sequence as the biologic product). The biologic parent may include a biologic synthesis process that generates one or more biologic products. The biologic parent may be selected based on at least one of the at two objectives selected for the biologic product (e.g., selecting a biologic parent that at least partially exhibits the at least two objectives, wherein the biologic product to be determined improves upon at least one of the at least two objectives of the biologic parent). The biologic parent may be selected based on an objective of improving at least one feature of the biologic parent (e.g., maintaining at least one desirable feature of the biologic parent and improving at least one undesirable feature of the biologic parent, or adding a new feature to the biologic parent).

The example flowchart of FIG. 28 may include a step 3506 of determining a set of variants of the biologic parent. The set of variants may be determined by including at least a portion of the biologic parent (e.g., a subsequence or a gene within a DNA sequence) and excluding another portion of the biologic parent (e.g., a deletion or deactivation of another subsequence or gene within the DNA sequence). The set of variants may be determined by selecting the biologic parent and introducing one or more edits (e.g., replacing a gene, DNA subsequence, or sequence of protein residues of the first biologic parent with a gene, DNA subsequence, or sequence of protein residues of the second biologic parent, and otherwise maintaining the features of the first biologic parent in the combination). The set of variants may be determined by altering and/or substituting at least one property or parameter of the biologic parent (e.g., altering and/or substituting a parent biologic synthesis process for producing a biologic product in a biologic fermentation tank by adding or substituting a reactant for an existing reactant of the parent biologic synthesis process). Each variant of the set of variants may include a number of edits with respect to the biologic parent (e.g., single edits of the biologic parent that involve changing one property, parameter, or feature of the biologic parent, such as replacing one DNA subsequence or set of protein residues with another DNA subsequence or set of protein residues, and/or double edits of the biologic parent that involve changing two distinct properties, parameters, or features of the biologic parent, such as replacing two DNA subsequences or sets of protein residues with other DNA subsequences or sets of protein residues). If the biologic parent and the variants are biologic synthesis processes, the edits may include a combination of one or more steps of the biologic parent with one or more other steps (e.g., a variant that combines all of the steps of the parent biologic synthesis process and one step of another biologic synthesis process, or a substitution of one step of the parent biologic synthesis process with one or more other steps).

The example flowchart of FIG. 28 includes a step 3508 of selecting, from the set of variants, a set of candidates for evaluation. The selecting may be based, for example, on an edit distance between each combination and the biologic parent (e.g., single edits vs. double edits, or more conservative and/or less numerous edits of a DNA subsequence, gene, sequence of protein residues, biologic synthesis process parameters, or the like vs. more extensive and/or more numerous edits of a DNA subsequence, gene, sequence of protein residues, biologic synthesis process parameters, or the like). The selecting may be based on a distance between each variant and the biologic parent in an embedding space, which may be based on a biologic product language model, such as a protein language model. The selecting may be based on a ranking of the variants (e.g., comparing previously untested variants and choosing those with a highest predicted performance).

The example flowchart of FIG. 28 includes a step 3510 of evaluating each variant of the set of candidates based on the at least two objectives. The evaluating may include, for example, a joint comparison of the at least two objectives of the biologic parent with the at least two objectives of each candidate. The evaluating may be based on a laboratory experiment that involves synthesizing each variant of the set of candidates and measuring the at least two objectives for each variant of the set of candidates. The evaluating may be based on a simulation of each variant of the set of candidates in a simulated environment and a measurement of the at least two objectives in the simulation for each variant of the set of candidates.

In embodiments, the platform 100 may use a machine learning model configured for multi-objective (also known as multitask) optimization of biological sequences. For example, the machine learning model may include one or more of an embedding layer that converts biological sequences into dense vector representations, multiple parallel prediction heads, which may each be specialized for a different objective/task (e.g., a different inference task based on different inputs, which may be any of the tasks and/or inputs described herein), and/or a multi-objective optimization layer that combines predictions using configurable weighting schemes. The machine learning model may be trained using multi-task learning approaches (e.g., using an objective function that combines multiple loss terms that may be weighted according to task importance). The platform 100 may implement caching mechanisms to store intermediate computational results and reuse the cached computational results when evaluating similar variants.

The example flowchart of FIG. 28 includes a step 3512 of identifying at least one high-performing variant of the set of candidates based on the evaluation. The identifying of high-performing variants may include, for instance, a comparison of one or more scores with each variant of the set of candidates (e.g., a sum and/or product of the scores of each of the at least two objectives for each variant). The identifying of high-performing variants may include comparing one or more scores of each variant with one or more thresholds (e.g., identifying high-performing variants that at least maintain, and preferably improve, each objective of the at least two objectives relative to the biologic parent). The identifying of high-performing variants may include mapping a vector representation of each variant to an embedding space and identifying the high-performing variants based on the locations of the variants within the embedding space. The identifying of high-performing variants may include ranking the variants (e.g., according to one or more scores of each variant) and selecting one or more variants as high-performing variants based on the ranking. Each variant that is identified as high-performing combinations may be added to a set of high-performing variants that also includes other high-performing variants from the same evaluation and/or other evaluations, such as prior evaluations of other sets of candidates.

The example flowchart of FIG. 28 includes a step 3514 of determining whether to continue evaluation of candidates of the set of variants. If the set of high-performing variants includes at least a desired or target number of high-performing variants, or if the set of high-performing variants includes at least one high-performing variant that satisfies at least one target criterion (e.g., at least maintaining a first objective of the at least two objectives and at least exhibiting a second objective of the at least two objectives), the evaluation may continue to step 3520. If the set of high-performing variants does not include at least a desired or target number of high-performing variants and/or does not include at least one high-performing variant that satisfies at least one target criterion, the evaluation may evaluate additional sets of candidates. If at least one high-performing variant has been identified, the evaluation may proceed to step 3518 by including, in the set of candidates, at least one additional variant that is based on at least one of the high-performing variants (e.g., a depth-based search in a proximity of the at least one high-performing variant). Alternatively or additionally, the evaluation may proceed to step 3516 by including, in the set of candidates, at least one additional variant from the set of variants (e.g., a breadth-based search of additional variants that are not in a proximity of the previously evaluated variants).

The example flowchart of FIG. 28 includes a step 3520 of outputting the high-performing variants as biologic products. The outputting may include, for example, presenting a report of the high-performing variants based on the evaluation. The outputting may include presenting a report of the performance of the high-performing variants (e.g., a result of a laboratory experiment and/or simulation that demonstrates the high performance of the identified high-performing variants). The outputting may include presenting an explanation of the high-performing variants (e.g., an explanation of the features of the biologic parent that are included in the high-performing variant, and/or an explanation of the manner in which the high-performing variant achieves the high performance). The outputting may include initiating one or more biologic synthesis processes to synthesize an amount of at least one of the high-performing variant (e.g., automatically initiating a biologic fermentation process to synthesize the high-performing variant for automated, human-supervised, and/or human-led evaluation). If the high-performing variants are biologic synthesis processes, the outputting may include initiating the biologic synthesis process to evaluate one or more results of the high-performing biologic synthesis process.

In embodiments, the platform 100 may implement a parallel evaluation pipeline that enables simultaneous assessment of multiple variants using different evaluation methods. For example, the platform 100 may simultaneously perform in silico predictions using machine learning models, run molecular dynamics simulations on specialized hardware, and/or interface with automated laboratory equipment for experimental validation. Simultaneous evaluation may reduce the total time required for variant assessments while providing better evaluations based on complementary data from multiple evaluation methods.

Determining Biologic Parents and Candidates for Evaluation

The comparative analysis approaches discussed herein (including those discussed in relation to FIGS. 25 and 26) include the selection of a first biologic parent and a second biologic parent and the determination of combinations as candidates for evaluation. As discussed in FIGS. 25 and 26, a biologic product may be determined based on a comparative analysis approach applied to a first biologic parent and a second biologic parent (e.g., combining at least a portion of the first biologic parent and the second biologic parent, thereby improving or at least maintaining a first feature of the first biologic parent and improving or at least maintaining a second feature of the second biologic parent). The biologic product may be determined and/or synthesized based on a comparative analysis approach that includes an evaluation of a combination based on a first feature of the first biologic parent and a second feature of the second biologic parent. Similarly, the multi-objective optimization approaches discussed herein (including those discussed in relation to FIGS. 27 and 28) include the selection of a biologic parent and the determination of variants as candidates for evaluation. As discussed in FIGS. 27 and 28, a biologic product may be determined based on a multi-objective optimization approach, in which two or more objectives are evaluated for variants of a biologic parent (e.g., generating a variant that includes one or more edits to a biologic parent and comparing each of the multiple objectives of the variant with the corresponding objective of the biologic parent). The biologic product may be determined and/or synthesized based on a multi-objective approach that includes an evaluation of a variant based on at least two objectives. Although distinct in some respects, the comparative analysis approaches and multi-objective optimization approaches have similar aspects that may vary in some example embodiments.

In these and other cases, the biologic product and/or biologic parent(s) may include (for example) a DNA sequence, an RNA sequence, a protein such as an enzyme protein, a non-enzyme protein, a plasmid, a metabolite, a cell line, a biologic strain of a microbe, or the like, or any combination of one or more such materials. The biologic products may be synthesized by a variety of biologic synthesis processes, including include (for example) a DNA synthesis process, an RNA synthesis process, a protein synthesis process, a metabolite synthesis process, a metabolic process, at least one pathway of a metabolic system, a plate growth process, a bioreactor process, or a downstream purification process, or any combination of one or more such processes. Alternatively or additionally, in these and other cases, the biologic product and/or biologic parent(s) may include (for example) a DNA synthesis process, an RNA synthesis process, a protein synthesis process, a metabolite synthesis process, a metabolic process, at least one pathway of a metabolic system, a plate growth process, a bioreactor process, or a downstream purification process, or any combination of one or more such processes.

In these and other cases, the features and/or objectives may include (for example) a reaction rate, a consistency, a feature expression, a feature activation, a reaction, an enzyme cleaning, stability, biocompatibility, a process rate, a process catalyzation rate, a process efficiency, a process cost, or a process yield, or any combination of one or more such features and/or objectives. For each combination and/or variant that is evaluated as a candidate for the biologic product, the objectives and/or features of the candidate may be evaluated by laboratory experiment and/or simulation, and may be evaluated and/or measured in a standalone manner and/or in relation to corresponding evaluation and/or measurements of one or more biologic parents and/or other candidates.

In these and other cases, one or more biologic parents may be selected in view of various features and/or objectives. For example, a biologic parent may include a DNA sequence including a gene that, when expressed, causes a protein product that is transcribed (from the first DNA sequence to a first mRNA sequence) and translated therefrom (from the first mRNA sequence to the protein product) to include a first feature and/or to exhibit a first objective, such as an activity of binding to a particular binding site, an inclusion in a metabolic process, a suitability as a precursor for another biologic process, or the like. A biologic parent may include a protein having a feature or objective that is to be included or exhibited in a protein product that is determined based on the protein, such as an activity of binding to a particular binding site, an inclusion in a metabolic process, a suitability as a precursor for another biologic process, or the like. A biologic parent may include a cell line or strain of a microbe having a feature or objective, such as an expression of a particular enzyme or other protein, a performance of a metabolic pathway, or a characteristic within an environment of the cell line or strain. A biologic parent may include a biologic synthesis process that produces a biologic product, such as a biological fermentation process occurring in a biological fermentation tank that produces the biologic product, wherein the biological fermentation process includes a feature or objective such as a yield, a reaction rate, or a consistency.

In some cases, the biologic synthesis process may be specifically intended and/or designed to synthesize one or more biologic parents may be directly selected for. As an example, the biologic synthesis process may be designed to synthesize the biologic parent or a variant thereof with a maintained or improved yield, activation, efficiency, or the like. For instance, a therapeutic composition, such as insulin, may be selected for synthesis and/or amplification, and the biologic synthesis process may be intended and/or designed to achieve and/or improve the synthesis of insulin with the objective of increasing the yield, rate, efficiency, and/or other features of the biologic synthesis process for insulin.

Alternatively or additionally, the biologic synthesis process may be specifically intended and/or designed to achieve one or more features or objectives (e.g., a binding to a binding site of a protein or enzyme, an activation or deactivation of a metabolic pathway, or a synthesis of a biologic product), and one or more biologic parents may be identified that may be included in the biologic synthesis process to achieve the one or more features or objectives (e.g., a biologic parent that exhibits a property of binding to the indicated binding site, of activating or deactivating the metabolic pathway, or of synthesizing the biologic product). As an example, a particular pathogen may be identified as being deactivated by causing an agent to bind to a particular binding site of the pathogen. One or more biologic parents may be identified as having a capability of binding to the binding site of the pathogen, but the one or more biologic parents may not be good therapeutic candidates, e.g., due to insufficient expression, activation, biocompatibility, or the like. The biologic synthesis process may be intended and/or designed with the objective of synthesizing a combination or variant of the one or more biologic parents that maintains or improves the feature of binding to the binding site of the pathogen, while also improving upon other features of the biologic parent(s), such as expression, activation, and/or biocompatibility.

In some cases, the biologic synthesis process may be intended and/or designed to add or amplify a desirable feature or objective to an existing biologic product, biologic synthesis process, metabolic pathway, or the like, or a class thereof. Alternatively or additionally, the biologic synthesis process may be intended and/or designed to mitigate or eliminate an undesirable feature or objective from an existing biologic product, biologic synthesis process, metabolic pathway, or the like, or a class thereof. As an example, a particular cell line may exhibit a property that is useful a variety of research and/or industrial processes, such as the synthesis of a particular metabolic product or the performance of a notable metabolic pathway. The property of the cell line may be determined to be sensitive to certain environmental conditions, such as temperature, pressure, and/or the presence or absence of certain enzymes, catalysts, nutrients, and/or contaminants, which may reduce the presentation and/or magnitude of the property. The biologic synthesis process may be intended and/or designed to improve a robustness of the cell line and/or an expression of the property by the cell line, and/or to reduce or eliminate the sensitivity of the cell line to the environmental conditions, thereby preserving and possibly amplifying the desirable property of the cell line. Accordingly, the biology synthesis process may be intended and/or designed to generate a biologic product that protects the cell line from the environmental conditions, such as increasing or decreasing the environmental temperature or pressure, or that increases or decreases the enzymes, catalysts, nutrients, and/or contaminants that affect the property of the cell line. One or more biologic parents may be selected that have the identified protective effects, and one or more biologic products that exhibit the protective effects and that are compatible with the cell line may be developed based on the one or more biologic parents. Alternatively or additionally, the one or more biologic parents may be used to modify a biologic synthesis process associated with the cell line, such as robustness or stability due to a cellular structure or metabolic product. The selection of the one or more biologic parents based on the objective of protecting the cell line may enable the inclusion of a feature in a variant of the cell line (e.g., engineering the cell line to include the cellular structure and/or to generate the metabolic product) and/or a variant of one or more biologic synthesis processes of the cell line parents (e.g., adding the metabolic product to the biologic synthesis and/or maintenance process of the cell line) to produce the protective effect for the cell line. In these cases, while the one or more biologic parents may not be directly included in combinations of biologic products of the biologic synthesis process, the features of the one or more biologic parents may be included in the biologic synthesis process to achieve one or more objectives thereof.

In some example embodiments, the selection of one or more biologic parents may include an identification of biologic products that include one or more features (e.g., binding to a particular binding site of a target such as a pathogen) and/or that exhibit properties related to one or more objectives (e.g., participation in a metabolic pathway that has a high yield). Based on an identification of a feature or property related to an objective, a search process may be performed over a data store of biologic products to identify one or more biologic products that may serve as biologic parents for the biologic synthesis process. For example, a database of cell lines may be searched to identify and select, as biologic parents, one or more cell lines that include a DNA sequence of interest and/or that have been observed to synthesize a particular biologic product of interest. As another example, one or more biologic products may be selected as biologic parents for a biologic synthesis process based on simulation of the biologic products in selected conditions (e.g., a simulated interaction of a database of proteins to identify and select biologic parents that may be capable of binding to a binding site of an pathogen, or a simulation of metabolic processes of various cell lines to identify those that may exhibit good performance at a particular temperature and/or pressure). As yet another example, one or more biologic products may be identified and selected as biologic parents for a biologic synthesis process based on laboratory experiments (e.g., a laboratory assay may be designed to expose a pathogen to a range of enzymes to identify, as biologic parents, one or more enzymes that deactivate the pathogen). As yet another example, one or more biologic products may be bioengineered to serve as a biologic parent. For instance, a cell line that is already used in a biologic synthesis process may be modified to include a particular gene for a desired protein, and the engineered cell line may be selected as a biologic parent for a further biologic product that can also synthesize the desired protein and that also exhibits features from another biologic parent and/or that achieves other objectives of an improved biologic synthesis process.

In some example embodiments, one or more biologic parents may be selected for a biologic process based on an objective of contributing and/or maintaining a feature of the one or more biologic parents. For example, a cell line may be determined to synthesize a particular protein of interest with a particular yield. The cell line may be selected as a biologic parent for the biologic synthesis process with an objective of causing and/or maintaining the synthesis of the protein of interest with the indicated yield. That is, the evaluation of candidates or variants and selection thereamong of a biologic product may be based on an objective or criterion of causing and/or maintaining the synthesis of the protein of interest with the indicated yield in the biologic synthesis process.

In some example embodiments, one or more biologic parents may be selected for a biologic process based on an objective of increasing or amplifying a desirable feature of the one or more biologic parents and/or of another biologic parent included in the biologic synthesis process. For example, a particular biologic process may involve the synthesis of a biologic product at a particular yield, and a biologic parent may be selected for inclusion the comparative analysis approach and/or multi-objective optimization based on an observation that the biologic parent increases the yield of the synthesized biologic product (e.g., by serving as a catalyst, by stimulating a metabolic pathway, and/or by enzymatically cleaning metabolic byproducts or contaminants). The cell line may be selected as a biologic parent for the biologic synthesis process with an objective of increasing or amplifying the desirable feature of the biologic synthesis process and/or biologic product included in the biologic synthesis process. That is, the evaluation of candidates or variants and selection thereamong of a biologic product may be based on an objective or criterion of increasing or amplifying the desirable feature of the synthesized biologic product through the biologic synthesis process.

In some example embodiments, one or more biologic parents may be selected for a biologic process based on an objective of decreasing or eliminating an undesirable feature of the one or more biologic parents and/or of another biologic parent included in the biologic synthesis process. For example, a biologic product may exhibit a therapeutic effect for certain diseases or conditions, but may also act as an antigen that triggers an immunologic response as an undesirable side-effect. An additional biologic product may be identified that reduces or prevents the triggering of the immunologic response by the biologic product and that reduces or eliminates the undesirable side-effects. The additional biologic product may be selected as a biologic parent for the biologic synthesis process with an objective of decreasing or eliminating the undesirable feature of the biologic synthesis process and/or biologic product included in the biologic synthesis process. That is, the evaluation of candidates or variants and selection thereamong of a biologic product may be based on an objective or criterion of decreasing or eliminating the undesirable side-effects of the synthesized biologic product generated through the biologic synthesis process.

As discussed, the comparative analysis approaches include the determination of a first biologic parent and a second biologic parent, followed by the determination of combinations thereof for evaluation based on a first feature of the first biologic parent and a second feature of the second biologic parent. Similarly, as discussed, the multi-objective optimization approaches include the determination of a biologic parent, followed by the determination of variants thereof for evaluation based on at least two objectives of a biologic synthesis process involving a protein product based on the biologic parent. In some example embodiments, the evaluation of the combinations and/or variants of one or more biologic parents may be performed selectively based on measurements and/or predictions of the features of the combinations and/or variants and/or objectives associated therewith.

The determination of combinations and variants in these approaches may be performed in various ways. In some example embodiments, a combination may be determined by selecting at least a portion of the first biologic parent and determining one or more modifications or edits based on the second biologic parent (e.g., inserting a gene in a genome of a second cell line as the second biologic parent into the genome of a first cell line as the first biologic parent). The modifications or edits may be directed (e.g., an organized, iterative, and/or stepwise series of single-edit modifications of a first biologic parent based on corresponding single portions of a second biologic parent) or random (e.g., a randomized combination of genes or portions of a second DNA sequence as the second biologic parent into a first DNA sequence as the first biologic parent, such as randomized mutation). The modifications or edits may be determined and/or specified by a user (e.g., the platform may receive, from a user, a list or selection of edits to include in various combinations or variants of a biologic parent) and/or a machine learning model (e.g., the platform may generate, by a machine learning model, various combinations or variants of a biologic parent based on effects predicted by the machine learning model). Alternatively or additionally, combinations and/or variants may be determined by applying a set of known edits or modifications to a biologic parent (e.g., generating combinations or variants by iteratively deleting, replacing, or adding various genes of a genome of a cell line, or by introducing various edits to a DNA sequence to produce predicted changes in the folding and shapes of proteins translated from the DNA sequence).

In some example embodiments, a combination or variant may be determined and selected for evaluation based on an objective of contributing and/or maintaining a feature of one or more biologic parents. For example, a biologic parent may include a cell line that synthesizes a particular protein of interest with a particular yield. Combinations and/or variants of the cell line may be selected for evaluation based on an objective of causing and/or maintaining the synthesis of the protein of interest with the indicated yield. That is, the evaluation of candidates or variants may be selected to preserve the gene that causes the synthesis of the protein of interest. Candidates or variants that do not contribute and/or maintain the feature of the one or more biologic parents (e.g., candidates or variants that include destructive edits or to or deletion of a gene that causes the synthesis of the protein of interests) may be excluded from evaluation.

In some example embodiments, a combination or variant may be determined and selected for evaluation based on an objective of increasing or amplifying a desirable feature of the one or more biologic parents and/or of another biologic parent included in the biologic synthesis process. For example, a particular biologic process may involve the synthesis of a biologic product at a particular yield, and a combination or variant may be selected for evaluation based on an increase of the yield of the biologic product (e.g., by increasing a production of or effectiveness as a catalyst, by increasing a stimulation of a metabolic pathway, and/or by increasing an enzymatic cleaning of metabolic byproducts or contaminants). The combination or variants may be selected for evaluation for the biologic synthesis process with an objective of increasing or amplifying the desirable features of the one or more biologic parents. That is, the evaluation of candidates or variants and selection thereamong of a biologic product may be based on an objective or criterion of increasing or amplifying the desirable feature of the biologic parents associated with the biologic synthesis process.

In some example embodiments, a combination or variant may be determined and selected for evaluation based on an objective of decreasing or eliminating an undesirable feature of the one or more biologic parents and/or of another biologic parent included in the biologic synthesis process. For example, a biologic product may exhibit a therapeutic effect for certain diseases or conditions, but may also act as an antigen that triggers an immunologic response as an undesirable side-effect. A biologic parent may be identified that reduces or prevents the triggering of the immunologic response by the biologic product and that reduces or eliminates the undesirable side-effects. Combinations or variants of the additional biologic product may be selected for evaluation with an objective of decreasing or eliminating the undesirable feature of the one or more biologic parents. That is, the evaluation of candidates or variants and selection thereamong for evaluation may be based on an objective or criterion of decreasing or eliminating the undesirable side-effects of the synthesized biologic product generated through the biologic synthesis process.

In some example embodiments, combinations may be determined and selected for evaluation in comparative analysis approaches based on multiple features, such as at least maintaining the first feature of the first biologic parent and also based on measurements or predictions of the addition of the second feature. That is, combinations may be generated and selected for evaluation for the biologic synthesis process only if they both maintain a feature of the first biologic parent and add a feature of the second biologic parent. Combinations that only achieve one of these results (e.g., maintaining or increasing the first feature of the first biologic parent but not adding the second feature of the second biologic parent, or adding the second feature of the second biologic parent but also failing to maintain the first feature of the first biologic parent) may be excluded from evaluation as candidates for the biologic product of the biologic synthesis process. Similarly, in some example embodiments, variants of a biologic parent may be determined and selected for evaluation in multi-objective based on multiple objectives, such as a first objective of maintaining a first feature of the biologic parent (e.g., a yield) and a second objective of increasing another feature of the biologic parent (e.g., a rate of a metabolic process). That is, variants may be generated and selected for evaluation for the biologic synthesis process only if they satisfy both the first objective and the second objective. Variants that only achieve one objective (e.g., maintaining a yield but failing to increase a rate of a metabolic process, or vice versa) may be excluded from evaluation as candidates for the biologic product of the biologic synthesis process.

In some example embodiments, combinations and/or variants of one or more biologic parents may be generated within a proximity of the one or more biologic parents. For example, combinations and/or variants of a biologic parent may be determined and selected for evaluation only within an edit distance of the one or more biologic parents (e.g., single edits of the biologic parents, or modifications of a variants of a protein that are within an edit distance of a protein serving as the biologic parent of the variants). Combinations or variants that are outside the proximity of the one or more biologic parents (e.g., exceeding a maximum number of edits and/or a maximum edit distance) may be excluded from evaluation as candidates for the biologic product of the biologic synthesis process. In some example embodiments, a variant of a biologic parent may be selected for evaluation based on an edit distance between the variant and the biologic parent being within an edit distance threshold. In some example embodiments, a combination of a first biologic parent and a second biologic parent may be selected for evaluation based on whether one or more edit distances between the combination and one or both of the biologic parents being within an edit distance threshold. The edit distance thresholds may be individually specified for each biologic parent, and the selection of the combination for evaluation may be based on whether the edit distance between the combination and each biologic parent is within the corresponding edit distance threshold. Alternatively or additionally, an edit distance threshold may be specified as an aggregate edit distance threshold between the combination and its biologic parents, and the selection of the combination for evaluation may be based on whether an aggregation of the edit distances between the combination and each biologic parent is within the aggregate edit distance threshold. The use of edit distance thresholds may promote the selective and/or preferential evaluation of variants and/or combinations that are similar to the one or more biologic parents thereof.

In some example embodiments, the proximity between a biologic parent and combinations and/or variants of the biologic parent may be determined based on distances within embedding space of the biologic parent and the combinations and/or variants. For example, an embedding space may be determined and/or learned based on measurements of various features of biologic products, wherein various embedding dimensions of the embedding space correspond to various features, combinations of features, derived values based on the provided features, or the like. The measurements of the features for a biologic product may be provided as input to an embedding model that generates an embedding of the biologic product as a vector representation of the biologic product within the embedding space. Distances between biologic products in the vector space may be used to identify clusters of biologic products that are within a mutual proximity, and that therefore represent a cluster of similar biologic products. Variants and/or combinations of a biologic product may change features of the biologic product, which may in turn change the vector representation of the variant or combination relative to the biologic product, thereby increasing the embedding distance between the variant or combination and the original biologic product. That is, embedding distances may be used as a measurement of similarity between various biologic products, which may guide the selection of combinations and/or variants to be evaluated (e.g., conserving a distance of the set of combinations variants or relative to at least one biologic parent).

Figure 29:
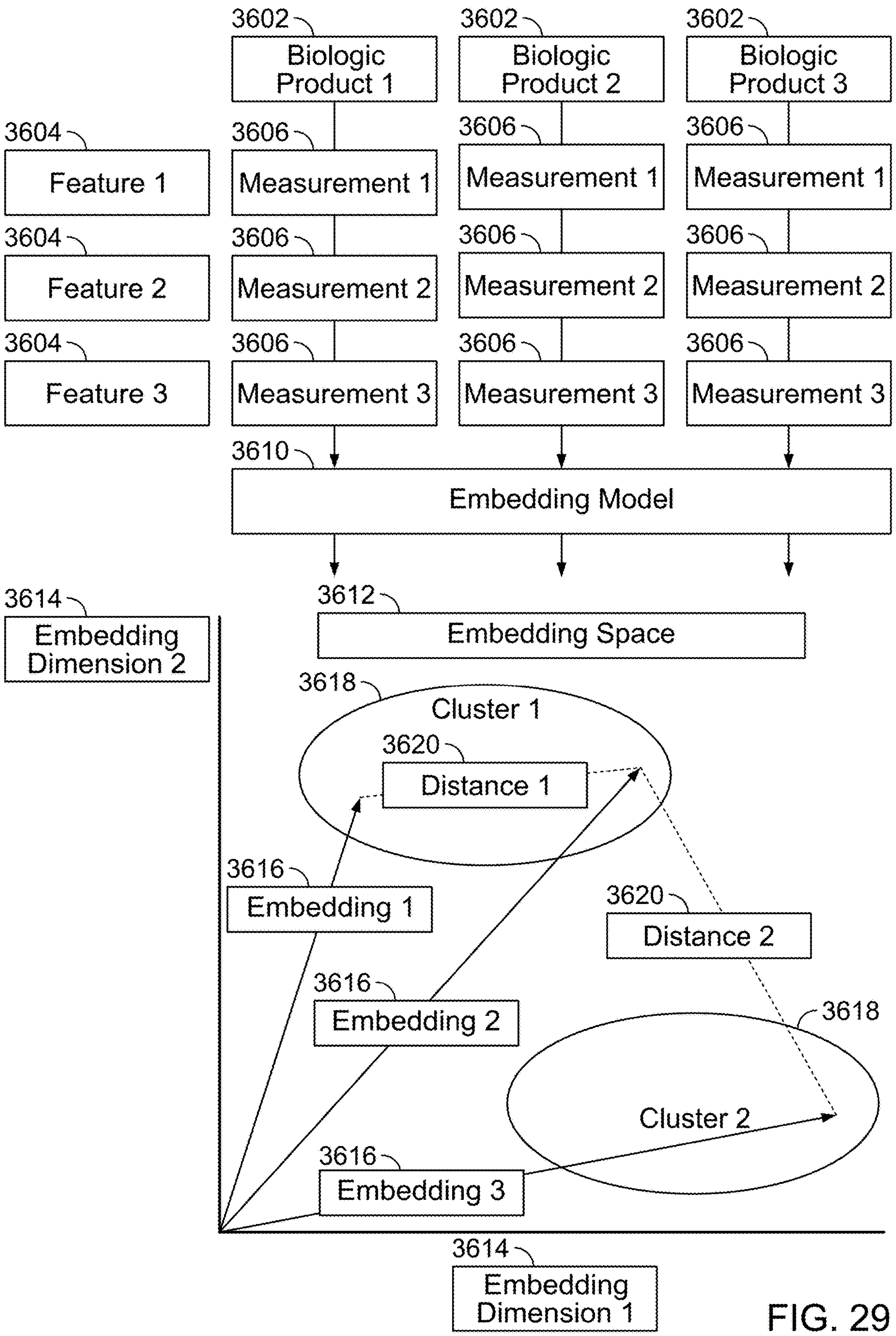
FIG. 29 is an example of an embedding space including vector representations of biologic products according to some example embodiments.

FIG. 29 is an example of an embedding space including vector representations of biologic products according to some example embodiments. As shown in FIG. 29, a set of biologic products 3602 are provided, each having various measurements 3606 of various features 3604 (e.g., an expression of respective biologic products 3602 by a strain or microbe, an activation of respective biologic products 3602 in various metabolic pathways, affinity of respective biologic products 3602 for various binding sites of other biologic products 3602, physical features such as size or protein folding features, or the like). For each biologic product 3602, the measurements 3606 of the features 3604 are provided as input to an embedding model 3610, which may have been trained (e.g., on the biologic products 3602 or other biologic products 3602) to generate an embedding 3616 as a vector representation of the combination of features 3604 of the biologic product 3602 within an embedding space 3612. The embedding space 3612 may include a number of embedding dimensions 3614, each embedding dimension 3614 representing a feature 3604 of the biologic products 3602, a combination of features 3604 of the biologic products 3602, a derived feature based on the features 3604 of the biologic products 3602, or the like. Within the embedding space 3612, the embedding distance 3620 between the locations of two or more embeddings 618 for two or more biologic products 3602 may represent an indicator of similarity between or among the two or more biologic products 3602. Each distance 3620 may be determined, for example, as a cosine similarity of the vector representations of the embeddings 3616 of the respective biologic products 3602 within the embedding space 3612. For example, a first distance 3620 between the vector representations of the embeddings 3616 for a first biologic product 3602 and a second biologic product 3602 may be small, indicating a proximity of the first biologic product 3602 and the second biologic product 3602 within the embedding space 3612 and a biologic similarity of the first biologic product 3602 and the second biologic product 3602. BY comparison, a second distance 3620 between the vector representations of the embeddings 3616 for the second biologic product 3602 and a third biologic product 3602 may be large, indicating a lack of proximity of the second biologic product 3602 and the third biologic product 3602 within the embedding space 3612 and a biologic dissimilarity of the second biologic product 3602 and the third biologic product 3602. Further, the locations of the embeddings 3616 within the embedding space 3612 may enable the determination of clusters 3618 of biologic products 3602 that share similar features, such as mutual participation in a metabolic pathway, mutual affinity for the binding sites of a class of biologic products 3602, or the like.

Although the embedding space 3612 in the example of FIG. 29 includes only two embedding dimensions 3614, other embedding spaces 3612 for other groups of biologic products 3602 may include a different and potentially large number of embedding dimensions 3614, each representing one or more features or derived features of the biologic products 3602, thereby enabling a rich representation of the biologic products 3602 according to their respective features 3604. Additionally, the embedding space 3612 may enable dimensionality reduction, wherein a large set of features 3604 is reduced to a small set of highly significant embedding dimensions 3614 and a lower dimensionality of the vector representations of the embeddings 3616. Due to a small number of dimensions 3614, the embedding model 3610 may be coerced to represent the respective biologic products 3602 only according to the most significant and distinctive features 3604 of the respective biologic products 3602 that indicate proximity or distance therebetween. The achieved dimensionality reduction may promote the generalization from learned associations to corresponding associations between biologic products 3602 that are superficially dissimilar, but that share key similarities that indicate mutual inclusion in a cluster 3618 of similar biologic products 3602.

In some example embodiments, combinations and/or variants of one or more biologic parents may be selected for evaluation based on the distances between the vector representations of the embeddings 3616 of the combinations and/or variants and the one or more biologic parents within the embedding space 3612. In some example embodiments, combinations and/or variants of one or more biologic parents may be generated within a proximity of the one or more biologic parents within the embedding space 3612. For example, combinations and/or variants of a biologic parent may be determined and selected for evaluation only within an embedding distance of the one or more biologic parents in the embedding space 3612. Combinations or variants that are not proximate to the one or more biologic parents within the embedding space 3612 (e.g., combinations or variants that are too different from the one or more biologic parents in terms of genotype, phenotype, activation, physical properties such as size or protein folding characteristics, or the like) may be excluded from evaluation as candidates for the biologic product of the biologic synthesis process. In some example embodiments, a variant of a biologic parent may be selected for evaluation based on whether an embedding distance between the variant and the biologic parent is within an embedding distance threshold. In some example embodiments, a combination of a first biologic parent and a second biologic parent may be selected for evaluation based on whether one or more embedding distances between the combination and one or both of the biologic parents within the embedding space 3612 are within an embedding distance threshold. The embedding distance thresholds may be individually specified for each biologic parent, and the selection of the combination for evaluation may be based on whether the embedding distance between the combination and each biologic parent within the embedding space 3612 is within the corresponding embedding distance threshold. Alternatively or additionally, an embedding distance threshold may be specified as an aggregate embedding distance threshold between the combination and its biologic parents within the embedding space 3612, and the selection of the combination for evaluation may be based on whether an aggregation of the embedding distances between the combination and each biologic parent is within the aggregate embedding distance threshold. The use of embedding distance thresholds within the embedding space 3612 may promote the selective and/or preferential evaluation of variants and/or combinations that are similar to the one or more biologic parents thereof.

In some example embodiments, a select number of combinations and/or variants may be determined and selected for evaluation. For example, based on a biologic parent featuring a genome including a set of genes, the combinations and/or variants based on the biologic parent may include at least one edit of each gene of the genome. The evaluation of combinations and/or variants may be limited based on a maximum number of the combinations and/or variants. The number of combinations and/or variants may be limited based on a maximum amount of time and/or computational and/or experimental resources involved in evaluating the combinations and/or variants (e.g., evaluating combinations and/or variants within a time window or measurable amount of computational processing). The evaluation of combinations and/or variants may be limited based on a proximity with regard to one or more biologic parents (e.g., only evaluating combinations and/or variants within a maximum edit distance of a biologic parent). The evaluation of combinations and/or variants may be limited based on a similarity of the combinations and/or variants to other combinations and/or variants that have been or will be evaluated (e.g., for two or more combinations and/or variants within a mutual edit distance of one another, such as multiple single edits to the same gene, only selecting one such combination and/or variant for evaluation, and excluding other combinations and/or variants from evaluation that are likely to perform similarly to the selected combination and/or variant). The evaluation of combinations and/or variants may be limited based on a predicted likelihood of performance (e.g., initially evaluating combinations and/or variants using a machine learning model that predicts a performance of each combination and/or variant, and further evaluating only the combinations and/or variants for which the machine learning model predicts at least a minimum performance and/or above a minimum predictive confidence level). Many such techniques may be used to determine and select combinations and/or variants of biologic parents for evaluation by the comparative analysis and/or multi-objective optimization approaches included in some example embodiments.

In some example embodiments, a combination or variant may be selected for evaluation based on a viability score of the combination or variant determined according to a biologic product language model, such as a protein language model. A biologic product language model may include a large language model (LLM) that has been trained to map descriptions of biologic products to particular features, such as the presence or absence of genes or variants thereof, rates of gene expression, participation in one or more metabolic pathways, structural features such as protein folding features, physical features such as size or hydrophilic or hydrophobic characteristics, inclusion and/or expression in various cell lines or strains of microbes, and/or association with various physiologic conditions such as disease causes, symptoms, and/or severity. A biologic product language model, such as a protein language model, may be developed by ingesting a training data corpus (e.g., journal articles that describe biologic products, databases of biologic product descriptions, annotated laboratory experiment data, annotated simulation data, knowledge graphs, or the like) and to map each biologic product included in the training data corpus to a set of features. The features may include binary indicators (e.g., Boolean indicators of gene presence or absence), quantitative numeric indicators (e.g., measurements of correlation strength between a biologic product and various metabolic processes, cell lines, strains of microbes, or the like), embeddings within an embedding space, structured tags (e.g., identifiers of the biologic product and/or indicators of the biologic product that describe features, associated metabolic pathways, or the like), textual descriptions, or the like. The mapping learned by the biologic product language model into a language embedding space may be used for determining the proximities and/or distances between various biologic products. For example, two biologic products that are described in different ways in scientific literature may be identified by the biologic product language model as having similar expression and/or function within a particular context (e.g., amplifying or mitigating a metabolic process). Examples of protein language models include ProGen, a language model that determines protein sequences and functions based on textual descriptions such as scientific articles; ProLLaMa, a protein language model that performs multi-task protein language processing, and ProtFlash, a protein language model based on an attention model. In some example embodiments, a biologic product language model generates, as part of the output for a biologic product, a viability score that indicates a likelihood of the biologic product (e.g., as a viable variant of a biologic parent, or as a viable combination of two or more biologic parents). The output of a biologic product language model for a biologic product (e.g., descriptive tags that associate the biologic product with various features, metabolic pathways, strains, or the like) may be used to compare the similarity of the biologic product to one or more biologic parents. Alternatively or additionally, the selection of biologic products for evaluation may be based on the viability score generated by the biologic product language model for the biologic product.

In some example embodiments, the selection of a set of variants or combinations of one or more parents may be performed by one or more machine learning models. For example, an artificial neural network may be developed and trained to determine and/or predict a feature or objective of a variant or combination based on set of properties of the variant or combination (e.g., a phenotype of a cell line or strain based on a genotype, or an activity of a protein based on a protein folding structure and/or a set of genes from which the protein is translated). The machine learning model may be developed and trained to predict a measurement of a feature or objective associated with each variant of a set of variants or of each combination of a set of combinations, and the variants or combinations having the highest predicted measurement of the set of variants or combinations may be selected first for evaluation, followed by additional variants or combinations having a next highest predicted measurement of the set of variants or combinations. The machine learning model may be developed and trained to select, among a set of variants or combinations, a subset of variants or combinations that are of interest in the context of one or more features or objectives. The selection may include conserving a number of selected variants or combinations having a similar performance of the features or objectives (e.g., among a plurality of variants or combinations having different edits that are likely to result in a similar performance of the plurality of variants or combinations, selecting only one such variants or combinations to avoid redundancy and/or conserve evaluation materials, such as laboratory resources). The machine learning model may select variants or combinations for evaluation based on the locations of the variants or combinations in an embedding space (e.g., a breadth-based evaluation that includes choosing one or two variants or combinations within each cluster of the embedding space; a depth-based evaluation that includes choosing a large number of variants or combinations within a particular cluster of the embedding space; or a combination of breadth-based and depth-based evaluation). The machine learning model may include active learning, in which the machine learning model performs the selection of variants and/or combinations to evaluate in order to improve an understanding of a cluster of variants or combinations, to explore the effect of a particular type of modification such as various edits of a gene, or to promote one or more objectives, such as choosing variants or combinations of a biologic parent that are likely to exhibit improved activity in a metabolic pathway as compared with the biologic parent.

In some example embodiments of comparative analysis approaches, the selection of a set of combinations of a first biologic parent and the second biologic parent for evaluation may include conserving a distance of the set of combinations relative to the first biologic parent. For example, combinations that are close to the first biologic parent within the embedding space 3612 may be selected first for evaluation, followed by combinations that are progressively more distant from the first biologic parent. The distance may include at least one of an edit distance between the first biologic parent and each combination, a number of edits between the first biologic parent and each combination, a degree of edits between the first biologic parent and each combination, a difference between a measure of the first feature of each combination relative to a measurement of the first feature of the first biologic parent, a structural feature of each combination relative to a corresponding structural feature of the first biologic parent, or a viability score of each combination relative to a corresponding viability score of the first biologic parent.

In some example embodiments of multi-objective approaches, the selection of a set of variants of a biologic parent for evaluation may include conserving a distance of the set of variants relative to the biologic parent. For example, variants that are close to the biologic parent within the embedding space 3612 may be selected first for evaluation, followed by variants that are progressively more distant from the first biologic parent. The distance may include at least one of an edit distance between the biologic parent and each variant, a number of edits between the biologic parent and each variant, a degree of edits between the biologic parent and each variant, a difference between a measure of the first feature of each variant relative to a measurement of the first feature of the biologic parent, a structural feature of each variant relative to a corresponding structural feature of the biologic parent, or a viability score of each variant relative to a corresponding viability score of the biologic parent.

Evaluating Candidates of Biologic Products

The comparative analysis approaches discussed herein (including those discussed in relation to FIGS. 25 and 26) include the evaluation of combinations of a first biologic parent and a second biologic parent. Similarly, the multi-objective optimization approaches discussed herein (including those discussed in relation to FIGS. 27 and 28) include the evaluation of variants of a biologic parent. In these and other cases, the evaluation of variants and combinations of biologic parents may include a variety of evaluation techniques that may be used individually or together.

In some example embodiments, an evaluation of a combination of two biologic parents may include the evaluation of one or more features of the combination. The one or more features may include, for example, a product expression feature, a product activation feature, a product reaction feature, an enzyme cleaning feature, a product stability feature, a product biocompatibility feature, a process rate feature, a process catalyzation rate feature, a process efficiency feature, a process cost feature, or a process yield feature. The evaluation of a feature may involve a binary determination of whether the feature is present or absent in the combination (e.g., whether or not the genotype of a cell line or strain of a microbe includes and/or expresses a particular gene; whether or not a protein is capable of binding to a binding site; or whether or not an enzyme is associated with a metabolic process). The evaluation of a feature may involve a quantitative determination of the presence, capability, availability, frequency, proficiency, and/or effectiveness of the feature (e.g., a frequency with which a cell line or a strain of a microbe expresses a particular gene; a degree of affinity between a protein and a binding site; and/or a degree to which an enzyme catalyzes a metabolic process). The evaluation of a feature may involve a determination of an association of a biologic product and other biologic materials (e.g., a location, form, and/or role of a protein in a cell, or a location, role, and/or function of an enzyme in a metabolic process). The evaluation of a feature may involve qualitative and/or quantitative determinations of fitness, suitability, viability, likelihood of occurrence or success, or the like, regarding one or more organisms (e.g., biocompatibility with a cell line or strain of a microbe), biologic processes (e.g., an effectiveness of a protein to serve as an enzyme in a metabolic process), and/or applications (e.g., a suitability of a pharmaceutical biologic product as a therapeutic candidate for a disease). The evaluation of a feature may involve a comparison of the feature in a variant or combination with the corresponding feature in at least one biologic parent (e.g., a determination of whether the variant or combination maintains, adds, increases, amplifies, reduces, or eliminates a feature as compared with the same feature in one or more biologic parents).

In some example embodiments, a variant or combination may be evaluated according to various objectives. For example, one or more variants or combinations of one or more parent enzymes may be evaluated to determine, verify, detect, measure, and/or quantify the degree to which the variants or combinations function as enzymes in particular conditions, such as a metabolic pathway. The one or more objectives may include, for example, a biologic product expression objective, a product activation objective, a product reaction objective, an enzyme cleaning objective, a product stability objective, a product biocompatibility objective, a process rate objective, a process catalyzation rate objective, a process efficiency objective, a process cost objective, or a process yield objective. The evaluation of an objective may involve a binary determination of whether the objective is met or not met in the variant or combination (e.g., whether or not a cell line or strain expresses a particular gene; whether or not a protein binds to a binding site; or whether or not an enzyme participates in a metabolic process). The evaluation of an objective may involve a quantitative determination of the degree to which the objective is met or not met (e.g., a frequency with which a cell line or a strain of a microbe expresses a particular gene; a likelihood of a protein to bind to a binding site; and/or a rate of catalyzation of a metabolic process by an enzyme). The evaluation of an objective may involve qualitative and/or quantitative determinations of fitness, suitability, viability, likelihood of occurrence or success, or the like, of the variant or combination for the objective (e.g., a suitability of a variant or combination to achieve a particular result in a metabolic process). The evaluation of an objective may involve a comparison of the objective in a variant or combination with the corresponding objective in at least one biologic parent (e.g., a determination of whether the variant or combination maintains, adds, increases, amplifies, reduces, or eliminates an objective as compared with the same objective in one or more biologic parents).

In some example embodiments, an evaluation of a variant or combination may be based on at least some of the same features or objectives by which the variant or combination was selected for generation and evaluation. For example, a variant or combination may be selected for evaluation and synthesized due to its predicted or likely enzymatic properties, and the evaluation of the variant or combination may involve a detection, verification, measurement, and/or quantification of the enzymatic properties of the variant or combination in various conditions. Alternatively or additionally, in some example embodiments, an evaluation of a variant or combination may be based on different features or objectives than the features or objectives by which the variant or combination was selected for generation and evaluation. For example, a variant or combination may be selected for evaluation and synthesized due to an edit distance or embedding distance between the variant or combination and one or more biologic parents (e.g., whether the edit distance or embedding distance is within a distance threshold). However, the evaluation of the selected and synthesized variant or combination may be based not on the edit distance or embedding distance, but on one or more features or objectives of the variant or combination (e.g., whether the variant or combination maintains, increases, amplifies, mitigates, and/or eliminates one or more features of a biologic parent).

In some example embodiments, an evaluation of a variant or combination may include laboratory experimentation, such as culturing a cell line, including a sample in one or more plate assays in specific conditions and/or time periods, and measuring various features of the plated samples. Alternatively or additionally, an evaluation of a variant or combination may include analytic techniques to evaluate one or more features or objectives of the variant or combination, such as an analysis of a DNA sequence to determine a likely structure of a protein resulting from a transcription and translation of the DNA sequence, or a comparison of a genotype of a cell line or a strain of a microbe with a gene database or scientific literature repository to predict the performance of the cell line or strain in various conditions, such as a bioreactor. Alternatively or additionally, an evaluation of a variant or combination may include a simulation of the variant or combination in various conditions, such as a simulation of an interaction between a protein and a binding site to predict a binding affinity, or a simulation of a cell line or a strain of a microbe in an environment with particular conditions to predict its viability. In some example embodiments, an evaluation of a variant or combination may include a combination of such techniques, such as an initial simulation of the variant or combination to predict at least a minimum likelihood of performance followed by laboratory experimentation to validate the prediction.

In some example embodiments, an evaluation of a variant or combination may include an evaluation of a single feature or objective. In other example embodiments, an evaluation of a variant or combination may include an individual evaluation of multiple features or objectives, such as a suitability of a variant or combination to exist in particular conditions (e.g., a fermentation tank featuring a particular range of temperatures and pressures) and an activity of the variant or combination in such conditions (e.g., an enzyme function of the variant or combination in the particular conditions). Each feature or objective of the variant or combination may be independently detected, measured, quantified, or the like, and the overall evaluation of the variant or combination may be based on the individual evaluations (e.g., whether the variant or combination possesses or does not possess each feature of a set of desirable features, or whether the variant or combination satisfies defined quantitative thresholds for each objective of a set of objectives).

In some example embodiments, an evaluation of a variant or combination may include a joint evaluation of multiple features or objectives. That is, the evaluation may evaluate a set of features or objectives together, particularly where such features and objectives are related. For example, for a cell line or a strain of a microbe that is selected to serve as a candidate for synthesizing a protein having a particular activity, a yield of the protein by the cell line or strain may be evaluated by jointly evaluating a frequency of expression of the protein by the cell line or strain in particular conditions and a measurement of the activity of the protein. A cell line or strain featuring high expression of the protein but poor activity of the protein may result in a negative evaluation; a cell line or strain featuring high activity of the protein but low expression may result in a negative evaluation; and a cell line or strain featuring both high expression of the protein and high activity of the protein may result in a positive evaluation. In some example embodiments, a joint evaluation of features or objectives of a variant or combination may include a measurement of a first feature of the variant or combination and a corresponding measurement of the first feature of at least one biologic parent (e.g., a first biologic parent of a combination) and a measurement of a second feature of the variant or combination and a corresponding measurement of the second feature of at least one biologic parent (e.g., a second biologic parent of the combination). In some cases, the joint evaluation may further include a measurement of a third feature of the variant or combination and a corresponding measurement of the third feature of at least one biologic parent. In some example embodiments that include a multi-objective optimization approach, the joint evaluation may include a measurement of an edit distance between a variant or combination and the biologic parent and/or a measurement of one or more objectives of the variant or combination and a corresponding measurement of the one or more objectives of the biologic parent.

A variety of techniques may be used in the joint evaluation of multiple features and/or objectives of a variant or combination. In some example embodiments, each feature may be independently evaluated (e.g., a first evaluation or measurement of a frequency of expression of a protein by a cell line or strain and a second evaluation or measurement of an activity of the expressed protein), and the evaluations may be combined to generate the joint evaluation of multiple features or objectives (e.g., adding or multiplying the frequency of expression and the measurement of the activity of the expressed protein). In some example embodiments, a joint evaluation of multiple features and/or objectives may include a composite evaluation of two or more features functioning together (e.g., a measurement of an enzymatic property of a protein expressed by a cell line or strain, as a composite measurement of the expression frequency of the protein and the activity of the expressed protein).

In some example embodiments, a joint evaluation of multiple features and/or objectives of a variant or combination of at least one biologic parent may include an evaluation of a location of a vector representation of an embedding of the variant or combination in an embedding space, where each location is a result of mapping one or more features and/or objectives of the variant or combination to the embedding dimensions of the embedding space. The evaluation may include a determination of whether the location of the vector representation of the embedding of the variant or combination in the embedding space is within a cluster of biologic products, such as a class of proteins that have various structural and/or functions features, or a class of proteins that are associated with one or more metabolic pathways. For example, the evaluation of may include jointly measuring a first feature of a variant or combination and the second feature of the variant or combination; determining the first feature of the variant or combination according to a first dimension of an embedding space; determining the second feature of the variant or combination according to a second dimension of the embedding space; and evaluating the variant or combination according to a vector representation in the embedding space, wherein the vector representation is based on the first feature according to the first dimension of the embedding space and the second feature according to the second dimension of the embedding space. Similarly, in some example embodiments featuring a multi-objective optimization approach, a joint evaluation of at least two objectives of a variant may include determining a first objective of the at least two objectives for the respective variant according to a first dimension of an embedding space, determining a second objective of the at least two objectives for the respective variant according to a second dimension of the embedding space, and evaluating the respective variant according to a vector representation in the embedding space, wherein the vector representation is based on a first objective of the at least two objectives according to the first dimension of the embedding space and the second objective according to the second dimension of the embedding space.

In some example embodiments, a joint evaluation of multiple features and/or objectives may include a weighted evaluation of multiple features and/or objectives. In some cases, while a joint evaluation may include individual evaluations, observations, and/or measurements of multiple features or objectives, the significance of each feature or objective in the joint evaluation may differ; e.g., a primary feature or objective may be more significant in the joint evaluation than a secondary feature or objective. For instance, a metabolic pathway may include an enzyme that is identified as a highly active and effective catalyst, such that only a small amount of the enzyme is needed to fully catalyze the metabolic pathway. Thus, a variant or combination of a cell line may be evaluated based on a primary feature or objective of a high activity of the expressed enzyme (e.g., determining and verifying that the variants or combinations maintain the high activity of the enzyme) and a secondary feature or objective of an expression of the enzyme (e.g., determining and verifying that at least a small amount of the variant or combination is expressed, while a high frequency of expression is not advantageous over a low but adequate frequency of expression). In such cases, a joint evaluation of multiple features or objectives of a variant or combination may include generating a weighted evaluation of the first feature of the respective combination according to a first weight associated with the first feature, generating a weighted evaluation of the second feature of the respective combination according to a second weight associated with the second feature, and evaluating the respective combination according to a combination of the weighted evaluation of the first feature and the weighted evaluation of the second feature. Similarly, in a multi-objective optimization approach, a joint evaluation of multiple objectives may include generating a weighted evaluation of the first objective of the at least two objectives for the respective variant according to a first weight associated with the first objective, generating a weighted evaluation of the second objective of the at least two objectives for the respective variant according to a second weight associated with the second objective, and evaluating the respective variant according to a combination of the weighted evaluation of the first objective and the weighted evaluation of the second objective. The weighs of the respective features or objectives may be assigned manually (e.g., by a technician or researcher), based on experimental data or results, based on heuristics or recommendations in scientific literature, etc. Alternatively or additionally, the weights of respective features or objectives may be learned as the parameters of a machine learning model (e.g., as part of the learned weights and biases of an artificial neural network that is developed and trained to classify variants or combinations based on a set of properties). Based on the weighted evaluations of the features or objectives, the evaluation may assign one or more scores to each variant and/or combination. For example, if the evaluation of each feature or objective includes a measurement, the measurements for a particular of a variant or combination may be normalized (e.g., to a common range or scale) and multiplied by the weight of the feature or objective, and the score of the variant or combination may be determined as an aggregation (e.g., sum, product, arithmetic mean, maximum, minimum, or the like) of the products of the normalized measurement and weight of each feature or objective. The determination of scores for the evaluation of the variants or combinations may enable comparisons and/or ranking that more fully reflects the relative significance of each feature or objective in the evaluation of candidates for the biologic synthesis process.

Alternatively or additionally, in some example embodiments, a joint evaluation of multiple features and/or objectives may include a determination of whether the multiple features and/or objectives satisfy one or more evaluation thresholds. For example, for each embedding dimension of an embedding space, an evaluation threshold may be determined, whereby the positive or negative evaluation of variants and/or combinations is based on a comparison of respective features of the vector representation of the variant or combination in the embedding space with the evaluation threshold of the corresponding embedding dimension. Because one or more embedding dimensions may correspond to multiple features or objectives (e.g., an embedding dimension involving an aggregation of features or objectives, or a derived feature or objective that is based on two or more features or objectives), a comparison of one feature of the vector representation of the variant or combination in the embedding space with the evaluation threshold of the corresponding one embedding dimension may involve a joint evaluation of the multiple features or objectives that are associated with the embedding dimension. In some example embodiments, a joint evaluation of a set of variants or combinations may be based on a first evaluation threshold of a first feature or objective of a respective variant or combination and/or a second evaluation threshold of a second feature or objective of the respective variant or combination. In some example embodiments featuring a multi-objective optimization approach, an evaluation of a variant or combination of a biologic parent may be based on an evaluation threshold of at least one objective of the at least two objectives for the respective variant or combination.

In some example embodiments, an evaluation of a variant or combination may be based on a biologic product language model, such as a protein language model. As a first example, a protein language model may be trained to map genotypes to phenotypes based on a corpus of scientific literature. The protein language model may receive, as input, an encoding of a set of genes included in a cell line or a strain of a microbe. The protein language model may generate, as output, a set of indicators of likely features of the variant or combination, based on the learned parameters of the protein language model that are based on the mapping of similar genotypes of other variants or combinations to observed or measured features of the other variants or combinations. As a second example, a protein language model may be trained to map amino acid sequences of a protein to expressed features of the protein, such as structural features of the folded protein, binding affinity for various binding sites, and/or participation and activity of the protein in various metabolic pathways. The protein language model may receive, as input, an amino acid sequence or portions thereof of a variant or combination of one or more biologic parents. The protein language model may generate, as output, a set of indicators of the structural features, activity, and/or metabolic pathway associations arising from the amino acid sequence of the variant or combination. In some example embodiments, a joint evaluation of a set of variants or combinations of one or more biologic parents may include generating a representation of a portion of a respective combination according to a biologic product language model (e.g., a protein language model), and evaluating the representation of the portion of the respective combination according to the biologic product language model. In some example embodiments that include a multi-objective optimization approach, a joint evaluation of a set of variants or combinations of one or more biologic parents may include generating a representation of a portion of a respective variant according to a biologic product language model, and evaluating the representation of the portion of a respective variant according to the biologic product language model.

In some example embodiments, a joint evaluation of features or objectives of a variant or combination may include a techno-economic analysis, including at least one technical feature or economic feature. For example, the techno-economic analysis may include an evaluation of an industrial-scale synthesis process from precursor materials (e.g., a cell line), the stages of the synthesis processes (e.g., the operation of a fermentation tank and the extraction of biologic products), and a final biologic product (e.g., a purification of an expressed protein). The techno-economic analysis may evaluate various technical features of the industrial-scale synthesis process (e.g., the complexity, reliability, consistency, efficiency, yield, and/or performance of a stage of the synthesis process). The techno-economic analysis may evaluate various economic features of the industrial-scale synthesis process (e.g., a cost and/or volume of resources to perform each stage of the industrial-scale synthesis process; an analysis of labor, equipment, and material supply chain issues related to the resources for each stage of the industrial-scale synthesis process; an efficiency, reliability, consistency, and/or volatility of the industrial-scale synthesis process; a value or market of one or more biologic products resulting from the industrial-scale synthesis process; and/or one or more externalities associated with the industrial-scale synthesis process, such as the generation and remediation of carbon emissions).

The evaluation of variations and/or combinations may result in an identification of suitable candidates for the biologic synthesis process. For example, one or more variants and/or combinations may be identified as having a high performance of the features and/or objectives included in the evaluation, and therefore may be selected as the final selections for the biologic synthesis process (e.g., the selected variants or combinations to be used as targets and/or products of the biologic synthesis process). In some example embodiments, it may be desirable to generate a set of variants or combinations having high performance as a range of options for the biologic synthesis process. For example, the high-performing variants or combinations may have different sets of features or objectives (e.g., a first variant may exhibit higher expression than a second variant, while the second variant may exhibit higher activity than the first variant). The high-performing variants or combinations may have different scores of various features or objectives. The high-performing variants or combinations may have different assessments according to a techno-economic analysis (e.g., a first variant may exhibit higher activity in a metabolic pathway and higher value than a second variant, but the biologic synthesis process of the first variant may be more costly, lower-yield, and/or more unreliable than the biologic synthesis process of the second variant). An output set of high-performing variants or combinations may include distinct variants or combinations that respectively feature a distinct advantage relative to the other variants or combinations of the output set (e.g., a first variant featuring high expression, a second variant featuring high activation, and a third variant featuring for which the biologic synthesis process exhibits a high yield). The output set of high-performing variants or combinations may be limited to avoid redundant or overly similar variants or combinations (e.g., among a set of high-performing variants or combinations within a proximity and/or cluster of an embedding space, the output set may include only one such variant or combination).

Iterative Development, Evaluation, and Selection of Candidate Biologic Products

The comparative analysis approaches discussed herein (including those discussed in relation to FIGS. 25 and 26) include the evaluation of combinations of a first biologic parent and a second biologic parent to determine one or more biologic products for the biologic synthesis process. Similarly, the multi-objective optimization approaches discussed herein (including those discussed in relation to FIGS. 27 and 28) include the evaluation of variants of a biologic parent to determine one or more biologic products for the biologic synthesis process. In these and other cases, the evaluation of variants and combinations of biologic parents may include an iterative approach to selecting and/or generating variants or combinations, evaluating the selected variants or combinations, and selecting additional variants and/or combinations for evaluation in order to produce an output set of variants and/or combinations for the biologic synthesis process. In some example embodiments, the evaluation may be based on a simulation of respective combinations and/or variants of a set of candidate combinations and/or variants. Alternatively or additionally, in some example embodiments, the evaluation may be based on evaluating an experimental result of respective combinations and/or variants of the first set of candidate combinations and/or variants.

In some example embodiments, an iterative development of a biologic synthesis process and/or a biologic product of a biologic synthesis process may include an initial determination of a set of variants and/or combinations to be evaluated (e.g., a range of edits to a first parent and/or a second parent, or combinations thereof). A first stage of evaluation may include a selection, from the set of variants and/or combinations, and evaluation of a first set of candidate biologic products. The candidate biologic products may include variants of a biologic parent and/or combinations of at least two biologic parents. The evaluation of the first set of candidate biologic products may result in the determination of high-performing candidate biologic products (e.g., a variant or combination that meets the one or more objectives of the evaluation and/or that features the one or more features of the evaluation). If the first group of candidate biologic products yields a sufficient number and/or variety of high-performing candidate biologic products, the evaluation may conclude with an output set of high-performing biologic products for the biologic synthesis process.

If the first group of candidate biologic products does not yield a sufficient number and/or variety of high-performing candidate biologic products, the evaluation may iteratively proceed with a second stage of selection and evaluation of a second set of candidate biologic products for evaluation. The second set of candidate biologic products may include further variants and/or combinations based on at least one candidate biologic product of the first set of candidate biologic products (e.g., further variants and/or combinations of a particular candidate biologic product that was evaluated as exhibiting an improved, but not yet sufficient, performance as compared with the one or more biologic parents and/or other candidate biologic products). That is, the second set of candidate biologic products may be based on a determination that the first set of candidate biologic products includes productive but not yet sufficient edits and/or modifications, wherein further edits and/or modifications may result in the determination of high-performing candidate variants or combinations that may be included in the output set.

In some example embodiments, the evaluation of the set of combinations or variants may be performed according to a ranking order of the set of variants or combinations. For example, the evaluation may assign a score to each variant or combination. The scores may be based on an aggregation (e.g., sum, product, arithmetic mean, maximum, or minimum) of the products of a normalized measurement for each feature or objective and a weight assigned to the corresponding feature or objective. The ranking order may be based on the scores of the combinations or variants (e.g., a ranking order according to a descending order of scores for the combinations or variants). The evaluation may be conducted as a first stage of evaluating a first candidate group of the highest-scoring n combinations or variants in the ranking order that have the highest scores. If the first stage does not produce enough high-performing combinations or variants, the evaluation may further include a second stage of evaluating a second candidate group of the next-highest-scoring n combinations or variants in the ranking order. The ranked evaluation of combinations or variants may continue in stages until a sufficient number of high-performing combinations or variants are produced and/or until no further combinations or variants are available for evaluation.

The evaluation may determine the ranking order of the set of combinations or variants by determining a score based on a comparison between the respective combination and at least one biologic parent, and determining the ranking order based on the score of the respective combination or variant. For example, the score may be adjusted to account for a distance between the combination or variant and each of the one or more biologic parents thereof. In some cases, it may be desirable to conserve a distance between the combination or variant and a biologic parent, and the score of the combination or variant may be scaled inversely with the distance. In other cases, it may be desirable to emphasize a distance between the combination or variant and a biologic parent (e.g., to generate combinations or variants that are not too similar to the biologic parent), and the score of the combination or variant may be scaled proportionally with the distance. The manner of adjusting the score may vary by biologic parent and/or by stage of evaluation based on the previous stages of evaluation.

In some example embodiments, the ranking order may be determined based on a collection of features or objectives of each combination and/or variant. For example, the evaluation may include selecting, from the set of combinations or variants, a first set of candidate combinations or variants based on the ranking order and evaluating the first set of candidate combinations or variants based on at least one of the first feature of respective combinations of the first set of candidate combinations and the second feature of respective combinations of the first set of candidate combinations. Further stages of evaluation may be based on the evaluation of the first set of candidate combinations or variants. For example, the second set of candidate combinations includes at least one variant of at least one candidate combination of the first set of candidate combinations and/or at least one combination of the set of combinations that is not included in the first set of candidate combinations.

In some example embodiments, the first set of candidate biologic products may include single edits of a biologic parent, and the second set of candidate biologic products may include alternative single edits of the biologic parent, wherein the alternative single edits may refine or further alter the features of the biologic parent in order to provide additional advantages. For example, the first set of candidate biologic products may include single edits of a biologic parent, and the second set of candidate biologic products may include alternative single edits of the biologic parent, wherein the alternative single edits may refine or further alter the features of the biologic parent in order to provide additional advantages. As another example, the first set of candidate biologic products may include single edits of a biologic parent, and the second set of candidate biologic products may include double edits of the biologic parent, wherein the double edits include the first single edit and a second additional edit of the biologic parent, which may result in additional (e.g., synergistic) features or improvements of the biologic parent.

Alternatively or additionally, in some example embodiments, the second set of candidate biologic products may include additional candidate biologic products selected from the set of variants and/or combinations that were not included in the first set of candidate biologic products. For example, the first set of candidate biologic products may result in a disappointing evaluation, such as a lack of improvement of the features of the one or more biologic parents (e.g., an unimproved expression and/or activity of a protein) and/or a loss of one or more features of the one or more biologic parents (e.g., an increased expression of a protein but a loss of activity). Instead of further evaluating the first set of candidate biologic products or refinements thereof, the iterative development process may next select and evaluate candidate biologic products that are quite different than those of the first set of candidate biologic products. For example, the first set of candidate biologic products may share a proximity and/or a cluster within an embedding space, and the second set of candidate biologic products may be selected as being distant from the proximity and/or cluster of the first set of candidate biologic products, and/or being located within a second proximity or cluster of the embedding space. In some example embodiments, the second set of candidate biologic products may include a mixed set of both further variants and/or combinations of the first set of candidate biologic products (e.g., refinements of improved but not sufficient candidate biologic products) as well as additional candidate biologic products that are quite different than those of the first set of candidate biologic products. The selection and evaluation of such mixed sets may enable the determination of additional candidate biologic products that are evaluated to be high-performing candidate biologic products (e.g., a biologic product including both a first edit that is refined from the first set of candidate biologic products and a second edit that is quite different than the first set of candidate biologic products).

Figure 30:
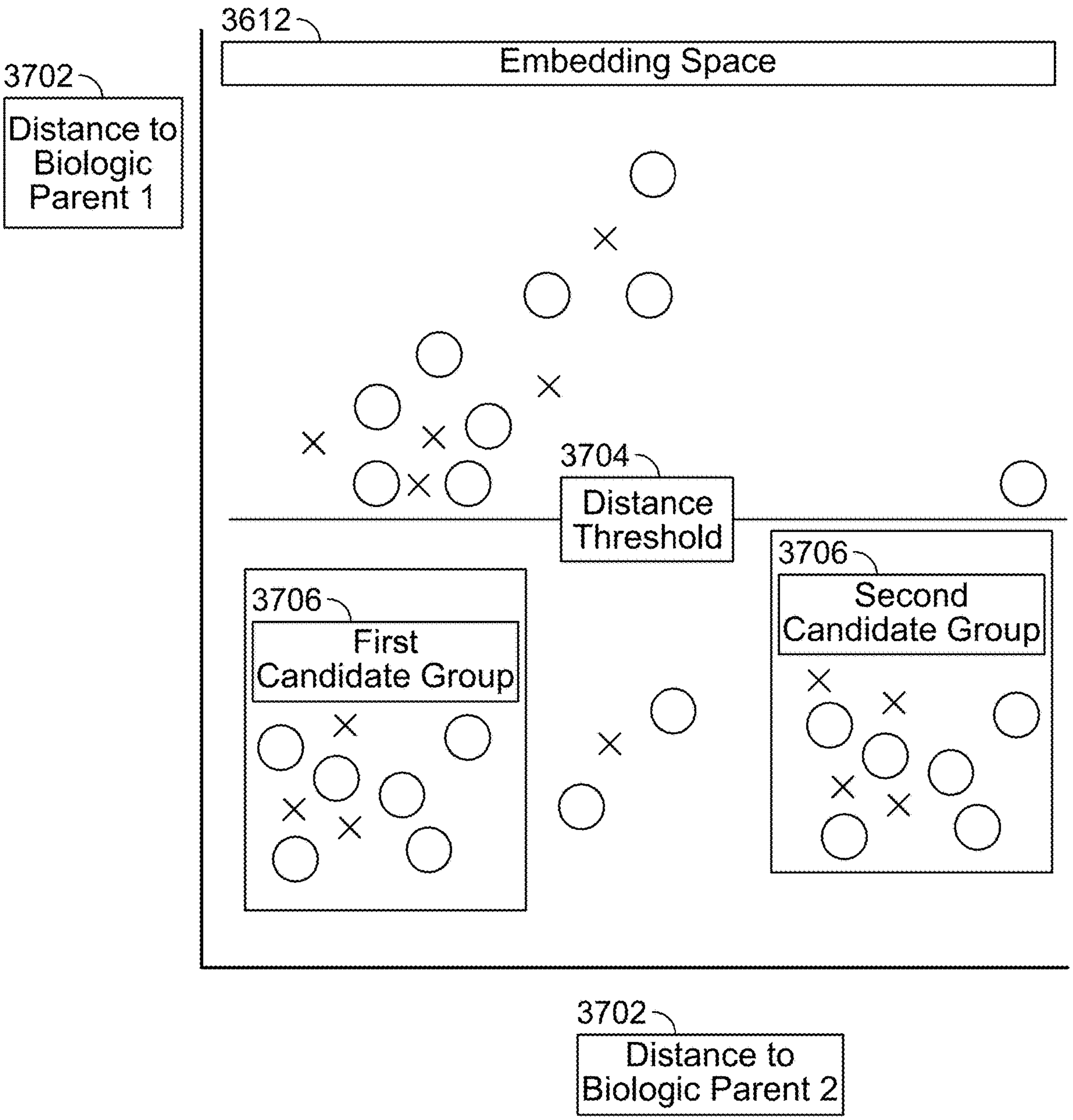
FIG. 30 is an illustration of an evaluation of a set of candidate biologic products according to some example embodiments.

FIG. 30 is an illustration of an evaluation of a set of candidate combinations according to some example embodiments. In FIG. 30, a set of combinations are determined and mapped into an embedding space 3612. The embedding space 612 in FIG. 30 includes, as a first dimensional axis, a distance 3702 of the respective combinations to a first biologic parent. The embedding space 612 in FIG. 30 includes, as a second dimensional axis, a distance 3702 of the respective combinations to a second biologic parent. Further, each combination is associated with a viability score. Combinations having a viability score above a viability score threshold (e.g., at least a minimum viability score indicating at least a minimum likelihood of representing a viable combination of the biologic parents) are shown in FIG. 30 as circles, which are eligible for evaluation as candidate biologic products of the biologic synthesis process. Combinations having a viability score below the viability score threshold (e.g., failing to satisfy a minimum viability score indicating a minimum likelihood of representing a viable combination of the biologic parents) are shown in FIG. 30 as crosses, and are excluded from evaluation as candidate biologic products of the biologic synthesis process.

As shown in FIG. 30, a first stage of evaluation includes a selection of combinations for a first candidate group 3706. The first candidate group 3706 may include the candidates having a comparatively small distance 3702 to both the first biologic parent (along the first dimensional axis) and the second biologic parent (along the second dimensional axis), and also having a viability score that satisfies the viability score threshold. The first candidate group 3706 may also be defined as being within a distance threshold 3704 of the first biologic parent (e.g., conserving a distance from the first biologic parent). The conserving may be based on an objective to maintain one or more features of the first biologic parent that are significant for the evaluation of high-performing candidate biologic products. An evaluation of the first candidate group 3706 may result in the determination of one or more high-performing candidates. In this case, further stages of evaluation may include the evaluation of additional combinations that are within a proximity of the first candidate group 3706 in the embedding space 3612. Alternatively or additionally, further stages of evaluation may include the evaluation of a second candidate group 3706 of combinations that are more distant from the second biologic parent 3702, but that are still within the distance threshold 3704 of the first biologic parent.

In some example embodiments, a first set of candidate combinations may include at least two alternative variants of a biologic parent having an edit location, wherein each of the at least two alternative variants includes a different edit of the edit location. For example, the combinations of the first set of candidate combinations may each include an edit of the same gene of the biologic parent, but the combinations may include different edits of the same gene. Alternatively or additionally, the first set of candidate combinations may include at least one combination that includes a single edit of the first biologic parent, and the second set of candidate combinations includes at least one combination that includes at least two edits of the first biologic parent. In this manner, the evaluation may include different kinds of combinations relative to one or more biologic parents. Alternatively or additionally, further stages of evaluation may include the evaluation of a second candidate group 706 of combinations that are more distant from the second biologic parent 702, but that are still within the distance threshold 704 of the first biologic parent.

Figure 31:
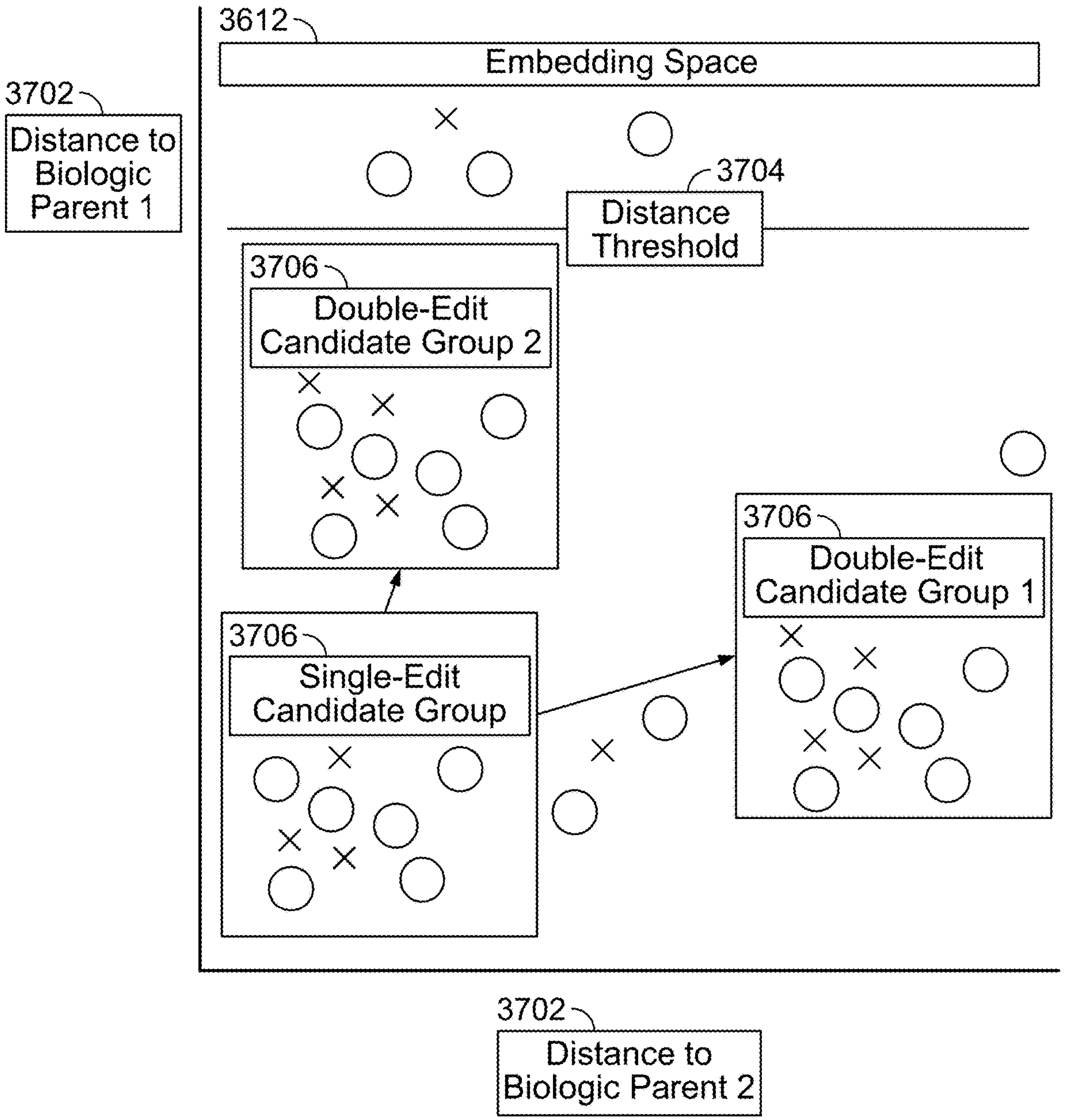
FIG. 31 is another illustration of an evaluation of a set of candidate biologic products according to some example embodiments.

FIG. 31 is another illustration of an evaluation of a set of candidate biologic products according to some example embodiments. As shown in FIG. 31, a first stage of evaluation includes a selection, for a first candidate group 3706, of single-edit combinations (e.g., replacing one gene of the first biologic parent with a corresponding gene of the second biologic parent). Based on the evaluation of the first candidate group 3706, a second stage evaluation includes a selection, for evaluation, of additional candidate groups 3706 that include double-edit combinations as further combinations of the first candidate group 3706. For example, for one or more single-edit combinations of the first candidate group 3706, a first double-edit candidate group 3706 may be identified that include an edit of the gene included from the second biologic parent, resulting in an increased distance 3702 of the combinations of the first double-edit candidate group 706 relative to the second biologic parent while not significantly affecting the distance 3702 to the first biologic parent within the embedding space 3612. Additionally, for one or more single-edit combinations of the first candidate group 3706, a second double-edit candidate group 3706 may be identified that include an edit of another gene of the first biologic parent, resulting in an increased distance 3702 of the combinations of the second double-edit candidate group 706 relative to the first biologic parent while not significantly affecting the distance 3702 to the second biologic parent within the embedding space 3612. The second stage of evaluation may include an evaluation of one or both of the double-edit candidate group 3706, which may result in the identification of additional high-performing combinations and/or additional candidate groups 3706 that may be further evaluated in further stages of the evaluation.

In some example embodiments, the evaluation of candidate combinations and/or variants may continue in stages until a sufficient number of high-performing combinations or variants are discovered. Alternatively or additionally, in some example embodiments, the evaluation of candidate combinations and/or variants may continue in stages until no further candidate combinations and/or variants remain to be evaluated. Alternatively or additionally, in some example embodiments, the evaluation of candidate combinations and/or variants may continue in stages until the likelihood of identifying additional improvements of the highest-performing combinations and/or variants is below a likelihood threshold. Alternatively or additionally, in some example embodiments, the evaluation of candidate combinations and/or variants may continue in stages until the evaluation reaches an evaluation threshold (e.g., a maximum number of evaluated combinations and/or variants; a maximum number of stages; and/or a maximum amount of experimental and/or computational resources have been used in the evaluation). Alternatively or additionally, in some example embodiments, the evaluation of candidate combinations and/or variants may be guided by one or more machine learning models that perform active learning by evaluating the candidate combinations and/or variants, and may continue in stages until the one or more machine learning models indicate a conclusion of the active learning. In some example embodiments, multiple criteria for concluding the evaluation may be identified and used to determine the conclusion of the evaluation. The criteria may be interrelated and/or dynamic (e.g., adjusting a maximum number of combinations and/or variants to evaluate based on a number of discovered high-performing combinations and/or variants).

In embodiments, the platform 100 may iteratively evaluate the candidate combinations and/or variants using techniques such as adaptive caching mechanisms that store intermediate results from previous evaluation stages (e.g., to reduce redundant calculations when evaluating similar variants), predictive pre-filtering using lightweight models to screen candidates before more computationally intensive evaluations, and/or dynamic batch sizing techniques that adjust the number of candidates evaluated simultaneously based on available computational resources and prediction confidence requirements.

AI-Guided Analytic Platform

In some example embodiments, an AI-guided analytic platform may perform the evaluation of combinations and/or variants of one or more biologic parents, by a comparative analysis approach and/or a multi-objective optimization approach as discussed herein.

In some example embodiments, an AI-guided analytic platform develops one or more biologic synthesis processes based on multi-objective optimization and/or comparative analysis. For example, the platform of FIG. 1 includes a multi-objective optimization module 3110 that operates in tandem with other elements and resources of the platform, such as foundation models 3102, a data store for synthetic biology sensor collection 2110, a workflow and service optimization module 208, and a workflow and service scaling module 210. One or more of these elements and/or modules may perform the respective functions using multi-objective optimization and/or comparative analysis, as illustrated in the flowcharts of FIGS. 25, 26, 27, and 28. For example, the automated model construction module 3108 may automatically generate at least one multi-objective evaluation artificial intelligence model that is configured to evaluate a biologic product according to each of at least two objectives. The AI-guided analytics discovery tool, digital twins, and simulation module 3112 may include at least one biologic synthesis simulation system that is configured to evaluate multiple objectives of biologic synthesis processes based on simulations of the biologic synthesis processes. The multi-objective optimization module 3110 may use the at least one multi-objective evaluation artificial intelligence model and/or the at least one biologic synthesis simulation to perform multi-objective optimizations of biologic synthesis processes. For example, the multi-objective optimization module 3110 may generate a set of variants of a biologic parent of the biologic product; simulate each variant of the set of variants using the at least one biologic synthesis simulation; and evaluate a performance of each variant of the set of variants for each objective of the at least two objectives using the at least one multi-objective evaluation artificial intelligence model, thereby determining one or more high-performing variants that may be identified as the biologic product.

The platform 100 may distribute execution of one or more models among multiple processing nodes, where each node may execute a specialized model (e.g., one of the protein language models, simulation models, and/or optimization models described herein). In embodiments, the platform 100 may dynamically manage the processing cores or other computational resources by assigning the various processing nodes to different models based on current processing tasks. The platform 100 may adaptively assign models based on input data characteristics (e.g., from real-time data streams being received by the platform 100) and/or optimization objectives that may be input by a user and/or needed by other components of the platform 100.

In some example embodiments, the AI-guided analytic platform may develop biologic synthesis processes such as a DNA synthesis process, an RNA synthesis process, a protein synthesis process, a metabolite synthesis process, a metabolic process, at least one pathway of a metabolic system, a plate growth process, or a fermentation process. Through such evaluation, the AI-guided analytic platform may develop biologic product such as (for example) an enzyme protein, a non-enzyme protein, a DNA sequence, an RNA sequence, a plasmid, a metabolite, or a biologic strain.

In some example embodiments, the AI-guided analytic platform may perform multi-objective optimization of multiple objectives of a biologic synthesis process. For example, the AI-guided analytic platform may include at least one of a set of machine learning systems, a set of artificial intelligence systems, and/or a set of neural networks. At least some of the machine learning systems, artificial intelligence systems, and/or neural networks may be designed and trained to simultaneously optimize a microbe, a bioreactor process, and a downstream purification process; to maximize production without minimizing growth; and/or to increase expression without loss of activity.

In some example embodiments, the AI-guided analytic platform may use a comparative analysis approach to evaluate multiple combinations as biologic products of a biologic synthesis process. For example, the AI-guided analytic platform may include at least one of a set of machine learning systems, a set of artificial intelligence systems, and/or a set of neural networks. At least some of the machine learning systems, artificial intelligence systems, and/or neural networks may be designed and trained to design towards a property using a protein language model; to determine a set of genetic modifications to make to a first protein such that the first protein exhibits one or more features of a second protein while maintaining one or more features of the first protein; to determine a genetic sequence similarity between a first protein and a second protein; to determine which residue positions differ between a first protein and a second protein; to generate a set of mutants of a protein based on each differing residue position between a first protein and a second protein; and/or to generate a set of mutants of a protein based on each differing residue position between a first protein and a second protein and having a set of protein language models that embed the set of mutants and calculate an embedding distance of each mutant to both proteins. In some example embodiments, the platform may calculate a viability score for each mutant in a set of mutants that represents a likelihood of each mutation, and may use a set of protein language models to calculate embedding distances for each mutation; and/or may build out multiple sets of mutations.

At the conclusion of the evaluation, the platform may generate an output set of high-performing combinations and/or variants. The platform may include, in the output set, annotations and/or descriptions of the high-performing combinations and/or variants (e.g., a comparative advantage of each high-performing combination or variant in the output set relative to at least one biologic parent and/or the other high-performing combinations or variants in the output set). The platform may generate a set of mutants of a protein based on each differing residue position between a first protein and a second protein and having a set of protein language models configured to embed the set of mutants, calculate an embedding distance of each mutant to both proteins, and graphically represent the embedding distance of each mutant to both proteins. The platform may automatically initiate and/or adapt a biologic synthesis process to synthesize the one or more biologic products.

Figure 32:
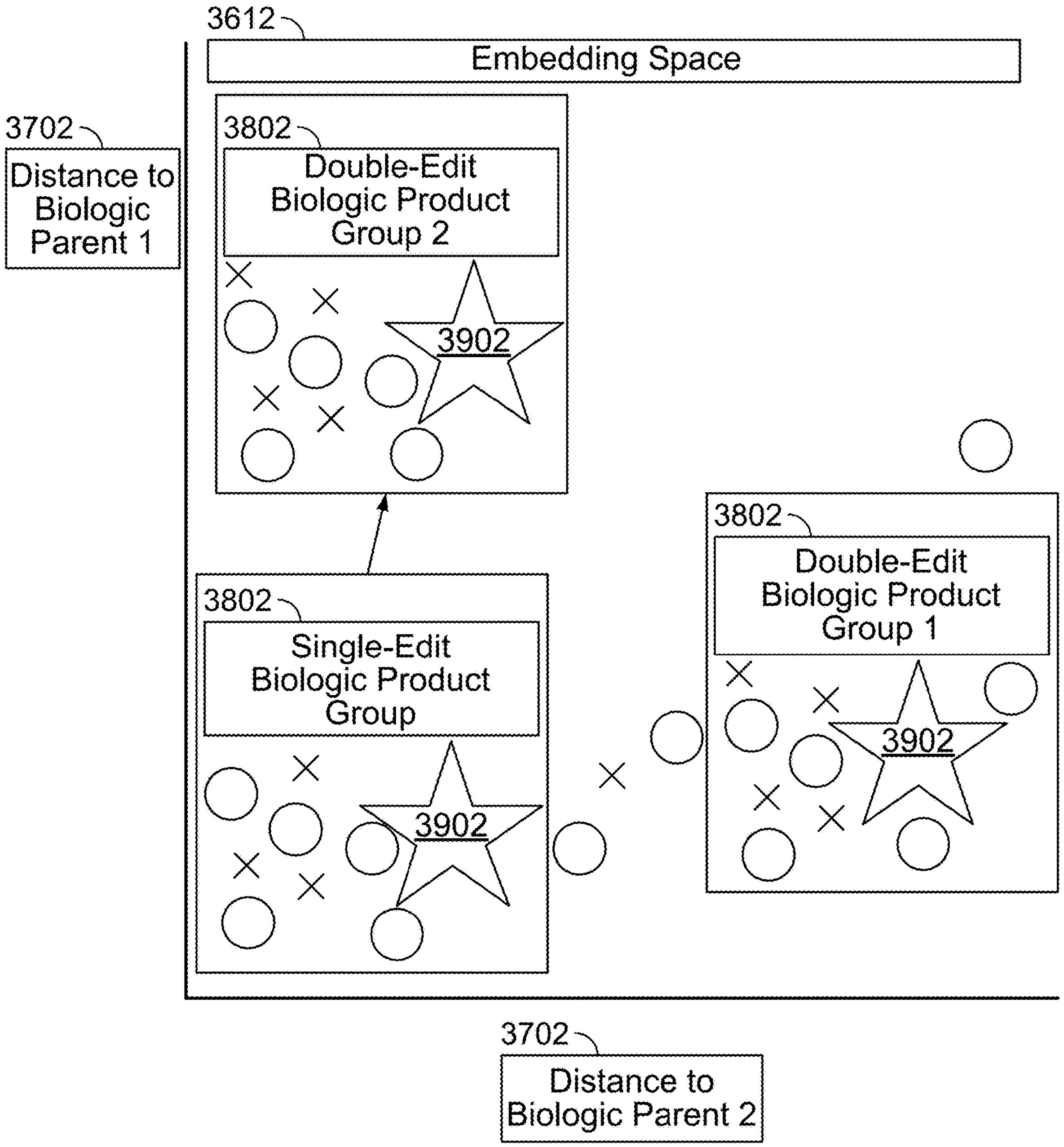
FIG. 32 is an illustration of a selection of biologic products resulting from an evaluation according to some example embodiments.

FIG. 32 is an illustration of a selection of biologic products resulting from an evaluation according to some example embodiments. As shown in FIG. 32, the evaluation of an embedding space 3612 of candidate combinations of a first biologic parent and a second biologic parent may include (in various stages) an evaluation of a single-edit biologic product group 3802; an evaluation of a first double-edit biologic product group 3802 that is based on the single-edit biologic product group 3802 (e.g., double edits including the same single edit as in the single-edit biologic product group 3802 and an additional edit); and an evaluation of a second double-edit biologic product group 3802 that is not based on the single-edit biologic product group 3802 (e.g., double edits that do not include the same single edit as in the single-edit biologic product group 3802). Based on the evaluation, the platform may present an output set of high-performing combinations 3902 as biologic products of the biologic synthesis process. Specifically, the output set may include one high-performing combination 3902 form each biologic product group 3802 (e.g., a highest-scoring single-edit combination in the single-edit biologic product group 3802; a highest-scoring double-edit combination in the first double-edit biologic product group 3802; and a highest-scoring double-edit combination in the second double-edit biologic product group 3802). The presentation of an output group including multiple high-performing biologic products may present options to a researcher or scientist for the selection of a biologic product and/or biologic synthesis process.

Additional Embodiments

In embodiments, a method of generating a biologic product of a biologic synthesis process includes selecting a first feature and a second feature of the biologic product; determining a first biologic parent having the first feature and not having the second feature, wherein the first feature is based on an aspect of the first biologic parent; determining a second biologic parent having the second feature and not having the first feature, wherein the second feature is based on an aspect of the first biologic parent, and the aspect of the second biologic parent can be combined with the aspect of the first biologic parent; and determining a biologic product having the first feature and the second feature, wherein the biologic product is determined based on an evaluation of a set of combinations of the aspect of the first biologic parent and the aspect of the second biologic parent.

In embodiments, the aspect of each biologic parent of the first biologic parent and the second biologic parent includes at least one of a portion of the biologic parent, a structural feature of the biologic parent, a functional feature of the biologic parent, a behavior of the biologic parent, a source of the biologic parent, a metabolic pathway associated with the biologic product, or a biologic condition associated with the biologic product.

In embodiments, the determination that the aspect of the second biologic parent can be combined with the aspect of the first biologic parent is based on at least one of a structural requirement of the aspect of each biologic parent, a functional requirement of the aspect of each biologic parent, an environmental requirement of the aspect of each biologic parent, a requirement of a source of the aspect of each biologic parent, a requirement of a metabolic pathway associated with the aspect of each biologic parent, or a requirement of a biologic condition associated with the aspect of each biologic parent.

In embodiments, the first biologic parent is determined by a machine learning model including an attention feature, and the attention feature associates the aspect of the first biologic parent with the first feature of the first biologic parent.

In embodiments, the second biologic parent is determined by a machine learning model including an attention feature, and the attention feature associates the aspect of the second biologic parent with the second feature of the second biologic parent.

In embodiments, determining the second biologic parent includes determining, by a machine learning model including an attention feature, that the aspect of the second biologic parent can be combined with the aspect of the first biologic parent.

In embodiments, the determination that the aspect of the second biologic parent can be combined with the aspect of the first biologic parent includes determining a modification of at least one of the aspect of the first biologic parent, the aspect of the second biologic parent, the biologic synthesis process, or the biologic product, the determination that the aspect of the second biologic parent cannot be combined with the aspect of the first biologic parent based on an absence of the modification, and the determination that the aspect of the second biologic parent can be combined with the aspect of the first biologic parent based on the modification.

In embodiments, determining the modification includes determining, by a machine learning model including an attention feature, and the attention feature associates the modification with at least one of the aspect of the first biologic parent, the aspect of the second biologic parent, the biologic synthesis process, or the biologic product.

For example, various biologic synthesis process may involve combinations of two or more biologic parents, each having a particular set of features to be included in a biologic product. For each biologic product, the respective feature may be due to a particular aspect of the biologic product, such as a particular gene of a strain or a particular structural feature of a protein that serves as a binding site with an affinity for another protein or other metabolic factor. In order to combine two or more biologic parents, it may be necessary to consider whether the aspects of the respective biologic parents that are associated with the respective features of the biologic products may be combined. For example, in some cases, a first structural aspect of a first protein may be combined with second structural aspect of a second protein, resulting in a protein that includes the features of both the first structural aspect and the second structural aspect. In other cases, a first structural aspect of a first protein may be incompatible with a second structural aspect of a second protein, such as variations of a single binding site that produce different features, where the binding site may be based on the first biologic parent or the second biologic parent but not both biologic parents. As another example, a first biologic parent may function only in a first environment (e.g., having a first range of temperature, pH, metabolic factors, or the like), and a second biologic parent may function only in a second environment (e.g., having a second range of temperature, pH, metabolic factors, or the like). In some cases, the range of environmental properties of the first biologic parent and the second biologic parent may overlap, which may indicate that a biologic product based on a combination of the first biologic parent and the second biologic parent may function within environments having the overlapping set of parameters. In other cases, the range of environmental properties of the first biologic parent and the second biologic parent may not overlap, which may indicate that a biologic product based on a combination of the first biologic parent and the second biologic parent cannot function in the range of environments relevant to the first biologic parent and the second biologic parent. A consideration of the compatibility of respective aspects of various biologic parents that are associated with relevant features may enable a refined selection of candidates and/or variants (e.g., excluding from evaluation any variants and/or candidates that are based on combinations of biologic parents that are incompatible).

In some cases, a modification of a biologic parent, biologic synthesis process, and/or biologic product may be determined, wherein the modification enables or improves a compatibility of biologic parents by a biologic synthesis process. For example, a biologic synthesis process for a first biologic parent may involve a particular temperature range, pH, metabolic factors, or the like, but these features may be incompatible with a second biologic parent to be combined with the first biologic parent. A modification of the biologic synthesis process (e.g., a modification of the temperature range, pH, metabolic factors, or the like) may improve the suitability of the biologic synthesis process for the inclusion of the second biologic parent without compromising the suitability of the biologic synthesis process for the inclusion of the first biologic parent.

In embodiments, the compatibility of various biologic parents, biologic synthesis processes, biologic products, or the like may be evaluated and/or modified by a machine learning model including an attention feature, such as a transformer layer. The attention model may associate various biologic parents, biologic synthesis processes, biologic products, or the like with various features, aspects, requirements, or the like. The attention model may enable the analysis of the biologic parents, biologic synthesis processes, biologic products, or the like to determine compatibility with other biologic parents, biologic synthesis processes, biologic products, or the like.

In embodiments, a method of generating a biologic product of a biologic synthesis process includes selecting a biologic parent of the biologic product, identifying at least two objectives of the biologic product, wherein each objective of the at least two objectives is based on a techno-economic analysis of the biologic synthesis process, and determining a variant of the biologic product based on the techno-economic analysis of the biologic synthesis process.

In embodiments, the techno-economic analysis includes an analysis of at least one techno-economic feature of the biologic synthesis process, and the at least one techno-economic feature of the biologic synthesis process includes at least one of an efficiency of the biologic synthesis process, a rate of the biologic synthesis process, an environment of the biologic synthesis process, a yield of the biologic synthesis process, a variance of the biologic synthesis process, a byproduct of the biologic synthesis process, or a feature of the biologic product of the biologic synthesis process, and at least one objective of the at least two objectives is based on the at least one techno-economic feature included in the techno-economic analysis.

In embodiments, the techno-economic analysis is based on a simulation of the biologic synthesis process, and the variant of the biologic product is determined based on a comparison of the simulation of the biologic synthesis process with a simulation of a variant biologic synthesis process including the variant.

In embodiments, the variant of the biologic product is determined based on a techno-economic analysis of the variant biologic synthesis process.

In embodiments, the techno-economic analysis of the biologic synthesis process includes an analysis of at least one techno-economic feature of the biologic synthesis process, the techno-economic analysis of the variant biologic synthesis process includes an analysis of the at least one techno-economic feature of the variant biologic synthesis process, and the variant of the biologic product is determined based on a comparison of the at least one techno-economic feature of the biologic synthesis process and the at least one techno-economic feature of the variant biologic synthesis process.

For example, a techno-economic analysis of a biologic synthesis process may involve an analysis of a set of biologic parents (e.g., availability, specificity, sensitivity, costs, or the like); the biologic synthesis process (e.g., rate, sensitivity, reliability, efficiency, byproducts, costs, or the like); and/or biologic products (e.g., yield, quality, availability, versatility, or the like). The techno-economic analysis may include an analysis of various properties of the biologic synthesis process (e.g., energy, physical space, time, attention, sensitivity to perturbation, or the like) and/or components of the biologic synthesis process (e.g., materials, bioreactors, sensors, storage tanks, human attention, automation, or the like). The techno-economic analysis may inform the selection of biologic parents (e.g., a selection, from a set of biologic parents that may be included in the biologic synthesis process, of particular biologic parents based on availability, quality, selectivity, cost, or the like). The techno-economic analysis may inform the planning of the biologic synthesis process (e.g., scheduling, timing, rate, scale, or the like). The techno-economic analysis may inform the selection of biologic products of the biologic synthesis process (e.g., a biologic synthesis process may be configured to generate variants of a set of biologic products, and particular biologic products may be selected based on quality, value, reliability, or the like). In some embodiments, techno-economic analyses may be performed for variants of the biologic parents, biologic synthesis process, biologic products, or the like, and features of the respective techno-economic analyses may be compared to choose, prioritize, schedule, and/or allocate resources among the variants of the biologic parents, biologic synthesis process, biologic products, or the like.

Pathway Optimization for Process Bottlenecks

Overview

In the field of biotechnology, many scenarios involve a biologic synthesis process for the production of a biologic product, such as a DNA sequence, an RNA sequence, a protein such as an enzyme, a metabolic precursor, a cell or cell line, a strain of a biological species, or the like. The biologic synthesis process may involve a research process, such as a generation of a microbe of a particular genotype and/or phenotype for testing, or a protein that may be a pharmaceutical candidate for the treatment of a biologic pathway associated with a disease. The biologic synthesis process may involve an industrial process to generate biologic materials for other purposes, such as the synthesis of a protein that is used as a precursor or catalyst in the synthesis of other biologic materials, or in other fields, such as an enzyme that degrades pollutants for remediation processes. The biologic synthesis process may involve a pharmaceutical process to generate pharmaceutically active materials to be dispensed in healthcare. The biologic synthesis processes may involve various synthesis settings (e.g., culturing strains on plates, replicating a DNA sequence via polymerase chain reaction (PCR), or fermentation processes occurring in biological fermentation tanks) and/or scales (e.g., small-scale synthesis for research, individual-scale synthesis for personalized medicine, and/or large-scale synthesis for mass production and distribution).

In such scenarios, a biologic synthesis process may be designed to promote and/or maintain a particular objective. Alternatively or additionally, the biologic synthesis process involving a biologic product may be designed to promote and/or maintain a particular feature of the biologic product.

For example, synthesis processes to generate a strain may be developed with the objective of amplifying the yield of the synthesis process per unit of time. Synthesis processes to generate an enzyme via a metabolic pathway may be developed with the objective of maintaining or increasing the effectiveness of the enzyme, such as the activity and/or rate of the enzyme to convert substrate materials into further biologic products. Synthesis processes to generate a pharmaceutical candidate may be developed with the objective of maintaining or increasing the effectiveness of treating a particular condition, such as a magnitude of increase or decrease of a metabolic pathway related to the condition. Synthesis processes involving the synthesis of a protein product from DNA and/or RNA may be developed with the objective of amplifying the rate of transcription and/or translation to increase the rate of production of the protein product. Many biologic synthesis processes begin with the identification of a biologic parent (e.g., a parent DNA or RNA sequence, a parent protein such as an enzyme, a parent cell line, or a parent strain of a microbe) having a particular feature, and the biologic synthesis process may be designed to promote and objective of the biologic synthesis process and/or a feature of the biologic parent. For example, a biologic synthesis process may produce a protein product that is commonly in a metabolic pathway and that may have an identified effect on the metabolic pathway. It may be desirable to modify the biologic synthesis process to promote an objective of the biologic synthesis process (e.g., to increase a yield of the protein product) or to promote a feature of the biologic product (e.g., to reduce unintended activity of the protein product that causes undesirable side-effects of the biologic synthesis process and/or a metabolic pathway in which the protein product is to be used). In order to promote an objective of the biologic synthesis process or to promote a feature of the biologic product, researchers may experiment with modifications of various parameters of the biologic synthesis process (e.g., temperature, pressure, the presence and components of reactants and/or nutrients, or the order and/or timing of steps of the biologic synthesis process) and may capture measurements of the experiments that indicate an effect of the modified parameters on the objective of the biologic synthesis process or the feature of the biologic product. Alternatively or additionally, researchers may conduct computer simulations of the biologic synthesis process with modifications of various parameters of the biologic synthesis process and may examine the results of the computer simulation to identify an effect of the modified parameters on the objective of the biologic synthesis process or the feature of the biologic product. The results of the experiments and/or simulations may enable the researchers to identify modifications of the biologic synthesis process that provide improvements of the objective of the biologic synthesis process or the feature of the biologic product.

In many biotechnology scenarios, the development of a biologic synthesis process for one or more objectives and/or features of a biologic product may be limited by a number of factors. As a first example, the biologic synthesis process may occur in conditions that limit a yield, rate, quality, or other feature of the biologic synthesis process. For instance, a biologic fermentation tank may require or reach a particular temperature and/or pressure, either initially or during the progression of the biologic synthesis process, may adversely affect the performance of the biologic synthesis process. As a second example, the biologic synthesis process may have side-effects or consequences that gradually and/or cumulatively limit the yield, rate, quality, or other feature of the biologic synthesis process. For instance, the biologic synthesis process may involve a metabolic pathway that produces a biologic product and one or more metabolic byproducts, and an accumulation of the metabolic byproducts may gradually and/or cumulatively limit the yield, rate, quality, or other feature of the biologic synthesis process. As a third example, the biologic synthesis process may consume and/or transform one or more materials of the biologic synthesis process, and a reduced availability and/or elimination of the one or more materials may adversely affect the performance of the biologic synthesis process. For instance, the biologic synthesis process may involve a metabolic pathway including an intermediate step that depends upon an enzyme, and while the enzyme may not be directly consumed by the intermediate step of the metabolic pathway, other features of the metabolic pathway may gradually cause a depletion of the enzyme that limits the performance of the biologic synthesis process. Further complications may occur due to differences between a model or understanding of the biologic synthesis process and a reality of the biologic synthesis process. For instance, a biologic parent, product, variant, combination, and/or biologic synthesis process may perform differently under experimental observation in plate assays than in biologic fermentation tanks for industrial-scale synthesis. As another example, a model or simulation of the biologic synthesis process may be accurate under some conditions (e.g., initial conditions in a biologic fermentation tank), but may unexpectedly vary under other conditions (e.g., later conditions in the biologic fermentation tank at a later point in the biologic synthesis process).

In these and other biotechnology scenarios, an outcome of a biologic synthesis process may be limited by one or more bottlenecks. The bottlenecks may include (for example) a growth rate bottleneck, a metabolite production rate bottleneck, a byproduct formation rate bottleneck, a protein expression level bottleneck, a process scale bottleneck, a process rate bottleneck, a product expression bottleneck, a product activation bottleneck, a process stability bottleneck, a process efficiency bottleneck, a process cost bottleneck, or a process yield bottleneck. The occurrence of the bottleneck may be discovered during the biology synthesis process, and may be difficult for researchers and scientists to understand due to an inability to observe the biology synthesis process without interfering with and altering the conditions that are associated with the bottleneck. Alternatively or additionally, the occurrence of the bottleneck may be discovered after the biology synthesis process, and may be difficult for researchers and scientists to understand due to a difference between the conditions during the biology synthesis process that caused the bottleneck and different conditions after the biology synthesis process that may be observed by researchers and scientists. The difficulty of optimizing biology synthesis processes through current methods and techniques, including by the identification, analysis, and resolution of bottlenecks, is a persistent source of inefficiency in biology synthesis processes.

Presented herein are techniques for optimizing biology synthesis processes, including the identification, analysis, and resolution of bottlenecks that may occur in such biology synthesis processes. The described techniques provides technical improvements to the technical field of biological synthesis processes by enabling process optimization to reduce the effects of bottlenecks and thus, e.g., improve the rate of production of valuable products generated by biological synthesis processes.

Optimization by Variants of the Biologic Synthesis Process

Figure 33:
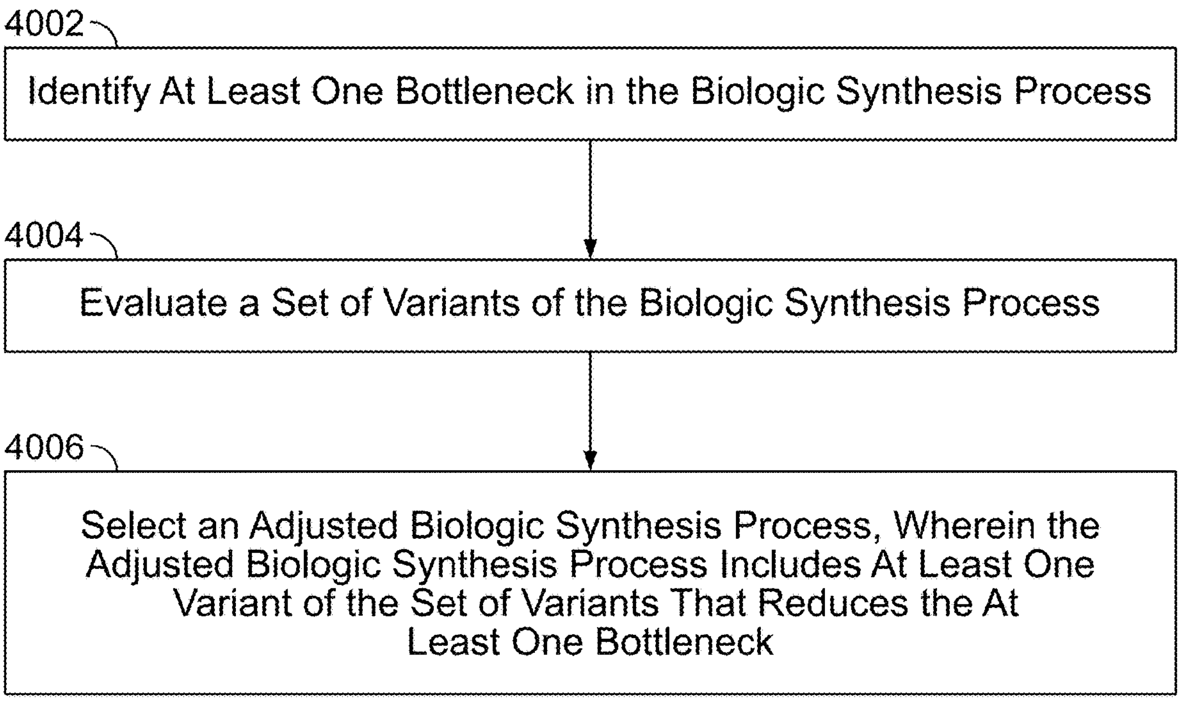
FIG. 33 is a flowchart that presents an example method of optimizing a biologic synthesis process according to some example embodiments.

FIG. 33 is a flowchart that presents an example method of optimizing a biologic synthesis process according to some example embodiments. The example method of FIG. 33 may be performed, for example, by the Optimize Workflows and Service Module 208 of the platform of FIG. 1.

The example flowchart of FIG. 33 includes a step 4002 of identifying at least one bottleneck in the biologic synthesis process. The biologic synthesis process may include (for example) a DNA synthesis process, an RNA synthesis process, a protein synthesis process, a metabolite synthesis process, a metabolic process, at least one pathway of a metabolic system, a plate growth process, a bioreactor process, or a downstream purification process. The biologic synthesis process may involve one or more biologic products, such as (for example) one or more biologic precursor of the biologic synthesis process, one or more reagents and/or starting materials of the biologic synthesis process, one or more biologic intermediaries of the biologic synthesis process, one or more enzymes and/or catalyst of the biologic synthesis process, and/or one or more biologic outputs of the biologic synthesis process. The biologic products may include (for example) an enzyme or non-enzyme protein, a DNA sequence, an RNA sequence, a plasmid, a metabolite, a cell line, a biologic strain of a microbe, or the like.

The biology synthesis process may be intended, designed, selected, and/or refined to generate one or more biologic products based on one or more objectives. The objectives may include, for example, an objective of synthesizing a biologic product with an activity of binding to a particular binding site, an inclusion in a metabolic process, a suitability as a precursor for another biologic process; an objective of synthesizing a biologic product that expresses a particular enzyme or other protein, that performs a metabolic pathway, or that exhibits a characteristic within an environment; an objective of determining a biologic synthesis process that includes an objective such as a yield, a reaction rate, or a consistency of a biologic product; a product expression objective; a product activation objective; a product reaction objective; an enzyme cleaning objective; a product stability objective; a product biocompatibility objective; a process rate objective; a process catalyzation rate objective; a process efficiency objective; a process cost objective; or a process yield objective.

A bottleneck of the biologic synthesis process may affect any of these objectives of the biologic synthesis process, and may be discovered, detected, monitored, and/or evaluated through the effect of the bottleneck of the biologic synthesis process on these and other objectives. In some cases, the bottleneck may be observed based on a downstream effect (e.g., a reduced yield of a biologic product of the biologic synthesis process), but the downstream effect may be caused by an upstream effect of the bottleneck on a preceding portion of the biologic synthesis process. For example, an instance of the biologic synthesis process may be observed to have a reduced yield as compared with an expected yield and/or a yield of previous instances of the biologic synthesis process, due to an apparent bottleneck at a final synthesis step of the biologic synthesis process. However, the bottleneck may actually occur during an intermediate step of the biologic synthesis process that limits the production of a biologic intermediary product that is an input to the final synthesis step of the biologic synthesis process. A review of the perceived effect of the bottleneck (e.g., measurements of the conditions of the biologic synthesis process during the final synthesis step) may reveal the occurrence of the bottleneck at another point in the biologic synthesis process (e.g., an unexpected depletion of the biologic intermediary product as input to the final synthesis step) and the actual cause of the bottleneck.

The example flowchart of FIG. 33 includes a step 4004 of evaluating a set of variants of the original biologic synthesis process. For example, a variant may include different process conditions than the original biologic synthesis process, such as a process temperature variant, a process pressure variant, a process volume variant, a process timing variant, a process order variant, a biologic product concentration variant, a biologic product addition variant, a biologic product substitution variant, a biologic product elimination variant, a biologic product expression variant, a biologic product activation variant, a biologic product activity variant, or a biologic product transformation variant. A variant may include a different material than the original biologic synthesis process, such as a different biologic precursor, a different reagent and/or starting material, a different substrate, a different biologic intermediary, a different enzyme and/or catalyst, and/or a different biologic output. A variant may include a different manner of performing the original biologic synthesis process, such as a different number of steps, a different order of steps, a different timing of steps, a different concurrency of steps, a different conditionality of steps, a substitution of a step for a different step, a merging of two or more steps, a partitioning of a step into two or more steps, a deletion or curtailment of a step, or an addition or extension of a step.

The example flowchart of FIG. 33 includes a step 4006 of selecting an adjusted biologic synthesis process, wherein the adjusted biologic synthesis process includes at least one variant of the set of variants, and the included at least one variant reduces the at least one bottleneck of the biologic synthesis process. The selection of the variant for inclusion in the adjusted biologic synthesis process may be based on a root cause analysis of the bottleneck of the biologic synthesis process, such as measurements and/or observations of the various features of respective steps of the biologic synthesis process that reveal the occurrence and/or cause of the bottleneck. The selection of the variant for inclusion in the adjusted biologic synthesis process may be based on a simulation of the biologic synthesis process, wherein measurements and/or observations of the various features of respective steps of the simulation of the biologic synthesis process reveal the occurrence and/or cause of the bottleneck. The selection of the variant for inclusion in the adjusted biologic synthesis process may be based on a machine learning analysis of the biologic synthesis process, wherein details and/or measurements of the biologic synthesis process may be processed by a machine learning model that is trained to identify and address bottlenecks arising in biologic synthesis processes. The selection of a variant may be based on experimental results that indicate a reduction or absence of the bottleneck in adjusted biologic synthesis processes that include the variant (e.g., experimental testing of the variants that results in an outcome indicating the reduction or absence of the bottleneck, even if the variant was not selected and/or predicted to reduce or eliminate the bottleneck and/or even if cause of the bottleneck and/or the causal relationship between the variant and the bottleneck are not fully understood). The selection of the adjusted biologic synthesis process including the determined variant enables a reduction or avoidance of the bottleneck in the biologic synthesis process.

Figure 34:
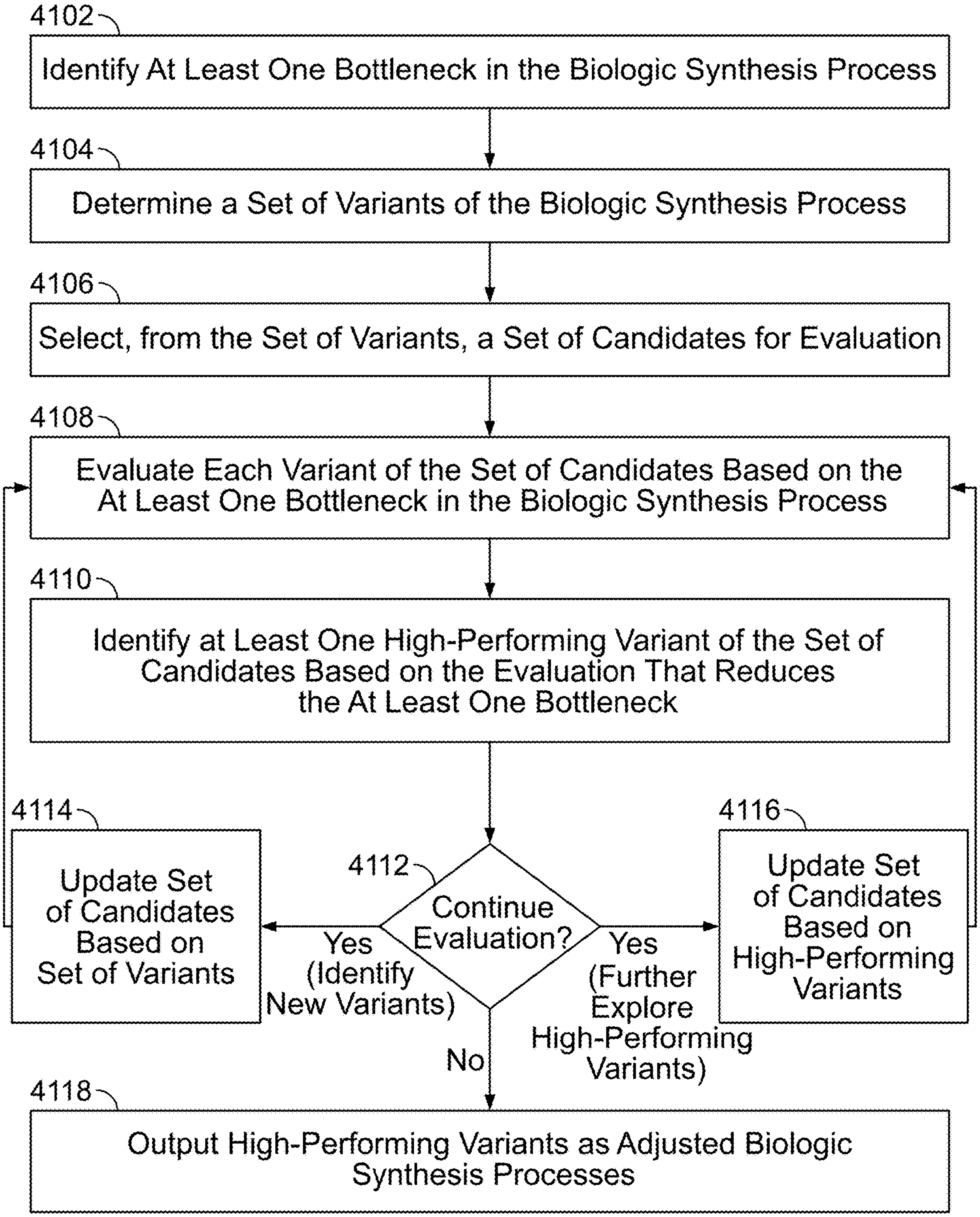
FIG. 34 is another flowchart that presents an example method of optimizing a biologic synthesis process according to some example embodiments.

FIG. 34 is another flowchart that presents an example method of optimizing a biologic synthesis process according to some example embodiments. The flowchart of FIG. 34 is a more detailed version of the flowchart of FIG. 33 that may be included and/or performed in some example embodiments. The example method of FIG. 34 may be performed, for example, by the Optimize Workflows and Service Module 208 of the platform of FIG. 1.

The example flowchart of FIG. 34 may relate to a biologic synthesis process including (for example) a DNA synthesis process, an RNA synthesis process, a protein synthesis process, a metabolite synthesis process, a metabolic process, at least one pathway of a metabolic system, a plate growth process, a bioreactor process, or a downstream purification process. The biologic synthesis process may involve one or more biologic products, such as (for example) one or more biologic precursor of the biologic synthesis process, one or more reagents and/or starting materials of the biologic synthesis process, one or more biologic intermediaries of the biologic synthesis process, one or more enzymes and/or catalyst of the biologic synthesis process, and/or one or more biologic outputs of the biologic synthesis process. The biologic products may include (for example) an enzyme or non-enzyme protein, a DNA sequence, an RNA sequence, a plasmid, a metabolite, a cell line, a biologic strain of a microbe, or the like.

The example flowchart of FIG. 34 includes a step 4102 of identifying at least one bottleneck in the biologic synthesis process. For example, the biology synthesis process may be intended, designed, selected, and/or refined to generate one or more biologic products based on one or more objectives. The objectives may include, for example, an objective of synthesizing a biologic product with an activity of binding to a particular binding site, an inclusion in a metabolic process, a suitability as a precursor for another biologic process; an objective of synthesizing a biologic product that expresses a particular enzyme or other protein, that performs a metabolic pathway, or that exhibits a characteristic within an environment; an objective of determining a biologic synthesis process that includes an objective such as a yield, a reaction rate, or a consistency of a biologic product; a product expression objective; a product activation objective; a product reaction objective; an enzyme cleaning objective; a product stability objective; a product biocompatibility objective; a process rate objective; a process catalyzation rate objective; a process efficiency objective; a process cost objective; or a process yield objective. A bottleneck of the biologic synthesis process may affect any of these objectives of the biologic synthesis process, and may be discovered, detected, monitored, and/or evaluated through the effect of the bottleneck of the biologic synthesis process on these and other objectives. The bottleneck may include (for example) a growth rate bottleneck, a metabolite production rate bottleneck, a byproduct formation rate bottleneck, a protein expression level bottleneck, a process scale bottleneck, a process rate bottleneck, a product expression bottleneck, a product activation bottleneck, a process stability bottleneck, a process efficiency bottleneck, a process cost bottleneck, or a process yield bottleneck.

The example flowchart of FIG. 34 may include a step 4104 of determining a set of variants of the biologic synthesis process. For example, a variant may include different process conditions than the original biologic synthesis process, such as a process temperature variant, a process pressure variant, a process volume variant, a process timing variant, a process order variant, a biologic product concentration variant, a biologic product addition variant, a biologic product substitution variant, a biologic product elimination variant, a biologic product expression variant, a biologic product activation variant, a biologic product activity variant, or a biologic product transformation variant. A variant may include a different material than the original biologic synthesis process, such as a different biologic precursor, a different reagent and/or starting material, a different substrate, a different biologic intermediary, a different enzyme and/or catalyst, and/or a different biologic output. A variant may include a different manner of performing the original biologic synthesis process, such as a different number of steps, a different order of steps, a different timing of steps, a different concurrency of steps, a different conditionality of steps, a substitution of a step for a different step, a merging of two or more steps, a partitioning of a step into two or more steps, a deletion or curtailment of a step, or an addition or extension of a step.

The example flowchart of FIG. 34 includes a step 4106 of selecting, from the set of variants, a set of candidates for evaluation. The selecting may be based, for example, on a likelihood of the features of the variant to be a cause of the bottleneck. The selecting may be based, for example, on a known variance of one or more features of the variant (e.g., a difficulty in controlling a temperature and/or pressure of the biologic synthesis process, and/or a volatility of a biologic precursor, parent, intermediary, enzyme, and/or catalyst of the biologic synthesis process).

The example flowchart of FIG. 34 includes a step 4108 of evaluating each variant of the set of candidates based on the at least one bottleneck in the biologic synthesis process. The evaluating may include, for example, evaluating a laboratory experiment and/or simulation of the biologic synthesis process to determine whether features of the variant that are related to the bottleneck match observed features of the laboratory experiment and/or simulation of the biologic synthesis process. The evaluating may include a comparison of an outcome of the variant of the biologic synthesis process with an observed outcome of an instance of the biologic synthesis that is associated with the bottleneck. The evaluating may include a determination of a possible cause and/or association between at least one feature of the variant (e.g., a divergence of a temperature and/or pressure during a step of the variant of the biologic synthesis process) and the bottleneck occurring in the biologic synthesis process. Evaluating the set of variants of the biologic synthesis process includes comparing a simulation of the biologic synthesis process with a simulation of each variant of the set of variants of the biologic synthesis process. Evaluating the set of variants may include comparing an experimental result of the biologic synthesis process with an experimental result of a respective experiment of each variant of the set of variants of the biologic synthesis process.

The example flowchart of FIG. 34 includes a step 4110 of identifying at least one high-performing variant of the set of candidates based on the evaluation. The identifying of high-performing variants may include, for instance, a comparison of one or more scores with each variant of the set of candidates (e.g., a sum and/or product of the scores of the similarity of various features of the variant of the biologic synthesis process and an instance of the biologic synthesis process during which the bottleneck occurred). The identifying of high-performing variants may include mapping a vector representation of each variant to an embedding space and identifying the high-performing variants based on the locations of the variants within the embedding space. The identifying of high-performing variants may include ranking the variants (e.g., according to one or more scores of each variant and/or a likelihood of the variant occurring during the biologic synthesis process) and selecting one or more variants as high-performing variants based on the ranking.

Each variant that is identified as high-performing combinations may be added to a set of high-performing variants that also includes other high-performing variants from the same evaluation and/or other evaluations, such as prior evaluations of other sets of candidates.

The platform 100 may evaluate variants using distributed and/or parallel computing to process multiple candidate variants simultaneously. For example, the platform 100 may use different computing nodes to simulate different variants of a process, then aggregate results (e.g., through a shared memory architecture). Using parallel processing can reduce evaluation time by a factor proportional to the number of available computing nodes. The platform may use processing cores (e.g., GPUs, NPUs, TPUs, FPGAs, etc.) for efficient processing of the multi-dimensional parameters involved in variant analysis, The example flowchart of FIG. 34 includes a step 1112 of determining whether to continue evaluation of candidates of the set of variants. If the set of high-performing variants includes at least a desired or target number of high-performing variants, or if the set of high-performing variants includes at least one high-performing variant that satisfies at least one target criterion (e.g., a likelihood of a cause of the bottleneck as indicated by the variant and/or a manner of reducing and/or avoiding the bottleneck during the biologic synthesis process due to one or more features of the variant), the evaluation may continue to step 4118. If the set of high-performing variants does not include at least a desired or target number of high-performing variants and/or does not include at least one high-performing variant that satisfies at least one target criterion, the evaluation may evaluate additional sets of candidates. If at least one high-performing variant has been identified, the evaluation may proceed to step 4116 by including, in the set of candidates, at least one additional variant that is based on at least one of the high-performing variants (e.g., a depth-based search in a proximity of the at least one high-performing variant). Alternatively or additionally, the evaluation may proceed to step 4114 by including, in the set of candidates, at least one additional variant from the set of variants (e.g., a breadth-based search of additional variants that are not in a proximity of the previously evaluated variants).

The example flowchart of FIG. 34 includes a step 4114 of outputting the high-performing variants as adjusted biologic synthesis processes. The outputting may include, for example, presenting a report of the high-performing variants of the biologic synthesis process based on the evaluation. The outputting may include presenting a report of the performance of the high-performing variants of the biologic synthesis process (e.g., a result of a laboratory experiment and/or simulation that demonstrates the occurrence of the bottleneck during the biologic synthesis process, a cause of the bottleneck in the biologic synthesis process, and/or a manner of reducing or avoiding the bottleneck of the biologic synthesis process). The outputting may include presenting an explanation of the high-performing variants of the biologic synthesis process (e.g., an explanation of the features of the variant that cause and/or contribute to the occurrence of the bottleneck during the biologic synthesis process). The outputting may include presenting a report of the determined cause of the bottleneck (e.g., a result of a laboratory experiment and/or simulation that demonstrates, explains, and/or verifies the determined cause of the bottleneck). The outputting may include presenting an explanation of the determined cause of the bottleneck (e.g., an explanation of the features of the biologic synthesis process that were determined to be the cause of the bottleneck). The outputting may include initiating the adjusted biologic synthesis processes, or altering an existing and/or ongoing biologic synthesis process according to the adjusted biologic synthesis process. The outputting may include initiating the adjusted biologic synthesis process to evaluate and/or verify the determined cause of the bottleneck.

In some example embodiments, evaluating the set of variants of the biologic synthesis process includes comparing a simulation of the biologic synthesis process with a simulation of each variant of the set of variants of the biologic synthesis process. Alternatively or additionally, evaluating the set of variants may include comparing an experimental result of the biologic synthesis process with an experimental result of a respective experiment of each variant of the set of variants of the biologic synthesis process.

In some example embodiments, evaluating the set of variants of the biologic synthesis process includes determining, within an embedding space, a location of each variant of the set of variants of the biologic synthesis process. For example, the embedding space may include at least two dimensions that respectively represent a feature of the biologic synthesis process. The location of a respective variant of the set of variants further comprises a vector within the embedding space, wherein respective dimensions of each vector correspond to a feature of the respective variant of the biologic synthesis process. Evaluating the set of variants of the biologic synthesis process may include identifying, within the embedding space, at least one region of variants that reduce at least one bottleneck of the biologic synthesis process. In some example embodiments, the evaluating may selectively focus on variants that are within at least one region of variants that reduce the at least one bottleneck of the biologic synthesis process. In some example embodiments, the embedding space may be represented as a heat map, wherein each location within the embedding space is associated with a temperature that is related to an effect of a variant at the location on the at least one bottleneck of the biologic synthesis process.

Figure 35:
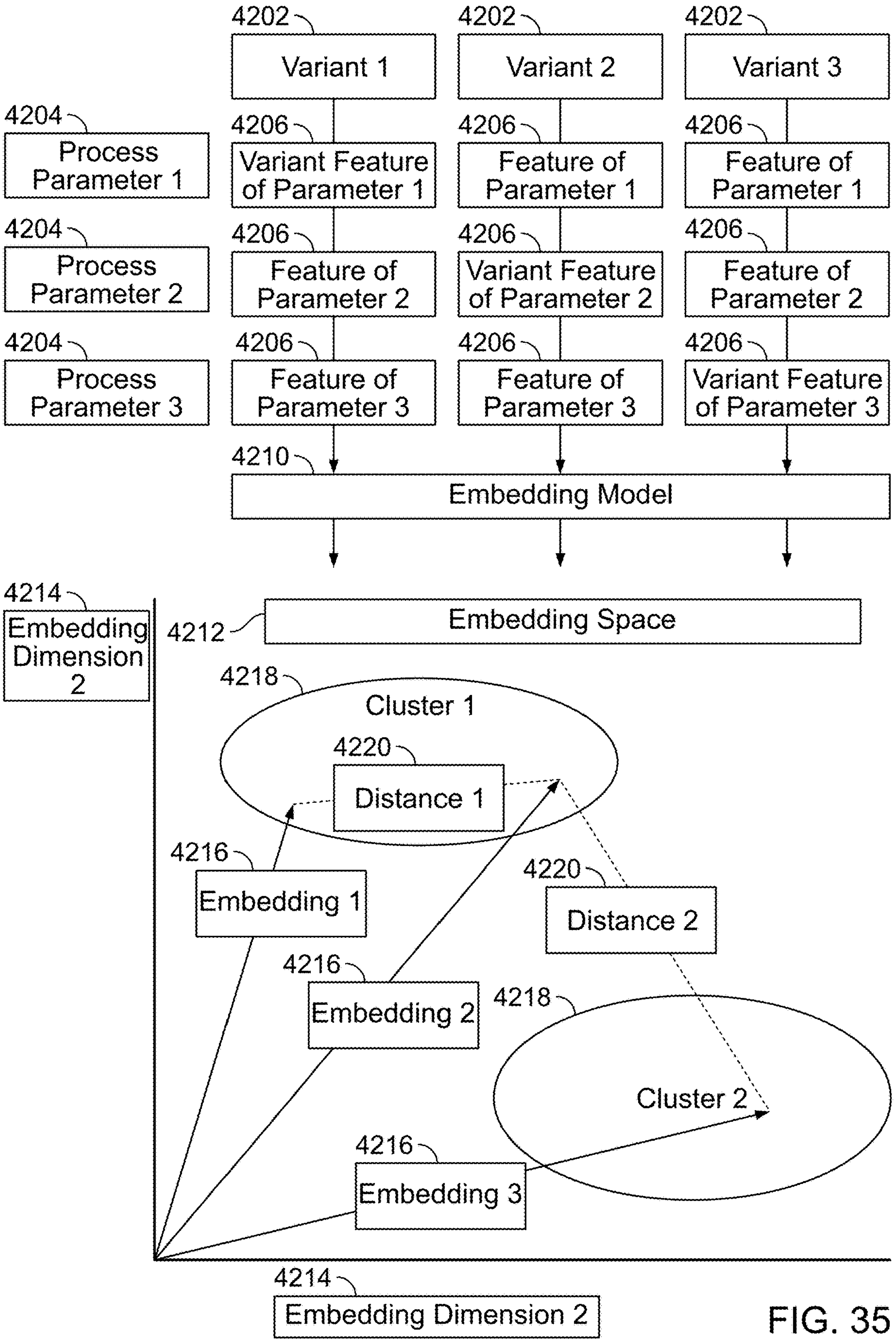
FIG. 35 is an example of an embedding space including vector representations of variants of a biologic synthesis process according to some example embodiments.

FIG. 35 is an example of an embedding space including vector representations of variants of a biologic synthesis process according to some example embodiments. As shown in FIG. 35, a set of variants 4202 of a biologic synthesis process are provided, each having a set of features 4206 of various parameters 4204 the biologic synthesis process that include one variant feature 4206. For each variant 4202, the features 4206 of the various process parameters 4204 are provided as input to an embedding model 4210, which may have been trained (e.g., on the biologic synthesis process 4202 or other biologic synthesis processes 4202) to generate an embedding 4216 as a vector representation of the features 4206 of the variant 4202 for the respective process parameters 4204 of the biologic synthesis process within an embedding space 4212. The embedding space 4212 may include a number of embedding dimensions 4214, each embedding dimension 4214 representing one or more process parameters 4204 of the biologic synthesis process, a combination of process parameters 4204 of the biologic synthesis process, a derived process parameter of the biologic synthesis process based on the process parameters 4204 of the biologic synthesis process, or the like. Within the embedding space 4212, the embedding distance 4220 between the locations of two or more embeddings 1218 for two or more variants 4202 may represent an indicator of similarity between or among the two or more variants 4202 of the biologic synthetic process. Each distance 4220 may be determined, for example, as a cosine similarity of the vector representations of the embeddings 4216 of the respective variants 4202 of the biologic synthesis process within the embedding space 4212. For example, a first distance 4220 between the vector representations of the embeddings 4216 for a first variant 4202 of the biologic synthesis process and a second biologic product 4202 may be small, indicating a proximity of the first variant 4202 and the second variant 4202 within the embedding space 3612 and an outcome similarity of the first variant 4202 and the second variant 4202. By comparison, a second distance 4220 between the vector representations of the embeddings 4216 for the second variant 4202 and a third variant 4202 may be large, indicating a lack of proximity of the second variant 4202 and the third variant 4202 within the embedding space 4212 and a dissimilarity of outcomes of the second variant 4202 and the third variant 4202. Further, the locations of the embeddings 4216 within the embedding space 4212 may enable the determination of clusters 4218 of variants 4202 that share similar outcomes and/or that may exhibit various bottlenecks, such as mutual execution of a metabolic pathway.

Although the embedding space 4212 in the example of FIG. 35 includes only two embedding dimensions 4214, other embedding spaces 4212 for other groups of variants 4202 may include a different and potentially large number of embedding dimensions 4214, each representing one or more variant features of the respective process parameters 4204 of the biologic synthesis process, thereby enabling a rich representation of the biologic synthesis process according to its respective process parameters 4204 and variants thereof. Additionally, the embedding space 4212 may enable dimensionality reduction, wherein a large set of process parameters 4204 is reduced to a small set of highly significant embedding dimensions 4214 and a lower dimensionality of the vector representations of the embeddings 4216. Due to a small number of dimensions 4214, the embedding model 4210 may be coerced to represent the respective variants 4202 only according to the most significant and distinctive features and variants thereof that indicate proximity or distance therebetween. The achieved dimensionality reduction may promote the generalization from learned associations related to the biologic synthesis process and bottlenecks arising therein to corresponding associations between variants 4202 that are superficially dissimilar, but that share key similarities that indicate mutual inclusion in a cluster 4218 of similar variants 4202. For example, a first variant 4202 may include a variant feature 4206 of a temperature parameter that increases a temperature of the biologic synthesis process, and a second variant 4202 may include a variant feature of a concentration of a material in the environment of the biologic synthesis process. While superficially dissimilar, the variant features of both variants 4202 may have a similar effect, e.g., a deactivation of an enzyme at a particular step in the biologic synthesis process, either due to a temperature difference that reduces the activity of the enzyme or due to a change in the concentration of a material that affects the enzyme. The similarity of the outcomes of the variants 4202, as indicated by a proximity within the embedding space 4212, despite their dissimilar variant features 4206, may serve as an indicator of the cause of the bottleneck and various adjustments of the biologic synthesis process that may reduce or avoid the bottleneck.

In some implementations, the generation and analysis of the embedding space may leverage distributed computing for efficient processing of high-dimensional data. For example, the platform 100 may calculate embedding vectors for large sets of variants using multiple processing nodes, with each node handling a subset of variants and their associated features. Similarly, the platform 100 may parallelize distance calculations between embeddings across multiple processing units, with each unit computing distances for a portion of the embedding space. In embodiments, matrix processing units (e.g., GPUs, NPUs, TPUs, FPGAs, etc.) may be employed for efficient calculation of embedding distances and cluster boundaries, reducing power consumption compared to general-purpose processors performing the same calculations.

In some example embodiments, combinations and/or variants of one or more variants of a biologic synthesis process may be selected for evaluation based on the distances between the vector representations of the embeddings 4216 of the variants and the one or more embedding dimensions 4214 within the embedding space 4212. In some example embodiments, variants of the biologic synthesis process may be generated within a proximity of within the embedding space 4212. For example, variants of the biologic synthesis process may be determined and selected for evaluation only within an embedding distance along one or more embedding dimensions 4214 in the embedding space 4212 that correspond to one or more process parameters 4204 of the biologic synthetic process. Variants that are not proximate within the embedding space 4212 (e.g., variants that are too different in process parameters 4204 and variant features 4206 thereof from the original biologic synthesis process) may be excluded from evaluation as candidates for the adjusted biologic synthesis process. In some example embodiments, a variant of the biologic synthesis process may be selected for evaluation based on whether an embedding distance between the variant and the original biologic synthesis process is within an embedding distance threshold. In some example embodiments, a variant of the biologic synthesis process may be selected for evaluation based on whether one or more embedding distances between the variant and the biologic synthesis process within the embedding space 3612 are within an embedding distance threshold. The embedding distance thresholds may be individually specified for each process parameter 4204 and/or embedding dimension 4214, and the selection of variants for evaluation may be based on whether the embedding distance between each variant and the biologic synthesis process within the embedding space 4212 is within the corresponding embedding distance threshold. Alternatively or additionally, an embedding distance threshold may be specified as an aggregate embedding distance threshold between the variant and the biologic synthesis process within the embedding space 4212, and the selection of the variant for evaluation may be based on whether an aggregation of the embedding distances between the variant and the biologic synthesis process is within the aggregate embedding distance threshold. The use of embedding distance thresholds within the embedding space 4212 may promote the selective and/or preferential evaluation of variants that are similar to the original biologic synthesis process.

Figure 36:
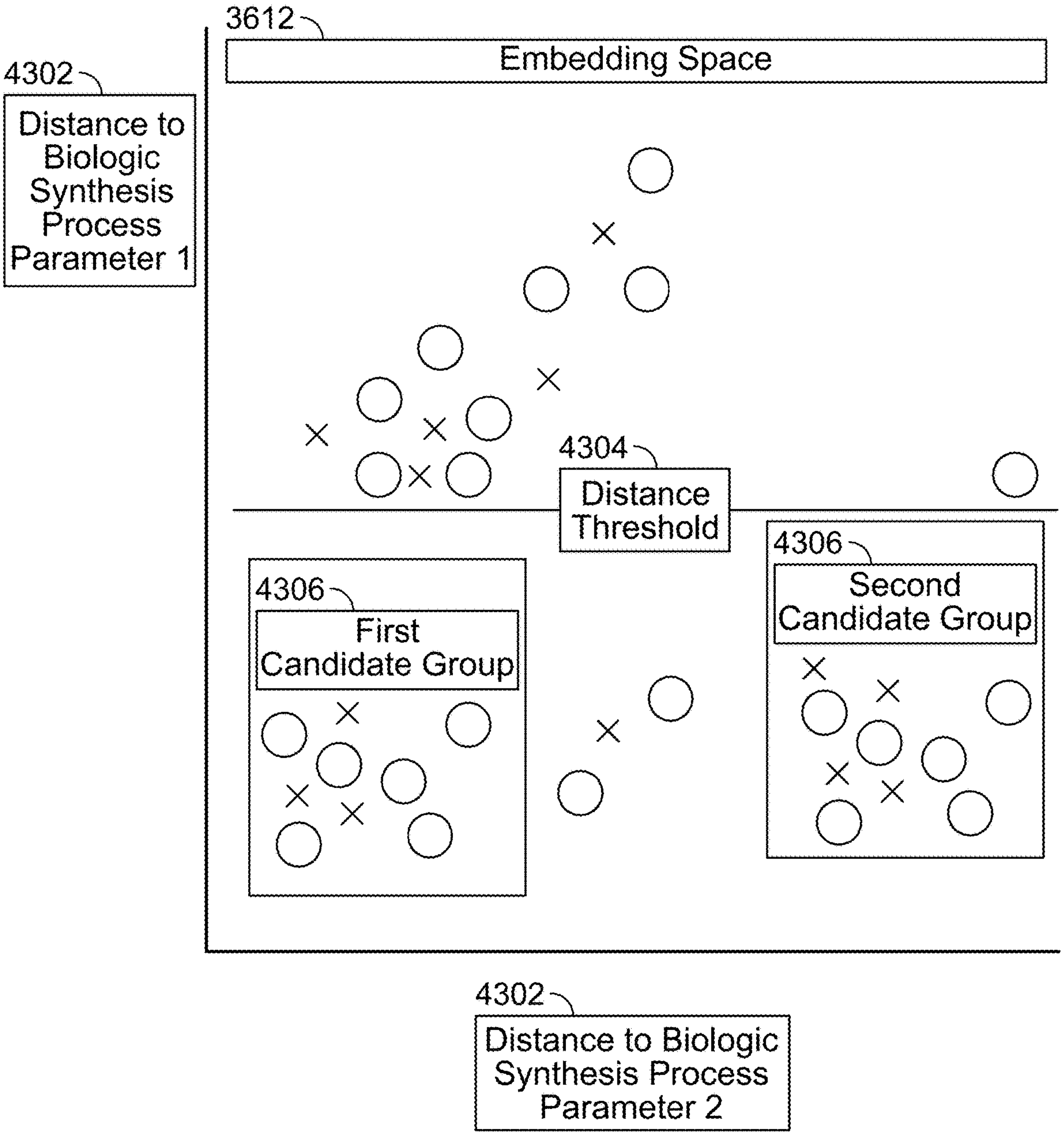
FIG. 36 is an illustration of an evaluation of a set of candidate variations according to some example embodiments.

FIG. 36 is an illustration of an evaluation of a set of candidate variants according to some example embodiments. In FIG. 36, a set of variants are determined and mapped into an embedding space 4212. The embedding space 1212 in FIG. 36 includes, as a first dimensional axis, a distance 4302 of the respective variants to a first process parameter of the biologic synthesis process. The embedding space 1212 in FIG. 36 includes, as a second dimensional axis, a distance 4302 of the respective variants to a second process parameter of the biologic synthesis process. Further, each variant is associated with a viability score. Combinations having a viability score above a viability score threshold (e.g., at least a minimum viability score indicating at least a minimum likelihood of an adjusted biologic synthesis process according to the variant) are shown in FIG. 36 as circles, which are eligible for evaluation as candidate variants of the biologic synthesis process. Combinations having a viability score below the viability score threshold (e.g., failing to satisfy a minimum viability score indicating a minimum likelihood of a success of an adjusted biologic synthesis process according to the variant) are shown in FIG. 36 as crosses, and are excluded from evaluation as candidate variants of the biologic synthesis process.

As shown in FIG. 36, a first stage of evaluation includes a selection of variants for a first candidate group 4306. The first candidate group 4306 may include the candidates having a comparatively small distance 4302 to both the first process parameter of the biologic synthesis process (along the first dimensional axis) and the second process parameter of the biologic synthesis process (along the second dimensional axis), and also having a viability score that satisfies the viability score threshold. The first candidate group 4306 may also be defined as being within a distance threshold 4304 of the first process parameter of the biologic synthesis process (e.g., not varying too far from the first process parameter of the original biologic synthetic process). An evaluation of the first candidate group 4306 may result in the determination of one or more high-performing candidates. In this case, further stages of evaluation may include the evaluation of additional variants that are within a proximity of the first candidate group 4306 in the embedding space 4212. Alternatively or additionally, further stages of evaluation may include the evaluation of a second candidate group 4306 of variants that are distant more distant from the second process parameter of the biologic synthetic process, but that are still within the distance threshold 33104 of the first process parameter of the biologic synthetic process.

In some example embodiments, a first set of candidate combinations may include at least two alternative variants of a process parameter of the biologic synthesis process, wherein each of the at least two alternative variants includes a different variant of the process parameter of the biologic synthesis process. For example, the combinations of the first set of candidate variants may each include a first variant feature of changing a temperature of the biologic synthesis process, but the variants may include different feature variants of the same process parameter (e.g., increasing vs. decreasing the temperature inside a biologic fermentation tank). Alternatively or additionally, the first set of candidate variants may include at least one combination that includes a single process variant of the biologic synthesis process, and the second set of candidate variants may include at least one variant that includes at least two process variations of the biologic synthesis process (e.g., a change to both a temperature and a pressure inside the biologic fermentation tank). In this manner, the evaluation may include different kinds of variants relative to the process parameters of the original biologic synthesis process. Alternatively or additionally, further stages of evaluation may include the evaluation of a second candidate group 1306 of variants that are more distant from the second process parameter of the biologic synthesis process, but that are still within the distance threshold 1304 of the first process parameter of the biologic synthesis process.

In some example embodiments, an evaluation of a set of variants of the biologic synthesis process may include evaluating respective variants of the set of variants according to a ranking order of the set of variants. For example, for a respective variant of the set of variants, the evaluation may include determining a score based on a comparison between the respective variant and the biologic synthesis process, and determining the ranking order based on the score of the respective variant. The comparison includes at least one of a distance between the respective variant and the biologic synthesis process, a feature of at least one process parameter of the respective variant and a corresponding feature of the process parameter of the biologic synthesis process, or a measurement of a feature of the respective variant and a corresponding measurement of the feature of the biologic synthesis process. The evaluation may include selecting, from the set of variants, a first set of candidate variants based on the ranking order; evaluating the first set of candidate variants based on at least one objective of respective variants of the first set of candidate variants; and based on evaluating the first set of candidate variants, selecting a second set of candidate variants for evaluation. For example, evaluating the first set of candidate variants may include evaluating a simulation of respective variants of the first set of candidate variants and/or evaluating an experimental result of respective variants of the first set of candidate variants. The second set of candidate variants includes at least one further variant of at least one variant of the first set of candidate variants and/or at least one variant of the set of variants that is not included in the first set of candidate variants. The first set of candidate variants may include at least two alternative variant feature of a process parameter of the biologic synthesis process, wherein each of the at least two alternative variants includes a different variant feature of the process parameter of the biologic synthetic process and/or at least one variant that includes a single variant feature of a process parameter of the biologic synthesis process, and the second set of candidate variants includes at least one variant that includes variant feature of at least two different process parameters of the biologic synthesis process. The adjusted biologic synthesis process may be selected based on an evaluation of a set of variants of the biologic synthesis process that reduces at least one bottleneck of the biologic synthesis process.

In some example embodiments, the evaluation may include generating an analysis and/or visual representation of the embedding space and/or variants included therein. For example, the evaluation may generate a heatmap that indicates, based on a visual style that is associated with heat (e.g., a red color), an association of various portions of the embedding space with one or more bottlenecks. The heatmap may visually signify and/or represent various process parameters in a "hot" region of the embedding space that are likely to be causes and/or effects of a bottleneck. Alternatively or additionally, the evaluation may include at least one explanation of at least one variant of the biologic synthesis process, wherein the at least one explanation may indicate an effect of the at least one variant on the at least one bottleneck of the biologic synthesis process.

In some example embodiments, an adjustment of a biologic synthesis process to reduce or avoid a first bottleneck may inadvertently create a second bottleneck. For example, increasing a temperature inside a fermentation tank to maintain an activity of an enzyme may reduce a bottleneck based on the enzyme, but the increased temperature may also increase a pressure inside the fermentation tank that reduces an activation of another enzyme that is more sensitive to pressure. Accordingly, in some example embodiments, the evaluation may include identifying at least one additional bottleneck in the adjusted biologic synthesis process. Based on the identification of the additional bottleneck, the evaluation may include evaluating a set of further variants of the adjusted biologic synthesis process, and selecting a further adjusted biologic synthesis process, wherein the further adjusted biologic synthesis process includes at least one variant of the set of further variants that reduces the at least one additional bottleneck of the adjusted biologic synthesis process. In this manner, multiple bottlenecks may be resolved by an iterative or stepwise evaluation that addresses each bottleneck through different variants and resulting adjustments of the biologic synthesis process.

Figure 37:
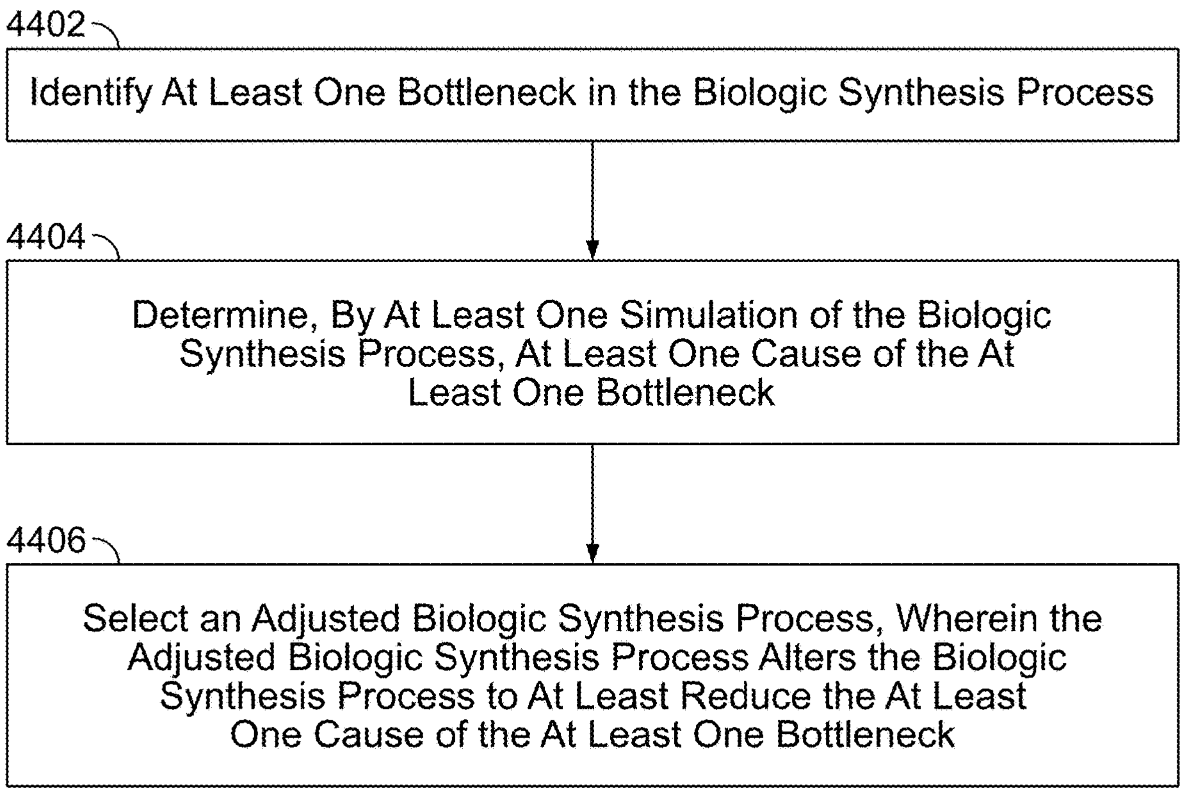
FIG. 37 is another flowchart that presents examples of methods of optimizing a biologic synthesis process according to some example embodiments.

Optimization by Simulating the Biologic Synthesis Process to Determine Cause of Bottlenecks FIG. 37 is another flowchart that presents an example method of optimizing a biologic synthesis process according to some example embodiments. The example method of FIG. 37 may be performed, for example, by the Optimize Workflows and Service Module 208 of the platform of FIG. 1.

The example flowchart of FIG. 37 includes a step 4402 of identifying at least one bottleneck in the biologic synthesis process. The biologic synthesis process may include (for example) a DNA synthesis process, an RNA synthesis process, a protein synthesis process, a metabolite synthesis process, a metabolic process, at least one pathway of a metabolic system, a plate growth process, a bioreactor process, or a downstream purification process. The biologic synthesis process may involve one or more biologic products, such as (for example) one or more biologic precursor of the biologic synthesis process, one or more reagents and/or starting materials of the biologic synthesis process, one or more biologic intermediaries of the biologic synthesis process, one or more enzymes and/or catalyst of the biologic synthesis process, and/or one or more biologic outputs of the biologic synthesis process. The biologic products may include (for example) an enzyme or non-enzyme protein, a DNA sequence, an RNA sequence, a plasmid, a metabolite, a cell line, a biologic strain of a microbe, or the like.

The biology synthesis process may be intended, designed, selected, and/or refined to generate one or more biologic products based on one or more objectives. The objectives may include, for example, an objective of synthesizing a biologic product with an activity of binding to a particular binding site, an inclusion in a metabolic process, a suitability as a precursor for another biologic process; an objective of synthesizing a biologic product that expresses a particular enzyme or other protein, that performs a metabolic pathway, or that exhibits a characteristic within an environment; an objective of determining a biologic synthesis process that includes an objective such as a yield, a reaction rate, or a consistency of a biologic product; a product expression objective; a product activation objective; a product reaction objective; an enzyme cleaning objective; a product stability objective; a product biocompatibility objective; a process rate objective; a process catalyzation rate objective; a process efficiency objective; a process cost objective; or a process yield objective. A bottleneck of the biologic synthesis process may affect any of these objectives of the biologic synthesis process. The bottleneck may include (for example) a growth rate bottleneck, a metabolite production rate bottleneck, a byproduct formation rate bottleneck, a protein expression level bottleneck, a process scale bottleneck, a process rate bottleneck, a product expression bottleneck, a product activation bottleneck, a process stability bottleneck, a process efficiency bottleneck, a process cost bottleneck, or a process yield bottleneck.

The example flowchart of FIG. 37 includes a step 4404 of determining, by at least one simulation of the biologic synthesis process, at least one cause of the at least one bottleneck. For example, the bottleneck may be monitored and/or evaluated through an effect of the bottleneck of the biologic synthesis process on these and other objectives. For example, the cause of the bottleneck may include a difference and/or change of at least one condition of the biologic synthesis process (e.g., a change of temperature and/or pressure, a change of the presence and components of reactants and/or nutrients, and/or a change of the order and/or timing of steps of the biologic synthesis process). The cause of the bottleneck may involve a side-effect or consequence of the biologic synthesis process that gradually and/or cumulatively limit the yield, rate, quality, or other feature of the biologic synthesis process, such as an accumulation of a metabolic byproducts that limits the yield, rate, quality, or other feature of the biologic synthesis process. The cause of the bottleneck may include a consumption and/or transformation of one or more materials of the biologic synthesis process, resulting in a reduced availability and/or elimination of the one or more materials that adversely affects the performance of the biologic synthesis process. The cause of the bottleneck may include one or more differences between a model or understanding of the biologic synthesis process and a reality of the biologic synthesis process. The cause of the bottleneck may include one or more differences between a performance of a model of the biologic synthesis process under some conditions (e.g., initial conditions in a biologic fermentation tank) and a different performance of the model under other conditions (e.g., later conditions in the biologic fermentation tank at a later point in the biologic synthesis process).

In step 4404, the cause of the bottleneck may be determined directly by the simulation. As a first such example, the simulation may include a digital twin of a biologic synthesis process, a biologic product, a metabolic pathway, a piece of equipment such as a fermentation tank, or the like. The simulation of the biologic synthesis process may include monitoring features of the digital twin during the simulation of the biological synthesis process to determine information about the bottleneck, such as a point at which the bottleneck occurs during the biological synthesis process and/or an effect of the bottleneck on another feature of the biologic synthesis process. The determination of the information about the bottleneck resulting from the simulation may inform a determination of the cause of the bottleneck.

As a second such example, features of the simulation of the biologic synthesis process may be compared with corresponding features of an instance of the biologic synthesis process in which the bottleneck occurs, such as a concurrently performed instance of the biologic synthesis process or a previous instance of the biologic synthesis process. Differences between the simulation of the biologic synthesis process and the performed instance of the biologic synthesis process may indicate information about the bottleneck, such as a point at which the bottleneck occurs during the biological synthesis process and/or an effect of the bottleneck on another feature of the biologic synthesis process. The determination of the information about the bottleneck resulting from the simulation may inform a determination of the cause of the bottleneck.

As a third such example, different simulations of the biologic synthesis process may be performed with variants of various features, such as at least one condition of the biologic synthesis process and/or at least one material included in the biologic synthesis process. For example, a first simulation of the biologic synthesis process may hold all properties of the original biologic synthesis process constant, while variant simulations of the biologic synthesis process may vary one or more properties of the original biologic synthesis process. Differences in the progression of the different variants of the biologic synthesis processes may produce information about the bottleneck, such as a point at which the bottleneck occurs during the biological synthesis process and/or an effect of the bottleneck on another feature of the biologic synthesis process. The determination of the information about the bottleneck resulting from the simulation may inform a determination of the cause of the bottleneck. For example, a bottleneck may involve a reduced rate of the biologic synthesis process. As compared with a first simulation of the biologic synthesis process, a variant simulation that reduces a temperature of the biologic synthesis process by a particular factor may closely match the conditions of a performed instance of the biologic synthesis process that includes an occurrence of the bottleneck, suggesting that a reduced temperature may be a cause of the bottleneck. A set of possible causes may be developed through variant simulations of the biologic synthesis process, and may be compared with corresponding measurements of a performed instance of the biologic synthesis process to determine the cause of the bottleneck. For instance, a measurement of the temperature of the biologic synthesis process at a particular point (e.g., within a biologic fermentation tank during a particular step of the biologic synthesis process) may reveal an unexpectedly reduced temperature. The matching of resulting features of the biologic synthesis process with corresponding features of the simulation variant of the biologic synthesis process may suggest and/or verify that the bottleneck is caused by the variant conditions of the simulation variant.

In embodiments, the platform 100 may execute the variant simulations (e.g., one or more simulations which may follow any of the above examples) using a distributed computing architecture that enables parallel simulation of multiple process variants. For example, different computing nodes may simulate different parameter combinations simultaneously, and the platform 100 may aggregate the results. In this example, each computing node may maintain a local cache of commonly accessed simulation parameters and/or intermediate results. The platform 100 may dynamically allocate computational resources to different variant simulations based on the complexity of the corresponding simulation, thereby reducing overall simulation time.

In some cases, the bottleneck may be observed based on a downstream effect (e.g., a reduced yield of a biologic product of the biologic synthesis process), but the downstream effect may be caused by an upstream effect of the bottleneck on a preceding portion of the biologic synthesis process. For example, an instance of the biologic synthesis process may be observed to have a reduced yield as compared with an expected yield and/or a yield of previous instances of the biologic synthesis process, due to an apparent bottleneck at a final synthesis step of the biologic synthesis process. However, the bottleneck may actually occur during an intermediate step of the biologic synthesis process that limits the production of a biologic intermediary product that is an input to the final synthesis step of the biologic synthesis process. A review of the perceived effect of the bottleneck (e.g., measurements of the conditions of the biologic synthesis process during the final synthesis step) may reveal the occurrence of the bottleneck at another point in the biologic synthesis process (e.g., an unexpected depletion of the biologic intermediary product as input to the final synthesis step) and the actual cause of the bottleneck.

The example flowchart of FIG. 37 includes a step 4406 of selecting an adjusted biologic synthesis process, wherein the adjusted biologic synthesis process alters the biologic synthesis process to at least reduce the at least one cause of the at least one bottleneck. The selecting may include, for example, presenting a report of the determined cause of the bottleneck due to the simulation. The outputting may include presenting a report of the determined cause of the bottleneck (e.g., a result of a laboratory experiment and/or simulation that demonstrates, explains, and/or verifies the determined cause of the bottleneck). The outputting may include at least one explanation of at least one variant of the biologic synthesis process, wherein the at least one explanation indicates an effect of the at least one variant on the at least one bottleneck of the biologic synthesis process. The outputting may include presenting an explanation of the determined cause of the bottleneck (e.g., an explanation of the features of the biologic synthesis process that were determined to be the cause of the bottleneck). The outputting may include initiating the adjusted biologic synthesis processes, or altering an existing and/or ongoing biologic synthesis process according to the adjusted biologic synthesis process. The outputting may include initiating the adjusted biologic synthesis process to evaluate and/or verify the determined cause of the bottleneck.

Additional Embodiments

In embodiments, a method of optimizing a biologic synthesis process includes identifying at least one bottleneck in a biologic synthesis process, selecting, from a set of optimization strategies, an optimization strategy for the biologic synthesis process, wherein the selected optimization strategy is associated with the at least one bottleneck, and selecting an adjusted biologic synthesis process, wherein the adjusted biologic synthesis process is based on applying the selected optimization strategy to the biologic synthesis process, and the adjusted biologic synthesis process reduces the at least one bottleneck of the biologic synthesis process.

In embodiments, the optimization strategy is selected by an optimize system that has been trained on at least one data set that indicates relationships between biologic synthesis processes and outcomes.

In embodiments, the optimization strategy is selected from an optimization strategy database, and the optimization strategy database indicates, for at least one optimization strategy, at least one of a source of the optimization strategy, a requirement of the optimization strategy, an application of the optimization strategy, an optimization effect of the optimization strategy, or a side-effect of the optimization strategy.

In embodiments, at least one optimization strategy included in the optimization strategy database is based on at least one of: at least one feature of at least one experiment associated with the optimization strategy, at least one feature of at least one industrial process associated with the optimization strategy, at least one feature of at least one simulation of a biologic synthesis process, wherein the at least one simulation is associated with the optimization strategy, or at least one feature of at least one report included in a natural-language knowledge, wherein the at least one report is associated with the optimization strategy.

In embodiments, the optimization strategy is selected by a reinforcement-learning-based machine learning model, the reinforcement-learning-based machine learning model has been trained to optimize biologic synthesis processes based on a reinforcement learning policy, and the selected optimization strategy is based on the reinforcement learning policy.

In embodiments, selecting the adjusted biologic synthesis process includes, performing a simulation of the adjusted biologic synthesis process, and comparing at least one feature of the simulation of the adjusted biologic synthesis process with a corresponding at least one feature of the biologic synthesis process, wherein the at least one feature is associated with the at least one bottleneck.

In embodiments, a method of optimizing a biologic synthesis process includes selecting at least one objective of the biologic synthesis process, identifying at least one bottleneck in the biologic synthesis process that relates to the at least one objective; and selecting an adjusted biologic synthesis process, wherein the adjusted biologic synthesis process includes at least one variant of a set of variants of the biologic synthesis process, each variant of the set of variants relates to the at least one bottleneck, and each variant of the set of variants reduces the at least one bottleneck of the at least one objective of the biologic synthesis process.

In embodiments, the at least one objective is associated with a techno-economic analysis of the biologic synthesis process, the at least one bottleneck in the biologic synthesis process is associated with the techno-economic analysis, and the set of variants is determined based on the techno-economic analysis.

In embodiments, selecting the adjusted biologic synthesis process includes performing a simulation of the adjusted biologic synthesis process, and performing a comparison of the biologic synthesis process and the simulation of the adjusted biologic synthesis process, wherein the comparison is based on the at least one bottleneck of the at least one objective.

In embodiments, selecting the adjusted biologic synthesis process includes, performing a simulation of the adjusted biologic synthesis process, and performing a comparison of the biologic synthesis process and the simulation of the adjusted biologic synthesis process, wherein the comparison includes a comparison of the at least one bottleneck of the at least one objective in the biologic synthesis process and a corresponding bottleneck of the at least one objective in the simulation of the adjusted biologic synthesis process.

In embodiments, the simulation of the adjusted biologic synthesis process is based on a digital twin of at least one component of the biologic synthesis process.

For example, an optimization strategy database may be generated based on optimizations of various biologic parents, biologic synthesis processes, biologic products, or the like, wherein the optimizations are determined from various sources, such as experiments, simulations, scientific journals, or the like. The optimization strategies may include, for example, variants and/or edits of biologic parents; variants of the biologic synthesis processes, such as changes to process parameters, components or equipment, metabolic factors, an order or scale of process steps, or the like; and/or variants and/or edits of biologic products. The optimization strategies may be associated with various objectives (e.g., improving yield, improving scale and/or scalability, improving efficiency, improving and/or controlling rate, improving quality or monitoring capability, or the like). The optimization strategies may be derived from a source (e.g., a first experiment, environment, simulation, strain, biologic parent(s), biologic synthesis process, biologic product, or the like) and may be applied to a target (e.g., a second experiment, experiment, environment, simulation, strain, biologic parent(s), biologic synthesis process, biologic product, or the like).

A biologic synthesis process may be adjusted based on one or more optimization strategies to reduce bottlenecks in the biologic synthesis process. For example, for a particular objective such as improving the yield of a biologic synthesis process, optimization strategies that relate to yield improvements may be identified, selected from an optimization strategy database, and applied to adjust the biologic synthesis process. The bottleneck may involve features of the biologic process that are determined to affect the policy, such as the features of biologic parents and/or the biologic synthesis process that create a bottleneck on scaling yield by scaling the biologic parents and/or biologic synthesis process.

In some cases, the identification may be based on a simulation of the adjusted biologic synthesis process (e.g., a simulation of a biologic synthesis process conducted through a digital twin of a bioreactor). The simulation of one or more adjusted biologic synthesis processes may inform the selection and/or comparison of various optimization strategies that may be applied to the biologic synthesis processes in furtherance of one or more objectives. Alternatively or objectively, the selection and/or analysis of optimization strategies for a biologic synthesis process may be performed by a reinforcement-learning-based machine learning model. For example, an RL-based machine learning model may be trained to evaluate biologic synthesis processes according to a policy, wherein the policy indicates various objectives of the biologic synthesis process and, optionally, a prioritization thereof. The RL-based machine learning model may apply different optimization strategies to the biologic synthesis process (e.g., by simulating the adjusted biologic synthesis processes according to the policy) and may conduct an analysis and/or comparison of how the optimization strategies affect the policy and the objectives indicated therein. Based on the analysis and/or comparisons, the RL-based machine learning model may be trained to select optimization strategies for biologic synthesis processes that promote the objectives of the policy. After the RL-based machine learning model is trained, a particular biologic synthesis process may be adjusted based on an optimization strategy determined by the RL-based machine learning model, wherein the RL-based machine learning model selects optimization strategies that address (e.g., reduce and/or eliminate) the objectives indicated in the policy.

AI-Guided Analytic Platform

In some example embodiments, an AI-guided analytic platform may perform the development of biologic synthesis processes as discussed herein. The AI-guided analytic platform may include one or more processors and a memory storing instructions that, when executed by the one or more processors, cause the AI-guided analytic platform to perform steps including identifying at least one bottleneck in a biologic synthesis process; evaluating a set of variants of the biologic synthesis process; and selecting an adjusted biologic synthesis process, wherein the adjusted biologic synthesis process includes at least one variant of the set of variants that reduces the at least one bottleneck of the biologic synthesis process. The biologic synthesis processes developed by the AI-guided analytic platform may include a DNA synthesis process, an RNA synthesis process, a protein synthesis process, a metabolite synthesis process, a metabolic process, at least one pathway of a metabolic system, a plate growth process, or a fermentation process.

In some example embodiments, the AI-guided analytic platform may run simulations to determine enzyme bottlenecks in pathway optimization. For example, the -guided analytic platform may execute a simulation including a digital twin of a biologic synthesis process, a biologic product, a metabolic pathway, a piece of equipment such as a fermentation tank, or the like. The simulation of the biologic synthesis process may include monitoring features of the digital twin during the simulation of the biological synthesis process to determine information about the bottleneck, such as a point at which the bottleneck occurs during the biological synthesis process and/or an effect of the bottleneck on another feature of the biologic synthesis process. The determination of the information about the bottleneck resulting from the simulation may inform a determination of the cause of the bottleneck.

In some example embodiments, the AI-guided analytic platform may develop biologic synthesis processes involved in various biotechnology scenarios, including (for example) protein optimization, genetic generalization, and/or predictions of laboratory experiments and/or industrial-scale synthesis in fermentation tanks. The AI-guided analytic platform may provide an explanation of an evaluation of the biologic synthesis process.

In some example embodiments, an AI-guided analytic platform for development of biologic synthesis processes may include one or more processors and a memory storing instructions that, when executed by the one or more processors, cause the AI-guided analytic platform to implement a system that evaluates the biologic synthesis processes, wherein the system includes at least one simulation system that is configured to simulate biologic synthesis processes to identify bottlenecks in the biologic synthesis processes. The biologic synthesis processes developed by the AI-guided analytic platform may include a DNA synthesis process, an RNA synthesis process, a protein synthesis process, a metabolite synthesis process, a metabolic process, at least one pathway of a metabolic system, a plate growth process, or a fermentation process.

In some example embodiments, the system may run the simulations to determine enzyme bottlenecks in pathway optimization. The simulation may include and/or be performed by a set of models configured to evaluate biologic synthesis processes wherein the set of models provides an explanation of an evaluation of the biologic synthesis processes. The simulation may include ranking variants of biologic synthesis processes in protein optimization; ranking variants of biologic synthesis processes in genetic generalization; and/or ranking variants of biologic synthesis processes in predictions in fermentation tanks.

At a conclusion of the evaluation, the platform may generate an output set of high-performing variants of the biologic synthesis process. The platform may include, in the output set, annotations and/or descriptions of the high-performing variants of the biologic synthesis process (e.g., a comparative advantage of each high-performing variant in the output set relative to other variants of the biologic synthesis process and/or the original biologic synthesis process).

AI-Driven Fermentation System

In embodiments, provided herein is an AI-guided synthetic biology development platform having a system for designing, optimizing, and/or manufacturing biosynthetic fuel.

In embodiments, the platform 100 may include an AI-driven fermentation system. The AI-driven fermentation system may include hardware and software components working together to enable AI-controlled fermentation. The fermentation system may include a fermentation chamber constructed from stainless steel, glass, and/or other biocompatible materials, configured to contain a fermentation medium.

A fermentation medium may refer to a liquid or semi-solid substrate that provides necessary nutrients and environmental conditions to support microbial growth and metabolic activities during fermentation. The medium typically contains carbon sources such as glucose, sucrose, or other metabolizable sugars; nitrogen sources including amino acids, proteins, or inorganic nitrogen compounds; trace elements such as iron, zinc, and manganese; vitamins and growth factors; and buffering agents to maintain optimal pH. The composition of the fermentation medium may be optimized for specific microorganisms and desired products, with components selected to maximize yield and productivity. The medium can be supplemented with precursor molecules, enzyme inducers, or other additives that enhance product formation. During fermentation, the medium composition changes as nutrients are consumed and metabolic products accumulate, requiring monitoring and potential supplementation to maintain optimal growth conditions. The physical properties of the medium, including viscosity, osmolality, and surface tension, can affect mass transfer and mixing characteristics within the fermentation chamber.

In embodiments, the fermentation system includes integrated ports for sensor mounting, sampling access, and media addition and/or removal capabilities. In embodiments, the fermentation chamber integrates with a rapid sampling system and/or an automated "omics" for generalization ("auto-OMG") system.

The fermentation system may include a plurality of sensors configured to measure fermentation parameters. Such sensors may include, but is not limited to, temperature sensors, pH sensors, dissolved oxygen sensors, biomass sensors, and substrate concentration sensors. The sensors may be implemented with specific hardware configurations. For example, the fermentation system may include a set of temperature sensors having a platinum RTD (PT100) probe mounted in a sanitary thermowell, which provides temperature measurements with ±0.1° C. accuracy. In another example, the fermentation system may include a set of pH sensors that may utilize industrial glass electrodes with built-in temperature compensation and digital signal processing, measuring pH from 2-12 with ±0.01 resolution. In yet another example, the fermentation system may include a set of oxygen sensors that employ optical sensing technology based on fluorescence quenching, enabling non-invasive measurement of dissolved oxygen from 0-100% saturation. In yet another example, the fermentation system may include a set of biomass sensors that implement real-time capacitance measurement at multiple frequencies (0.1-10 MHz) to determine viable cell density independent of media conditions. In yet another example, the fermentation system may include a set of substrate concentration sensors that use near-infrared (NIR) spectroscopy (e.g., near-infrared (NIR) sensors) with multivariate calibration models to monitor key metabolites. In yet another example, the substrate concentration sensors may use Raman spectroscopy (e.g., Raman sensors) with AI-driven multivariate analysis to correlate Raman spectral data with known substrate concentrations. In embodiments, the fermentation system may include additional sensors to enable comprehensive process monitoring and control, including redox sensors, optical sensors, infrared sensors, pressure sensors, precision flow meters, conductivity sensors, turbidity sensors, fluorescence-based detection systems, enzymatic electrodes, biosensors, weight sensors, acoustic sensors, ion-selective electrodes, heat flux sensors, and imaging sensors, among many others. Advanced redox sensors utilizing platinum electrodes can measure oxidation-reduction potential, providing insight into metabolic states. Foam detection may be achieved through conductivity or optical sensors that monitor foam formation and trigger control responses. Gas composition analysis can be performed using mass spectrometry or infrared sensors to measure oxygen, carbon dioxide, and other gases in the exhaust stream. Pressure sensors monitor both headspace and internal vessel conditions, while precision flow meters measure media addition and removal rates. Conductivity sensors track ionic content and media composition changes throughout the fermentation process. Turbidity sensors employing optical scatter methods provide additional data on cell density, while specialized viscosity sensors monitor the rheological properties of the fermentation broth. Cell viability may be assessed through fluorescence-based detection systems, and specific metabolites can be measured using enzymatic electrodes or biosensors. Gravimetric monitoring is enabled by weight sensors, while acoustic sensors can track cell density and bubble size distributions. Multiple-frequency capacitance measurements offer alternative approaches to biomass quantification. UV-Vis spectrophotometry enables both optical density measurements and metabolite analysis. Ion-selective electrodes provide specific ion monitoring capabilities, while heat flux sensors measure metabolic activity. Advanced imaging sensors based on microscopy techniques can analyze cell morphology in real-time, providing detailed information about cellular states and population dynamics.

In embodiments, the fermentation system may include a control system that is operatively coupled to the fermentation chamber and the plurality of sensors. The control system may include one or more processors and memory storing instructions that, when executed by the one or more processors, cause the control system to receive sensor data from the plurality of sensors, process the sensor data using a set of AI-based learning models to determine optimal fermentation parameters, generate control signals based on the desired optimal fermentation parameters, and adjust operating conditions of the fermentation chamber based on the control signals. In some embodiments, the control system may include one or more processors and memory storing instructions that, when executed by the one or more processors, cause the control system to receive sensor data from the plurality of sensors, process the sensor data using a set of AI-based learning models to determine a set of fermentation parameters, wherein the determined set of fermentation patterns are configured to generate additional training data for improving the set of AI-based learning models, generate control signals based on the desired optimal fermentation parameters, adjust operating conditions of the fermentation chamber based on the control signals, collect response data indicating the effects of the adjusted operating conditions, and update the set of AI-based learning models using the collected response data as additional training data.

The control system may execute its functions by receiving sensor data through industrial communication protocols, pre-processing data to remove noise and normalize values, feeding processed data through the set of AI-based learning models, converting model outputs into specific control actions, implementing control actions through actuators and control elements, and logging all operations for traceability.

In embodiments, the control system may be configured to analyze historical fermentation data through automated data mining algorithms that identify correlations between process parameters and fermentation outcomes. Pattern recognition may be implemented using statistical methods and/or neural network feature extraction. The prediction of optimal parameters utilizes reinforcement learning techniques to maximize a defined yield objective function.

The set of AI-based learning models may comprise various architectures and approaches to machine learning, including but not limited to: transformer models, convolutional neural networks, deep learning models, supervised models, semi-supervised models, unsupervised models, reinforcement models, long short-term memory (LSTM) models, multi-layer perceptron, lin-log models, large language models, large protein models, and protein language models.

The AI-based learning models may be implemented using various architectural configurations and combinations to optimize performance for specific tasks. In an example, the AI-based learning models may be implemented as a deep neural network architecture with input layers processing standardized sensor data streams, multiple LSTM layers for temporal pattern recognition, dense hidden layers with dropout for robust feature extraction, and output layers predicting optimal control parameters. The models may be trained on historical fermentation data using supervised learning with recorded process parameters and yield data as training examples. Continuous model updating may be achieved through online learning algorithms that incorporate new sensor data and fermentation results to refine model weights and biases.

The platform 100 may execute the set of AI-based learning models using adaptive computation techniques that dynamically adjust a model's computational complexity based on input complexity. For example, when processing simple parameter sets, the platform 100 may execute the AI-based learning model using a reduced number of layers or attention heads to conserve computational resources. Conversely, for complex parameter sets requiring more detailed analysis, the platform 100 may dynamically configure the AI-based learning model to activate additional layers and/or computational pathways.

Fermentation parameters may refer to measurable physical, chemical, and biological variables that characterize and influence the fermentation process conditions, cellular metabolism, and product formation. These parameters serve as quantifiable indicators used to monitor, control, and optimize fermentation processes to achieve desired outcomes in terms of growth, productivity, and product quality. In embodiments, fermentation parameters may include temperature of the fermentation medium, pH level of the fermentation medium, dissolved oxygen concentration, pressure within the fermentation chamber, agitation rate, nutrient feed rate, substrate concentration, metabolite concentration, cell density, gas flow rate, foam level, viscosity of the fermentation medium, redox potential, carbon dioxide evolution rate, oxygen uptake rate, osmotic pressure, specific growth rate, product formation rate, yield coefficients, mass transfer coefficients, power input, mixing time, shear stress, and/or biomass morphology, among others.

In embodiments, the fermentation system implements precise control through automated adjustment signals that regulate multiple operational parameters of the fermentation process. The control signals enable dynamic modification of critical process variables including agitation speed via impeller control, temperature regulation through heating and cooling elements, and automated pump control for nutrient feed, pH adjustment solutions, and antifoam agents. The system may manage gas exchange through sparger flow rate adjustments and maintains optimal pressure conditions within the fermentation chamber. Additional control mechanisms may regulate substrate feed rate, harvest timing, mixing operations, aeration levels, and recirculation patterns to maintain ideal growth conditions, among many others.

The control signals enable a sophisticated response system that can rapidly adapt to changing fermentation conditions. For example, when dissolved oxygen levels decrease, the system may simultaneously adjust multiple parameters such as increasing agitation speed, modifying aeration rate, and adjusting pressure to restore optimal oxygen transfer conditions. This coordinated control approach enables precise maintenance of desired setpoints while responding to process disturbances and changing metabolic requirements of the culture. The control architecture supports both feedback and feedforward control strategies, allowing for both reactive and predictive process optimization based on real-time parameter measurements and learned process dynamics.

In embodiments, the AI-based learning models may be continuously refined and improved through an iterative training process that incorporates new operational data collected during fermentation runs. The fermentation system collects response data indicating the effects of control adjustments on fermentation parameters and process outcomes. This response data may include changes in metabolite concentrations, cell density measurements, productivity metrics, and other key performance indicators that result from specific control actions.

The fermentation system's control system may implement online learning algorithms that enable real-time model updates based on newly acquired fermentation data. As the fermentation system observes the outcomes of its control decisions, it can refine its predictive capabilities by adjusting model weights and biases to better reflect actual process dynamics. This continuous learning approach allows the models to adapt to changing conditions and improve their prediction accuracy over time.

The platform may employ transfer learning techniques to leverage knowledge gained from previous fermentation runs when optimizing new processes. Historical response data from similar fermentation conditions or strains can be used to initialize model parameters, accelerating the learning process for new applications. The fermentation system may maintain a database of process responses and corresponding control actions, enabling the AI models to identify patterns and relationships that inform future optimization strategies.

In implementations, the fermentation system's control system may utilize reinforcement learning frameworks where the model receives feedback on the effectiveness of its control decisions through defined reward functions based on process performance metrics. This allows the fermentation system to systematically explore different control strategies while exploiting successful patterns identified from previous operations. The learning process may incorporate both feedback and feedforward control strategies, enabling both reactive and predictive process optimization based on real-time parameter measurements and learned process dynamics.

The fermentation system's adaptive computation techniques can dynamically adjust model complexity based on the quality and quantity of available training data. For simpler parameter sets with limited training data, the fermentation system may utilize reduced model architectures, while more complex scenarios with rich historical data enable the activation of additional computational pathways for more sophisticated control strategies.

In embodiments, the fermentation system may be configured as a mobile laboratory unit designed for deployment at client sites, enabling on-site fermentation process development and optimization. Such mobile laboratory unit may be alternatively referred to as a "fermentation system kit" and/or a "fermentation system in-a-box." The mobile configuration may integrate the fermentation chamber, sensor arrays, control systems, and/or rapid sampling capabilities into a self-contained, transportable unit that maintains the same sophisticated monitoring and control capabilities as stationary systems. The mobile unit may be housed within a customized container or vehicle that provides necessary utilities including power supply, climate control, and clean air handling systems to maintain appropriate operating conditions.

The mobile laboratory configuration may include specialized features to ensure stability and reliability during transport and operation at various locations. These features may include shock-absorbing mounting systems for sensitive equipment, redundant power systems with uninterruptible power supply (UPS) backup, integrated water purification and waste handling systems, and rapid sterilization capabilities for maintaining sterile operations. The system may also incorporate quick-connect interfaces for rapid setup of utilities and support systems at client sites, enabling efficient deployment and initialization of fermentation processes.

The mobile platform may be equipped with secure data transmission capabilities to enable remote monitoring and control while maintaining data integrity and security. This allows for real-time collaboration between on-site operators and remote experts, facilitating rapid troubleshooting and process optimization. The mobile system's AI-based control architecture may include specialized algorithms to account for site-specific variables such as local environmental conditions, available utilities, and facility constraints, ensuring consistent performance across different deployment locations.

In embodiments, the platform may include a simulation engine that is configured to generate and execute simulations for different process scenarios in which the biological strain produces the functional output, wherein each process scenario has different modifications to genes, environmental parameters, biological pathways, and/or proteins or enzymes associated with the biological strain. The simulation engine can generate multiple simulated process scenarios, where each scenario tests different modifications. The simulation engine executes these scenarios and generates simulation data based on the results.

The simulation data generated from these simulations can be received as additional input by the set of AI-based learning models. This simulation data, along with other data inputs, can be used by the set of AI-based learning models to generate recommendations. The recommendations can be based at least in part on analyzing the outcomes and results captured in the simulation data. In some embodiments, the simulation data may be integrated with other data by the data integration facilities before being provided to the set of AI-based learning models.

The simulation engine may employ distributed computing techniques to parallelize the execution of simulations across multiple computing nodes. For example, each node may be responsible for simulating specific aspects of a biological system (e.g., metabolic pathways, environmental conditions, genetic expressions, etc.). The platform may then aggregate results using a synchronization layer that maintains temporal consistency across simulations.

The simulation engine may be configured to perform sensitivity analysis across multiple parameters simultaneously. This capability enables the platform to identify which combinations of modifications have the most significant impact on the desired functional output. The engine can systematically vary parameters within defined ranges while monitoring system responses, generating comprehensive sensitivity maps that highlight key control points in the biological system.

In embodiments, the simulation engine incorporates machine learning-based prediction models that can estimate the outcomes of proposed modifications before running full simulations. These predictive capabilities help optimize the simulation pipeline by prioritizing the most promising scenarios for detailed analysis. The prediction models are continuously refined using both historical simulation results and real experimental data to improve their accuracy over time.

The platform's simulation engine may also include specialized modules for modeling stochastic biological processes. These modules account for the inherent randomness and variability in biological systems by incorporating probabilistic elements into the simulations. This stochastic modeling capability provides more realistic predictions of system behavior and helps identify potential failure modes or edge cases that deterministic approaches might miss.

Allocation of AI-Based Experiment Evaluations

In the field of biotechnology, many scenarios involve the planning, execution, and evaluation of experiments to explore various features of a biologic process. For example, a biologic process may involve a natural or synthesized metabolic pathway that transforms precursors, such as amino acids, proteins, reagents, enzymes, cell lines, organisms, or the like, into one or more biologic products, such as proteins, DNA sequences, transformed cell lines, transformed organisms, or the like. Various alterations to the biologic process may affect the performance of the biologic process, such as the yield, rate, consistency, quality of biologic product, sensitivity of the biologic process to perturbation, or the like. As a first example, a biologic process that involves the synthesis of a particular protein may be sensitive to a folding feature of the protein, such as a configuration of a binding site that may affect a compatibility and/or selectivity of the protein for an enzyme of the biologic process. Changes to the protein may alter the folding feature of the protein and may increase or decrease the compatibility and/or selectivity of the protein for the enzyme, which may accordingly increase or decrease the yield, rate, consistency, quality, or other features of the biologic process. As a second example, a cell line or organism may include a gene that is associated with a certain phenotypic feature of the cell line or organism, such as a performance, rate, and/or quality of a metabolic process that produces one or more biologic products. Alterations of the gene (e.g., excising, mutating, or the like) may alter the phenotypic feature of the cell line or organism and, by extension, the performance, rate, and/or quality of the metabolic process and the resulting one or more biologic products.

The range of available experiments in the field of biotechnology may be large. For example, a biologic process may occur in many variants of a cell line or organism, and/or may be carried out in various environments and with various experimental parameters to synthesize a protein such as an enzyme or a pharmaceutical candidate. It may be desirable to evaluate a large set of experiments to identify adjustments of a biologic process that may improve the yield, rate, consistency, quality of biologic product, sensitivity of the biologic process to perturbation, or the like. Such evaluation may be performed retrospectively (e.g., evaluating performed experiments, designed around various hypotheses relating to the field of biotechnology, and experimental outcomes of the performed experiments in order to identify improvements of the biologic process). Alternatively or additionally, such evaluation may be performed prospectively (e.g., evaluating and/or generating proposals for new experiments that may test and/or validate various hypotheses associated with the field of biotechnology that may yield improvements to the biologic process). For example, hypotheses that involve altering the structure of a protein to improve compatibility and/or selectivity for an enzyme, and/or altering the genotype of a cell line or organism to improve the performance of a metabolic process, may be demonstrated and/or validated by experiments. However, the number of candidate experiments that could be performed and/or the number of previously performed experiments may greatly exceed the resources available for such evaluation, such as the available attention of human researchers who are proficient in the relevant field of biotechnology. Additionally, the number of candidate experiments that could be performed in a laboratory may greatly exceed the laboratory resources that are available to perform various experiments.

Presented herein are techniques for applying agentic AI to the retrospective and/or prospective evaluation of experiments in the field of biotechnology. In accordance with the techniques presented herein, an AI-based platform may include an experiment data set including records that respectively represent a synthetic biology experiment. Each record may indicate at least one hypothesis associated with the synthetic biology experiment and an experiment definition based on the at least one hypothesis. An AI-based agent may be configured to perform an evaluation of respective records of each synthetic biology experiment, and generate, based on the evaluation, at least one observation about the at least one hypothesis associated with the synthetic biology experiment represented by each of the respective records.

More particularly, in many such scenarios, the number of candidate experiments that could be performed and/or the number of previously performed experiments may greatly exceed even the computational resources that are available to the AI agents to perform retrospective and/or prospective evaluations of experiments, in addition to other steps such as generating experimental designs for various experiments. Therefore, in accordance with some embodiments of the techniques presented herein, the AI-based agent may be associated with a set of resources (e.g., computational resources to evaluate the experiment and/or laboratory resources to cause the experiment to be performed). The AI-based agent may be further configured to perform the evaluation of respective records by allocating the set of resources over the records of the experiment data set, wherein each allocation associates a subset of the set of resources to the evaluation of a respective record of the experiment data set.

Figure 38:
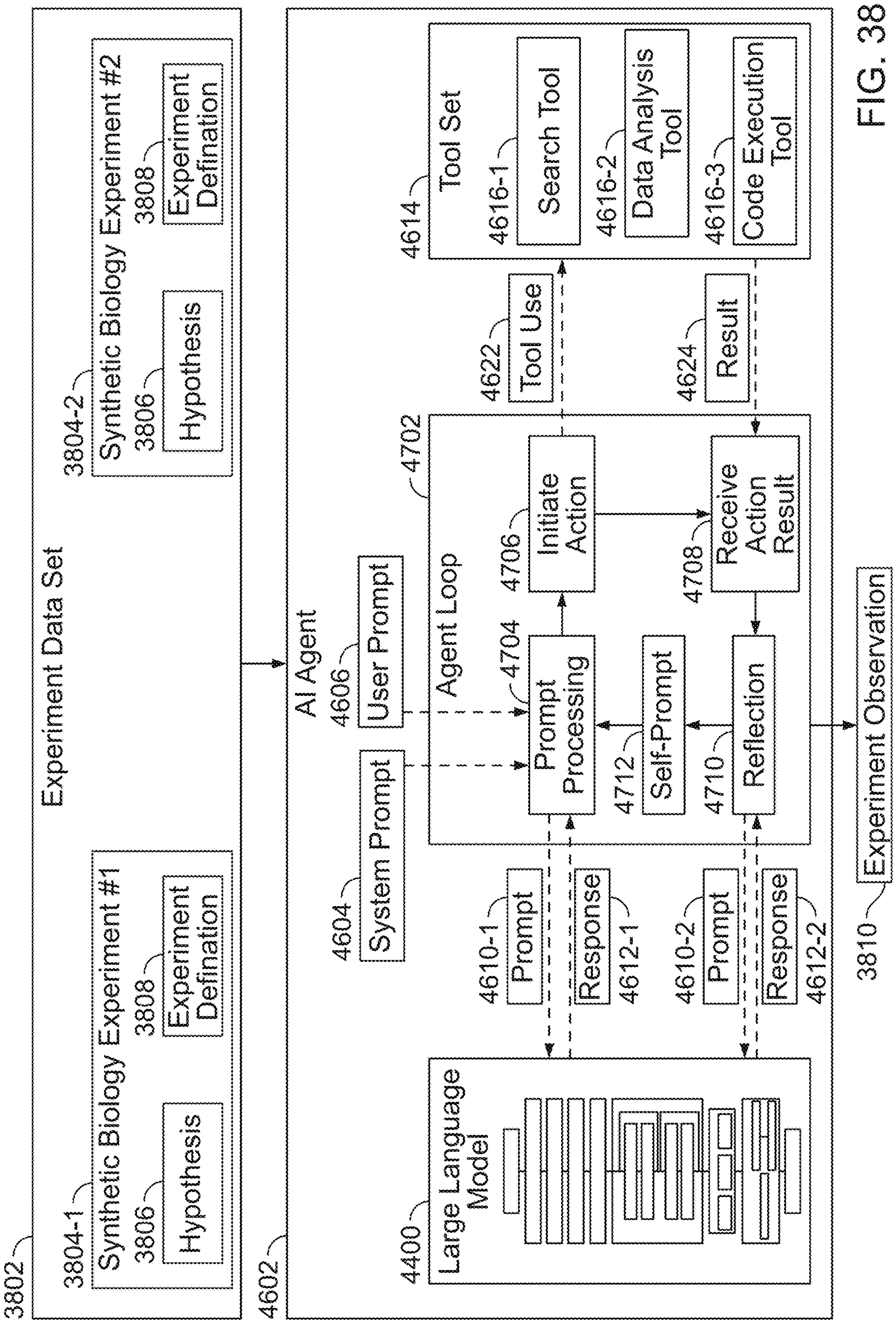
FIG. 38 is a schematic diagram detailing experiment evaluation by an AI agent according to some example embodiments.

FIG. 38 illustrates an example scenario featuring experiment evaluation by an AI agent 4602 according to some example embodiments. The example scenario of FIG. 38 may be understood in view of the additional coverage of topics related to artificial intelligence, such as the discussion of FIGS. 40 through 48.

As shown in FIG. 38, an experiment data set 3802 includes a set of records 3804 of synthetic biology experiments. One or more records 3804 of the experiment data set 3802 may represent a previously conducted synthetic biology experiment, such as a report of a synthetic biology experiment in a scientific journal, a laboratory journal, or an experiment database. The record may include at least one outcome of the previously conducted synthetic biology experiment, such as measurements, observations, findings, and/or products of the previously conducted synthetic biology experiment. Alternatively or additionally, one or more records 3804 of the experiment data set 3802 may represent a proposed synthetic biology experiment, such as a proposal to alter an amino acid sequence of a protein to alter the configuration of a binding site, or a proposal to test an edit of a genotype of a cell line or organism to observe resulting changes of the phenotype of the cell line or organism. The record 3804 of the experiment data set 3802 may include at least one prediction of at least one outcome of the proposed synthetic biology experiment, such as a hypothesis 3806 involving a predicted effect of changing the physical folding structure of a protein and/or the predicted effect on the phenotype of the cell line or organism resulting for the edit of the genotype of the cell line or organism. As shown in the example of FIG. 38, each record 3804 also indicates one or more hypotheses 3806 that may have been or might be tested and/or validated by the experiment. As further shown in the example of FIG. 38, each record 3804 also includes an experiment definition 3808 that indicates how the experiment was and/or might be conducted.

The experiment data set 3802 may be evaluated by an AI agent 4602 to perform an evaluation of respective records 3804 of each synthetic biology experiment and to generate, based on the evaluation, at least one observation 3810 about the hypothesis 3806 associated with the synthetic biology experiment represented by each of the respective records 3804. For example, as shown in FIG. 38, the AI agent 4602 may include a large language model 4400 that serves as a logic engine for the AI agent 4602. The AI agent 4602 may also include a tool set 4614 of tools 4616 for performing certain tasks during the evaluation of an experiment, such as a search tool 4616-1 that can be invoked to search for supplemental information related to a hypothesis 3806 and/or experiment definition 3808, a data analysis tool 4616-2 to perform data analyses of various data associated with the experiment, and a code execution tool 4616-3 to execute instructions (e.g., Python scripts) in relation to the evaluation of an experiment. The AI agent 4602 may be configured by a system prompt 4604, which may specify instructions for evaluating each of the records 3804 included in the experiment data set 3802 and/or for generating observations 3810.

In order to evaluate an experiment, the AI agent 4602 may engage an agent loop 4702 that iteratively evaluates respective features of a record 3804 to generate one or more observations 3810 about the related experiment. For example, the AI agent 4602 may receive a user prompt 4606 that includes a description of the experiment represented by a record 3804 of the experiment data set 3802, the hypothesis 3806 associated with the experiment, and the experiment definition 3808 of the experiment (e.g., the protocol, resources, and/or data collection techniques associated with the experiment). The AI agent 4602 may first perform a prompt processing stage 4704 to generate an initial evaluation of the experiment represented by the record 3804. During the prompt processing stage 4704, the AI agent 4602 may generate a first prompt 4610-1 for the large language model 4400 that requests an initial evaluation of the record 3804 and an indication of one or more actions that may further inform the evaluation. For example, the system prompt 4604 may describe each of the tools 4616 of the tool set 4614, may provide examples in which the respective tools 4616 can be effectively used to generate information of value to the evaluation of experiments, and instructions for how the large language model 4400 should evaluate the experiment, including examples of the evaluation of other experiments of the experiment data set 3802. Based on the first prompt 4610-1, the large language model 4400 may generate a first response 4612-1 including a first evaluation of the record 3804 of the experiment. The first response 4612-1 may indicate one or more actions 4620 to be taken, such as instances of tool use 4622 that might generate additional information for evaluation during subsequent iterations of the agent loop 4702. During an initiate action stage 4706, the AI agent 4602 may extract the requested actions 4620 from the first response 4612-1 and may initiate tool use 4622 therefor, such as invoking the search tool 4616-1 to search a scientific literature database for other experiments that may relate to the record 3804 and/or other features of an area of synthetic biology associated with the experiment. In a receive action result stage 4708, the AI agent 4602 may receive a result 4624 generated by one or more tools 4616 during and/or after the tool use 4622, such as retrieved information that matches a search query. During a reflection stage 4710, the AI agent 4602 may evaluate the record 3804 together with the result 4624 of the tool use. In particular, the AI agent 4602 may generate a second prompt 4610-2 that includes the system prompt 4604, the user prompt 4606, details of the record 3804, the first prompt 4610-1, the first response 4612-1, a description of the actions 4620 and tool use 4622 performed during the initiate action stage 4706, and/or the result 4624 of the tool use 4622. The second prompt 4610-2 may be provided to the large language model 4400 with a request to determine a next step in the agent loop 4702 and to generate a self-prompt 4712 for a next iteration of the agent loop 4702. The large language model 4400 may generate the self-prompt 4712, and the AI agent 4602 may initiate a second iteration of the agent loop 4702 by processing the self-prompt 4712 by the large language model 4400.

The iteration of the agent loop may continue until the large language model 4400 has completed its evaluation of the record 3804 and is ready to generate a record of one or more observations 3810 of the record 3804, the associated experiment, and the hypothesis 3806 associated with the experiment. For example, the observations 3810 may include (without limitation) a rating of the at least one hypothesis, an indicator of a prioritization of the synthetic biology experiment represented by the respective record, wherein the prioritization is relative to a respective synthetic biology experiment represented by another record of the experiment data set, a validation of the at least one hypothesis, an identification of an issue with the experiment definition based on the at least one hypothesis, a prediction of at least one outcome of the respective synthetic biology experiment, wherein the prediction is based on the at least one hypothesis, or an explanation of at least one outcome of the respective synthetic biology experiment, wherein the at least one outcome is included in the respective record, and the explanation is based on the at least one hypothesis. The large language model 4400 may incrementally accumulate the information and/or observations about the record 3804 through each of one or more iterations of the agent loop 4702 and/or one or more actions 4620, such as one or more instances of tool use 4622 of the tools 4616 of the tool set 4614. When the large language model 4400 determines (during a reflection stage 4710) that the evaluation of a record 3804 is complete, the large language model 4400 may generate (during the prompt processing stage 4704) the set of observations 3810 to be provided as the output of the AI agent 4602 for the experiment and an indicator that the agent loop 4702 for the record 3804 is complete. The AI agent 4602 may extract the one or more observations 3810 about the record 3804, the hypothesis 3806, and/or the experiment and may output the observations 3810. For example, the AI agent 4602 may store the one or more observations 3810 in a log of experimental evaluations; attach the one or more observations 3810 to the record 3804 as an annotation and/or recommendation; and/or present the one or more observations 3810 to a human researcher, such as a laboratory manager who may choose and schedule experiments to be conducted in a laboratory.

The example scenario of FIG. 38 may include a number of variations based on the nature of the experiment data set 3802, the records 3804 of experiments, the related hypotheses 3806, or the like. The following variations may be included in various embodiments of the techniques herein, some of which may alter some details of example scenario shown in FIG. 38.

In various embodiments, the AI agent 4602 may use many kinds of large language models 4400, agent loops 4702, and/or tool sets 4614 in the evaluation of the experiment data set 3802. For example, the large language model 4400 may be or may include a foundation model that is not particularly trained on an understanding of the area of synthetic biology, but may be configured and/or informed (e.g., by retrieval-augmented generation (RAG), the use of the search tool 4616-1, or the like) with domain-specific knowledge and information that enables the large language model 4400 to evaluate the experiment data set 3802 and to generate relevant observations 3810. Alternatively, the large language model 4400 may be specifically trained (e.g., initially or by fine-tuning and/or transfer learning) using documents that relate to the domain of synthetic biology, such as scientific literature, and may perform its evaluation of the experiment data set 3802 and generate observations 3810 in an informed manner. As a second example, the agent loop 4702 may be executed in an ad-hoc manner, where each iteration of the agent loop 4702 determines, during the reflection stage 4710, the incremental advance of the next iteration of the agent loop 4702 in the evaluation of a record 3804 of the experiment data set 3802. Alternatively, the agent loop 4702 may be organized according to a workflow for evaluating the records 3804, experiments, and hypotheses 3806 of the experiment data set 3802, where such a workflow may be specified in the system prompt 4604, discovered by the AI agent 4602 (e.g., using the search tool 4616-1), and/or generated by a first iteration of the agent loop 4702. As a third example, the tool set 4614 of the AI agent 4602 may include a variety of tools 4616, such as tools 4616 that communicate with one or more human researchers to supplement and/or collaborate on the evaluation of the record 3804 of an experiment, and/or one or more simulation tools 4616 that perform simulations of experiments to deduce, predict, and/or validate a recorded and/or predicted experimental outcome associated with a record 3804 of the experiment data set 3802. Many such variations and techniques of AI agents 4602 are discussed herein and/or are known to those of ordinary skill in the art, and may be included in various embodiments of the techniques presented herein.

In various embodiments, the AI agent 4602 may perform various types of evaluations of the records 3804 and associated experiments, hypotheses 3806, and/or experiment definitions 3808 of the experiment data set 3802. For example, the evaluation may include searching one or more experimental databases (e.g., via the search tool 4616-1) to identify other performed and/or proposed experiments that relate to the experiment of a particular record 3804. The evaluation may include searching one or more synthetic biology databases (e.g., via the search tool 4616-1) to identify knowledge about the field of synthetic biology that relates to the experiment of a particular record 3804, e.g., in order to supplement the evaluation, verify, and/or critique certain presumptions, requirements, observations, and/or conclusions of the experiment associated with a record 3804. The evaluation may include performing data analyses (e.g., via the data analysis tool 4616-2) of supporting, initial, predicted, and/or related data that is associated with a proposed experiment of a record 3804 and/or of data included in a record 3804 of a performed experiment. The evaluation may include executing code (e.g., through the code execution tool 4616-3) to generate computational analyses and/or results that relate to an experiment associated with a record 3804, such as protein folding simulations, protein interaction simulations, and/or cell line or organism simulations to predict and/or verify one or more outcomes associated with the experiment of a record 3804.

In various embodiments, the AI agent 4602 may generate many types of observations 3810 about a record 3804, experiment, hypothesis 3806, and/or experiment definition 3808 of the experiment data set 3802. For example, the AI agent 4602 may generate a rating, score, or the like of the at least one hypothesis. The AI agent 4602 may generate indicators of the prioritization of respective synthetic biology experiments represented by respective records 3804 of the experiment data set 3802, wherein the prioritization indicated for a record 3804 is relative to a respective synthetic biology experiment represented by other records 3804 of the experiment data set 3802. The AI agent 4602 may generate validations of hypotheses 3806 associated with the experiments represented by various records 3804 of the experiment data set 3804. The AI agent 4602 may identify issues with the experiment definitions of one or more records 3804 based on the associated hypotheses 3806 (e.g., errors in an experiment protocol that may prevent the results of an experiment from informing the hypothesis 3806 of the experiment). The AI agent 4602 may generate predictions of outcomes of the synthetic biology experiments of respective records 3804, wherein the prediction is based on the at least one hypothesis 3806 of the record 3804. Where respective records 3804 include at least one observed outcome of an experiment, the AI agent 4602 may generate explanations of the outcomes of the synthetic biology experiments of respective records 3804 based on the at least one hypothesis 3806. These and many other types of observations 3810 may be generated by the AI agent 4602 during the evaluation of the records 3804 of the experiments of the experiment data set 3802.

In some embodiments, the AI agent 4602 may be associated with a set of resources, and may be further configured to perform the evaluation of respective records 3804 by allocating the set of resources over the records 3804 of the experiment data set 3802. Each allocation may associate a subset of the set of resources to the evaluation of a respective record 3804 of the experiment data set 3802. As a first such example, the set of resources may include a set of computational resources that is available to the AI agent 4602, such as processing time, memory, storage, hardware provisions such as tensor processing units (TPUs) and/or graphics processing units (GPUs), large language models 4400 with various forms of specialization and/or training, and/or computational resources for using respective tools 4616 of the tool set 4614 to perform searches, data analyses, and/or code execution such as simulations. The computational resources may be provisioned, allocated, and/or measured in various ways (e.g., units and/or amounts of computation and/or storage, credits that the AI agent 4602 may spend in various ways, a duration of performing the evaluation of a set of records 3804 and that may be chronologically allocated over the experiment data set 3802, or the like). The AI agent 4602 may allocate the set of resources over the records 3804 of the experiment data set 3802 by determining an amount of computational resources to be spent by the AI agent 4602 in the evaluation of respective synthetic biology experiments of the experiment data set 3802. For example, the AI agent 4602 may choose an allocation of a portion (e.g., a specific amount and/or a percentage) of the computational resources to evaluate a particular record 3804. For example, the AI agent 4602 may determine that the experiment associated with a first record 3804-1 is of high priority (e.g., due to a high likelihood of success and/or significance of the outcomes of the experiment) and may allocate a large portion of computational resources to the evaluation of the experiment associated with the first record 3804-1. The AI agent 4602 may determine that the experiment associated with a second record 3804-2 is of low priority (e.g., due to a low likelihood of success and/or insignificance of the outcomes of the experiment) and may allocate a small portion of computational resources to the evaluation of the experiment associated with the second record 3804-2. The AI agent 4602 may adjust the allocation of computational resources to one or more records 3804 during the iterative processing of the agent loop 4702 (e.g., expanding the allocation of computational resources to records 3804 associated with experiments that an initial evaluation reveals to be promising and/or relevant, and/or reducing the allocation of computational resources to records 3804 associated with experiments that an initial evaluation reveals to be underwhelming and/or inconsequential). The AI agent 4602 may request adjustments of the overall allocation of computational resources, optionally based on a presentation of an initial evaluation of one or more records 3804 of the experiment data set 3802.

In some embodiments, the AI agent 4602 may allocate a set of experimental resources over the records 3804 of the experiment data set 3802. For example, the experimental resources may include laboratory physical space, access to laboratory machines for performing various steps of experimental protocols (e.g., reaction tanks, incubators, freezers, or the like), consumable materials such as reagents and supplies, time in a laboratory schedule of available resources, laboratory personnel that may be assigned to various experiments, computational time required by an experimental protocol for data analysis, sampling, or simulations, or the like. The AI agent 4602 may determine an amount of experimental resources to be allocated to performing respective synthetic biology experiments of the experiment data set 3802. For example, the AI agent 4602 may determine that the experiment associated with a first record 3804-1 is of high priority (e.g., due to a high likelihood of success and/or significance of the outcomes of the experiment) and may allocate a large portion of experimental resources to the experiment associated with the first record 3804-1. The AI agent 4602 may determine that the experiment associated with a second record 3804-2 is of low priority (e.g., due to a low likelihood of success and/or insignificance of the outcomes of the experiment) and may allocate a small portion of experimental resources to the experiment associated with the second record 3804-2. The AI agent 4602 may adjust the allocation of experimental resources to one or more records 3804 during the iterative processing of the agent loop 4702 (e.g., expanding the allocation of experimental resources to records 3804 associated with experiments that an initial evaluation reveals to be promising and/or relevant, and/or reducing the allocation of experimental resources to records 3804 associated with experiments that an initial evaluation reveals to be underwhelming and/or inconsequential). The AI agent 4602 may request adjustments of the overall allocation of experimental resources, optionally based on a presentation of an initial evaluation of one or more records 3804 of the experiment data set 3802.

In some embodiments, the AI agent 4602 may allocate computational resources for the evaluation of experiments and/or experimental resources for the performance of experiments based on a variety of considerations. For example, the AI agent 4602 may allocate computational and/or experimental resources to respective records 3804 of the experiment data set 3802 based on preliminary evaluations of the synthetic biology experiments associated with respective records 3804 of the experiment data set 3802. The AI agent 4602 may allocate computational and/or experimental resources to respective records 3804 of the experiment data set 3802 based on priorities associated with the at least one hypothesis on which respective synthetic biology experiments are based (e.g., prioritizing the evaluation and/or performance of experiments associated with high-priority hypotheses over those associated with low-priority hypotheses). The AI agent 4602 may allocate computational and/or experimental resources to respective records 3804 of the experiment data set 3802 based on associations between a subject matter domain of the respective hypotheses and a subject matter domain of the AI agent 4602 (e.g., allocating more computational time to perform a more comprehensive evaluation of experiments that are within a knowledge domain of the AI agent 4602). The AI agent 4602 may allocate computational and/or experimental resources to respective records 3804 of the experiment data set 3802 based on observations about the hypothesis generated by another AI agent 4602 (e.g., a high rating or priority assigned to an experiment by another AI agent 4602 of a set of AI-based agents, and/or a recommendation or referral of an experiment from another AI agent 4602 to the AI agent 4602).

In some embodiments, an AI agent 4602 may interact with one or more human researchers in the evaluation of experiments and/or the generation of observations 3810. As a first example, the AI agent 4602 may present, to a human researcher, at least one recommendation to perform at least one synthetic biology experiment of the experiment data set 3802. The recommendation may be based, for example, on observations 3810 indicating a high likelihood of success of the experiment and/or a high significance of the hypothesis 3806 and/or outcome of the experiment to the AI agent 4602 and/or the human researcher. As a second example, the AI agent 4602 may receive, for a synthetic biology experiment, an experiment definition that was developed by a human researcher. The AI agent 4602 may generate an evaluation of the experiment definition for the synthetic biology experiment and present the evaluation of the experiment definition to the human researcher (e.g., validation of the experiment definition, a predicted outcome of the experiment definition, and/or a proposed modification of the experiment definition to avoid one or more potential issues and/or to improve one or more objectives of the experiment, such as increasing yield, rate, quality, and/or consistency of a biologic product).

In some embodiments, the AI agent 4602 may be associated with an evaluation performance metric that indicates a proficiency of the AI agent 4602 in evaluating various experiments and generating various observations 3810. The evaluation performance metric of the AI agent may be updated based on an assessment of the observations 3810 generated by the AI agent 4602 about each experiment of the experiment data set 3802. As a first example, an AI platform may perform a comparison of the observations 3810 of the AI agent 4602 about the hypothesis 3806 of a synthetic biology experiment with at least one observed and/or measured outcome of the synthetic biology experiment, and may update the evaluation performance metric of the AI agent 4602 according to the comparison. As a second example, at least one record 3804 of the experiment data set 3802 may include at least one predicted outcome of a synthetic biology experiment that is generated by the AI agent 4602, and an AI platform may perform a comparison of the predicted outcomes of the synthetic biology experiment with at least one observed outcome of the respective synthetic biology experiment. The AI platform and the respective AI agents 4602 may critique, rate, rank, compete, and/or otherwise evaluate the other AI agents 4602 of a set of AI agents 4602. Such ratings, rankings, or the like may adjust the resources that each AI agent 4602 may allocate over the evaluation and/or performance of experiments associated with respective records 3804 of the experiment data set 3802.

In some embodiments, the AI agent 4602 may be configured to, for a synthetic biology experiment of a selected record of the experiment data set, generate an experiment definition for the synthetic biology experiment based on a model of a biologic process associated with the synthetic biology experiment. The AI agent 4602 may cause the synthetic biology experiment to be performed based on the experiment definition, and update the model of the biologic process based on the evaluation. Some such embodiments may utilize reinforcement learning techniques to model the biologic process.

As a first example, a reinforcement learning model may include a reinforcement learning policy based on the biologic process. Based on the evaluation and observations 3810 of the synthetic biology experiment, the AI agent 4602 may update the model of the biologic process by updating the reinforcement learning policy through a reinforcement learning process. Updating the reinforcement learning policy may enable the AI agent 4602 to reconcile the model of the biologic process with at least one outcome of the synthetic biology experiment (e.g., incorporating a hypothesis into the model of the biologic process, adapting one or more assertions or presumptions of the model of the biologic process based on experimental results, and/or using experimental results to validate, dispute, clarify, extend, or otherwise adapt various assertions or presumptions of the model of the biologic process).

As a second example, if the reinforcement learning policy is based on at least one experimental perturbation involved in the synthetic biology experiment. Based on the evaluation and observations 3810 of the synthetic biology experiment, the AI agent 4602 may update the reinforcement learning policy by updating the experimental perturbation involved in the synthetic biology experiment based on at least one outcome of the synthetic biology experiment. For instance, if the synthetic biology experiment involves applying a new edit to a genotype of a cell line or an organism, the outcomes of the synthetic biology experiment and the observations 3810 of the AI agent 4602 may enable the AI agent 4602 to update the model of the biologic process to indicate the effects of the edit.

As a third example, the reinforcement learning policy may be based on at least one objective associated with the synthetic biology experiment (e.g., an objective to increase a yield, rate, quality, and/or consistency of a fermentation process). Based on the evaluation and observations 3810 of the synthetic biology experiment, the AI agent 4602 may update the objective based on one or more outcomes of the synthetic biology experiment (e.g., indicating an effect of a particular process parameter of a fermentation process on the yield, rate, quality, and/or consistency of the fermentation process).

As a fourth example, the reinforcement learning policy may be based on at least one performance metric associated with the synthetic biology experiment. For example, the synthetic biology experiment may be based on a score, rank, rating, and/or measurement of one or more features of a biologic process, such as a yield, rate, quality, and/or consistency of synthesized biologic products. Based on the evaluation and observations 3810 of the synthetic biology experiment, the AI agent 4602 may update the at least one performance metric associated with the synthetic biology experiment. These and other variations may enable the AI agent 4602 to use the evaluation and observations 3810 of respective experiments to update a repository or model of knowledge about a subject matter domain of synthetic biology and/or various biologic processes related thereto.

Model-In-the-Loop Synthetic Biology

In the field of biotechnology, many scenarios involve an iterative process of planning, execution, and evaluation of experiments to explore various features of a biologic process. For example, a first experiment may involve an initial attempt to synthesize a biologic product through a metabolic process of a cell line, and may result in a failure to synthesize a biologic product due to various observed features of the metabolic process. Observations of the first experiment may inform the design of a second experiment involving a revised attempt to synthesize the biologic product through the metabolic process of the cell line, and may result in a successful synthesis of the biologic product. Observations of the second experiment may inform the design of a third experiment with adjusted process parameters (e.g., temperature, pressure, presence and/or concentrations of nutrients, the presence or absence of catalysts, edits to the genotype of the cell line, or the like), which may result in improved synthesis of the biologic product (e.g., increased eld, rate, quality, and/or consistency of the synthesized biologic product). The iterative experimental process is sometimes referred to as a "Design/Build/Test/Learn" or "DBTL" cycle, wherein each iteration of the synthetic biology DBTL cycle produces observations and insights that may inform the development of the next and future iterations of the synthetic biology DBTL cycle in the development of biologic products.

Conventionally, human researchers were involved in each stage of each experiment, including the experimental conception, design, performance, collection and analysis of data, generation of observations and conclusions, and conception of adjustments of the experiment in pursuit of various objectives. However, the heavy reliance on the availability, attention, and effort of trained human researchers for each step of the experimental process might limit, complicate, delay, protract, or otherwise detrimentally affect the performance of experiments. Such reliance and the resulting detrimental effects may slow the rate of progress in the acquisition of knowledge in the field of synthetic biology and/or the production of needed biologic products, such as pharmaceuticals, vaccines, medical supplies, or the like.

Presented herein are techniques for incorporating agentic AI in the synthetic biology DBTL cycle used to develop a biologic product. In accordance with the techniques presented herein, an experiment data set may define a synthetic biology experiment based on a model of a biologic process. An AI agent may be configured to participate in the synthetic biology DBTL cycle of the biologic process. For example, the AI agent may generate an experiment definition for the synthetic biology experiment based on the model of the biologic process ("Design"); cause the synthetic biology experiment to be performed based on the experiment definition ("Build"); perform an evaluation of at least one outcome of the synthetic biology experiment ("Test"); and update the model of the biologic process based on the evaluation ("Learn"). The participation of the AI agent in various aspects of the synthetic biology DBTL cycle may increase a rate, number, efficiency, quality, and/or consistency of the performance of experiments that advance and accelerate the accumulation of knowledge regarding the biologic process and the development of biologic products.

Figure 39:
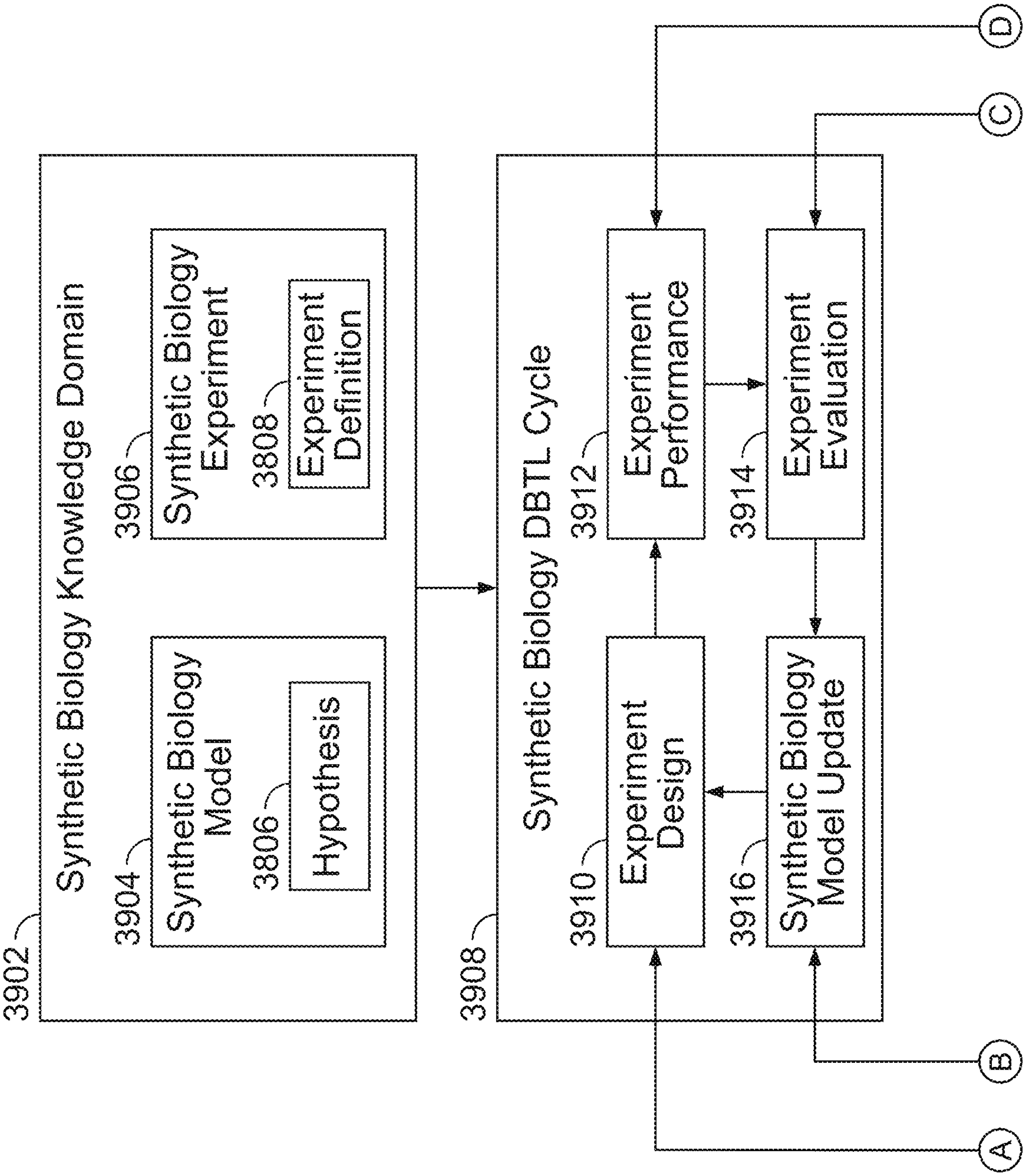
FIG. 39 is a schematic diagram detailing participation of an AI agent in the synthetic biology DBTL cycle during the development of a biologic process for synthesizing biologic products according to some example embodiments.
Figure 39:
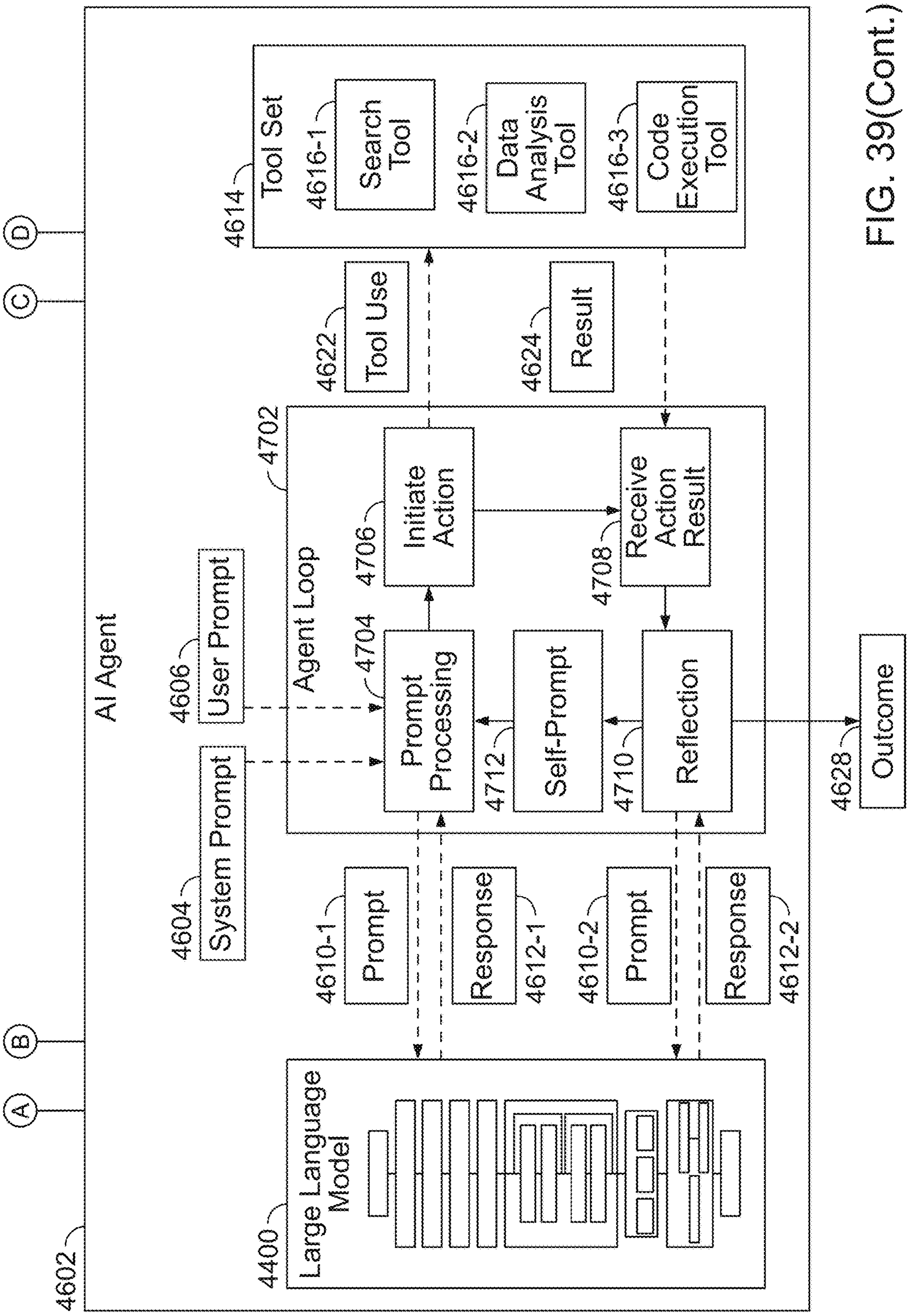

FIG. 39 illustrates an example scenario featuring participation of an AI agent 4602 in the synthetic biology DBTL cycle during the development of a biologic process for synthesizing biologic products according to some example embodiments. The example scenario of FIG. 39 may be understood in view of the additional coverage of topics related to artificial intelligence, such as the discussion of FIGS. 40 through 48.

As shown in FIG. 39, a synthetic biology knowledge domain 3902 includes a synthetic biology model 3904 of a biologic process, such as a metabolic process of a cell line or organism that causes the synthesis of a biologic product. The synthetic biology model 3904 may be represented, for example, as a natural-language repository of journal articles, experimental observations and results, educational analyses or summaries of various aspects of the synthetic biology knowledge domain 3902, or the like. The synthetic biology model 3904 may include one or more data sets, such as data collected during experiments, simulations, or inference by predictive models. The synthetic biology model 3904 may include representations of various features of the synthetic biology knowledge domain 3902, such as machine instructions that simulate the behavior of cell lines, organisms, and/or biologic processes in various conditions. The synthetic biology knowledge domain 3902 also includes one or more records 3906 of synthetic biology experiments that relate to the synthetic biology knowledge domain 3902. One or more records 3906 of the synthetic biology knowledge domain 3902 may represent a previously conducted synthetic biology experiment, such as a report of a synthetic biology experiment in a scientific journal, a laboratory journal, or an experiment database. The record may include at least one outcome of the previously conducted synthetic biology experiment, such as measurements, observations, findings, and/or products of the previously conducted synthetic biology experiment. Alternatively or additionally, one or more records 3906 of the synthetic biology knowledge domain 3902 may represent a proposed synthetic biology experiment, such as a proposal to alter an amino acid sequence of a protein to alter the configuration of a binding site, or a proposal to test an edit of a genotype of a cell line or organism to observe resulting changes of the phenotype of the cell line or organism. The record 3906 of an experiment may include at least one prediction of at least one outcome of the proposed synthetic biology experiment, such as a hypothesis 3806 involving a predicted effect of changing the physical folding structure of a protein and/or the predicted effect on the phenotype of the cell line or organism resulting for the edit of the genotype of the cell line or organism. One or more records 3906 of synthetic biology experiments (particularly previously performed experiments) may include an experiment definition 3808 of the experiment (e.g., the protocol, resources, and/or data collection techniques associated with the experiment).

The synthetic biology knowledge domain 3902 may be advanced by performing one or more iterations of a synthetic biology DBTL cycle 3908. The synthetic biology DBTL cycle 3908 includes an experiment design stage 3910 wherein the experiment definition 3808 of a synthetic biology experiment is selected, refined, critiqued, and finalized for execution, based on the synthetic biology model 3904 and one or more hypotheses 3806 to be tested, observed, measured, proven, disproven, or otherwise investigated by the experiment. The synthetic biology DBTL cycle 3908 includes an experiment performance stage 3912 wherein a synthetic biology experiment is prepared, initiated, performed, monitored, and concluded. The synthetic biology DBTL cycle 3908 includes an experiment evaluation stage 3914 wherein various data collected during the monitoring of the synthetic biology experiment is analyzed, visualized, verified, and otherwise inspected to extract knowledge about the synthetic biology knowledge domain 3902. The synthetic biology DBTL cycle 3908 includes a synthetic biology model update stage 3916 wherein knowledge of the biologic process and/or biologic product that was extracted during the experiment evaluation stage 3914 is used to update the synthetic biology model 3904. Completion of a first iteration of the synthetic biology DBTL cycle 3908 may inform the design, performance, and/or objectives of a second or later iteration of the synthetic biology DBTL cycle 3908.

In example embodiments and as shown in FIG. 39, an AI agent 4602 may participate in each phase of the synthetic biology DBTL cycle 4908. For example, during the experiment design stage 3910, the AI agent 4602 may generate the experiment definition 3808 for the synthetic biology experiment based on the synthetic biology model 3904, including one or more hypotheses 3806 to be investigated by the synthetic biology experiment. During the experiment performance stage 3912, the AI agent 4602 may cause the synthetic biology experiment to be performed based on the experiment definition 3808. During the experiment evaluation stage 3914, the AI agent 4602 may perform an evaluation of at least one outcome of the synthetic biology experiment, such as performing data analyses, generating observations, and/or extracting or synthesizing knowledge about the synthetic biology knowledge domain 3902. During the synthetic biology model update stage 3916, the AI agent 4602 may update the synthetic biology model 3904 based on the evaluation of the experiment. During each stage of each iteration the synthetic biology DBTL cycle 3908 for a given synthetic biology experiment, the AI agent 4602 may operate autonomously and independently; may operate in collaboration with one or more human researchers; and/or may operate alongside and in collaboration with one or more other AI agents 4602, devices, services, or the like. In this manner, the AI agent 4602 may supplement, extend, or substitute for the availability, attention, and effort of trained human researchers.

More specifically, as shown in FIG. 39, the AI agent 4602 may include a large language model 4400 that serves as a logic engine for the AI agent 4602. The AI agent 4602 may also include a tool set 4614 of tools 4616 for performing certain tasks during the evaluation of an experiment, such as a search tool 4616-1 that can be invoked to search for supplemental information related to a hypothesis 3806 and/or experiment definition 3808, a data analysis tool 4616-2 to perform data analyses of various data associated with the experiment, and a code execution tool 4616-3 to execute instructions (e.g., Python scripts) in relation to the evaluation of an experiment. The AI agent 4602 may be configured by a system prompt 4604, which may specify instructions for evaluating each of the records 3804 included in the experiment data set 3802 and/or for generating observations 3810.

In order to participate in any stage of the synthetic biology DBTL cycle 3908, the AI agent 4602 may engage an agent loop 4702 that iteratively performs the tasks involved in the current stage of the synthetic biology DBTL cycle 3908. Specifically, the AI agent 4602 may receive a user prompt 4606 that indicates a current stage of the synthetic biology DBTL cycle 3908 and any supplemental information, such as one or more hypotheses 3806 related to the current stage of the synthetic biology DBTL cycle. For example, during the experiment design stage 3910, the AI agent 4602 may receive a user prompt 4606 requesting an experiment definition 3808 for the synthetic biology experiment based on the synthetic biology model 3904, including one or more hypotheses 3806 to be investigated by the synthetic biology experiment. During the experiment performance stage 3912, the AI agent 4602 may receive a user prompt 4606 instructing and/or authorizing the AI agent 4602 to cause the synthetic biology experiment to be performed based on the experiment definition 3808. During the experiment evaluation stage 3914, the AI agent 4602 may receive a user prompt 4606 requesting an evaluation of at least one outcome of the synthetic biology experiment, such as performing data analyses, generating observations, and/or extracting or synthesizing knowledge about the synthetic biology knowledge domain 3902. During the synthetic biology model update stage 3916, the AI agent 4602 may receive a user prompt 4606 requesting an update of the synthetic biology model 3904 based on the evaluation of the experiment.

In order to participate in a current stage as indicated in the user prompt 4606, the AI agent 4602 may perform one or more iterations of the agent loop 4702. For example, the AI agent 4602 may first perform a prompt processing stage 4704 to generate an initial evaluation of the task requested by the user prompt 4606 for the current stage of the synthetic biology DBTL cycle 3908. During the prompt processing stage 4704, the AI agent 4602 may generate a first prompt 4610-1 for the large language model 4400 that directs the large language model 4400 to determine a manner of performing one or more tasks associated with the current stage of the synthetic biology DBTL cycle 3908. The first prompt 4610-1 may include an indication of one or more actions 4620 that may further inform the evaluation. For example, the system prompt 4604 may describe each of the tools 4616 of the tool set 4614, may provide examples in which the respective tools 4616 can be effectively used to generate information of value to the evaluation of experiments, and instructions for how the large language model 4400 should evaluate the experiment, including examples of the evaluation of other experiments of the experiment data set 3802. Based on the first prompt 4610-1, the large language model 4400 may generate a first response 4612-1 including instructions for performing one or more tasks associated with the current stage of the synthetic biology DBTL cycle 3908. The first response 4612-1 may indicate one or more actions 4620 to be taken to perform one or more tasks associated with the current stage of the synthetic biology DBTL cycle 3908, such as instances of tool use 4622 that might generate additional information for subsequent iterations of the agent loop 4702. During an initiate action stage 4706, the AI agent 4602 may extract the requested actions 4620 from the first response 4612-1 and may initiate tool use 4622 therefor to perform one or more tasks associated with the current stage of the synthetic biology DBTL cycle 3908, such as invoking the search tool 4616-1 to search a scientific literature database for other experiments that may relate to the record 3804 and/or other features of an area of synthetic biology associated with the experiment. In a receive action result stage 4708, the AI agent 4602 may receive a result 4624 generated by one or more tools 4616 in during and/or after the tool use 4622, such as retrieved information that matches a search query. During a reflection stage 4710, the AI agent 4602 may evaluate the record 3804 together with the result 4624 of the tool use in the context of the one or more tasks associated with the current stage of the synthetic biology DBTL cycle 3908. In particular, the AI agent 4602 may generate a second prompt 4610-2 that includes the system prompt 4604, the user prompt 4606, details of the record 3804, the first prompt 4610-1, the first response 4612-1, a description of the actions 4620 and tool use 4622 performed during the initiate action stage 4706, and/or the result 4624 of the tool use 4622. The second prompt 4610-2 may be provided to the large language model 4400 with a request to determine a next step in the agent loop 4702 to perform the one or more tasks associated with the current stage of the synthetic biology DBTL cycle 3908. The second prompt 4610-2 may also instruct the large language model 4400 to generate a self-prompt 4712 for a next iteration of the agent loop 4702. The large language model 4400 may generate the self-prompt 4712, and the AI agent 4602 may initiate a second iteration of the agent loop 4702 by processing the self-prompt 4712 by the large language model 4400 to continue the incremental completion of the one or more tasks associated with the current stage of the synthetic biology DBTL cycle 3908.

The iteration of the agent loop 4702 may continue until the large language model 4400 has completed the one or more tasks associated with the current stage of the synthetic biology DBTL cycle 3908. Instead, the large language model 4440 may generate a record of the completion of the one or more tasks associated with the current stage of the synthetic biology DBTL cycle 3908, such as log entries and/or one or more outcomes, recordings, and/or descriptions of the one or more tasks. The large language model 4400 may incrementally perform respective tasks of a current stage of the synthetic biology DBTL cycle 3908 until the current stage is complete, and may then proceed to a next stage of the synthetic biology DBTL cycle 3908 for further processing (e.g., independently, in collaboration with one or more human researchers, and/or in collaboration with one or more other AI agents 4602, devices, services, or the like). When the large language model 4400 determines (during a reflection stage 4710) that the tasks of a current stage of the synthetic biology DBTL cycle 3908 are all complete, the large language model 4400 may generate (during the prompt processing stage 4704) the set of outcomes of the current stage of the synthetic biology DBTL cycle 3908 and an indicator that the agent loop 4702 for the current stage of the synthetic biology DBTL cycle 3908 is complete. The AI agent 4602 may extract the one or more outcomes 3918 about the current stage of the synthetic biology DBTL cycle 3908, which may include observations about the synthetic biology knowledge domain 3902 and/or the hypothesis 3806 associated with the experiment, and may output the outcomes 3918. For example, the AI agent 4602 may store the one or more outcomes 3918 in a log of experimental evaluations; attach the one or more outcomes 3918 to the record 3804 as an annotation and/or recommendation; and/or present the one or more outcomes 3918 to a human researcher, such as a laboratory manager who may choose and schedule experiments to be conducted in a laboratory.

The example scenario of FIG. 39 may include a number of variations based on the nature of the synthetic biology knowledge domain 3902, the synthetic biology model 3904 and hypotheses 3806 relating thereto, the record 3906 of the synthetic biology experiments, and/or the experiment definitions 3808 thereof. The following variations may be included in various embodiments of the techniques herein, some of which may alter some details of example scenario shown in FIG. 39.

In various embodiments, the AI agent 4602 may use many kinds of large language models 4400, agent loops 4702, and/or tool sets 4614 to participate in respective stage of the synthetic biology DBTL cycle 3908. For example, the large language model 4400 may be or may include a foundation model that is not particularly trained on an understanding of the area of synthetic biology, but may be configured and/or informed (e.g., by retrieval-augmented generation (RAG), the use of the search tool 4616-1, or the like) with domain-specific knowledge and information that enables the large language model 4400 to perform tasks for the respective stage of the synthetic biology DBTL cycle 3908 and to generate relevant outcomes 3918. Alternatively, the large language model 4400 may be specifically trained (e.g., initially or by fine-tuning and/or transfer learning) using documents that relate to the synthetic biology knowledge domain 3902, such as scientific literature, and may perform the tasks of the respective stage of the synthetic biology DBTL cycle 3908 in an informed manner. As a second example, the agent loop 4702 may be executed in an ad-hoc manner, where each iteration of the agent loop 4702 determines, during the reflection stage 4710, the incremental advance of the next iteration of the agent loop 4702 in the performance of one or more tasks of respective stage of the synthetic biology DBTL cycle 3908. Alternatively, the agent loop 4702 may be organized according to a workflow for performing one or more of the tasks of the respective stage of the synthetic biology DBTL cycle 3908, where such a workflow may be specified in the system prompt 4604, discovered by the AI agent 4602 (e.g., using the search tool 4616-1), and/or generated by a first iteration of the agent loop 4702. As a third example, the tool set 4614 of the AI agent 4602 may include a variety of tools 4616, such as tools 4616 that communicate with one or more human researchers to supplement and/or collaborate on the performance of tasks of a respective stage of the synthetic biology DBTL cycle 3908, and/or one or more simulation tools 4616 that perform simulations of experiments to deduce, predict, and/or validate a recorded and/or predicted experimental outcome as part of a task of a respective stage of the synthetic biology DBTL cycle 3908. Many such variations and techniques of AI agents 4602 are discussed herein and/or are known to those of ordinary skill in the art, and may be included in various embodiments of the techniques presented herein.

In some embodiments, the AI agent 4602 may adapt the agent loop 4702 to participate in the experiment design stage 3910 of the synthetic biology DBTL cycle 3908. Specifically, the AI agent 4602 may adapt the agent loop 4702 to generate at least one hypothesis 3806 about the synthetic biology model 3904. Alternatively or additionally, the AI agent 4602 may adapt the agent loop 4702 to generate the experiment definition 3808 for the synthetic biology experiment in order to test at least one hypothesis 3806 about the synthetic biology model 3904. For instance, the AI agent 4602 may adapt the agent loop 4702 by receiving, selecting, discovering, and/or generating one or more workflows for the generation of hypotheses 3806 and/or experiment definitions 3808, wherein the workflow guides the sequence of iterations of the agent loop 4702 to complete one or more tasks of the experiment design stage 3910 of the synthetic biology DBTL cycle 3908.

As a first such example, the AI agent 4602 may use a workflow to generate an experiment definition 3808 for the synthetic biology experiment by receiving a description of at least one hypothesis 3806 about the synthetic biology model 3904, wherein the description is developed by a human researcher. The AI agent 4602 may execute additional iterations of the agent loop 4702 according to the workflow to generate the experiment definition 3808 for the synthetic biology experiment in order to test the at least one hypothesis 3806 about the synthetic biology model 3904 provided by the human researcher.

As a second such example, the AI agent 4602 may use a workflow to analyze an experiment definition 3808 generated by a human researcher. For instance, the AI agent 4602 may receive the experiment definition 3808 for the synthetic biology experiment from a human researcher. Executing additional iterations of the agent loop 4702 according to the workflow may enable the AI agent 4602 to generate an evaluation of the experiment definition 3808 for the synthetic biology experiment, such as predicting one or more outcomes of the experiment if conducted according to the experiment definition 3808, identifying potential issues with the experiment definition 3808, and/or generating recommendations to adjust the experiment definition 3808 to improve the outcomes of the synthetic biology experiment. The AI agent 4602 may execute additional iterations of the agent loop 4702 according to the workflow to present the evaluation of the experiment definition 3808 to the human researcher.

In some embodiments, the AI agent 4602 may adapt the agent loop 4702 to participate in the experiment performance stage 3912 of the synthetic biology DBTL cycle 3908. For instance, the AI agent 4602 may adapt the agent loop 4702 by receiving, selecting, discovering, and/or generating one or more workflows that guide the sequence of iterations of the agent loop 4702 to complete one or more tasks of the experiment performance stage 3912 of the synthetic biology DBTL cycle 3908. Specifically, the AI agent 4602 may adapt the agent loop 4702 to present, to a human researcher, a recommendation to perform the synthetic biology experiment. The recommendation may include an explanation of a basis of the synthetic biology experiment, such as one or more hypotheses 3806 about the synthetic biology model 3904 to be tested, a prediction of one or more outcomes of the synthetic biology experiment, and/or a basis to prioritize performing the synthetic biology experiment over other synthetic biology experiments that the human researcher may be considering. Alternatively or additionally, the AI agent 4602 may adapt the agent loop 4702 to initiate one or more automated experimental processes to initiate, perform, monitor, record, analyze, and/or conclude one or more steps of the synthetic biology experiment according to the experiment definition 3808.

In some embodiments, the AI agent 4602 may adapt the agent loop 4702 to participate in the experiment evaluation stage 3914 of the synthetic biology DBTL cycle 3908. For instance, the AI agent 4602 may adapt the agent loop 4702 by receiving, selecting, discovering, and/or generating one or more workflows that guide the sequence of iterations of the agent loop 4702 to complete one or more tasks of the experiment evaluation stage 3914 of the synthetic biology DBTL cycle 3908. Specifically, the AI agent may adapt the agent loop 4702 to present the evaluation of one or more outcomes of the synthetic biology experiment to a human researcher. The presentation of the evaluation may include a summary of the synthetic biology experiment, an explanation of the conclusions of the evaluation, a visualization of data collected during or after the synthetic biology experiment, or the like.

In some embodiments, the AI agent 4602 may adapt the agent loop 4702 to participate in the synthetic biology model update stage 3916 of the synthetic biology DBTL cycle 3908. For instance, the AI agent 4602 may adapt the agent loop 4702 by receiving, selecting, discovering, and/or generating one or more workflows that guide the sequence of iterations of the agent loop 4702 to complete one or more tasks of the synthetic biology model update stage 3916 of the synthetic biology DBTL cycle 3908.

As a first example, the AI agent may execute some iterations of the agent loop 4702 according to the workflow to perform a comparison of at least one hypothesis about the biologic process with the at least one outcome of the synthetic biology experiment. The AI agent may execute additional iterations of the agent loop 4702 according to the workflow to update the synthetic biology model 3904 based on the comparison.

As a second example, the AI agent may receive an evaluation by a human researcher of at least one hypothesis about the biologic process based on at least one outcome of the synthetic biology experiment. The AI agent may execute iterations of the agent loop 4702 according to the workflow to update the synthetic biology model 3904 based on the evaluation by the human researcher.

In some embodiments, the synthetic biology model 3904 may be represented as a reinforcement learning policy of a reinforcement learning model. For example, the reinforcement learning model may include, as an environment, a template of a synthetic biology experiment that may be designed to explorer one or more hypotheses 3806. The reinforcement learning model may include, as an objective function, a scoring protocol for measuring and/or evaluating outcomes of the synthetic biology experiment, such as measurements of experimental yield, rate, quality, or the like. The reinforcement learning model may include, as a set of actions, perturbations of the synthetic biology experiment that may affect, and possibly improve the outcomes of the synthetic biology experiment. For instance, the actions may involve adjustments to the process parameters of the synthetic biology experiment (e.g., temperature, pressure, presence and/or concentrations of nutrients, the presence or absence of catalysts, edits to the genotype of the cell line, or the like). Alternatively or additionally, for a synthetic biology experiment involving a cell line or an organism, the actions may involve edits to a genotype of the cell line or organism that may affect, and possibly improve, the outcomes of the synthetic biology experiment. The reinforcement learning model may be trained (e.g., by reinforcement learning techniques) to learn a policy of selecting actions that introduce perturbations of an experiment definition 3808 that are likely to improve the outcomes of the synthetic biology experiment.

As a first example, during the experiment design stage 3910 of the synthetic biology DBTL cycle 3908, AI agent 4602 may be configured to generate an experiment definition 3808 based on the reinforcement learning model. For instance, the AI agent 4602 may execute iterations of the agent loop 4702 to update at least one experimental perturbation involved in the synthetic biology experiment based on the at least one outcome of the synthetic biology experiment. That is, based on the selection of an action by the reinforcement learning model to apply a perturbation the synthetic biology experiment, the AI agent 4602 may execute one or more iterations of the agent loop 4702 to adjust the experiment definition 3808 to include the perturbation associated with the action.

As a second example, during the experiment performance stage 3912 of the synthetic biology DBTL cycle 3908, the AI agent 4602 may cause the synthetic biology experiment to be performed based on the experiment definition based on the reinforcement learning model.

As a third example, during the experiment evaluation stage 3914 of the synthetic biology DBTL cycle 3908, the AI agent 4602 may execute iterations of the agent loop 4702 to update at least one objective associated with the synthetic biology experiment based on the at least one outcome of the synthetic biology experiment. For example, based on measurements of an objective of the synthetic biology experiment such as a yield, rate, quality, and/or consistency of a biologic process, the AI agent 4602 may execute iterations of the agent loop 4702 to update the reinforcement learning policy of the reinforcement learning model to associate a particular action (e.g., a perturbation of the synthetic biology experiment included in the experiment definition 3808) with at least one objective (e.g., the action or perturbation causes the synthetic biology experiment to increase a rate and yield of the biologic process, but to decrease a consistency of the biologic process). As another example, the AI-based agent may execute iterations of the agent loop 4702 to generate at least one observation about the at least one hypothesis 3806 of the synthetic biology model 3904 based on at least one outcome 3918 of the synthetic biology experiment. Such observations may include, for example (without limitation), a rating of the at least one hypothesis, an indicator of a prioritization of the synthetic biology experiment relative to other synthetic biology experiments, a validation of the at least one hypothesis, an identification of an issue with the experiment definition based on the at least one hypothesis, a prediction of at least one outcome of the synthetic biology experiment based on the at least one hypothesis, and/or an explanation of at least one outcome of the synthetic biology experiment based on the at least one hypothesis.

As a fourth example, during the synthetic biology model update stage 3916 of the synthetic biology DBTL cycle 3908, the AI agent 4602 may execute iterations of the agent loop 4702 to update the reinforcement learning model based on outcomes of the synthetic biology experiment. For example, the reinforcement learning model may include a reinforcement learning policy based on the synthetic biology knowledge domain 3902. The AI agent 4602 may execute iterations of the agent loop 4702 to update the reinforcement learning policy through a reinforcement learning process to reconcile the synthetic biology model 3904 with at least one outcome of the synthetic biology experiment (e.g., increasing a probability of actions associated with perturbations of the synthetic biology experiment that improve the outcomes of the synthetic biology experiment, and/or decreasing a probability of actions associated with perturbations of the synthetic biology experiment that do not improve the outcomes of the synthetic biology experiment). As another example, the reinforcement learning policy may include one or more performance metrics associated with the synthetic biology experiment (e.g., estimated measurements of a yield of a biologic process included in the synthetic biology experiment). The AI agent 46702 may execute iterations of the agent loop 4702 to update the at least one performance metric associated with the synthetic biology experiment based on the at least one outcome of the synthetic biology experiment (e.g., updating the estimates of the yield based on the observed yield of the biologic process).

Other variations of the AI agent 4602 (e.g., according to one or more workflows) may improve a collaboration of the AI agent 4602 based on an allocation of resources to the synthetic biology experiment. For example, during the experiment design stage 3910 of the synthetic biology DBTL cycle 3908, the AI agent 4602 may execute iterations of the agent loop 4702 to allocate a portion of a set of resources to the synthetic biology experiment. The allocated resources may include experimental resources (e.g., laboratory physical space, access to laboratory machines for performing various steps of experimental protocols (e.g., reaction tanks, incubators, freezers, or the like), consumable materials such as reagents and supplies, time in a laboratory schedule of available resources, laboratory personnel that may be assigned to various experiments, computational time required by an experimental protocol for data analysis, sampling, or simulations, or the like). Alternatively or additionally, the allocated resources may include computational resources (e.g., processing time, memory, storage, hardware provisions such as tensor processing units (TPUs) and/or graphics processing units (GPUs), large language models 4400 with various forms of specialization and/or training, and/or computational resources for using respective tools 4616 of the tool set 4614 to perform searches, data analyses, and/or code execution such as simulations). The AI agent 4602 may determine the allocation of resources based on at least one of a preliminary evaluation of the synthetic biology experiment, a priority associated with at least one hypothesis on which the synthetic biology experiment is based, an association between a subject matter domain of at least one hypothesis on which the synthetic biology experiment is based and a subject matter domain of the AI agent 4602, and/or at least one observation, by anther AI agent, about at least one hypothesis on which the synthetic biology experiment is based.

In some embodiments, the AI agent 4602 may be associated with an evaluation performance metric. During one or more stages of the synthetic biology DBTL cycle 3908, the AI agent 4602 may update the evaluation performance metric based on observations about the synthetic biology experiment (e.g., based on a comparison of the at least one predicted outcome of the synthetic biology experiment by the AI agent 4602 with at least one observed outcome of the synthetic biology experiment). These and other variations may enable the AI agent 4602 to participate in various stages of the synthetic biology DBTL cycle 3908.

Additional Embodiments

In embodiments, provided herein is an AI-guided synthetic biology development platform having a system for designing, optimizing, and/or manufacturing biosynthetic fuel.

In embodiments, provided herein is an AI-guided synthetic biology development platform having a system for designing, optimizing, and/or manufacturing biosynthetic methanol.

In embodiments, provided herein is an AI-guided synthetic biology development platform having a system for designing, optimizing, and/or manufacturing biosynthetic ethanol.

In embodiments, provided herein is an AI-guided synthetic biology development platform having a system for designing, optimizing, and/or manufacturing biodiesel.

In embodiments, provided herein is an AI-guided synthetic biology development platform having a system for designing, optimizing, and/or manufacturing biobutanol.

In embodiments, provided herein is an AI-guided synthetic biology development platform having a system for designing, optimizing, and/or manufacturing biosynthetic fuel additives.

In embodiments, provided herein is an AI-guided synthetic biology development platform having a system for designing, optimizing, and/or manufacturing biosynthetic isooctane.

In embodiments, provided herein is an AI-guided synthetic biology development platform having a system for designing, optimizing, and/or manufacturing biosynthetic lubricants.

In embodiments, provided herein is an AI-guided synthetic biology development platform having a system for designing, optimizing, and/or manufacturing biosynthetic industrial enzymes.

In embodiments, provided herein is an AI-guided synthetic biology development platform having a system for designing, optimizing, and/or manufacturing biosynthetic dyes and/or pigments.

In embodiments, provided herein is an AI-guided synthetic biology development platform having a system for designing, optimizing, and/or manufacturing biosynthetic commodity chemicals.

In embodiments, provided herein is an AI-guided synthetic biology development platform having a system for designing, optimizing, and/or manufacturing biosynthetic alkanediols.

In embodiments, provided herein is an AI-guided synthetic biology development platform having a system for designing, optimizing, and/or manufacturing biosynthetic 1,4-Butanediol (BDO).

In embodiments, provided herein is an AI-guided synthetic biology development platform having a system for designing, optimizing, and/or manufacturing biosynthetic purified terephthalic acid (PTA)

In embodiments, provided herein is an AI-guided synthetic biology development platform having a system for designing, optimizing, and/or manufacturing biosynthetic peroxides and/or organic acids.

In embodiments, provided herein is an AI-guided synthetic biology development platform having a system for designing, optimizing, and/or manufacturing biopolymers.

In embodiments, provided herein is an AI-guided synthetic biology development platform having a system for designing, optimizing, and/or manufacturing biosynthetic biodegradable plastics.

In embodiments, provided herein is an AI-guided synthetic biology development platform having a system for designing, optimizing, and/or manufacturing biosynthetic biodegradable polyhydroxyalkanoates (PHA).

In embodiments, provided herein is an AI-guided synthetic biology development platform having a system for designing, optimizing, and/or manufacturing biosynthetic biosurfactants.

In embodiments, provided herein is an AI-guided synthetic biology development platform having a system for designing, optimizing, and/or manufacturing biosynthetic sophorolipids.

In embodiments, provided herein is an AI-guided synthetic biology development platform having a system for designing, optimizing, and/or manufacturing biosynthetic building materials.

In embodiments, provided herein is an AI-guided synthetic biology development platform having a system for designing, optimizing, and/or manufacturing biosynthetic cement.

In embodiments, provided herein is an AI-guided synthetic biology development platform having a system for designing, optimizing, and/or manufacturing biosynthetic hydrophobic materials.

In embodiments, provided herein is an AI-guided synthetic biology development platform having a system for designing, optimizing, and/or manufacturing a biosynthetic product that digests plastics.

In embodiments, provided herein is an AI-guided synthetic biology development platform having a system for designing, optimizing, and/or manufacturing a biosynthetic product that processes waste material.

In embodiments, provided herein is an AI-guided synthetic biology development platform having a system for designing, optimizing, and/or manufacturing biosynthetic negative carbon materials.

In embodiments, provided herein is an AI-guided synthetic biology development platform having a system for designing, optimizing, and/or manufacturing biosynthetic textiles.

In embodiments, provided herein is an AI-guided synthetic biology development platform having a system for designing, optimizing, and/or manufacturing biosynthetic fibers.

In embodiments, provided herein is an AI-guided synthetic biology development platform having a system for designing, optimizing, and/or manufacturing biosynthetic polyester.

In embodiments, provided herein is an AI-guided synthetic biology development platform having a system for designing, optimizing, and/or manufacturing biosynthetic polyamide.

In embodiments, provided herein is an AI-guided synthetic biology development platform having a system for designing, optimizing, and/or manufacturing biosynthetic polypropylene.

In embodiments, provided herein is an AI-guided synthetic biology development platform having a system for designing, optimizing, and/or manufacturing biosynthetic cellulosics.

In embodiments, provided herein is an AI-guided synthetic biology development platform having a system for designing, optimizing, and/or manufacturing biosynthetic natural fibers.

In embodiments, provided herein is an AI-guided synthetic biology development platform having a system for designing, optimizing, and/or manufacturing biosynthetic spider silk.

In embodiments, provided herein is an AI-guided synthetic biology development platform having a system for designing, optimizing, and/or manufacturing biosynthetic silkworm silk.

In embodiments, provided herein is an AI-guided synthetic biology development platform having a system for designing, optimizing, and/or manufacturing biosynthetic wool.

In embodiments, provided herein is an AI-guided synthetic biology development platform having a system for designing, optimizing, and/or manufacturing biosynthetic cotton.

In embodiments, provided herein is an AI-guided synthetic biology development platform having a system for designing, optimizing, and/or manufacturing a biosynthetic product for mineral extraction.

In embodiments, provided herein is an AI-guided synthetic biology development platform having a system for designing, optimizing, and/or manufacturing a biosynthetic product for bioremediation.

In embodiments, provided herein is an AI-guided synthetic biology development platform having a system for designing, optimizing, and/or manufacturing biosynthetic sensors.

In embodiments, provided herein is an AI-guided synthetic biology development platform having a system for designing, optimizing, and/or manufacturing biosynthetic fertilizers.

In embodiments, provided herein is an AI-guided synthetic biology development platform having a system for designing, optimizing, and/or manufacturing biosynthetic pesticides.

In embodiments, provided herein is an AI-guided synthetic biology development platform having a system for designing, optimizing, and/or manufacturing biosynthetic herbicides.

In embodiments, provided herein is an AI-guided synthetic biology development platform having a system for designing, optimizing, and/or manufacturing biosynthetic fungicides.

In embodiments, provided herein is an AI-guided synthetic biology development platform having a system for designing, optimizing, and/or manufacturing biosynthetic nematicides.

In embodiments, provided herein is an AI-guided synthetic biology development platform having a system for designing, optimizing, and/or manufacturing biosynthetic crop protection agents.

In embodiments, provided herein is an AI-guided synthetic biology development platform having a system for designing, optimizing, and/or manufacturing microbes configured for nitrogen optimization and/or fixation in crops.

In embodiments, provided herein is an AI-guided synthetic biology development platform having a system for designing, optimizing, and/or manufacturing biosynthetic product for carbon sequestration.

In embodiments, provided herein is an AI-guided synthetic biology development platform having a system for designing, optimizing, and/or manufacturing biosynthetic products for aquaculture applications.

In embodiments, provided herein is an AI-guided synthetic biology development platform having a system for designing, optimizing, and/or manufacturing biosynthetic animal feed.

In embodiments, provided herein is an AI-guided synthetic biology development platform having a system for designing, optimizing, and/or manufacturing biosynthetic animal probiotics.

In embodiments, provided herein is an AI-guided synthetic biology development platform having a system for designing, optimizing, and/or manufacturing biosynthetic animal medicines.

In embodiments, provided herein is an AI-guided synthetic biology development platform having a system for designing, optimizing, and/or manufacturing biosynthetic bioluminescent plants.

In embodiments, provided herein is an AI-guided synthetic biology development platform having a system for designing, optimizing, and/or manufacturing biosynthetic food.

In embodiments, provided herein is an AI-guided synthetic biology development platform having a system for designing, optimizing, and/or manufacturing biosynthetic beverages.

In embodiments, provided herein is an AI-guided synthetic biology development platform having a system for designing, optimizing, and/or manufacturing biosynthetic palm oils.

In embodiments, provided herein is an AI-guided synthetic biology development platform having a system for designing, optimizing, and/or manufacturing biosynthetic flavors.

In embodiments, provided herein is an AI-guided synthetic biology development platform having a system for designing, optimizing, and/or manufacturing biosynthetic milk components.

In embodiments, provided herein is an AI-guided synthetic biology development platform having a system for designing, optimizing, and/or manufacturing biosynthetic milk proteins.

In embodiments, provided herein is an AI-guided synthetic biology development platform having a system for designing, optimizing, and/or manufacturing biosynthetic casein.

In embodiments, provided herein is an AI-guided synthetic biology development platform having a system for designing, optimizing, and/or manufacturing biosynthetic human milk sugar (HMO)

In embodiments, provided herein is an AI-guided synthetic biology development platform having a system for designing, optimizing, and/or manufacturing biosynthetic meat substitutes.

In embodiments, provided herein is an AI-guided synthetic biology development platform having a system for designing, optimizing, and/or manufacturing biosynthetic personal care products.

In embodiments, provided herein is an AI-guided synthetic biology development platform having a system for designing, optimizing, and/or manufacturing biosynthetic cosmetics.

In embodiments, provided herein is an AI-guided synthetic biology development platform having a system for designing, optimizing, and/or manufacturing biosynthetic retinol.

In embodiments, provided herein is an AI-guided synthetic biology development platform having a system for designing, optimizing, and/or manufacturing biosynthetic fragrances.

In embodiments, provided herein is an AI-guided synthetic biology development platform having a system for designing, optimizing, and/or manufacturing biosynthetic skin care products.

In embodiments, provided herein is an AI-guided synthetic biology development platform having a system for designing, optimizing, and/or manufacturing biosynthetic home care products.

In embodiments, provided herein is an AI-guided synthetic biology development platform having a system for designing, optimizing, and/or manufacturing biosynthetic cleaning materials.

In embodiments, provided herein is an AI-guided synthetic biology development platform having a system for designing, optimizing, and/or manufacturing biosynthetic laundry detergent.

In embodiments, provided herein is an AI-guided synthetic biology development platform having a system for designing, optimizing, and/or manufacturing biosynthetic vitamins.

In embodiments, provided herein is an AI-guided synthetic biology development platform having a system for designing, optimizing, and/or manufacturing biosynthetic antioxidants.

In embodiments, provided herein is an AI-guided synthetic biology development platform having a system for designing, optimizing, and/or manufacturing biosynthetic phytochemicals.

In embodiments, provided herein is an AI-guided synthetic biology development platform having a system for designing, optimizing, and/or manufacturing biosynthetic cannabinoids.

In embodiments, provided herein is an AI-guided synthetic biology development platform having a system for designing, optimizing, and/or manufacturing biosynthetic carotenoids.

In embodiments, provided herein is an AI-guided synthetic biology development platform having a system for designing, optimizing, and/or manufacturing biosynthetic flavonoids.

In embodiments, provided herein is an AI-guided synthetic biology development platform having a system for designing, optimizing, and/or manufacturing biosynthetic terpenes.

In embodiments, provided herein is an AI-guided synthetic biology development platform having a system for designing, optimizing, and/or manufacturing biosynthetic polyunsaturated fatty acids.

In embodiments, provided herein is an AI-guided synthetic biology development platform having a system for designing, optimizing, and/or manufacturing biosynthetic pharmaceuticals.

In embodiments, provided herein is an AI-guided synthetic biology development platform having a system for designing, optimizing, and/or manufacturing enzymes that act as biocatalysts in active pharmaceutical ingredient (API) manufacturing.

In embodiments, provided herein is an AI-guided synthetic biology development platform having a system for designing, optimizing, and/or manufacturing cell therapies.

In embodiments, provided herein is an AI-guided synthetic biology development platform having a system for designing, optimizing, and/or manufacturing biosynthetic vaccines and/or vaccine components.

In embodiments, provided herein is an AI-guided synthetic biology development platform having a system for designing, optimizing, and/or manufacturing biosynthetic squalene.

In embodiments, provided herein is an AI-guided synthetic biology development platform having a system for designing, optimizing, and/or manufacturing therapeutic enzymes.

In embodiments, provided herein is an AI-guided synthetic biology development platform having a system for designing, optimizing, and/or manufacturing biosynthetic heparin.

In embodiments, provided herein is an AI-guided synthetic biology development platform having a system for designing, optimizing, and/or manufacturing therapeutic bacteria.

In embodiments, provided herein is an AI-guided synthetic biology development platform having a system for designing, optimizing, and/or manufacturing living medicines.

In embodiments, provided herein is an AI-guided synthetic biology development platform having a system for designing, optimizing, and/or manufacturing biosynthetic probiotics.

In embodiments, provided herein is an AI-guided synthetic biology development platform having a system for designing, optimizing, and/or manufacturing biosynthetic antibody therapeutics.

In embodiments, provided herein is an AI-guided synthetic biology development platform having a system for designing, optimizing, and/or manufacturing biosynthetic personalized medicines.

In embodiments, provided herein is an AI-guided synthetic biology development platform having a system for designing, optimizing, and/or manufacturing biosynthetic medical devices.

In embodiments, provided herein is an AI-guided synthetic biology development platform having a system for designing, optimizing, and/or manufacturing biosynthetic medical diagnostic devices.

In embodiments, provided herein is an AI-guided synthetic biology development platform having a system for designing, optimizing, and/or manufacturing biosynthetic medical diagnostic sensors.

In embodiments, provided herein is an AI-guided analytic platform for synthetic biology development.

In embodiments, provided herein is a synthetic biology development-as-a-service (SBDaaS) platform.

In embodiments, provided herein is an AI-guided synthetic biology techno-economic analysis (tea) platform.

In embodiments, provided herein is a synthetic biology techno-economic analysis-as-a-service platform.

In embodiments, provided herein is an AI-guided synthetic biology prototyping platform.

In embodiments, provided herein is a synthetic biology prototyping-as-a-service platform.

In embodiments, provided herein is an AI-guided synthetic biology optimization platform.

In embodiments, provided herein is a synthetic biology optimization-as-a-service platform.

In embodiments, provided herein is an AI-guided synthetic biology pathway optimization platform.

In embodiments, provided herein is an AI-guided synthetic biology protein optimization platform.

In embodiments, provided herein is an AI-guided synthetic biology design for scale optimization platform.

In embodiments, provided herein is an AI-guided synthetic biology scaling platform.

In embodiments, provided herein is a synthetic biology scaling-as-a-service platform.

In embodiments, provided herein is an AI-guided synthetic biology screening management platform.

In embodiments, provided herein is a screening management-as-a-service platform.

In embodiments, provided herein is an AI-guided analytic platform for synthetic biology development having an AI-guided development toolkit.

In embodiments, provided herein is an AI-guided analytic platform for synthetic biology development having an AI-guided intellectual property (IP) toolkit.

In embodiments, provided herein is an AI-guided analytic platform for synthetic biology development having a strain IP exploration tool configured to recommend gene edits associated with an existing strain that will not impact performance of the existing strain.

In embodiments, provided herein is an AI-guided analytic platform for synthetic biology development having a system for analyzing the similarities of strains.

In embodiments, provided herein is an AI-guided synthetic biology development platform having a workflow definition system that monitors interactions of a set of designated human users performing a set of tasks and learns respective workflows to automate the set of tasks in an iterative, semi-supervised manner wherein the set of tasks are associated with synthetic biology development.

In embodiments, provided herein is an AI-guided synthetic biology development platform having a workflow management system that accesses a plurality of workflows learned by a workflow definition system and that deploys one or more of the plurality of workflows in connection with a synthetic biology development task.

In embodiments, provided herein is a synthetic biology strain, physical biological asset, and/or genetic modification.

In embodiments, provided herein is a synthetic biology process environment and/or parameters.

In embodiments, provided herein is a set of hardware assets associated with synthetic biology development.

In embodiments, provided herein is a system having a set of robots and/or robotic handling systems configured to perform screening tasks and/or other synthetic biology development tasks.

In embodiments, provided herein is a system having an AI system-on-chip (SoC) configured to perform tasks associated with synthetic biology development.

In embodiments, provided herein is a system having a plate having an AI system-on-chip (SoC) configured to perform tasks associated with synthetic biology development.

In embodiments, provided herein is a system having a tank having an AI system-on-chip (SoC) configured to perform tasks associated with synthetic biology development.

In embodiments, provided herein is a system having a controller having an AI system-on-chip (SoC) configured to perform tasks associated with synthetic biology development.

In embodiments, provided herein is a system having a fermenter controlled by a set of models.

In embodiments, provided herein is a system having a system configured to control fermentation in real-time to estimate model parameters using a turbidostat.

In embodiments, provided herein is a system having a system configured to control fermentation in real-time to estimate model parameters using a chemostat.

In embodiments, provided herein is a system having a set of smart plates configured for synthetic biology development tasks.

In embodiments, provided herein is a system having a set of smart tanks configured for synthetic biology development tasks and/or biomanufacturing tasks.

In embodiments, provided herein is a system having a set of automated laboratories configured for synthetic biology development tasks and/or experiments.

In embodiments, provided herein is a system having an extended reality (XR) system configured for providing an XR environment associated with synthetic biology development.

In embodiments, provided herein is a system having an augmented reality (AR) system configured for providing an AR environment associated with synthetic biology development.

In embodiments, provided herein is a system having a virtual reality (VR) system configured for providing a VR environment associated with synthetic biology development.

In embodiments, provided herein is a system having a mixed reality (MR) system configured for providing an MR environment associated with synthetic biology development.

In embodiments, provided herein is a system having a machine vision system configured to perform machine vision tasks associated with synthetic biology development and/or biomanufacturing.

In embodiments, provided herein is a system having a 3D printing system configured to print biosynthetic products.

In embodiments, provided herein is a system having a system configured for the design, synthesis, processing, and/or recycling of 3D printed biosynthetic products.

In embodiments, provided herein is a system having a system configured for the design, manufacturing, and/or operation of devices that use 3D-printed biosynthetic products.

In embodiments, provided herein is a system having software and/or firmware associated with 3D-printed biosynthetic products.

In embodiments, provided herein is an AI-guided analytic platform for synthetic biology development having a data intake pipeline configured to manage the intake of data associated with synthetic biology development.

In embodiments, provided herein is an AI-guided analytic platform for synthetic biology development having a customer data ingestion toolkit configured for processing customer data associated with synthetic biology development.

In embodiments, provided herein is an AI-guided analytic platform for synthetic biology development having a data intake pipeline having a schema definition system configured to infer a consistent schema configuration for a set of data files.

In embodiments, provided herein is an AI-guided analytic platform for synthetic biology development having a data intake pipeline having a system for validating genotypes.

In embodiments, provided herein is an AI-guided analytic platform for synthetic biology development having a data intake pipeline having a system for generating an analytical measure associated with quality control (QC) for data associated with synthetic biology development.

In embodiments, provided herein is an AI-guided analytic platform for synthetic biology development having a data intake pipeline having a system configured to identify outliers in a dataset wherein the dataset is associated with synthetic biology development.

In embodiments, provided herein is an AI-guided analytic platform for synthetic biology development having a data intake pipeline having a system for prioritizing control strains.

In embodiments, provided herein is an AI-guided analytic platform for synthetic biology development having a data intake pipeline having a system configured to design a set of experiments associated with synthetic biology development.

In embodiments, provided herein is an AI-guided analytic platform for synthetic biology development having a data intake pipeline having a queryable strain registry.

In embodiments, provided herein is an AI-guided analytic platform for synthetic biology development having a data intake pipeline having a system for importing a new dataset associated with synthetic biology development.

In embodiments, provided herein is an AI-guided analytic platform for synthetic biology development having a data intake pipeline having a system for updating a dataset with new data wherein the new data is associated with synthetic biology development.

In embodiments, provided herein is an AI-guided analytic platform for synthetic biology development having a data intake pipeline having a system for storing model parameters and/or outputs wherein the models are associated with synthetic biology development.

In embodiments, provided herein is an AI-guided analytic platform for synthetic biology development having a data collection system configured to automatically collect data wherein the data is associated with synthetic biology development.

In embodiments, provided herein is an AI-guided analytic platform for synthetic biology development having a data aggregation system configured to automatically aggregate data wherein the data is associated with synthetic biology development.

In embodiments, provided herein is an AI-guided analytic platform for synthetic biology development having a data processing system configured to automatically process data wherein the data is associated with synthetic biology development.

In embodiments, provided herein is an AI-guided analytic platform for synthetic biology development having a data storage system configured to store data wherein the data is associated with synthetic biology development.

In embodiments, provided herein is an AI-guided analytic platform for synthetic biology development having a distributed ledger system configured to store data wherein the data is associated with synthetic biology development.

In embodiments, provided herein is an AI-guided analytic platform for synthetic biology development having a blockchain system configured to store data wherein the data is associated with synthetic biology development.

In embodiments, provided herein is an AI-guided analytic platform for synthetic biology development having a blockchain system configured to represent strain lineage.

In embodiments, provided herein is an AI-guided analytic platform for synthetic biology development having a data normalization system configured for normalizing data associated with synthetic biology development.

In embodiments, provided herein is an AI-guided analytic platform for synthetic biology development having a data normalization system configured to perform Bayesian data normalization for data associated with synthetic biology development.

In embodiments, provided herein is an AI-guided analytic platform for synthetic biology development having a data normalization system configured for normalizing data associated with synthetic biology development having a system configured to identify the optimal model of data generation.

In embodiments, provided herein is an AI-guided analytic platform for synthetic biology development having a data normalization system configured for normalizing data associated with synthetic biology development having a system configured to estimate batch effects.

In embodiments, provided herein is an AI-guided analytic platform for synthetic biology development having a system for automatically collecting biological parameters and measurements.

In embodiments, provided herein is an AI-guided analytic platform for synthetic biology development having a system configured to generate an analytical measure associated with fermentation.

In embodiments, provided herein is an AI-guided analytic platform for synthetic biology development having a system configured to generate an analytical measure associated with carbon balance in fermentation.

In embodiments, provided herein is an AI-guided analytic platform for synthetic biology development having a system configured to estimate normalized yield associated with fermentation.

In embodiments, provided herein is an AI-guided analytic platform for synthetic biology development having a system configured to monitor flow rate and/or other metrics associated with fermentation.

In embodiments, provided herein is an AI-guided analytic platform for synthetic biology development having a sensor and/or data fusion system configured to combine data from multiple sensors and/or data sources wherein the data is associated with synthetic biology development.

In embodiments, provided herein is an AI-guided analytic platform for synthetic biology development having a model output tracking system configured for tracking model outputs wherein the model outputs are associated with synthetic biology development.

In embodiments, provided herein is an AI-guided analytic platform for synthetic biology development having a model output tracking system having a database to store model predictions wherein the model predictions are associated with synthetic biology development.

In embodiments, provided herein is an AI-guided analytic platform for synthetic biology development having a model output tracking system having an application programming interface (API).

In embodiments, provided herein is an AI-guided analytic platform for synthetic biology development having a model output tracking system having a system for running a model against candidate strains to obtain a list of scored design candidate strains.

In embodiments, provided herein is an AI-guided analytic platform for synthetic biology development having a model output tracking system having a system for analyzing and/or filtering a list of scored candidate strains.

In embodiments, provided herein is an AI-guided analytic platform for synthetic biology development having a model output tracking system having a candidate strain scoring system.

In embodiments, provided herein is an AI-guided analytic platform for synthetic biology development having a multi-objective optimization system for performing multi-objective optimizations in synthetic biology development tasks.

In embodiments, provided herein is an AI-guided analytic platform for synthetic biology development having a machine learning system, artificial intelligence system, and/or set of neural networks configured to simultaneously optimize a microbe, a bioreactor process, and a downstream purification process.

In embodiments, provided herein is an AI-guided analytic platform for synthetic biology development having a hybrid model system having a plurality of models wherein a set of models of the plurality of models are configured to generate a set of outputs associated with synthetic biology development.

In embodiments, provided herein is an AI-guided analytic platform for synthetic biology development having a hybrid model system having a plurality of models wherein a set of models of the plurality of models are configured to generate a set of outputs associated with synthetic biology development wherein the set of models use sensor and/or data fusion to generate the set of outputs.

In embodiments, provided herein is an AI-guided analytic platform for synthetic biology development having a hybrid model system having a plurality of models wherein a set of models of the plurality of models are configured to generate a set of outputs associated with synthetic biology development in a low data regime.

In embodiments, provided herein is an AI-guided analytic platform for synthetic biology development having a hybrid model system having a plurality of models wherein a set of models of the plurality of models are configured to generate a set of outputs associated with synthetic biology development in a high data regime.

In embodiments, provided herein is an AI-guided analytic platform for synthetic biology development having a hybrid model system having a machine learning system, artificial intelligence system, and/or neural network system configured to select a model from a plurality of models wherein the plurality of models are associated with synthetic biology development.

In embodiments, provided herein is an AI-guided analytic platform for synthetic biology development having a hybrid model system having a machine learning system, artificial intelligence system, and/or neural network system configured to select a plurality of models from a set of models wherein the set of models are associated with synthetic biology development.

In embodiments, provided herein is an AI-guided analytic platform for synthetic biology development having a hybrid model system having a set of models wherein the models operate in parallel.

In embodiments, provided herein is an AI-guided analytic platform for synthetic biology development having a hybrid model system having a plurality of models wherein a set of models of the plurality of models operate in a sequence and having a system for sequencing the order of execution of the set of models.

In embodiments, provided herein is an AI-guided analytic platform for synthetic biology development having a hybrid model system having a plurality of models wherein at least one of the plurality of models is a machine learning model.

In embodiments, provided herein is an AI-guided analytic platform for synthetic biology development having a hybrid model system having a plurality of models wherein at least one of the plurality of models is a tabular machine learning model.

In embodiments, provided herein is an AI-guided analytic platform for synthetic biology development having a hybrid model system having a plurality of models wherein at least one of the plurality of models is a zero-shot machine learning model.

In embodiments, provided herein is an AI-guided analytic platform for synthetic biology development having a hybrid model system having a plurality of models wherein at least one of the plurality of models is a one-shot machine learning model.

In embodiments, provided herein is an AI-guided analytic platform for synthetic biology development having a hybrid model system having a plurality of models wherein at least one of the plurality of models is a few-shot machine learning model.

In embodiments, provided herein is an AI-guided analytic platform for synthetic biology development having a hybrid model system having a plurality of models wherein at least one of the plurality of models is a deep learning model.

In embodiments, provided herein is an AI-guided analytic platform for synthetic biology development having a hybrid model system having a plurality of models wherein at least one of the plurality of models is a long short-term memory (LSTM) model.

In embodiments, provided herein is an AI-guided analytic platform for synthetic biology development having a hybrid model system having a plurality of models wherein at least one of the plurality of models is a multilayer perceptron (MLP) model.

In embodiments, provided herein is an AI-guided analytic platform for synthetic biology development having a hybrid model system having a plurality of models wherein at least one of the plurality of models is a transformer model.

In embodiments, provided herein is an AI-guided analytic platform for synthetic biology development having a set of hybrid models having a set of process models and a set of neural networks wherein the set of hybrid models are configured to simulate the behavior of a fermentation process.

In embodiments, provided herein is an AI-guided analytic platform for synthetic biology development having a set of neural networks and a set of hybrid models for combining plate and tank data.

In embodiments, provided herein is an AI-guided analytic platform for synthetic biology development having a set of fully differentiable kinetic models configured to execute strain and/or process engineering tasks.

In embodiments, provided herein is an AI-guided analytic platform for synthetic biology development having a set of fully differentiable kinetic models configured to execute strain and/or process engineering tasks wherein the fully differentiable kinetic model is optimized for fit to data.

In embodiments, provided herein is an AI-guided analytic platform for synthetic biology development having a set of fully differentiable kinetic models configured to execute strain and/or process engineering tasks wherein the fully differentiable kinetic model is optimized for genetic edits.

In embodiments, provided herein is an AI-guided analytic platform for synthetic biology development having a set of fully differentiable kinetic models configured to execute strain and/or process engineering tasks wherein the fully differentiable kinetic model is optimized for media formulation.

In embodiments, provided herein is an AI-guided analytic platform for synthetic biology development having a set of fully differentiable kinetic models configured to execute strain and/or process engineering tasks wherein the fully differentiable kinetic model is optimized for control processes.

In embodiments, provided herein is an AI-guided analytic platform for synthetic biology development having a system configured for enabling ensemble modeling.

In embodiments, provided herein is an AI-guided analytic platform for synthetic biology development having an automated model construction system configured to automate the construction of a set of pathway models associated with synthetic biology development.

In embodiments, provided herein is an AI-guided analytic platform for synthetic biology development having an automated model construction system configured to automate the construction of a set of pathway models associated with synthetic biology development having a system for defining a set of pathways, enzymes, and/or reactions to include in the set of models.

In embodiments, provided herein is an AI-guided analytic platform for synthetic biology development having an automated model construction system configured to automate the construction of a set of pathway models associated with synthetic biology development having a system for defining a set of pathways, enzymes, and/or reactions to include in the set of models, a system for automatically collecting data associated with the set of pathways, enzymes, and or reactions, and a system for automatically configuring the set of models based on the automatically collected data.

In embodiments, provided herein is an AI-guided analytic platform for synthetic biology development having an automated model construction system configured to automate the construction of a set of pathway models associated with synthetic biology development having a system for setting default parameter values and initial states for the set of pathway models.

In embodiments, provided herein is an AI-guided analytic platform for synthetic biology development having an automated model construction system configured to automate the construction of a set of pathway models associated with synthetic biology development having a system for adjusting the parameter values for the set of pathway models based on experimental data.

In embodiments, provided herein is an AI-guided analytic platform for synthetic biology development having an automated model construction system having a system for adjusting the knowledge base data to a given model.

In embodiments, provided herein is an AI-guided analytic platform for synthetic biology development having an automated model construction system having a user interface.

In embodiments, provided herein is an AI-guided analytic platform for synthetic biology development having a set of foundation models associated with synthetic biology.

In embodiments, provided herein is an AI-guided analytic platform for synthetic biology development having a set of protein models configured to design and/or optimize a set of proteins to have desired properties and/or functions.

In embodiments, provided herein is an AI-guided analytic platform for synthetic biology development having a set of protein language models configured to represent and/or predict the structures and/or functions of a set of proteins based on a set of amino acid sequences.

In embodiments, provided herein is an AI-guided analytic platform for synthetic biology development having a set of gene embedding models configured to represent a gene as a vector in high-dimensional space.

In embodiments, provided herein is an AI-guided analytic platform for synthetic biology development having a strain embedding model configured to represent a strain as a vector in high-dimensional space.

In embodiments, provided herein is an AI-guided analytic platform for synthetic biology development having a system configured to automatically collect a functional description of a gene from a database and input the functional description of the gene into a protein language model to output the gene embedding data for the gene.

In embodiments, provided herein is an AI-guided analytic platform for synthetic biology development having a system configured to automatically collect a protein sequence from a database and input the protein sequence into a protein language model to output a prediction of an enzyme, the enzyme's function in a cell, and/or a function-aware embedding of a protein sequence.

In embodiments, provided herein is an AI-guided analytic platform for synthetic biology development having a system configured to automatically collect text and/or a protein sequence from a database and input the protein sequence into a protein language model to output embedding data.

In embodiments, provided herein is an AI-guided analytic platform for synthetic biology development having a system configured to automatically fuse gene embedding data from different models.

In embodiments, provided herein is an AI-guided analytic platform for synthetic biology development having a system for combining protein language models with supervised learning.

In embodiments, provided herein is an AI-guided analytic platform for synthetic biology development having a set of active learning models.

In embodiments, provided herein is an AI-guided analytic platform for synthetic biology development having a system configured to optimize the genetics of a strain for performance at a target scale based on a set of ensemble supervised models and active learning.

In embodiments, provided herein is an AI-guided analytic platform for synthetic biology development having a system for using a strain embedding to identify untested potential high performers, a system for identifying model signatures in plate data, a system for predicting tank performance using the identified model signatures, a set of neural networks and a set of hybrid models configured to combine plate and tank data, an ensemble model system, and an active learning system.

In embodiments, provided herein is an AI-guided analytic platform for synthetic biology development having a set of active learning models configured to prioritize experiments associated with synthetic biology development.

In embodiments, provided herein is an AI-guided analytic platform for synthetic biology development having a set of mechanistic models configured to simulate the behavior of a set of biological systems under a set of conditions.

In embodiments, provided herein is an AI-guided analytic platform for synthetic biology development having a set of genome scale models configured to represent the metabolic network of an organism at the scale of its entire genome.

In embodiments, provided herein is an AI-guided analytic platform for synthetic biology development having a set of kinetic models configured to simulate the behavior of a biological pathway.

In embodiments, provided herein is an AI-guided analytic platform for synthetic biology development having a set of kinetic models that use dynamic and responsive boundaries.

In embodiments, provided herein is an AI-guided analytic platform for synthetic biology development having a set of kinetic models having a system that deconstruct enzymatic reaction mechanisms into component steps.

In embodiments, provided herein is an AI-guided analytic platform for synthetic biology development having a set of kinetic models having a system configured for parameter modeling and/or prediction.

In embodiments, provided herein is an AI-guided analytic platform for synthetic biology development having a set of process models configured to simulate the behavior of a fermentation process.

In embodiments, provided herein is an AI-guided analytic platform for synthetic biology development having a machine learning system, artificial intelligence system, and/or set of neural networks configured to perform techno-economic analysis (TEA).

In embodiments, provided herein is an AI-guided analytic platform for synthetic biology development having a machine learning system, artificial intelligence system, and/or set of neural networks configured to perform prototyping tasks associated with synthetic biology development.

In embodiments, provided herein is an AI-guided analytic platform for synthetic biology development having a machine learning system, artificial intelligence system, and/or set of neural networks configured to select a base strain.

In embodiments, provided herein is an AI-guided analytic platform for synthetic biology development having a machine learning system, artificial intelligence system, and/or set of neural networks configured to select a base strain wherein the base strain is designed to produce a plurality target molecules.

In embodiments, provided herein is an AI-guided analytic platform for synthetic biology development having a machine learning system, artificial intelligence system, and/or set of neural networks configured for pathway selection.

In embodiments, provided herein is an AI-guided analytic platform for synthetic biology development having a machine learning system, artificial intelligence system, and/or set of neural networks configured for enzyme selection.

In embodiments, provided herein is an AI-guided analytic platform for synthetic biology development having a set of pathway models.

In embodiments, provided herein is an AI-guided analytic platform for synthetic biology development having a set of neural networks configured to perform a biological pathway optimization.

In embodiments, provided herein is an AI-guided analytic platform for synthetic biology development having a system for enabling ensemble modeling using a set of models configured to perform a pathway optimization.

In embodiments, provided herein is an AI-guided analytic platform for synthetic biology development having a genetic generalization system configured to predict the effects of a set of unseen genetic edits while holding a set of process conditions constant.

In embodiments, provided herein is an AI-guided analytic platform for synthetic biology development having a system configured to generate a set of recommendations related to potential genetic edits to a strain in optimizing the strain for performance at target scale.

In embodiments, provided herein is an AI-guided analytic platform for synthetic biology development having a system configured to optimize the genetics of a strain for performance at a target scale.

In embodiments, provided herein is an AI-guided analytic platform for synthetic biology development having a set of gene function models configured to represent and/or predict the function of a gene.

In embodiments, provided herein is an AI-guided analytic platform for synthetic biology development having a system configured to automatically combine a gene function model and a pathway function model.

In embodiments, provided herein is an AI-guided analytic platform for synthetic biology development having a set of gene knockout models configured to predict the behavior from single gene edits from phenotypes of edits of other genes.

In embodiments, provided herein is an AI-guided analytic platform for synthetic biology development having a system configured to optimize the genetics of a strain for performance at a target scale based on supervised modeling.

In embodiments, provided herein is an AI-guided analytic platform for synthetic biology development having a system configured to optimize the genetics of a strain for performance at a target scale based on a set of supervised models configured to generalize tank and/or plate performance data based on strain gene functions and/or embeddings.

In embodiments, provided herein is an AI-guided analytic platform for synthetic biology development having a system configured to optimize the genetics of a strain for performance at a target scale based on a set of supervised models configured to generalize tank performance data based on plate data signature for edits.

In embodiments, provided herein is an AI-guided analytic platform for synthetic biology development having a system configured to optimize the genetics of a strain for performance at a target scale based on a set of supervised models that combine gene embeddings and rich plate data.

In embodiments, provided herein is an AI-guided analytic platform for synthetic biology development having a set of design for scale models.

In embodiments, provided herein is an AI-guided analytic platform for synthetic biology development having a knowledge and discovery engine configured to determine the conditions for optimizing the genetics of a strain for performance at a target scale.

In embodiments, provided herein is an AI-guided analytic platform for synthetic biology development having a system configured to optimize the genetics of a strain for performance at a target scale having a system configured to analyze a set of parameters associated with a target condition and replicate the set of parameters in a scale-down model.

In embodiments, provided herein is an AI-guided analytic platform for synthetic biology development having a system configured to optimize the genetics of a strain for performance at a target scale having a system configured to collect the genomics, transcriptomics, proteomics, metabolomics, lipidomics, and/or phenomics to characterize the strain biology at a set of target conditions.

In embodiments, provided herein is an AI-guided analytic platform for synthetic biology development having a system configured to optimize the genetics of a strain for performance at a target scale having a system configured to design a platform host for robustness across a plurality of conditions.

In embodiments, provided herein is an AI-guided analytic platform for synthetic biology development having a system configured to identify a set of optimal fermentation processes for a strain in a set of experiments.

In embodiments, provided herein is an AI-guided analytic platform for synthetic biology development having a system to identify the environmental conditions of the host that depend on the genetic modifications of the host to make the product.

In embodiments, provided herein is an AI-guided analytic platform for synthetic biology development having a machine learning system, artificial intelligence system, and/or set of neural networks configured to select, recommend, and/or rank a set of synthetic biology screening experiments.

In embodiments, provided herein is an AI-guided analytic platform for synthetic biology development having a machine learning system, artificial intelligence system, and/or set of neural networks configured to scale the production of a molecule from a set of plates to a set of tanks.

In embodiments, provided herein is an AI-guided analytic platform for synthetic biology development having a machine learning system, artificial intelligence system, and/or set of neural networks configured to understand the transition from a set of plates to a set of tanks in the production of a molecule.

In embodiments, provided herein is an AI-guided analytic platform for synthetic biology development having a system for using a gene embedding to identify untested potential high performers and having a set of neural networks and a set of hybrid models for combining plate and tank data.

In embodiments, provided herein is an AI-guided analytic platform for synthetic biology development having a system for using a strain embedding to identify untested potential high performers and having a set of neural networks and a set of hybrid models for combining plate and tank data.

In embodiments, provided herein is an AI-guided analytic platform for synthetic biology development having a system for identifying model signatures in plate data, a system for predicting tank performance using the identified model signatures, and a set of neural networks and a set of hybrid models configured to combine plate and tank data.

In embodiments, provided herein is an AI-guided analytic platform for synthetic biology development having a machine learning system, artificial intelligence system, and/or set of neural networks configured to optimize a set of biomanufacturing processes.

In embodiments, provided herein is an AI-guided analytic platform for synthetic biology development having a set of models for scaling the design of a biosynthetic product.

In embodiments, provided herein is an AI-guided analytic platform for synthetic biology development having a process generalization system configured to predict the effects of a set of process conditions while holding the genotype of a strain constant.

In embodiments, provided herein is an AI-guided analytic platform for synthetic biology development having a system configured to predict the performance of a strain in producing a molecule in a set of tanks from the performance of the strain in producing the molecule in a set of plates.

In embodiments, provided herein is an AI-guided analytic platform for synthetic biology development having a system configured to predict the optimal process conditions for a strain to produce a target molecule in a set of tanks.

In embodiments, provided herein is an AI-guided analytic platform for synthetic biology development having a system configured to determine a set of technical, economic, and/or physical limitations of a scaled production process for a product molecule.

In embodiments, provided herein is an AI-guided analytic platform for synthetic biology development having a system configured to determine a set of properties of a product molecule and/or required downstream processing in a scaled production process for the product molecule.

In embodiments, provided herein is an AI-guided analytic platform for synthetic biology development having a system configured to determine a set of environmental requirements of a host strain that are independent from a target product molecule of the host strain.

In embodiments, provided herein is an AI-guided analytic platform for synthetic biology development having a machine learning system, artificial intelligence system, and/or set of neural networks configured to optimize the yield of a target molecule.

In embodiments, provided herein is an AI-guided analytic platform for synthetic biology development having a machine learning system, artificial intelligence system, and/or set of neural networks configured to optimize the performance of a target molecule.

In embodiments, provided herein is an AI-guided analytic platform for synthetic biology development having a machine learning system, artificial intelligence system, and/or set of neural networks configured to optimize the purification of a target molecule.

In embodiments, provided herein is an AI-guided analytic platform for synthetic biology development having a set of machine learning systems, a set of artificial intelligence systems, a set of neural networks, and/or a set of other models configured for scaling tasks associated with synthetic biology.

In embodiments, provided herein is an AI-guided analytic platform for synthetic biology development having a system for modeling the behaviors of a set of nonmodal organisms.

In embodiments, provided herein is an AI-guided analytic platform for synthetic biology development having a feedstock exploration system configured to generate feedstock recommendations associated with a synthetic biology product.

In embodiments, provided herein is an AI-guided analytic platform for synthetic biology development having a set of models configured to look for patterns in historical data associated with synthetic biology development.

In embodiments, provided herein is an AI-guided analytic platform for synthetic biology development having an analytics system configured to generate an analytic measure associated with synthetic biology development.

In embodiments, provided herein is an AI-guided analytic platform for synthetic biology development having a search and discovery system for searching data and discovering patterns in data associated with synthetic biology development.

In embodiments, provided herein is an AI-guided analytic platform for synthetic biology development having a system configured to perform flux balance analysis (FBA).

In embodiments, provided herein is an AI-guided analytic platform for synthetic biology development having a system configured to perform flux balance analysis (FBA) having a system configured to precisely simulate sections of a metabolic network.

In embodiments, provided herein is an AI-guided analytic platform for synthetic biology development having a system configured to perform flux balance analysis (FBA) having a system for modifying an objective function of FBA metabolism to include an upstream supply generated in upstream sub-units and a downstream demand generated within downstream sub-units in the production network, and iteratively solving FBA metabolism and the upstream and downstream sub-units with updated initial conditions to produce a time series solution to the production network.

In embodiments, provided herein is an AI-guided analytic platform for synthetic biology development having a system configured to perform flux balance analysis (FBA) having a system configured to simplify a metabolic network to reduce the size of the computational problem.

In embodiments, provided herein is an AI-guided analytic platform for synthetic biology development having a system configured to perform flux balance analysis (FBA) having a system configured to store a database structured as a bipartite graph.

In embodiments, provided herein is an AI-guided analytic platform for synthetic biology development having a system configured to perform flux variability analysis (FVA).

In embodiments, provided herein is an AI-guided analytic platform for synthetic biology development having a system configured to perform gene essentiality analysis.

In embodiments, provided herein is an AI-guided analytic platform for synthetic biology development having an AI-guided digital twin system for enabling digital twins associated with synthetic biology development.

In embodiments, provided herein is an AI-guided analytic platform for synthetic biology development having an AI-guided digital twin system having a set of base strain digital twins for digitally representing a set of base strains.

In embodiments, provided herein is an AI-guided analytic platform for synthetic biology development having an AI-guided digital twin system having a set of gene digital twins for digitally representing a set of genes.

In embodiments, provided herein is an AI-guided analytic platform for synthetic biology development having an AI-guided digital twin system having a set of genome digital twins for digitally representing a set of genomes.

In embodiments, provided herein is an AI-guided analytic platform for synthetic biology development having an AI-guided digital twin system having a set of protein digital twins for digitally representing a set of proteins.

In embodiments, provided herein is an AI-guided analytic platform for synthetic biology development having an AI-guided digital twin system having a set of enzyme digital twins for digitally representing a set of enzymes.

In embodiments, provided herein is an AI-guided analytic platform for synthetic biology development having an AI-guided digital twin system having a set of feedstock digital twins for digitally representing a set of feedstocks.

In embodiments, provided herein is an AI-guided analytic platform for synthetic biology development having an AI-guided digital twin system having a set of plate digital twins for digitally representing a set of plates.

In embodiments, provided herein is an AI-guided analytic platform for synthetic biology development having an AI-guided digital twin system having a set of bioreactor digital twins for digitally representing a set of bioreactors.

In embodiments, provided herein is an AI-guided analytic platform for synthetic biology development having an AI-guided digital twin system having a set of tank digital twins for digitally representing a set of tanks.

In embodiments, provided herein is an AI-guided analytic platform for synthetic biology development having an AI-guided digital twin system having a set of biomanufacturing plant digital twins for digitally representing a set of biomanufacturing plants.

In embodiments, provided herein is an AI-guided analytic platform for synthetic biology development having an AI-guided digital twin system having a set of laboratory infrastructure digital twins for digitally representing laboratory infrastructure.

In embodiments, provided herein is an AI-guided analytic platform for synthetic biology development having an AI-guided digital twin system having a set of screening robotics digital twins for digitally representing a set of robots and/or robotic handling systems configured to perform screening tasks.

In embodiments, provided herein is an AI-guided analytic platform for synthetic biology development having an AI-guided digital twin system having a set of biosynthetic pathway digital twins for digitally representing a set of biosynthetic pathways.

In embodiments, provided herein is an AI-guided analytic platform for synthetic biology development having an AI-guided digital twin system having a set of biomanufacturing process digital twins for digitally representing a set of biomanufacturing processes.

In embodiments, provided herein is an AI-guided analytic platform for synthetic biology development having an AI-guided digital twin system having a system for representing a set of strain performance metrics in a set of digital twins associated with synthetic biology development.

In embodiments, provided herein is an AI-guided analytic platform for synthetic biology development having an AI-guided digital twin system having a system for representing a set of financial metrics in a set of digital twins associated with synthetic biology development.

In embodiments, provided herein is an AI-guided analytic platform for synthetic biology development having an AI-guided digital twin system having a system for representing a set of process parameters in a set of digital twins associated with synthetic biology development.

In embodiments, provided herein is an AI-guided analytic platform for synthetic biology development having a simulation system used to model the behavior of a system associated with synthetic biology development.

In embodiments, provided herein is an AI-guided analytic platform for synthetic biology development having an AI-guided simulation system used to model the behavior of a system associated with synthetic biology development.

In embodiments, provided herein is an AI-guided analytic platform for synthetic biology development having a simulation system used to model the behavior of a system associated with synthetic biology development having a system for performing a heuristic evaluation and/or ranking associated with a set of simulations.

In embodiments, provided herein is an AI-guided analytic platform for synthetic biology development having a simulation system used to model the behavior of a system associated with synthetic biology development having a system for providing a set of visualizations associated with a set of simulation results.

In embodiments, provided herein is an AI-guided analytic platform for synthetic biology development having a simulation system used to model the behavior of a system associated with synthetic biology development having a system for initializing parameters and/or states for simulations executed during model training.

In embodiments, provided herein is an AI-guided analytic platform for synthetic biology development having a simulation system configured for performing digital cell design simulations.

In embodiments, provided herein is an AI-guided analytic platform for synthetic biology development having a simulation system configured to execute a set of simulations associated with the performance of a strain in a set of plates.

In embodiments, provided herein is an AI-guided analytic platform for synthetic biology development having a simulation system configured to execute a set of simulations associated with the performance of a strain in a set of bioreactors and/or tanks.

In embodiments, provided herein is an AI-guided analytic platform for synthetic biology development having a simulation system configured to execute a set of simulations associated with biosynthetic pathway optimizations.

In embodiments, provided herein is an AI-guided analytic platform for synthetic biology development having a user interface configured to provide a user with access to the platform.

In embodiments, provided herein is an AI-guided analytic platform for synthetic biology development having a research interface configured to provide a researcher and/or research institution user with access to the platform.

In embodiments, provided herein is an AI-guided analytic platform for synthetic biology development having a web stack used to create and deliver web applications.

In embodiments, provided herein is an AI-guided analytic platform for synthetic biology development having a DevOps stack configured to automate the development, deployment, and/or operations of software.

In embodiments, provided herein is an AI-guided analytic platform for synthetic biology development having a big data stack configured to collect, store, and/or analyze large amounts of data.

In embodiments, provided herein is an AI-guided analytic platform for synthetic biology development having a cloud stack configured to build and deploy applications on a cloud computing platform.

In embodiments, provided herein is an AI-guided analytic platform for synthetic biology development having a microservices architecture.

In embodiments, provided herein is an AI-guided analytic platform for synthetic biology development having an extract, transform, load (ETL) system that moves data from one system to another system.

In embodiments, provided herein is an AI-guided analytic platform for synthetic biology development having a software development kit (SDK) having libraries, code samples, documentation, and/or tools that enable development of applications for a platform.

In embodiments, provided herein is an AI-guided analytic platform for synthetic biology development having an application programming interface (API).

In embodiments, provided herein is an AI-guided analytic platform for synthetic biology development having a safety and governance system associated with synthetic biology development configured for managing the safety and/or governance associated with synthetic biology development.

In embodiments, provided herein is an AI-guided analytic platform for synthetic biology development having a safety and governance system associated with synthetic biology development wherein the governance system applies one or more governance analyses to the output of a machine learning system, an artificial intelligence system, a set of neural networks, and/or other models such to ensure the output complies with a set of applicable governance standards.

In embodiments, provided herein is an AI-guided analytic platform for synthetic biology development having a safety and governance system having a system for automating policy and governance associated with a set of models associated with synthetic biology development.

In embodiments, provided herein is an AI-guided analytic platform for synthetic biology development having a safety and governance system having a risk management system configured to manage risk associated with synthetic biology products and/or processes.

In embodiments, provided herein is an AI-guided analytic platform for synthetic biology development having a machine learning system, artificial intelligence system, and/or set of neural networks configured to reduce the cost of materials in a synthetic biology manufacturing process.

In embodiments, provided herein is an AI-guided analytic platform for synthetic biology development having a machine learning system, artificial intelligence system, and/ or set of neural networks configured to optimize, recommend, and/or select feedstock for a synthetic biology manufacturing process.

In embodiments, provided herein is an AI-guided analytic platform for synthetic biology development having a machine learning system, artificial intelligence system, and/or set of neural networks configured to optimize the sustainability of a synthetic biology manufacturing process.

In embodiments, provided herein is an AI-guided analytic platform for synthetic biology development having a machine learning system, artificial intelligence system, and/or set of neural networks configured to improve health benefits associated with a molecule produced by a synthetic biology manufacturing process.

In embodiments, provided herein is an AI-guided analytic platform for synthetic biology development having a machine learning system, artificial intelligence system, and/or set of neural networks configured to improve the price stability of a molecule produced by a synthetic biology manufacturing process.

In embodiments, provided herein is an AI-guided analytic platform for synthetic biology development having a machine learning system, artificial intelligence system, and/or set of neural networks configured to improve the energy efficiency of a synthetic biology manufacturing process.

In embodiments, provided herein is an AI-guided analytic platform for synthetic biology development having a machine learning system, artificial intelligence system, and/or set of neural networks configured to improve land use associated with a synthetic biology manufacturing process.

In embodiments, provided herein is an AI-guided analytic platform for synthetic biology development having a machine learning system, artificial intelligence system, and/or set of neural networks configured to improve the profit margins of a molecule produced by a synthetic biology manufacturing process.

In embodiments, provided herein is an AI-guided analytic platform for synthetic biology development having a machine learning system, artificial intelligence system, and/or set of neural networks configured to optimize the design of a set of biomanufacturing plants based on models associated with strain performance.

In embodiments, provided herein is an AI-guided analytic platform for synthetic biology development having a machine learning system, artificial intelligence system, and/or set of neural networks configured to generate a prediction associated with synthetic biology development.

In embodiments, provided herein is an AI-guided analytic platform for synthetic biology development having a machine learning system, artificial intelligence system, and/or set of neural networks configured to predict risk associated with a synthetic biology product and/or process.

In embodiments, provided herein is an AI-guided analytic platform for synthetic biology development having a machine learning system, artificial intelligence system, and/or set of neural networks configured to perform predictive maintenance on a set of reactors and/or machines associated with synthetic biology development.

In embodiments, provided herein is an AI-guided analytic platform for synthetic biology development having a machine learning system, artificial intelligence system, and/or set of neural networks configured to perform a classification associated with synthetic biology development.

In embodiments, provided herein is an AI-guided analytic platform for synthetic biology development having a machine learning system, artificial intelligence system, and/or set of neural networks to control and/or configure a set of plates and/or tanks associated with synthetic biology development.

In embodiments, provided herein is an AI-guided analytic platform for synthetic biology development having a machine learning system, artificial intelligence system, and/or set of neural networks to generate a recommendation associated with synthetic biology development.

In embodiments, provided herein is an AI-guided analytic platform for synthetic biology development having a system for providing interpretability, explainability, and/or knowledge extraction associated with a machine learning system, artificial intelligence system, and/or set of neural networks associated with synthetic biology development.

In embodiments, provided herein is an AI-guided synthetic biology development platform having a robotic software process automation (RPA) system to automate workflows associated with synthetic biology development.

In embodiments, provided herein is an AI-guided synthetic biology development platform having an expert system configured to perform tasks associated with synthetic biology development.

Computer-Based Implementations

Introduction

The methods and/or processes described in the disclosure, and steps associated therewith, may be realized in hardware, software or any combination of hardware and software suitable for a particular application. The hardware may include a general-purpose computer and/or dedicated computing device or specific computing device or particular aspect or component of a specific computing device. The processes may be realized in one or more microprocessors, microcontrollers, embedded microcontrollers, programmable digital signal processors or other programmable devices, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine-readable medium.

The elements described and depicted herein, including in flow charts and block diagrams throughout the figures, imply logical boundaries between the elements. However, according to software or hardware engineering practices, the depicted elements and the functions thereof may be implemented on machines through computer executable code using a processor capable of executing program instructions stored thereon as a monolithic software structure, as standalone software modules, or as modules that employ external routines, code, services, and so forth, or any combination of these, and all such implementations may be within the scope of the disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices, artificial intelligence, computing devices, networking equipment, servers, routers and the like. Furthermore, the elements depicted in the flow chart and block diagrams or any other logical component may be implemented on a machine capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described in the disclosure may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

Special-Purpose Systems

A special-purpose system includes hardware and/or software and may be described in terms of an apparatus, a method, or a computer-readable medium. In various embodiments, functionality may be apportioned differently between software and hardware. For example, some functionality may be implemented by hardware in one embodiment and by software in another embodiment. Further, software may be encoded by hardware structures, and hardware may be defined by software, such as in software-defined networking or software-defined radio.

In this application, including the claims, the term module refers to a special-purpose system. The module may be implemented by one or more special-purpose systems. The one or more special-purpose systems may also implement some or all of the other modules. In this application, including the claims, the term "module" may be replaced with the term "controller" or the term "circuit." In this application, including the claims, the term platform refers to one or more modules that offer a set of functions. In this application, including the claims, the term system may be used interchangeably with module or with the term special-purpose system.

The special-purpose system may be directed or controlled by an operator. The special-purpose system may be hosted by one or more of assets owned by the operator, assets leased by the operator, and third-party assets. The assets may be referred to as a private, community, or hybrid cloud computing network or cloud computing environment. For example, the special-purpose system may be partially or fully hosted by a third-party offering software as a service (SaaS), platform as a service (PaaS), and/or infrastructure as a service (IaaS). The special-purpose system may be implemented using agile development and operations (DevOps) principles. In embodiments, some or all of the special-purpose system may be implemented in a multiple-environment architecture. For example, the multiple environments may include one or more production environments, one or more integration environments, one or more development environments, etc.

A special-purpose system may be partially or fully implemented using or by a mobile device. A special-purpose system may be partially or fully implemented using or by a network device. A special-purpose system may be partially or fully implemented using a computer having a variety of form factors and other characteristics. For example, the computer may be characterized as a personal computer, as a server, etc. The computer may be portable, as in the case of a laptop, netbook, etc. The computer may or may not have any output device, such as a monitor, line printer, liquid crystal display (LCD), light emitting diodes (LEDs), etc. The computer may or may not have any input device, such as a keyboard, mouse, touchpad, trackpad, computer vision system, barcode scanner, button array, etc. The computer may run a general-purpose operating system, such as the WINDOWS operating system from Microsoft Corporation, the MACOS operating system from Apple, Inc., or a variant of the LINUX operating system.

A special-purpose system may be distributed across multiple different software and hardware entities. Communication within a special-purpose system and between special-purpose systems may be performed using networking hardware. The distribution may vary across embodiments and may vary over time. For example, the distribution may vary based on demand, with additional hardware and/or software entities invoked to handle higher demand. In various embodiments, a load balancer may direct requests to one of multiple instantiations of the special purpose system. The hardware and/or software entities may be physically distinct and/or may share some hardware and/or software, such as in a virtualized environment. Multiple hardware entities may be referred to as a server rack, server farm, data center, etc.

Hardware

The term "hardware" encompasses components such as processing hardware, storage hardware, networking hardware, and other general-purpose and special-purpose components. Note that these are not mutually exclusive categories. For example, processing hardware may integrate storage hardware and vice versa.

Multiple components of the hardware may be integrated, such as on a single die, in a single package, or on a single printed circuit board or logic board. For example, multiple components of the hardware may be implemented as a system-on-chip. A component, or a set of integrated components, may be referred to as a chip, chipset, chiplet, or chip stack.

The hardware may integrate and/or receive signals from sensors. The sensors may allow observation and measurement of conditions including temperature, pressure, wear, light, humidity, deformation, expansion, contraction, deflection, bending, stress, strain, load-bearing, shrinkage, power, energy, mass, location, temperature, humidity, pressure, viscosity, liquid flow, chemical/gas presence, sound, and air quality. A sensor may include image and/or video capture in visible and/or non-visible (such as thermal) wavelengths, such as a charge-coupled device (CCD) or complementary metal-oxide semiconductor (CMOS) sensor.

Some or all features of hardware may be defined using a language for hardware description, such as IEEE Standard 1364-2005 (commonly called "Verilog") and IEEE Standard 1076-2008 (commonly called "VHDL"). The hardware description language may be used to manufacture and/or program hardware.

The methods and systems described herein may transform physical and/or intangible items from one state to another. The methods and systems described herein may also transform data representing physical and/or intangible items from one state to another.

Storage Hardware and Computer-Readable Media

Storage hardware is or includes a computer-readable medium. The term computer-readable medium, as used in this disclosure, encompasses both nonvolatile storage and volatile storage, such as dynamic random-access memory (DRAM). The term computer-readable medium only excludes transitory electrical or electromagnetic signals propagating through a medium (such as on a carrier wave). A computer-readable medium in this disclosure is therefore non-transitory and may also be considered tangible. The storage hardware may include cache memory, which may be collocated with or integrated with processing hardware.

Storage hardware may have read-only, write-once, or read/write properties. Storage hardware may be random access or sequential access. Storage hardware may be location-addressable, file-addressable, and/or content-addressable.

Processing Hardware and Architecture

The methods and systems described herein may be deployed in part or in whole through machines that execute computer software, program codes, and/or instructions on processing hardware (also referred to as a "processor"). The disclosure may be implemented as a method on the machine(s), as a system or apparatus as part of or in relation to the machine(s), or as a computer program product embodied in a computer readable medium executing on one or more of the machines. In embodiments, the processor may be part of a server, cloud server, client, network infrastructure, mobile computing platform, stationary computing platform, or other computing platforms. A processor may be any kind of computational or processing device capable of executing program instructions, codes, binary instructions and the like, including a central processing unit (CPU), a general processing unit (GPU), a logic board, a chip (e.g., a graphics chip, a video processing chip, a data compression chip, or the like), a chipset, a controller, a system-on-chip (e.g., an RF system on chip, an AI system on chip, a video processing system on chip, or others), an integrated circuit, an application specific integrated circuit (ASIC), a field programmable gate array (FPGA), an approximate computing processor, a quantum computing processor, a parallel computing processor, a neural network processor, or other type of processor. The processor may be or may include a signal processor, digital processor, data processor, embedded processor, microprocessor or any variant such as a co-processor (math co-processor, graphic co-processor, communication co-processor, video co-processor, AI co-processor, and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more threads. The thread may spawn other threads that may have assigned priorities associated with them; the processor may execute these threads based on priority or any other order based on instructions provided in the program code. The processor, or any machine utilizing one, may include non-transitory memory that stores methods, codes, instructions and programs as described herein and elsewhere. The processor may access a non-transitory storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache, network-attached storage, server-based storage, and the like.

A processor may include one or more cores that may enhance speed and performance of a multiprocessor. In embodiments, the process may be a dual core processor, quad core processors, other chip-level multiprocessor and the like that combine two or more independent cores (sometimes called a die).

The processor may enable execution of multiple threads. These multiple threads may correspond to different programs. In various embodiments, a single program may be implemented as multiple threads by the programmer or may be decomposed into multiple threads by the processing hardware. The threads may be executed simultaneously to enhance the performance of the processor and to facilitate simultaneous operations of the application.

A processor may be implemented as a packaged semiconductor die. The die includes one or more processing cores and may include additional functional blocks, such as a cache. In various embodiments, the processor may be implemented by multiple dies, which may be combined in a single package or packaged separately.

Networking Hardware and Infrastructure

The methods and systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements. The methods and systems described herein may be adapted for use with any kind of private, community, or hybrid cloud computing network or cloud computing environment, including those which involve features of software as a service (SaaS), platform as a service (PaaS), and/or infrastructure as a service (IaaS).

The methods, program codes, and instructions described herein and elsewhere may be implemented on a cellular network with multiple cells. The cellular network may either be frequency division multiple access (FDMA) network or code division multiple access (CDMA) network. The cellular network may include mobile devices, cell sites, base stations, repeaters, antennas, towers, and the like. The cell network may be a GSM, GPRS, 3G, 4G, 5G, LTE, EVDO, mesh, or other network types.

The networking hardware may include one or more interface circuits. In some examples, the interface circuit(s) may implement wired or wireless interfaces that connect, directly or indirectly, to one or more networks. A wide-area network may also be referred to as a distributed communications system (DCS). The networks may include one or more of point-to-point and mesh technologies. Data transmitted or received by the networking components may traverse the same or different networks. Networks may be connected to each other over a WAN or point-to-point leased lines using technologies such as Multiprotocol Label Switching (MPLS) and virtual private networks (VPNs).

Software

Software includes instructions that are machine-readable and/or executable. Instructions may be logically grouped into programs, codes, methods, steps, actions, routines, functions, libraries, objects, classes, etc. Software may be stored by storage hardware or encoded in other hardware. Software encompasses (i) descriptive text to be parsed, such as HTML (hypertext markup language), XML (extensible markup language), and JSON (JavaScript Object Notation), (ii) assembly code, (iii) object code generated from source code by a compiler, (iv) source code for execution by an interpreter, (v) bytecode, (vi) source code for compilation and execution by a just-in-time compiler, etc. As examples only, source code may be written using syntax from languages including C, C++, JavaScript, Java, Python, R, etc. The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the devices described in the disclosure, as well as heterogeneous combinations of processors, processor architectures, or combinations of different hardware and software, or any other machine capable of executing program instructions. Computer software may employ virtualization, virtual machines, containers, dock facilities, portainers, and other capabilities. In example embodiments, methods described in the disclosure and combinations thereof may be embodied in computer executable code that, when executing on one or more computing devices, performs the steps thereof. In another aspect, the methods may be embodied in systems that perform the steps thereof and may be distributed across devices in a number of ways, or all of the functionality may be integrated into a dedicated, standalone device or other hardware. In another aspect, the means for performing the steps associated with the processes described in the disclosure may include any of the hardware and/or software described in the disclosure. All such permutations and combinations are intended to fall within the scope of the disclosure.

Software also includes data. However, data and instructions are not mutually exclusive categories. In various embodiments, the instructions may be used as data in one or more operations. As another example, instructions may be derived from data. The functional blocks and flowchart elements in this disclosure serve as software specifications, which can be translated into software by the routine work of a skilled technician or programmer. Software may include and/or rely on firmware, processor microcode, an operating system (OS), a basic input/output system (BIOS), application programming interfaces (APIs), libraries such as dynamic-link libraries (DLLs), device drivers, hypervisors, user applications, background services, background applications, etc. Software includes native applications and web applications. For example, a web application may be served to a device through a browser using hypertext markup language 5th revision (HTML5).

Software may include artificial intelligence systems, which may include machine learning or other computational intelligence. For example, artificial intelligence may include one or more models used for one or more problem domains. When presented with many data features, identification of a subset of features that are relevant to a problem domain may improve prediction accuracy, reduce storage space, and increase processing speed. This identification may be referred to as feature engineering. Feature engineering may be performed by users or may only be guided by users. In various implementations, a machine learning system may computationally identify relevant features, such as by performing singular value decomposition on the contributions of different features to outputs. Examples of the models include recurrent neural networks (RNNs) such as long short-term memory (LSTM), deep learning models such as transformers, decision trees, support-vector machines, genetic algorithms, Bayesian networks, and regression analysis. Examples of systems based on a transformer model include bidirectional encoder representations from transformers (BERT) and generative pre-trained transformer (GPT). Training a machine-learning model may include supervised learning (for example, based on labelled input data), unsupervised learning, and reinforcement learning. In various embodiments, a machine-learning model may be pre-trained by their operator or by a third party. Problem domains include nearly any situation where structured data can be collected, and includes natural language processing (NLP), computer vision (CV), classification, image recognition, etc.

Entities recording transactions, such as in a blockchain, may reach consensus using an algorithm such as proof-of-stake, proof-of-work, and proof-of-storage. Elements of the present disclosure may be represented by or encoded as non-fungible tokens (NFTs). Ownership rights related to the non-fungible tokens may be recorded in or referenced by a distributed ledger. Transactions initiated by or relevant to the present disclosure may use one or both of fiat currency and cryptocurrencies, examples of which include bitcoin and ether.

Artificial Intelligence

The following sections provide an overview of selected topics in artificial intelligence that may be included in and/or relate to some example embodiments. It is to be appreciated that additional artificial intelligence models, concepts, techniques, and the like may vary from those discussed herein in some respects, such as model architecture, software architecture supporting various models, training techniques, performance measurements, or the like, and may function equivalently to those discussed herein when included in various embodiments of the techniques presented herein. All such artificial intelligence models, concepts, techniques, and the like that are functionally equivalent to those presented herein, as may be appreciated by at least a person of ordinary skill in the art, are intended to be included and to be included in the range of example embodiments of the techniques presented herein.

Artificial Neural Networks

Some example embodiments may include one or more artificial neural networks. The following discussion presents an overview of artificial neural networks, which may supplement the discussion of other artificial intelligence topics.

As a general overview, an artificial neural network (frequently referred to simply as a “neural network”) is a computational unit that is architecturally similar to a set of neurons in a biological organism, such as the human brain. Like a biological neuron, each neuron in an artificial neural network receives one or more inputs, such as input data received from outside of the artificial neural network and/or one or more outputs from one or more other neurons of the artificial neural network. Each neuron processes the one or more inputs (e.g., using an internal “activation function”), which may have been refined by learning or “training” to perform such processing in accordance with a task or objective of the neural network. Each neuron generates one or more outputs based on the processing. Each of the one or more outputs may be received as input by one or more other neurons of the neural network and/or may be provided as one or more outputs of the neural network. Once trained (e.g., using a training data set that indicates a correct or desired set of outputs for each of one or more sets of inputs), the neural network may perform similar processing on new sets of input, including sets of input that the neural network has not previously processed. In this manner, the neural network may learn to perform tasks and/or achieve objectives even if the computer hosting the neural network has not been programmed to do so by conventional techniques, such as task-specific machine instructions and/or executable scripts.

More specifically, a neural network includes a group of connected nodes, which also can be referred to as neurons or perceptrons, organized into one or more layers. Neural networks that include multiple layers can be referred to as "deep" networks. A deep network can include an input layer, an output layer, and one or more hidden layers positioned between the input layer and the output layer. The neurons of the neural network can be connected or non-fully connected. A neural networks can be or include one or more feed-forward neural networks. In feed-forward networks, the connections between neurons do not form a cycle. For example, each connection can connect a neuron from an earlier layer to a neuron from a later layer.

As a simple example, a two-layer neural network includes an input layer including I input neurons $n_i$, j∈I and an output layer including J output neurons $n_j$, j∈J. In a "dense" configuration, each output neuron is connected to each input neuron by a connection that includes a weight, wherein the weight of the connection between each input neuron $n_i$, i∈I, and each output neuron $n_j$, j∈J, can be represented as $w_{ij}$. Additionally, each output $n_j$, j∈J, includes an activation function $f(x)$, which may be a step function such as the Heaviside step function, a linear function such as $f(x)=mx+b$, a rectified linear (ReLU) function such as $f(x)=\max(0, x)$, an exponential or polynomial function, a transcendental function such as $f(x)=\tan h(x)$, or a logarithmic function, such as $f(x)=\ln(x)$, or the like. Finally, the output layer includes a bias B that is applied to all of the output neurons.

Each input neuron receives an input and passes it through as output, optionally with preprocessing such as normalizing the input (e.g., scaling the input to a range such as between 0 and 1, optionally based on the inputs of one or more other input neurons and/or the input of the input neuron $n_i$ for other sets of input). Each output neuron $n_j$, j∈J, receives an input $i_i$ from each input neuron $n_i$, i∈I. Each output neuron $n_j$, j∈J, determines the sum of the bias B and, for each input neuron $n_i$, i∈I, the product of the input $i_i$ received from the input neuron $n_i$ and the weight $w_{ij}$ of the connection between the input neuron $n_i$ and the output neuron $n_j$. Each output neuron $n_j$ then processes this sum with its activation function $f(x)$ and provides the output of the activation function $f(x)$ as the output of the output neuron $n_j$.

The output of the activation function $f(x)$ of each output neuron $n_j$ may be passed through as the output of the output neuron $n_j$. Some such neural networks may perform linear regression calculations, where the output is simply a linear combination or weighed sum of the inputs and, optionally, a bias of the output layer. Alternatively or additionally, output of the activation function $f(x)$ of each output neuron $n_j$ may be postprocessed (e.g., scaling the output to a range such as between 0 and 1, optionally based on the outputs of one or more other output neurons and/or the output of the output neuron $n_j$ for other sets of inputs). The output of an output neuron $n_j$ may be continuous over a range. Alternatively or additionally, the output of an output neuron $n_j$ may be quantized to one of several discrete values. For example, an output of an output neuron $n_j$ may be translated to a binary value by comparing the output of the activation function $f(x)$ with a binary threshold value, wherein values of the output of the output neuron $n_j$ that are equal to or greater than the binary threshold value are interpreted as a positive binary output (e.g., True or 1) and values of the output of the output neuron $n_j$ that are less than the binary threshold value are interpreted as a negative binary output (e.g., False or 0). Such comparisons may be used for classification, e.g., where an output neuron $n_j$ determines and outputs either a value of True or 1 indicating that the inputs correspond to the features of a particular class of inputs, or a value of False or 0 indicating that the inputs do not correspond to the features of the particular class of inputs. Some neural networks perform include two or more output neurons $n_j$ may receive a set of inputs and may output a set of classifications k for each class $c_k$ in a set of K classes, where each neuron indicates whether the inputs correspond to class $c_k$, k∈K. In some neural networks that are configured as multilabel classification, a given set of inputs is processed independently by each of two or more output neurons $n_j$, j∈J. That is, the classification determination for each class $c_k$ by each output neuron $n_{j1}$ is independent of the classification determination for each other class $c_{k2}$ by each other output neuron $n_{j2}$. As a result, a given set of inputs may be classified into any number of classes between 0 and k, including a single class or multiple classes. In some other neural networks that are configured for multiclass classification, rather than outputting k independent classifications for each class $c_k$, k∈K, the neural network may output a confidence of the classification of the set of inputs for each class $c_k$, k∈K, and the most likely single classification among the set of K classes may be determined as the highest probability or confidence for all $c_k$ classes in the set of K classes. Some such neural networks postprocess all of the outputs by scaling the output by the logit function, $f(x)=\ln(p/(1-p))$, and the scaled output of each output neurons $n_j$, j∈J, indicates the probability (between 0 and 1) that the set of inputs belongs to the class associated with the output neuron $n_j$. The multiclass classification of the output may then be interpreted as the classification having the highest probability based on the output of all output neurons $n_j$, j∈J. Many such neural networks included in various embodiments may process input by these and other processing techniques.

Other neural networks, known as "shallow" neural networks, include one "hidden" layer of neurons between the input layer and the output layer, where the hidden layer and the output layer include the same number of neurons J. The hidden layer of neurons may encapsulate the activation function $f(x)$ and associated processing performed by each output neuron $n_j$, j∈J, in the previous simple example. Each output neuron $n_j$, j∈J, may receive as input only the output of one corresponding neuron of the hidden layer and may perform a postprocessing step as described above, such as scaling the output to a range. In some multiclass classification neural networks, the output layer operates as a "softmax" normalization layer, whereby each output neuron $n_j$, j∈J, scales its inputs (i.e., the output of a corresponding neuron of the hidden layer) by the logit function, $f(x)=\ln(p/(1-p))$, and the scaled output of each output neurons $n_j$, j∈J, indicates the probability (between 0 and 1) that the set of inputs belongs to the class associated with the output neuron $n_j$. It is to be appreciated that such shallow neural networks still involve only one layer of processing (i.e., the hidden layer) that performs neuron-based calculation as the output of the activation function applied to the weighted sum of the inputs, and the output layer is provided to postprocess the output, such as quantizing to a range of values (e.g., 0 or 1) and/or scaling to a range (e.g., multiclass probabilities between 0 and 1).

Still other neural networks, known as "deep" neural networks, include a sequence of two or more "hidden" layers between the input layer and the output layer. Each hidden layer may include a number of neurons, each of which may be connected to one or more neurons of a previous layer in the sequence of layers (i.e., either the input layer or a previous hidden layer). The number of neurons in each hidden layer may be the same as or different than the number of neurons in a preceding layer from which the hidden layer receives its input (i.e., either the input layer or a previous hidden layer). The number of neurons in each hidden layer may be the same as or different than the number of neurons in a following layer to which the hidden layer provides its output as the input of the following layer (i.e., either a following hidden layer or the output layer). The introduction of multiple hidden layers enables richer mathematical processing of each set of inputs than a "shallow" neural network in which each set of inputs is processed only by one layer of activation functions. The richer mathematical processing of deep neural networks may enable greater neural "capacity" that provides a number of improvements over shallow neural networks, such as an expanded number of concepts learned during training that enables more nuanced classification, better handling of correlated inputs, recognition of patterns involving greater numbers of features, or the like.

Figure 40:
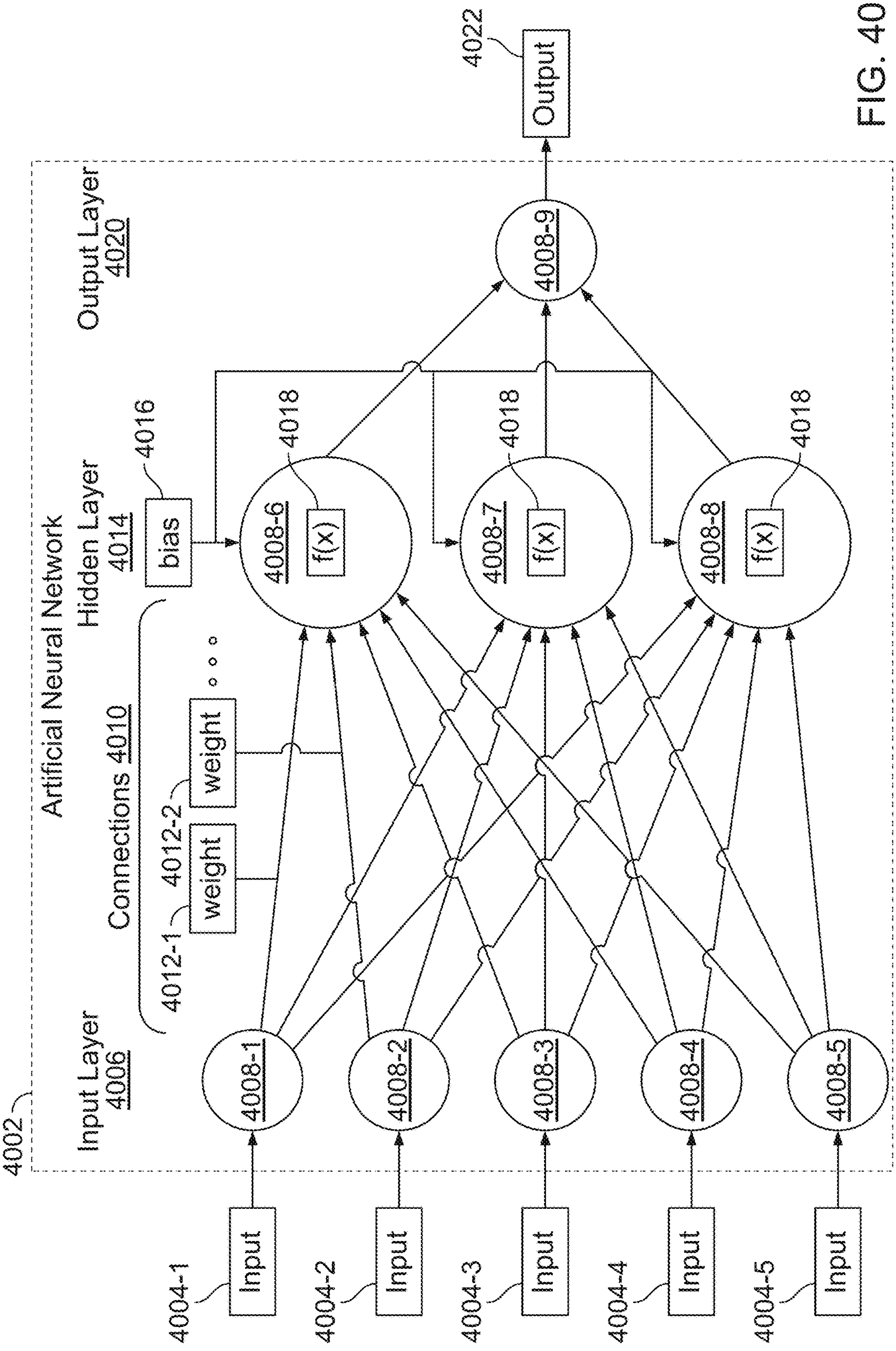
FIG. 40 is a schematic diagram detailing an example artificial neural network with multiple layers according to some example embodiments.

FIG. 40 illustrates an example artificial neural network with multiple layers. Artificial neural network 4002 includes an input layer 4006, a hidden layer 4014, and an output layer 4020 with each layer comprising a plurality of nodes or neurons 4008 that respond to different combinations of inputs 4004 from the previous layers. In this "densely connected" artificial neural network 4002, each neuron 4008 of each layer has a connection 4010 to each neuron 4008 in the preceding layer and/or each neuron 4008 in the following layer. Further, each connection 4010 between each pair of neurons 4008 has a numeric weight 4012 that determines how much relative effect an input from the neuron 4008 in the preceding layer has on the output value of the neuron 4008 in the following layer. Further, the hidden layer includes a numeric bias 4016 that is associated with each neuron 4008 of the hidden layer 4014. The number of layers, number of neurons in each layer, and the like are often referred to as the architecture or "hyperparameters" of the artificial neural network 4002, are selected to initialize the artificial neural network 4002 and generally remain fixed. The weights 4012 and biases 4016 of the artificial neural network 4002 are referred to as the "parameters" of the artificial neural network 4002, and are initialized to arbitrary values (e.g., to zero or to random values). The artificial neural network 4002 is optimized or "trained" by adjusting the weights 4012 and biases 4016 of the artificial neural network 4002 to generate output 4022 that corresponds to a set of inputs 4004.

Input layer 4006 may include a plurality of input neurons 4008-1, 4008-2, 4008-3, 4008-4, 4008-5, each of which receives a corresponding input 4004-1, 4004-2, 4004-3, 4004-4, 4004-5 that may provide information from the outside world or input data (e.g., sensor data, image data, text data, audio data, etc.) to the artificial neural network 4002. The input data may be from different sources and may include library data, simulation data, user input data, training data, outcome data, or the like. The input neurons 4008-1, 4008-2, 4008-3, 4008-4, 4008-5 may pass on the information to the hidden layer 4014, and no computation may be performed by the input nodes. Hidden layers may include a plurality of neurons, such as neurons 4008-6, 4008-7, and 4008-8. The neurons 4008-6, 4008-7, 4008-8 in the hidden layer 4014 process the information from the input layer 4006 based on the weights 4012 of the connections 4010 between the input layer 4006 and the hidden layer 4014 and the bias 4016 associated with the hidden layer 4014. More specifically, each neuron 4008-6, 4008-7, 4008-8 receives, as input, the input 4004 of each neuron 4008-1, 4008-2, 4008-3, 4008-4, 4008-5 of the input layer 4006, and multiplies each input 4004 by the weight 4012 of the corresponding connection 4010 between the respective neuron 4008 of the input layer 4006 and the neuron 4008 of the hidden layer 4014. Each neuron 4008 of the hidden layer 4014 determines a sum of these products and the bias 4016 of the hidden layer 4014. Each neuron 4008 of the hidden layer 4014 then processes this sum by the activation function 4018 associated with the neuron 4008 and outputs the output of the activation function 4018 as the output of the neuron 4008. Similarly, the output layer 4020 includes an output neuron 4008-9 that processes information based on the weights 4012 of the connections 4010 between the neurons 4008 of the hidden layer 4014 and the neuron 4008-9 of the output layer 4020. The output of the output neuron 4008-9 is provided as the output 4022 of the artificial neural network 4002.

Some artificial neural networks 4002 include two or more hidden layers 4014. The hidden layers 4014 are connected in series, wherein each hidden layer 4014 receives input from a preceding layer (e.g., either the input layer 4006 or a preceding hidden layer 4014), and each hidden layer 4014 generates output for a following layer (e.g., a following hidden layer 4014 or the output layer 4020). A first hidden layer 4014 may detect a set of primitive patterns in the input 4004 (e.g., low-level visual features of an image). A second hidden layer 4014 may detect patterns within the output of the first hidden layer 4014. A third hidden layer 4014 may detect patterns of patterns within the output of the second hidden layer 4014. In this manner, the artificial neural network 4002 may be designed to analyze patterns of increasing sophistication, composed of successive hierarchies of sub-patterns.

In some artificial neural networks 4002, a neuron 4008 may have connections 4010 to all neurons 4008 in the preceding layer and the following layer. Thus, the layers may be referred to as fully-connected or "dense" layers. In some artificial neural networks 4002, a neuron 4008 may have connections to only some of the neurons 4008 in the preceding layer and the following layer. Thus, the layers may be referred to as sparsely-connected layers. Each neuron 4008 in the artificial neural network 4002 determines a weighted linear combination of its inputs and the computation on each neural network layer may be described as a multiplication of an input matrix and a weight matrix. A bias matrix is then added to the resulting product matrix to account for the threshold of each neuron in the next level. Further, an activation function 4018 is applied to each resultant value, and the resulting values are placed in the matrix for the next layer. Thus, the output from a neuron i in the artificial neural network 4002 may be represented as:

$$yi = f\left(\sum xiwi + bi\right)$$

where f is the activation function. Σxiwi is the weighted sum of input matrix, and bi is the bias matrix.

The activation function 4018 of each neuron 4008 determines the activity level or excitation level generated in the neuron 4008 as a result of an input signal of a particular size. The purpose of the activation function 4018 is to introduce non-linearity into the output of a neuron 4008 because most real-world functions are non-linear and it is desirable that the neurons 4008 can learn these non-linear representations. Several activation functions 4018 may be used in an artificial neural network 4002. One example activation function 4018 is the sigmoid function σ(x), which is a continuous S-shaped monotonically increasing function that asymptotically approaches fixed values as the input approaches plus or minus infinity. The sigmoid function σ(x) takes a real-valued input and transforms it into a value between 0 and 1:

$$\sigma(x) = 1/(1+\exp(-x)).$$

Another example activation function 4018 is the tanh function, which takes a real-valued input and transforms it into a value within the range of [−1, 1]:

$$\tanh(x) = 2\sigma(2x) - 1$$

A third example activation function 4018 is the rectified linear unit (ReLU) function. The ReLU function takes a real-valued input and thresholds it above zero (i.e., replacing negative values with zero):

$$f(x) = \max(0, x).$$

The above activation functions 4018 are provided as examples and in various embodiments, and that artificial neural networks 4002 may utilize a variety of activation functions 4018 including (but not limited to) identity, binary step, logistic, soft step, tan h, arctan, softsign, rectified linear unit (ReLU), leaky rectified linear unit, parameteric rectified linear unit, randomized leaky rectified linear unit, exponential linear unit, s-shaped rectified linear activation unit, adaptive piecewise linear, softplus, bent identity, soft exponential, sinusoid, sinc, gaussian, softmax, maxout, and/or a combination of activation functions 4018.

In the example artificial neural network 4002 of FIG. 40, neurons 4008-1, 4008-2, 4008-3, 4008-4, 4008-5 in the input layer 4006 may take external inputs 4004-1, 4004-2, 4004-3, 4004-4, 4004-5, which may be numerical values depending upon the input dataset. While only five inputs 4004 are shown in FIG. 40, in various implementations, an input neuron 4008 may receive tens, hundreds, thousands, or more 4004. In the example artificial neural network 4002 of FIG. 40, no computation is performed on the input layer 4006, and thus the outputs from neurons 4008-1, 4008-2, 4008-3, 4008-4, 4008-5 of the input layer 4006 are the same as the inputs 4004-1, 4004-2, 4004-3, 4004-4, 4004-5, respectively, which are fed into the hidden layer 4014. The output of each neuron 4008 in the hidden layer 4014 depends on the outputs from the neurons 4008-1, 4008-2, 4008-3, 4008-4, 4008-5 of the input layer 4006, the weights 4012 associated with the connections 4010 between the neuron 4008 of the hidden layer 4014 and the neurons 4008-1, 4008-2, 4008-3, 4008-4, 4008-5 of the input layer 4006, the bias 4016 of the hidden layer 4014, and the activation function 4018 of the neuron 4008. Thus, the output from each neuron 4008 of the hidden layer 4014 may be computed as:

$$Y_{4008} = f(x_1w_1 + x_2w_2 + x_3w_3 + x_4w_4 + x_5w_5 + b_{4016}).$$

The neuron 4008-08 in the output layer 4020 may perform similar computations (using weights associated with the connections 4010 between each neuron 4008 of the hidden layer 4014 and the neuron 4008-9 of the output layer 4020 and a bias 4016 associated with the output layer 4020):

$$Y_{4008-9} = f(x_6w_6 + x_7w_7 + x_8w_8 + b_{4016}).$$

where $Y_{4008-8}$ is the output of the neuron 4008-9 of the output layer 4020, and is also provided as the output 4022 of the artificial neural network 4002.

As mentioned, the connections between neurons 4008 in the artificial neural network 4002 have associated weights 4012, which determine how much relative effect an input value has on the output value of the neuron 4008 in question. Before the artificial neural network 4002 is trained, random values are selected for each of the weights 4012. The weights 4012 are adjusted during the training process and this adjustment of weights to determine the best set of weights 4012 that maximize the accuracy of the artificial neural network 4002 is referred to as training. For every input in a training dataset, the output of the artificial neural network 4002 may be observed and compared with the expected output, and the error between the expected output and the observed output may be propagated back to the previous layer. The weight 4012 of each connection 4010 and the bias 4016 associated with each layer may be adjusted based on the error. This process is repeated until the output error is below a predetermined threshold.

Backpropagation (e.g., backward propagation of errors) can be utilized with an optimization method such as gradient descent to adjust the weights 4012 and biases 4016 and update the characteristics of the artificial neural network 4002. Backpropagation may be a supervised training scheme that learns from labeled training data and errors at the neurons 4008 by changing parameters of the artificial neural network 4002 to reduce the errors. For example, a result of feedforward propagation (e.g., output activation value(s)) determined using training input data is compared against a corresponding known reference output data to calculate a loss function gradient. The gradient may be then utilized in an optimization method to determine new updated weights 4012 and biases 4016 in an attempt to minimize a loss function. For example, to measure error, the mean square error is determined using the equation:

$$E = (\text{target} - \text{output})2$$

To determine the gradient for a weight "w," a partial derivative of the error with respect to the weight 4012 may be determined, where:

$$\text{gradient} = \partial E/\partial w$$

The calculation of the partial derivative of the errors with respect to the weights 4012 may flow backwards through the neurons 4008 of the artificial neural network 4002. Then a portion (e.g., ratio, percentage, etc.) of the gradient is subtracted from the weight 4012 to determine the updated weight 4012. The portion may be specified as a learning rate "a." Thus an example equation of determining the updated weight is given by the formula:

$$w_{new} = w_{old} - \alpha(\partial E/\partial w)$$

The learning rate must be selected such that it is not too small (e.g., a rate that is too small may lead to a slow convergence to the desired weights 4012) and not too large (e.g., a rate that is too large may cause the weights 4012 to not converge to the desired weights 4012). Similar updating is performed for the bias 4016 of each layer. After the adjustment of weights 4012 and biases 4016, the artificial neural network 4002 generates output 4022 that is closer to the expected output for each set of inputs 4004.

Figure 41:
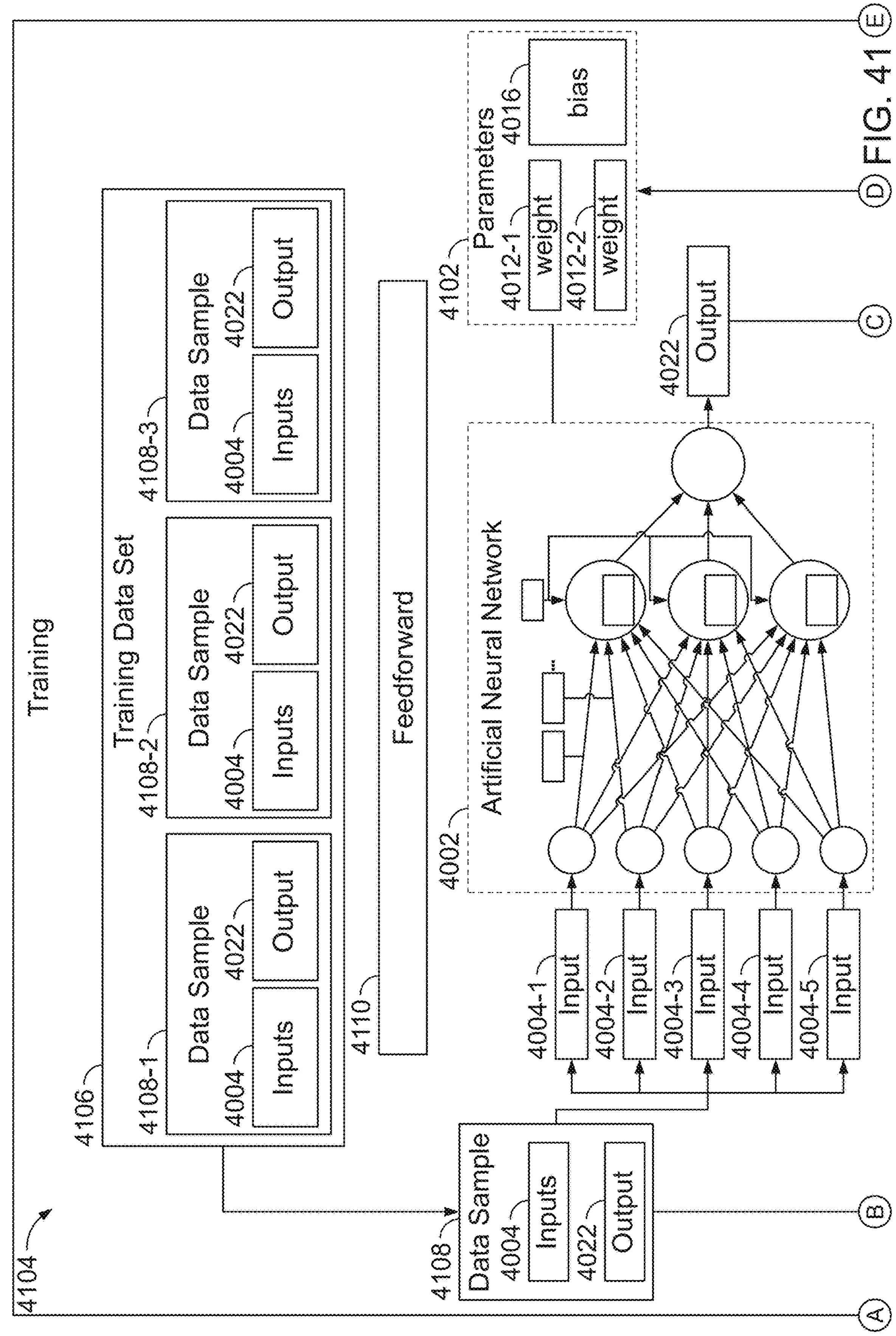
FIG. 41 is a schematic diagram detailing an example of training and inference of an example artificial neural network according to some example embodiments.
Figure 41:
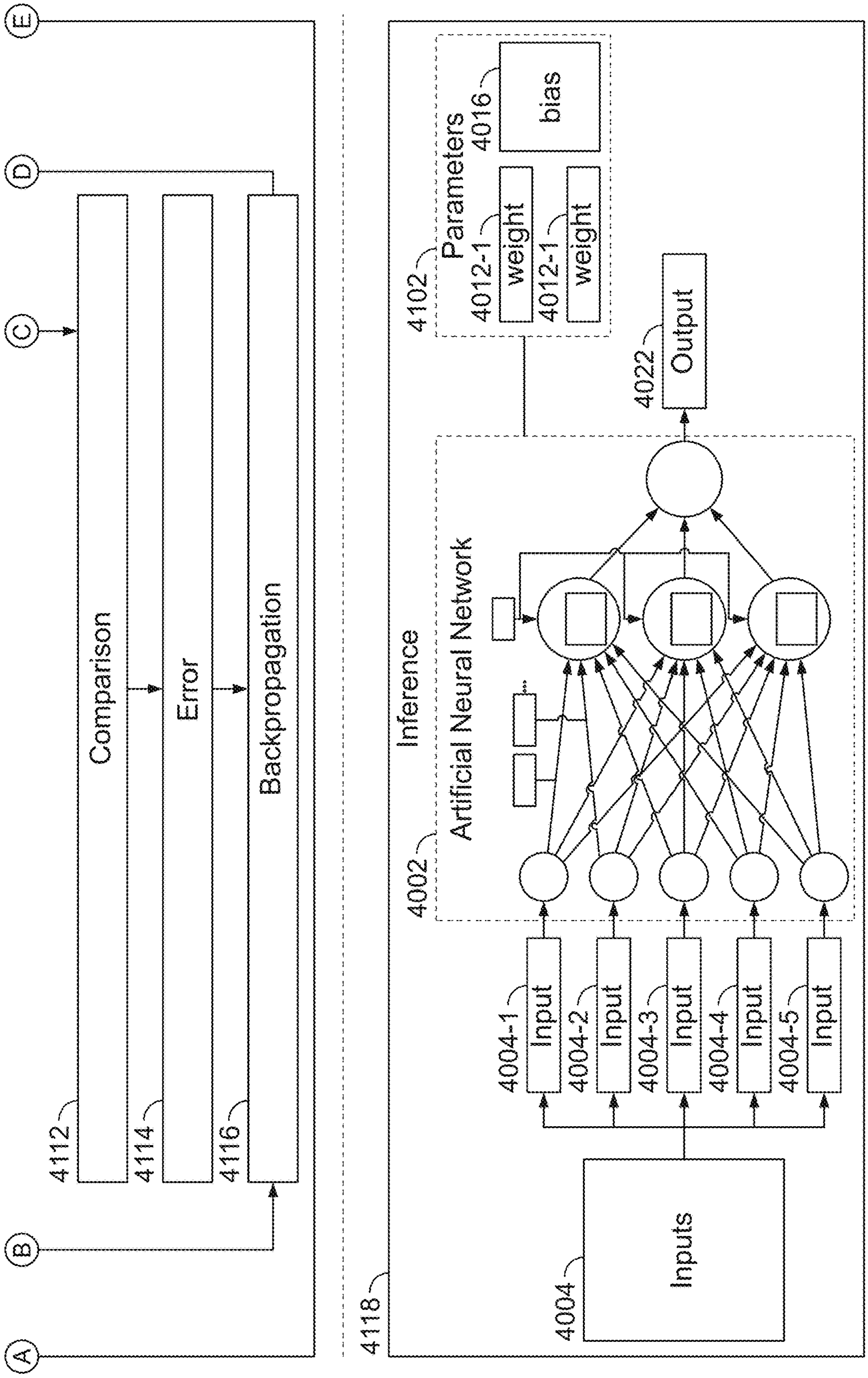

FIG. 41 illustrates an example of a training 4104 and inference 4118 of an example artificial neural network 4002. The artificial neural network 4002 of FIG. 41 may be the same as or similar to the artificial neural network 4002 of FIG. 40.

During a type of training 4104 known as "supervised" training, a training data set 4106 is provided that includes a number of data samples 4108, wherein each data sample 4108-1, 4108-2, 4108-3 includes a set of inputs 4004 and an expected output 4022 of the artificial neural network 4002. For example, to train an artificial neural network 4002 to classify data into one or more classes of patterns (e.g., classifying email into "spam" and "not spam" classes), the training data set 4106 may include a number of data samples 41008 that provide an example set of inputs 4004 and output 4022 that indicates the classification or "label" associated with the example set of inputs 4004 (e.g., an example set of keywords included in an email message and either a "spam" label or "not spam" label for the email message). As another example, to train an artificial neural network 4002 to perform regression over continuous and/or discrete inputs 4004 (e.g., determining a value of a real estate property based on factors such as size, age, features, and location), the training data set 4106 may include data samples 4108 that associate an example set of inputs 4004 with the expected regression output 4022 (e.g., the size, age, features, and/or location of a particular real estate property, and an estimate of the value of the real estate property based on the inputs). As yet another example, to train an artificial neural network 4002 to classify a content of an image (e.g., indicating a type of animal present in the image, such as a dog, cat, or bird, the training data set 4106 may include data samples 4108 that respectively associate a set of inputs 4004 that indicate the content of the image (e.g., the pixel values and/or detected features such as vector representations of lines and boundaries) and an output 4022 indicating one or more labels to be generated by the artificial neural network 4002 for the respective image (e.g., the labels of one or more classes of animals represented by the inputs 4004 of the image).

The training 4104 of an artificial neural network 4002 may involve a set of rounds or "epochs" in which each data sample 4108 of the training data set 4106 is processed by the artificial neural network 4002, and the parameters 4102 of the artificial neural network 4002 (e.g., the weights 4012 and/or biases 4016 of respective neurons 4008 and layers of the artificial neural network 4002) are adjusted so that the output 4022 of the artificial neural network 4002 for a data sample 4108 is closer to the output 4022 of the data sample 4108. For example, during a feedforward step 4110, the inputs 4004 of a first data sample 4108-1 may be provided as input to the input layer 4006 of the artificial neural network 4002, and may be processed through one or more hidden layer(s) 4014 and the output layer 4020 to produce one or more outputs 4022. The training 4104 may then perform a comparison 4112 output 4022 of the artificial neural network 4002 may be compared with the output 4022 of the first data sample 4108-1 to determine an error 4114. Based on the comparison 4112 and the error 4114, backpropagation 4116 may be performed to adjust the parameters 4102 of the artificial neural network 4002 to reduce the error 4114 between the output 4022 generated by the artificial neural network 4002 for the inputs 4004 of the first data sample 4108-1 and the output 4022 included in the first data sample 4108-1. Specifically, the backpropagation 4116 may involve first adjusting the weights 4012 and/or bias 4016 of the output layer 4020 based on the differential gradient of the activation function of the neuron 4008 of the output layer 4020, the error 4114, the inputs to the neuron 4008 of the output layer 4020 received from the hidden layer 4014, the weights 4012 of the connections 4010 between the neuron 4008 of the output layer 4020 and the neurons 4008 of the hidden layer 4014, and optionally a learning rate. Next, the backpropagation 4116 may involve adjusting the weights 4012 and/or bias 4016 of each neuron 4008 of the last hidden layer 4014 based on the differential gradient of the activation function of each neuron 4008 of the last hidden layer 4014, the error 4114, the inputs to each neuron 4008 of the last hidden layer 4014 received from the preceding layer (e.g., a preceding hidden layer 4014 or the input layer 4006), the weights 4012 of the connections 4010 between each neuron 4008 of the last hidden layer 4014 and the neurons 4008 of the preceding layer, and optionally the learning rate. The backpropagation 4116 may continue backward through the artificial neural network 4002 until all of the parameters 4102 have been updated to reduce the error 4114 for the first data sample 4108-1.

After processing the first data sample 4108-1, the training 4104 may involve similar processing of the other data samples 4108-2, 4108-3 of the training data set 4106. The adjustment of the artificial neural network 4002 by each data sample 4108 of the training data set 4106 may complete an "epoch" of training 4104. The training 4104 may involve multiple epochs (e.g., iterations of adjustments over the training data set 4106). The progress of training 4104 may be evaluated and monitored based on the changes in the error 4114 over the entire training data set 4106 (e.g., the sum of the error for each data sample 4108 before updating the parameters 4102). The training 4104 may involve adjusting the learning rate as the error 4114 of the artificial neural network 4002 over the entire training data set 4106 changes (e.g., reducing the learning rate as the artificial neural network 4002 converges on the expected outputs 4022, thereby making smaller adjustments that refine the precision of the analyses and outputs 4022). The training 4104 may be considered complete when the overall error 4114 of the entire training data set 4106 is below a threshold error 4114, indicating that the artificial neural network 4002 has achieved a desirable level of accuracy and precision in its processing of the inputs 4004 of the training data set 4106.

The training 4104 of artificial neural networks 4002 may involve many techniques and/or adjustments to improve the speed of training 4104 and/or the resulting performance of the trained artificial neural network 4002. As a first example, rather than performing backpropagation 4116 to adjust the parameters 4102 of the artificial neural network 4002 for each data sample 4108, the training 4104 may involve "batch" processing of the training data set 4106, wherein batches of data samples 4108 are analyzed, and backpropagation 4116 is performed over an accumulation of the error 4114 for the entire batch. As a second example, rather than determining completion of training 4104 when the error 4114 is below a threshold, the training 4104 may involve monitoring a rate of change of the error 4114, and may be considered complete when the rate of change is below a threshold rate of change of the error 4114. Such consideration may reduce the likelihood and/or magnitude of "overtraining," where the parameters 4102 of the artificial neural network 4002 are excessively adjusted or "overfit" to the training data set 4106, which may reduce the performance of the artificial neural network 4002 over data samples 4108 that are not included in the training data set 4106. That is, the parameters 4102 may cause the artificial neural network 4002 to generate outputs 4022 that are very close to the expected outputs 4022 of the inputs 4004 for the data samples 4108 of the training data set 4106, but that exhibit considerable error over similar inputs 4004 that are not included in the training data set 4016. As a third example, rather than training on the entire training data set 4106, the artificial neural network 4002 may partition the training data set 4106 into a "training" set that is used to train the artificial neural network 4002, a "validation" set that is used to monitor the performance of the artificial neural network 4002 over unseen data during training (e.g., in order to detect the beginning of overfitting), and a "test" set that is used to evaluate the performance of the fully trained artificial neural network 4002 after the completion of training. Further techniques that may be included in the training 4104 of an artificial neural network 4002, as may be known to persons of ordinary skill in the art, include bootstrap aggregation or "bagging" (e.g., training an artificial neural network 4002 repeatedly over different splits of the training data set 4106 between training, validation, and test sets), regularization (e.g., applying various techniques to prevent individual weights 4012 and/or biases 4016 from becoming too large, such as L1 or "lasso" regularization, L2 or "ridge" regularization, and "dropout" regularization in which random subsets of neurons 4008 are deactivated during training 4104), few-shot learning (e.g., training 4104 an artificial neural network 4002 to perform classification wherein at least one class has a very small number of data samples 4108 in the training data set 4106), and fine-tuning (e.g., broadly training an artificial neural network 4002 on a generalized training data set 4106, and then specifically training the artificial neural network 4002, and in particular selectively training only one or more final layers of the artificial neural network 4002, on a more specific training data set 4106 for a specialized task and/or a specialized knowledge domain).

After the completion of training 4104, an artificial neural network 4002 may be used for inference 4118, that is, for the analysis of set of inputs 4004 that were not included in the training 4104, and that may not have an expected output 4022. For example, an artificial neural network 4002 that has been trained for anomaly detection may be deployed to a production environment to detect anomalies in the input received from a device. An artificial neural network 4002 that has been trained to classify email as "spam" or "not spam" may be deployed to an email client to classify incoming email as "spam" or "not spam." An artificial neural network 4002 that has been trained to classify images based on their content may be deployed to an image database to analyze the content of images and generate labels for respective images of the image database. Due to the training 4104, the artificial neural network 4002 may generate outputs 4022 for various inputs 4004 based on similar logical criteria that associated the inputs 4004 and expected outputs 4022 of each data sample 4108 of the training data set 4106.

Further techniques that may be utilized during inference 4118 of an artificial neural network 4002, as may be known to persons of ordinary skill in the art, include zero-shot learning (e.g., providing an artificial neural network 4002 with a classification task involving at least one class that was completely unrepresented by even one data sample 4108 in the training data set 4106, and providing a description of the class during inference 4118 so that the artificial neural network 4002 can still correctly classify an input 4004 as belonging to the class) and transfer learning (e.g., training an artificial neural network 4002 on one task and/or knowledge domain, and then using the artificial neural network 4002 for inference 4118 in a different or related task and/or knowledge domain).

In some cases, the training 4104 of the artificial neural network 4002 may continue after deployment and/or concurrently with inference 4118. For example, as new inputs 4004 are received that are different than the inputs 4004 of the training data set 4106, new data samples 4108 may be provided that associate the new inputs 4004 with expected outputs 4022. The artificial neural network 4002 may be further trained and/or retrained on the new data samples 4108, optionally in combination with the data samples 4108 of the original training data set 4106. As another example, the performance of the artificial neural network 4002 may be detected to vary from the performance of the fully trained artificial neural network 4002 over the training data set 4106 (e.g., due to overfitting, a variance between the training data set 4016 and new data samples 4108, and/or changes in the performance of the artificial neural network 4002 over the data samples 4108 of the training data set 4106 due to continued training). In such cases, often known as "drift." the artificial neural network 4002 may be further trained, retrained, reinitialized for supplemental training, combined with one or more other artificial neural networks 4002 and/or other AI models, and/or replaced by one or more other artificial neural networks 4002 and/or other AI models.

Artificial neural networks 4002 can be or include one or more recurrent neural networks. In some instances, at least some of the neurons 4008 of a recurrent neural network can form a cycle. Recurrent neural networks can be especially useful for processing input data that is sequential in nature. In particular, in some instances, a recurrent neural network can pass or retain information from a previous portion of the input data sequence to a subsequent portion of the input data sequence through the use of recurrent or directed cyclical connections between and among the neurons 4008.

In some artificial neural networks 4002, sequential input data can include time-series data (e.g., sensor data versus time or imagery captured at different times). For example, a recurrent neural network can analyze sensor data versus time to detect or predict a swipe direction, to perform handwriting recognition, etc. Sequential input data may include words in a sentence (e.g., for natural language processing, speech detection or processing, etc.); notes in a musical composition; sequential actions taken by a user (e.g., to detect or predict sequential application usage); sequential object states; etc. In some example embodiments, recurrent neural networks include long short-term (LSTM) recurrent neural networks; gated recurrent units; bi-direction recurrent neural networks; continuous time recurrent neural networks; neural history compressors; echo state networks; Elman networks; Jordan networks; recursive neural networks; Hopfield networks; fully recurrent networks; sequence-to-sequence configurations; etc.

Some artificial neural networks 4002 can be or include one or more convolutional neural networks. In some instances, a convolutional neural network can include one or more convolutional layers that perform convolutions over input data using learned filters. Filters can also be referred to as kernels. Convolutional neural networks can be especially useful for vision problems such as when the input data includes imagery such as still images or video. However, convolutional neural networks can also be applied for natural language processing.

Some artificial neural networks 4002 may be or include autoencoders. In some instances, the aim of an autoencoder is to learn a representation (e.g., a lower-dimensional encoding) for a set of data, often for the purpose of dimensionality reduction. For example, in some instances, an autoencoder can seek to encode the input data and then provide output data that reconstructs the input data from the encoding. In some neural networks, the autoencoder can include additional losses beyond reconstructing the input data.

Some artificial neural networks 4002 may be or include one or more other forms of artificial neural networks 4002 such as, for example, deep Boltzmann machines; deep belief networks; stacked autoencoders; etc. Any of the neural networks described herein can be combined (e.g., stacked) to form more complex networks.

Artificial neural networks 4002 may be trained and used for a variety of analytic tasks. In analytic tasks, the output of the artificial neural network 4002 is understood and used to encode an analysis of the inputs provided to the artificial neural network 4002, such as an indication of a classification, a product of a regression calculation over the input data, or an indication of an object or pattern recognized in the input data. Examples of analytic tasks performed by an artificial neural network 4002 including (without limitation) pattern recognition, regression, classification, visual object recognition (using convolutional neural networks), data clustering, and anomaly detection. Persons of ordinary skill in the art may be familiar with a variety of analytic AI models and techniques.

Artificial neural networks 4002 may also be trained and used for a variety of "generative" tasks. In generative tasks, the output of the artificial neural network 4002 is understood and used as new content that has been generated by the artificial neural network 4002, such as new text, images, sounds, data, or the like. The new content may be based on the inputs 4004 of the artificial neural network 4002 (such as a prompt that requests features of the generated content, or an example of content that the generated content should resemble) and/or may be based on randomization of the artificial neural network 4002 (e.g., perturbation of the latent space that specifies features of the generated content). Types of artificial neural networks 4002 that may be useful as generative AI include (without limitation) autoencoders. Markov chain generators, generative adversarial networks ("GANs"), diffusion-based models, and transformers. Persons of ordinary skill in the art may be familiar with a variety of generative AI models and techniques.

Some AI models include a combination or "ensemble" of two or more artificial neural networks 4002. As a first example, two or more artificial neural networks 4002 may be connected in series, such that at least a portion of the output of a first artificial neural network 4002 may be provided as at least a portion of the input of a second artificial neural network 4002. A series architecture of artificial neural networks may enable smaller artificial neural networks 4002 that are trained for selective tasks to be combined into a larger AI model that performs more sophisticated tasks based on the combination of artificial neural network 4002. For instance, a first artificial neural network 4002 may be configured to classify input data into various types of classes based on patterns in the data, and a second artificial neural network 4002 (e.g., a recurrent neural network) may evaluate a set of classifications of the input data over time to determine trends and/or chronological patterns based on the classifications over time. As a second example, two or more artificial neural network 4002 may be combined in parallel to perform the same, similar, or different types of analyses of input data. For example, a first artificial neural network 4002 may be trained to detect and classify a first type of pattern in input data, and a second artificial neural network 4002 may be trained to detect and classify a second type of pattern in input data. The combined output of these artificial neural networks 4002 and the processing of a set of input data by both artificial neural networks 4002 may enable a detection of multiple types and/or classifications over the input data. As a third example, two or more artificial neural network 4002 may be combined in parallel to perform the same, similar, or different types of analyses over different portions of input data. For example, an input data set may be partitioned into two or more subsets of input data, each subset of input data may be concurrently processed by a different artificial neural network 4002, and the concurrently generated outputs of the artificial neural networks 4002 may be combined into an aggregate output over the entire input data set. Such combinations may enable data analysis to be performed faster and/or over discrete sections of the input data set based on the partitioning. As a fourth example known as "boosting," an AI model may include two or more simple or "weak" artificial neural networks 4002 that are individually trained (e.g., over small and/or distinct sets of training data, or using only a brief training period), and the output of the AI model may include a combination of the outputs of the simple or "weak" artificial neural networks 4002 to generate a stronger (e.g., more accurate and/or precise) output based on the consensus of the "weak" artificial neural networks 4002. Some AI models may combine artificial neural networks 4002 of different types (e.g., a recurrent neural network that generates individual outputs for respective time points, followed by a densely connected artificial neural network 4002 to classify outputs over a set of time points). Some AI models may combine one or more artificial neural networks 4002 with one or more other types of AI models, such as decision trees, rule-based expert systems, k-means clustering models, k-nearest-neighbor models, or the like.

Attention

Some artificial intelligence systems, machine learning models, or the like may comprise, integrate, link to, or include an attention feature. Attention may be generally described as a determination, among a set of inputs, of the relatedness of each input to the other inputs in the set of inputs. In "self-attention," the input includes a sequence of elements, and attention is determined between each pair of elements in the sequence. As a first example, the set of inputs includes a sequence of words in a language, and attention is applied to determine, for each word in the sequence, the relatedness of the word to each other word in the sequence. As a second example, an input includes an image comprising a set of pixels, and attention is applied to determine, for each group of pixels in the image, the relatedness of the group of pixels to each other group of pixels in the image. Attention can also be applied between sets of input, wherein attention is determined between each element of a first set of input and each element of a second set of input. For example, the set of inputs can include a first sequence of words in a first language and a second sequence of words in a second language, and attention can be determined to indicate how each word in the first sequence is related to each word in the second sequence.

Figure 42:
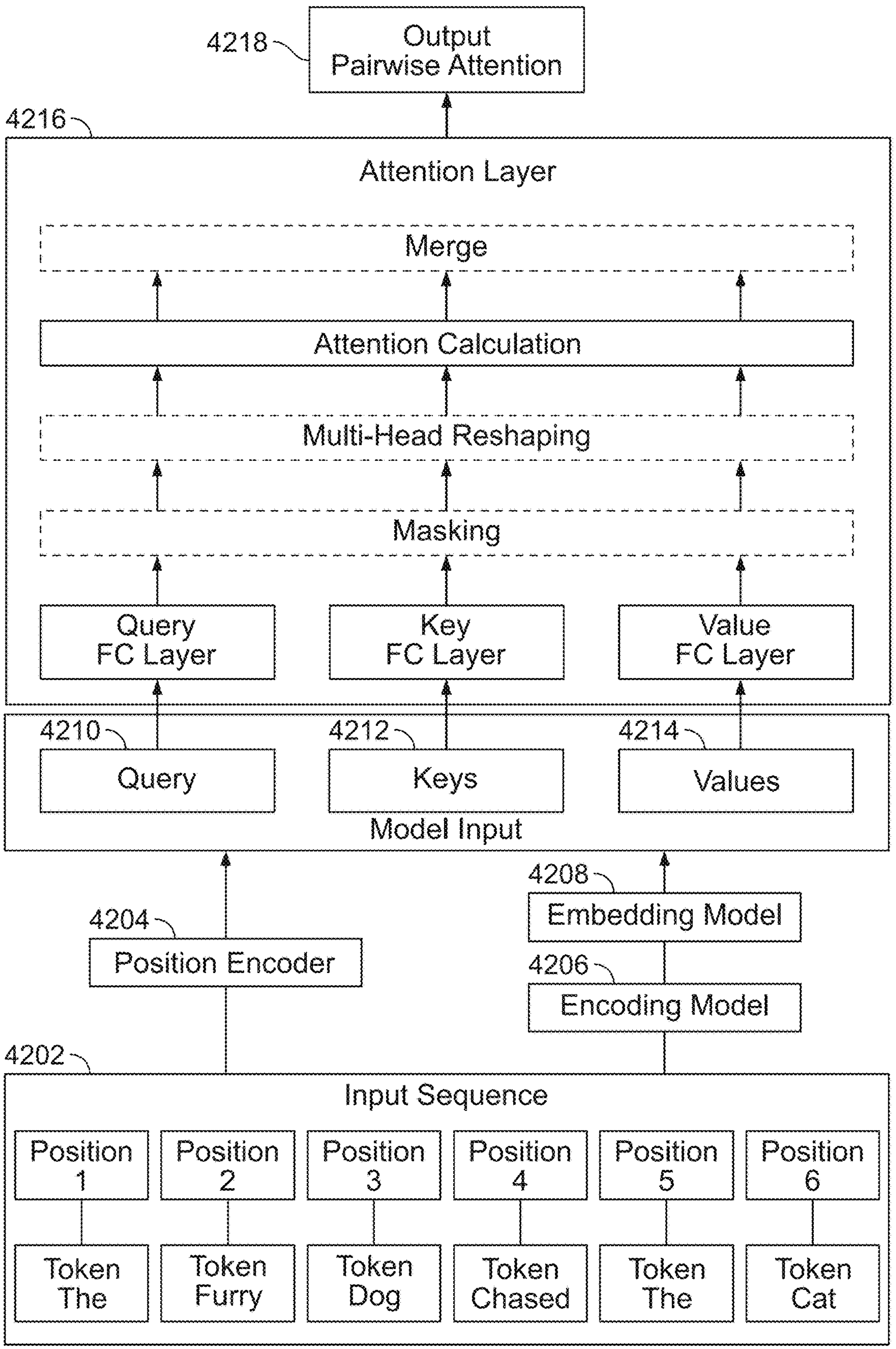
FIG. 42 is a schematic diagram detailing an example of a determination of attention by a machine learning model according to some example embodiments.

FIG. 42 presents an example of a determination of attention by a machine learning model. In the example of FIG. 42, an input sequence 4202 includes a set of tokens, each representing a word ("The", "Furry", "Dog". "Chased", "The", "Cat"). Each token includes an indicator of a position of the token in the sequence. In various embodiments, the tokens of the input sequence 4202 may include complete words, portions of words (e.g., a first token indicating a word root and a second token indicating a modifier of the word root), punctuation, or the like. Some tokens may indicate metadata, such as a start-of-sequence token, an end-of-sequence token, or a null token indicating a padding of the sequence or a mask that hides a token of the sequence.

The input sequence 4202 may be processed by a position encoder 4204 that determines, for each token, an encoding of the position of the token in the input sequence 4202. The position encoding may include an ordinal numerical value that indices the ordinal position of each token in the sequence, such as an index beginning at zero or one. The position encoding may include a relative numerical value that indicates a position of each token in the sequence relative to a fixed position, such as a current word (encoded position 0), an immediately preceding word (encoded position −1), or an immediately following word (encoded position 1). The position encoding may include non-integer values and/or multiple values, such as a first index indicating a sine calculation (with a given frequency) of the position of each token and a second index indicating a cosine calculation (with a same or different frequency) of the position of each token.

The input sequence 4202 may also be translated into an encoded sequence according to a language-specific encoding model 4206. For example, an encoding model 4206 for the English language may assign integer values to various words, tokens such as word stems and punctuation, proper nouns, and the like. The integers may be arbitrarily assigned, e.g., according to the ordinal positions of the tokens in a sorting (e.g., alphabetic ordering) of the tokens. A received input sequence, such as an English-language expression, may be broken into tokens (e.g., separating the word "cats" into the token "cat" and the token "s" indicating a pluralization of the preceding token "cat"), and each token may be translated into its assigned integer according to the encoding model. The encoding integers may be concatenated to represent the input expression as a sequence of integers, which may be more easily processed by the attention layer 4216 than the native symbolic grammar of the language that may involve a variable number of letters, symbols, and grammatic rules.

After being translated into an encoding sequence with position encoding, the input sequence 4202 (e.g., the sequence of integers according to the encoding model and corresponding positional encodings) may be processed by an embedding model 4208. The embedding model 4208 determines, for each token in the input sequence 4202, a mapping of the token into a latent space representation of the input (e.g., a latent space representation of a language). The latent space may position each token along a plurality of n dimensions, wherein each dimension represents a distinct type of relationship among the elements of the language. The embedding model 4208 clusters the tokens such that related tokens are positioned closer to each other within the latent space. For example, along one dimension of the latent space, the words "Cat" and "Dog" may be positioned close together as being words that describe animals, while also being positioned apart from words that do not describe animals, such as "Baseball" and "School." Along another dimension of the latent space, the words "Dog" and "Furry" may be positioned close together as words that commonly occur in the context of dogs, while also being positioned apart from words that do not describe dogs, including "Cat." For each token of the input sequence, the embedding model 4208 generates one or more values that indicate the position of the token within the latent space. The values may be encoded as a vector, and the proximity of two tokens within the latent space may be determined based on vector proximity calculations, such as cosine similarity. While the encoding sequence by the encoding model 4206 simply maps the low-level letters and symbols of an expression into regularized integers, the processing of the input sequence by the embedding model 4208 supplements the input sequence with semantic context, such as semantic similarity between tokens.

The positions encoded by the position encoder 4204 and the embeddings determined by the embedding model 4208 serve as the input of the input sequence 4202 to the attention layer 4216. As shown in FIG. 42, the input to the attention layer 4216 includes a query 4210, a set of keys 4212, and a set of values 2214. As an example, the query 4210 may include an indicator of a particular token in the input sequence, such as the sixth token ("Cat"). The keys 4212 may include the position encodings of respective preceding tokens of the input sequence 4202, as determined by the position encoder 4204, and a corresponding embedding of the respective token as determined by the embedding model 4208. The values may indicate additional data features of the tokens of the input sequence 4202. As an example, the values may indicate, for each token of the input sequence 4202, a determined sentiment (e.g., a ranking between −1, indicating very negative words, and +1, indicating very positive words). In some attention layers 4126, no additional data features are available, and the values 4214 are identical to the keys 4212.

The model input is received and processed by an attention layer 4216. In FIG. 42, the attention layer 4216 first includes a set of fully-connected layers: a first fully-connected layer processes the query of the model input; a second fully-connected layer processes the keys of the model input; and a third fully-connected layer processes the values of the model input. Each fully-connected layer includes a bias and a set of weights that adjust the values of the query, key, or value, respectively. The bias and weights of each fully-connected layer are model parameters that are initialized (e.g., to random values) and then incrementally adjusted during training.

In some attention layers 4216, the outputs of the fully-connected layers are further processed by a masking layer. The masking layer removes one or more values from the model input adjusted by the fully-connected layers. As a first example, the masking layer can reduce to zero the values of the key and/or value at a given position, such as a token at a current position to be predicted, or a token at a position following the current position that is to be hidden from the model. As a second example, the masking layer can reduce to zero the values of particular keys and/or values, such as padding values that are provided to adapt the size of the model input to a size of input that the attention layer 4126 is configured to receive and process. The masking layer can produce output for certain tokens (e.g., reduced to zero) for the indicated tokens (e.g., the current token, future tokens, and/or padding tokens) and that is the same as the input for the remaining tokens.

In some attention layers 4216, the outputs of the masking layer are further processed by a multi-head reshaping layer. The multi-head reshaping layer can reshape an input vector comprising the weighted and/or masked model input such that subsets of the input can be processed in parallel by different attention heads. As an example, an attention layer 4216 may include two attention heads, and the input can be reshaped such that each attention head is applied to only half of the inputs. The multi-head attention model can enable attention determinations over different subsets of the input (e.g., a first attention head can determine the relatedness of a first token to a first subset of tokens of the input sequence, and a second attention head can determine the relatedness of the same first token to a second subset of tokens of the input sequence). Alternatively or additionally, the multi-head attention model can enable different types of attention determinations among the tokens of the input sequence (e.g., a first attention head can determine a first type of relatedness of a first token to a subset of tokens of the input sequence, and a second attention head can determine a second type of relatedness of the same first token to the same or different subset of tokens of the input sequence). The multi-head attention model may enable parallel processing of the input sequence (e.g., the input for each attention head can be processed by a different processing core).

The attention layer 4216 includes an attention calculation that determines, based on the model input, the attention of a token of the input sequence with respect to other tokens of the input sequence. The attention calculation may include an additive attention ("Bahdanau Attention") calculation, in which attention is determined as a sum of weighted calculations of the distances of the tokens along each dimension of the latent space. The attention calculation may include a dot product determination, as a comparison of the distances between the vectors of the tokens within the latent space. The attention calculation may be performed over the query, keys, and values of the model input, optionally after processing with a masking layer. The attention calculation may be performed for each of a plurality of attention heads, each of which processes a particular subset of the tokens of the input sequence.

In embodiments that include multi-head reshaping, the output of the attention calculation is further processed by a merge operation that merges the attention calculations for the respective attention heads. The merge operation may include a concatenation and/or interleaving of the attention calculations of the attention heads. The merge operation may include an arithmetic operation applied to the attention calculations of the attention heads, such as an arithmetic mean, median, min, and/or max calculation.

The attention layer 4216 outputs, for at least one token of the input sequence, a determination of pairwise attention 4218 between the token and at least one other token of the input sequence. The output of the attention layer 4216 may include a vector that indicates, for at least one token of the input sequence, the determinations of attention between the token and a set of other tokens of the input sequence. The output of the attention layer 4216 may include a set of vectors that indicate, for respective tokens of the input sequence, the determinations of attention between the respective token and at least one other token of the input sequence. The output of the attention layer 4216 may indicate, for a token of a first sequence, the attention of the token to one or more tokens of a second sequence. As shown in FIG. 42, the output of the attention layer 4216 includes determinations of pairwise attention 4218 between pairs of tokens (e.g., each pair including a current token in an input sequence and each preceding token in the input sequence). The pairwise determinations may be further processed, for example, by applying a softmax calculation to normalize the pairwise attention determinations based on a desired range of output values (e.g., probability values between 0.0 and 1.0, with a 1.0 sum over the set of output values).

The attention layer 4216 may be trained by providing sets of training input sequences 4202 and comparing the outputs of the attention layer 4216 with expected outputs. Alternatively or additionally, the attention layer 4216 may be trained by incorporating the attention layer 4216 into a larger model (e.g., a transformer model) and adjusting the parameters of the attention layer 4216 (e.g., the parameters of the fully-connected layers) for a given training input sequence 4202 in order to adjust the output of the attention layer 4216 toward a desired output for the training input sequence 4202. As an example, in a backpropagation training process, the output of the attention layer 4216 is provided as input to a succeeding layer. The output of the model including the attention layer 4216 and the succeeding layer may be compared with a desired output for the training input sequence 4202. Based on this comparison, adjustments of the output of the succeeding layer (e.g., based on an error calculation) may inform a determination of desired adjustments of the input of the succeeding layer, which correspond to adjustments of the output of the attention layer 4126. The adjustments of the output may be achieved by internally adjusting the parameters of the attention layer 4126 (e.g., the weights and/or biases of the fully-connected or "FC" layers shown in FIG. 42) such that the attention layer 4126 subsequently generates output for the training input sequence 4202 that more closely corresponds to the desired input for the succeeding layer. Incremental training over a set of training input sequences 4202 can cause the attention layer 4216 to generate output that corresponds to the desired output for the training input sequences 4202. As an example, if the input sequences are sentences in a language and the desired output of the model includes the probabilities of words in the language that could follow a given set of input words, the attention layer 4216 can be incrementally adjusted to indicate the attention (e.g., relatedness) between the next word in the input sequence and the preceding words in the input sequence.

It is to be appreciated that the attention layer 4126 shown in FIG. 42 presents only one example, and that attention layers 4126 may include a variety of variations with respect to the example of FIG. 42. For example, attention layers 4126 may include, without exception, additional layers or sub-layers that perform one or more of: normalization; randomization; regularization (e.g., dropout); one or more sparsely-connected layers; one or more additional fully-connected layers; additional masking; additional reshaping and/or merging; pooling; sampling; recurrent or reentrant features, such as gated recurrence units (GRUs), long short-term memory (LSTM) units, or the like; and/or alternative layers, such as skip layers. Alternatively or additionally, the architecture of the attention layer 4126 shown in FIG. 42 may vary in numerous respects. For example, masking may be applied to the model input instead of to the outputs of the fully-connected layers. One or more fully-connected layers may be omitted, replaced with a sparsely-connected layer, and/or provided as multiple fully-connected layers, including a sequence of two or more fully-connected layers; or the like. Model parameters (e.g., weights and biases) and/or hyperparameters (e.g., layer counts, sizes, and/or embedded calculations) may be modified and/or replaced with variant parameters and/or hyperparameters. Many such variations may be included in attention layers 4126 that are incorporated in a variety of machine learning models to process a variety of types of input sequences.

Transformer Models

In embodiments, an artificial intelligence system, machine learning model, or the like, of any of the types disclosed herein, may comprise, integrate, link to, or include a transformer model, that is, a neural network that learns context and meaning by tracking relationships in a set of sequential data inputs. Transformer models may include one or more attention layers, including (but not limited to) the attention layer 4126 shown in FIG. 42.

Figure 43:
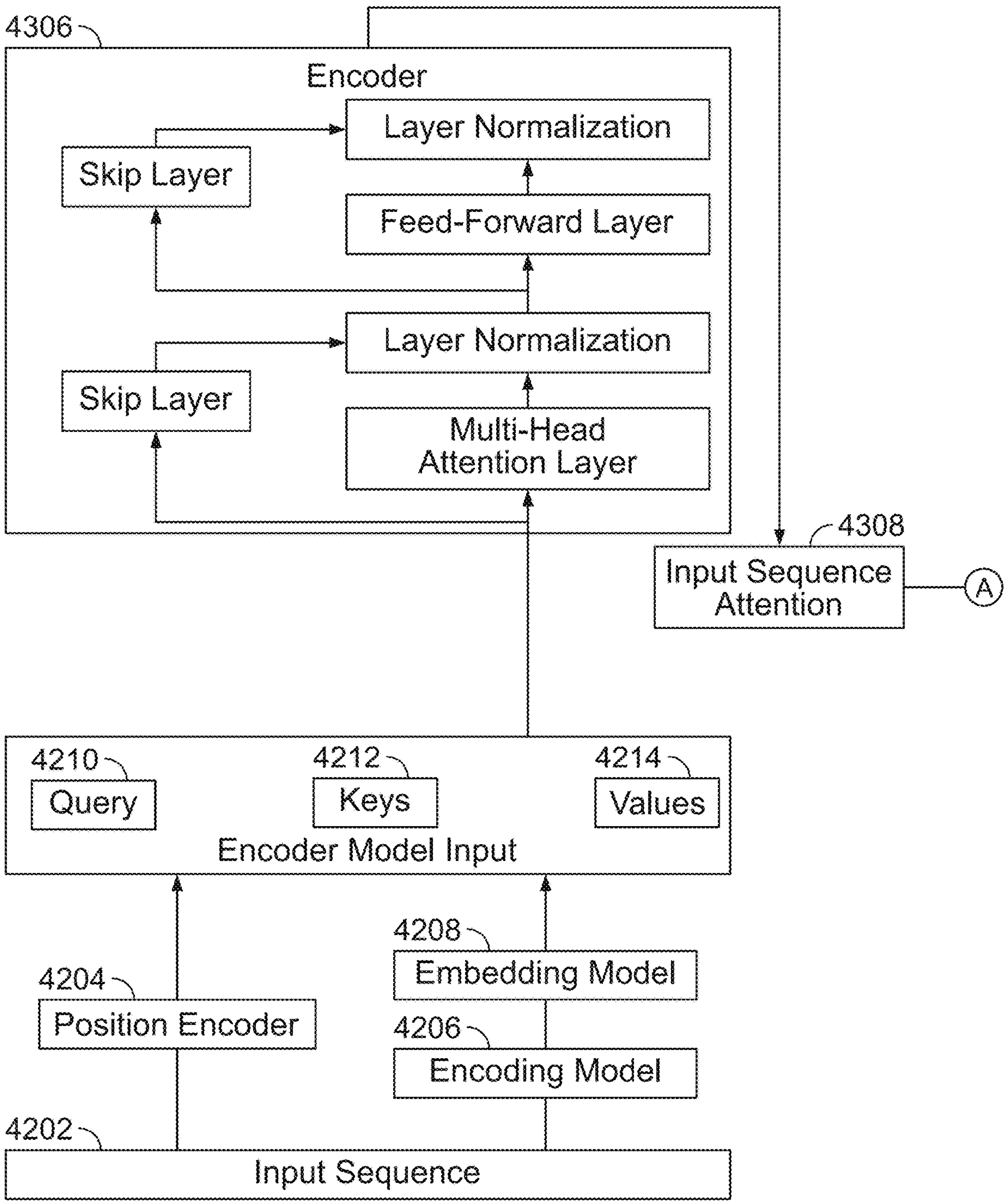
FIG. 43 is a schematic diagram detailing an example transformer model according to some example embodiments.
Figure 43:
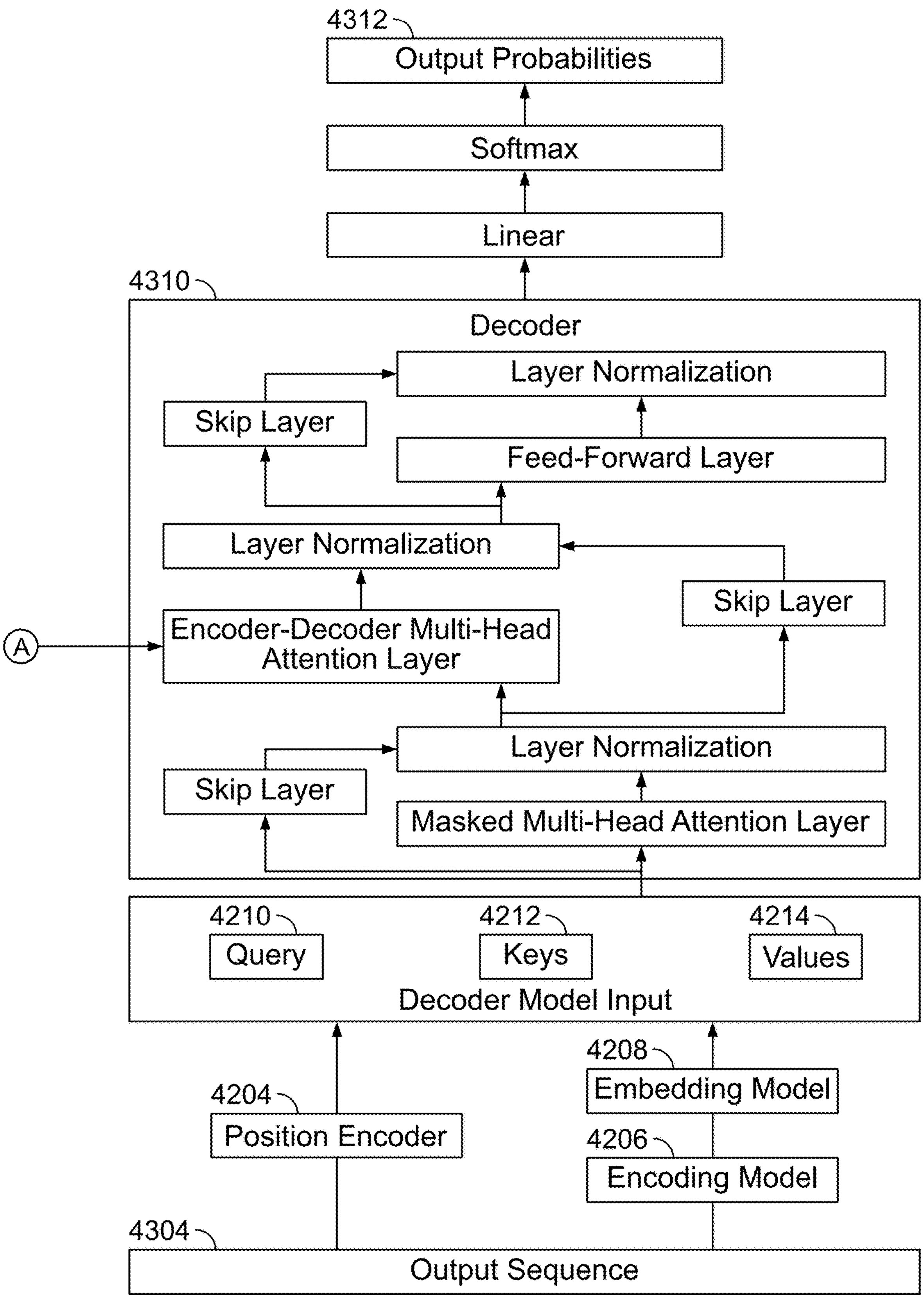

FIG. 43 presents an example of a transformer model 4302. The transformer model of FIG. 43 is based on an encoder-decoder architecture in which an encoder 4306 processes an input sequence 4202 and a decoder 4310 processes an output sequence 4304 to generate a set of output probabilities 4312. As a first example, the input sequence 4202 may include a sequence of words in a first language; the output sequence 4304 may include a sequence of words in a second language corresponding to a translation of the input sequence; and the output probabilities 4312 may include the probabilities of words in the second language for a particular position in the translation. As a second example, the input sequence 4202 may include a sequence of words in a language that represent a query or prompt; the output sequence 4304 may include a sequence of words in the same language that represent a portion of a response to the query or prompt; and the output probabilities 4312 may include the probabilities of next words in the response to the query or prompt to follow the given portion of the response. In some cases, the output sequence includes only the tokens up to a particular position (e.g., the first n−1 tokens of the output sequence), and the output probabilities 4312 represent the probabilities of tokens in the language that could follow the output sequence 4304 (e.g., the nth token in the output sequence 4304, based on previously determined tokens 1 through n−1 in the output sequence 4304). In some cases, the output sequence 4304 includes all of the tokens except the token a particular position (e.g., all of the tokens except the nth token of the output sequence), and the output probabilities 4312 represent the probabilities of tokens in the language of the output sequence 4304 that could represent the missing token in the output sequence 4304 (e.g., the nth token in the output sequence 4304, based on all of the tokens in the output sequence 4304 except the nth token).

The encoder 4306 receives an input sequence 4202 comprising a set of tokens. The input sequence 4202 may be padded to a given length corresponding to a configured input size for the encoder 4306. The input sequence 4202 is processed by a position encoder 4204 to encode the positions of the respective tokens of the input sequence. The input sequence 4202 is also processed by an encoding model 4206 to determine the encodings of the tokens corresponding to natural-language words and symbols of the input sequence 4202. The input sequence 4202 (specifically, the sequence of encodings generated by the encoding model 4206) is also processed by an embedding model 4208 to determine the embeddings of the tokens of the input sequence 4202. The encoded positions and embeddings are used to generate an encoder model input to the encoder 4306, including a query 4210 (e.g., a position of one or more tokens in the input sequence), a set of keys 4212 (e.g., the encoded positions and embeddings for each token of the input sequence), and a set of values 4214 (e.g., additional language features of the tokens such as outputs of sentiment analysis). The set of values 4214 may be a copy of the set of keys 4212 if no additional data features are available. The input to the encoder 4306 is processed by a multi-head attention layer, such as an instance of the attention layer 4126 shown in FIG. 42. The multi-head attention layer determines self-attention within the input sequence 4202 (e.g., the pairwise relatedness of a respective token of the input sequence to each other token of the input sequence). The output of the multi-head attention layer is received and processed by a layer normalization component. Additionally, a skip layer is provided that passes the encoder model input through to the layer normalization component. The layer normalization component combines the output of the multi-head attention layer with the encoder model input (e.g., via arithmetic mean, median, min, max, addition, multiplication, or the like) and normalizes the combined output to within a desired range. The encoder 4306 may include a sequence of two or more instances of this combination of multi-head attention layers, skip layer, and layer normalization components. The encoder 4306 also includes a feed-forward layer (e.g., a fully-connected layer and/or a sparsely-connected layer) including a set of trainable parameters. The output of the feed-forward layer is provided to another layer normalization component, along with the output of the preceding layer normalization component via a skip layer. The encoder 4306 outputs an input sequence attention 4308, which indicates, for each of one or more tokens of the input sequence 4202, the relatedness of each other token of the input sequence 4202.

The decoder 4310 features an architecture that is similar to the encoder 4306, but that includes additional components to incorporate the input sequence attention 4308 generated by the encoder 4306. The decoder 4310 receives an output sequence 4304 comprising a set of tokens. The output sequence 4304 may be padded to a given length corresponding to a configured input size for the decoder 4310. The output sequence 4304 is processed by a position encoder 4204 to encode the positions of the respective tokens of the output sequence. The output sequence 4304 is also processed by an encoding model 4206 to determine the encodings of the tokens corresponding to natural-language words and symbols of the output sequence 4304. The output sequence 4304 (specifically, the sequence of encodings generated by the encoding model 4206) is also processed by an embedding model 4208 to determine the embeddings of the tokens of the output sequence 4304. The encoded positions and embeddings are used to generate input to the decoder 4310, including a query 4210 (e.g., a position of one or more tokens in the output sequence 4304), a set of keys 4212 (e.g., the encoded positions and embeddings for each token of the output sequence 4304), and a set of values 4214 (e.g., additional language features of the tokens such as outputs of sentiment analysis). The set of values 4214 may be a copy of the set of keys 4212 if no additional data features are available. The input to the decoder 4310 is processed by a masked multi-head attention layer, such as an instance of the attention layer 4126 shown in FIG. 42. In addition to determining attention, the masked multi-head attention layer masks the input values of a current token of the output sequence and any tokens of the output sequence that follow the current token. The masked multi-head attention layer determines self-attention within the output sequence (e.g., the relatedness of a respective token of the output sequence to each preceding token of the output sequence). The output of the multi-head attention layer is received and processed by a layer normalization component. Additionally, a skip layer is provided that passes the encoder model input through to the layer normalization component. The layer normalization component combines the output of the multi-head attention layer with the input to the decoder 4310 (e.g., via arithmetic mean, median, min, max, addition, multiplication, or the like) and normalizes the combined output to within a desired range. The decoder 4310 may include a sequence of two or more instances of this combination of multi-head attention layers, skip layer, and layer normalization components. The decoder 4310 further includes an encoder-decoder multi-head attention layer that receives both the output of the preceding layer normalization component and the input sequence attention 4308 generated by the encoder 4306. The encoder-decoder multi-head attention layer does not determine self-attention within the output sequence 4304, but, rather, determines the attention between the tokens of the output sequence 4304 and the corresponding tokens of the input sequence 4202. The output of the encoder-decoder multi-head attention unit is also received and processed by a second layer normalization component. Additionally, a skip layer is provided that passes the input to the encoder-decoder multi-head attention layer through to the second layer normalization component. The second layer normalization component combines the output of the multi-head attention layer with the input to the encoder-decoder multi-head attention unit (e.g., via arithmetic mean, median, min, max, addition, multiplication, or the like) and normalizes the combined output to within a desired range. The decoder 4310 also includes a feed-forward layer (e.g., a fully-connected layer and/or a sparsely-connected layer) including a set of trainable parameters. The output of the feed-forward layer is provided to a third layer normalization component, along with the output of the preceding layer normalization component via a skip layer. The output of the decoder 4310 is processed by a fully-connected layer and a softmax normalization layer based on a cross-entropy determination.

The output of the softmax normalization layer includes a set of output probabilities 4312 for each possible token of a language of the output sequence for the current token. As a first example, the input sequence 4202 may include a sequence of words in a first language; the output sequence 4304 may include a sequence of words in a second language corresponding to a translation of the input sequence, up to a current (nth) word in the translation; and the output probabilities 4312 may include the probabilities of words in the second language for the nth word in the translation. As a second example, the input sequence 4202 may include a sequence of words in a language that represent a query or prompt; the output sequence 4304 may include a sequence of words in the same language that represent a response to the query or prompt, up to a current (nth) word in the response; and the output probabilities 4312 may include the probabilities of words in the language for the nth word in the response.

During training 4104, the transformer model 4302 may be provided with a set of input sequences 4202 and complete corresponding output sequences 4304. As a first example involving language translation, the transformer model 4302 may be provided with a training data set 4106 including (as inputs 4004) a first corpus of sentences in a first language and (as outputs 4022) a second corpus of sentences in a second language that respectively correspond to the sentences in the first language. As a second example involving a generative model, the transformer model 4302 may be provided with a training data set 4016 including (as inputs 4004) a first corpus of queries or prompts in a language and (as outputs 4022) a second corpus of responses in the language that correspond to the respective queries or prompts. For each data sample 4108 of the training data set 4106, a pair of sentences of the first corpus and second corpus are selected. The encoder 4306 is provided with the first (input) sentence, and the transformer model 4302 determines the first word in the second (output) sentence. In this case, the output sequence 4304 provided to the decoder 4310 is completely masked so that the decoder 4310 cannot make predictions based on the expected words in the second sentence. The word probabilities determined by the decoder 4310 are compared with the actual first word in the output sequence 4304, and backpropagation 4116 is applied through the decoder 4310 and the encoder 4306 to increase the likelihood of outputting the expected word. The backpropagation 4116 includes adjusting the parameters 4102 of the attention layers 4126 to increase the attention between the first word and related words of the input sequence 4202. The encoder 4306 is then provided again with the first (input) sentence, and the transformer model 4302 determines the second word in the second (output) sentence. In this case, the output sequence 4304 provided to the decoder 4310 includes the unmasked first word, but masks all words after the first word. The output probabilities 4312 determined by the decoder 4310 are compared with the actual second word in the output sequence 4304, and backpropagation 4116 is applied through the decoder 4310 and the encoder 4306 to increase the likelihood of outputting the expected word. The backpropagation 4116 includes adjusting the parameters 4102 of the attention layers 4126 to increase the attention between the second word, the known first word of the output sequence 4304, and related words of the input sequence 4202. In this manner, the transformer model 4302 performs autoregressive prediction, wherein the output probability 4312 of each nth token of the output sequence 4304 is based on the input sequence 4202, the previously predicted tokens of the output sequence 4304, and the encoder-decoder attention therebetween. Training 4104 continues over the entirety of the first and second corpora to improve the output probabilities 4312 generated by the transformer model 4302.

In many cases, the training of the transformer model 4302 occurs in batches. For example, the previous (simplified) training example described an incremental training of the transformer model 4302 over each corresponding pair of sentences of the first and second corpora, wherein the parameters 4102 of the transformer model 4302 are adjusted via backpropagation 4116 after each instance of processing. In batch training, the input and output sequences are vectorized, as are the layers of the transformer model, such that predictions over each word of the output sequence 43-4 are predicted in parallel. During backpropagation 4116, parameter adjustment is performed for each batch of the training data set 4106, based on the outputs for all of the pairwise inputs of each batch of the training data set 4106.

After training 4104, the transformer model 4302 can be used to predict an output sequence 4304 based on an input sequence 4202. First, the input sequence 4202 is processed by the position encoder 4204, the encoding model 4206, and the embedding model 4208 to generate input to the encoder 4306. Next, the encoder 4306 processes the input, while the decoder 4310 processes the input sequence attention 4308 generated by the encoder 4306 and a null output sequence (e.g., an output sequence 4304 in which all outputs are initially nulled and/or masked by the masked multi-head attention layer 4126). The output probabilities 4312 generated by the decoder 4310 are used to determine a first token of the output sequence. In any such case, the transformer model 4302 is then applied to the same input sequence 4202 and an updated output sequence 4304 including only the determined first token of the output sequence 4304, and the output probabilities 4312 generated by the decoder 4310 determine the second token of the output sequence 4304. This process continues until reaching an output token cap and/or upon determining, as the output of the decoder 4310, an end-of-sequence token. In this manner, the transformer model 4302 is applied over the input sequence 4202 to generate, in serial and autoregressive manner, the sequence of tokens of the output sequence 4304.

It is to be appreciated that the transformer model 4302 shown in FIG. 43 presents only one example, and that transformer models 4302 may include a variety of variations with respect to the example of FIG. 43. For example, the architecture of the encoder 4306 and/or decoder 4310 may include, without exception, additional layers or sub-layers that perform one or more of: normalization; randomization; regularization (e.g., dropout); one or more sparsely-connected layers; one or more additional fully-connected layers; additional masking; additional reshaping and/or merging; pooling; sampling; recurrent or reentrant features, such as gated recurrence units (GRUs), long short-term memory (LSTM) units, or the like; and/or alternative layers, such as skip layers. Alternatively or additionally, the architecture of the encoder 4306 and/or decoder 4310 shown in FIG. 43 may vary in numerous respects. For example, masking may be applied directly to the output sequence 4304 instead of within the multi-head attention models. One or more fully-connected layers may be omitted, replaced with a sparsely-connected layer, and/or provided as multiple fully-connected layers, including a sequence of two or more fully-connected layers; or the like. Model parameters (e.g., weights and biases) and/or hyperparameters (e.g., layer counts, sizes, and/or embedded calculations) may be modified and/or replaced with variant parameters and/or hyperparameters. Many such variations may be included in transformer models 4302 to process a variety of types of input and output sequences.

In particular, transformer models 4302 may vary in the manner of selecting a token from the output probabilities 4312 generated by each iteration of the transformer model 4302. For example, some transformer models 4302 may simply choose, for each token of the output sequence 4304, the token having the highest output probability 4312 as determined by the current iteration of the transformer model 4302. Because the output probabilities 4312 does not vary for a given input sequence 4202 and a given sequence of previously generated tokens of the output sequence 4304, such transformer models 4302 will generate the same output sequence 4304 for any given input sequence 4202. In other transformer models 4302, the selection of a token for each iteration is based on a random sampling over the output probabilities 4312. Such transformer models 4302 may exhibit a stochastic property, wherein processing of the same input sequence 4202 may produce a multitude of output sequence 4304, each based on a different random sampling of the stepwise generation of tokens. Further, because the stochastic nature at each step affects the determination of output probabilities 4312 for the next iteration over the output sequence 4304, repeated processing of the same input sequence 4202 may result in output sequences 4304 that are very different from one another, including output sequences 4304 that head in different conceptual directions. Still other transformer models 4302 may provide a controllable feature ("temperature") that scales the output probabilities 4312 before stochastic selection, wherein a low "temperature" amplifies the highest output probabilities 4312 and restricts the generated output sequence 4304 to a range of similarity, and a high "temperature" permits a broader selection among the top output probabilities 4312 and broadens the differences between generated output sequences 4304.

Transformer models 4302, including the example transformer model 4302 shown in FIG. 43, may be applied in a variety of circumstances. As an example, transformer models 4302 may be trained on and/or configured to process a variety of types of input sequences and/or output sequences. Sequential data inputs and/or outputs can include a wide variety of types described herein, such as strings of text, sequences of sensor data from or about an entity, sequences of steps in a process (e.g., chemical, physical, biological, and many others) or flow (e.g., a human workflow, information technology traffic flow, physical traffic flow, sequences of user behavior (e.g., attention to content, clickstream behavior, shopping behavior (digital and real world), and many others. Any of these, and others can be provided as inputs to train a transformer model, which may be alternatively described herein as a self-attention model, a foundation model, or the like. A range of mathematical self-attention techniques can be applied to detect how data elements in sequential data mutually affect each other (such as in feed-forward, feedback, and other forms of influence and dependency). In various embodiments described herein and in the documents incorporated by reference herein, a set of transformer models may be deployed for a wide range of use cases, including for predictive text applications (e.g., generating a next token of text based on a previous set of tokens, such as for intelligent agent dialog, responses to queries, and the like); for extraction of information (such as extraction of meaningful elements from sensor data, signal data, and the like, such as analog signal data from sensors on machines, wearable devices, infrastructure sensors, edge and IoT devices, and many others); for analysis of human factors, such as emotional response, sentiment, satisfaction, opinion, and the like; for summarizing data (such as providing summaries of text, images, video, sensor data, and many other streams of data of the type collected and processed as described herein); for trend detection, prediction and forecasting (and hence also for anomaly detection, such as fraud in financial transactions), including for a wide range of trends, including health (human, animal, mental, financial, machine condition, and others), performance (wellness, financial, physical, and many others), and many others; for recognition of entities and behaviors (such as objects appearing in video or image data, objects captured in LIDAR and other point-cloud rendering systems, objects located by SLAM systems, and many others); for generation and execution of instructions (e.g., recipes, control instructions, rules, regulations, governance instructions, and many others); and for many other uses.

An input data set, such as an analog or digital sensor data stream, a body of text, a set of images, a set of structured data (such as data from a graph database or other form of database noted herein, a sequence of blockchain or distributed ledger entries (or other ledger data, such as accounting, financial, health or other data), a set of signals (of the various types noted herein), may be provided in order to train a transformer model 4302. Initial training may include a step of facilitating compression of the input data, such as by constraining the size of the transformer neural network and/or its outputs, to dimensionality that is significantly smaller (or less granular, etc.) than that of the input data. By requiring the output of the constrained transformer model 4302 to match, within a required metric of fidelity, the input data, the transformer model is caused to generate an "embedding" of the input data into a more compressed, efficient format. A decoding neural network may then be trained to operate on the output of the constrained, embedding transformer model 4302, such that it can reproduce the input data from the output of the constrained model within the required metric, thereby assuring that the data is compressed without losing critical meaning.

Once the embedding transformer model 4302 is so trained, the decoding neural network can be removed and replaced by one or more of a set of use-case-specific decoding models, each of which is trained to operate on the output of the embedding model to produce a target outcome, such as performing any of the use cases noted above to a satisfactory degree. These use-case decoding models can be fine-tuned iteratively over time with feedback from users, outcomes, or the like. Thus, a trained embedding foundation/transformer model, once created, can be used across many different use cases that may benefit from understanding the meaning of the input data set.

Transformer models 4302 may include features and/or techniques such as deep learning, self-learning, self-organizing, or the like, and may enable various self-learning, self-organization, or other self-referential capabilities. They may also be supervised, semi-supervised, or the like. Transformer models may be coupled with, integrated with, linked to, or the like, in series, parallel or other more complex workflows, with other AI types, such as other neural network types (e.g., CNNs, RNNs, and others). For example, a transformer model 4302 operating on sequential data may be coupled with a model suited to operate on non-sequential data (e.g., for pattern recognition) to achieve a use case.

Transformer models 4302 may discover patterns in large bodies of data by application of a set of mathematical functions, optionally operating in parallel processing configurations, thereby eliminating or reducing the need for human labeling (and thereby greatly expanding the set of available data that can be used to train a model).

Self-attention may be accomplished in a transformer model 4302 by introducing a set of positional encoders that tag data elements entering and exiting a neural network and inserting a set of attention units at appropriate places in the encoding and decoding framework of an AI system. The attention units generate a mathematical map of interrelationships among data elements. Multi-headed attention units may be deployed, executing a matrix of equations in parallel to determine the interrelationships. Transformer models 4302, using self-attention, may display strong capabilities to provide outputs that are consistent with how humans find patterns and meaning in data.

Transformer models 4302 may be embodied with very large numbers of parameters (e.g., hundreds of millions, billions, trillions, or more) operating on very large sets of parallel processors. For example, the Megatron-Turing Natural Language Generation Model by NVIDIA and Microsoft is reported to have 530 billion parameters. As noted above, from a foundational model, various use-case specific models (decoders, projections, and the like) can be purpose-built for specific applications. Accordingly, a set of transformer models 4302 may be deployed using advanced computational techniques and/or processing architectures, such as ones that simplify or converge processors, simplify I/O, and the like. For example, 3D chipset or chiplet architectures may facilitate much higher density, faster computation, making transformer models more cost-effective. Quantum computation may also facilitate massively parallel processing in form factors that are faster, more energy efficient, or the like. Similarly, some machine learning models may use a tensor-engine GPU chip with a specific transformer engine, such as the NVIDIA H100 Tensor Core GPU. Another example of a transformer model is the Google switch transformer model, a trillion-parameter model that uses sparsity and a mixture-of-experts architecture to enable gains in performance and reductions in training speed.

Some smaller or more constrained transformer models 4302 may be trained to generate embeddings, particularly for very complex data sets, such as granular analog data.

Some transformer models 4302 may be configured to operate on structured data processing systems, such as on results from queries that are directed to a database, results of inputs directed to a set of APIs, or the like. This may facilitate better understanding of what meaning a transformer model is recognizing in a data pattern, which can be critical to ensuring quality (e.g., where a model may, due to flaws in underlying data, generate poor conclusion, such as replicating historical racial bias, missing critical balancing information, failing to understand formal logical constructs, or the like). As noted elsewhere in this disclosure and the documents incorporated herein, governance of AI in general, is a need, and the scale and complexity of transformer models likely compounds problems recognized with other neural networks, including their "black box" nature, uncertainty about input quality, and the like.

Large Language Models

Transformer models 4302 (such as the transformer model described in relation to FIG. 43) and attention mechanisms (such as the attention layer 4126 described in relation to FIG. 42) enable a class of artificial intelligence systems known as language models or large language models ("LLMs"). An artificial intelligence system, machine learning model, or the like, of any of the types disclosed herein, may comprise, integrate, link to, or include a large language model.

A language model may be a model that is specifically configured to understand, process, and generate sequences of human language as well as (in some cases) other types of inputs and outputs (e.g., for multimodal models as described in more detail below). A language model may operate by predicting subsequent elements (e.g., tokens, which may represent words, sub-words, or characters as described above for transformer models) of a sequence based on preceding elements. For example, a language model may analyze an input sequence of text, determine probabilities for one or more potential next tokens, and output the one or more potential next tokens based on the probabilities. By training on textual data sets, language models can learn statistical patterns, syntactical structures, and semantic relationships that are inherent in the training data, thereby acquiring abilities to perform various language processing tasks.

Large language models often have a large scale, meaning the model is trained on large data sets (e.g., data sets comprising petabytes of text, code, and/or other sequential data) and the model possesses a large number of adjustable parameters (e.g., ranging from billions to trillions of parameters). This scale enables a large language model 4400 to develop a broad, generalized understanding of language, acquire knowledge spanning numerous domains, and exhibit emergent abilities (e.g., complex capabilities or behaviors that were not explicitly programmed or directly trained but which arise as a consequence of the scale of the model and the richness of its training data). Although the encoder-decoder architecture (as shown in FIG. 43) may be useful for different types of transformer models, large language models 4400 (especially when used for generative tasks such as interactive dialogue and instruction-following) may use a decoder-only architecture because they may predict subsequent tokens based on preceding tokens without a distinct source sequence requiring a separate encoder.

Figure 44:
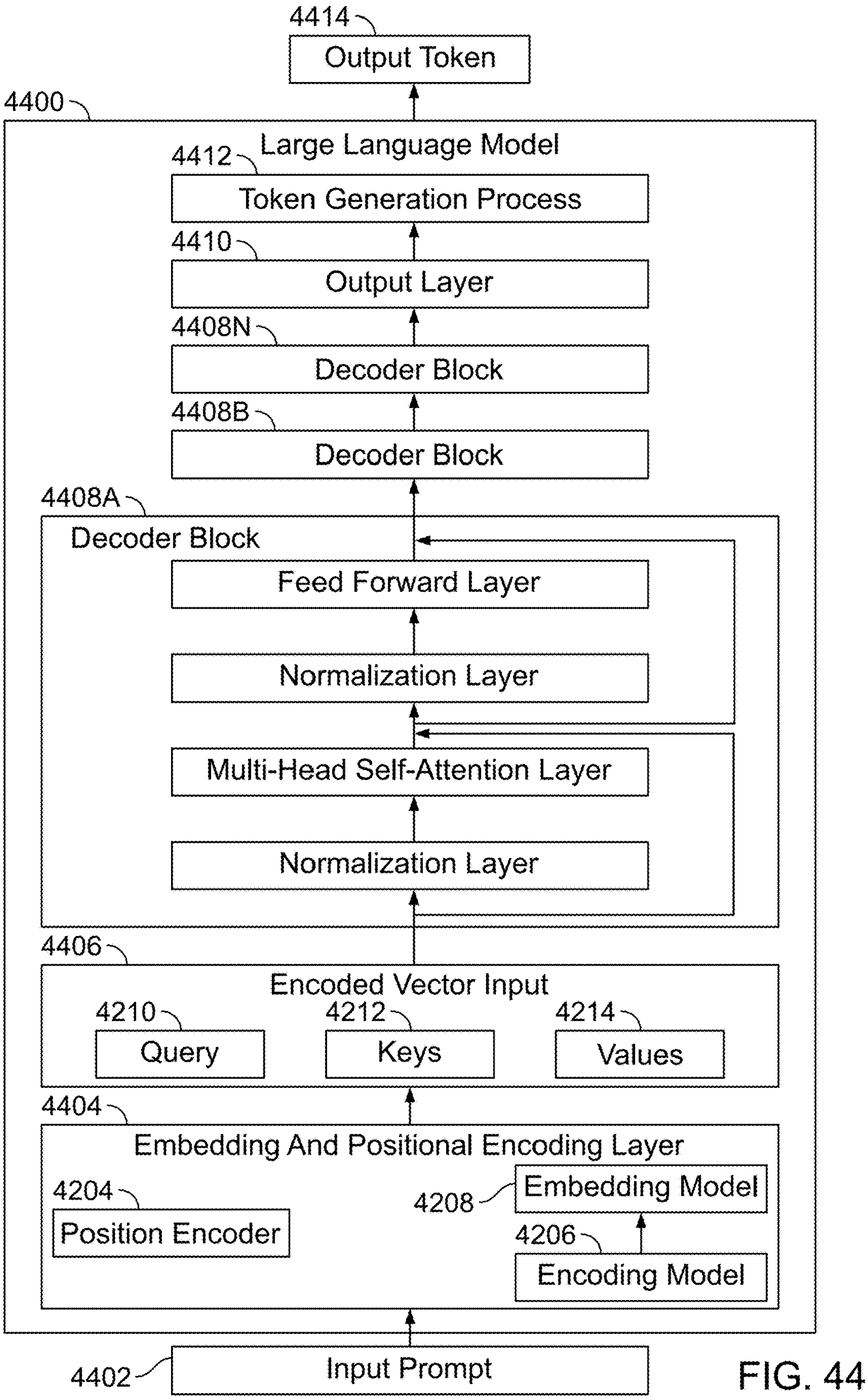
FIG. 44 is a schematic diagram detailing an example large language model, depicted as an example decoder-only architecture according to some example embodiments.

FIG. 44 presents a simplified block diagram of a large language model 4400, depicted as an example decoder-only architecture. In the large language model 4400 of FIG. 44, an input prompt 4402 (e.g., a sequence of text provided by a user or another system) is received and processed by an embedding and positional encoding layer 4404. The embedding component of the embedding and positional encoding layer 4404 maps each token in the input prompt 4402 to a high-dimensional vector representation (similar to the embedding model described above for FIGS. 42 and 43), and the positional encoding component of the embedding and positional encoding layer 4404 adds information about the position of each token within the sequence (as described above for FIGS. 42 and 43). The outputs of the embedding and positional encoding layer 4404 may be structured as a sequence of encoded vectors 4406 that may be provided as input to one or more decoder blocks 4408. Each decoder block 4408 may include a self-attention mechanism (e.g., a multi-head self-attention layer) and a feed-forward neural network layer (which may operate as described for FIG. 43). The decoder blocks 4408 may also include normalization layers and residual connections (as described above for FIG. 43). The decoder blocks 4408 may process the input sequence layer by layer, passing the output of one decoder block 4408 to the input of another decoder block 4408. The output from the final decoder block 4408 may then be passed to an output layer 4410 (e.g., a linear layer followed by a softmax function) that generates a probability distribution over a vocabulary of possible next tokens, as described above. A token generation process 4412 then selects or samples a token based on this distribution, and the selected generated token 4414 can be appended to the input sequence for generating subsequent tokens in an autoregressive fashion (e.g., the output token appended to the input sequence becomes the subsequent input sequence), continuing until a desired output length is reached or a stop-sequence token is generated.

Large language models 4400 may be configured using various configuration parameters and settings that control processing of inputs and generation of outputs. In some cases, a large language model 4400 may be configured to use a particular size of context window (e.g., the maximum sequence length). A context window defines the maximum number of tokens that the model can simultaneously consider when processing an input prompt and generating a response. For example, the positional encoding scheme of the model and attention mechanisms may be configured to handle a specific maximum sequence length of tokens (e.g., by having learned positional embeddings for each position up to this maximum), which defines the context window. As a specific example, if a large language model 4400 has a context window of 4,096 tokens, it can attend to (e.g., process and generate vectors for) the information contained within the most recent 4,096 tokens of the combined input (including the user prompt, any preceding conversational turns, and/or other items in the input sequence) and its own generated output. Information outside the context window may not be directly accessible to the model during a given processing step, which can affect its ability to maintain long-range coherence or recall information from earlier, extensive interactions. It should be noted that current hardware and research supports operation of large language models 4400 with large context windows of up to 1 million tokens, and future large language models 4400 will likely operate with even greater context windows.

A larger context window enables a large language model 4400 to process longer passages of generated text and/or more extended conversational interactions. The large language model 4400 can thus "remember" and refer to information presented earlier in the input even for long input sequences, thereby leading to more contextually relevant and informed responses. Long context windows may be important for complex tasks that require agentic behavior, which may require the large language model 4400 to process and synthesize large amounts of background information, generate "thinking" tokens (as described more below), consider hypotheses, analyze pros and cons of each hypothesis, use tools and evaluate tool results, and/or the like. For example, in a Design-Build-Test-Learn (DBTL) cycle for experimental research, an AI agent based on a large language model 4400 can generate hypotheses or design subsequent experiments, and may need to consider a long history of prior experimental hypotheses, goals, methods, results, and learned insights, which may require a sufficiently large context window.

When the cumulative length of an input sequence (e.g., a conversational history or a lengthy document) exceeds the configured context window size of a large language model 4400, various strategies may be employed by a system interfacing with the large language model 4400, or by the architecture of the large language model 4400, to manage the available context. A simple strategy is truncation, where the oldest tokens in the sequence that extend beyond the context window limit are discarded. However, truncation may result in the loss of potentially relevant earlier information. Another strategy is programmatic summarization, where segments of the input sequence (e.g., earlier parts of a conversation) are periodically summarized (e.g., by the same large language model 4400 in a separate process or by a dedicated summarization model), and this summary is then re-injected into the active context window (e.g., replacing the summarized portion of the token sequence with the summary sequence), thereby shortening the active token sequence to allow additional information to fit within the context window while still preserving a condensed representation of past information.

Alternatively or additionally, some systems may use a sliding context window mechanism to process long sequences in manageable chunks, for example by sequentially processing segments of the long input that fit the native context window of the model, where the window "slides" across the sequence, often with an overlap between consecutive segments to maintain contextual flow. Another technique is retrieval-based context management, where the entirety or portions of a token sequence is stored in an external memory or vector database, and a retrieval mechanism (e.g., as described below for the retrieval component 404 of the RAG system in relation to FIG. 45) is used to select and inject the most relevant segments from the external memory into the context window based on a user prompt or conversational turn. These and other techniques may enable the large language model 4400 to access longer sequences of information and/or more context data that may exceed a native context window capacity, enabling greater coherence and more informed responses based on large sets of context data.

A large language model 4400 (such as the example large language model 4400 shown in FIG. 44) may generate outputs by predicting a probability distribution over possible next tokens (e.g., via the output layer 4410 and token generation process 4412). The large language model 4400 may use various parameters to control which specific token is selected from a distribution. These parameters therefore allow a user or system to control aspects of the output of the large language model 4400, such as its degree of randomness, creativity, or determinism. These parameters may be used to adjust the token generation process 4412 at run time (e.g., during inference). One such control parameter is referred to as "temperature." When a low temperature setting (e.g., a value close to 0, such as 0.1 or 0.2) is used, the token generation process 4412 is more likely to select the top-ranked (e.g., most probable) token from the output distribution generated by the output layer 4410, thereby providing a more deterministic output. In some cases, a low temperature setting may lead to outputs that are more predictable and factual but potentially less creative. Conversely, a higher temperature setting (e.g., a value greater than 0.7, such as 0.8 or 1.0) may cause the large language model 4400 to be more likely to select tokens of lower probability, which may result in more creative, surprising, or exploratory responses. Thus, the choice of temperature may be application or task dependent based on whether precision/predictability or creativity is preferred. The temperature setting therefore controls the amount of randomness used by the token generation process 4412 when it samples from the output distribution.

Other sampling strategies may be used by the token generation process 4412 (e.g., in addition to temperature) to control the token selection process. For example, top-k sampling may be used to restrict the token selection of the large language model 4400 to the k most probable tokens from the output distribution, followed by resampling from the reduced top-k set (which may use temperature to control the resampling). Another technique is top-p sampling (also known as nucleus sampling), where the token generation process 4412 considers the smallest set of tokens with a cumulative probability that exceeds a threshold p and then samples from the reduced set. These and other methods thereby allow users or systems to control the characteristics of text generated by a large language model 4400, for example to optimize for characteristics such as coherence, creativity, and/or adherence to specific constraints, depending on the desired outcome of the task or application.

Interactions between users or automated systems and large language models 4400 may be mediated using textual input sequences known as prompts. The nature of prompts may significantly influence the quality, relevance, and utility of the responses of the large language model 4400. A prompt may include textual input provided to a large language model 4400 to elicit a specific response or to guide its behavior. A prompt can range in complexity from a simple question or a few keywords up to a highly detailed set of instructions, examples, and/or other contextual information. The large language model 4400 processes a prompt (e.g., via its embedding and positional encoding layer 4404 and decoder blocks 4408 as shown in FIG. 44) as input and then autoregressively generates a subsequent sequence of tokens as its output, as described above.

Large language models 4400 may be trained to accept prompts of varying types, and may learn to prioritize or handle different types of prompts in different ways via post-training. Some large language models 4400 are configured to accept a "system prompt" that describes a set of instructions that define a persona, role, overall goal, constraints, style, or other configuration that may be used by the large language model 4400 for generation of each of its responses throughout an interaction or a series of interactions (e.g., a conversation). Thus, the system prompt may describe a context that may reused for a set of subsequent interactions, and the large language model 4400 may be trained (e.g., using fine-tuning, reinforcement learning, etc.) to adhere to the system prompt over several turns of back and forth interaction. By contrast, a user prompt may refer to a specific, individual turn-by-turn prompt that includes an input, question, or instruction provided by the user during an interaction. For example, following the system prompt above, a user may ask a specific question or include a specific instruction. The large language model 4400 may formulate a response to the question/instruction that is based on both the system prompt (e.g., following any rules for responding in the system prompt) as well as the immediate user prompt (which may include the question that the large language model 4400 answers or instruction that the large language model 4400 follows).

The practice of designing, refining, and optimizing prompts to elicit desired and accurate responses from large language models 4400 may be termed "prompt engineering." Effective prompt engineering can enhance the performance of the large language model 4400 on specific tasks without requiring modification of the underlying model parameters (e.g., weights learned during pre-training or fine-tuning). Thus, prompt engineering techniques may be used by human users and/or by automated systems, such as by experimenting with different prompting strategies to generate multiple large language model 4400 outputs for various purposes. Prompt engineering techniques may include providing different wording or levels of detail for questions or instructions, specifying various desired output formats, (e.g., text formatting, desired output length, file formats, use of markup syntax, etc.), using few-shot prompting (e.g., including one or more examples of the task being performed successfully, such as input-output pairs demonstrating an example task completion or response style), employing techniques such as chain-of-thought (CoT) prompting, where the large language model 4400 is instructed to "think step-by-step" or to articulate its reasoning process before arriving at a final answer, and the like. These and other prompt engineering strategies may be used when large language models 4400 act as agents in complex, multi-step workflows, where control over the reasoning and/or output of the large language model 4400 may enhance quality and capability of the agent.

After an initial pre-training where a large language model 4400 is trained using large data sets (which may operate as described for training generative transformer models), one or more post-training techniques may be used to add capabilities to the large language model 4400. Post-training techniques may improve controllability of the large language model 4400, align its behavior more closely with human preferences and intentions, improve performance on certain types of tasks, or otherwise enhance performance in some way. The one or more post-training techniques may include instruction tuning, where a pre-trained large language model 4400 may be fine-tuned on a data set that includes instructions (e.g., explicit commands or questions) and corresponding desired responses. This type of fine-tuning may enable the large language model 4400 to better understand how to respond to various human questions and instructions across a wide range of tasks. Alternatively or additionally, the refinement techniques may include alignment procedures, such as Reinforcement Learning from Human Feedback (RLHF). In an RLHF process, human evaluators assess and provide feedback (e.g., by ranking or rating different model-generated responses to a given prompt) on the outputs of the large language model 4400. The human feedback may be used to train a separate reward model to predict the quality or preferability of a model response. The large language model 4400 itself may then be fine-tuned using reinforcement learning techniques, with the reward model optimizing the large language model 4400 for generating outputs that are more preferable to humans (e.g., because they are more helpful, harmless, coherent, etc.). It should be noted that other reinforcement learning techniques are described in more detail elsewhere herein.

Some large language models 4400 are explicitly trained or fine-tuned to generate a sequence of "reasoning tokens" or "thinking tokens" prior to producing a final response. These models may be called reasoning models or Reasoning Language Models (RLMs). Reasoning models build on insights derived from prompting techniques like chain-of-thought to elicit reasoning from a general-purpose large language model 4400. For example, the generation of tokens representing intermediate cognitive steps may be incorporated directly into a training objective of the large language model 4400 (e.g., using supervised fine-tuning techniques). For example, the training data may include queries or problems paired with answers and also with human-written or automatically generated detailed reasoning examples. The large language model 4400 is thereby configured to use a more structured problem-solving process by being trained to generate intermediate reasoning as part of its output sequence. The explicit generation of thought processes can enhance transparency, allow models to try out various solutions or reasoning paths before responding, think about potential errors prior to responding, etc. Outputting reasoning tokens may therefore improve an ability of the large language model 4400 to solve more complex multi-step problems (e.g., logical, mathematical, or programmatic tasks).

The reasoning performance of large language models 4400 may also be adjusted by configuring test-time compute parameters, which may control an amount of computational resources that are used during inference. For example, a large language model 4400 may be configured to use best-of-N sampling, which involves prompting the same model multiple times to generate multiple (e.g., a configurable number N) candidate reasoning traces or solutions for a given problem. Then, a verifier (which may be a rule-based checker for tasks with easily verifiable answers or another large language model 4400 or other model that is trained to assess solution quality) may be used to rank and select the best output from the candidates. Another technique is self-consistency, which may involve generating multiple candidate outputs (e.g., a configurable number N) and selecting an answer that appears most frequently or through a consensus mechanism. These and other inference-time techniques may be used to improve reasoning by using additional compute to explore more of a solution space.

After the completion of training on a large and general-purpose corpus of text, a large language model 4400 may exhibit generalized reasoning capabilities, such as the ability to apply logic to a problem or scenario and to provide a logical solution or analysis. Due to such generalized reasoning capabilities, such broadly trained large language models 4400 are often referred to as "foundation models" that can be applied to a large variety of tasks and circumstances. Such large language models 4400 can often be applied to a particular problem or scenario in a specialized domain that was not covered in the training of the large language models 4400 (e.g., a niche area of knowledge or science, or a peculiar circumstance), but that nevertheless benefits from the generalized reasoning skills acquired by the large language models 4400 in a variety of generalized domains. In such specialized domains, the large language models 4400 may perform adequately without retraining, but by providing the large language models 4400 with information about the specialized domain in the input prompt 4402 (e.g., in a system prompt or user prompt), by providing supplemental information about the specialized domain as part of retrieval-augmented generation (RAG), and/or by equipping the large language model 4400 with an information retrieval tool that the large language model 4400 can use to retrieve and ingest information about the specialized domain. Alternatively or additionally, the large language model 4400 may be fine-tuned for the specialized domain by continued training on a corpus of documents within the specialized domain, such as research papers, conversations, or examples arising within the specialized domain.

Although the development and improvement of very large-scale large language models 4400 has brought significant advancements in AI capabilities, substantial effort is also being directed to the creation and optimization of smaller, more efficient large language models 4400. These smaller models may be configured to deliver good performance on specific tasks and/or may allow execution in environments with limited computing resources (e.g., on-device applications or other edge computing scenarios that may prioritize low latency, token generation speed, data privacy, and/or other benefits of local execution). Several techniques may enable the development of smaller and more efficient but still capable large language models 4400. For example, knowledge distillation techniques may be used to train a smaller "student" model to mimic the output behavior and/or internal representations of a larger, more capable "teacher" model. Knowledge distillation techniques may involve training the student model using ground truth labels (e.g., the correct/target outputs for given inputs from an original training data set, such as a correct next word in a sequence) while using the output probabilities and/or intermediate activations of the teacher model as additional information for a training loss function, thereby enabling the student model to better learn the reasoning patterns of the teacher model. Alternatively or additionally, quantization techniques may be used to reduce the numerical precision of the parameters of a model in order to decrease a size of the model in memory and/or accelerate computation. Quantization may involve converting floating-point numbers (e.g., 32-bit or 16-bit) for model parameters into lower-precision formats, such as 8-bit integers, thereby reducing the memory footprint of the model (which may allow the use of less RAM for executing the model) and enabling faster arithmetic operations. Alternatively or additionally, pruning techniques may be used to identify and remove less important parameters or connections within a neural network by evaluating the contribution of individual weights or entire structured groups of weights (e.g., neurons or attention heads) to outputs and setting the values of less important weights to zero, thereby "sparsifying" the model to reduce its size and computational complexity. Alternatively or additionally, specialized fine-tuning on domain-specific or task-specific data sets may be used to optimize smaller models for particular tasks.

Large language models 4400 may be accessible via systems that provide chat interfaces or APIs that facilitate interactive, multi-turn conversations between a user (or system) and the large language model 4400. Such a chat system may be used for multi-turn conversations where subsequent responses are based on the most recent user prompt and also on the preceding dialogue (e.g., such that each turn of the conversation is appended to the previous input sequence to maintain a token sequence that covers all or part of the chat conversation). For example, a conversational input sequence may begin with a system prompt that provides context for the processing and output of the large language model 4400, such as a role of the large language model 4400, a context in which user prompts are to be received and evaluated, and/or an expected format or content of the output. The conversational input sequence may also include a first user prompt, which may include or relate to a question, a topic, a request, or the like. The large language model 4400 may receive the conversational input sequence, process the system prompt and the first user prompt, and generate a first response. The first response may be presented to the user and added to the conversational input sequence and presented to the user. The large language model 4400 may then receive from the user a second user prompt, which may be in response to the first response of the large language model 4400, an extension or alteration of the first user prompt, and/or a prompt involving a new question, topic, request, or the like. The large language model 4400 may generate a second response based on the system prompt, the first user prompt, the first response, and the second user prompt. In this manner, the large language model 4400 may engage the user in a series of interactions and may build up the token sequence over time. Chat systems may manage the conversational token sequence for the user or client device, thus removing the need of the user or client to store the token sequence, repeatedly send past prompts and responses (e.g., over a network), manage context windows, and/or the like. In such large language models, the chat system may cache the previous conversation token sequence, append new output of the large language model 4400, and append incoming user prompts to maintain a token sequence. However, it should be noted that a back-and-forth conversation may not require a chat system because a user or client system may handle caching and updating of the token sequence, management of the context window, etc.

A chat interface or API may be used for complex, iterative tasks, including agentic tasks. For example, a large language model 4400 agent may engage in an ongoing dialogue with a user or an automated system, where the user or automated system may iteratively provide more context, such as answers to questions posed by the large language model 4400 agent, additional data such as updated experimental and/or sensor data, additional instructions in response to changing context, and/or the like. The large language model 4400, in turn, may respond to each new prompt provided by the user or automated system, thereby modifying its outputs to take the most recent data into account while maintaining the context of the conversation. Thus, chat systems provide an iterative and stateful interface for collaborative problem-solving or knowledge generation.

Large language models 4400 may be trained to operate on multimodal tokens, meaning it may be trained to understand, process, and/or generate information from multiple types of data formats other than and/or in addition to text. For example, multimodal large language models 4400 may integrate information from and/or produce outputs in modalities such as images, audio, video, structured data, sensor data (e.g., in continuous or discrete formats), or the like, including any of the data described above in connection with transformer models. For example, a multimodal large language model 4400 may be configured to accept an image or other non-textual data as part of its input alongside a textual prompt and/or it may be capable of generating an image or other non-textual data as its output in response to a text prompt. Multimodal capabilities may be added to large language models 4400 using various techniques and/or architecture modifications. As an example, a large language model 4400 designed to process images may incorporate components such as a vision transformer or a convolutional neural network (CNN) that convert an input image into a sequence of embeddings that may be processed by the transformer layers together with the text embeddings. For generating images, a large language model 4400 may output a sequence of tokens that may be interpreted by a separate image generation model (e.g., a diffusion model) to produce a visual output. As another example, for processing audio input (e.g., spoken language, environmental sounds), a system including a large language model 4400 may employ a speech-to-text (STT) component to transcribe the audio into a textual sequence, which may then be provided as input to the large language model 4400 in the same way as other text prompts. Alternatively or additionally, a multimodal large language model 4400 may be configured to directly process audio data using an audio encoder (e.g., a neural network module such as a CNN that is adapted for audio and/or transformer-based audio encoders) that converts raw audio waveforms or their spectral representations (e.g., spectrograms) into a sequence of audio embeddings that can be processed by the main transformer layers of the large language model 4400. For generating audio output (e.g., synthesized speech), a large language model 4400 may generate a textual response that is subsequently converted into audible speech by a separate text-to-speech (TTS) component. Alternatively or additionally, a large language model 4400 may be trained to directly generate representations (e.g., acoustic tokens or parameters) that can be synthesized into speech.

In some multimodal large language models 4400, the different modalities may be unified within the decoder blocks 4408 of the large language model 4400. For example, a multimodal large language model 4400 may convert each modality into a separate sequence of embedding vectors (e.g., one sequence of text token embeddings, a separate sequence of image patch embeddings from a vision encoder, a separate sequence of audio frame embeddings from an audio encoder, etc.). The large language model 4400 may project the different embeddings into a compatible dimensional space (e.g., such that different types of embeddings may be transformed to have the same dimensionality, such as by using a learned linear transformation layer). The separate embedding sequences may then be concatenated and/or interleaved into a single embedding sequence that is fed into the decoder blocks 4408 of the large language model 4400. Within the decoder blocks, the self-attention mechanism may then operate across all types of tokens, allowing the model to learn direct correlations and dependencies between, for example, specific words in a textual prompt and particular regions or features in an accompanying image within the same processing pipeline.

Multimodal capabilities can broaden the scope of tasks a large language model 4400 can address. For example, a user may provide a multimodal large language model 4400 with an image and a textual prompt asking the large language model 4400 to describe or operate based on data in the image, answer specific questions about the image content, identify features or anomalies in the image, or the like. Multimodal capabilities may allow a large language model 4400 agent to, for example, analyze visual, audio, or other data collected by sensors, process spoken instructions or dictations, analyze and operate on continuous data, sequential data, discrete data, and/or any other type of data.

Large language models 4400 may use retrieval augmented generation (RAG) to obtain additional context data from a knowledge base that may be added to an input sequence to enable better responses. For example, the large language model 4400 may use RAG to access knowledge that was not available in the data the large language models 4400 were trained on (e.g., private data, sensor data, experimental data, etc.). The knowledge base may store any type of information that may be useful to the large language model 4400 in formulating responses.

Figure 45:
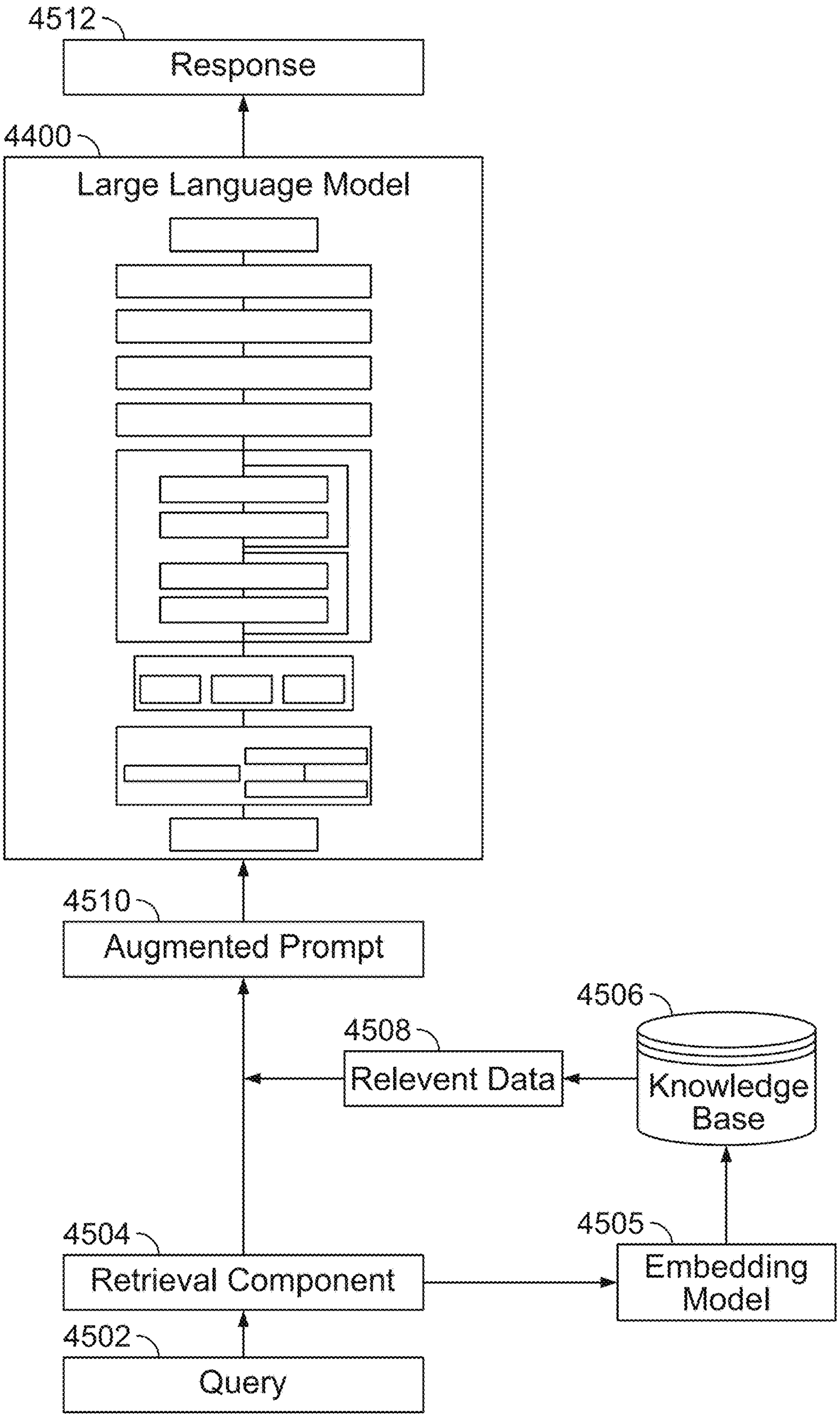
FIG. 45 is a schematic diagram detailing an example system that uses large language models and has a RAG capability according to some example embodiments.

FIG. 45 presents a high-level schematic of an exemplary system 4500 that uses large language models 4400 and has a RAG capability. The RAG system 4500 may receive a query 4502 from a user or an automated system. Prior to submitting the query 4502 as a prompt to the large language model 4400, the RAG system 4500 may first process the query using a retrieval component 4504. The retrieval component 404 may be configured to search an external knowledge base 4506 to find relevant data 4508 (including textual and/or non-textual data) that is relevant to the query 4502 of the user. This retrieval may be performed using various techniques, such as semantic search based on embeddings, keyword matching, hybrid approaches, or other search techniques. Semantic search refers to generating embeddings using the query 4502 and comparing the query embeddings to pre-stored embeddings generated for different chunks of data in the knowledge base 4506. The embeddings for semantic search may be generated using an embedding model 4505, which may be the same embedding model used for the large language model 4400 or a different one. Semantic search may involve the use of cosine similarity, which is a measure of the similarity of the vector corresponding to the query embeddings and the respective vector corresponding to each chunk from the knowledge base using the cosine function, or may use an alternative vector similarity metric. When the query embeddings are similar enough (e.g., above a threshold similarity), the chunk of relevant data 4508 from the knowledge base may be a "hit" for the semantic search and therefore may be retrieved from the knowledge base and added to the query 4502 as additional context. Alternatively or additionally, other techniques such as keyword search may be used to retrieve relevant data 4508.

The one or more items of relevant data 4508 (e.g., one or more relevant data chunks from the knowledge base) may be combined with the original user query 4502 to form an augmented prompt 4510 for the large language model 4400. The system 4500 may then provide the augmented prompt 4510 to the large language model 4400 (which may be an example of the large language model 4400 4400 described in FIG. 44). The large language model 4400 may then generate a response 4512 that takes into account its internal pre-trained knowledge as well as the specific, contextual information from the relevant data 4508.

Retrieval-augmented generation may improve the accuracy or utility of large language models 4400 responses by grounding them in specific information from the knowledge base 4506. RAG may reduce hallucinations because the large language model 4400 is guided by the retrieved data 4508 rather than relying solely on memory from its trained weights. RAG may also enable large language models 4400 to provide responses that are more up-to-date than the data used in their pre-training and that have access to proprietary data, depending on what data is stored in the knowledge base.

The semantic search performed by the retrieval component 4504 may use a vector database, which is a specialized database that provides functions for storing, managing, and/or querying vector embeddings. Vector databases may use indexing algorithms that support approximate nearest neighbor (ANN) search for retrieving the embeddings (and their associated data chunks) that are most similar (e.g., by cosine similarity, Euclidean distance, or another similarity metric) to a given query embedding derived from a query. This structure provides a fast retrieval for RAG systems, thereby reducing latency for finding contextual information and providing it to the large language model 4400.

Agentic AI

Some large language models may be included in and/or used by an AI agent. Whereas some large language models are provided to engage in conversation with a user and/or as interfaces to other machine learning models, other large language models are incorporated in an architecture that enables an AI-based agent to perform tasks, such as organizing data, initiating and executing interactions with other services and devices, and reasoning through a problem in a scenario, "Agentic AI" generally refers to AI techniques in which an AI-based model, or "AI agent," uses a foundational model, such as a large language model, as a logic and reasoning engine in order to accomplish one or more objectives, such as completing tasks, engaging interactions, and/or exploring and presenting solutions to problems.

Many AI agents exhibit a wider range of capabilities than basic large language models 4400, including a large language model 4400 that is incorporated in the AI agent would exhibit if utilized apart from the structure and features of the AI agent. For example, while many large language models 4400 are limited to a turn-taking sequence of interactions with a user, many AI agent may interact with other devices and services, including other machine learning models and AI agents. While many large language models 4400 are limited to generating language output for the user, many AI agents can initiate or execute functional actions, such as organizing data, causing devices to perform actions or movements, and/or executing financial transactions. While many large language models 4400 occupy an idle state while passively awaiting a user prompt of a user and also reenter an idle state after providing a single response to the user, many AI agents can actively perform reasoning, respond to stimuli, and take actions autonomously rather than in direct response to a user prompt. While many large language models 4400 are limited to a single round of processing to generate a response to a user prompt, many AI agents can break down a problem, objective, or request into a series of steps such as a workflow, iteratively perform each step, and provide reflexive feedback at each step to inform the next iteration until the AI agent determines that its own processing is complete. Finally, while many large language models 4400 and machine learning models are designed, trained, and/or configured to perform a single specific task, many AI agents may be assigned to a role, may decide and self-learn how to perform a variety of tasks, and may initiate, execute, and/or critique he execution of workflows to accomplish both familiar tasks and new tasks for emerging problems or novel requests. In these and other ways, agentic AI expands the roles, capabilities, and uses of AI agents beyond those of large language models 4400, including the capabilities of the large language model 4400 that operates as the logic and reasoning engine of the AI agent.

AI Agent Tool Use

Many AI agents are equipped with a set of tools that respectively enable the AI agent to take various actions. An AI agent may receive a description of each tool of a set of tools and their capabilities, initiate the use of a tool to accomplish a particular function at a particular point in a workflow, and receive a result of an instance of tool use for further consideration in its processing of a task, objective, and/or request.

As a first example, an AI agent may be configured (e.g., by examples provided in a system prompt) to generate search queries for an Internet search engine. For example, given a user prompt including a natural-language request for help finding a certain kind of information (e.g., "how do I erase all of the information on my phone?"). The AI agent may process the user prompt and a system prompt that provides pairwise examples of input (e.g., examples of user requests for various kinds of information) and output (e.g., examples of search queries that may be submitted to an Internet search engine to retrieve the information requested by one of the example user requests). The AI agent may submit the user prompt and the system prompt to a large language model 4400 and may receive, as output from the large language model 4400, a search query that is likely to retrieve the requested information through a particular search engine (e.g., "phone 'factory reset' erase data instructions"). The AI agent may present the generated search query to the user, optionally with instructions for submitting the search query to a search engine (e.g., the URL of the search engine and stepwise instructions for submitting the query). Alternatively, the AI agent may further generate a complete URL of a search engine that also encodes the generated search query (e.g., as an encoded set of HTTP GET parameters appended to the URL of the search engine as URL parameters), such that the user may execute the search by clicking on the generated URL or by copy-and-pasting it into the address bar of a web browser. Alternatively, the AI agent may directly submit the generated search query to the search engine and may return, to the user, a web page of search results generated by the search engine. In these ways and in particularly by the last example, the AI agent uses the search engine as a tool for retrieving information for users.

As a second example, an AI agent may aid a user with tasks associated with a file system. For example, the file system may include files identified by filenames, file types, and content, and a hierarchical set of folders that organize the files into logical groups. A user may submit a variety of natural-language related to the file system, such as a request to find files having certain content, a request to copy files from a first folder to a second folder, a request to generate a compressed archive files in a certain location and/or of a certain type, or a request to reorganize a particular portion of the file system based on some user-specified criteria. The AI agent may have access to a file system tool that performs certain actions in the file system, such as listing the contents of a folder or location; creating, viewing, or editing the contents of a file; moving, copying, renaming, or deleting one or more identified files or folders; describing the contents of a file or folder; or generating compressed archives containing a set of identified files or folders. A user may not know how to use the file system tool, but may be able to express requests related to the file system (e.g., "please create a compressed archive of all photos included in my file system," "please find the photos of my trip last week," or "please identify all files related to my project and move them to a new folder called 'My Project'"). The AI agent may be informed of the availability of the file system tool, its capabilities (e.g., the set of actions that it supports), and the manner of using it (e.g., the format of requests that correspond to various actions). For example, the file system tool may include an application programming interface (API) that receives requests in a certain format, and the AI agent may be provided with examples of the format for various actions and the resulting effects on the file system. The examples may be included in a system prompt along with other instructions for using the file system tool (e.g., a list of operating-system-specific files that should not be renamed, moved, or deleted, and a general instruction to record all file system actions in a log file). When presented with a user prompt including a user request that involves the file system, the AI agent may submit the system prompt and the user prompt to a large language model 4400 and may receive, from the large language model 4400, a list of one or more file system actions to perform with the file system tool to fulfill the request of the user. For example, the large language model 4400 may generate a list of API calls, including their names and arguments or parameters, to invoke through the API of the file system tool to perform the task requested by the user. The AI agent may present the list of instructions to the user as an informative guide of how the user may use the file system tool to achieve the request of the user. Alternatively, the AI agent may directly submit each instruction of the list of instructions to the file system tool (e.g., executing a series of calls through an API of the file system tool), thereby directly using the file system tool to execute the request of the user.

As a third example, an AI agent may aid a user with communicating with other individuals, organizations, services, and the like using a communication tool. For example, the communication tool may be capable of generating, sending, and receiving email messages, simple message service (SMS) messages, and messages through a group chat service. An AI agent may be informed of the availability of the communication tool, its capabilities (e.g., the types of communication channels that the tool can use for communication), its limitations (e.g., whether or not the communication tool can send attachments through each type of communication channel), and examples of the manner of performing various kinds of communication (e.g., the format of a request to be submitted to the communication tool to perform a particular type of communication, such as sending an email, sending an SMS message, and/or communicating with other users via the chat service). For example, the AI agent may be provided with a system prompt that lists the details of the communication tool, optionally including examples of invocations that correspond to various natural-language requests. A user may not know how to use each of these communication services, or may not wish to do so directly. Instead, the user may submit communication requests to the AI agent as natural-language expressions (e.g., "please send the project file to my colleagues," "please let my friend know that I am arriving at the theater," or "please read any communication I have not yet read or received"). The AI agent may receive the request from the user and may submit the request and the system prompt to a large language model 4400, and may receive, from the large language model 4400, a list of one or more invocations of the communication tool that can be performed to fulfill the request of the user. The AI agent may automatically initiate each such invocation through the communication tool to complete the request of the user.

Some AI agents may include a tool set with a variety of tools having different capabilities and usable in different circumstances. For example, an AI agent may have access to a set of tools including a web search tool, a file system tool, and a communication tool. A system prompt may indicate the identity, name, capabilities, limitations, and manner of accessing each tool, optionally including examples in which a request of a user may be fulfilled by a particular invocation of a tool with a particular format. Such an AI agent may be capable of fulfilling a variety of requests using each of the available tools, such as a first natural-language request to search the Internet for a particular type of information, a second natural-language request to search the local file system of a device for a certain file, or a third natural-language request to communicate with one or more individuals.

Further, an AI agent having access to a multitude of tools may use the available tools together to fulfill a request of a user. For example, a user may ask the AI agent to send a particular file to an individual, but the user may not know or indicate the manner of contacting the individual. The AI agent may submit the request and the system prompt to the large language model 4400, and may receive, from the large language model 4400, a list of invocations of the various tools (e.g., instructions generated by the large language model 4400 to first use a file system tool to retrieve the identified file from the file system, then use the web search tool to identify contact information for the individual (e.g., retrieving an email address of the individual from a website or social media profile of the individual), and finally use the communication tool to generate and send the identified file to the individual (e.g., generating and sending an email to the retrieved email address of the individual, wherein the generated email includes the retrieved file as an attachment)). The AI agent may show the generated instructions to the user, or may directly execute each of the invocations through the respective tools to fulfill the request of the user.

Various AI agents may interact with tools in different ways, as mediated by the software architecture supporting the large language model 4400 within the AI agent. As a first example, an AI agent may provide, to a large language model 4400, a system prompt that includes descriptions of various tools of a tool set. The system prompt may include the names and functions of tools, the manner of invoking each tool, a manner of operation of each tool, the effects and side-effects of each tool, a result of uses of the tool in various contexts, and/or one or more examples of the use of a tool in a one or more contexts. A user prompt to the large language model 4400 may indicate a particular context (e.g., at a particular step of a workflow), and the large language model 4400 may generate a response that indicates the use of a particular tool of the tool set. For example, if a step of a workflow indicates that a particular device needs some data, the large language model 4400 may indicate that a data transfer tool should be used to transmit the data to the particular device. The AI agent may receive the response of the large language model 4400, extract the portion of the response indicating the use of the data transfer tool, and invoke the data transfer tool as indicated by the large language model 4400. As a second example, an AI agent may provide to the large language model 4400, as part of the system prompt, instructions by which the large language model 4400 can indicate a use of a tool in its response. For example, the system prompt may indicate a format of the response for invoking a tool, such as a format of an XML document or JSON object that, if included in the response of the large language model 4400, causes the AI agent to invoke a particular tool. The format of the XML document or JSON object may indicate, for example, the names of one or more tools to be invoked, one or more parameters to be used in the invocation of a tool (e.g., the names and/or values of parameters of a function call), and/or one or more ways of handling a result of using the tool (e.g., where to store a value or object returned by the tool, or one or more function handlers to invoke when the use of the tool is complete). The large language model 4400 may receive the system prompt and may format its response as an XML document or JSON object that indicates the use of one or more tools. The AI agent may translate the XML document or JSON object into the indicated tool and may invoke the tool as indicated in the XML document or JSON object. As a third example, some large language models 4400 include a direct interface to a tool set including one or more tools that may be invoked for various purposes, and may be trained and/or otherwise informed of the tool set. The AI agent may permit, monitor, manage, and/or use the result of the invocation of various tools by the large language model 4400 through its direct interface to the tool set.

Some AI agents may have access to one or more tools that produce one or more results, such as effects, side-effects, logs, exceptions, returned values such as objects, or the like. For example, a communication tool may receive requests to communicate with other devices and/or users, and each invocation of the communication tool may result in one or more results that indicate the success, failure, duration, bitrate, error, or the like of an attempt to communicate with another device and/or user. In such cases, the AI agent may store, log, process, and/or use the result of the invocation of a tool. In some cases, the AI agent may invoke the large language model 4400 with the result of an invocation. The large language model 4400 may generate a response that indicates an interpretation of the result and/or one or more additional steps to take based on the result. For example, after invoking a communication tool to perform a task as indicated by the large language model 4400, the AI agent may receive an error or exception from the tool indicating that attempt to perform the task failed, and optionally including metadata that indicates one or more reasons for the failure. The AI agent may provide the error or exception to the large language model 4400, which may interpret the error or exception and may provide, as a response, a modified invocation of the communication tool that is likely to avoid the one or more reasons for the failure. The AI agent may perform a second use of the communication tool based on the modified invocation to complete the task.

Figure 46:
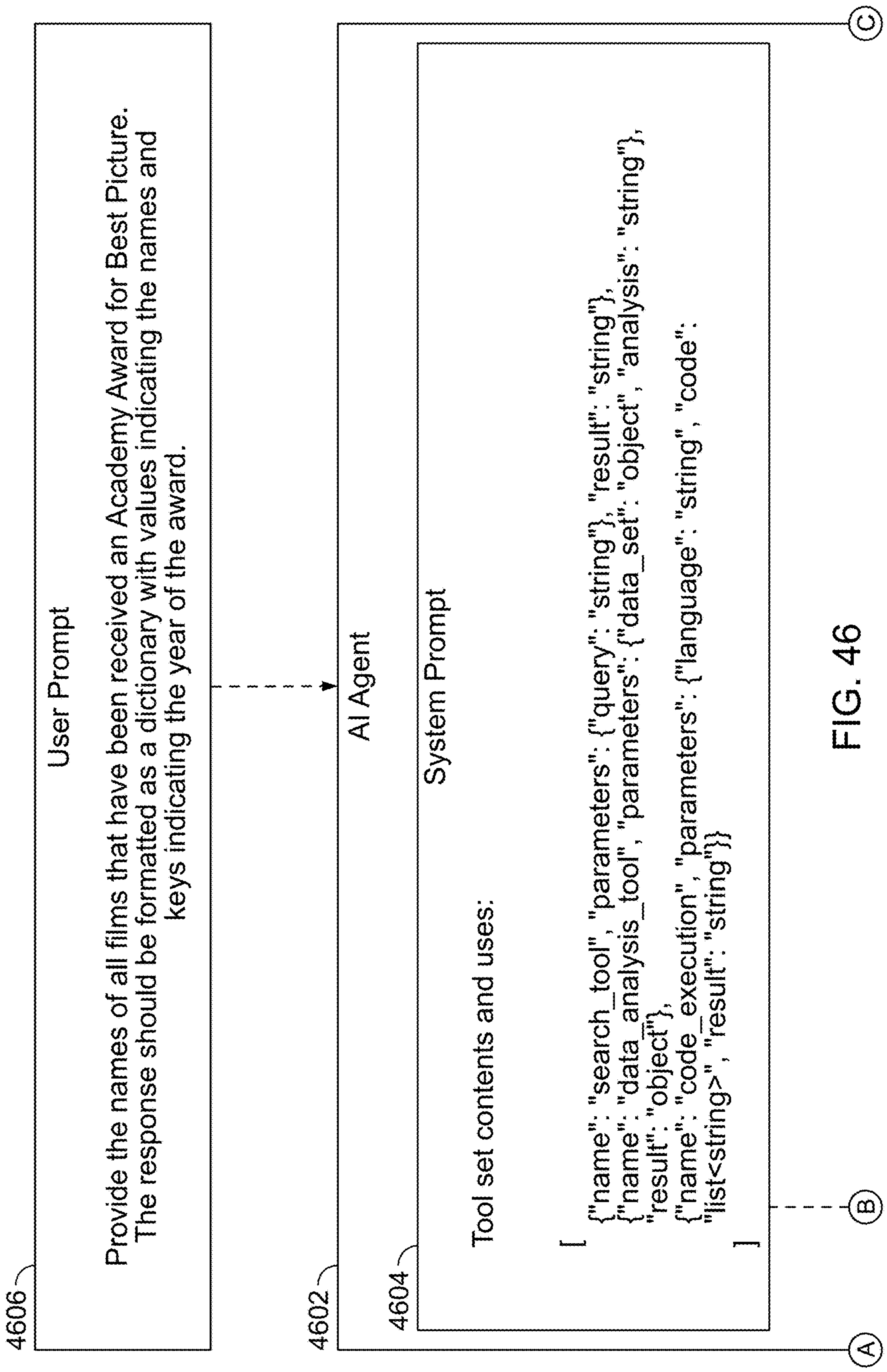
FIG. 46 is a schematic diagram detailing an example of tool use by an example AI agent according to some example embodiments.
Figure 46:
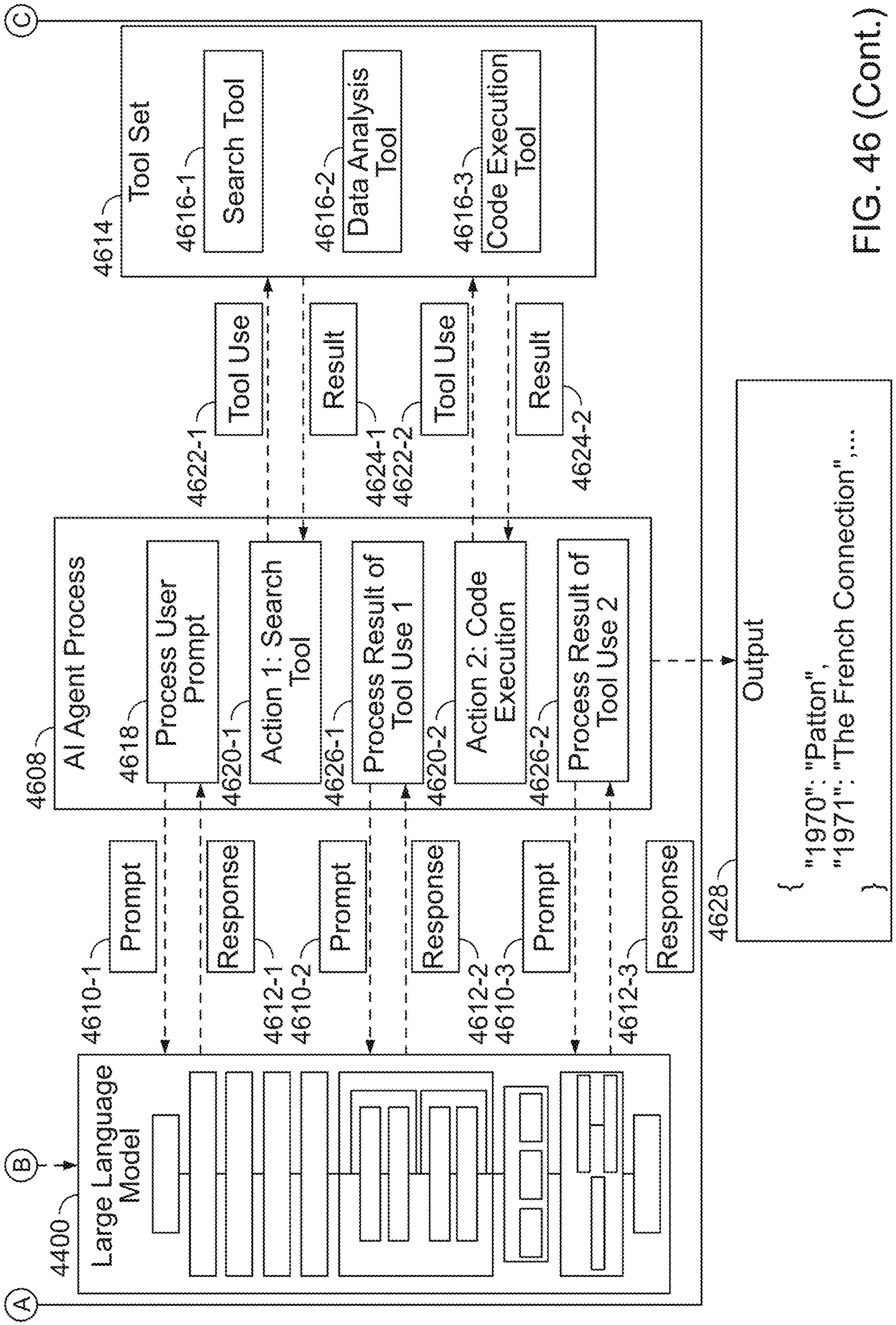

FIG. 46 presents an illustration of tool use by an example AI agent 4602. In the example shown in FIG. 46, an AI agent 4602 includes a large language model 4400. The large language model 4400 may be integrated and/or provided with the AI agent 4602, and/or may be external to the AI agent 4602 but accessible to the AI agent 4602, such as through an application programming interface (API). The AI agent 4602 also includes a tool set 4614 involving a set of tools 4616, including a search tool 4616-1 that can be invoked to perform searches (e.g., via a search engine), a data analysis tool 4616-2 that can be invoked to analyze data (e.g., via a data analysis or statistics library), and a code execution tool 4616-3 that can be invoked to execute code (e.g., a Python script). Respective tools 4616 of the tool set 4614 may be integrated and/or provided with the AI agent 4602, and/or may be external to the AI agent 4602 but accessible to the AI agent 4602, such as through an application programming interface (API). The AI agent 4602 also includes a system prompt 4604 that provides instructions and/or contextual information to guide the processing of the large language model 440 while processing the prompt 4610 and generating a response 4612. In the example of FIG. 46, the system prompt 4604 of the AI agent 4602 informs the large language model 4400 of the tool set 4614, including, for each tool 4616, the name of the tool 4616, the manner of invoking the tool 4616 with a set of parameters, and a format of a result of an invocation of the tool 4616. The system prompt 4604 specifies the details of each tool 4616 in a JSON object that the large language model 4400 may understand and use to invoke each took 4616. The AI agent 4602 invokes the large language model 4400 with prompts 4610 that respectively include the system prompt 4604 and one or more user prompts 4606. For example, the AI agent 4602 may generate each prompt 4610 by combining it with the user prompt 4606, and/or as a list that begins with the system prompt 4604 and then a user prompt 4606. For second-and-alter prompts 4610 in a sequence of prompts 4610 (such as shown in FIG. 46), the prompt 4610 may include an interleaved sequence of previous prompts 4610 and corresponding previously generated responses 4612, and may end with the latest prompt 4610 to be processed by the large language model 4400 to generate a latest response 4612.

The AI agent 4602 receives a user prompt 4606 that includes a request that involves the tool set 4614. For example, the AI agent 4602 may receive a user prompt 4606 including a request for a list of the names of films that have received an Academy Award for Best Picture, and specifying a particular JSON object format for the output 4628 of the AI agent 4602. The AI agent 4602 may process the user prompt 4606 by engaging in an AI agent process 4608 that uses the large language model 4400 and the tool set 4614. First, the AI agent process 4608 performs a step 4618 of processing the user prompt 4606 by providing both the user prompt 4606 and the system prompt 4604 to the large language model 4400 (e.g., as a first prompt 4610-1). The large language model 4400 may first determine that a list of the films requested in the user prompt 4606 is needed, and may generate a first response 4612-1 indicating an action 4620-1 of the search tool 4616-1. Specifically, the large language model 4400 may generate the first response 4612-1 according to the system prompt 4604 by including an invocation of the search tool 4616-1 according to its use as indicated in the system prompt 4604 (e.g.: search_tool (“query”: “films academy award best picture”)). The AI agent process 4608 may receive the first response 4612-1, extract the formatted request to use the search tool 4616-1, and perform an action 4620-1 of executing a tool use 4622-1 of the search tool 4616-1. The search tool 4616-1 may execute the search query (e.g., using a RAG database, an Internet search engine, a file search engine, or the like) and may return a first result 4624-1 of the first tool use 4622-1, such as a string that contains the requested data. The AI agent process 4608 may perform a step 4626-1 of receiving a first result 4624-1 from the search tool 4616-1 and may pass the first result 4624-1 to the large language model 4400 in a second prompt 4610-2. The large language model 4400 may receive the second prompt 4610-2 and determine that the first result 4624-1 contains the requested data, and may be capable of extracting the content. However, the extracted content may not be in the format requested by the user prompt 4606. The large language model 4400 may then determine that the list of the films included in the first result 4624-1 can be properly formatted by processing it with code (e.g., a small Python script that generates dictionaries). The large language model 4400 may generate a second response 4612-2 indicating a tool use 4622-2 of the code execution tool 4616-3. Specifically, the large language model 4400 may generate the second response 4612-2 according to the system prompt 4604 by including an invocation of the code execution tool 4616-3 according to its use as indicated in the system prompt 4604 (e.g.: code_execution(“language”: “python”, “code”: (list of Python instructions that format the list as a dictionary)). The AI agent process 4608 may receive the second response 4612-2, extract the formatted request to use the code execution tool 4616-3, and perform an action 4620-2 of executing a tool use 4622-2 of the code execution tool 4616-3. The code execution tool 4616-3 may receive, from the large language model 4400, the data extracted from the first result 4624-1 and the Python code to execute using the data, and may execute the code and return the formatted dictionary as a second result 4624-2 of the tool use 4622-2. The AI agent process 4608 may perform a step 4626-2 of receiving the second result 4624-2 from the code execution tool 4616-3 and may pass the second result 4624-2 to the large language model 4400 in a third prompt 4610-3. The large language model 4400 may determine that the second result 4624-2 fulfills the request of the user prompt 4606, and may generate a response 4612-3 indicating that the second result 4624-2 can be provided as an outcome 4628 of processing the user prompt 4606. Accordingly, the AI agent 4602 can produce the second result 4624-2 as an outcome 4628 of processing the user prompt 4606. In this manner, the AI agent 4602, driven by the large language model 4400 as a logic engine, can invoke a sequence of tools 4616 of the tool set 4614 described in the system prompt 4604 to fulfill a request indicated in a user prompt 4606.

AI Agent Loops

As previously discussed, large language models 4400, particularly those configured in a chat-style interface, typically operate in a sequential, turn-taking manner, where each user prompt 4606 is fulfilled by iteratively generating the output tokens 4414 for the output sequence 4304. At the end of generating an output sequence 4304 through a single iterative process, the large language model 440 typically enters an idle state and awaits the receipt of a next user prompt 4606. By contrast, AI agents are often configured to fulfill a request by operate in an agent loop, wherein each iteration of the agent loop incrementally advances the fulfillment of the request. Each iteration of the agent loop may involve four steps: a receipt and processing of a prompt, an invocation of a tool based on a response to the prompt, a receipt of a result of the invocation of the tool, and a reflection on the result of the invocation of the tool and the state of the request. At each iteration of the agent loop, the AI agent evaluates the current state of the request in view of the past iterations of the agent loop; determines a next step to be taken toward fulfilling the request; and determines how to proceed at the conclusion of the current iteration of the agent loop. The use of a large language model 4400 to receive the relevant information, logically evaluate the state of the request, and make decisions as to the next step for the current iteration of the agent loop enables the AI agent to work through the request in an incremental, stepwise manner and the capability of logically adapting to unexpected events.

Figure 47:
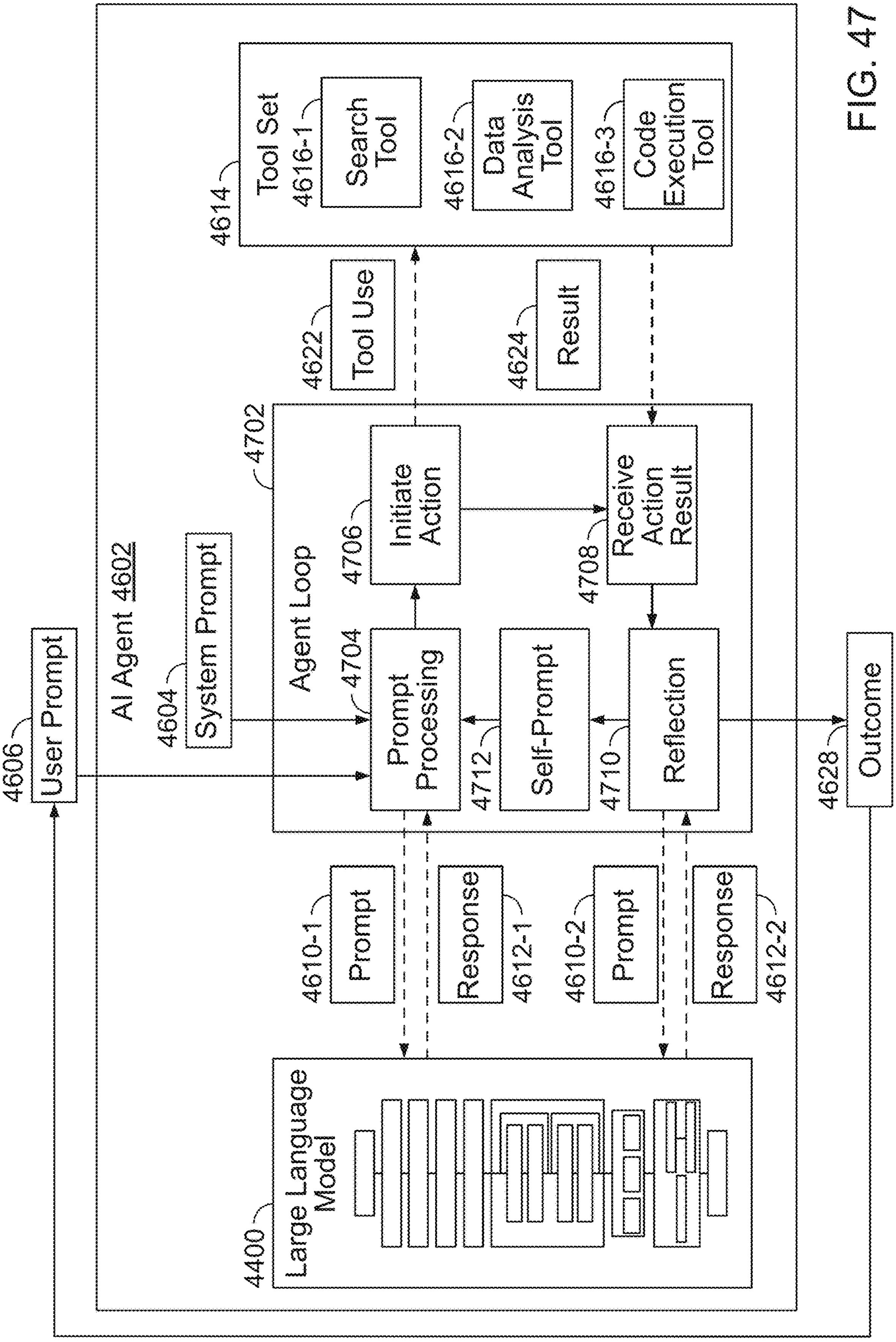
FIG. 47 is a schematic diagram detailing an example AI agent featuring an agent loop according to some example embodiments.

FIG. 47 illustrates an example scenario featuring an AI agent 4602 featuring an agent loop 4702. Like the AI agent 4602 of FIG. 46, the AI agent 4602 of FIG. 47 includes (e.g., incorporates, is provided with, and/or has access to) a large language model 4400, and also includes (e.g., incorporates, is provided with, and/or has access to) a tool set 4614 including a search tool 4616-1, a data analysis tool 4616-2, and a code execution tool 4616-3. The AI agent 4602 of FIG. 47, the AI agent 4602 also includes an agent loop 4702 that can be executed, in an iterative and repeated manner, to fulfill a user prompt 4606. The AI agent 4602 also stores a system prompt 4604 that is provided with any prompt 4610 to the large language model 4400, wherein the system prompt 4604 provides instructions and/or contextual information to guide the processing of the large language model 440 while processing the prompt 4610 and generating a response 4612.

As shown in FIG. 47, the agent loop 4702 includes a cyclic sequence of four stages: a prompt processing stage 4704, an initiate action stage 4706, receive action result stage 4708, and a reflection stage 4710. The AI agent 4602 may receive a user prompt 4606, such as a request to perform a task or answer a question.

In a first instance of the prompt processing stage 4704, the AI agent 4602 may initiate a first iteration of the agent loop 4702 by executing, wherein the user prompt 4606 and the system prompt 4604 are combined to generate a first prompt 4610-1 that is provided to the large language model 4400. The large language model 4400 may generate a first response 4612-1 to the first prompt 4610-1 that includes an indication of at least one action 4620. The action 4620 may include one or more instances of tool use 4622 of one or more tools 4616 of the tool set 4614. The large language model 4400 may specify the actions 4620 involving tool use 4622 in a particular format as instructed by the system prompt 4604 (e.g., similar to invocation of functions in a programming language such as C or Python, wherein each tool use 4622 is specified as a function name and a list of arguments or parameters).

In an initiate action stage 4706, the agent loop 4702 may initiate one or more actions 4620 as indicated in the first response 4612-1 of the large language model 4400, such as one or more instances of tool use 4622 of one or more tools 4616 of the tool set 4614. For example, the AI agent 4602 may synchronously execute one or more functions that are specified in the response 4612, and may await a result 4624 of the function. Alternatively or additionally, the AI agent 4602 may asynchronously execute one or more functions that are specified in the response 4612, and may perform other processing while awaiting a result 4624 of the function.

In a receive action result stage 4708, the agent loop 4702 may receive a result 4624 of an action 4620 executed by the AI agent 4602 as indicated by the first response 4612-1. For example, the agent loop 4702 may receive, from one or more tools 4616, a returned value (e.g., a primitive value or an object); a message describing the execution of the tool use 4622, such as a success or failure value and/or a success or error message; and/or one or more exceptions or errors that may have occurred during the tool use 4622. In some cases, the agent loop 4702 may process the result 4624, such as logging the result 4624, retrying a failed tool use 4622 a number of times, and/or storing, inspecting, reporting on, and/or curating an object included in the result 4624.

In a reflection stage 4710, the agent loop 4702 provides the result 4624 of the one or more actions 4620 to the large language model 4400. For example, the agent loop 4702 may generate a second prompt 4610-2 that includes the first prompt 4610-1, the first response 4612-1, a description of the actions 4620 executed by the AI agent 4602 based on the first response 4612-1, and one or more results 4624 of the respective actions 4620. The large language model 4400 may respond to the second prompt 4610-2 with a second response 4612-2 that reflects on the second prompt 4610-2 and indicates a state of the agent loop 4702. For example, the second response 4612-2 may include a self-prompt 4712 that the AI agent 4602 uses in a second iteration of the agent loop 4702, e.g., as the latest prompt 4610-1 to be evaluated by the large language model 4400 in the second iteration of the agent loop 4702. The self-prompt 4712 may include, for example, an evaluation of the result 4624 of the one or more actions 4620, such as a determination of whether or not each action 4620 succeeded based on an evaluation of the result 4624; a reason for an error or exception occurring during the action 4620 and indicated in the result 4624, or of an unexpected result 4624 in response to an action 4620; and/or an indication of how the action 4620 could be differently performed to improve upon the execution of the action 4620 in the next iteration of the agent loop 4702. The self-prompt 4712 may include at least a portion of the result 4624 (e.g., content extracted from a web page retrieved by the search tool 4616-1; a result of a data analysis performed by the data analysis tool 4616-2; and/or a result of code execution performed by the code execution tool 4616-3) and/or a description of what the next iteration of the agent loop 4702 should do with the at least a portion of the result 4624 (e.g., the next iteration of the agent loop 4702 should format retrieved content as indicated in the system prompt 4604). During the reflection stage 4710, the large language model 4400 may be configured (e.g., by instructions in the system prompt 4604) to determine whether the agent loop 4702 is complete or the agent loop 4702 is incomplete and should continue (e.g., to process a self-prompt 4712 generated by the large language model 4400 for the next iteration of the agent loop 4702). The large language model may indicate such determination in the second response 4612-2. If the second response 4612-2 indicates continuation of the agent loop 4702, the AI agent 4602 may initiate a second iteration of the agent loop 4702 by executing the prompt processing stage 4704 with a new prompt 4610-1 (e.g., by appending the self-prompt 4712 to the system prompt 4604, the user prompt 4707, the first prompt 4610-1, the first response 4612-1, and/or the second prompt 4610-2). If the second response 4612-2 indicates that the agent loop 4702 is complete, the AI agent 4602 may provide an outcome 4628 of the AI agent 4602 in response to processing the user prompt 4606, such as various determinations by the large language model 4440 and/or one or more effects or results of one or more actions 4620 executed by the AI agent 4602 during the processing of the user prompt 4606. In this manner, the iterative execution of the agent loop 4702 may enable a stepwise, incremental processing of the user prompt 4606 by repeated invocation of the large language model 4400.

Some AI agents 4602 may include and/or use agent loops 4702 that are different in some ways than the agent loop 4702 shown in FIG. 47. As a first example, some agent loops 4702 may not feature a tool set 4614, or may feature a different kind of tool set 4614 than the tool set 4614 shown in FIG. 47. For instance, a tool set 4614 may include communications with other devices, processes, services, or other AI models, including other AI agents 4602. A tool set 4614 may include, as one or more tools 4616, one or more invocations of the same AI agent 4602 and/or the large language model 4400, such as sub-loops of the agent loop 4702 that perform more fine-grained processing for a particular iteration of the agent loop 4702 based on a specialized system prompt 4604. A tool set 4614 may include, as one or more tools 4616, interaction with one or more humans, such as a presentation of data and/or visualizations to a user, a presentation of a recommendation and/or authorization for an action 4620 by the user, and/or a request for input or participation by the user. For example, the tool 4616 may cause a question, prompt, message, user interface, or the like to be presented to a human (e.g., a human who submitted the user prompt, a human expert in a particular field, and/or an administrator of the AI agent 4602), and may receive information from the human. In particular, before performing an action 4620 having significant effects (e.g., making changes to a file system, sending a message on behalf of an individual, and/or executing a financial transaction), the tool 4616 may request and receive authorization from the action 4620 from a human, and may perform the action 4620 during the next iteration of the agent loop 4702 if such authorization is received from the human. Such a tool 4616 may enable a collaborative and/or supervised processing of user prompts and execution of actions 4620. As a second example, some agent loops 4702 may include one or more tools 4616 that are executed asynchronously. For instance, an action 4620 may involve starting or initiating a tool use 4622, and upon completion and/or transmission of a request to initiate the tool use 4622, the agent loop 4702 may continue with a next iteration of the agent loop 4702 while the tool use 4622 concurrently occurs. A following iteration of the agent loop 4702 may involve checking on a status and/or progress of a concurrently executing tool use 4622, retrieving a result of a concurrently executed tool use 4622 that has completed, and/or stopping a concurrently executed tool use 4622 in response to an error and/or timeout condition. As a third example, some agent loops 4702 may not include a specific reflection stage 4710 that includes a second prompt 4610-2 processed by the large language model 4400 for each iteration of the agent loop 4702. Rather, the agent loops 4702 may generate a self-prompt 4712 for a next iteration of the agent loop 4702 that includes the result 4624 of the one or more actions 4620 performed during the current iteration of the agent loop 4702. As a fourth example, rather than completion of the agent loop 4702 being determined by the large language model 4400 during a reflection stage 4710, the large language model 4400 may indicate a completion of the agent loop 4702 in its response 4612-1 to a first prompt 4610-1 of the agent loop 4702 during the prompt processing stage 4704. Alternatively or additionally, the AI agent 4602 may determine the completion of the agent loop 4702 as a result 4724 of one or more actions 4620, e.g., by determining that an action 4620 produced a result 4624 that indicates the completion of the agent loop 4702. As another alternative, some AI agents 4602 may run an agent loop 4702 indefinitely, e.g., until receiving a request or instruction from a user, device, process, or AI model to stop the agent loop 4702 and return an outcome 4628. As a fifth example, some agent loops 4702 may provide one or more outcomes 4628 to the user prompt 4606 before the agent loop 4702 is complete, such as partial results, incomplete results, and/or status updates about the ongoing agent loop 4702, such as the progress of the agent loop 4702 in fulfilling a request stated in the user prompt 4606.

Agent loops 4702 may include a variety of techniques that may aid and/or inform the performance of the AI agent 4602. The following description covers a few such techniques that may be included in various AI agents 4602, individually or together with other such techniques.

AI Agent Reasoning Patterns

Some AI agents 4602 may be configured (e.g., by prompt engineering of a system prompt 4604 and/or user prompt 4606, retrieval-augmented generation (RAG) techniques, and/or self-configuration by the use of search tools) to operate according to one or more reasoning patterns. Many such reasoning patterns may be included in various AI agents 4602.

As a first example, an AI agent 4602 may exhibit an inversion-of-control pattern wherein the AI agent solicits information from a source of a request. For example, some AI agents 4602 may be used in an iterative manner, wherein a user submits a series of user prompts 4606 featuring requests and/or questions that are respectively fulfilled by the AI agent 4602. In some cases, the processing of a user prompt 4606 may require the AI agent 4602 to request further information and/or actions from the user who submitted the user prompt 4606. For example, in order to answer a question of the user included in the user prompt 4606 (e.g., "what should I cook for dinner tonight?"), the AI agent 4602 may first generate a series of questions to gather additional information that may inform the processing of the user prompt 4606 (e.g., "what foods do you like? what ingredients are available for preparing food? do you have any dietary restrictions?") The "inversion" of a familiar pattern where a user asks questions and the AI agent 4602 provides responses may enable the AI agent 4602 to solicit information that improves the quality of the outcome 4628 of the original user prompt 4606. As another example, some user prompts 4606 ask the AI agent 4602 to perform a task by receiving user prompts 4606 requesting specific actions 4620 and each iteration of the agent loop 4702 performing an action 4620. However, some user prompts 4606 may include a request for the AI agent 4602 to inform, assist, and/or supervise a human in performing a task. The AI agent 4602 may fulfill the request by causing each iteration of the agent loop 4702 to generate, as an intermediate outcome 4628, an instruction for the human to perform one step of the task, optionally including information about how to perform the step (e.g., informative images and/or videos). Each following user prompt 4606 may include an indication by the human and/or the user of whether the human successfully performed the step of the latest iteration of the agent loop 4702 or whether the human encountered a problem. The AI agent 4602 and the human may therefore engage in an "inversion" of the interaction where the AI agent 4602 performs actions 4620 as requested by the user.

As a second example, an AI agent 4602 may use a question refinement pattern to improve a fulfillment of a user prompt 4606. For example, a particular user prompt 4606 may include a request to perform a task (e.g., "please manage my files"), but the AI agent 4602 may be able to interpret the request in different ways, and/or may not have enough information about the task that the user would like the AI agent 4602 to perform. Instead, the AI agent 4602 may provide, to the user, a list of more specific user prompts 4606 that the user may select to perform variants of the task (e.g., "Would you like me to organize your files into folders by name or subject, organize your files by recency or use, or backup your files to a backup location?") The selection of a refined question or user prompt 4606 by the user may improve the likelihood that the outcome of the agent loop 4702 is consistent with the intent of the user.

As a third example, an AI agent 4602 may use a template pattern to generate output according to an expected template. For example, a system prompt 4604 may specify a format for an outcome 4628 of an execution of the agent loop 4702, such as data to be provided according to a specified schema of an XML document or a JSON object. A system prompt 4604 may indicate a particular order of presenting information in an outcome 4628 for particular types of user prompts 4606 (e.g., "if the user prompt 4606 includes a math story problem, the outcome 4628 should first state an answer to the math story problem, and then provide an explanation of the reasoning of the answer"). By relying on a template patter, the AI agent 4602 may generate outcomes 4628 including output that is more consistent and/or that matches an expectation of the user that submitted each user prompt 4606.

AI Agent Roles

Some AI agents 4602 may be configured (e.g., by prompt engineering of a system prompt 4604 and/or user prompt 4606, retrieval-augmented generation (RAG) techniques, and/or self-configuration by the use of search tools) to embody a particular role while processing a query 4502 or prompt 4610. While an AI agent 4602 without a specified role may evaluate a user prompt through the cognitive lens of a person of average or common knowledge or skill, an AI agent 4602 operating in the context of a specified role may adopt and exhibit the language, customs, experience, and know-how of an individual in the specified role.

For example, in order to perform a specialized task such as generating code, the AI agent 4602 may be requested to occupy a role of an experienced software developer, and to apply its processing based on the knowledge, principles, experience, cognitive skills, and/or habits of an experienced software developer. As a result, the AI agent 4602 may evaluate a user prompt involving the generation of code (e.g., a request to generate code based on particular objectives, features, technologies, uses, or the like) through the cognitive model of an experienced software developer. Accordingly, the AI agent 4602 may analyze the features specified in the user prompt as software requirements, and may follow a logical framework or process used by software developers to design software that conforms to the given set of software requirements.

As another example, given a prompt involving a request relevant to an organization such as a company (e.g., a request by an employee to undertake a particular project), an AI agent 4602 without a role might generally respond to the request with generalized knowledge and public information about the organization. If the AI agent 4602 is instructed to consider the request in the specific role of an experienced information technology (IT) professional for the company, the output of the AI agent 4602 may specifically address the information technology (IT) needs and/or considerations associated with the request (e.g., the allocation of computational resources for the project, the availability of IT-related capabilities of the company that may relate to the project, and/or any cybersecurity risks or considerations associated with the project). If the AI agent 4602 is instructed to consider the request in the specific role of a sales professional for the company, the output of the AI agent 4602 may specifically address the marketing and/or sales needs and/or considerations associated with the request (e.g., the value proposition of the project to the customers and/or clients of the company or the ability of the project to enhance the performance and/or value of commercial features of existing products and/or services). If the AI agent 4602 is instructed to consider the request in the specific role of a legal officer for the company, the output of the AI agent 4602 may specifically address the legal needs and/or considerations associated with the request (e.g., legal risks to the company that may arise in connection with the project and/or legal frameworks that may be established to validate the project and/or protect the company from legal risk associated with the project).

Some AI agents 4602 may assign particular roles to particular iterations of the agent loop 4702. For example, a user prompt 4606 may involve a problem that requires multiple perspectives and/or skills (e.g., a project request within a company that requires evaluation through the perspectives of an IT professional, a sales professional, and a legal officer). The AI agent 4602 may perform respective iterations of the agent loop 4702 in a particular role that corresponds to a purpose, objective, or sub-task of the iteration of the agent loop 4702. For example, at the conclusion of each agent loop 4702, the reflection stage 4710 may involve the determination of a sub-task to be performed by the next iteration of the agent loop 4702, as well as a skill and/or perspective that the AI agent 4602 may need to perform the sub-task. The self-prompt 4712 generated by the large language model 4400 may instruct the next iteration of the agent loop 4702 to perform the next sub-task, and may also indicate a role that the AI agent 4602 is to adopt while performing the next iteration of the agent loop 4702, wherein the role enables the AI agent 4602 to adopt the skills and/or perspectives of the role that are needed for the sub-task. The role associated with one iteration of the agent loop 4702 may differ from the role associated with a next iteration of the agent loop 4702 (e.g., the iterations may involve different roles, or one iteration may involve a role and the other iteration may not involve any role). In this manner, the AI agent 4602 may switch into, out of, and between roles in the performance of sequential iterations of the agent loop 4702.

AI Agent Chain-of-Thought Reasoning

Some AI agents 4602 are configured to perform chain-of-thought reasoning. In chain-of-thought reasoning, when given a user prompt 4606 featuring a complex problem, the AI agent 4602 may avoid attempting a complete analysis of the complex problem and a determination of the outcome 4628 through a single iteration of the large language model 4400 (e.g., a single iteration of an agent loop 4702). Instead, the AI agent 4602 may be configured (e.g., by prompt engineering of the system prompt and/or user prompt, retrieval-augmented generation (RAG) techniques, and/or self-configuration by the use of search tools) to perform a stepwise, incremental analysis of the problem, wherein each of several iterations of the agent loop 4702 incrementally advances the analysis of the problem. Such configuration may be achieved by providing examples of stepwise analyses of given problems, which the AI agent 4602 and large language model 4400 may emulate in its processing of user prompts 4606 that involve similar problems through several iterations of the agent loop 4702.

For example, a user prompt 4606 for an AI agent 4602 may include a complicated logical prompt, such as a math story problem. If the AI agent 4602 is not provided with any cognitive methodology for solving the math story problem, the AI agent 4602 may attempt to process the entire math story problem with the large language model 4400 in one iteration. However, the logic required to analyze the math story problem and generate a correct answer may exceed the logical processing capabilities of the large language model 4400, similar to asking an individual to add a set of numbers in a short time period without the aid of a calculator or writing paper. As a result, the response 4612 of the large language model 4400 may be incorrect, incomplete, or even nonsensical. Instead, the AI agent 4602 may be informed (e.g., by prompt engineering of the system prompt and/or user prompt, retrieval-augmented generation (RAG) techniques, and/or self-configuration by the use of search tools) to follow a particular stepwise methodology when solving problems that are similar to the math story problem.

Instead, a system prompt 4604 for the AI agent 4602 may include one or more examples of prototypical math story problems and the specific logical steps that can be performed to break down each math story problem to generate a solution. For instance, the examples provided by the system prompt 4604 may include the following: "John has twice as many apples as Jane. If John gives half of his apples to Jane, how many apples does Jane now have relative to John?—Answer: John has twice as many apples as Jane. Therefore, half of John's apples equals the number of apples that Jane currently has. If John gives half of his apples to Jane, John would have the same number of apples that Jane has now, and Jane would have twice as many applies as Jane has now. Thus, Jane would then have twice as many apples as John." If the system prompt 4604 provided to the AI agent 4602 includes several such examples of stepwise or "chain-of-thought" reasoning, the large language model 4400 of the AI agent 4602 may perform each iteration of the agent loop 4702 to perform one step in the demonstrated chain-of-thought reasoning.

An AI agent 4602 may apply such chain-of-thought reasoning in the processing of user prompts 4606. For example, a user prompt 4606 may include a new math story problem (e.g.: "John was six years old when Jane was two years old. If Jane is now ten years old, how old will John be three years from now?") Even if the details of the math story problem of the user prompt 4606 does not closely resemble the details of the example math story problems included in the configuration of the AI agent 4602 (e.g., chain-of-thought examples given in the system prompt 4604), the AI agent 4602 may use a similar stepwise manner as the examples provided in the system prompt 4604 while analyze the new math story problem. During a first iteration of the agent loop 4702, the large language model 4400 may analyze the first sentence and generate a first determination that John is (and will always be) four years older than Jane. This first determination may be included in the response 4612 of the language model 4400, which may be serially included in the prompts 4610 provided to the large language model 4400 for each following iteration of the agent loop 4702. During a second iteration of the agent loop 4702, the large language model 4400 may generate a second determination that if Jane is now ten years old, and if John is four years older than Jane, then John is now fourteen years old. This second determination may also be included in the response 4612 of the language model 4400, which may be serially included in the prompts 4610 provided to the large language model 4400 for each following iteration of the agent loop 4702. During a third iteration of the agent loop 4702, the large language model 4400 may generate a third determination that if John is now fourteen years old, then in three years, John will be seventeen years old. The large language model 4400 may also determine that this third determination may be provided as the answer to the math story problem included in the user prompt 4606. As a result, the response 4612 of the large language model 4400 may indicate the third determination should be provided as the outcome 4628 of the AI agent 4602 in response to the user prompt 4606. The agent loop 4702 may therefore provide the third determination (e.g., "in three years. John will be seventeen years old") as the outcome 4628 of the AI agent 4602 in response to the user prompt 4606. Optionally, the agent loop 4702 may also include, in the outcome 4628, a description of the stepwise process by which the AI agent 4602 generated the third determination and/or the intermediate determinations by the AI agent 4602 for the first and intermediate iterations of the agent loop 4702. In this manner, the AI agent 4602 may be configured to perform chain-of-thought reasoning to analyze user prompts 4606 in accordance with the iterative nature of the agent loop 4702.

AI Agent Self-Critique

In many scenarios, large language models 4400 may process a user prompt 4606 and may initiate actions 4620 and/or generate outcomes 4628 based on certain express, implied, and/or determined logical deductions, facts, or the like. As a first example, a user prompt 4606 may request information about a topic (e.g., the names and years of films that were awarded an Academy Award for Best Picture), and the outcome 4628 of the AI agent 4602 may include statements of the names and years of such films. As a second example, a user prompt 4606 may state a logical problem, such as a math story problem, and the outcome 4628 of the AI agent 4602 may include an answer and/or explanation of the math story problem. As a third example, a user prompt 4606 may assert certain facts in the context of a question (e.g., a request for geographic information about Paris as the capital of Spain), and the outcome 4628 of the AI agent 4602 may echo the asserted facts in its response to the question. As a fourth example, a user prompt 4606 may request the completion of a certain task, and the AI agent 4602 may determine and/or rely on a number of contextual facts and logical principles in the invocation of actions 4620 and tools 4616 to complete the task.

However, many large language models 4400 have exhibited a trait of "hallucination," or of fabricating facts, logical principles, or the like during the processing of a user prompt 4606 and the generation of an outcome 4628. As a first example, while processing a user prompt 4606 that requests information about a topic (e.g., the names and years of films that were awarded an Academy Award for Best Picture), the AI agent 4602 may fabricate or "hallucinate" the names of films that do not exist and/or that were not awarded an Academy Award for Best Picture, and/or may misstate the year of such an award. As a second example, while processing a user prompt 4606 that states a logical problem, such as a math story problem, the AI agent 4602 may commit errors, such as intermediate determinations that are mathematically erroneous, internally inconsistent, inaccurate facts from the math story problem, or logically unsupported. Such errors may or may not be explicitly stated and/or apparent in the outcome 4628. As a third example, while processing a user prompt 4606 that asserts an incorrect fact in the context of a question (e.g., a request for geographic information about Paris as the capital of Spain), the AI agent 4602 may fail to detect the error, may echo the error in its response to the question, and/or may fabricate additional fictitious statements in support of the error. As a fourth example, while processing a user prompt 4606 that requests the completion of a certain task, the AI agent 4602 may use incorrect contextual facts and logical principles in the invocation of actions 4620 and tools 4616 (e.g., reporting an action 4620 as having been successfully completed despite the associated tool 4616 indicating an error). As one well-known example of "hallucination," when asked to indicate the occurrences of the letter "R" in the word "strawberry," some large language models 4400 incorrectly report two such occurrences, and may even maintain and support the incorrect fact with evidently incorrect explanations. As a further problem, such "hallucinations" may occur only intermittently and/or transiently due to the stochastic nature of the transformer models 4302 included in some large language models 4400.

In order to reduce the problem of hallucination, an AI agent 4602 may be configured to perform (e.g., as one or more iterations of the agent loop 4702) a self-critique process, wherein the AI agent 4602 identifies, investigates, and verifies or corrects certain facts, determinations, and/or logical consistency in and among the steps of its previous processing (e.g., previous iterations of the agent loop 4702).

As a first example, before processing a user prompt 4606 that asserts certain facts, the AI agent 4602 may spend one or more iterations of the agent loop 4702 verifying the accuracy of the provided facts (e.g., using a search tool 4616 to query a data source, such as a RAG database or an Internet search engine, to verify the facts). If any facts provided in the user prompt 4606 are determined to be incorrect, the AI agent 4602 may generate an outcome 4628 that notes the incorrect provided fact and, optionally, explains the basis of the determination of the error (e.g., citing a reliable information source that corrects the fact).

As a second example, after executing a tool 4616 and receiving a result 4624, the AI agent 4602 may perform one or more iterations of the agent loop 4702 to inspect and verify the content of the result 4624 provided by the tool 4616 and the interpretation of the result 4624 by the AI agent 4602. For instance, if a first iteration of the agent loop 4702 executes a search tool 4616 and receives a result 4624 that includes information retrieved from a data source (such as the Internet), a second iteration of the agent loop 4702 may compare the received information with other information sources (e.g., to determine whether information extracted from the result 4624 is incorrect, ambiguous, or incorrectly interpreted). If the information extracted from the result 4624 is determined to be inconsistent with other information available to the AI agent 4602 (e.g., if a result 4624 indicates the name of a film reported as having been received the Academy Award in a particular year, but another information source accessible to the AI agent 4602 indicates a different film as having received the award in the given year and/or raises doubt on the existence of the identified film), the AI agent 4602 may spend additional iterations of the agent loop 4702 retrieving and evaluating additional information from other sources to correct the error before indicating a corresponding fact in the outcome 4628 of the processing.

As a third example, if an iteration of the agent loop 4702 results in a determination that may be relied upon for following iterations of the agent loop 4702 and/or may be included in the outcome 4628, the AI agent 4602 may spend one or more iterations of the agent loop 4702 verifying the determination (e.g., comparing it with information in the user prompt 4606, the system prompt 4604, and/or other intermediate determinations by the agent loop 4702). Such verifying iterations of the agent loop 4702 or "sanity checks" may enable the AI agent 4602 to detect one or more factual and/or logical errors in the determination, such as contradictions, internal inconsistencies, or implications of the determination that seem implausible or counterintuitive. In response to such detection, the AI agent 4602 may use one or more additional iterations of the agent loop 4702 to investigate and/or correct the factual and/or logical error (e.g., repeating previous iterations of the agent loop 4702 with different prompts 4610 that may reduce causes of ambiguity, include supplemental information, and/or provide additional instructions to the large language model 4400). Alternatively or additionally, the AI agent 4602 may include, in the outcome 4628, a description of the factual and/or logical error, and a basis for the detection of the factual and/or logical error. Such an outcome 4628 may enable a user to provide an updated user prompt 4606 that can be processed by the AI agent 4602 without a recurrence of the factual and/or logical error.

In these and other cases, the AI agent 4602 may exhibit greater performance (e.g., more reliable, consistent, and error-free outcomes 4628 of processing various user prompts 4606) due to the configuration of the AI agent 4602 to include one or more self-critique iterations of the agent loop 4702. Such configurations may be achieved, e.g., through chain-of-thought system prompts 4604 that include, in its examples of chain-of-thought reasoning, one or more self-critique steps. Such configurations may be achieved, e.g., through system prompting 4604 that explicitly instructs the AI agent 4602 to perform self-critique iterations of the agent loop 4702 (e.g., an instruction to verify and/or correct each fact included in an outcome 4628 before outputting the outcome 4628 in response to the user prompt 4606). Such configurations may be achieved, e.g., through internal configuration of the AI agent 4602 (e.g., one or more postprocessing steps provided at the conclusion of the agent loop 4702 to verify and/or correct the contents of the outcome 4628 before outputting the outcome 4628 in response to the user prompt 4606).

AI Agent Workflows

As discussed in relation to FIG. 47, an AI agent 4602 may perform a sequence of iterations of the agent loop 4702, wherein each iteration concludes with a reflection stage 4710 during which the large language model 4400 determines a next step in the agent loop 4702. That is, in the example of FIG. 47, the AI agent 4602 does not perform iterations of the agent loop 4702 according to pre-planning or organization, but, rather, determines the context of its next iteration of the agent loop 4702 at the conclusion of each preceding iteration of the agent loop 4702. That is, the execution of the agent loop 4702 in such AI agents 4602 may involve an unplanned or ad-hoc sequence of iterations of the agent loop 4702. For example, in a chain-of-thought reasoning model, each iteration of the agent loop 4702 may conclude with a reflection stage 4710 in which the AI agent 4602 compares its progress in processing the use prompt 4606 with the stepwise processing demonstrated in the chain-of-thought examples in a system prompt 4604, determines a next reasoning step that is analogous to the stepwise reasoning demonstrated in the chain-of-thought examples in a system prompt 4604, and generate a self-prompt 4712 that causes the next iteration of the agent loop 4702 to perform the identified next reasoning step.

Other AI agents 4602 may be differently configured to pre-plan one or more iterations of the agent loop 4702. In particular, the AI agent 4602 may operate according to a workflow that indicates a stepwise process for processing the user prompt 4606 and generating an outcome 4628. In contrast with the unplanned, ad-hoc examples, an AI agent 4602 that follows a workflow may perform a proscriptive, pre-planned stepwise methodology for processing the user prompt 4606, and may select and perform iterations of the agent loop 4702 according to the stepwise instructions of the workflow.

In some AI agents 4602, a workflow may be provided to the AI agent 4602. As first example, the workflow for a particular task may be indicated in the system prompt 4604, the user prompt 4606, and/or the operating instructions (e.g., configuration and/or programming) of the AI agent 4602. As a second example, an AI agent 4602 may discover and/or retrieve a workflow for processing a user prompt 4606. For example, while processing a user prompt 4606 involving an unfamiliar and/or novel type of problem or request (e.g., an engineering task that involves a reverse kinematics analysis), a first iteration of the agent loop 4702 may use a search tool 4616-1 to search for a workflow for processing such types of problems or requests (e.g., a workflow for performing reverse kinematics analyses). As a third example, the AI agent 4602 may generate its own workflow for processing a user prompt 4606. For example, if the AI agent 4602 receives a system prompt 4604 that includes several chain-of-thought examples, a first iteration of the agent loop 4702 may determine a workflow as a set of steps for reasoning through the problem provided in the user prompt 4606, wherein the workflow resembles the stepwise reasoning provided in the examples of the system prompt. In some such AI agents 4602, the system prompt 4604 may indicate the workflow associated with each chain-of-thought example, and/or may instruct the AI agent 4602 to use the first iteration of the agent loop 4702 to generate a workflow to organize the following iterations of the agent loop 4702. In these and other cases, the AI agent 4602 may organize the iterations of the agent loop 4702 based on the given workflow. For example, during the reflection stage 4710, the large language model 4400 may determine a current step of the given workflow and may generate a self-prompt 4712 that directs the next agent loop 4702 to perform a next step of the given workflow. The AI agent 4602 may include, in the outcome 4628, a description of the performed workflow and/or a description of the performance of each step of the performed workflow (e.g., one or more actions 4620, tools 4616, results 4624, and/or intermediate determinations associated with one or more steps of the performed workflow).

Some AI agents 4602 may follow a received, discovered, and/or generated workflow without deviation in the processing of a user prompt 4606. Alternatively, an AI agent 4602 may dynamically adjust a workflow during processing of the workflow during or after one or more iterations of the agent loop 4702. As a first example, if the AI agent 4602 determines that a step of the workflow is unnecessary (e.g., a workflow step of sorting data that is already sorted), the AI agent 4602 may skip the step of the workflow and may refrain from spending one or more iterations of the agent loop 4702 on the step of the workflow. As a second example, if the AI agent 4602 encounters an unexpected occurrence during the processing of a step of the workflow (e.g., performing an action 4620 with a tool 4616 and receiving a result 4624 of the action 4620 that includes an exception, an error, or an unexpected result such as an unexpected type of data), the AI agent 4602 may alter the workflow to address the unexpected occurrence (e.g., repeating the step of the workflow in one or more additional iterations of the agent loop 4702 until a cause of the unexpected occurrence is addressed). As a third example, if the AI agent 4602 encounters an issue during the processing of a workflow (e.g., an intermediate determination that is internally inconsistent with an earlier determination, the system prompt 4604, the user prompt 4606, or the like), the AI agent 4602 may insert additional steps into the workflow, reverse execution and return to an earlier point in the workflow where the issue may have originated, and/or provide an outcome 4628 indicating the issue instead of completing the workflow. As a fourth example, if the AI agent 4602 determines that a first workflow is not suitable for processing a user prompt 4606 (e.g., if a request included in the user prompt 4606 is impossible, incompatible with the tool set 4614 accessible to the AI agent 4602, and/or cannot be adequately fulfilled by the current workflow), the AI agent 4602 may request, receive, discover, and/or generate a substitute workflow for the user prompt 4606. The substitute workflow may completely replace the first workflow, the AI agent 4602 may start over with the substitute workflow. Alternatively, the substitute workflow may replace the first workflow from a current workflow step on, and the AI agent 4602 may divert its processing of the user prompt 4606 based on the substitute workflow. The AI agent 4602 may include, in the outcome 4628, an indication of the dynamic adjustment of the workflow and/or a description of the adjustments made to the workflow during processing.

Some AI agents 4602 may associate one or more roles with respective steps of a workflow. For example, a workflow may involve a first step to be performed without any particular role, a second step to be performed in a first role, and a third step to be performed in a second role. For example, the role of each step may be indicated in a workflow provided by the system prompt 4604 and/or user prompt 4606, may be included in a workflow discovered by the use of tools 4616, and/or may be determined by the AI agent 4602 during an initial review of the workflow. At the conclusion of each iteration of the agent loop 4702, the AI agent 4602 may determine a step of the workflow that is associated with the next iteration of the agent loop 4702 and whether any role is associated with the step of the workflow. The AI agent 4602 may generate a self-prompt 4712 that instructs the next iteration of the agent loop 4702 to perform the step of the workflow in the role associated with the step of the workflow.

Some AI agents may use a plurality of possible workflows to process a user prompt 4606. For example, in a "tree-of-thought" architecture, an AI agent 4602 may generate a group of possible workflows by which a user prompt 4606 may be fulfilled. Given a set of candidate workflows, one or more iterations of the agent loop 4702 may select one or more of the candidate workflows for exploration during the same and/or future iterations of the agent loop 4702. For instance, given a request for a solution to a problem, the AI agent 4602 could invoke a search tool 4616-1 to search for informative answers to similar problems; a data analysis tool 4616-2 to extract details of the problem that may inform the determination of a solution; and/or a code execution tool 4616-3 to apply one or more programming libraries, automation techniques, or the like to generate an automated solution to the problem. During a first iteration of the agent loop 4702, the AI agent 4602 may identify the set of possible workflows and may choose one (e.g., the search tool 4616-1) as a first attempt to fulfill the user prompt 4606. The AI agent 4602 may spend one or more iterations of the agent loop 4702 on the first selected workflow (e.g., invoking the search tool 4616-1, receiving its result 4624, and extracting and further processing information contained in the result 4624). If the first selected workflow does not yield an adequate outcome 4628, a following iteration of the agent loop 4702 may cause the AI agent 4602 to suspend execution of the first selected workflow and to begin execution of a second selected workflow (e.g., invoking the data analysis stool 4616-2). Some of the candidate workflows may share a common starting point (e.g., using the search tool 4616-1 to receive information) and may then diverge further along the workflow (e.g., different techniques for processing and/or considering the result 4624 of the invocation of the search tool 4616-1). Some AI agents 4602 may select and execute the candidate workflows in a breadth-first manner (e.g., iteratively spending on or more agent loops 4702 on each candidate workflow until one of the candidate workflows is complete and returns an acceptable outcome 4628). Some AI agents 4602 may select and execute the candidate workflows in a depth-first manner (e.g., fully exploring a first candidate workflow until successful completion or failure, and then determining whether to provide the outcome 4628 of the first candidate workflow or to initiate exploration of a second candidate workflow). Some AI agents 4602 may dynamically adjust the candidate workflows, such as bifurcating a candidate workflow into two or more candidate workflows (e.g., receiving a result of a search tool 4616-1 and generating a set of offshoot candidate workflows with different techniques for analyzing a result 4624 of the search tool 4616-1), merging two or more partially explored candidate workflows (e.g., merging the result 4624 of an invocation of a search tool 4616-1 during a first candidate workflow and the result 4624 of an invocation of a data analysis tool 4616-2 during a second candidate workflow), or the like. The AI agent 4602 may include, in the outcome 4628, an indication of the selected candidate workflows that the AI agent 4602 explored, a reasoning for such selection, a description of the execution of the selected candidate workflows, and/or the outcomes of the executed candidate workflows.

Reinforcement Learning

Some artificial neural networks 4002 may be applied to problems that are difficult to evaluate by techniques such as backpropagation 4116 and supervised learning, wherein a training data set 4106 associates respective inputs 4004 with one or more expected outputs 4022. For example, an artificial neural network 4002 may be trained to play chess, but the vast number of combination of states of a chess board (conservatively estimated as 10120 possible states, according to a calculation known as the Shannon number) prevents training with even a minimally comprehensive training data set 4106. Further, the strategic nature of chess prevents the association of particular states of the board (as inputs 4004) with a specific evaluation or recommendation of an action to be taken in that state (as output 4022). Similar problems may arise for various problems where the artificial neural network 4002 is provided to interact with an environment that may have a large and possibly indeterminate number of states, and may take various actions in such states that may have various intended consequences and side-effects. Such scenarios include simulations, games, and complex domains such as robotic movement and autonomous vehicle navigation.

In such scenarios, techniques in the field of reinforcement learning may be used to train an artificial neural network 4002 to select actions. More specifically, the artificial neural network 4002 may be configured to select actions that are likely to advance, improve, or otherwise serve an objective, such as achieving certain outcomes of a simulation, improving a circumstance of a player in a game, or developing a solution to a problem in a complex domain such as robotic movement or autonomous vehicle navigation. The artificial neural network 4002 may be provided a state of an environment, a set of actions that may be taken in the state of the environment, and an objective function to be pursued or optimized (e.g., a goal to be achieved and/or a measurement of the environment to be maximized by the actions of the artificial neural network 4002). The artificial neural network 4002 may select, among the available actions, one or more actions to be executed to pursue or optimize the objective function. The selected action may be executed, the environment may be adjusted and/or reevaluated in response to the action, and the objective function may be reassessed to determine how the selected action affected the objective function (e.g., whether the state of the environment improved, worsened, or did not change the objective function). As a reinforcement learning step, the parameters 4102 of the artificial neural network 4002 that affect its selection of actions may be altered to increase the likelihood of selecting actions that improve the objective function and to decrease the likelihood of selecting actions that do not improve the objective function. In this manner, reinforcement learning may provide a less direct and more computationally expensive training process than backpropagation 4116, but may enable the development of an artificial neural network 4002 for more complex scenarios to which backpropagation 4116 cannot be effectively applied.

More specifically, reinforcement learning causes an artificial neural network 4002 to learn a policy that governs the selection of actions for respective states of an environment. The learned policy causes the artificial neural network 4002 to determine a probability of taking each action in view of a given state of an environment. During training, the parameters 4102 of the artificial neural network 4002 that determine the probabilities of the respective actions of the policy may be adjusted so that the probabilities of actions that would or might improve the objective function in the given state of an environment are increased, and so that the probabilities of actions that would not or might not improve the objective function in the given state of an environment are decreased. During each iteration of training, a given state of the environment may cause the artificial neural network 4002 to generate the probabilities of the available actions. The training process may choose any (including several) of the available actions for evaluation. The highest-probability action may indicate the action that the policy determines to have the highest probability of improving the objective function, and the training process may explore this action to refine the policy based on the ongoing and ultimate outcomes of the environment due to the action. However, lower-probability actions may indicate previously untested actions in view of the current environment, and such untested actions may yield unexpected results, including an unexpectedly large improvement in the objective function. For example, given a particular state of a chess board, an artificial neural network may apply a policy to determine a first chess move that is likely to increase the objective function (e.g., improving the strategic condition of the chess board in favor of the artificial neural network). The training may choose to explore the first chess move to determine various outcomes of executing the selected action (e.g., the first chess move). The training may update the probability of choosing the first chess move in the given state of the chess board according to the explored outcomes of the first chess move. However, a second chess move that has not yet been fully evaluated might create additional options for future states of the chess board, which may yield strategic advances that outperform the outcomes of the first chess move. On the other hand, the second chess move might cause unforeseen consequences for the strategic position of the artificial neural network 4002, such as a chess "blunder" that may only be apparent several moves later. The training process may choose to explore the second chess move to evaluate the outcomes. The training may update the probability of choosing the second chess move in the given state of the chess board according to the explored outcomes of the second chess move. In this manner, the reinforcement learning process trains the artificial neural network 4002 to develop a policy based on both continued exploration and refinement of previously evaluated actions that are likely to advance the objective function and novel exploration of previously unevaluated actions that might yield even better options for advancing the objective function.

Figure 48:
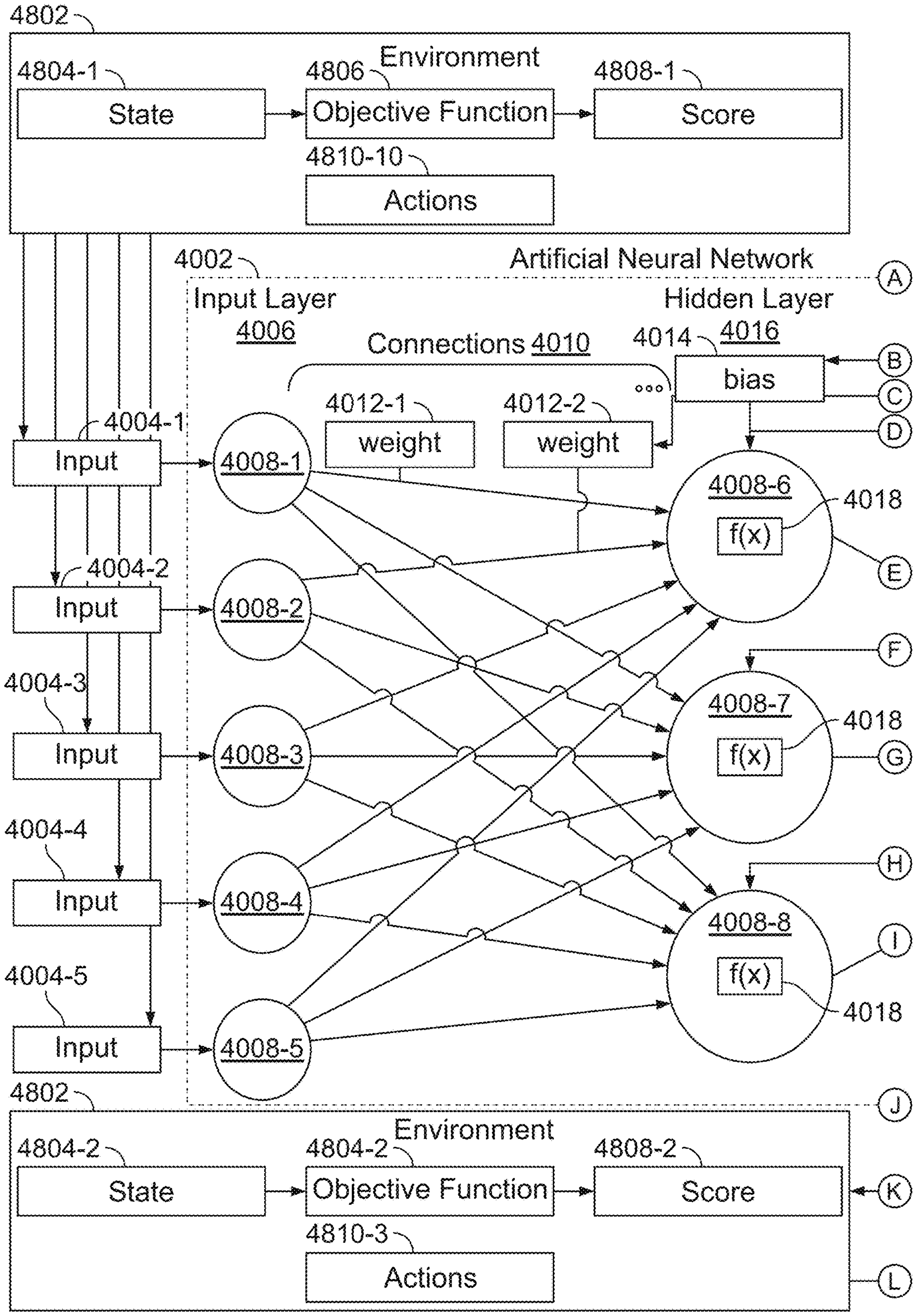
FIG. 48 is a schematic diagram detailing a development of an artificial neural network by reinforcement learning according to some example embodiments.

FIG. 48 illustrates an example scenario featuring a development of an artificial neural network 4002 by reinforcement learning. In the example scenario of FIG. 48, the artificial neural network 4002 interacts with an environment

4802 (e.g., a simulation, a game, a real-world area such as a factory or a road, an experimental scientific process, or the like) through a set of actions 4810 (e.g., movements or actions performed by an entity in the environment 4802 and controlled by the artificial neural network 4002, or the selection and/or adjustment of parameters of the environment 4802 and/or experimental scientific process). More particularly, at each point in time, the environment 4802 may exist in a state 4804, and the set of actions 4810 that can be selected by the artificial neural network 4002 may be based on the current state 4804 of the environment 4802. That is, some actions 4810 may be available to the artificial neural network 4002 for use during a first state 4804 of the environment 4802, but may not be available to the artificial neural network 4002 for use during a second state 4804 of the environment 4802. Further, the artificial neural network 4002 may be configured to maximize an objective function 4806, such as an achievement of a goal or objective within the environment 4802 and/or a score, rank, or other type of assessment of the state 4804 of the environment 4802. In the example scenario of FIG. 48, the objective function 4806 can determine a score 4808 for a current state 4804 of the environment 4802, and the artificial neural network 4002 is to be trained to take actions 4810 that change the state 4804 of the environment 4802 in a way that is likely to increase the score 4808 of the objective function 4806.

As shown in FIG. 48, the environment 4802 is initially in a first state 4804-1, for which the objective function 4806 returns a first score 4808-1. The first state 4804-1 of the environment 4802 also determines a first set of actions 4810-1 that the artificial neural network 4002 may choose to change the state 4804 of the environment 4802. The artificial neural network 4002 may receive, as input 4004, the first state 4804-1 of the environment 4802, the first score 4808-1 of the first state 4804-1 as determined by the objective function 4806-1, and the set of actions 4810-1 among which the artificial neural network 4002 may choose during the first state 4804-1. For the given set of inputs 4004, the artificial neural network 4002 may generate, as the output of the neuron 4008 of the output layer 4020, a set of probabilities 4812 of the first set of actions 4810-1 that are available at the first state 4804-1. Initially, the artificial neural network 4002 may be incapable of predicting how such actions 4810 might affect the state 4804 of the environment 4802 and/or the score 4808 of the objective function 4806, as the weights 4012 and biases 4016 of the neurons 4008 may have initially been zeroed or randomized. Thus, the probabilities 4812 may initially be equal and/or randomized. Over time, as the artificial neural network 4002 is trained to learn a policy, the probabilities 4812 of the available actions 4810 are proportional to the learned likelihood that a selection of each such action 4810 in the given state 4804 of the environment 4802 would increase the score 4808 of the objective function 4806.

Based on the probabilities 4812 (e.g., a random selection among the first set of actions 4810-1, wherein the random selection is weighted based on the probabilities 4812 of the respective actions 4810-1), the artificial neural network 4002 selects one of the actions 4810-2. The environment 4802 is updated based on the selected action 4810-2, resulting in a second state 4804-2, for which the objective function 4806 determines a second score 4808-2 for comparison with the first score 4808-1 associated with the first state 4804-1. The second score 4808-2 may be higher than the first score 4808-1, indicating that the selected action 4810-2 favorably affected the state 4804 of the environment 4802. Alternatively, the second score 4808-2 may be the same as or less than the first score 4808-1, indicating that the selected action 4810-2 did not favorably affected the state 4804 of the environment 4802. Based on the comparison, the training of the artificial neural network 4002 involves a policy update 4814 of the weights 4012 and/or biases 4016 of the artificial neural network 4002, wherein the policy update 4814 adjusts the probability 4812 of the selected action 4810-2 (relative to the other actions 4810 of the first set of actions 4810-1) of selecting the action 4810-2 when the environment 4802 is in the first state 4804-1. If the selected action 4810-2 favorably affected the state 4804 of the environment 4802, the policy update 4814 adjusts the weights 4012 and/or biases 4016 of the artificial neural network 4002 to increase the probability 4812 of selecting the selected action 4810-2 when the environment 4802 is in a state 4804 similar to the first state 4804-1. If the selected action 4810-2 did not favorably affect the state 4804 of the environment 4802, the policy update 4814 adjusts the weights 4012 and/or biases 4016 of the artificial neural network 4002 to maintain or decrease the probability 4812 of selecting the selected action 4810-2 when the environment 4802 is in a state 4804 similar to the first state 4804-1. The training may continue with a selection of another action 4810 from the first set of actions 4810-1 for evaluation in view of the first state 4804-1 of the environment 4802. Alternatively or additionally, the training may continue with the determination of a second set of actions 4810-3 in view of the second state 4804-2 of the environment 4802 following the application of the selected action 4810-2. By iteratively performing policy updates 4814 of the weights 4012 and/or biases 4016 of the artificial neural network 4002, the reinforcement learning process may incrementally adjust the policy learned by the artificial neural network 4002, such that the probabilities 4812 of the actions 4810 determined by the artificial neural network 4002 in view of a given state 4804 of the environment 4802 match the likelihood that each such action 4810, if selected and performed with regard to the environment 4802, would improve the score 4808 of the updated state 4804 of the environment 4802 by the objective function 4806.

The example reinforcement learning process shown in FIG. 48 may vary in many ways based on the nature of the environment 4802 and actions 4810 (e.g., a type of simulation, game, real-world environment, and/or scientific experiment in which the artificial neural network 4002 is to operate), the objective function 4806, and/or the structure and/or performance of the artificial neural network 4002 in the environment 4802, including a role of the artificial neural network 4002 in the environment 4802.

As a first example, some reinforcement learning scenarios involve complex objective functions 4806 in which several parameters are to be concurrently optimized and/or several goals are to be concurrently pursued. For instance, in a simulation of an industrial manufacturing process, the objective functions 4806 may include separate scores 4808 for a quality of manufactured products to be maximized, the rate of production of manufactured products to be maximized, a cost of manufactured products to be minimized, a set of safety standards to be met, and/or a set of pollution measurements to be minimized. The policy update 4814 may be performed based on the effects of each action 4810 on a prioritized and/or weighted combination of the scores 4808 (e.g., highly prioritizing compliance with safety standards and maximization product quality, secondarily prioritizing maximization of production rates and minimization of costs, and tertiarily prioritizing minimization of pollution).

As a second example, comparatively simple environments 4802 and/or objective functions 4806 may involve scoring 4808 and policy updates 4814 based only on a current state 4804 of the environment 4802, and each action 4810 may be considered only to change a current state 4804 of the environment 4802 to an updated state of the environment 4802. Accordingly, the selection of actions 4810-2 for further consideration may be performed as a breadth-first evaluation, e.g., evaluating all of the available actions 4810 for a first state 4804 of the environment 4802 before evaluating any of the actions 4810 that would be available for each or any updated state 4804 of the environment 4802. However, comparatively complex environments 4802 and/or objective functions 4806 may involve longer-term implications; for example, the strategy required in chess often requires considering the consequences of each action 4810 in view of the following combinations of actions available to each player at each future step (often referred to as a "ply"). Accordingly, the selection of actions 4810-2 for further consideration may be performed as a depth-first evaluation, e.g., evaluating each action 4810 in view of an extended subset of further states 4804 of the environment 4802 (e.g., the chess board) after the action 4810 is taken at a first time before evaluating any of the other actions 4810 that are available at the first time.

As a third example, due to the potentially enormous number of states 4804 of the environment 4802 and the actions 4810 that may be available in each state 4804, the search space that is open for consideration by the reinforcement learning process may be practically unbounded, such that the reinforcement learning process may run indefinitely and may still be able to explore only a minuscule portion of the search space. Thus, different reinforcement learning processes may use different strategies for selecting an action 4810 for evaluation for a given state 4804 of the environment 4802 and a given set of available actions 4810. In particular, each strategy for a reinforcement learning process is based on a balance between selecting for evaluation, among the set of available actions 4810 for the given state 4804 of the environment 4802, the current best action 4810 for a given state 4804 (e.g., the action 4810 that is currently predicted to have the greatest likelihood of changing the state 4804 of the environment 4802 in a way that improves the objective function 4806) and/or other actions 4810 in the set of available actions 4810 that might produce an even greater likelihood of changing the state 4804 of the environment 4802 in a way that improves the objective function 4806. That is, each strategy for reinforcement learning balances the reinforcement learning goals of verifying and/or refining the current policy or of experimenting with alternative actions to discover even better policies based on a different selection of action 4810. As another consideration, each reinforcement learning policy balances the value of a short-term improvement in the score 4808 of the objective function 4806 for the immediately following state 4804 of the environment 4802 in response to a selected action 4810 against the prospective longer-term or future improvement in the score 4808 of the objective function 4806 for several future following states 4804 of the environment 4802 in response to the selected action 4810. For instance, a chess move that results in capturing the queen of an opponent may yield a very large increase in the score 4808 of the chess board, but the cost of such capture may sacrifice one or more other chess pieces and/or positional advantages that have a greater long-term decrease in the score 4808 of the chess board.

One such reinforcement learning strategy, known as Q-learning, is based on the Bellman equation, expressed as follows:

$$Q^{new}(S_t, A_t) \leftarrow (1-\alpha)\cdot Q(S_t, A_t) + \alpha\cdot(R_{t+1} + \gamma\cdot \max_a Q(S_{t+1}, a)),$$

wherein,

- $S_t$ represents the state 4804 of the environment 4802 at time t,
- $A_t$ represents the set of actions 4810 that are available in the environment 4802 at time t,
- $Q(S_t,A_t)$ represents a quality or probability of taking each action $A_t$ in the environment 4802 at time t,
- $\alpha$ represents a learning rate of adjusting the probabilities of the policy,
- $R_{t+1}$ represents a "reward" or improvement of the objective function 4806 in response to taking an action in the environment 4802 at time t,
- $\gamma$ represents a "discount factor" indicating a weight given to the prospect of future improvements of the objective function 4806 in response to taking an action in the environment 4802 at time t,
- $\max_a Q(S_{t+1},a)$ represents the maximum possible "reward" or improvement of the objective function 4806 for any further action(s) 4810 that could be taken in the environment 4802 after taking an action in the environment 4802 at time t, and
- $Q^{new}(S_t,A_t)$ represents the updated quality or probability of taking each action $A_t$ in the environment 4802 at time t, that is, the adjusted probabilities 4812 in response to the probability update 4814 of the reinforcement learning model.

In Q-learning, the "discount factor" $\gamma$ balances the exploration of actions that may have long-term value in pursuing the objective function 4806 in the environment 4802 against the exploration of actions having short-term value in increasing the score 4808 of the objective function 4806 in the environment 4802. Also, Q-learning provides a as an adjustable learning rate to adjust the rate at which the probabilities 4812 of the respective actions 4810 of the policy are updated. Many such reinforcement learning strategies for training artificial neural networks 4002 to perform reinforcement learning tasks may be known to persons of ordinary skill in the art of reinforcement learning.

Reinforcement learning may be used in a wide variety of circumstances. For example, reinforcement learning may be applied to train an artificial neural network 4002 to control one or more entities in a simulation, such as cognitive entities in a biological simulation. Reinforcement learning may be applied to train an artificial neural network 4002 to make decisions in a complex environment 4802, such as a game or the management of the machinery of an industrial manufacturing facility. Reinforcement learning may be applied in various transit environments 4802 to train an artificial neural network 4002 to control the movement of robotic machines in a particular environment 4802 such as an industrial manufacturing facility and/or the navigation and routing decisions of autonomous vehicles. Reinforcement learning may be applied in various scientific environments to generate, explore, and evaluate various perturbations of scientific experiments. Many such scenarios for the application of reinforcement learning techniques may be known to persons of ordinary skill in the art of reinforcement learning.

Architectures

The methods and systems described herein may be deployed in part or in whole through machines that execute computer software on various devices including a server, client, firewall, gateway, hub, router, switch, infrastructure-as-a-service, platform-as-a-service, or other such computer and/or networking hardware or system. The software may be associated with a server that may include a file server, print server, domain server, internet server, intranet server, cloud server, infrastructure-as-a-service server, platform-as-a-service server, web server, and other variants such as secondary server, host server, distributed server, failover server, backup server, server farm, and the like. The server may include one or more of memories, processors, computer readable media, storage media, ports (physical and virtual), communication devices, and interfaces capable of accessing other servers, clients, machines, and devices through a wired or a wireless medium, and the like. The methods, programs, or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers, social networks, and the like. Additionally, this coupling and/or connection may facilitate remote execution of programs across the network. The networking of some or all of these devices may facilitate parallel processing of a program or method at one or more locations without deviating from the scope of the disclosure. In addition, any of the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

A software program may be associated with a client that may include a file client, print client, domain client, internet client, intranet client and other variants such as secondary client, host client, distributed client and the like. The client may include one or more of memories, processors, computer readable media, storage media, ports (physical and virtual), communication devices, and interfaces capable of accessing other clients, servers, machines, and devices through a wired or a wireless medium, and the like. The methods, programs, or codes as described herein and elsewhere may be executed by the client. In addition, other devices required for the execution of methods as described in this application may be considered as a part of the infrastructure associated with the client.

The client may provide an interface to other devices including, without limitation, servers, other clients, printers, database servers, print servers, file servers, communication servers, distributed servers and the like. Additionally, this coupling and/or connection may facilitate remote execution of programs across the network. The networking of some or all of these devices may facilitate parallel processing of a program or method at one or more locations without deviating from the scope of the disclosure. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

In a client-server model, some of the software executes on first hardware identified functionally as a server, while other of the software executes on second hardware identified functionally as a client. The identity of the client and server is not fixed: for some functionality, the first hardware may act as the server while for other functionality, the first hardware may act as the client. In different embodiments and in different scenarios, functionality may be shifted between the client and the server. In one dynamic example, some functionality normally performed by the second hardware is shifted to the first hardware when the second hardware has less capability. In various embodiments, the term "local" may be used in place of "client," and the term "remote" may be used in place of "server."

Some or all of the software may run in a virtual environment rather than directly on hardware. The virtual environment may include a hypervisor, emulator, sandbox, container engine, etc. The software may be built as a virtual machine, a container, etc. Virtualized resources may be controlled using, for example, a DOCKER™ container platform, a pivotal cloud foundry (PCF) platform, etc.

Some or all of the software may be logically partitioned into microservices. Each microservice offers a reduced subset of functionality. In various embodiments, each microservice may be scaled independently depending on load, either by devoting more resources to the microservice or by instantiating more instances of the microservice. In various embodiments, functionality offered by one or more microservices may be combined with each other and/or with other software not adhering to a microservices model.

Some or all of the software may be arranged logically into layers. In a layered architecture, a second layer may be logically placed between a first layer and a third layer. The first layer and the third layer would then generally interact with the second layer and not with each other. In various embodiments, this is not strictly enforced—for example, some direct communication may occur between the first and third layers.

The methods, program codes, and instructions described herein and elsewhere may be implemented on or through mobile devices. The mobile devices may include navigation devices, cell phones, mobile phones, mobile personal digital assistants, laptops, palmtops, netbooks, pagers, electronic book readers, music players and the like. These devices may include, apart from other components, a storage medium such as flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer-to-peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

EXAMPLES

Examples of hardware components include integrated circuits (ICs), application specific integrated circuit (ASICs), digital circuit elements, analog circuit elements, combinational logic circuits, gate arrays such as field programmable gate arrays (FPGAs), digital signal processors (DSPs), and complex programmable logic devices (CPLDs).

Examples of servers include a file server, print server, domain server, internet server, intranet server, cloud server, infrastructure-as-a-service server, platform-as-a-service server, web server, secondary server, host server, distributed server, failover server, and backup server.

Examples of mobile devices include navigation devices, cell phones, smart phones, mobile phones, mobile personal digital assistants, palmtops, netbooks, pagers, electronic book readers, tablets, and music players.

Examples of network devices include switches, routers, firewalls, gateways, hubs, base stations, access points, repeaters, head-ends, user equipment, cell sites, antennas, and towers.

Examples of processing hardware include a central processing unit (CPU), a graphics processing unit (GPU), an approximate computing processor, a quantum computing processor, a parallel computing processor, a neural network processor, a signal processor, a digital processor, a data processor, an embedded processor, a microprocessor, and a co-processor. The co-processor may provide additional processing functions and/or optimizations, such as for speed or power consumption. Examples of a co-processor include a math co-processor, a graphics co-processor, a communication co-processor, a video co-processor, and an artificial intelligence (AI) co-processor.

Examples of a system-on-chip include a radio frequency (RF) system-on-chip, an artificial intelligence (AI) system-on-chip, a video processing system-on-chip, an organ-on-chip, a quantum algorithm system-on-chip, etc.

Examples of storage hardware and/or computer-readable media include computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g., USB sticks or keys), floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, network-attached storage, network storage, NVME-accessible storage, PCIE connected storage, and distributed storage.

Examples of storage implemented by the storage hardware include a database (such as a relational database or a NoSQL database), a data store, a data lake, a column store, and a data warehouse.

Example of storage hardware include nonvolatile memory devices, volatile memory devices, magnetic storage media, a storage area network (SAN), network-attached storage (NAS), optical storage media, printed media (such as bar codes and magnetic ink), and paper media (such as punch cards and paper tape).

Examples of nonvolatile memory devices include flash memory (including NAND and NOR technologies), solid state drives (SSDs), an erasable programmable read-only memory device such as an electrically erasable programmable read-only memory (EEPROM) device, and a mask read-only memory device (ROM).

Examples of volatile memory devices include processor registers and random-access memory (RAM), such as static RAM (SRAM), dynamic RAM (DRAM), synchronous DRAM (SDRAM), synchronous graphics RAM (SGRAM), and video RAM (VRAM).

Example of magnetic storage media include analog magnetic tape, digital magnetic tape, and rotating hard disk drive (HDDs).

Examples of optical storage media include a CD (such as a CD-R, CD-RW, or CD-ROM), a DVD, a Blu-ray disc, and an Ultra HD Blu-ray disc.

Examples of storage implemented by the storage hardware include a distributed ledger, such as a permissioned or permissionless blockchain.

Examples of networks include a cellular network, a local area network (LAN), a wireless personal area network (WPAN), a metropolitan area network (MAN), and/or a wide area network (WAN).

Examples of local area networks (LANs) include Institute of Electrical and Electronics Engineers (IEEE) Standard 802.11-2020 (also known as the Wi-Fi wireless networking standard) and IEEE Standard 802.3-2018 (also known as the ETHERNET wired networking standard).

Examples of a WPAN include IEEE Standard 802.15.4, including the ZIGBEE standard from the ZigBee Alliance. Further examples of a WPAN include the BLUETOOTH wireless networking standard, including Core Specification versions 3.0, 4.0, 4.1, 4.2, 5.0, and 5.1 from the Bluetooth Special Interest Group (SIG).

Examples of cellular networks include GSM, GPRS, 3G, 4G, 5G, LTE, and EVDO. The cellular network may be implemented using frequency division multiple access (FDMA) network or code division multiple access (CDMA) network.

Examples of wide-area networks (WANs) include the Internet.

Further Information and Use of Terms

The background description is presented simply for context, and is not necessarily well-understood, routine, or conventional. Further, the background description is not an admission of what does or does not qualify as prior art. In fact, some or all of the background description may be work attributable to the named inventors that is otherwise unknown in the art.

While only a few embodiments of the disclosure have been shown and described, it will be obvious to those skilled in the art that many changes and modifications may be made thereunto without departing from the spirit and scope of the disclosure as described in the following claims. All patent applications and patents, both foreign and domestic, and all other publications referenced herein are incorporated herein in their entireties to the full extent permitted by law.

The detailed description includes specific examples for illustration only, and not to limit the disclosure or its applicability. The examples are not intended to be an exhaustive list, but instead simply demonstrate possession by the inventors of the full scope of the currently presented and envisioned future claims. Variations, combinations, and equivalents of the examples are within the scope of the disclosure. No language in the specification should be construed as indicating that any non-claimed element is essential or critical to the practice of the disclosure. Although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of multiple embodiments remain within the scope of this disclosure. No language in the specification should be construed as indicating any non-claimed element as essential to the practice of the disclosure.

All methods described herein can be performed in any suitable order unless otherwise indicated herein or otherwise clearly contradicted by context. For example, one or more elements (e.g., steps within a method, instructions, actions, or operations) may be executed in a different order (and/or concurrently) without altering the principles of the present disclosure. Unless technically infeasible, elements described as being in series may be implemented partially or fully in parallel. Similarly, unless technically infeasible, elements described as being in parallel may be implemented partially or fully in series.

While the disclosure describes structures corresponding to claimed elements, those elements do not necessarily invoke a means plus function interpretation unless they explicitly use the signifier "means for." Unless otherwise indicated, recitations of ranges of values are merely intended to serve as a shorthand way of referring individually to each separate value falling within the range, and each separate value is hereby incorporated into the specification as if it were individually recited.

Physical (such as spatial and/or electrical) and functional relationships between elements (for example, between modules, circuit elements, semiconductor layers, etc.) are described using various terms. Unless explicitly described as being "direct," when a relationship between first and second elements is described, that relationship encompasses both (i) a direct relationship where no other intervening elements are present between the first and second elements and (ii) an indirect relationship where one or more intervening elements are present between the first and second elements. Example relationship terms include "adjoining," "transmitting," "receiving," "connected," "engaged," "coupled," "adjacent," "next to," "on top of," "above," "below," "abutting," and "disposed."

While the drawings divide elements of the disclosure into different functional blocks or action blocks, these divisions are for illustration only. According to the principles of the present disclosure, functionality can be combined in other ways such that some or all functionality from multiple separately-depicted blocks can be implemented in a single functional block; similarly, functionality depicted in a single block may be separated into multiple blocks. Unless explicitly stated as mutually exclusive, features depicted in different drawings can be combined consistent with the principles of the present disclosure.

In the drawings, reference numbers may be reused to identify identical elements or may simply identify elements that implement similar functionality. Numbering or other labeling of instructions or method steps is done for convenient reference, not to indicate a fixed order. In the drawings, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. As one example, for information sent from element A to element B, element B may send requests and/or acknowledgements to element A.

While the foregoing written description enables one skilled to make and use what is considered presently to be the best mode thereof, those skilled in the art will understand and appreciate the existence of variations, combinations, and equivalents of the specific embodiment, method, and examples herein. The disclosure should therefore not be limited by the above-described embodiment, method, and examples, but by all embodiments and methods within the scope and spirit of the disclosure. The spirit and scope of the disclosure is not to be limited by the foregoing examples, but is to be understood in the broadest sense allowable by law.

The use of the terms "a" and "an" and "the" and similar referents in the context of describing the disclosure (especially in the context of the following claims) is to be construed to cover both the singular and the plural, unless otherwise indicated herein or clearly contradicted by context. The phrase "at least one of A, B, and C" should be construed to mean a logical (A OR B OR C), using a non-exclusive logical OR, and should not be construed to mean "at least one of A, at least one of B, and at least one of C," The terms "comprising," "with," "including," and "containing" are to be construed as open-ended terms (i.e., meaning "including, but not limited to.") unless otherwise noted. Recitations of ranges of values herein are merely intended to serve as a shorthand method of referring individually to each separate value falling within the range, unless otherwise indicated herein, and each separate value is incorporated into the specification as if it were individually recited herein. The term "exemplary" simply means "example" and does not indicate a best or preferred example. The use of any and all examples, or exemplary language (e.g., "such as") provided herein, is intended merely to better illuminate the disclosure and does not pose a limitation on the scope of the disclosure unless otherwise claimed. The term "set" may include a set with a single member. The term "set" does not necessarily exclude the empty set—in other words, in some circumstances a "set" may have zero elements. The term "non-empty set" may be used to indicate exclusion of the empty set—that is, a non-empty set must have one or more elements. The term "subset" does not necessarily require a proper subset. In other words, a "subset" of a first set may be coextensive with (equal to) the first set. Further, the term "subset" does not necessarily exclude the empty set—in some circumstances a "subset" may have zero elements.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

In this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using a machine learning framework, e.g., a TensorFlow framework, or a Jax framework.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network.

Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

The invention claimed is:

1. A rapid sampling system for obtaining samples from a fermentation system, comprising:
- a sample inlet fluidly connected to the fermentation system;
- a pump fluidly connected to the sample inlet and configured to draw a sample from the fermentation system;
- a first valve fluidly connected to an outlet of the pump;
- a second valve fluidly connected to a liquid nitrogen chamber;
- a multi-well filter plate, wherein an individual well of the multi-well filter plate is configured to collect and filter the sample;
- a motorized base operatively connected to the multi-well filter plate configured to adjust a position of the multi-well filter plate; and
- a control unit including one or more processors and one or more memories operatively connected to the pump, the first valve, the second valve, and the motorized base, the control unit configured to automatically initiate and perform a plurality of sampling operations at predetermined time intervals, wherein each sampling operation comprises:
  - controlling the operation of the pump to obtain the sample,
  - controlling the operation of the first valve to dispense the sample into a first well of the multi-well filter plate;
  - controlling the operation of the second valve to dispense liquid nitrogen into the first well of the multi-well filter plate; and
  - controlling the operation of the motorized base to move the multi-well filter plate to position a second well beneath the first valve and the second valve.

2. The rapid sampling system of claim 1, further comprising a purge compressed air inlet fluidly connected to the first valve and operatively connected to the control unit, wherein the control unit is further configured to control operation of the first valve to dispense compressed air into a selected well before receiving the sample.

3. The rapid sampling system of claim 1, further comprising a purge solvent inlet fluidly connected to the first valve and operatively connected to the control unit wherein the control unit is further configured to control operation of the first valve to dispense solvent into a selected well before obtaining the sample.

4. The rapid sampling system of claim 1, further comprising a vacuum base wherein the vacuum base is operatively connected to the multi-well filter plate and operatively connected to the control unit wherein the control unit is further configured to control operation of the vacuum base to filter one or more wells of the multi-well filter plate.

5. The rapid sampling system of claim 1, further comprising a carbon source inlet fluidly connected to the fermentation system and configured to dispense a carbon source into the fermentation system wherein the carbon source inlet is operatively connected to the control unit and wherein the initiation of the plurality of sampling operations is dependent on a dispensing of carbon by the carbon source inlet.

6. The rapid sampling system of claim 1, further comprising a sampling loop.

7. The rapid sampling system of claim 1, wherein the rapid sampling system is configured for a pilot scale.

8. The rapid sampling system of claim 1, wherein the rapid sampling system is configured for industrial scale.

9. The rapid sampling system of claim 1, wherein the first valve is an HPLC valve.

10. The rapid sampling system of claim 1, wherein the second valve is a cryogenic valve.

11. The rapid sampling system of claim 1, wherein the rapid sampling system is represented as a digital twin.

12. The rapid sampling system of claim 1, wherein the rapid sampling system is integrated with a mass and/or optical analytical system and an automated omics for generalization system.

* * * * *